(12) United States Patent
Bennett et al.

(10) Patent No.: US 11,827,898 B2
(45) Date of Patent: Nov. 28, 2023

(54) GENE THERAPY FOR OCULAR DISORDERS

(71) Applicant: The Trustees of the University of Pennsylvania, Philadelphia, PA (US)

(72) Inventors: Jean Bennett, Bryn Mawr, PA (US); Junwei Sun, Philadelphia, PA (US); Jeannette Bennicelli, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 642 days.

(21) Appl. No.: 16/621,627

(22) PCT Filed: Jun. 14, 2018

(86) PCT No.: PCT/US2018/037592
§ 371 (c)(1),
(2) Date: Dec. 11, 2019

(87) PCT Pub. No.: WO2018/232149
PCT Pub. Date: Dec. 20, 2018

(65) Prior Publication Data
US 2020/0172929 A1 Jun. 4, 2020

Related U.S. Application Data

(60) Provisional application No. 62/519,821, filed on Jun. 14, 2017.

(51) Int. Cl.
*C12N 15/86* (2006.01)
*C07K 14/47* (2006.01)
*A61K 48/00* (2006.01)

(52) U.S. Cl.
CPC ............ *C12N 15/86* (2013.01); *A61K 48/005* (2013.01); *A61K 48/0075* (2013.01); *C07K 14/4705* (2013.01); *C12N 2750/14143* (2013.01); *C12N 2750/14171* (2013.01)

(58) Field of Classification Search
CPC .......... C12N 15/86; C12N 2750/14143; C12N 2750/14171; C07K 14/47; C07K 14/4705; C07K 14/705; A61K 48/005; A61K 48/0075
See application file for complete search history.

(56) References Cited

U.S. PATENT DOCUMENTS

| | | | |
|---|---|---|---|
| 5,139,941 A | 8/1992 | Muzyczka et al. | |
| 5,478,745 A | 12/1995 | Samulski et al. | |
| 5,741,683 A | 4/1998 | Zhou et al. | |
| 6,057,152 A | 5/2000 | Samulski et al. | |
| 6,204,059 B1 | 3/2001 | Samulski et al. | |
| 6,268,213 B1 | 7/2001 | Samulski et al. | |
| 6,491,907 B1 | 12/2002 | Rabinowitz et al. | |
| 6,596,535 B1 | 7/2003 | Carter | |
| 6,660,514 B1 | 12/2003 | Zolotukhin et al. | |
| 6,951,753 B2 | 10/2005 | Shenk et al. | |
| 7,094,604 B2 | 8/2006 | Snyder et al. | |
| 7,125,717 B2 | 10/2006 | Carter | |
| 7,172,893 B2 | 2/2007 | Rabinowitz et al. | |
| 7,201,898 B2 | 4/2007 | Monahan et al. | |
| 7,229,823 B2 | 6/2007 | Samulski et al. | |
| 7,282,199 B2 | 10/2007 | Gao et al. | |
| 7,439,065 B2 | 10/2008 | Ferrari et al. | |
| 7,456,683 B2 | 11/2008 | Takano et al. | |
| 7,588,772 B2 | 9/2009 | Kay et al. | |
| 7,629,322 B2 | 12/2009 | Kleinschmidt et al. | |
| 7,790,449 B2 | 9/2010 | Gao et al. | |
| 7,906,111 B2 | 3/2011 | Wilson et al. | |
| 8,147,823 B2 | 4/2012 | Acland et al. | |
| 2004/0022766 A1* | 2/2004 | Acland | C12N 15/86 424/93.2 |
| 2007/0036760 A1 | 2/2007 | Wilson et al. | |
| 2009/0197338 A1 | 8/2009 | Vandenberghe et al. | |
| 2011/0305772 A1 | 12/2011 | Cameron | |
| 2013/0317091 A1 | 11/2013 | Ye et al. | |
| 2014/0010861 A1 | 1/2014 | Bancel et al. | |
| 2014/0087444 A1* | 3/2014 | Bennett | C12N 15/86 435/254.2 |

(Continued)

FOREIGN PATENT DOCUMENTS

EP 1310571 2/2006
WO WO 2002/057454 A2 7/2002

(Continued)

OTHER PUBLICATIONS

Kingdoms of Life, waynesword.palomar.edu/trfeb98.htm, last visited Nov. 26, 2007.*
Mammal, en.wikipedia.org/wiki/Mammal, last visited Aug. 31, 2022.*
Fumoto et al., Targeted Gene Delivery: Importance of Administration Routes, INTECH, Novel Gene Therapy Approaches, p. 3-31; editors Wei and Good, publisher Books on Demand, 2013.*
Daya et al., Gene Therapy Using Adeno-Associated Virus Vectors, Clin. Microbiol. Rev. 21(4): 583-593, 2008.*
Mingozzi and High, Immune responses to AAV vectors: overcoming barriers to successful gene therapy, Blood 122(1): 23-36, 2013.*

(Continued)

*Primary Examiner* — Kevin K Hill
(74) *Attorney, Agent, or Firm* — Howson & Howson LLP; Colleen M. Schaller

(57) ABSTRACT

Compositions and methods are provided for treating ocular disorders in a subject are provided. In one aspect, an adeno-associated viral vector is provided which includes a nucleic acid molecule comprising a sequence encoding CNGA3. In another aspect, an adeno-associated viral vector is provided which includes a nucleic acid molecule comprising a sequence encoding CNGB3. In another aspect, an adeno-associated viral vector is provided which includes a nucleic acid molecule comprising a sequence encoding REP-1. In desired embodiments, the subject is human, cat, dog, sheep, or non-human primate.

14 Claims, 74 Drawing Sheets

Specification includes a Sequence Listing.

(56) References Cited

U.S. PATENT DOCUMENTS

| | | | |
|---|---|---|---|
| 2015/0259395 | A1 | 9/2015 | Chalberg et al. |
| 2016/0206704 | A1 | 7/2016 | MacLaren |

FOREIGN PATENT DOCUMENTS

| | | |
|---|---|---|
| WO | WO 2003/042397 | 5/2003 |
| WO | WO 2005/033321 | 4/2005 |
| WO | WO 2006/110689 | 10/2006 |
| WO | WO 2010/005533 | 1/2010 |
| WO | WO 2011/034947 A2 | 3/2011 |
| WO | WO 2011/126808 | 10/2011 |
| WO | WO 2012/094560 | 7/2012 |
| WO | WO-2012/094560 A2 | 7/2012 |
| WO | WO 2012/114090 | 8/2012 |
| WO | WO 2012/158757 | 11/2012 |
| WO | WO 2013/049493 | 4/2013 |
| WO | WO 2013/063601 | 5/2013 |
| WO | WO 2013/086515 | 6/2013 |
| WO | WO 2014/011210 | 1/2014 |
| WO | WO 2014/124282 | 8/2014 |
| WO | WO 2014/170480 A1 | 10/2014 |
| WO | WO 2015/092440 | 6/2015 |
| WO | WO 2015/160893 | 10/2015 |
| WO | WO 2017/106202 | 6/2017 |

OTHER PUBLICATIONS

Kattenhorn et al., Adeno-Associated Virus Gene Therapy for Liver Disease, Human Gene Therapy 27(12): 947-961, Nov. 28, 2016.*
Perrin, Make Mouse Studies Work, Nature (507): 423-425, 2014.*
Ye et al., Rescue of Cone ERG Function by Treatment with AAV-hCNGB3 Vectors in CNGB3 Knockout Mice, Invest. Ophthalmol. & Visual Sci. 56 (5477), ARVO Annual Meeting Abstract, Jun. 2015; abstract only.*
Beltran et al., rAAV2/5 gene-targeting to rods:dose-dependent efficiency and complications associated with different promoters, Gene Therapy, vol. 17(9):1162-1174, Sep. 2010.
Buchholz et al., Rapid and Efficient Directed Differentiation of Human Pluripotent Stem Cells Into Retinal Pigmented Epithelium, Stem Cells Translational Medicine, vol. 2151:384-93, May 2013.
Buning et al., Recent developments in adeno-associated virus vector technology, Journal of Genetic Medicine, vol. 10(7):717-733, Jul. 2008.
Cai et al., A 350 bp region of the proximal promoter of Rds drives cell-type specific gene expression, Experimental Eye Research, vol. 91(2):186-94, Aug. 2010.
Carvalho et al., Long-term and age-dependent restoration of visual function in a mouse model of CNGB3-associated achromatopsia following gene therapy, Human Molecular Genetics, vol. 20(16): 3161-3175, Aug. 2011.
Cereso et al., Proof of concept for AAV2/5-mediated gene therapy in iPSC-derived retinal pigment epithelium of a choroideremia patient, Molecular Therapy—Methods & Clinical Development, vol. 1:14011, Apr. 2014.
Coussa et al., Choroideremia: a review of general findings and pathogenesis, Ophthalmic Genetics, vol. 33(2):57-65, Jun. 2012.
Cronin et al., Dark-rearing the rd10 mouse: implications for therapy, Advances in Experimental Medicine and Biology, vol. 723:129-36, 2012.
Daber et al., A novel molecular switch, Journal of Molecular Biology, vol. 391(4):661-70, Aug. 2009.
Dalkara et al, In Vivo—Directed Evolution of a New Adeno—Associated Virus for Therapeutic Outer Retinal Gene Delivery from the Vitreous, Science Translational Medicine, vol. 5(189):189ra76, Jun. 2013.
Damdindorj et al, A Comparative Analysis of Constitutive Promoters Located in Adeno-Associated Viral Vectors, PloS ONE, vol. 9(8): e106472, Aug. 2014.
Diehl et al, A good practice guide to the administration of substances and removal of blood, including routes and volumes, Journal Applied Toxicology, vol. 21(1):15-23, Jan. 2001.
Dyka et al., Cone specific promoter for use in gene therapy of retinal degenerative diseases, Adv Exp Med Biol. 2014;801:695-701.
Fisher et al., Transduction with recombinant adeno-associated virus for gene therapy is limited by leading-strand synthesis, Journal of Virology, vol. 70(1):520-532, Jan. 1996.
Grieger & Samulski, Adeno-associated virus as a gene therapy vector: Vector development, production and clinical applications, Advanced Biochemical Engineering/Biotechnology, vol. 99: 119-145, 2005.
Guo et al., Rapid and simplified purification of recombinant adeno-associated virus, J Virol Methods, vol. 183(2):139-146, Aug. 2012.
Kachi et al., Equine infectious anemia viral vector-mediated codelivery of endostatin and angiostatin driven by retinal pigmented epithelium-specific VMD2 promoter inhibits choroidal neovascularization, Human Gene Therapy, vol. 20(1):31-9, Jan. 2009.
Lambard et al., Expression of Rod-Derived Cone Vability Factor: Dual Role of CRX in Regulation Promoter Activity and Cell-Type Specificity, PloS One, vol. 5(10):e13025, Oct. 2010.
Li et al., Craft CM. Retinoic acid upregulates cone arrestin expression in retinoblastoma cells through a Cis element in the distal promoter region, Invest Ophthalmology & Visual Science, vol. 43(5):1375-1383, May 2002.
Lock et al., Absolute Determination of Single-Stranded and Self-Complementary Adeno-Associated Viral Vector Genome Titers by Droplet Digital PCR, Human Gene Therapy Methods, vol. 25(2):115-25, Apr. 2014.
Lyubarsky et al., Recovery phase of the murine rod photoresponse reconstructed from electroretinographic recordings, Journal of Neuroscience, vol. 16(2):563-571, Jan. 1996.
Marmor et al. "Standard for clinical electroretinography (2004 update)." Documenta Ophthalmologica, vol. 108(2):107-14, Mar. 2004.
McCarty et al., Self-complementary recombinant adeno-associated virus (scAAV) vectors promote efficient transduction independently of DNA synthesis, Gene Therapy, vol. 8(16):1248-1254, Aug. 2001.
McLaughlin et al., Adeno-associated virus general transduction vectors: analysis of oroviral structures, vol. 62(6):1963-1973, Jun. 1988.
Morrissey et al., PRE-1, a cis element sufficient to enhance cone- and rod—specific expression in differentiating zebrafish photoreceptors, BMC Dev, Biol, vol. 11:3, Jan. 2011.
Mowat et al., Tyrosine capsid-mutant AAV vectors for gene delivery to the canine retina from a subretinal or intravitreal approach, Gene Therapy, vol. 21(1):96-105, Jan. 2014.
Mussolino et al., AAV-mediated photoreceptor transduction of the pig cone-enriched retina, Gene Therao , 18(7):637-45, Jul. 2011.
Nagata et al., Codon Optimization Effect on Translational Efficiency of DNA Vaccine in Mammalian Cells: Analysis of Plasmid DNA Encoding a CTL Epitope Derived from Microorganisms, Biochem Biophys Res Commun. Aug. 2, 1991;261(2):445-51.
Nathans and Hogness, Isolation and nucleotide sequence of the gene encoding human rhodospin, PNAS, vol. 81(15):4851-4855, Aug. 1984.
Nicoud et al., Development of photoreceptor—specific promoters and their utility to investigate EIAV lentiviral vector mediated gene transfer to photoreceptors, Journal Genetic Medicine, vol. 9(12):1015-23, Dec. 2007.
Ogueta et al., The Human cGMP-PDE β-Subunit Promoter Region Directs Expression of the Gene to Mouse Photoreceptors, Invest Ophthalmology & Visual Science, vol. 41(13):4059-63, Dec. 2000.
Shu, X et al., Functional characterization of the human RPGR proximal promoter, Invest Ophthalmolo & Visual Science, vol. 53(7):3951-8, Jun. 2012.
Sochor et al., An Autogenously Regulated Expression System for Gene Therapeutic Ocular Applications, Scientific Reports, vol. 24(5):17105, Nov. 2015.
Sun et al., Gene Therapy with a Promoter Targeting Both Rods and Cones Rescues Retinal Degeneration Caused by AIPL1 Mutations, Gene Therapy, vol. 17(1):117-131, Jan. 2010.
Tolmachova, et al., CHM/REP1 cDNA delivery by lentiviral vectors provides functional expression of the transgene in the retinal pigment epithelium of choroideremia mice, The Journal of Gene Medicine, vol. 14(3):158-168, Mar. 2012.

(56) References Cited

OTHER PUBLICATIONS

Vasireddy et al., AAV-mediated gene therapy for choroideremia: preclinical studies in personalized models. PLoS One, vol. 8(5):e61396, May 2013.

Zhang et al., Adenovirus-adeno-associated virus hybrid for large-scale recombinant adeno-associated virus production, Human Gene Therapy, vol. 20(9):922-929, Sep. 2009.

NCBI Reference Sequence: NM_000390.2, *Homo sapiens* CHM, Rab escort protein 1 (CHM), transcript variant 1, mRNA (Apr. 23, 2017).

NCBI Reference Sequence: NM_0012982, *Homo sapiens* cyclic nucleotide gated channel subunit alpha 3 (CNGA3), transcript variant 1, mRNA (May 20, 2017).

NCBI Reference Sequence: XM_011510554.1, Predicted: *Homo sapiens* cyclic nucleotide gated channel alpha 3 (CNGA3), transcript variant X1, mRNA (Mar. 12, 2015).

International Search Report and Written Opinion issued in International Patent Application No. PCT/US18/37592, dated Nov. 5, 2018.

International Search Report and Written Opinion issued in International Patent Application No. PCT/US16/066402, dated Jul. 31, 2017.

Du et al., "Vitreal delivery of AAV vectored Cnga3 restores cone function in CNGA3-/-/Nr1-/- mice, an all-cone model of CNGA3 achromatopsia," Human Molecular Genetics, vol. 24(13):3699-3707, Apr. 2015.

Accession No. GSN:AAD58492, XP55774683, "Human CNG channel alpha 3 potassium channel (KCNQ2) DNA,"Jun. 2007.

UniProtKB, XP055775654, "Protein Cyclic nucleotide-gated 1,2 cation channel beta-3 UniProtKB-Q9NQW8 (CNGB3_HUMAN),"Ap. 2004.

Extended European Search Report, dated Feb. 19, 2021, issued on European Patent Application No. 20183330.8.

Extended European Search Report, dated Feb. 22, 2021, issued on European Patent Application No. 18817402.3.

Office Action issued on Brazilian Patent Application No. BR112018011838-9, dated Mar. 30, 2021.

Dominguez et al., Intravenous scAAV9 delivery of a codon-optimized SMN1 sequence rescues SMA mice, Human Molecular Genetics, vol. 20(4):681-693, Nov. 2011.

Non-Final Office Action issued in U.S. Appl. No. 16/061,530, dated Nov. 27, 2020.

English translation of Office Action issued in Japanese Patent Application No. 2018-531202, dated Dec. 2, 2020.

Petit et al. Advances in Gene Therapy for Diseases of the Eye, Hum Gene Ther. Aug. 2016;27(8):563-79.

Ye et al. Cone-Specific Promoters for Gene Therapy of Achromatopsia and Other Retinal Diseases, Hum Gene Ther. Jan. 2016;27(1):72-82.

Office Action in Japanese Patent Application No. 2019-569784 dated May 11, 2022, with translation provided by local agent.

Office Action in European Patent Application No. 2019-569784 dated May 11, 2022, with translation provided by local agent.

Office Action dated Jun. 7, 2023 issued in corresponding Japanese Patent Application No. 2022-063749, with unofficial English translation provided by local Agent.

\* cited by examiner

QUERY = Native REP-1 (SEQ ID NO: 3)
SUBJECT = Codon-optimized REP-1 (SEQ ID NO: 1)

| Score | Expect | Identities | Gaps | Strand |
|---|---|---|---|---|
| 1267 bits(1404) | 0.0 | 1455/1955(74%) | 4/1955(0%) | Plus/Plus |

```
Query  1    ATGGCGGATACTCTCCCTTCGGAGTTTGATGTGATCGTAATAGGGACGGGTTTGCCTGAA  60
            ||||| ||||| |||||| || ||||||||||| ||||| || |||||| || |||||||
Sbjct  1    ATGGCTGATACCCTGCCCTCTGAATTCGACGTGATTGTGATTGGAACCGGACTCCCTGAA  60

Query  61   TCCATCATTGCAGCTGCATGTTCAAGAAGTGGCCGGAGAGTTCTGCATGTTGATTCAAGA  120
            ||||||||| |||||||| |||  || ||||||||  | |||||| |||| |||| ||||
Sbjct  61   TCGATCATCGCCGCGGCCTGTTCCCGGTCCGGCCGTGTCCGGCGCGTGCTGCACGTCGATTCGAGA  120

Query  121  AGCTACTATGGAGGAAAACTGGGCCAGTTTTTCAGGACTATTGTCCTGGCTAAAG  180
            |||||||| || |||||||||||||||||||| |||||| || ||||||||| ||
Sbjct  121  AGCTACTACGGAGGGAATTGGGCCTCATTCTCCTTCTCCGGACTGCTCTCCTGGCTGAAG  180

Query  181  GAATACCAGGAAAAACAGTGACATTGTAAGTGACAGTCCAGTGTGGCAAGACCAGATCCTT  240
            ||||||||||||||| |||||||| || ||| | ||||||||||||||||||||||| |
Sbjct  181  GAGTATCAGGAGAACTCCGACTTGTCTCCGACTCACCTGTGTGGCAGGACCAGATCCTG  240

Query  241  GAAAATGAAGAAGCCATTGCTCTTAGCAGGAAGGACAAAACTATTCAACATGTGGAAGTA  300
            ||||| ||||| ||||||| | ||||||| |||||||| ||| |||||||||||| |
Sbjct  241  GAAAACGAGGAAGCCAATAGCCCCTGAGCCGGAAGCAATGCCCGAAGACCATCCAGCACGTGGAGGTG  300
```

FIG. 2A

```
Query  301  TTTTGTTATGCCAGTCAGGATTTGCATGAAGATGTCGAAGAAGCTGGTGCACTGCAGAAA  360
             ||||||||||  |||||||||||||||||||||||||||||||| ||||| ||||||||
Sbjct  301  TTCTGTTATGCCTCCCAAGACCTCCATGAGGACGTGGAAGAGGCTGGAGAGCGTTGCAGAAG  360

Query  361  AATCATGCCTCTTGTGACATCTGCAAACTCCACAGAAGCTGCAGATTCTGCCTTCCTGCCT  420
             ||||||||||  |||| ||  |||| ||| |||| ||||| |||||  |||||| ||||
Sbjct  361  AATCATGCCCTCGTGACCTCCTAACTCCACCGAGGCCAGCCCGACAGCGCCTTCCTGCCG  420

Query  421  ACGGAGGATGAGTCATTAAGCACTATGAGCTGTGAAATGCTCACAGAACAAACTCCAAGC  480
             ||||||||||| |||   | ||||||  ||||||| ||||| ||||| || |||||||
Sbjct  421  ACCGAGGATGAATCCCTGTCAACTATGTCGTGCGAAATGCTGACCGAACAGACTCCGAGC  480

Query  481  AGCGATCCAGAGAATGCGCTAGAAGTAAATGGTGCTGAAGTGACAGGGGAAAAAGAAAAC  540
             |||||||||||| |||| | |||| | ||||||| |||| | |||  |||||  |||||
Sbjct  481  TCCGACCCCGAAAACGCCCTGGAAGTGAACGGAGCGGAAGTGACCGGCGAAAAGGAGAAC  540

Query  541  CATTGTGATGATAAAACTTGTGTGCCATCAACTTCAGCAGAAGACATGAGTGAAAATGTG  600
             ||||||  ||||||| |||||||||||||  ||||||| ||| |||||| ||||||||| 
Sbjct  541  CATTGCGACAAGATACCACAGAGCAACCAAAGAAAAACAGAATTACTTACTCACAAATT  600

Query  601  CCTATAGCAGAAGATACCACAGAGCAACCAAAGAAAAACAGAATTACTTACTCACAAATT  660
             ||||| |||||||||||||||||| |||||||| ||||||| || ||||| |||||||
Sbjct  601  CCTATCGCCGAGGACACCACCGAGCCCAAGAAGAACAGAATCACGTACAGCCAGATC  660

Query  661  ATTAAAGAAGGCAGGAGATTTAATATTGATTTAGTATCAAAGCTGCTGTATTCTCGAGGA  720
```

FIG. 2B

```
Sbjct  661   ATCAAGGAGGGGCGGAGGTTTAACATCGATCTGGTGTGTCGAAGCTGCTGTACAGCCGCGGT  720
             ||||||||||||||||||||||||||||||||||||||||||||||||||||||||||||
Query  721   TTACTAATTGATCTTCTAATCAAATCTAAATGTTAGTCGATAT--GCAGAGTTTAAAAATA  778
             ||||||||||||||||||||||||||||||||||||||||||  ||||||||||||||||
Sbjct  721   CTGCTGATCGATCTGCTCATTAAGTCGAAACGT---GTCGAGATACGCCGAGTTCAAGAACA  778

Query  779   TTACCAGGATTCTTGCATTTCGAGAAGGACGAGTGGAACAGGTTCCGTGTTCCAGAGCAG  838
             ||||||||||||||||||||||||||||||||||||||||||||||||||||||||||||
Sbjct  779   TCACAAGGATTCTCGCCTTCCGGGAAGGAAGAGTGGAACAAGTGCCGTGCTCCCGGGCCG  838

Query  839   ATGTCTTTAATAGCAAACAACTTACTATGGTAGAAAAAGCGAATGCTAATGAAATTTCTTA  898
             ||||||||||||||||||||||||||||||||||||||||||||||||||||||||||||
Sbjct  839   ACGTGTTCAACTCAAAGCAACTTACCATGGTGGAAAAGCGCATGCTGATGAAATTCCTGA  898

Query  899   CATTTTGTATGGAATATGAGAAATATCCTGATGAATATAAAGGATATGAAGAGATCACAT  958
             ||||||||||||||||||||||||||||||||||||||||||||||||||||||||||||
Sbjct  899   CCTTCTGCATGGAGTACGAAAAGTACCCTGATGAGTACAAGGGTTACGAAGAAATTACTT  958

Query  959   TTTATGAATATATTTAAAGACTCAAAAATTAACCCCAACCTCCAATATATTGTCATGCATT  1018
             ||||||||||||||||||||||||||||||||||||||||||||||||||||||||||||
Sbjct  959   TCTACGAGTACCTCAAGACCTCAAGAAGCTGACCCCGAATCTGCAGTACATTGTGATGCACT  1018

Query  1019  CAATTGCAATGACATCAGAGACATCGAGCACCATAGATGGTCTCAAAGCTACCAAAA  1078
             ||||||||||||||||||||||||||||||||||||||||||||||||||||||||
Sbjct  1019  CAATCGCAATGACCTCCGAAATCGCCGCCTCCTGACCATCGACGGGCTCAAGGCCACCAAGA  1078

Query  1079  ACTTTCTTCACTGTCTTGGGCGTATGCAACACTCCATTTTGTTCCTTTATATGGCC  1138
```

FIG. 2C

```
Sbjct  1079                                        ACTTCCTGCACTGTTTGGGGCGCTACGGCAACACTCCGTTCCTCTTCCCGCTGTACGGCC  1138

Query  1139  AAGGAGAACTCCCCCAGTGTTTCTGCAGGATGTGTCTGTGTTTGGTGGTGAATTTATTGTC  1198
Sbjct  1139  AGGGAGAGCTGCCTCAGTGTTTCTGCCGGATGTGCCCGTGTTCGGCGGAATCTACTGTC   1198

Query  1199  TTCGCCATTCAGTACAGTGCCTTGTAGTGGACAAAGAATCCAGAAAATGTAAAGCAATTA  1258
Sbjct  1199  TCCGGCCACTCGGTCCAGTGCCTGGTGGTGGACAAGGAATCCAGGAAGTGCAAAGCCATTA  1258

Query  1259  TAGATCAGTTTGGTCAGAGAATAATCTCTGAGCATTTCCTCGTGGAGGACAGTTACTTTC  1318
Sbjct  1259  TTGACCAGTTCGGACAACGGATCATTTCCGAGCACTTCTTGTGGAGGACTCATACTTCC   1318

Query  1319  CTGAGAACATGTGCTCACGTGTGCAATACAGGCAGATCTCCAGGCAGTGCTGATTACAG   1378
Sbjct  1319  CGGAGAACATGTGCTCTCGGGTCCAGTATCGACAGATTTCCAGGGCGGTGCTCATTACTG  1378

Query  1379  ATAGATCTGTCCTAAAAACAGATTCAACAGATTTCCATTTTGACAGTGCCAGCAG      1438
Sbjct  1379  ACCGGAGCGTCCTCAAGACCGATAGCGACCAGCAGATCTCCATCCTGACCGTGCCGGCGG  1438

Query  1439  AGGAACCAGGAACTTTTGCTGTGTTCGGGTCATTGAGTTATGTTCTTCAACGATGACATGCA  1498
Sbjct  1439  AAGAACCCGGCACTTTGCCGTGCGCGTGATCGAGCTTTGCTCATCCACCATGACTTGCA  1498
```

FIG. 2D

| | | | |
|---|---|---|---|
| Query | 1499 | TGAAAGGCACCTATTTGGTTCATTTGACTTGCACATCTTCTAAAACAGCAAGAGAAGATT | 1558 |
| Sbjct | 1499 | TGAAAGGCACCTATTTGGTTCATTTGACTTGCACATCTTCTAAAACAGCAAGAGAAGATT | 1558 |
| Query | 1559 | TGAAAAGGCACTTACCTGGTGCACCTGCACGTGCACCTCATCGAAAACCGTAGAGAGGACC | 1618 |
| Sbjct | 1559 | TGAAAAGGCACTTACCTGGTGCACCTGCACGTGCACCTCATCGAAAACCGTAGAGAGGACC | 1618 |
| Query | 1619 | TAGAATCAGTTGTGCAGAAATTGTTTGTTCCATATACTGAAATGGAGATAGAAAATGAAC | 1678 |
| Sbjct | 1619 | TAGAATCAGTTGTGCAGAAATTGTTTGTTCCATATACTGAAATGGAGATAGAAAATGAAC | 1678 |
| Query | 1679 | TGGAATCCGTCGTCCAAAAGCTGTTCGTGCCTTACACCGAGATGGAAATTGAAAACGAAC | 1738 |
| Sbjct | 1679 | TGGAATCCGTCGTCCAAAAGCTGTTCGTGCCTTACACCGAGATGGAAATTGAAAACGAAC | 1738 |
| Query | 1739 | AAGTAGAAAAAGCCAAGAATTCTGTGGGCTCTTTTACTTCAATATGAGAGATTCGTCAGACA | 1798 |
| Sbjct | 1739 | AAGTAGAAAAAGCCAAGAATTCTGTGGGCTCTTTTACTTCAATATGAGAGATTCGTCAGACA | 1798 |
| Query | 1799 | AAGTGGAGAAGCCCCGCATCCTTTGGGCCCGTACTTTAACATGCGATTCCTCCGATA | 1858 |
| Sbjct | 1799 | AAGTGGAGAAGCCCCGCATCCTTTGGGCCCGTACTTTAACATGCGATTCCTCCGATA | 1858 |
| Query | 1859 | TCAGCAGGAGCTGTTATAATGATTTACCATCCAACGTTTATGTCTGCTCTGCCCAGATT | 1918 |
| Sbjct | 1859 | TCAGCAGGAGCTGTTATAATGATTTACCATCCAACGTTTATGTCTGCTCTGCCCAGATT | 1918 |
| Query | 1919 | TCTCGCGGTCCTGCTATAACGACTTGCCTTCGAACGTCTACGTCTGCTCCGGGCCAGACT | 1978 |
| Sbjct | 1919 | TCTCGCGGTCCTGCTATAACGACTTGCCTTCGAACGTCTACGTCTGCTCCGGGCCAGACT | 1978 |
| Query | 1979 | GTGGTTTAGGAAATGATAATGCAGTCAAGACTCAAACACAGGCTGAAACACTTTTCCAGGAAATCTGCC | 2038 |
| Sbjct | 1979 | GTGGTTTAGGAAATGATAATGCAGTCAAGACTCAAACACAGGCTGAAACACTTTTCCAGGAAATCTGCC | 2038 |
| Query | 2039 | GCGGTCTTGGCAACGACAATGCCGTGAAGCAGGCGGGAAACACTGTTCCAAGAGATCTGCC | 2098 |
| Sbjct | 2039 | GCGGTCTTGGCAACGACAATGCCGTGAAGCAGGCGGGAAACACTGTTCCAAGAGATCTGCC | 2098 |
| Query | 2099 | CCAATGAAGATTTCTGTCCCCCTCCACCAAAATCCTGAAGACATTATCCTTGATGGAGACA | 2158 |
| Sbjct | 2099 | CCAATGAAGATTTCTGTCCCCCTCCACCAAAATCCTGAAGACATTATCCTTGATGGAGACA | 2158 |
| Query | 2159 | CTAACGAGGATTTTTGCCCGCCCCCAAACCCGAGATATCATCTTGACGGAGACA | 2218 |
| Sbjct | 2159 | CTAACGAGGATTTTTGCCCGCCCCCAAACCCGAGATATCATCTTGACGGAGACA | 2218 |
| Query | 2219 | GTTTACAGCCAGAGGCTTCAGAATCCAGTGCCATACCAGAGGCTAACTCGGAGACTTTCA | 2278 |
| Sbjct | 2219 | GTTTACAGCCAGAGGCTTCAGAATCCAGTGCCATACCAGAGGCTAACTCGGAGACTTTCA | 2278 |
| Query | 2279 | GCCTGCAGCCAGAAGCATCCGAGTCCAGCGCCATCCCGGAGGCCAACAGCGAAACCTTCA | 2338 |
| Sbjct | 2279 | GCCTGCAGCCAGAAGCATCCGAGTCCAGCGCCATCCCGGAGGCCAACAGCGAAACCTTCA | 2338 |

FIG. 2E

```
Query  1919  AGGAAAGCACAAACCTTGGAAACCTAGAGGAGTCC  1953
             ||||| |||| ||||| || ||||| || ||||||
Sbjct  1919  AGGAGAGCACTAACCTGGGCAACCTGGAAGAGTCC  1953
```

FIG. 2F

Codon optimized (Query) SEQ ID NO: 9 vs. Native (subject) SEQ ID NO: 13 CNGA3

| Score | Expect | Identities | Gaps |
|---|---|---|---|
| 1856 bits(2058) | 0.0 | 1678/2108(80%) | 2/2108(0%) |

```
Query  1    GCGGCCGCCACCATGGCTAAGATTAACACCCAGTACTCACATCCATCCGCACTCACCTC  60
            ||||||||||||||||| |||||||| ||||||||||| || |||||| || |||||||
Sbjct  1    GCGGCCGCCACCATGGCCAAGATCAACACACCCAGTCAACATCCCCACCCCTCCACCTC  60

Query  61   AAAGTCAAGACCTCCGATCGGGATCTGAACCGGGCTGAGAATGGGCTGTCGCGGCCCAC  120
            || ||||||| |||||||| |||||| |||| ||| || || ||||||| || ||||||
Sbjct  61   AAGGTAAAGACCTCAGACCGGGATCTCAATCGCGCTGAAAATGGCCTCAGAGAGCCCAC  120

Query  121  TCGTCGTCCGAGGAAACCAGCAGC-GTGCTCCAGCCGGGCATGCCATGGAAACTAGGGG  179
            |||||  |||||| || || |||| |||||| ||| ||||| ||  ||||| || ||||
Sbjct  121  TCGTCAAGTGAGGAGAC-ATCGTCAGTGCTGCTGCAGCCGGGATCGCCATGGAGACCAGAGG  179

Query  180  GCTGGGGACTCCGGACAGGGATCCTTCACTGGACAGGGTATTGCCCGGCTGAGCAGACT  239
            |||||||||| ||||| ||||| || ||||||  || ||  || ||||| || ||
Sbjct  180  ACTGGCTGACTCCGGGCAGGGATCCTCCTTCACCGGCCAGGGGATCGCCAGGCTGTCGCGCCT  239

Query  240  GATCTTCCTGCTTCGCCGCTGGGCGGCCAGACACGTGCACCATCAGGACCAGGACCTGA  299
            |||||| ||||||| ||||||||||| |||||||||||| ||  || ||||| ||| ||
Sbjct  240  CATCTTCTTGCTGCGCAGGTGGCGCGGCCAGGCATGTGCACCAGGACCAGGACCGGA  299
```

FIG. 3A

```
Query  300  TAGCTTCCCCGACCGCTTTAGGGGAGCCGAGCTGAAAGAAGTGTCAAGCCAGGAGTCAAA  359
            ||||||||||||||||||||||||||||||||||||||||||||||||||||||||||||
Sbjct  300  TAGCTTCCCCGACCGCTTTAGGGGAGCCGAGCTGAAAGAAGTGTCAAGCCAGGAGTCAAA  359

Query  360  CTCTTTTCCTGATCGTTTCCGTGGAGCCGAGCTTAAGGAGTGTCCAGCCAAGAAAGCAA   419
            ||||||||||||||||||||||||||||||||||||||||||||||||||||||||||
Sbjct  360  CTCTTTTCCTGATCGTTTCCGTGGAGCCGAGCTTAAGGAGTGTCCAGCCAAGAAAGCAA   419

Query  420  CGCGCAGGCCAACGTCGGCAGCCAAGAGAGCCTGCAGACCGGGGACGCTCGGCATGGCCGCT  479
            ||||||||||||||||||||||||||||||||||||||||||||||||||||||||||||
Sbjct  420  CGCGCAGGCCAACGTCGGCAGCCAAGAGAGCCTGCAGACCGGGGACGCTCGGCATGGCCGCT  479

Query  480  TGCCCAGGCAAATGTGGGCAGCCAGGAGCCAGCAGACAGAGGAGAAGCGCCTGGCCCCT    539
            ||||||||||||||||||||||||||||||||||||||||||||||||||||||||
Sbjct  480  TGCCCAGGCAAATGTGGGCAGCCAGGAGCCAGCAGACAGAGGAGAAGCGCCTGGCCCCT    539

Query  540  CGCAAAGTGCAACACTAACACTTCCAACAACACCGAAGAGGAAAAGAAAACCAAGAAGAA  599
            ||||||||||||||||||||||||||||||||||||||||||||||||||||||||||
Sbjct  540  CGCAAAGTGCAACACTAACACTTCCAACAACACCGAAGAGGAAAAGAAAACCAAGAAGAA  599

Query  600  GGCCAAATGCAACACTAACACCAGCAACAACACGGAGGAGGAAGAAGAGAAAAAGAA    659
            ||||||||||||||||||||||||||||||||||||||||||||||||||||||
Sbjct  600  GGCCAAATGCAACACTAACACCAGCAACAACACGGAGGAGGAAGAAGAGAAAAAGAA    659

Query  660  GGATGCAATTGTGGTGGACCCTTCCCTCCAACCTGTACTACCGCTGGTTGACCGCCATCGC  719
            ||||||||||||||||||||||||||||||||||||||||||||||||||||||||||||
Sbjct  660  GGATGCAATTGTGGTGGACCCTTCCCTCCAACCTGTACTACCGCTGGTTGACCGCCATCGC  719

Query  720  GGATGCGATCGTGGTGGACCCGTCCAGCAACCTGTACTACCGCTGGCTGACCGCCATCGC  779
            ||||||||||||||||||||||||||||||||||||||||||||||||||||||||||
Sbjct  720  GGATGCGATCGTGGTGGACCCGTCCAGCAACCTGTACTACCGCTGGCTGACCGCCATCGC  779

Query  780  CCTCCCGGTCTTTTACAATTGGTATCTCCTTATCTGCCGGGCCTGCTTCGACGAACTGCA  839
            ||||||||||||||||||||||||||||||||||||||||||||||||||||||||||
Sbjct  780  CCTCCCGGTCTTTTACAATTGGTATCTCCTTATCTGCCGGGCCTGCTTCGACGAACTGCA  839

Query  840  CCTGCCTGTGTCTTCTATAACTGGTATCTGCTTATTTGCAGGGCCTGCTGTTTCGATGAGCTGCA  899
            ||||||||||||||||||||||||||||||||||||||||||||||||||||||||||
Sbjct  840  CCTGCCTGTGTCTTCTATAACTGGTATCTGCTTATTTGCAGGGCCTGCTGTTTCGATGAGCTGCA  899

Query  900  ATCAGAGTACCTGATGCTGTGGCTGGACTATAGCGCCGATGTGCTCTACGTCCT    959
            ||||||||||||||||||||||||||||||||||||||||||||||||||||
Sbjct  900  ATCAGAGTACCTGATGCTGTGGCTGGACTATAGCGCCGATGTGCTCTACGTCCT    959

Query  960  GTCCGAGTACCTGATGCTGTGGCTGGTCCTGGCAGATGTCCTGTATGTCTT    1019
            |||||||||||||||||||||||||||||||||||||||||||||||||
Sbjct  960  GTCCGAGTACCTGATGCTGTGGCTGGTCCTGGCAGATGTCCTGTATGTCTT    1019

Query  1020 GGATGTGCTCGTGCGCGCCCGGACCGGATTCTTGGAACAAGGCCTGATGGTGTCCGACAC  1079
            ||||||||||||||||||||||||||||||||||||||||||||||||||||||||||
Sbjct  1020 GGATGTGCTCGTGCGCGCCCGGACCGGATTCTTGGAACAAGGCCTGATGGTGTCCGACAC  1079

Query  1080 GGATGTGCTTGTACGAGCTCGGACACAGGTTTTCTTGAGCAAGGCTTAATGGTCAGTGATAC  1139
            ||||||||||||||||||||||||||||||||||||||||||||||||||||||||||
Sbjct  1080 GGATGTGCTTGTACGAGCTCGGACACAGGTTTTCTTGAGCAAGGCTTAATGGTCAGTGATAC  1139
```

FIG. 3B

```
Query  720   GAATAGACTGTGGCAGCACTATAAGACCACAACCAGTTCAAGCTTGACGTGCTCAGCCT   779
             ||||||||||||||||||||||||||||||||||||||||||||||||||||||||||||
Sbjct  720   GAATAGACTGTGGCAGCACTATAAGACCACAACCAGTTCAAGCTTGACGTGTGTTGTCCCT   779

Query  780   CAACAGGCTGTGGCAGCATTACAAGACGACCACGCAGTTCAAGCTGGATGTGTTGTCCCT   839
             ||||||||||||||||||||||||||||||||||||||||||||||||||||||||||||
Sbjct  780   TGTGCCGACTGACCTGGCCTACCTGAAAGTCGGAACTAACTACCCGGAAGTCAGATTCAA   839

Query  840   GGTCCCCACCGACCTGGCTTACTTAAAGGTGGCACAAAACTACCAGAAGTGAGGTTCAA   899
             ||||||||||||||||||||||||||||||||||||||||||||||||||||||||||||
Sbjct  840   CCGACTCCTGAAGTTCAGCAGGCTGTGTTCGAGTTCTCTTTGACCGCACCGAGACTCGGACCAA   899

Query  900   CCGCCTACTGAAGTTTTCCCGGCTCTCTTTGAATTCTTTGACCGCACAGAGACAAGGACCAA   959
             ||||||||||||||||||||||||||||||||||||||||||||||||||||||||||||
Sbjct  900   CTACCCTAACACATGTTCCGGATCGGAAATCTGGTGCTCTACATACTGATTATCATCCATTG   959

Query  960   CTACCCCAATATGTTCAGGATTGGGAACTTGGTCTTGTACATTCTCATCATCCACTG   1019
             ||||||||||||||||||||||||||||||||||||||||||||||||||||||||||||
Sbjct  960   GAACGCCTGTATCTATTTCGCCATTTCGAAGTTCATCGGTTCGGAACCGATTCCTGGGT   1019

Query  1020  GAATGCCTGCATCTACTTTGCCATTTCCAAGTTCATTGGTTTTGGGACAGACTCCTGGGT   1079
             ||||||||||||||||||||||||||||||||||||||||||||||||||||||||||||
Sbjct  1020  GTACCCCAACACATTCGATCCCGAACACGGTCGCCTGTCCCGGAAGTACATCTACTCCCT   1079

Query  1080  CTACCCAAACATCTCAATCCCAGAGCATGGGCGCCTCTCCAGGAAGTACATTTACAGTCT   1139
             ||||||||||||||||||||||||||||||||||||||||||||||||||||||||||||
Sbjct  1080  GTACTGGTCCACTCTGACTCTGACCACGATCGGGGAAACCCCTCCACCCGTGAAGGACGA   1139

Query  1140  CTACTGGTCCACCTTGACCCTTACCACCATTGTGAGACCCCACCCCGTGAAAGATGA   1139
```

FIG. 3C

```
Query  1140  AGAGTACCTGTTCGTGGTGGTGGACTTCCTGGTCGGAGTGTTGATTTTCGCCACCATTGT  1199
             ||||||||||||||||||||||||||||||||||||||||||||||||||||||||||||
Sbjct  1140  AGAGTACCTGTTCGTGGTGGTGGACTTCCTGGTCGGAGTGTTGATTTTCGCCACCATTGT  1199

Query  1200  GGAGTATCTCTTGTGGTCGTAGACTTCTTGGTGGGTGTTCTGATTTTTGCCAAGCCAA    1259
             ||||||||||||||||||||||||||||||||||||||||||||||||||||||||||||
Sbjct  1200  GGGAAAACGTGGGCTCCATGATCTCCAACATGAACGCGTCGAGAGCTGAGTTCCAAGCCAA  1259

Query  1260  GGGCAATGTGGGCTCCATGATCTCGAATATGAATGCCTCACGGGCAGAGTTCCAGGCCAA  1319
             ||||||||||||||||||||||||||||||||||||||||||||||||||||||||||||
Sbjct  1260  GATCGACTCCATTAAGCAGTACATGCAGTTCAGAAAGGTCACCAAGGACCTGGAAACCAG  1319

Query  1320  GATTGATTCCATCAAGCAGTACATGCAGTTCCGCAAGGTCACCAAGGACTTGGAGACGCG  1379
             ||||||||||||||||||||||||||||||||||||||||||||||||||||||||||||
Sbjct  1320  GGTCATCCGCTGGTTCGACTACCTGTGGGCCAACAAAAAGACTGTGACGAAAAGGAAGT  1379

Query  1380  GGTTATCCGGTGGTTTGACTACCTGTGGGCCAACAAGACGGTGGATGAGAAGGAGGT    1439
             ||||||||||||||||||||||||||||||||||||||||||||||||||||||||||||
Sbjct  1380  GCTGAAGTCGCTGCCGGATAAGCTGAAGGCCGAAATCGCCATTAACGTGCACCTTGACAC  1439

Query  1440  CCTGAAGAAAGTCCGGATCTTCCAAGACTGTGAAGCCGCCTCCTGGTTGGAGCTGTGCT  1499
             ||||||||||||||||||||||||||||||||||||||||||||||||||||||||||||
Sbjct  1440  GCTGAAGAAGGTTCGCATCTTCCAGGACTGTGAGGCAGGGCTGCTGGTGGAGCTGTGCT  1499

Query  1500  CAAGCTGCGCCCACCGTGTTCAGCGGAGATTACATTTGCAAGAAGGGCGATATCGG     1559
             ||||||||||||||||||||||||||||||||||||||||||||||||||||||||||||
Sbjct  1500  GAAGCTGCGACCACTGTGTTCAGCCCTGGGGATTATATCTGCAAGAAGGGAGATATTGG  1559
```

FIG. 3D

```
Query  1560  CAAAGAGATGTACATCATCAACGAGGGAAAGCTGGCCGTGGTTCGCGGACGACGGGCGTGAC  1619
             |||||||||||||||||||||||||||||||||||||||||||||||||||||||||||||
Sbjct  1560  GAAGGAGATGTACATCATCAACGAGGGAAAGCTGGCCGTGGTTGCTGATGATGGGGTCAC   1619

Query  1620  CCAGTTCGTGGTGCTGTCCGACGGATCCTACTTCGGTGAAATCTCAATCCTCAACATCAA  1679
             |||||||||||||||||||||||||||||||||||||||||||||||||||||||||||
Sbjct  1620  CCAGTTCGTGGTCCTCAGCGATGGGACGTACTTCGGGGAGATCAGCATTCTGAACATCAA  1679

Query  1680  GGGGTCCAAGTCCGGCAACCGAGAGAACTGCCAACATTCGCTCCATCGGATACAGCGACCT  1739
             |||||||||||||||||||||||||||||||||||||||||||||||||||||||||||
Sbjct  1680  GGGGAGCAAGTCGGGGAACCGCAGGAGCCAACATCCGCAGCATTGGCTACTCAGACCT   1739

Query  1740  GTTTTGCCCTGTCCAAGGATGACCTGATGGAGGCTCTGACTGAGTACCCTGAAGCGAAGAA  1799
             |||||||||||||||||||||||||||||||||||||||||||||||||||||||||||
Sbjct  1740  GTTCTGCCTCTCAAAGGACGATCTCATGGAGGCCCTCACCGAGTACCCCGAAGCCAAGAA  1799

Query  1800  GGCTTTGGAGGAAAAGGGGCGGCAGATTCTGATGAAGGACAATTTGATCGACGAGGAGCT  1859
             |||||||||||||||||||||||||||||||||||||||||||||||||||||||||||
Sbjct  1800  GGCCCTGGAGGAGAAAGGACGCCAGATCCTGATGAAAGACAACCTGATCGATGAGGAGCT  1859

Query  1860  CGCACGGGCCCGGCCCGACCCCCAAGGATCTCGAAGAGAAGGTCGAACAGCTGGGTTCTTC  1919
             |||||||||||||||||||||||||||||||||||||||||||||||||||||||||||
Sbjct  1860  GGCCAGGGCGCGGGCGGACCCCAAGGACCTTGAGGAGAAAGTGAGCAGCTGGGGTCCTC  1919

Query  1920  GCTTGATACCCTGCAAACCCGATTCGCGGCGGCTGCGCCGAGTACAAACGCGACCCAGAT  1979
             |||||||||||||||||||||||||||||||||||||||||||||||||||||||||||
Sbjct  1920  CCTGGACACCCTGCAGACCAGTTTGCACGCCTCCTGCTGAGTACACGCCACCCAGAT   1979
```

FIG. 3E

```
Query  1980  GAAGATGAAGCAGAGACTGTCACAGTTGGAATCCCAAGTCAAGGGCGGAGGCGACAAGCC  2039
             ||||||||||||||||||  ||  |   ||||||   |||   ||  ||  ||||||||
Sbjct  1980  GAAGATGAAGCAGCGTCTCAGCCAACTGGAAAGCCAGGTGAAGGGTGGTGGGACAAGCC  2039

Query  2040  GCTGGGCGGACGGGGAAGTGCCCGGGGACGCCACCAAGACTGAGGACAAGCAGCAGTGATC  2099
             |||||  ||   ||  ||||   ||||||| |   |   |  |  ||| | |  ||||||
Sbjct  2040  CCTGGCTGATGGGGAAGTTCCCGGGGATGCTACAAAAACAGAGGACAAACAACAGTGATC  2099

Query  2100  ATAGATCT  2107
             ||||||||
Sbjct  2100  ATAGATCT  2107
```

Locations of silent mutations are highlighted
CLUSTAL W (1.83) multiple sequence alignment
CNGB3_with_modified_ends - SEQ ID NO: 23
CNGB3_modified_ORF - SEQ ID NO: 21
native_CNGB3_ORF - SEQ ID NO: 19

```
CNGB3_with_modified       GCGGCCCGCCACCATGTTTAAATCGCTGACAAAAGTCAACAAGGTGAAGCCTATAGGAGAG
CNGB3_modified_ORF        ------------ATGTTTAAATCGCTGACAAAAGTCAACAAGGTGAAGCCTATAGGAGAG
native_CNGB3_ORF          ------------ATGTTTAAATCGCTGACAAAAGTCAACAAGGTGAAGCCTATAGGAGAG
                                      ************************************************

CNGB3_with_modified       AACAATGAGAATGAACAAAGTTCTCGTCGGAATGAAGAAGGCTCTCACCCAAGTAATCAG
CNGB3_modified_ORF        AACAATGAGAATGAACAAAGTTCTCGTCGGAATGAAGAAGGCTCTCACCCAAGTAATCAG
native_CNGB3_ORF          AACAATGAGAATGAACAAAGTTCTCGTCGGAATGAAGAAGGCTCTCACCCAAGTAATCAG
                          ************************************************************

CNGB3_with_modified       TCTCAGCAAACCACAGCCACAGGAAGAGAAAACAAAGGTGAAGAGAAATCTCTCAAAACCAAG
CNGB3_modified_ORF        TCTCAGCAAACCACAGCCACAGGAAGAGAAAACAAAGGTGAAGAGAAATCTCTCAAAACCAAG
native_CNGB3_ORF          TCTCAGCAAACCACAGCCACAGGAAGAGAAAACAAAGGTGAAGAGAAATCTCTCAAAACCAAG
                          ************************************************************

CNGB3_with_modified       TCAACTCCAGTCACGTCTGAAGAGCCACCACCACCAAGACCAAGACAAACATACAAGACAAAACTCTCCAAGAAA
CNGB3_modified_ORF        TCAACTCCAGTCACGTCTGAAGAGCCACCACCACCAAGACCAAGACAAACATACAAGACAAAACTCTCCAAGAAA
native_CNGB3_ORF          TCAACTCCAGTCACGTCTGAAGAGCCACCACCACCAAGACCAAGACAAACATACAAGACAAAACTCTCCAAGAAA
                          ************************************************************

CNGB3_with_modified       AATTCCTCTGGAGATCTGACCACACAAACCCTGACCCTCAAAATGCAGCAGAACCAACTGGA
CNGB3_modified_ORF        AATTCCTCTGGAGATCTGACCACACAAACCCTGACCCTCAAAATGCAGCAGAACCAACTGGA
native_CNGB3_ORF          AATTCCTCTGGAGATCTGACCACACAAACCCTGACCCTCAAAATGCAGCAGAACCAACTGGA
                          ************************************************************

CNGB3_with_modified       ACAGTGCCAGAGCAGAGGAAATGGACCCCGGGAAAGAAGGTCCAAACAGCCACAAAAC
CNGB3_modified_ORF        ACAGTGCCAGAGCAGAGGAAATGGACCCCGGGAAAGAAGGTCCAAACAGCCACAAAAC
native_CNGB3_ORF          ACAGTGCCAGAGCAGAGGAAATGGACCCCGGGAAAGAAGGTCCAAACAGCCACAAAAC
                          ************************************************************

CNGB3_with_modified       AAACCGGCCAGCAGTCCTGTTATAAATGAGTATGCCGATGCCCAGCTACACAACCTGGTG
```

```
native_CNGB3_ORF              TTTGTAAGAGGAGGAGAGACATAATAGTGATTCAAATGAGCTAAGGAAACACTACAGGACT CNGB3_with_modified_ORF       TCTACAAAATTTCAGTTGGATGTGCGATCGCATCAATAATACCATTTGATATTTGCTACCTCTTC
CNGB3_modified_ORF            TCTACAAAATTTCAGTTGGATGTGCGATCGCATCAATAATACCATTTGATATTTGCTACCTCTTC
native_CNGB3_ORF              TCTACAAAATTTCAGTTGGATGTGCGATCGCATCAATAATACCATTTGATATTTGCTACCTCTTC
                              ************************************************************

CNGB3_with_modified_ORF       TTTGGGTTTAATCCAATGTTTAGAGCAAATAGGATGTTAAAGTACACTTCATTTTTTGAA
CNGB3_modified_ORF            TTTGGGTTTAATCCAATGTTTAGAGCAAATAGGATGTTAAAGTACACTTCATTTTTTGAA
native_CNGB3_ORF              TTTGGGTTTAATCCAATGTTTAGAGCAAATAGGATGTTAAAGTACACTTCATTTTTTGAA
                              ************************************************************

CNGB3_with_modified_ORF       TTTAATCATCACCTAGAGTCTATAATGGACAAAGCATATATCTACAGAGTTATTCGAACA
CNGB3_modified_ORF            TTTAATCATCACCTAGAGTCTATAATGGACAAAGCATATATCTACAGAGTTATTCGAACA
native_CNGB3_ORF              TTTAATCATCACCTAGAGTCTATAATGGACAAAGCATATATCTACAGAGTTATTCGAACA
                              ************************************************************

CNGB3_with_modified_ORF       ACTGGATACTTGCTGTTTATTCTGCACATTAATGCCTGTGTTTATTACTGGGCTTCAAAC
CNGB3_modified_ORF            ACTGGATACTTGCTGTTTATTCTGCACATTAATGCCTGTGTTTATTACTGGGCTTCAAAC
native_CNGB3_ORF              ACTGGATACTTGCTGTTTATTCTGCACATTAATGCCTGTGTTTATTACTGGGCTTCAAAC
                              ************************************************************

CNGB3_with_modified_ORF       TATGAAGGAATTGGCACTACTAGATGGGTGTATGATGGGAAGGAAACGAGTATCTGAGA
CNGB3_modified_ORF            TATGAAGGAATTGGCACTACTAGATGGGTGTATGATGGGAAGGAAACGAGTATCTGAGA
native_CNGB3_ORF              TATGAAGGAATTGGCACTACTAGATGGGTGTATGATGGGAAGGAAACGAGTATCTGAGA
                              ************************************************************

CNGB3_with_modified_ORF       TGTTATTATTGGGCAGTTCGAACTTTAATTACCATTGGTGGCCTTCCAGAACCACAAACT
CNGB3_modified_ORF            TGTTATTATTGGGCAGTTCGAACTTTAATTACCATTGGTGGCCTTCCAGAACCACAAACT
native_CNGB3_ORF              TGTTATTATTGGGCAGTTCGAACTTTAATTACCATTGGTGGCCTTCCAGAACCACAAACT
                              ************************************************************

CNGB3_with_modified_ORF       TTATTTGAAATTGTTTTTCAACTCTTGAATTTTTTTCTGGAGTTTTTGTGTTCTCCAGT
CNGB3_modified_ORF            TTATTTGAAATTGTTTTTCAACTCTTGAATTTTTTTCTGGAGTTTTTGTGTTCTCCAGT
native_CNGB3_ORF              TTATTTGAAATTGTTTTTCAACTCTTGAATTTTTTTCTGGAGTTTTTGTGTTCTCCAGT
                              ************************************************************

CNGB3_with_modified_ORF       TTAATTGGTCAGATGAGAGATGTGATTGGAGCAGCAGCTACAGCCAATCAGAACTACTTCCGC
CNGB3_modified_ORF            TTAATTGGTCAGATGAGAGATGTGATTGGAGCAGCAGCTACAGCCAATCAGAACTACTTCCGC
native_CNGB3_ORF              TTAATTGGTCAGATGAGAGATGTGATTGGAGCAGCAGCTACAGCCAATCAGAACTACTTCCGC
                              ************************************************************
```

```
CNGB3_with_modified    AGAGGGACTTCTCGTCAATCACTCATTATCAGCATGGCTCCTTCTGCTGAGGGCGGAGAA
CNGB3_modified_ORF     AGAGGGACTTCTCGTCAATCACTCATTATCAGCATGGCTCCTTCTGCTGAGGGCGGAGAA
native_CNGB3_ORF       AGAGGGACTTCTCGTCAATCACTCATTATCAGCATGGCTCCTTCTGCTGAGGGCGGAGAA
                       ************************************************************

CNGB3_with_modified    GAGGTTCTTACTATTGAAGTCAAAGAAAAGGCTAAGCAATGATCATAACTGCAG-MDIFI
CNGB3_modified_ORF     GAGGTTCTTACTATTGAAGTCAAAGAAAAGGCTAAGCAATGA------------------
native_CNGB3_ORF       GAGGTTCTTACTATTGAAGTCAAAGAAAAGGCTAAGCAATAA------------------
                       *****************************************  *
```

Version 2a (V2a)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| KanR | 4631...5440 | 810 | => |
| pUC ori | 5612...6200 | 589 | => |
| lamba stuffer | 6437...11,503 | 5067 | == |
| CAP binding site | 11,555...11,576 | 22 | == |
| lac promotor | 11,591...11,621 | 31 | == |
| lac operator | 11,629...11,645 | 17 | == |

Version 2b (V2b)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| KanR | 4631...5440 | 810 | => |
| pUC ori | 5612...6200 | 589 | => |
| CAP binding site | 6488...6509 | 22 | == |
| lac promotor | 6524...6554 | 31 | == |
| lac operator | 6562...6578 | 17 | == |

Version 3a (V3a)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| FRT (minimal) | 4264...4297 | 34 | <= |
| bla txn terminator | 4330...4630 | 301 | == |
| pTF3 | 4421...4446 | 26 | == |
| p15A ori | 5077...5622 | 546 | <= |
| lamba stuffer | 5643...10,709 | 5067 | == |
| KanR | 10,715...11,524 | 810 | <= |
| rrnB1 B2 T1 txn terminator | 11,703...11,877 | 175 | <= |
| pTR | 11,778...11,794 | 17 | == |
| FRT (minimal) | 11,909...11,942 | 34 | => |

Version 3a (V3a)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| FRT (minimal) | 4264...4297 | 34 | <= |
| bla txn terminator | 4330...4630 | 301 | == |
| pTF3 | 4421...4446 | 26 | == |
| p15A ori | 5077...5622 | 546 | <= |
| KanR | 5644...6453 | 810 | <= |
| rrnB1 B2 T1 txn terminator | 6632...6806 | 175 | <= |
| pTR | 6707...6723 | 17 | == |
| FRT (minimal) | 6838...6871 | 34 | => |

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Human native CHM (REP-1) | 1861...3822 | 1962 | => |
| bGH poly(A) signal | 3836...4043 | 208 | == |
| 3' ITR | 4093...4222 | 130 | == |
| ITR D segment | 4093...4110 | 18 | == |
| FRT (minimal) | 4250...4283 | 34 | <= |
| bla txn terminator | 4316...4616 | 301 | == |
| pTF3 | 4407...4432 | 26 | == |
| lamba stuffer | 4752...9818 | 5067 | == |
| M13 fwd | 9824...9840 | 17 | <= |
| pUC ori | 10,110...10,698 | 589 | <= |
| KanR | 10,822...11,631 | 810 | <= |
| rrnB1 B2 T1 txn terminator | 11,810...11,984 | 175 | <= |
| pTR | 11,885...11,901 | 17 | == |
| FRT (minimal) | 12,016...12,049 | 34 | == |

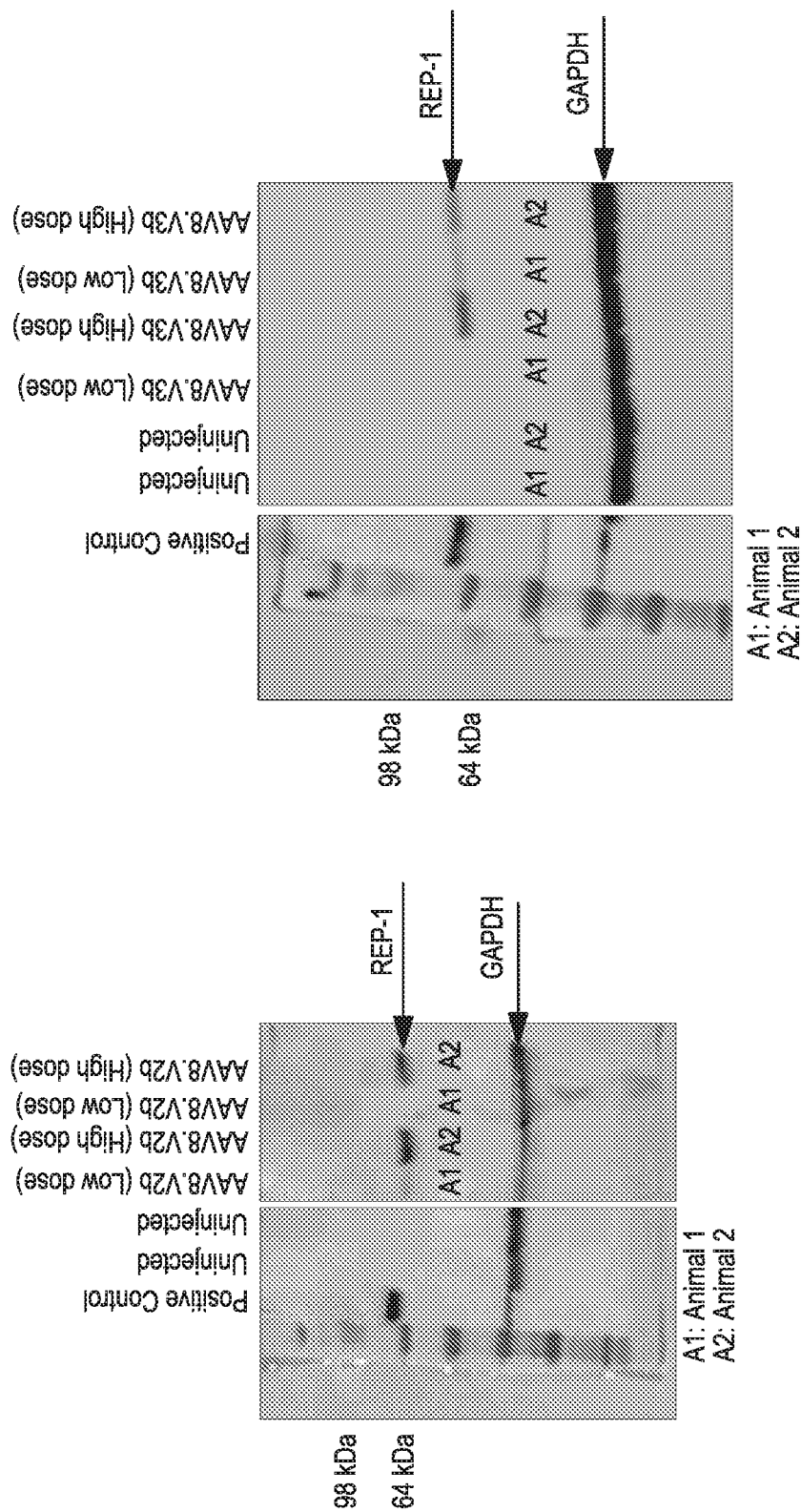

P982 Features:

| Feature | Location | Size | Directionality |
|---|---|---|---|
| 5' ITR | 1..130 | 130 | == |
| ITR D segment | 113..130 | 18 | == |
| RK1 promoter | 175..684 | 510 | => |
| native CNGA3 | 685..2790 | 2106 | => |
| BGH polyA | 2796..3012 | 217 | == |
| 3' ITR | 3060..3189 | 130 | == |
| ITR D segment | 3060..3077 | 18 | == |
| bla txn terminator | 3283..3583 | 301 | => |
| rpn txn terminator | 3590..3703 | 114 | => |

| lambda stuffer | 3719..8785 | 5067 | => |
| pUC ori | 8946..9749 | 804 | <= |
| KanR | 9798..10592 | 795 | <= |
| rrnB1 B2 T1 txn terminator | 10777..10951 | 175 | <= |

FIG. 13B pAAV-RK1-codonoptimizedCNGA3 (p983)

P983 Features:

| Feature | Location | Size | Directionality |
|---|---|---|---|
| 5' ITR | 1..130 | 130 | == |
| ITR D segment | 113..130 | 18 | == |
| RK1 promoter | 175..684 | 510 | => |
| CNGA3opt | 685..2790 | 2106 | => |
| BGH polyA | 2796..3012 | 217 | == |
| 3' ITR | 3060..3189 | 130 | == |
| ITR D segment | 3060..3077 | 18 | == |

| | | | |
|---|---|---|---|
| bla txn terminator | 3283..3583 | 301 | => |
| rpn txn terminator | 3590..3703 | 114 | => |
| lambda stuffer | 3719..8785 | 5067 | => |
| pUC ori | 8946..9749 | 804 | <= |
| source | 9790..9789 | 11041 | == |
| KanR | 9798..10592 | 795 | <= |
| rrnB1 B2 T1 txn terminator | 10777..10951 | 175 | <= |

FIG. 14B

P984 Features:

| Feature | Location | Size | Directionality |
|---|---|---|---|
| 5' ITR | 1..130 | 130 | == |
| ITR D segment | 113..130 | 18 | == |
| RK1 promoter | 175..684 | 510 | => |
| CNGA3_opt_variant3 | 685..2955 | 2271 | => |
| BGH polyA | 2961..3177 | 217 | == |
| 3' ITR | 3225..3354 | 130 | == |

| ITR D segment | 3225..3242 | 18 | == |
| bla txn terminator | 3448..3748 | 301 | => |
| rpn txn terminator | 3755..3868 | 114 | => |
| lambda stuffer | 3884..8950 | 5067 | => |
| pUC ori | 9111..9914 | 804 | <= |
| source | 9955..9954 | 11206 | == |
| KanR | 9963..10757 | 795 | <= |
| rrnB1 B2 T1 txn terminator | 10942..11116 | 175 | <= |

FIG. 15B pAAV-hCAR-CNGA3 native (p1070)

P1070 Features:

| Feature | Location | Size | Directionality |
|---|---|---|---|
| 5' ITR | 1..130 | 130 | === |
| ITR D segment | 113..130 | 18 | === |
| hCAR promoter sequence | 181..1078 | 898 | === |
| native CNGA3 | 1081..3184 | 2104 | => |
| exon | 1185..1191 | 7 | === |
| BGH polyA | 3190..3406 | 217 | === |

| 3' ITR | 3454..3583 | 130 | == |
| ITR D segment | 3454..3471 | 18 | == |
| bla txn terminator | 3677..3977 | 301 | => |
| rpn txn terminator | 3984..4097 | 114 | => |
| lambda stuffer | 4113..9179 | 5067 | => |
| pUC_ori | 9340..10143 | 804 | <= |
| KanR | 10192..10986 | 795 | <= |
| rrnB1 B2 T1 txn terminator | 11171..11345 | 175 | <= |
| wt ITRcassette | 11420..175 | 191 | => |

FIG. 16B pAAV-hCAR-codonoptimizedCNGA3 (p1071)

Features of p1071:

| Feature | Location | Size | Directionality |
|---|---|---|---|
| 5' ITR | 1..130 | 130 | == |
| ITR D segment | 113..130 | 18 | == |
| hCAR promoter sequence | 181..1078 | 898 | == |
| CNGA3opt | 1081..3184 | 2104 | => |
| BGH polyA | 3187..3403 | 217 | == |
| 3' ITR | 3451..3580 | 130 | == |
| ITR D segment | 3451..3468 | 18 | == |

| bla txn terminator | 3674..3974 | 301 | => |
|---|---|---|---|
| rpn txn terminator | 3981..4094 | 114 | => |
| lambda stuffer | 4110..9176 | 5067 | => |
| pUC ori | 9337..10,140 | 804 | <= |
| KanR | 10189..10983 | 795 | <= |
| rrnB1 B2 T1 txn terminator | 11168..11342 | 175 | <= |

FIG. 17B

Features of p1072:

| Feature | Location | Size | Directionality |
|---|---|---|---|
| 5' ITR | 1..130 | 130 | == |
| ITR D segment | 113..130 | 18 | == |
| hCAR promoter sequence | 181..1078 | 898 | == |
| CNGA3_opt_variant3 | 1081..3349 | 2269 | => |
| BGH polyA | 3355..3571 | 217 | == |
| 3' ITR | 3619..3748 | 130 | == |

| ITR D segment | 3619..3636 | 18 | == |
| bla txn terminator | 3842..4142 | 301 | => |
| rpn txn terminator | 4149..4262 | 114 | => |
| lambda stuffer | 4278..9344 | 5067 | => |
| pUC ori | 9505..10308 | 804 | <= |
| KanR | 10357..11151 | 795 | <= |
| rrnB1 B2 T1 txn terminator | 11336..11510 | 175 | <= |

FIG. 18B

Features of p1065:

| Feature | Location | Size | Directionality |
|---|---|---|---|
| 5' ITR | 1..130 | 130 | == |
| ITR D segment | 113..130 | 18 | == |
| CMV enhancer | 241..544 | 304 | == |
| chicken beta-actin promoter | 546..823 | 278 | => |
| CBA exon1 and intron | 824..1795 | 972 | => |

| | | | |
|---|---|---|---|
| native CNGA3 | 1855..3958 | 2104 | => |
| bGH poly(A) signal | 3971..4178 | 208 | == |
| 3' ITR | 4228..4357 | 130 | == |
| ITR D segment | 4228..4245 | 18 | == |
| bla txn terminator | 4451..4751 | 301 | => |
| rpn txn terminator | 4758..4871 | 114 | => |
| lambda stuffer | 4887..9953 | 5067 | => |
| M13 fwd | 9959..9975 | 17 | <= |
| pUC ori | 10245..10833 | 589 | <= |
| KanR | 10957..11766 | 810 | <= |
| rrnB1 B2 T1 txn terminator | 11945..12119 | 175 | <= |
| FRT (minimal) | 12151..12184 | 34 | => |

FIG. 19B

| 3' ITR | 4228..4357 | 130 | == |
| ITR D segment | 4228..4245 | 18 | == |
| bla txn terminator | 4451..4751 | 301 | => |
| rpn txn terminator | 4758..4871 | 114 | => |
| lambda stuffer | 4887..9953 | 5067 | => |
| pUC ori | 10114..10917 | 804 | <= |
| KanR | 10966..11760 | 795 | <= |
| rrnB1 B2 T1 txn terminator | 11945..12119 | 175 | <= |

FIG. 20B pAAV-CMV-CBA-codonoptimizedCNGA3Variant3(p1104)

Features of p1104:

| Feature | Location | Size | Directionality |
|---|---|---|---|
| 5' ITR | 1..130 | 130 | == |
| ITR D segment | 113..130 | 18 | == |
| CMV/CBA hybrid promoter | 191..1852 | 1662 | => |
| CNGA3_opt_variantX | 1855..4123 | 2269 | => |
| BGH polyA | 4129..4345 | 217 | == |

| 3' ITR | 4393..4522 | 130 | == |
| ITR D segment | 4393..4410 | 18 | == |
| bla txn terminator | 4616..4916 | 301 | => |
| rpn txn terminator | 4923..5036 | 114 | => |
| lambda stuffer | 5052..10118 | 5067 | => |
| pUC ori | 10279..11082 | 804 | <= |
| KanR | 11131..11925 | 795 | <= |
| rrnB1 B2 T1 txn terminator | 12110..12284 | 175 | <= |

FIG. 21B pAAV-RK1-hCNGB3 native (p995)

P995 Features:

| Feature | Location | Size | Directionality |
|---|---|---|---|
| 5' ITR | 1..130 | 130 | == |
| ITR D segment | 113..130 | 18 | == |
| RK1 promoter | 175..685 | 511 | => |
| native CNGB3 with flanking sites and silent mut | 686..3139 | 2454 | => |
| BGH polyA | 3144..3360 | 217 | == |
| 3' ITR | 3408..3537 | 130 | == |
| ITR D segment | 3408..3425 | 18 | == |
| bla txn terminator | 3631..3931 | 301 | => |
| pTF3 | 3722..3747 | 26 | == |

| rpn txn terminator | 3938..4051 | 114 | => |
| --- | --- | --- | --- |
| lambda stuffer | 4067..9133 | 5067 | => |
| pUC_ori | 9294..10,097 | 804 | <= |
| source | 10,138..10,137 | 11389 | == |
| Kanamycin | 10,146..10,940 | 795 | <= |
| rnB1 B2 T1 txn terminator | 11,125..11,299 | 175 | <= |
| 5' ITR | 1..130 | 130 | == |

FIG. 22B

| ITR D segment | 3407..3424 | 18 | == |
| --- | --- | --- | --- |
| bla txn terminator | 3630..3930 | 301 | => |
| pTF3 | 3721..3746 | 26 | == |
| rpn txn terminator | 3937..4050 | 114 | => |
| lambda stuffer | 4066..9132 | 5067 | => |
| pUC_ori | 9293..10,096 | 804 | <= |
| source | 10,137..10,136 | 11388 | == |
| Kanamycin | 10,145..10,939 | 795 | <= |
| rrnB1 B2 T1 txn terminator | 11,124..11,298 | 175 | <= |

FIG. 23B pAAV-hCAR-hCNGB3 native (p1054)

P1054 Features

| Feature | Location | Size | Directionality |
|---|---|---|---|
| 5' ITR | 1..130 | 130 | == |
| ITR D segment | 113..130 | 18 | == |
| hCAR promoter sequence | 181..1078 | 898 | == |
| native CNGB3 with flanking sites and silent mut | 1081..3532 | 2452 | => |
| BGH polyA | 3537..3753 | 217 | == |
| 3' ITR | 3801..3930 | 130 | == |
| ITR D segment | 3801..3818 | 18 | == |

| bla txn terminator | 4024..4324 | 301 | => |
| rpn txn terminator | 4331..4444 | 114 | => |
| lambda stuffer | 4460..9526 | 5067 | => |

FIG. 24B pAAV-hCAR-hCNGB3 codon optimized (p1055)

P1055 Features:

| Feature | Location | Size | Directionality |
|---|---|---|---|
| 5' ITR | 1..130 | 130 | == |
| ITR D segment | 113..130 | 18 | == |
| hCAR promoter sequence | 181..1078 | 898 | == |
| codon opt CNGB3 with flanking sites | 1081..3532 | 2452 | => |
| BGH polyA | 3537..3753 | 217 | == |
| 3' ITR | 3801..3930 | 130 | == |
| ITR D segment | 3801..3818 | 18 | == |
| bla txn terminator | 4024..4324 | 301 | => |
| rpn txn terminator | 4331..4444 | 114 | => |

| lambda stuffer | 4460..9526 | 5067 | => |
| pUC_ori | 9687..10,490 | 804 | <= |

FIG. 25B pAAV-CMV/CBA-hCNGB3 native (p1105)

P1105 Features

| Feature | Location | Size | Directionality |
|---|---|---|---|
| 5' ITR | 1..130 | 130 | == |
| ITR D segment | 113..130 | 18 | == |
| CMV/CBA hybrid promoter | 191..1852 | 1662 | => |
| CBA promoter | 543..824 | 282 | => |
| CBA exon1 and intron | 823..1795 | 973 | => |
| native CNGB3 with flanking and silent mut | 1855..4306 | 2452 | => |
| BGH polyA | 4311..4527 | 217 | == |
| 3' ITR | 4575..4704 | 130 | == |

| ITR D segment | 4575..4592 | 18 | == |
| bla txn terminator | 4798..5098 | 301 | => |

FIG. 26B pAAV-CMV/CBA-hCNGB3 codon optimized (p1066)

P1066 Features:

| Feature | Location | Size | Directionality |
|---|---|---|---|
| 5' ITR | 1..130 | 130 | == |
| ITR D segment | 113..130 | 18 | == |
| CMV/CBA hybrid promoter | 191..1852 | 1662 | => |
| CBA promoter | 543..824 | 282 | => |
| CBA exon1 and intron | 823..1795 | 973 | => |

| | | | |
|---|---|---|---|
| codon opt CNGB3 with flanking sites | 1855..4305 | 2451 | => |
| BGH polyA | 4311..4527 | 217 | == |
| 3' ITR | 4575..4704 | 130 | == |
| ITR D segment | 4575..4592 | 18 | == |
| bla txn terminator | 4798..5098 | 301 | => |
| pTF3 | 4889..4914 | 26 | == |
| rpn txn terminator | 5105..5218 | 114 | => |
| lambda stuffer | 5234..10,300 | 5067 | => |
| pUC_ori | 10,461..11,264 | 804 | <= |
| Kanamycin | 11,313..12,107 | 795 | <= |
| rrnB1 B2 T1 txn terminator | 12,292..12,466 | 175 | <= |

FIG. 27B

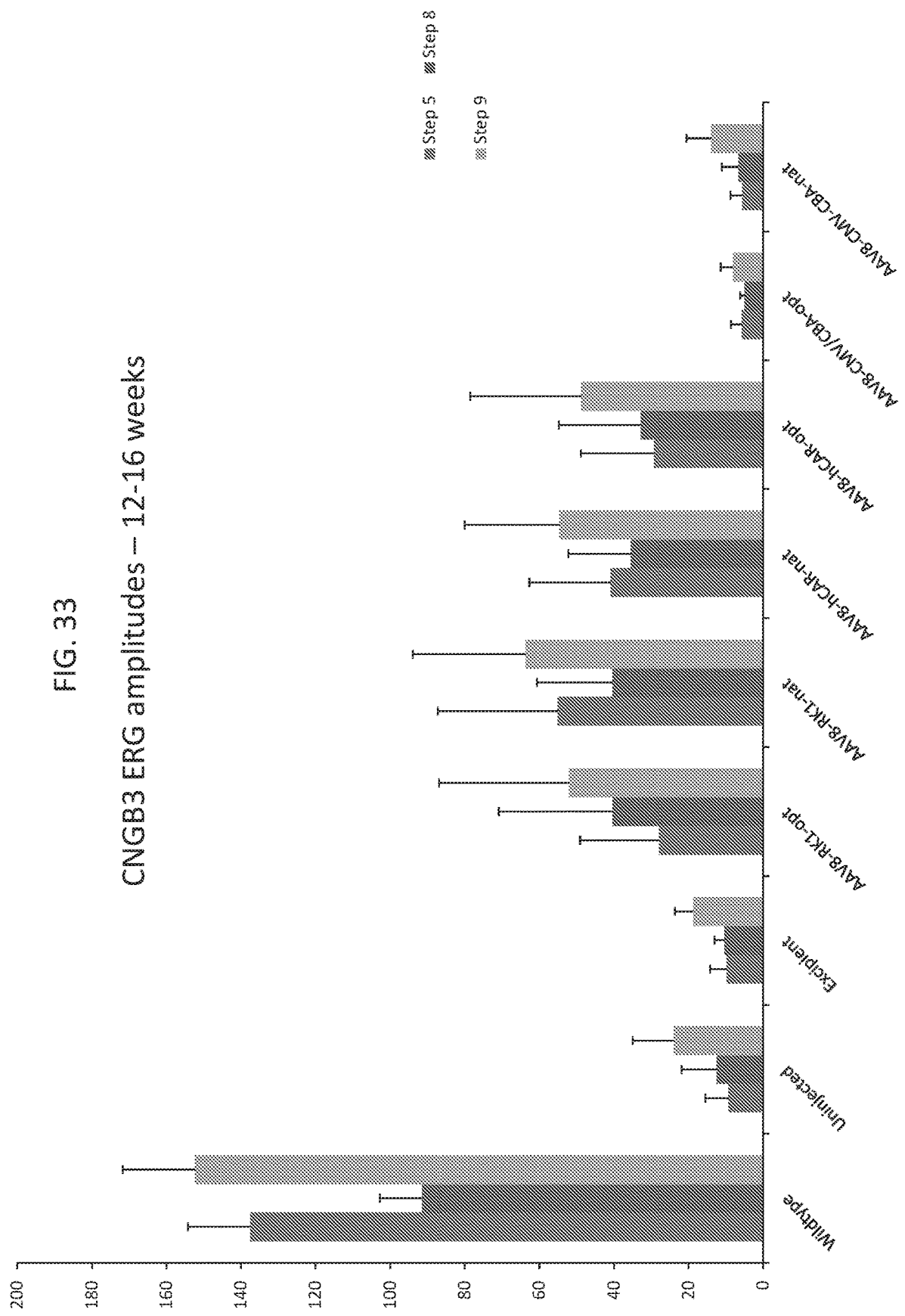

5E8 vg/eye

5E9 vg/eye pAAV-hCAR-native-CNGA3-WPRE (p1122)

P1122 Features:

| Feature | Location | Size | Directionality |
|---|---|---|---|
| 5' ITR | 1..130 | 130 | == |
| ITR D segment | 113..130 | 18 | == |
| hCAR promoter | 181..1078 | 898 | => |
| native CNGA3 | 1091..3181 | 2091 | => |
| WPRE | 3209..3750 | 542 | => |
| BGH polyA | 3756..3976 | 221 | == |
| 3' ITR | 4025..4154 | 130 | == |
| ITR D segment | 4025..4042 | 18 | == |

| | | | |
|---|---|---|---|
| bla txn terminator | 4248..4548 | 301 | => |
| rpn txn terminator | 4555..4668 | 114 | => |
| lambda stuffer | 4684..9750 | 5067 | => |
| pUC ori | 9911..10,714 | 804 | <= |
| KanR | 10,731..11,557 | 795 | <= |
| rrnB1 B2 T1 txn terminator | 11,742..11,916 | 175 | <= |

FIG. 45B

GENE THERAPY FOR OCULAR DISORDERS

CROSS-REFERENCE TO RELATED APPLICATIONS

This is a National Stage Entry under 35 U.S.C. 371 of International Patent Application No. PCT/US2018/037592, filed Jun. 14, 2018, which claims priority to U.S. Provisional Patent Application No. 62/519,821, filed Jun. 14, 2017. These applications are incorporated by reference herein.

INCORPORATION-BY-REFERENCE OF MATERIAL SUBMITTED IN ELECTRONIC FORM

Applicant hereby incorporates by reference the Sequence Listing file labeled "17-8318PCT_Seq_Listing_ST25.txt" (created Mar. 29, 2022, 512,366 bytes).

BACKGROUND OF THE INVENTION

Choroideremia (CHM) is an X-linked inherited retinal disease characterized by the degeneration of photoreceptors, retinal pigment epithelium (RPE) and choriocapillaris. Symptoms develop in the 1st or 2nd decade of life with complaints of poor night vision (nyctalopia) and progressive loss of peripheral vision. Visual fields constrict as the disease progresses. This culminates with loss of central vision (visual acuity) and blindness as early as the fourth decade of life. More than 140 mutations in the CHM gene have been found to cause choroideremia. Mutations may lead to the production of an abnormally small, nonfunctional and/or unstable Rab escort protein-1 (REP-1) protein, a decrease in the protein's function or loss of REP-1 protein production. Lack of normal REP-1 disrupts the ability of Rab proteins to aid in intracellular trafficking. The immobility of proteins and organelles within the cell causes the cells to function poorly and to die prematurely.

The choroideremia gene, CHM, encodes Rab Escort Protein-1 (REP-1), a 653 amino acid protein involved in regulation of membrane trafficking. Since the CHM locus is on the X-chromosome, choroideremia is typically only diagnosed in males. Although female carriers of the disease are usually asymptomatic, retinal exams often reveal a patchy degeneration of the retina and RPE and female individuals can be affected depending on the extent of X-inactivation of the normal X chromosome (lyonization). Coussa, R G, Traboulsi, E I (2012) Choroideremia: a review of general findings and pathogenesis, Ophthalmic Genet 33(2):57-65, which is incorporated herein by reference. See also, Vasireddy et al, AAV-mediated gene therapy for choroideremia: preclinical studies in personalized models. PLoS One. 2013 May 7; 8(5):e61396, which is incorporated herein by reference.

Achromatopsia is a heterogeneous group of autosomal recessive inherited retinal diseases characterized by early onset reduced visual acuity, impaired or complete color blindness, nystagmus, photoaversion and loss of cone photoreceptor function. About 80% of achromatopsia patients show mutations in the alpha or beta subunit (A3 and B3) of the cGMP controlled cation channel cyclic nucleotide-gated channel (CNG) of cone photoreceptors. Homologous to the human disease, Cnga3 deficient mice reveal a loss of cone specific functionality leading to malfunction and degeneration of affected cone photoreceptors.

Therefore, compositions useful for expressing REP-1, CNGA3 or CNGB3 in human subjects are needed.

SUMMARY OF THE INVENTION

Choroideremia (CHM) is an X-linked retinal degeneration that is symptomatic in the 1st or 2nd decade of life causing nyctalopia and loss of peripheral vision. The disease progresses through mid-life, when most patients become blind. CHM is a favorable target for gene augmentation therapy, as the disease is due to loss of function of a protein necessary for retinal cell health, Rab Escort Protein 1 (REP1), which is encoded by the CHM gene. The CHM cDNA can be packaged in recombinant adeno-associated virus (rAAV), which has an established track record in human gene therapy studies. In addition, there are sensitive and quantitative assays to document REP1 activity, including its ability to prenylate Rab proteins such as Rab27 and to correct a defect in Rab27 localization and trafficking due to lack of prenylation in REP-1 deficient cells.

In one aspect, a codon optimized cDNA sequence encoding Rab Escort Protein-1 (REP-1) is provided. In one embodiment, the codon optimized cDNA sequence is a variant of SEQ ID NO: 3. In another embodiment, the codon optimized cDNA sequence is SEQ ID NO: 1. In another embodiment, the cDNA sequence is codon optimized for expression in humans.

In another aspect, an expression cassette includes a codon optimized nucleic acid sequence that encodes REP-1. In one embodiment, the expression cassette includes the cDNA sequence of SEQ ID NO: 1. In still other embodiments, the REP-1 encoding sequence is positioned between 5' and 3' AAV ITR sequences. In one embodiment, the vector genome includes all of the nucleic acid sequence between, and including, the 5' ITR and 3' ITR.

In another embodiment, an adeno-associated virus (AAV) vector is provided. The AAV vector includes an AAV capsid and a nucleic acid sequence comprising AAV inverted terminal repeat sequences and a nucleic acid sequence encoding human Rab Escort Protein-1 (REP-1), and expression control sequences that direct expression of the REP-1 in a host cell. In one embodiment, the REP-1 sequence encodes a full length REP-1 protein. In one embodiment, the REP-1 sequence is the protein sequence of SEQ ID NO: 2.

In one aspect, a codon optimized cDNA sequence encoding cyclic nucleotide gated channel alpha 3 (CNGA3) is provided. In one embodiment, the codon optimized cDNA sequence is a variant of SEQ ID NO: 13 or SEQ ID NO: 15. In another embodiment, the codon optimized cDNA sequence is SEQ ID NO: 9 or SEQ ID NO: 11. In another embodiment, the cDNA sequence is codon optimized for expression in humans.

In another aspect, a codon optimized cDNA sequence encoding CNGB3 is provided. In one embodiment, the codon optimized cDNA sequence is a variant of SEQ ID NO: 19 or 21 or 23. In another embodiment, the codon optimized cDNA sequence is SEQ ID NO: 45. In another embodiment, the cDNA sequence is codon optimized for expression in humans.

In another aspect, an expression cassette includes a codon optimized nucleic acid sequence that encodes cyclic nucleotide gated channel alpha 3 (CNGA3). In one embodiment, the expression cassette includes the cDNA sequence of SEQ ID NO: 9, SEQ ID NO: 11, SEQ ID NO: 13, or SEQ ID NO: 15. In still other embodiments, the CNGA3 encoding sequence is positioned between 5' and 3' AAV ITR sequences.

In another aspect, an expression cassette includes a codon optimized nucleic acid sequence that encodes cyclic nucleotide gated channel beta 3 (CNGB3). In one embodiment, the expression cassette includes the cDNA sequence of SEQ ID NO: 19 or SEQ ID NO: 21 or SEQ ID NO: 23 or SEQ ID NO: 45. In still other embodiments, the CNGB3 encoding sequence is positioned between 5' and 3' AAV ITR sequences.

In another embodiment, an adeno-associated virus (AAV) vector is provided. The AAV vector includes an AAV capsid and a nucleic acid sequence comprising AAV inverted terminal repeat sequences and a nucleic acid sequence encoding human CNGA3, and expression control sequences that direct expression of the CNGA3 in a host cell. In one embodiment, the CNGA3 sequence encodes a full length CNGA3 protein. In one embodiment, the CNGA3 sequence is the protein sequence of SEQ ID NO: 10, SEQ ID NO: 12 or SEQ ID NO: 14.

In another embodiment, an adeno-associated virus (AAV) vector is provided. The AAV vector includes an AAV capsid and a nucleic acid sequence comprising AAV inverted terminal repeat sequences and a nucleic acid sequence encoding human CNGB3, and expression control sequences that direct expression of the CNGB3 in a host cell. In one embodiment, the CNGB3 sequence encodes a full length CNGB3 protein. In one embodiment, the CNGB3 sequence is the protein sequence of SEQ ID NO: 20.

In another aspect, an adeno-associated virus (AAV) vector is provided which comprises an AAV8 capsid and an expression cassette, wherein said expression cassette comprises nucleic acid sequences encoding REP-1, inverted terminal repeat sequences and expression control sequences that direct expression of REP-1 in a host cell. In one embodiment, the expression control sequences include a Chicken Beta Actin (CBA) promoter with a cytomegalovirus (CMV) enhancer. In one embodiment, the nucleic acid sequence comprises SEQ ID NO: 1.

In yet another aspect, an adeno-associated virus (AAV) vector is provided which comprises an AAV8 capsid and an expression cassette, wherein said expression cassette comprises nucleic acid sequences encoding CNGA3, inverted terminal repeat sequences and expression control sequences that direct expression of CNGA3 in a host cell. In one embodiment, the expression control sequences include a rhodopsin kinase promoter. In one embodiment, the expression control sequences include a human cone arrestin promoter. In one embodiment, the nucleic acid sequence comprises SEQ ID NO: 9. In one embodiment, the nucleic acid sequence comprises SEQ ID NO: 11.

In yet another aspect, an adeno-associated virus (AAV) vector is provided which comprises an AAV8 capsid and an expression cassette, wherein said expression cassette comprises nucleic acid sequences encoding CNGB3, inverted terminal repeat sequences and expression control sequences that direct expression of CNGB3 in a host cell.

In another aspect, an adeno-associated virus (AAV) vector is provided which comprises an AAV2 capsid and an expression cassette, wherein said expression cassette comprises nucleic acid sequences encoding REP-1, inverted terminal repeat sequences and expression control sequences that direct expression of REP-1 in a host cell. In one embodiment, the expression control sequences include a CBA promoter with a CMV enhancer. In one embodiment, the nucleic acid sequence comprises SEQ ID NO: 1.

In yet another aspect, an adeno-associated virus (AAV) vector is provided which comprises an AAV2 capsid and an expression cassette, wherein said expression cassette comprises nucleic acid sequences encoding CNGA3, inverted terminal repeat sequences and expression control sequences that direct expression of CNGA3 in a host cell. In one embodiment, the expression control sequences include a rhodopsin kinase promoter. In one embodiment, the expression control sequences include a human cone arrestin promoter. In one embodiment, the nucleic acid sequence comprises SEQ ID NO: 9. In one embodiment, the nucleic acid sequence comprises SEQ ID NO: 11.

In yet another aspect, an adeno-associated virus (AAV) vector is provided which comprises an AAV2 capsid and an expression cassette, wherein said expression cassette comprises nucleic acid sequences encoding CNGB3, inverted terminal repeat sequences and expression control sequences that direct expression of CNGB3 in a host cell.

In yet another aspect, an adeno-associated virus (AAV) vector is provided which comprises an AAV9 capsid and an expression cassette, wherein said expression cassette comprises nucleic acid sequences encoding CNGA3, inverted terminal repeat sequences and expression control sequences that direct expression of CNGA3 in a host cell. In one embodiment, the expression control sequences include a rhodopsin kinase promoter. In one embodiment, the expression control sequences include a human cone arrestin promoter. In one embodiment, the nucleic acid sequence comprises SEQ ID NO: 9. In one embodiment, the nucleic acid sequence comprises SEQ ID NO: 11.

In yet another aspect, an adeno-associated virus (AAV) vector is provided which comprises an AAV9 capsid and an expression cassette, wherein said expression cassette comprises nucleic acid sequences encoding CNGB3, inverted terminal repeat sequences and expression control sequences that direct expression of CNGB3 in a host cell.

In another aspect, an adeno-associated virus (AAV) vector is provided which comprises an AAV9 capsid and an expression cassette, wherein said expression cassette comprises nucleic acid sequences encoding REP-1, inverted terminal repeat sequences and expression control sequences that direct expression of REP-1 in a host cell. In one embodiment, the expression control sequences include a CBA promoter with a CMV enhancer. In one embodiment, the nucleic acid sequence comprises SEQ ID NO: 1.

In another aspect, a pharmaceutical composition is provided which includes a pharmaceutically acceptable carrier, diluent, excipient and/or adjuvant and a least a viral vector as described herein.

In yet a further aspect a pharmaceutical composition comprises a pharmaceutically acceptable carrier, diluent, excipient and/or adjuvant and the nucleic acid sequence, a plasmid, a vector, or a viral vector, such as the rAAV, described specifically herein.

In another aspect, a method for treating choroideremia is provided. In one embodiment, the method includes administering a composition which includes the AAV vector which encodes REP-1, as described herein, to a subject in need thereof.

In another aspect, a method for treating achromatopsia is provided. In one embodiment, the method includes administering a composition which includes the AAV vector which encodes CNGA3, as described herein, to a subject in need thereof.

In another aspect, a method for treating achromatopsia is provided. In one embodiment, the method includes administering a composition which includes the AAV vector which encodes CNGB3, as described herein, to a subject in need thereof.

In yet another aspect, a plasmid for producing an AAV vector is provided. In one embodiment, the plasmid includes the codon optimized cDNA sequence encoding REP-1 as described herein. In another embodiment, the plasmid includes the codon optimized cDNA sequence encoding CNGA3 as described herein. In another embodiment, the plasmid includes a codon optimized cDNA sequence encoding CNGB3 which is a sequence sharing at least 70% identity with SEQ ID NO: 19 or SEQ ID NO: 21. In yet another embodiment, the plasmid includes the codon optimized cDNA sequence encoding CNGB3 as described herein. In one embodiment, the plasmid is modular.

In another aspect, a method of generating a rAAV virus is provided. The method includes culturing a packaging cell carrying the plasmid described herein in the presence of sufficient viral sequences to permit packaging of the gene expression cassette viral genome into an infectious AAV envelope or capsid. In another, aspect, a recombinant AAV produced according to the method is provided.

Other aspects and advantages of the invention will be readily apparent from the following detailed description of the invention.

BRIEF DESCRIPTION OF THE DRAWINGS

FIG. 2A to FIG. 2F provide an alignment of the native REP-1 coding sequence of SEQ ID NO: 1 vs. the codon optimized REP-1 coding sequence of SEQ ID NO: 3.

FIG. 3A to FIG. 3F provide an alignment of the native CNGA3 coding sequence of SEQ ID NO: 13 vs. the codon optimized CNGA3 coding sequence of SEQ ID NO: 9.

FIG. 4A to FIG. 4F provide an alignment of CNGB3 native ORF (SEQ ID NO: 19) vs. CNGB3 modified ORF (SEQ ID NO: 21) vs. CNGB3 modified orf with modified ends (SEQ ID NO: 23). Point mutations are highlighted.

FIG. 12A is a western blot showing human anti-REP-1 antibody detection of a protein of ~75-80 kDa in ocular tissues of CD-1 mice injected with AAV8.2b at 5E9 (High dose) vector genome copies. Animals injected with AAV8.2b at 5E8 (Low dose) showed a very faint protein band at ~75-80 kDa.

FIG. 12B is a Western blot analysis of ocular tissues of AAV8.3b injected CD1 mice (2 mice/group) detected with anti-REP-1 antibody, which revealed the presence of a protein of ~75-80 kDa in one eye injected with low dose and in both eyes injected with high dose of AAV8.3b. In the ocular tissues of uninjected mice there was no REP-1 expression detected.

FIG. 13A to FIG. 13B provide a plasmid map of pAAV-RK1-nativeCNGA3, described herein. The sequence is shown in SEQ ID NO: 30.

FIG. 14A to FIG. 14B provide a plasmid map of pAAV-RK1-codon optimized CNGA3, described herein. The sequence is shown in SEQ ID NO: 31.

FIG. 15A to FIG. 15B provide a plasmid map of pAAV-RK1-codon optimized CNGA3 variant 3, described herein. The sequence is shown in SEQ ID NO: 32.

FIG. 16A to FIG. 16B provide a plasmid map of pAAV-hCAR-nativeCNGA3, described herein. The sequence is shown in SEQ ID NO: 33.

FIG. 17A to FIG. 17B provide a plasmid map of pAAV-hCAR-codon optimized CNGA3, described herein. The sequence is shown in SEQ ID NO: 34.

FIG. 18A to FIG. 18B provide a plasmid map of pAAV-hCAR-codon optimized CNGA3 variant 3, described herein. The sequence is shown in SEQ ID NO: 35.

FIG. 19A to FIG. 19B provide a plasmid map of pAAV-CMV-CBA-nativeCNGA3, described herein. The sequence is shown in SEQ ID NO: 36.

FIG. 20A to FIG. 20B provide a plasmid map of pAAV-CMV-CBA-codon optimized CNGA3, described herein. The sequence is shown in SEQ ID NO: 37.

FIG. 21A to FIG. 21B provide a plasmid map of pAAV-CMV-CBA-codon optimized CNGA3 variant 3, described herein. The sequence is shown in SEQ ID NO: 38.

FIG. 22A to FIG. 22B provide a plasmid map of pAAV-RK1-native CNGB3, described herein. The sequence is shown in SEQ ID NO: 39.

FIG. 23A to FIG. 23B provide a plasmid map of pAAV-RK1-codon optimized CNGB3, described herein. The sequence is shown in SEQ ID NO: 40.

FIG. 24A to FIG. 24B provide a plasmid map of pAAV-hCAR-native CNGB3, described herein. The sequence is shown in SEQ ID NO: 41.

FIG. 25A to FIG. 25B provide a plasmid map of pAAV-hCAR-codon optimized CNGB3, described herein. The sequence is shown in SEQ ID NO: 42.

FIG. 26A to FIG. 26B provide a plasmid map of pAAV-CMV-CBA-native CNGB3, described herein. The sequence is shown in SEQ ID NO: 43.

FIG. 27A to FIG. 27B provide a plasmid map of pAAV-CMV-CBA-codon optimized CNGB3, described herein. The sequence is shown in SEQ ID NO: 44.

FIG. 33 is a bar graph showing the results of cone ERG for CNGB3 null mice treated with the noted vectors, as described in Example 9.

FIG. 45A and FIG. 45B provide a plasmid map of pAAV-hCAR-native-CNGA3-WPRE (p1122), described herein. The sequence of pAAV-hCAR-native-CNGA3-WPRE (p1122) is shown in SEQ ID NO: 46.

DETAILED DESCRIPTION OF THE INVENTION

Figure 1A:
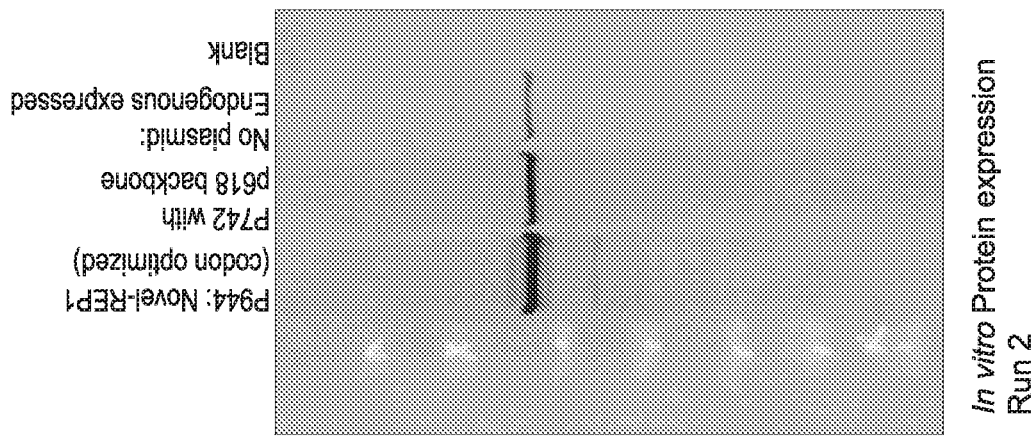
FIG. 1A and FIG. 1B are gels showing REP-1 protein expression in vitro after transfection of cultured 84-31 HEK cells. The first lane of each gel shows expression of codon-optimized REP-1 as described herein, expressed from plasmid p944. The second lane shows expression of native REP-1 from plasmid p742. The third lane shows endogenous expression of REP-1 by 84-31 cells that were not transfected with a plasmid. The last lane is a blank. The gels demonstrate that the codon-optimized REP-1 sequence, as described herein, results in a higher level of protein expression than the native REP-1 sequence, and that levels of expression from the exogenously transfected plasmids are many-fold higher than endogenous REP-1 expression.

The methods and compositions described herein include compositions and methods for delivering optimized CHM encoding REP-1 to mammalian subjects for the treatment of ocular disorders, primarily blinding diseases such as choroideremia. In addition, methods and compositions described herein involve compositions and methods for delivering optimized CNGA3 or CNGB3 to mammalian subjects for the treatment of ocular disorders, primarily blinding diseases such as achromatopsia. In one embodiment, such compositions involve codon optimization of the REP-1, CNGA3 or CNGB3 coding sequence. It is believed that these features increase the efficacy of the product, and increase safety, since a lower dose of reagent is used. It is anticipated that this optimization of the transgene cassette could theoretically maximize the level of production of the experimental protein compared to levels that can be generated using the endogenous sequence. However, also encompassed herein are compositions which include the native REP1, CNGA3, and CNGB3 coding sequences, as shown in SEQ ID NO: 3, SEQ ID NO: 13 and SEQ ID NO: 19, respectively. It is to be understood that when an embodiment is described for either REP-1, CNGA3 or CNGB3, a similar embodiment is intended to be recited for the other.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

The choroideremia gene, CHM, encodes Rab Escort Protein-1 (REP-1), a 653 amino acid protein thought to be involved in membrane trafficking. As used herein, the terms "REP-1" and "CHM" are used interchangeably when referring to the coding sequence. Since the CHM locus is on the X-chromosome, choroideremia is typically only diagnosed in males. Although female carriers of the disease are usually asymptomatic, retinal exams often reveal a patchy degeneration of the retina and RPE and female individuals can be affected depending on the extent of X-inactivation of the normal X chromosome (lyonization). See, Coussa, cited above. The native amino acid sequence encoding human REP-1 is reported at GenBank accession number P24386, and reproduced here in SEQ ID NO: 2. The native human nucleic acid sequence of CHM is reproduced here at SEQ ID NO: 3 (accession no. NM_000390.2).

Cyclic nucleotide-gated (CNG) ion channels are key mediators underlying signal transduction in retinal and olfactory receptors. Genetic defects in CNGA3 and CNGB3, encoding two structurally related subunits of cone CNG channels, are known to lead to achromatopsia. CNGA3 is a 694 amino acid protein. CNGB is an 809 amino acid protein.

Achromatopsia is a heterogeneous group of congenital, autosomal recessive retinal disorders that manifest by early onset cone photoreceptor dysfunction, severely reduced visual acuity, impaired or complete color blindness and photophobia. The native nucleic acid sequence encoding human CNGA3 is reported at GenBank accession no. XM_011210554.1, and reproduced in SEQ ID NO: 13. The native nucleic acid sequence encoding human CNGA3 is reported at GenBank accession no. XM_011210554.1, and reproduced in SEQ ID NO: 13. The native nucleic acid sequence for the human CNGA3 X1 variant, which includes an additional exon, is reported at GenBank accession no. NM_001298.2, and reproduced in SEQ ID NO: 15. The native nucleic acid sequence encoding human CNGB3 is reproduced in SEQ ID NO: 19.

In certain embodiments of this invention, a subject has an "ocular disorder", for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

As used herein "ocular disorder" includes, cone-rod dystrophies and retinal diseases including, without limitation, Stargardt disease (autosomal dominant or autosomal recessive), retinitis pigmentosa, and pattern dystrophy. In one embodiment, the subject has achromatopsia. In another embodiment, the subject has choroideremia or an X-linked hereditary retinal degeneration. Clinical signs of such ocular diseases include, but are not limited to, decreased peripheral vision, decreased central (reading) vision, decreased night vision, loss of color perception, reduction in visual acuity, decreased photoreceptor function, pigmentary changes, and ultimately blindness.

As used herein, the term "treatment" or "treating" is defined encompassing administering to a subject one or more compounds or compositions described herein for the purposes of amelioration of one or more symptoms of an ocular disease. "Treatment" can thus include one or more of reducing onset or progression of an ocular disease, preventing disease, reducing the severity of the disease symptoms, or retarding their progression, including the progression of blindness, removing the disease symptoms, delaying onset of disease or monitoring progression of disease or efficacy of therapy in a given subject.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

The terms "percent (%) identity", "sequence identity", "percent sequence identity", or "percent identical" in the context of nucleic acid sequences refers to the bases in the two sequences which are the same when aligned for correspondence. The percent identity is determined by comparing two sequences aligned under optimal conditions over the sequences to be compared. The length of sequence identity comparison may be over the full-length of the REP-1, CNGA3 or CNGB3 coding sequence, or a fragment of at least about 100 to 150 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Commonly available sequence analysis software, more specifically, BLAST or analysis tools provided by public databases may also be used.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

By "engineered" is meant that the nucleic acid sequences encoding the REP-1 or CNGA3 or CNGB3 protein described herein are assembled and placed into any suitable genetic element, e.g., naked DNA, phage, transposon, cosmid, episome, etc., which transfers the REP-1 or CNGA3 or CNGB3 sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

The term "transgene" as used herein means an exogenous or engineered protein-encoding nucleic acid sequence that is under the control of a promoter or expression control sequence in an expression cassette, rAAV genome, recombinant plasmid or production plasmid, vector, or host cell described in this specification. In certain embodiments, the transgene is a human CHM (REP-1) sequence, encoding a functional REP-1 protein. In some embodiments, the transgene is a codon optimized nucleic acid CHM (REP-1) encoding the REP-1 amino acid sequence set forth in SEQ ID NO: 2. In certain embodiments, the transgene is encoded by the sequence set forth in SEQ ID NO: 1. In certain embodiments, the REP-1 transgene is encoded by the sequence set forth in SEQ ID NO: 5. SEQ ID NO: 5 includes modified ends, which include restriction sites for cloning into a plasmid, such as a production plasmid described herein.

In certain embodiments, the transgene is a human CNGA3 sequence, encoding a functional CNGA3 protein. In certain embodiments, the transgene is a codon optimized CNGA3 encoding sequence SEQ ID NO: 10. In certain embodiments, the transgene is encoded by the sequence set forth in SEQ ID NO: 9. In one embodiment, the transgene includes modified ends, such as that shown in SEQ ID NO: 16, SEQ IDNO 17 or SEQ ID NO: 18, which include restriction sites for cloning into a plasmid, such as a plasmid described herein. In certain embodiments, the transgene is a codon optimized CNGA3 encoding sequence SEQ ID NO: 12. In certain embodiments, the transgene is encoded by the sequence set forth in SEQ ID NO: 11. In certain embodiments, the transgene is encoded by the native coding sequence of CNGA3, which is set forth in SEQ ID NO: 13.

In certain embodiments, the transgene is a human CNGB3 sequence, encoding a functional CNGB3 protein. In certain embodiments, the transgene is a codon optimized CNGB3 encoding sequence which is a sequence sharing at least 70% identity with SEQ ID NO: 19 or 21. In certain embodiments, the transgene is encoded by the sequence set forth in SEQ ID NO: 23. SEQ ID NO: 23 includes modified ends, which include restriction sites for cloning into a plasmid, such as a production plasmid described herein. Nucleotides 13 to 2448 of SEQ ID NO: 23 provide the ORF for CNGB3. In certain embodiments, the transgene is a codon optimized CNGB3 encoding sequence SEQ ID NO: 20. In certain embodiments, the transgene is encoded by the sequence set forth in SEQ ID NO: 19. In certain embodiments, the transgene is encoded by the sequence set forth in SEQ ID NO: 21. In certain embodiments, the transgene includes modified ends for cloning into a plasmid, such as the plasmids described herein. SEQ ID NO: 21 is a novel cDNA sequence in which certain silent mutations have been made to the native coding sequence. In certain embodiments, the CNGB3 sequence is the codon optimized sequence set forth in SEQ ID NO: 45. Further modifications to the native sequence, as described herein, are contemplated by the invention.

In one embodiment, the nucleic acid sequence encoding REP-1, CNGA3 or CNGB3 further comprises a nucleic acid encoding a tag polypeptide covalently linked thereto. The tag polypeptide may be selected from known "epitope tags" including, without limitation, a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes." Certain plasmids are described herein.

"Virus vectors" are defined as replication defective viruses containing the exogenous or heterologous CHM (REP-1) or CNGA3 or CNGB3 nucleic acid transgene(s). In one embodiment, an expression cassette as described herein may be engineered onto a plasmid which is used for drug delivery or for production of a viral vector. Suitable viral vectors are preferably replication defective and selected from amongst those which target ocular cells. Viral vectors may include any virus suitable for gene therapy, including but not limited to adenovirus; herpes virus; lentivirus; retrovirus; parvovirus, etc. However, for ease of understanding, the adeno-associated virus is referenced herein as an exemplary virus vector.

A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In still another embodiment, the expression cassette, including any of those described herein is employed to generate a recombinant AAV genome.

As used herein, the term "host cell" may refer to the packaging cell line in which a recombinant AAV is produced from a production plasmid. In the alternative, the term "host cell" may refer to any target cell in which expression of the transgene is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion.

In certain embodiments herein, the term "host cell" refers to cultures of ocular cells of various mammalian species for in vitro assessment of the compositions described herein. In other embodiments herein, the term "host cell" refers to the cells employed to generate and package the viral vector or recombinant virus. Still in other embodiments, the term "host cell" is intended to reference the ocular cells of the subject being treated in vivo for the ocular disease.

As used herein, the term "ocular cells" refers to any cell in, or associated with the function of, the eye. The term may refer to any one of photoreceptor cells, including rod photoreceptors, cone photoreceptors and photosensitive ganglion cells, retinal pigment epithelium (RPE) cells, Mueller cells, choroidal cells, bipolar cells, horizontal cells, and amacrine cells. In one embodiment, the ocular cells are the photoreceptor cells. In another embodiment, the ocular cells are RPE cells.

"Plasmids" generally are designated herein by a lower case p preceded and/or followed by capital letters and/or numbers, in accordance with standard naming conventions that are familiar to those of skill in the art. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the REP-1 or CNGA3 or CNGB3 and/or expression control sequences that act in trans or at a distance to control the transcription and expression thereof.

The term "AAV" or "AAV serotype" as used herein refers to the dozens of naturally occurring and available adeno-associated viruses, as well as artificial AAVs. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, AAV1, AAV2, AAV3, AAV4, AAV5, AAV6, AAV7, AAV8, AAV9, AAV8 bp, AAV7M8 and AAVAnc80, variants of any of the known or mentioned AAVs or AAVs yet to be discovered or variants or mixtures thereof. See, e.g., WO 2005/033321, which is incorporated herein by reference. In another embodiment, the AAV capsid is an AAV8 bp capsid, which preferentially targets bipolar cells. See, WO 2014/024282, which is incorporated herein by reference. In another embodiment, the AAV capsid is an AAV7m8 capsid, which has shown preferential delivery to the outer retina. See, Dalkara et al, In Vivo—Directed Evolution of a New Adeno-Associated Virus for Therapeutic Outer Retinal Gene Delivery from the Vitreous, Sci Transl Med 5, 189ra76 (2013), which is incorporated herein by reference. In one embodiment, the AAV capsid is an AAV8 capsid. In another embodiment, the AAV capsid an AAV9 capsid. In another embodiment, the AAV capsid an AAV5 capsid. In another embodiment, the AAV capsid an AAV2 capsid.

As used herein, relating to AAV, the term variant means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used.

The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, VA). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors.

"Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

By "administering" as used in the methods means delivering the composition to the target selected cell which is characterized by the ocular disease. In one embodiment, the method involves delivering the composition by subretinal injection to the RPE, photoreceptor cells or other ocular cells. In another embodiment, intravitreal injection to ocular cells is employed. In still another method, injection via the palpebral vein to ocular cells may be employed. Still other methods of administration may be selected by one of skill in the art given this disclosure. By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. Direct delivery to the eye (optionally via ocular delivery, subretinal injection, intra-retinal injection, intravitreal, topical), or delivery via systemic routes, e.g., intraarterial, intraocular, intravenous, intramuscular, subcutaneous, intradermal, and other parental routes of administration. The nucleic acid molecules and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

Certain compositions described herein are isolated, or synthetically or recombinantly engineered nucleic acid sequences that provide novel codon-optimized sequences encoding REP-1 or CNGA3 or CNGB3. In one embodiment, an isolated or engineered codon optimized nucleic acid sequence encoding human REP-1 is provided. In one embodiment, the codon-optimized sequence is SEQ ID NO: 1. In another embodiment, the codon optimized sequence includes N-terminal and C-terminal restriction sites for cloning. In one embodiment, such as that disclosed in SEQ ID NO: 5, the REP-1 coding sequence includes an N-terminal NotI restriction site and a C-terminal BamHI restriction site, in addition to a Kozak consensus sequence. In addition, the codon optimized sequence, in some embodiments, includes one or more additional restriction sites to allow for addition of markers, such as an epitope tag. When aligned with the native nucleic acid sequence, the codon optimized REP-1 may have a percent identity of at least 50%, or at least 60%, or at least 70%, or at least 80% or at least 90%, including any integer between any of those ranges. In one embodiment, the codon optimized REP-1 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In one embodiment, when aligned with the native nucleic acid sequence SEQ ID NO: 3, it is revealed that codon optimized REP-1 (SEQ ID NO: 1) has a percent sequence identity of only 74% (see FIG. 2).

In another embodiment, an isolated or engineered codon optimized nucleic acid sequence encoding human CNGA3 is provided. In one embodiment, the codon-optimized sequence is SEQ ID NO: 9. In one embodiment, the codon-optimized sequence is a CNGA3 variant shown in SEQ ID NO: 11. In another embodiment, the codon optimized sequence includes N-terminal and C-terminal restriction sites for cloning. In one embodiment, the CNGA3 coding sequence includes an N-terminal NotI restriction site and a C-terminal BglII restriction site, in addition to a Kozak consensus sequence. Examples of CNGA3 sequences which include such modifications can be found in SEQ ID NO: 16, SEQ ID NO: 17 and SEQ ID NO: 18. In addition, the codon optimized sequence, in some embodiments, includes one or more additional restriction sites to allow for addition of markers, such as an epitope tag. When aligned with the native nucleic acid sequence, the codon optimized CNGA3 may have a percent identity of at least 50%, or at least 60%, or at least 70%, or at least 80% or at least 90%, including any integer between any of those ranges. In one embodiment, the codon optimized CNGA3 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In one embodiment, when aligned with the native nucleic acid sequence SEQ ID NO: 13, it is revealed that codon optimized CNGA3 (SEQ ID NO: 9) has a percent sequence identity of only 80% (see FIG. 3).

In another embodiment, an isolated or engineered codon optimized nucleic acid sequence encoding human CNGB3 is provided. In one embodiment, the codon-optimized sequence is a sequence sharing at least 70% identity with SEQ ID NO: 19 or SEQ ID NO 21. In one embodiment, the codon optimized sequence is that set forth in SEQ ID NO: 45, which shares about 76% identity with the modified CNGB3 sequence of SEQ ID NO: 21. In another embodiment, the codon optimized sequence includes N-terminal and C-terminal restriction sites for cloning, for example, as shown in SEQ ID NO: 23. In addition, the codon optimized sequence, in some embodiments, includes one or more additional restriction sites to allow for addition of markers, such as an epitope tag. When aligned with the native nucleic acid sequence (as shown in SEQ ID NO: 19) or the modified sequence of SEQ ID NO: 21, the codon optimized CNGB3 may have a percent identity of at least 50%, or at least 60%, or at least 70%, or at least 80% or at least 90%, including any integer between any of those ranges. In one embodiment, the codon optimized CNGB3 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%.

In one embodiment, the optimized nucleic acid sequences encoding the REP-1 or CNGA3 or CNGB3 constructs described herein are engineered into any suitable genetic element, e.g., naked DNA, phage, transposon, cosmid, RNA molecule (e.g., mRNA), episome, etc., which transfers the REP-1 or CNGA3 or CNGB3 sequences carried thereon to a host cell, e.g., for generating nanoparticles carrying DNA or RNA, viral vectors in a packaging host cell and/or for delivery to a host cells in subject. In one embodiment, the genetic element is a plasmid.

The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

A variety of expression cassettes are provided which employ SEQ ID Nos. 1 or 5 for expression of the REP-1 protein. In one embodiment, an example of a plasmid containing such an expression cassette is shown in SEQ ID NO. 25. In one embodiment, an example of a plasmid containing such an expression cassette is shown in SEQ ID NO. 26. In one embodiment, an example of a plasmid containing such an expression cassette is shown in SEQ ID NO. 27. In one embodiment, an example of a plasmid containing such an expression cassette is shown in SEQ ID NO. 28. As used herein, the "vector genome" is the nucleic acid sequence which is packaged between the 5' and 3' ITRs, including the ITRs themselves. In some embodiments, the term "vector genome" is used interchangeably with "expression cassette". Thus, in one embodiment, the vector genome includes a 5' ITR, a CMV enhancer, a Chicken beta-actin promoter, CBA exon 1 and intron, a Kozak sequence, a codon optimized CHM, bGH poly A and a 3' ITR. In one embodiment, the vector genome comprises nt 1 to 4233 of SEQ ID NO: 25. In another embodiment, the vector genome comprises nt 1 to 4233 of SEQ ID NO: 26. In another embodiment, the vector genome comprises nt 1 to 4233 of SEQ ID NO: 27. In another embodiment, the vector genome comprises nt 1 to 4233 of SEQ ID NO: 28.

In another embodiment, a variety of expression cassettes are provided which employ SEQ ID Nos. 9, 11 or 13 for expression of the CNGA3 protein. In one embodiment, an example of a plasmid containing such an expression cassette is shown in SEQ ID NOs. 30-38. In one embodiment, the vector genome includes a 5' ITR, a RK1 promoter, a codon optimized CNGA3, bGH poly A and a 3' ITR. In another embodiment, the vector genome includes a 5' ITR, a RK1 promoter, a native CNGA3, bGH poly A and a 3' ITR. In another embodiment, the vector genome includes a 5' ITR, a RK1 promoter, a codon optimized CNGA3 variant 3, bGH poly A and a 3' ITR. Thus, in one embodiment, the vector genome includes a 5' ITR, a hCAR promoter, a codon optimized CNGA3, bGH poly A and a 3' ITR. In another embodiment, the vector genome includes a 5' ITR, a hCAR promoter, a native CNGA3, bGH poly A and a 3' ITR. In another embodiment, the vector genome includes a 5' ITR, a hCAR promoter, a codon optimized CNGA3 variant 3, bGH poly A and a 3' ITR. Thus, in one embodiment, the vector genome includes a 5' ITR, a CMV enhancer, a Chicken beta-actin promoter, CBA exon 1 and intron, a codon optimized CNGA3, bGH poly A and a 3' ITR. In another embodiment, the vector genome includes a 5' ITR, a CMV enhancer, a Chicken beta-actin promoter, CBA exon 1 and intron, a native CNGA3, bGH poly A and a 3' ITR. In another embodiment, the vector genome includes a 5' ITR, a CMV enhancer, a Chicken beta-actin promoter, CBA exon 1 and intron, a codon optimized CNGA3 variant 3, bGH poly A and a 3' ITR.

In one embodiment, the vector genome comprises nt 1 to 3189 of SEQ ID NO: 30. In another embodiment, the vector genome comprises nt 1 to 3189 of SEQ ID NO: 31. In another embodiment, the vector genome comprises nt 1 to 3354 of SEQ ID NO: 32. In another embodiment, the vector genome comprises nt 1 to 3583 of SEQ ID NO: 33. In another embodiment, the vector genome comprises nt 1 to 3580 of SEQ ID NO: 34. In another embodiment, the vector genome comprises nt 1 to 3748 of SEQ ID NO: 35. In another embodiment, the vector genome comprises nt 1 to 4357 of SEQ ID NO: 36. In another embodiment, the vector genome comprises nt 1 to 4357 of SEQ ID NO: 37. In another embodiment, the vector genome comprises nt 1 to 4522 of SEQ ID NO: 38.

In another embodiment, a variety of expression cassettes are provided which employ SEQ ID Nos. 19, 21, 23 or 45 for expression of the CNGB3 protein.

In one embodiment, an example of a plasmid containing such an expression cassette is shown in SEQ ID NOs. 39-44. In one embodiment, the vector genome includes a 5' ITR, a RK1 promoter, a codon optimized CNGB3, bGH poly A and a 3' ITR. In another embodiment, the vector genome includes a 5' ITR, a RK1 promoter, a native CNGB3, bGH poly A and a 3' ITR. In one embodiment, the vector genome includes a 5' ITR, a hCAR promoter, a codon optimized CNGB3, bGH poly A and a 3' ITR. In another embodiment, the vector genome includes a 5' ITR, a hCAR promoter, a native CNGB3, bGH poly A and a 3' ITR. In one embodiment, the vector genome includes a 5' ITR, a CMV enhancer, a Chicken beta-actin promoter, CBA exon 1 and intron, a codon optimized CNGB3, bGH poly A and a 3' ITR. In another embodiment, the vector genome includes a 5' ITR, a CMV enhancer, a Chicken beta-actin promoter, CBA exon 1 and intron, a native CNGB3, bGH poly A and a 3' ITR.

In one embodiment, the vector genome comprises nt 1 to 3537 of SEQ ID NO: 39. In another embodiment, the vector genome comprises nt 1 to 3536 of SEQ ID NO: 40. In another embodiment, the vector genome comprises nt 1 to 3930 of SEQ ID NO: 41. In another embodiment, the vector genome comprises nt 1 to 3930 of SEQ ID NO: 42. In another embodiment, the vector genome comprises nt 1 to 4704 of SEQ ID NO: 43. In another embodiment, the vector genome comprises nt 1 to 4704 of SEQ ID NO: 44. In another embodiment, the vector genome comprises nt 1 to 4154 of SEQ ID NO: 46.

As used herein, an "expression cassette" refers to a nucleic acid molecule which comprises coding sequences for the optimized REP-1 or CNGA3 or CNGB3 proteins, promoter, and may include other regulatory sequences therefor, which cassette may be engineered into a genetic element or plasmid, and/or packaged into the capsid of a viral vector (e.g., a viral particle).

In one embodiment, an expression cassette comprises a codon optimized nucleic acid sequence that encodes REP-1. In one embodiment, the cassette provides the codon optimized REP-1 operatively associated with expression control sequences that direct expression of the codon optimized nucleic acid sequence that encodes REP-1 in a host cell.

In another embodiment, an expression cassette comprises a codon optimized nucleic acid sequence that encodes CNGA3. In one embodiment, the cassette provides the codon optimized CNGA3 operatively associated with expression control sequences that direct expression of the codon optimized nucleic acid sequence that encodes CNGA3 in a host cell.

In another embodiment, an expression cassette comprises a codon optimized nucleic acid sequence that encodes CNGB3. In one embodiment, the cassette provides the codon optimized CNGB3 operatively associated with expression control sequences that direct expression of the codon optimized nucleic acid sequence that encodes CNGB3 in a host cell.

In another embodiment, an expression cassette for use in an AAV vector is provided. In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the codon optimized nucleic acid sequence that encodes REP-1 or CNGA3 or CNGB3, optionally with additional sequences which direct expression of the codon optimized nucleic acid sequence that encodes REP-1 or CNGA3 or CNGB3 in a host cell. Thus, as described herein, a AAV expression cassette is meant to describe an expression cassette as described above flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (AITR), are used for convenience and to accelerate regulatory approval. However, ITRs from other AAV sources may be selected. Each rAAV genome can be then introduced into a production plasmid. In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

One type of production plasmid is that shown in SEQ ID NO: 7, which is termed p584. This plasmid is used in the examples for generation of the rAAV-REP-1 vector. Such a plasmid is one that contains a 5' AAV ITR sequence; a selected promoter; a polyA sequence; and a 3' ITR; additionally, it also contains a stuffer sequence, such as lambda. In one embodiment, a non-coding lambda stuffer region is included in the vector backbone. The nucleic acid sequence encoding REP-1, CNGA3 or CNGB3 are inserted between the selected promoter and the polyA sequence, or a similar, plasmid. An example of p584 which includes the REP-1 encoding sequence can be found in SEQ ID NO: 8. In another embodiment, the production plasmid is modified to optimized vector plasmid production efficiency. Such modifications include addition of other neutral sequences, or deletion of portion(s) of or the entire lambda stuffer sequence to modulate the level of supercoil of the vector plasmid. Such modifications are contemplated herein. In other embodiments, terminator and other sequences are included in the plasmid.

In still a further embodiment, a recombinant adeno-associated virus (AAV) vector is provided for delivery of the REP-1, CNGA3 and CNGB3 constructs and optimized sequences described herein. An adeno-associated virus (AAV) viral vector is an AAV Dnase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). Each of these documents is incorporated by reference in its entirety. In some embodiments, the AAV capsids are generated using the nucleic acid sequences described in the listed documents. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used. In one embodiment, it is desirable to utilize an AAV capsid, which shows tropism for the desired target cell, e.g., photoreceptors, RPE or other ocular cells. In one embodiment, the AAV capsid is a tyrosine capsid-mutant in which certain surface exposed tyrosine residues are substituted with phenylalanine (F). Such AAV variants are described, e.g., in Mowat et al, Tyrosine capsid-mutant AAV vectors for gene delivery to the canine retina from a subretinal or intravitreal approach, Gene Therapy 21, 96-105 (January 2014), which is incorporated herein by reference.

For packaging an expression cassette or rAAV genome or production plasmid into virions, the ITRs are the only AAV components required in cis in the same construct as the transgene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or engineered obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

The rAAV vectors comprise an AAV capsid and an AAV expression cassette comprising sequences encoding REP-1 or CNGA3 or CNGB3, such as described above. In certain embodiments, the rAAV expression cassette comprises AAV inverted terminal repeat sequences and a codon optimized nucleic acid sequence that encodes REP-1 or CNGA3 or CNGB3, and expression control sequences that direct expression of the encoded proteins in a host cell. The rAAV expression cassette, in other embodiments, further comprises one or more of an intron, a Kozak sequence, a polyA, and post-transcriptional regulatory elements. Such rAAV vectors for use in pharmaceutical compositions for delivery to the eye, may employ a capsid from any of the many known AAVs identified above.

Other conventional components of the expression cassettes and vectors include other components that can be optimized for a specific species using techniques known in the art including, e.g, codon optimization, as described herein. The components of the cassettes, vectors, plasmids and viruses or other compositions described herein include a promoter sequence as part of the expression control sequences. In another embodiment, the promoter is cell-specific. The term "cell-specific" means that the particular promoter selected for the recombinant vector can direct expression of the optimized REP-1 or CNGA3 or CNGB3 transgene in a particular ocular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In one embodiment, the photoreceptor-specific promoter is a human rhodopsin kinase promoter. The rhodopsin kinase (RK1) promoter has been shown to be active in both rods and cones. See, e.g., Sun et al, Gene Therapy with a Promoter Targeting Both Rods and Cones Rescues Retinal Degeneration Caused by AIPL1 Mutations, Gene Ther. 2010 January; 17(1): 117-131, which is incorporated herein by reference in its entirety. In one embodiment, the promoter is modified to add one or more restriction sites to facilitate cloning. In one embodiment, the RK1 promoter is shown in nt 175-684 of SEQ ID NO: 30.

Human cone arrestin (hCAR) promoter has been identified and utilized in AAV transduction experiments and in gene replacement studies. See, e.g. Li A, Zhu X, Craft C M. Retinoic acid upregulates cone arrestin expression in retinoblastoma cells through a Cis element in the distal promoter region. Invest Ophthalmol Vis Sci. 2002; 43(5):1375-1383; and Carvalho, Livia. S., et al, "Long-term and age-dependent restoration of visual function in a mouse model of CNGB3-associated achromatopsia following gene therapy." *Human molecular genetics* 20.16 (2011): 3161-3175. In experiments performed in animals aimed at characterizing gene expression, human cone arrestin promoters drove strong expression in retina. See, Dyka, Frank M., et al. "Cone specific promoter for use in gene therapy of retinal degenerative diseases." *Retinal Degenerative Diseases*. Springer New York, 2014. 695-701. Dyka el al also report that the specificity of hCAR promoter was poor, with rods and RPE clearly being transduced. Sequences of hCAR promoter are accessible via publicly available literatures, database and commercially available products. In one embodiment, the nucleic acid sequence of hCAR promoter is reproduced in nt 175 to nt 1078 of SEQ ID NO: 33. In another embodiment, the nucleic acid sequence of hCAR promoter is reproduced in nt 181 to nt 1078 of SEQ ID NO: 33.

In another embodiment, the promoter is a human rhodopsin promoter. In one embodiment, the promoter is modified to include restriction on the ends for cloning. See, e.g, Nathans and Hogness, Isolation and nucleotide sequence of the gene encoding human rhodopsin, PNAS, 81:4851-5 (August 1984), which is incorporated herein by reference in its entirety. In another embodiment, the promoter is a portion or fragment of the human rhodopsin promoter. In another embodiment, the promoter is a variant of the human rhodopsin promoter.

Other exemplary promoters include the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference in its entirety). In another preferred embodiment, the promoter is the human interphotoreceptor retinoid-binding protein proximal (IRBP) promoter. In one embodiment, the promoter is a 235 nt fragment of the hIRBP promoter. In one embodiment, the promoter is the RPGR proximal promoter (Shu et al, IOVS, May 2102, which is incorporated by reference in its entirety). Other promoters useful in the invention include, without limitation, the rod opsin promoter, the red-green opsin promoter, the blue opsin promoter, the cGMP-β-phosphodiesterase promoter (Qgueta et al, IOVS, Invest Ophthalmol Vis Sci. 2000 December; 41(13):4059-63), the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PloS One, October 2010, 5(10): e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein in its entirety. In another embodiment, the promoter is selected from human human EF1α promoter, rhodopsin promoter, rhodopsin kinase, interphotoreceptor binding protein (IRBP), cone opsin promoters (red-green, blue), cone opsin upstream sequences containing the red-green cone locus control region, cone transducing, and transcription factor promoters (neural retina leucine zipper (Nrl) and photoreceptor-specific nuclear receptor Nr2e3, bZIP).

In another embodiment, the promoter is a ubiquitous or consistutive promoter. An example of a suitable promoter is a hybrid chicken β-actin (CBA) promoter with cytomegalovirus (CMV) enhancer elements. In one embodiment, the nucleic acid sequence of the CBA promoter, with CMV enhancer elements is shown in nt 1 to nt 544 of SEQ ID NO: 36. In one embodiment, the promoter includes CBA exon 1 and intron sequences such as that shown in nt 546 to nt. 823 of SEQ ID NO: 36.

In another embodiment, the promoter is the CB7 promoter. Other suitable promoters include the human β-actin promoter, the human elongation factor-1a promoter, the cytomegalovirus (CMV) promoter, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PloS ONE 9(8): e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. In one embodiment, the promoter is of a small size, under 1000 bp, due to the size limitations of the AAV vector. In another embodiment, the promoter is under 400 bp. Other promoters may be selected by one of skill in the art. In one embodiment, the REP-1 construct incorporates a ubiquitous promoter. In another embodiment, the CNGA3 construct incorporates a photoreceptor-specific promoter. In one embodiment, the REP-1 construct includes a CBA promoter with CMV enhancer elements.

In another embodiment, the promoter is an inducible promoter. The inducible promoter may be selected from known promoters including the rapamycin/rapalog promoter, the ecdysone promoter, the estrogen-responsive promoter, and the tetracycline-responsive promoter, or heterodimeric repressor switch. See, Sochor et al, An Autogenously Regulated Expression System for Gene Therapeutic Ocular Applications. Scientific Reports, 2015 Nov. 24; 5:17105 and Daber R, Lewis M., A novel molecular switch. J Mol Biol. 2009 Aug. 28; 391(4):661-70, Epub 2009 Jun. 21 which are both incorporated herein by reference in their entirety.

In other embodiments, the cassette, vector, plasmid and virus constructs described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. In another embodiment, a Woodchuck hepatitis virus post-transcriptional regulatory element (WPRE) is included. The expression cassette or vector may contain none, one or more of any of the elements described herein. Examples of suitable polyA sequences include, e.g., SV40, bovine growth hormone (bGH), and TK polyA. Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), amongst others. In one embodiment, a Kozak sequence is included upstream of the transgene coding sequence to enhance translation from the correct initiation codon. In another embodiment, CBA exon 1 and intron are included in the expression cassette. In one embodiment, the transgene is placed under the control of a hybrid chicken β actin (CBA) promoter. This promoter consists of the cytomegalovirus (CMV) immediate early enhancer, the proximal chicken β actin promoter, and CBA exon 1 flanked by intron 1 sequences. See, nt 1 to 823 of SEQ ID NO: 36.

An adeno-associated virus (AAV) vector comprising an AAV capsid and a nucleic acid sequence comprising AAV inverted terminal repeat sequences and the nucleic acid sequence of SEQ ID NO: 1 encoding human Rab Escort Protein-1 (REP-1), and expression control sequences comprising a CBA promoter with a CMV enhancer that direct expression of the REP-1 in a host cell.

In one embodiment, an adeno-associated virus (AAV) vector is provided which includes an AAV capsid having packaged therein a nucleic acid sequence comprising AAV inverted terminal repeat sequences and the nucleic acid sequence of SEQ ID NO: 9 or SEQ ID NO: 11, encoding human cyclic nucleotide gated channel alpha 3 (CNGA3), and expression control sequences that direct expression of the CNGA3 in a host cell. In one embodiment, the CNGA sequence comprises SEQ ID NO: 9 and a rhodopsin kinase 1 (RK1) promoter. In another embodiment, the RK1 promoter sequence is nt 175-684 of SEQ ID NO: 30. In another embodiment, the CNGA sequence comprises SEQ ID NO: 11 and a human cone arrestin (hCAR) promoter. In another embodiment, the hCAR promoter sequenced is that shown in nt 175 to nt 1078 of SEQ ID NO: 33 or nt 181 to nt 1078 of SEQ ID NO: 33.

In another embodiment, an adeno-associated virus (AAV) vector is provided which includes an AAV capsid having packaged therein a nucleic acid sequence comprising AAV inverted terminal repeat sequences and the nucleic acid sequence SEQ ID NO. 45 encoding human cyclic nucleotide gated channel beta 3 (CNGB3), and expression control sequences that direct expression of the CNGB3 in a host cell. In one embodiment, the expression control sequences comprise a CMV/CBA promoter, RK1 promoter or hCAR promoter. In another embodiment, the expression cassette contains a 5' ITR, CBA promoter, CMV enhancer, CBA exon 1 and intron, kozak sequence, human codon optimized CHM sequence (SEQ ID NO: 1), bGH poly A and 3' ITR.

In yet other aspects, these nucleic acid sequences, vectors, expression cassettes and rAAV viral vectors are useful in a pharmaceutical composition, which also comprises a pharmaceutically acceptable carrier, buffer, diluent and/or adjuvant, etc. Such pharmaceutical compositions are used to express the optimized REP-1 or CNGA3 or CNGB3 in the ocular cells through delivery by such recombinantly engineered AAVs or artificial AAVs.

To prepare these pharmaceutical compositions containing the nucleic acid sequences, vectors, expression cassettes and rAAV viral vectors, the sequences or vectors or viral vector is preferably assessed for contamination by conventional methods and then formulated into a pharmaceutical composition suitable for administration to the eye. Such formulation involves the use of a pharmaceutically and/or physiologically acceptable vehicle or carrier, particularly one suitable for administration to the eye, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In one exemplary specific embodiment, the composition of the carrier or excipient contains 180 mM NaCl, 10 mM NaPi, pH7.3 with 0.0001%-0.01% Pluronic F68 (PF68). The exact composition of the saline component of the buffer ranges from 160 mM to 180 mM NaCl. Optionally, a different pH buffer (potentially HEPES, sodium bicarbonate, TRIS) is used in place of the buffer specifically described. Still alternatively, a buffer containing 0.9% NaCl is useful.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The pharmaceutical compositions containing at least one replication-defective rAAV virus, as described herein, can be formulated with a physiologically acceptable carrier, diluent, excipient and/or adjuvant, for use in gene transfer and gene therapy applications. In the case of AAV viral vectors, quantification of the genome copies ("GC"), vector genomes ("VG"), or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with Dnase to eliminate un-encapsidated AAV genome DNA or contaminating plasmid DNA from the production process. The Dnase resistant particles are then subjected to heat treatment to release the genome from the capsid. The released genomes are then quantitated by real-time PCR using primer/probe sets targeting specific region of the viral genome (usually poly A signal). In another method the effective dose of a recombinant adeno-associated virus carrying a nucleic acid sequence encoding the optimized REP-1 or CNGA3 or CNGB3 transgene is measured as described in S. K. McLaughlin et al, 1988 J. Virol., 62:1963, which is incorporated by reference in its entirety.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the codon optimized nucleic acid sequences encoding REP-1 or CNGA3 or CNGB3 as described herein that is in the range of about $1.0 \times 10^6$ GC to about $1.0 \times 10^{15}$ GC including all integers or fractional amounts within the range. In one embodiment, the compositions are formulated to contain at least $1 \times 10^7$, $2 \times 10^7$, $3 \times 10^7$, $4 \times 10^7$, $5 \times 10^7$, $6 \times 10^7$, $7 \times 10^7$, $8 \times 10^7$, or $9 \times 10^7$ GC per dose including all integers or fractional amounts within the range. In one embodiment, the compositions are formulated to contain at least $1 \times 10^8$, $2 \times 10^8$, $3 \times 10^8$, $4 \times 10^8$, $5 \times 10^8$, $6 \times 10^8$, $7 \times 10^8$, $8 \times 10^8$, or $9 \times 10^9$ GC per dose including all integers or fractional amounts within the range. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10\beta$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range. All dosages may be measured by any known method, including as measured by oqPCR or digital droplet PCR (ddPCR) as described in, e.g., M. Lock et al, Hum Gene Ther Methods. 2014 April; 25(2):115-25. Doi: 10.1089/hgtb.2013.131, which is incorporated herein by reference.

These above doses may be administered in a variety of volumes of carrier, excipient or buffer formulation, ranging from about 25 to about 1000 microliters, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

In one embodiment, the viral constructs may be delivered in doses of from at least $1\times10^7$ to about least $1\times10^{11}$ GCs in volumes of about 1 µL to about 3 µL for small animal subjects, such as mice. For larger veterinary subjects having eyes about the same size as human eyes, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the particular ocular disorder and the degree to which the disorder, if progressive, has developed.

Yet another aspect described herein is a method for treating, retarding or halting progression of blindness in a mammalian subject having, or at risk of developing, choroideremia. In one embodiment, a rAAV carrying the REP-1 codon optimized sequences, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of ocular diseases, and may also involve administration via the palpebral vein or other intravenous or conventional administration routes.

Yet another aspect described herein is a method for treating, retarding or halting progression of blindness in a mammalian subject having, or at risk of developing, achromatopsia. In one embodiment, an rAAV carrying the CNGA3 or CNGB3 native, modified or codon optimized sequence, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of ocular diseases, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. The dosages, administrations and regimens may be determined by the attending physician given the teachings of this specification. In one embodiment, the composition is administered in a single dosage selected from those above listed in a single affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages). In another embodiment, multiple injections are made in different portions of the same eye. In another embodiment, a second administration of an rAAV including the selected expression cassette (e.g., CHM containing cassette) is performed at a later time point. Such time point may be weeks, months or years following the first administration. Such second administration is, in one embodiment, performed with an rAAV having a different capsid than the rAAV from the first administration. In another embodiment, the rAAV from the first and second administration have the same capsid.

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention it is desirable to perform non-invasive retinal imaging and functional studies to identify areas of the rod and cone photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described herein, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged ocular cells is impacted. In another embodiment, the volume and/or concentration of the rAAV composition is a greater amount, in order reach larger portions of the eye, including non-damaged photoreceptors.

In one embodiment of the methods described herein, a one-time intra-ocular delivery of a composition as described herein, e.g., an AAV delivery of an optimized REP-1 cassette, is useful in preventing vision loss and blindness in a subject at risk of developing choroideremia. In another embodiment of the methods described herein, a one-time intra-ocular delivery of a composition as described herein, e.g., an AAV delivery of an optimized CNGA3 or CNGB3 cassette, is useful in preventing vision loss and blindness in a subject at risk of developing achromatopsia.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the rod and/or cones or photoreceptors are functioning or remaining, as compared to a non-diseased eye.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference, optical coherence tomography (to measure thickness of various layers of the retina), histology (retinal thickness, rows of nuclei in the outer nuclear layer, immunofluorescence to document transgene expression, cone photoreceptor counting, staining of retinal sections with peanut agglutinin—which identifies cone photoreceptor sheaths).

Specifically for human subjects, following administration of a dosage of a composition described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics laser scanning ophthalmoscopy, mobility testing, test of reading speed and accuracy, microperimetry and/or ophthalmoscopy. These and other efficacy tests are described in U.S. Pat. No. 8,147,823; in co-pending International patent application publication WO 2014/011210 or WO 2014/124282, incorporated by reference.

In yet another embodiment, any of the above described methods is performed in combination with another, or secondary, therapy. In still other embodiments, the methods of treatment of these ocular diseases involve treating the subject with the composition described in detail herein in combination with another therapy, such as antibiotic treatment, palliative treatment for pain, and the like. The additional therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In one embodiment, a method of generating a recombinant rAAV comprises obtaining a plasmid containing an AAV expression cassette as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver the codon optimized REP-1 or CNGA3 or CNGB3 in the expression cassettes and genomes described above and in the examples below.

In yet another embodiment, a vector comprising any of the expression cassettes described herein is provided. As described above, such vectors can be plasmids of variety of origins and are useful in certain embodiments for the generation of recombinant replication defective viruses as described further herein.

In one another embodiment, the vector is a plasmid that comprises an expression cassette, wherein the expression cassette comprises AAV inverted terminal repeat sequences and a codon optimized nucleic acid sequence that encodes REP-1, and expression control sequences that direct expression of the encoded protein in a host cell.

In another embodiment, the vector is a plasmid that comprises an expression cassette, wherein the expression cassette comprises AAV inverted terminal repeat sequences and a codon optimized nucleic acid sequence that encodes CNGA3, and expression control sequences that direct expression of the encoded protein in a host cell.

In another embodiment, the vector is a plasmid that comprises an AAV expression cassette, wherein the expression cassette comprises AAV inverted terminal repeat sequences and a codon optimized nucleic acid sequence that encodes CNGB3, and expression control sequences that direct expression of the encoded protein in a host cell.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Example 1: Differentiation of Pluripotent Stem Cells into RPE

Choroideremia lacks a relevant mouse model and there is no canine model, therefore, transduction and expression is tested in a human retinal cell model of the disease. Because it is impossible to obtain retinal cells from a living patient, RPE are generated from induced pluripotent stem cells. Pluripotent stem cells are directed to RPE using the protocol described by Buchholz et al, Rapid and Efficient Directed Differentiation of Human Pluripotent Stem Cells Into Retinal Pigmented Epithelium, Stem Cells Translational Medicine, 2013; 2:384-393 which is incorporated by reference in its entirety. See also, Cereso et al, Proof of concept for AAV2/5-mediated gene therapy in iPSC-derived retinal pigment epithelium of a choroideremia patient, Molecular Therapy—Methods & Clinical Development (2014) 1, 14011, which is incorporated by reference in its entirety. Other methods for producing RPE are known in the art.

Briefly, the human induced pluripotent stem cell line is maintained in Dulbecco's Modified Eagle's Medium: Nutrient Mixture F-12 (DMEM/F12) containing 2mMGlutaMAX-I, 20% knockout serum replacement, 0.1 mM Modified Eagle's Medium Non-Essential Amino Acids (MEM NEAA), 0.1 mM β-mercaptoethanol and 4 ng/ml bFGF on a mitomycin C-treated or irradiated mouse embryonic fibroblast feeder layer.

Pluripotent stem cells are passaged directly onto Matrigel (BD Biosciences) in DMEM/F12 with 1×B27, 1×N2, and 1×NEAA (Invitrogen). From days 0 to 2, 50 ng/ml Noggin, 10 ng/ml Dkk1, 10 ng/ml IGF1 and 10 mM nicotinamide are added to the base medium. From days 2 to 4, 10 ng/ml Noggin, 10 ng/ml Dkk1, 10 ng/ml IGF1, 5 ng/ml bFGF and 10 mM nicotinamide are added to the base medium. From days 4 to 6, 10 ng/ml Dkk1, 10 ng/ml IGF1 and 100 ng/ml Activin A (R&D Systems) are added to the base medium. From days 6 to 14, 100 ng/ml Activin A, 10 μM SU5402 (EMD Millipore, Darmstadt, Germany), and 1 mM VIP are added to the base medium. Control experiments are performed in base media alone (DMEM/F12, B27, N2, and NEAA).

The cells are mechanically enriched by scraping away cells with non-RPE morphology. Subsequently, the remaining RPE are digested using TrypLE Express (Invitrogen) for 5 minutes at 37° C. The cells are passed through a 30-μm single-cell strainer and seeded onto Matrigel-coated tissue culture plastic, Transwell membranes or CC2-treated chambered slides. Enriched cells are cultured in DMEM-high glucose with 1% fetal bovine serum (FBS), GlutaMAX, and sodium pyruvate for 30 days.

Example 2: Cells Transduced with AAV-REP-1

Briefly, AAV2/8CMV.CBA-REP-1 viral vector incorporating REP-1 codon optimized sequences are produced by transient transfection of HEK293 cells, and the viral particles are precipitated from either the supernatant using polyethylene glycol. See, e.g., Guo et al, Rapid and simplified purification of recombinant adeno-associated virus, J Virol Methods. 2012 August; 183(2): 139-146, which is incorporated herein by reference. The vectors are purified by double CsCl centrifugation, dialyzed, and titered by dot blot assay.

For the prenylation experiments, RPE are seeded in 24-well plates, and $1.2 \times 10^6$ cells are estimated at confluence. Cells are transduced with 100,000 vg per cell, and prenylation assays are performed at 4 weeks post transduction. Experiments are performed in triplicate.

Example 3: Prenylation

An in vitro prenylation assay is performed as described in Vasireddy et al, PloS One. 2013 May 7; 8(5):e61396, cited above, using [3F1]-geranylgeranyl pyrophosphate (GGPP) (Perkin Elmer, Boston, MA, USA) as a prenyl group donor, in the presence of recombinant Rab geranylgeranyl transferase and RAB27. Incorporation of radiolabeled prenyl groups into the RAB27 protein is measured by scintillation counting. For consistency the control values are normalized to 100 and used as the base value. All experiments are performed in triplicate, and statistical comparison of prenylation between experimental and control groups is evaluated using the two-tailed unpaired student's t-test.

Briefly, 48 hr post transduction, transduced REP cells are washed with cold PBS. Cell pellets are collected and washed thoroughly with cold PBS. Cells are lysed on ice for 30 min using RIPA+Protease inhibitors. In an alternative protocol, cells are sonicated. Cytosolic fractions are collected by centrifuging the lysate at 75,000-100 000 g for 1-2 h at 4° C.

Stocks are prepared for the prenylation reaction as follows.

|  | STOCKS prepared | FINAL CONCENTRATION REQUIRED |
|---|---|---|
| Rab GGTase | 16.63 uM - (GGTAse-a) 14.59 uM- (GGTASE-b) | 0.05 uM |
| Rab 27a | 25.93 uM | 4 uM |
| 3H GGPP | 22.2 | 5 uM |
| NP40 |  | 1 mM |
| DTT | 10 mM | 1 mM |
| HEPES | 1M | 50 mM |
| Mgcl2 | 100 mM | 5 mM |

Final reaction volume used for prenylation is 25 μL

| Rab GGTase a | 0.075 ul |
|---|---|
| Rab Ggtaseb | 0.085 ul |
| [³H]-geranylgeranyl pyrophosphate (GGPP) | 5.68 ul |
| NP40 | 0.15 ul |
| DTT | 2.5 ul |
| HEPES | 1.25 ul |
| MgCl2 | 1.25 ul |

| | |
|---|---|
| Rab 27a | 3.12 ul |
| Cytosolic Fraction (Cell lysate) | 10.89 ul |

The reaction mixture is incubated at 37° C. for 30 min. The reaction is stopped by adding 9:1 ethanol/HCL, and incubated for 30 minutes. The proteins are collected on glass fiber filter papers (Whatman papers) by vacuum filtration (0.1 ml). The filters are washed carefully with cold phosphate buffer −3 times to remove unbound material. The membranes are dried carefully. The filters are placed in 5 ml scintillation cocktail and scinitillation counting is performed. See also, Tolmachova et al, CHM/REP1 cDNA delivery by lentiviral vectors provides functional expression of the transgene in the retinal pigment epithelium of choroideremia mice, The Journal of Gene Medicine, 2012; 14-158-68, which is incorporated herein by reference in its entirety.

Assays for CNGA3 or CNGB3 proof-of-concept may include use of a spontaneous mutant animal model (for example, the Cnga3−/− mouse or the Awassi sheep). The mouse model could be bred with an "all-cone" photoreceptor mouse, the Nrl−/− mouse, to obtain double knockouts. The latter (Cnga3−/−Nrl−/−) mouse may expedite identification of efficacy. Efficacy could be measured by pupillometry, measures of visual acuity and contrast (for example, using optokinetics), electroretinograms, and visual behavior. Ultimately, histology will document expression of the transgene with improved outcomes on the other measures. Hsitologic approaches will also be used to document any effects of the intervention on cone photoreceptors (total number of cone photoreceptors, density, location, etc).

Similar to choroideremia as discussed above, assays for proof-of-concept for gene augmentation therapy for CNGA3- or CNGB3-associated achromatopsia may include use of induced pluripotent stem cell (iPSC) models. The iPSC models, generated from patients with achromatopsia due to CNGA3 or CNGB3 mutations, will be differentiated into retinal precursors and/or photoreceptor cells in vitro. The wildtype CNGA3 (or CNGB3) cDNA will be delivered to these cells using recombinant AAV and the cells will be analyzed for biogenesis and preservation of function of the relevant (Cyclic nucleotide-gated, CNG) channel comprised by these subunits. Channel function will be assessed by electrophysiology on membrane patches. Restoration of the channel should rescue cGMP-activated currents. Additional studies can test for sensitivity of channel function before and after delivery of the wildtype CNG cDNA to physiological ligands.

Example 4: In Vitro Expression of AAV.Codon-Optimized Human CHM

The objective of this study was to evaluate the ability of AAV mediated CHM expression after gene delivery using a series of next generation AAV 2 and AAV8 vectors encoding the codon optimized CHM gene (SEQ ID NO: 1) in 84-31 and COS-7 cell lines.

To maximize the expression of CHM, a codon optimized CHM sequence was produced (SEQ ID NO: 1). The codon optimized plasmid was synthesized and used in the creation of all the next generation CHM transgene expression cassettes. To overcome the potential problem of contamination of non-functional AAV genomes, a non-coding lambda stuffer region was included in the vector backbone. Incorporation of stuffer not only increases the length of the plasmid, but also diminishes the possibility of plasmid DNA backbone contamination while packaging the AAV. The impact of incorporating a stuffer region in the vector backbone to eliminate the plasmid DNA impurities was carried out as an independent study. Two recombinant AAV proviral plasmids (high and low copy) backbones were used to generate the different constructs. The high copy plasmid was designed based on the pUC vector origin. The low copy plasmid was designed based on the p15A origin. To further enhance the translation from the correct initiation codon, a Kozak sequence upstream of the start codon was incorporated.

A total of four plasmids have been engineered for the current study and those described in the following examples (Table 1). In addition, a plasmid carrying the CHM native sequence, which is currently being used in a clinical trial, was also generated (version 1). Plasmid maps for each of Version 2a, 2b, 3a and 3b, and Version 1 are shown in FIGS. 6-10, respectively.

TABLE 1

Plasmid features

| Name | REP Sequence | Lambda insert | Kozak Sequence | Origin | Copy number | Promoter/Intron |
|---|---|---|---|---|---|---|
| Version 1 (V1) | Native | Present | Absent | pUC | High copy | CMV-CBA promoter + Enhancer extension |
| Version 2a (V2a) | Codon-optimized | Present | present | pUC | High copy | CMV-CBA promoter + Enhancer extension |
| Version 2b (V2b) | Codon-optimized | Not Present | present | pUC | High copy | CMV-CBA promoter + Enhancer extension |
| Version 3a (V3a) | Codon-optimized | Present | present | P15A | Low copy | CMV-CBA promoter + Enhancer extension |
| Version 3b (V3b) | Codon-optimized | Not Present | present | P15A | Low copy | CMV-CBA promoter + Enhancer extension |

The in vitro expression of these constructs was tested in COS-7 and 84-31 cell lines. The engineered features of the next-generation CHM constructs are depicted in Table. 1.

Recombinant AAV proviral high and low copy plasmids were generated by cloning the codon optimized human CHM cDNA (hCHM) (SEQ ID NO: 1) into the transgene cassette. The transgene was placed under the control of a hybrid chicken β actin (CBA) promoter. This promoter consists of the cytomegalovirus (CMV) immediate early enhancer, the proximal chicken β actin promoter, and CBA exon 1 flanked by intron 1 sequences. The proviral high and low copy number plasmids also contain AAV inverted terminal repeats and a PolyA sequence. The next generation plasmid backbones used in the current study contain a lambda phage fragment stuffer followed by the kanamycin bacterial selection gene. Additional plasmids lack the stuffer but contain the kanamycin selection gene. The high-copy number vector is similar to that of pUC plasmids (~300 copies/bacterial cell). The low copy number plasmid (~10 copies/bacterial cell) has an origin of p15A. To enhance translation from the correct initiation codon, all next generation constructs contain a KOZAK consensus sequence upstream of the start codon, ATG. The generated plasmids are sequence verified using primers that can specifically target either the promoter+enhancer extension sequence or the codon optimized CHM sequence. The plasmid maps and sequences of all five constructs are shown in FIGS. 6-10. Standard triple transfection with calcium phosphate was used to generate AAV vectors listed below (see Table 2 for vector qualification). Both AAV2 and AAV8 serotypes of the vectors were generated to ensure the results are serotype-independent.

TABLE 2

Summary of AAV2 and AAV8 vectors generated and concentration of viral stocks.

| Name | Serotype | Plasmid name | Lot number | Stock Conc. (vg/ml) |
|---|---|---|---|---|
| AAV2.V1 | AAV 2 | Version 1 (V1) | KA 892* | 4.47E+12 |
| AAV2.V2a | AAV 2 | Version 2a (V2a) | CT 239 | 2.16E+12 |
| AAV2.V2b | AAV 2 | Version 2b (V2b) | CT 238 | 7.40E+12 |
| AAV2.V3a | AAV 2 | Version 3a (V3a) | CT 258 | 4.82E+12 |
| AAV2.V3b | AAV 2 | Version 3b (V3b) | CT 256 | 5.91E+12 |
| AAV8.V1 | AAV 8 | Version 1 (V1) | KA 808* | 1.39E+13 |
| AAV8.V2a | AAV 8 | Version 2a (V2a) | CT 245 | 1.40E+13 |
| AAV8.V2b | AAV 8 | Version 2b (V2b) | CT 244 | 1.11E+13 |
| AAV8.V3a | AAV 8 | Version 3a (V3a) | CT 259 | 8.67E+12 |
| AAV8.V3b | AAV 8 | Version 3b (V3b) | CT 255 | 1.36E+13 |

The 84-31 cell line is a subclone of 293 HEK cell line (human embryonic kidney cells) and constitutively expresses adenovirus E4 proteins to enhance transduction of AAV virus. COS-7 cells are fibroblast like cell lines that are derived from monkey kidney tissues. Both 84-31 cells and COS-7 cells were plated, separately, in 6-well cell culture plates and transduced with one of the ten test articles (either AAV2 or AAV8) at five different multiplicity of infection (MOIs). After 36-48 hours, cells were harvested, lysed and protein samples were prepared for SDS-PAGE followed by Western blot analysis to detect the expression of exogenous CHM.

Both 84-31 and COS-7 cells were cultured in Dulbecco's modified Eagle medium (DMEM)-high glucose with 10% fetal bovine serum, and 1% penicillin/streptomycin at 37° C. in an environment supplied with 5% $CO_2$. The day before transduction (18-24 h before) cells at a density of 3E5 were seeded in 2 ml of cell culture media in each well of a 6-well cell culture dish. Seeded cells were incubated at 37° C. in an environment supplied with 5% $CO_2$. Wells of both COS-7 and 84-31 cells were infected with AAV vectors listed below at various multiplicities of infection (MOI) (Table 3 and Table 4). No virus was added to negative control cells (untransduced cells). Briefly, the tissue culture media was removed and a fresh 2 ml aliquot of media was added to each well of the 6 well culture dish. Then the predetermined amount of AAV vector was measured (directly from the stock) and added to each well (Table 3 and Table 4). For an MOI of 1E4, 1 µL of respective virus stock was diluted to 10 µL with cell culture media. From this solution, the predetermined volume of the virus was added to respective well (Table 3 and 4). Cells were incubated with the AAV virus for 36-48 hours at 37° C. with 5% $CO_2$ till harvesting. Cells were observed under microscope before harvesting to check for abnormalities.

TABLE 3

Infection does of four next generation AAV2 and AAV8 hCHM vectors in COS-7 cells.

| Vector Used | Cell Line | Cell Density | Vector Used (µL) | MOI |
|---|---|---|---|---|
| No AAV | COS-7 | 3E5 | — | — |
| AAV2.V2a | COS-7 | 3E5 | 1.5 | 1E4 |
| | COS-7 | 3E5 | 15 | 1E5 |
| | COS-7 | 3E5 | 45 | 3E5 |
| | COS-7 | 3E5 | 75 | 5E5 |
| | COS-7 | 3E5 | 150 | 1E6 |
| AAV2.V2b | COS-7 | 3E5 | 4.2 (from a 1 to 10 dilution of the stock) | 1E4 |
| | COS-7 | 3E5 | 4.2 | 1E5 |
| | COS-7 | 3E5 | 12.6 | 3E5 |
| | COS-7 | 3E5 | 21 | 5E5 |
| | COS-7 | 3E5 | 42 | 1E6 |
| AAV8.V2a | COS-7 | 3E5 | 2.9 (from a 1 to 10 dilution of the stock) | 1E4 |
| | COS-7 | 3E5 | 2.88 | 1E5 |
| | COS-7 | 3E5 | 8.65 | 3E5 |
| | COS-7 | 3E5 | 14.42 | 5E5 |
| | COS-7 | 3E5 | 28.85 | 1E6 |
| AAV8.V2b | COS-7 | 3E5 | 2.7 (from a 1 to 10 dilution of the stock) | 1E4 |
| | COS-7 | 3E5 | 2.7 | 1E5 |
| | COS-7 | 3E5 | 8.1 | 3E5 |
| | COS-7 | 3E5 | 13.5 | 5E5 |
| | COS-7 | 3E5 | 27 | 1E6 |

TABLE 4

Infection rates of four next generation AAV2 and AAV8 hCHM vectors in 84-31 cells

| Vector Used | Cell Line | Cell Density | Vector Used (µL) | MOI |
|---|---|---|---|---|
| No AAV | 84-31 | 3E5 | — | — |
| AAV2.V2a | 84-31 | 3E5 | 1.5 | 1E4 |
| | 84-31 | 3E5 | 15 | 1E5 |
| | 84-31 | 3E5 | 45 | 3E5 |
| | 84-31 | 3E5 | 75 | 5E5 |
| | 84-31 | 3E5 | 150 | 1E6 |
| AAV2.V2b | 84-31 | 3E5 | 4.2 (from a 1 to 10 dilution of the stock) | 1E4 |
| | 84-31 | 3E5 | 4.2 | 1E5 |
| | 84-31 | 3E5 | 12.6 | 3E5 |
| | 84-31 | 3E5 | 21 | 5E5 |
| | 84-31 | 3E5 | 42 | 1E6 |
| AAV8.V2a | 84-31 | 3E5 | 2.9 (from a 1 to 10 dilution of the stock) | 1E4 |
| | 84-31 | 3E5 | 2.88 | 1E5 |
| | 84-31 | 3E5 | 8.65 | 3E5 |
| | 84-31 | 3E5 | 14.42 | 5E5 |
| | 84-31 | 3E5 | 28.85 | 1E6 |
| AAV8.V2b | 84-31 | 3E5 | 2.7 (from a 1 to 10 dilution of the stock) | 1E4 |
| | 84-31 | 3E5 | 2.7 | 1E5 |
| | 84-31 | 3E5 | 8.1 | 3E5 |
| | 84-31 | 3E5 | 13.5 | 5E5 |
| | 84-31 | 3E5 | 27 | 1E6 |

First, both, the COST and 84-31 cell lines were used to test if the in vitro expression of CHM is cell line independent. Once the independence was established, all subsequent experiments were carried out only in 84-31 cells, which have shown superior transduction efficiency with AAV. Wells of 84-31 cells were infected with the AAV vectors listed below at various MOI (see table 3 and 4).

Western blot analysis: 1. Cell lysates were prepared. The AAV transduced cells along with the untreated control cells, were harvested 36-48 h post-infection after a thorough PBS wash. Cells were then lysed on ice using RIPA buffer with protease inhibitors. Cell lysates were cleared by centrifuging at 13,000 rpm for 10 min. 2. Quantification and preparation of proteins. Protein quantification of the cell lysates was carried out using ThermoFisher Micro BCA™ Protein Assay Kit following manufacturer's instructions. Protein concentration was determined by taking OD reading at 562 nm. To evaluate the in vitro expression of CHM, between 40-60 ug of measured protein was loaded on 4-12% Bis-Tris gels. 3. SDS-PAGE and blotting SDS-PAGE and western blot analysis were carried out according to known protocols. Briefly, the protein gels were transferred on to a nitrocellulose membrane, blocked in milk and incubated with the primary antibodies. Antihuman REP-1 2F1 antibody (2F1, 1:1000 dilution) and one of the following: anti-GAPDH antibody (1:1000 dilution), anti actin antibody (1:1000 dilution) or anti-Tubulin antibody (1:5000 dilution) was used as primary antibodies for each blot. After washing the blot, HRP conjugated anti-mouse IgG antibody and/or anti-rabbit IgG antibody at a concentration of 1:5000 were used as secondary antibodies. The blots were developed by chemiluminescence using ECL reagents according to the manufacturer's instructions. Controls: 1. Loading controls: One of the following: anti-Actin antibody, anti-tubulin antibody or anti-GAPDH antibody was used as a loading control to demonstrate equal loading of protein in each well of the gels. Anti-Tubulin antibody detects a protein of ~51 kDa. Anti-Actin antibody detects a protein of ~42 kDa, and anti-GAPDH antibody detects a protein of ~39 kDa. Initial blots were probed with either anti-tubulin antibody or anti-Actin antibody or anti-GAPDH antibody depending up on their availability. After initial experiments, to be consistent, anti-GAPDH antibody was used as the loading control. 2. Positive control: After the production of hREP-1 protein was established in AAV2.V2a transduced COS-7 cells, the AAV2.V2a-Cos-7 cell lysates were used as positive control in later western blot experiments. 3. Negative control: Untreated cells were used as negative control. Analyses of western blot results of REP-1 protein production in various cell lines are summarized in Table. 5.

TABLE 5

Figure 1B:
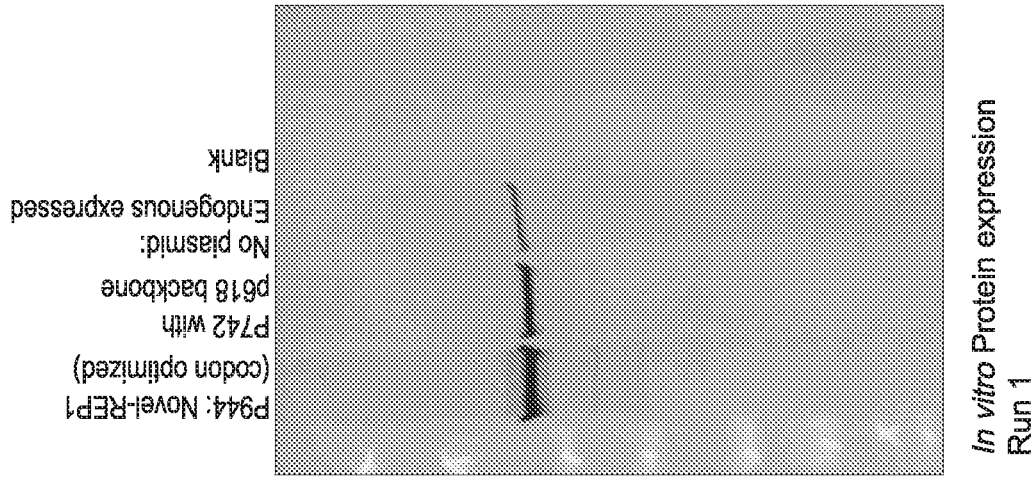
Figure 4B:
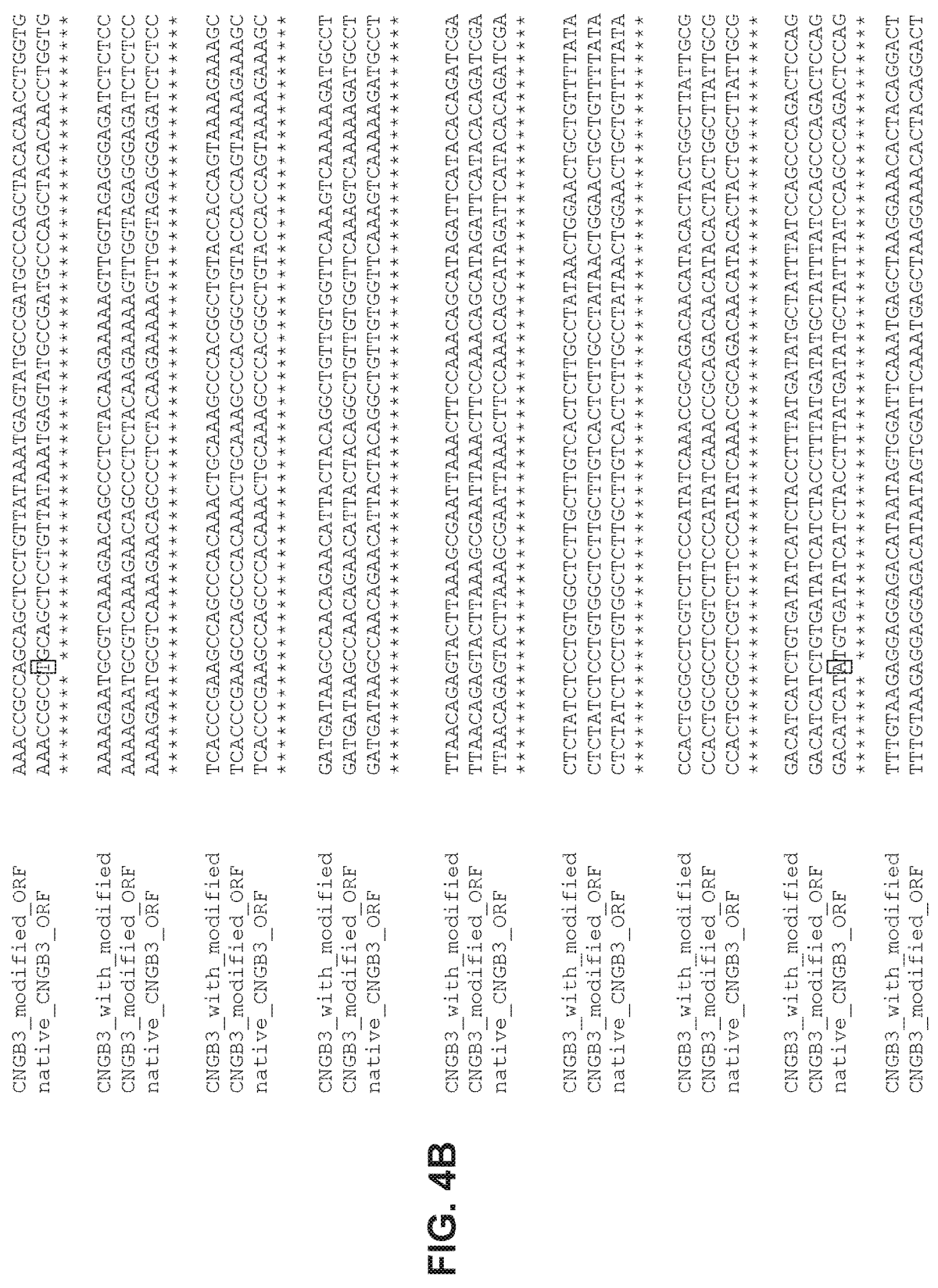
Figure 4E:
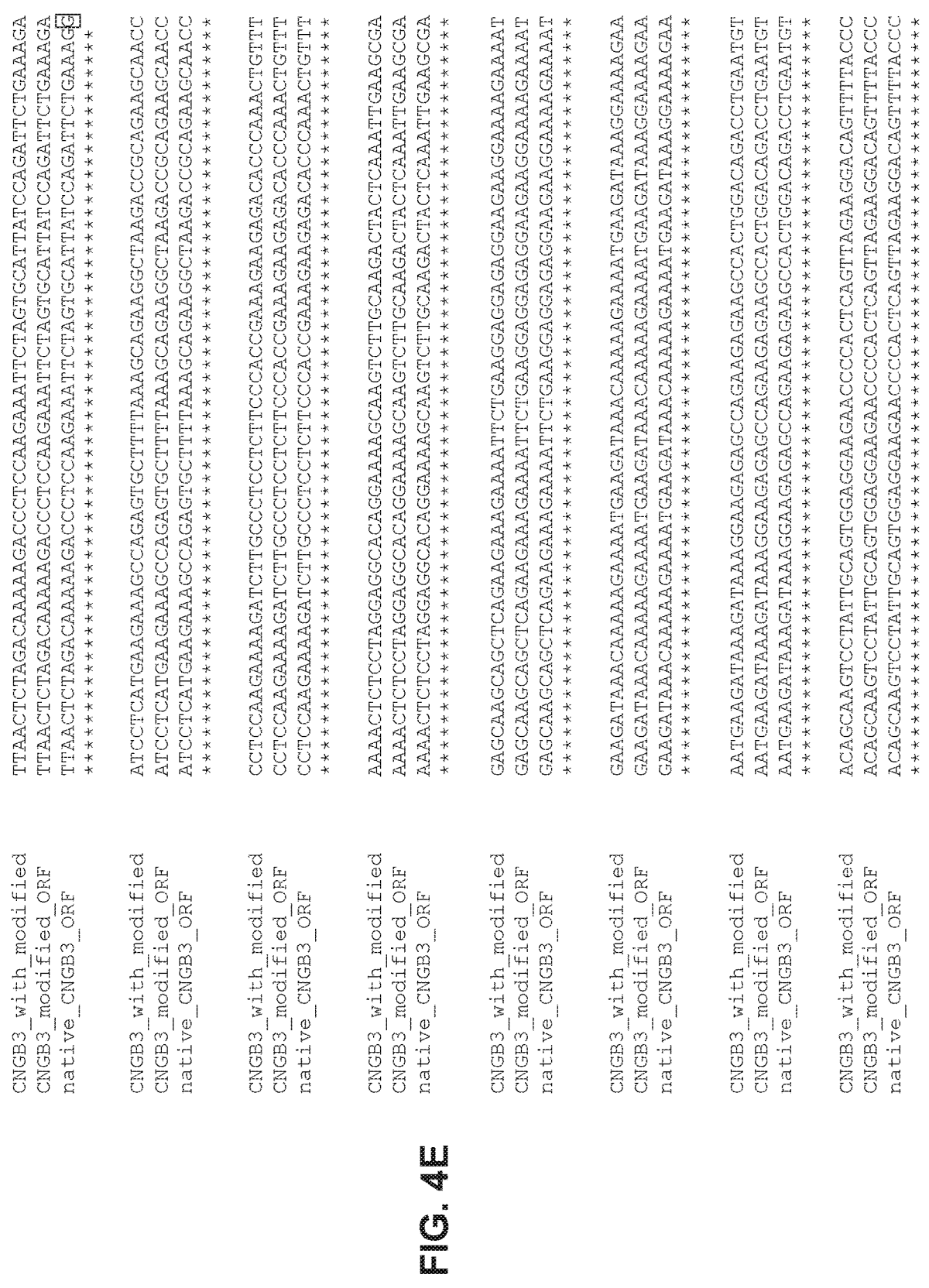
Figure 5:
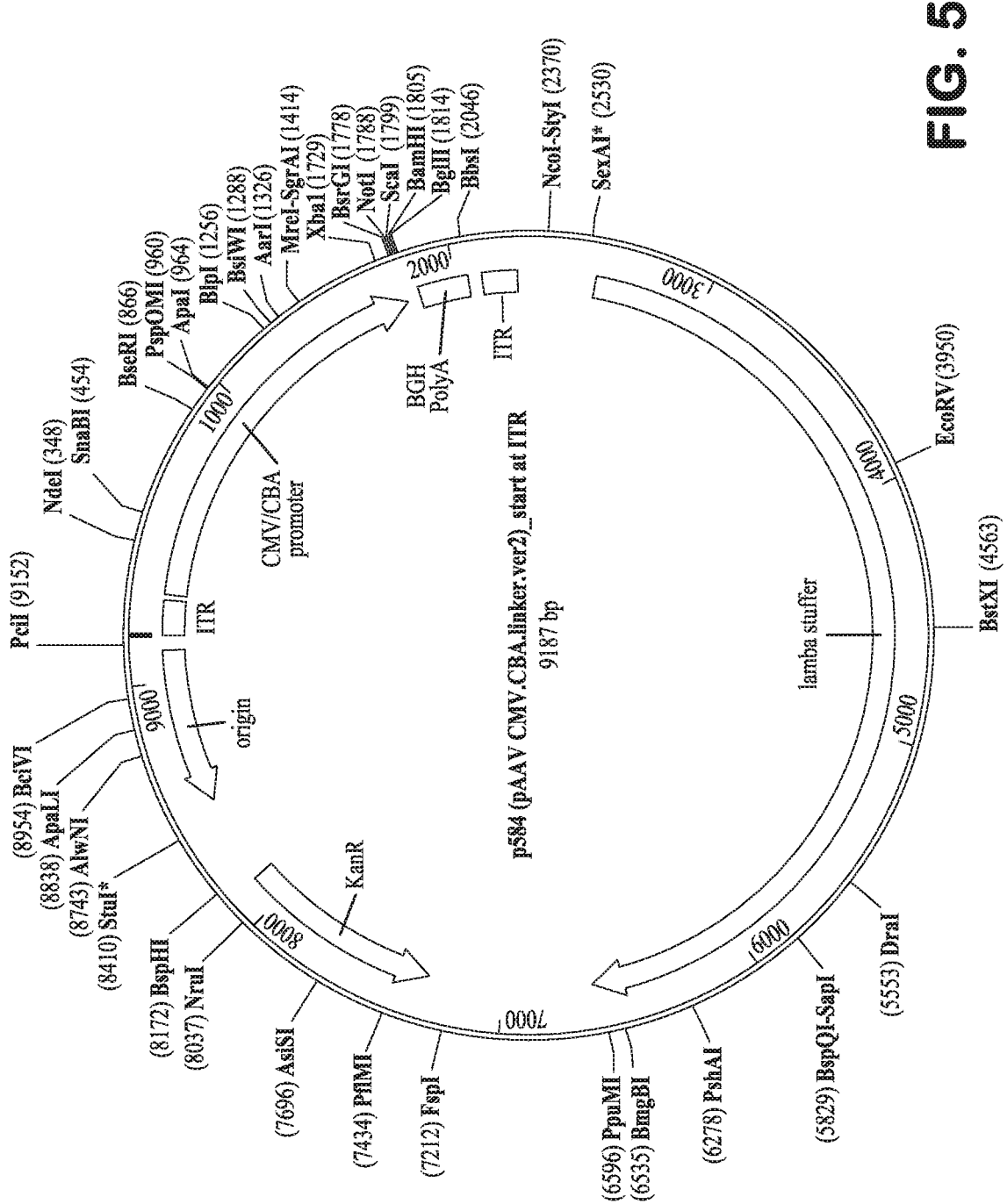
FIG. 5 is a plasmid map of p584, described herein. The sequence of p584 is shown in SEQ ID NO: 7.

| Name | Serotype | Cell Line | FIG. | MOI Used | CHM Expression (Observation) |
|---|---|---|---|---|---|
| AAV2.V2a | AAV2 | COS-7 | FIG. 1 | IE4–IE6 | Detectable expression of CHM at all MOIs tested |
| AAV2.V2a | AAV2 | 84-31 | FIG. 1 | IE4–IE6 | |
| AAV2.V2b | AAV2 | COS-7 | FIG. 2 | IE4–IE5 | |
| AAV2.V2b | AAV2 | 84-31 | FIG. 2 | IE4–IE6 | |
| AAV2.V3a | AAV2 | 84-31 | FIG. 3 | IE4–IE6 | |
| AAV2.V3b | AAV2 | 84-31 | FIG. 3 | 1E4–IE6 | |
| AAV8.V2a | AAV8 | COS-7 | FIG. 4 | IE4–IE6 | Detectable expression of CHM at MOI of IE5–1E6. |
| AAV8.V2a | AAV8 | 84-31 | FIG. 4 | IE4–IE6 | |
| AAV8.V2b | AAV8 | COS-7 | FIG. 5 | IE4–IE6 | Detectable expression of CHM above |
| AAVS.V2b | AAV8 | 84-31 | FIG. 5 | IE4–IE6 | |

TABLE 5-continued

Figure 6:
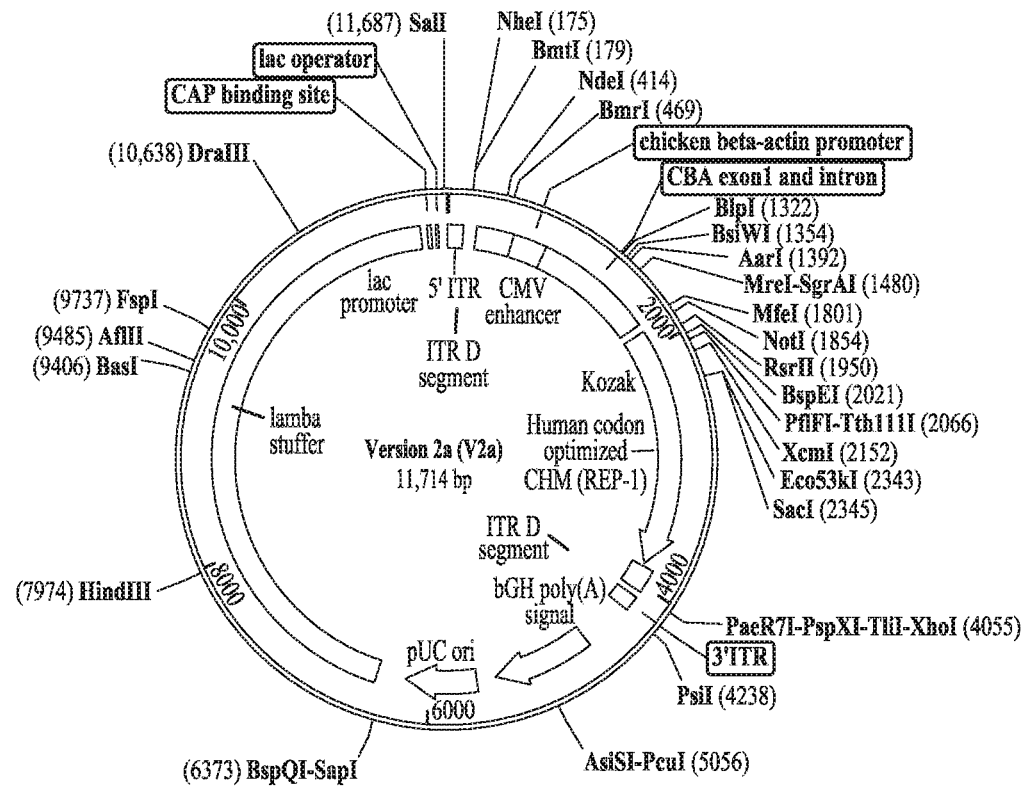
FIG. 6 is a plasmid map of AAV.hCHMco.Version 2a, described herein. The sequence of Version 2a is shown in SEQ ID NO: 25.
Figure 7:
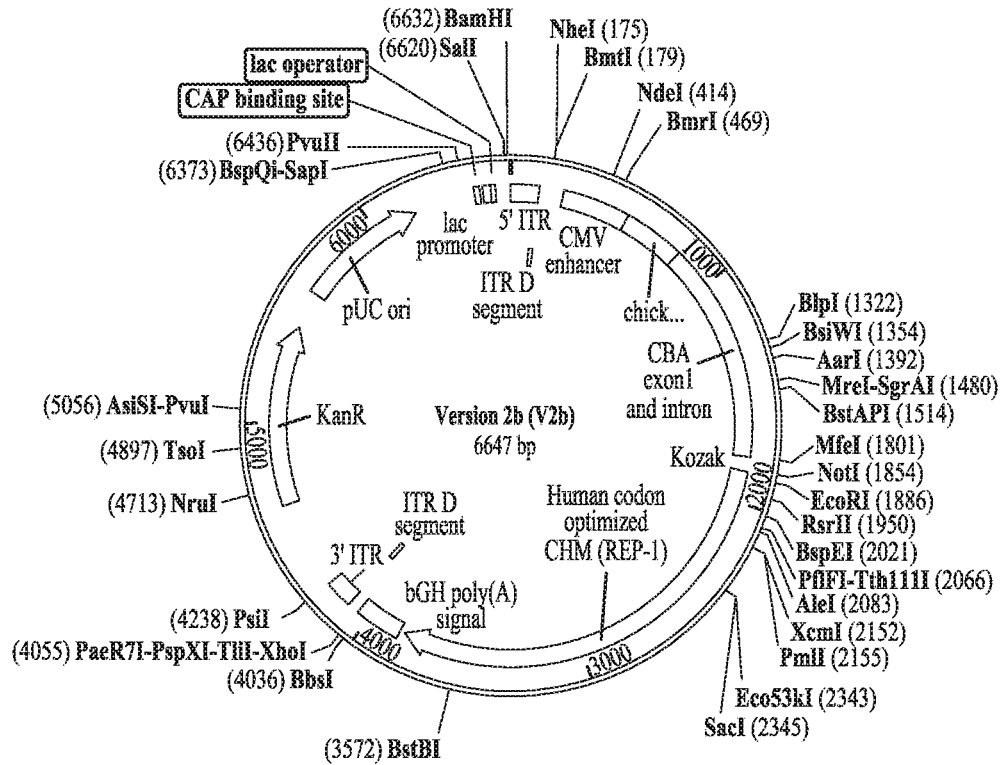
FIG. 7 is a plasmid map of AAV.hCHMco.Version 2b, described herein. The sequence of Version 2b is shown in SEQ ID NO: 26.
Figure 8:
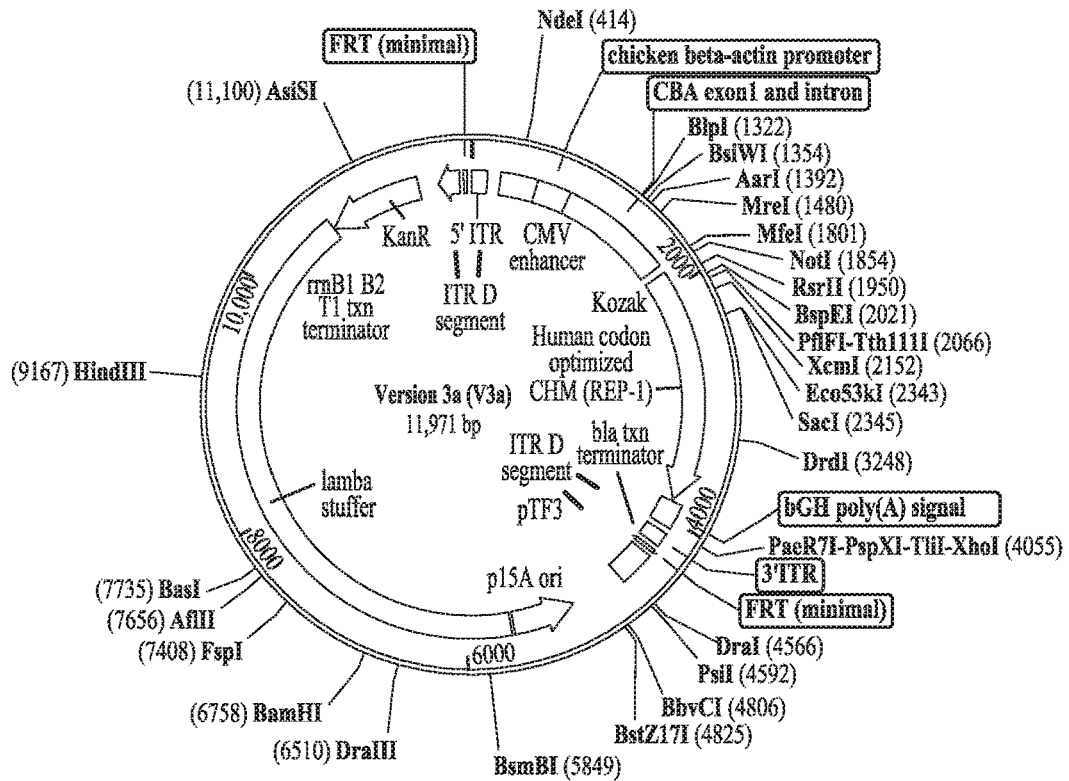
FIG. 8 is a plasmid map of AAV.hCHMco.Version 3a, described herein. The sequence of Version 3a is shown in SEQ ID NO: 27.
Figure 9:
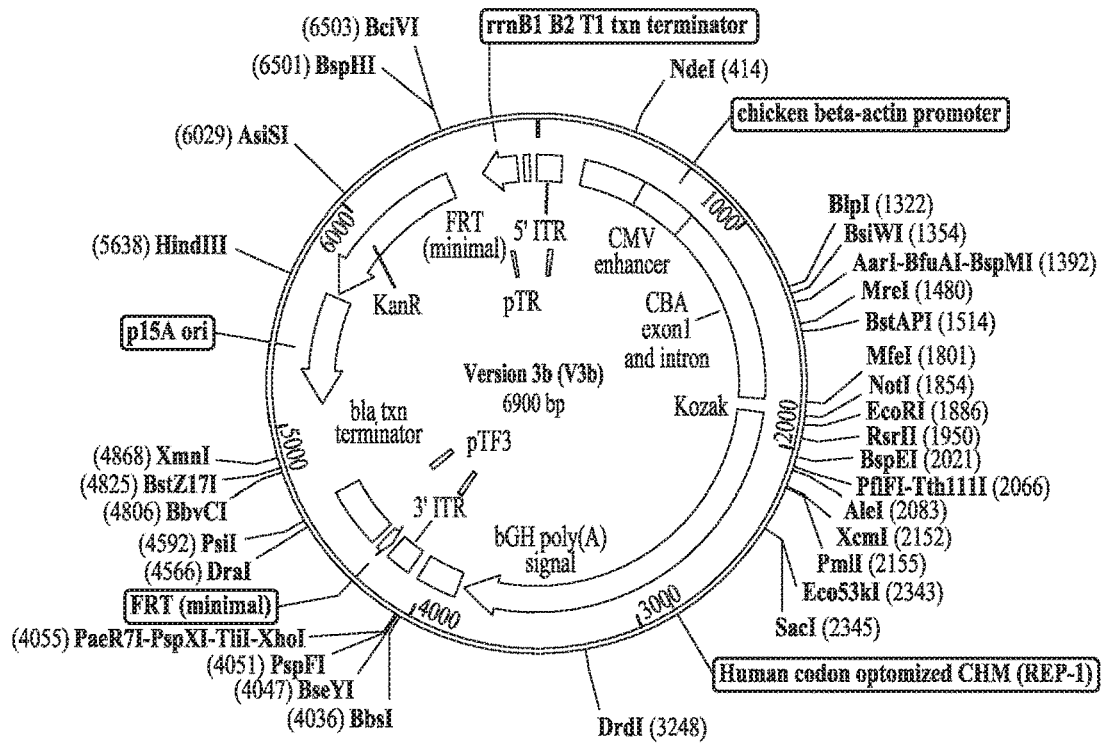
FIG. 9 is a plasmid map of AAV.hCHMco.Version 3b, described herein. The sequence of Version 3b is shown in SEQ ID NO: 28.
Figure 10:
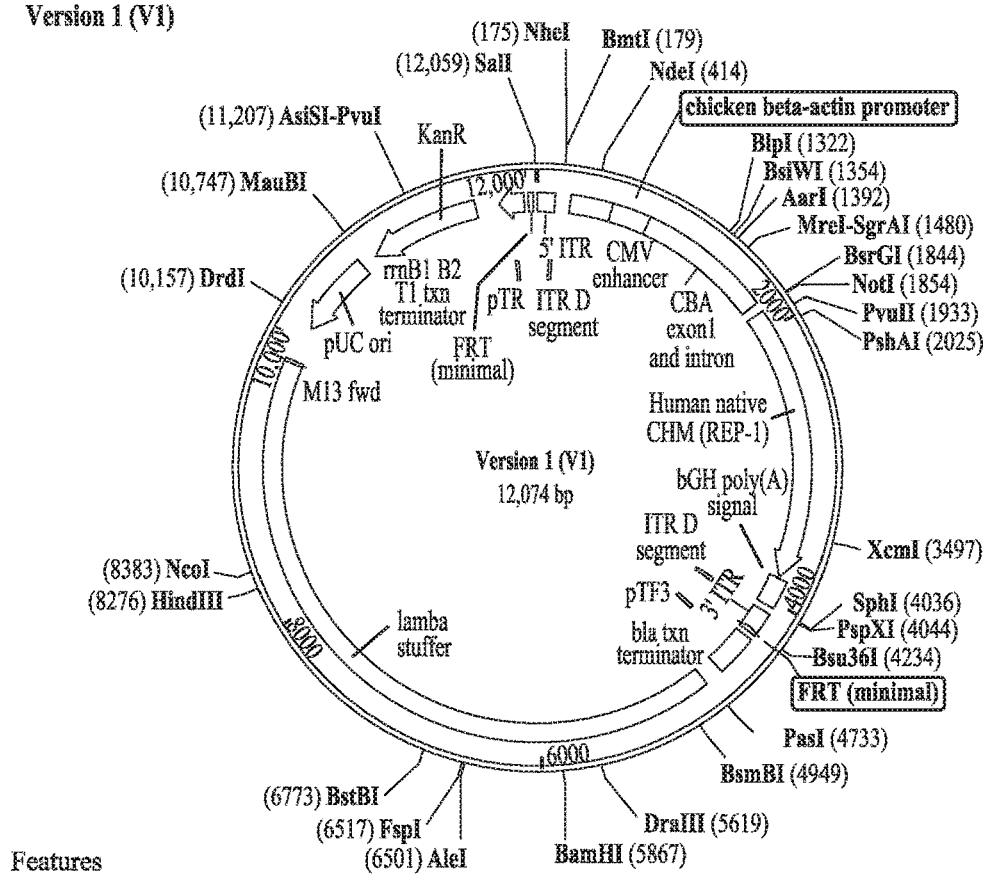
FIG. 10 is a plasmid map of AAV.hCHM.Version 1, described herein. The sequence of Version 1 is shown in SEQ ID NO: 29.

| Name | Serotype | Cell Line | FIG. | MOI Used | CHM Expression (Observation) |
|---|---|---|---|---|---|
| AAV8.V3a | AAV8 | 84-31 | FIG. 6 | IE4–IE6 | MOI of 3E5–1E6 Detectable expression of CHM above MOI of 3E5–IE6 |
| AAV8.V3b | AAV8 | 84-31 | FIG. 6 | IE4–1E6 | |

Monoclonal human REP-1-specific antibody, detected one single ~75-80 kDa hREP-1 protein in cells transduced with next generation AAV2.copt.CHM/AAV8.copt.CHM. A 75-80 kDa band was not observed in cell lysates of untreated control cells. Probing of the blots with either anti-Actin/antitubulin/anti-GAPDH antibody showed a band of equal density in all lanes of the western blot including in untreated controls. Anti-actin antibody detected a protein molecular weight band at ~42 kDa, anti-tubulin antibody detected a protein at ~51 kDa, and anti-GAPDH antibody detected a protein at ~39 kDa. All antibodies detected only specific bands of expected size molecular weight. No nonspecific bands were observed in any of the blots. A pre-stained molecular weight marker was used to compare the molecular weights of protein of interest.

Briefly, REP-1 protein was observed at the expected size in COS-7 and 84-31 cells transduced with AAV2.V2a, AAV2.V2b, AAV2.hCHM.V3a and AAV2.hCHM.V3b. Untreated controls did not reveal the presence of expected size human REP-1 protein. Labeling the blot with anti-actin antibody detected a protein band of equal intensity in all lanes of the gel at ~42 kDa. Pre-stained protein ladder was used to compare the molecular weights of REP-1 and Actin. Data not shown.

The results indicate that AAV2 and AAV8 serotype vectors containing next generation plasmids are able to transduce 84-31 and COS-7 cells efficiently. Expression of CHM in the next generation plasmids was in the detectable range, and demonstrated a dose dependent trend. Transduction of cells with the next generation hCHM viruses resulted in production of REP-1 protein of the predicted size.

Example 5: Comparison of In Vitro Protein Expression of AAV.Codon-Optimized.Human CHM with AAV Native.Human CHM The objective of this study was to delineate transduction efficiency of AAV vectors (serotype 2 and 8) containing various versions of the CHM-containing transgene cassettes by measuring levels of REP-1 protein in a 84-31 cell line based study model.

Plasmids and Vectors: A total of 5 transgene plasmids were compared either in AAV2 or AAV8: Version 1 (previously being used in an on-going clinical trial) and four next generation versions (V2a, V2b, V3a, and V3b). The plasmids were engineered as described in Example 4, and the features thereof are shown in Table 1. Table 2 above shows a summary of AAV2 and AAV8 vectors generated and concentration of viral stocks.

Study Design (e.g. Treatment Groups)

1. In a pilot experiment, COS-7 and 84-31 cells were transduced with AAV2.hCHM.Version1, Version2a and Version 2b. Western blot was performed to compare transduction efficiency levels in the two cells lines.

2. 84-31 cells, plated in 6-well plates were transduced with one of the 10 test articles (Version 1, 2a, 2b, 3a and 3b in either AAV2 or AAV8 background) at an MOI of 3E5. After 36-48 hours, cells were harvested and lysed. The lysate was loaded on SDS-PAGE, and subjected to further Western blot analyses. Levels of REP-1 protein are compared amongst all construct versions. Two separate plates were setup for each AAV2.CHM or AAV8.CHM experiments were analyzed, separately.

Test Material Administration 3.4.1 Cell Culture 83-41 cells and COS-7, both were cultured in Dulbecco's modified Eagle medium (DMEM)-high glucose with 10% fetal bovine serum, and 1% penicillin/streptomycin at 37° C. in an environment supplied with 5% CO2.

3.4.2 Preparation of Cells for Transduction:

The day before transduction (18-24 h before) 83-41 and COS-7 cells were seeded at a density of 3E5 in 2 ml of cell culture media per well in a 6-well cell culture dish. The seeded cells were incubated at 37° C. in an environment supplied with 5% CO2.

3.4.3 Transduction:

Wells of 84-31 cells and Cos-7 were infected with AAV vectors as described below at an MOI of 3E5 (see Table 6 for the pilot experiment and Table 7 for the second set of experiments). No virus was added to the negative (untransduced) control. Briefly, first, the tissue culture media was removed and replaced with 2 ml fresh media/well in each the wells in the 6 well cell culture dish. Then the predetermined amount of AAV vector (see table 2 for vector volumes used for transduction) was measured (from the stock) and directly added to each well. Cells were incubated with the AAV virus for 36-48 hours at 37° C. with 5% CO2 until harvesting. Cells were observed under microscope before harvesting to check any abnormality. Western blot analysis was performed as described in Example 4.

TABLE 6

Pilot Experiment: Infection doses of AAV2.hCHM.V1, 2a, 2b in 84-31 and COS-7 cells.

| Vector Used | Cell Line | Cell density | Vector used (µL) | MOI |
| --- | --- | --- | --- | --- |
| None | 84-31 | 3E5 | 0 | 0 |
| AAV2.V1 | 84-31 | 3E5 | 13.42 | 3E5 |
| AAV2.V2b | 84-31 | 3E3 | 8.11 | 3E5 |
| AAV2.V2e | 84-31 | 3E5 | 27.78 | 3E5 |
| AAV2.V1 | COS-7 | 3E5 | 13.42 | 3E5 |
| AAV2.V2B | COS-7 | 3E5 | 8.11 | 3E5 |
| AAV2.V2a | COS-7 | 3E5 | 27.78 | 3E5 |
| None | COS-7 | 3E5 | 0 | 0 |

TABLE 7

Infection doses of AAV.hCHM next generation vectors and V1 (AAV2 and AAV8) in 84-31 cells

| Vector Used | Cell Line | Cell density | Vector used (µL) | MOI |
| --- | --- | --- | --- | --- |
| None | 84-31 | 3E5 | 0 | 0 |
| AAV8.V2a | 84-31 | 3E5 | 5.77 | 3E5 |
| AAV8.V2b | 84-31 | 3E5 | 5.41 | 3E5 |
| AA.V8.V3a | 84-31 | 3E5 | 6.92 | 3E5 |
| AAV8.V3b | 84-31 | 3E5 | 4.41 | 3E5 |
| AAV8.V1 | 84-31 | 3E5 | 4.32 | 3E5 |
| None | 84-31 | 3E5 | 0 | 0 |
| AAV2.V2a | 84-31 | 3E5 | 27.78 | 3E5 |
| AAV2.V2b | 84-31 | 3E5 | 8.11 | 3E5 |
| AAV2.V3a | 84-31 | 3E5 | 12.45 | 3E5 |
| AAV2.V3b | 84-31 | 3E5 | 10.15 | 3E5 |
| AAV2.V1 | 84-31 | 3E5 | 13.42 | 3E5 |

Results: Comparison of the expression of native hCHM (AAV2.hCHM.V1) versus codon-optimized CHM AAV2a and 2b vectors in 84-31 and COS-7 cells In this experiment 84-31 and COS-7 cells were transduced with either no vector (untreated control), AAV2.hCHM.Version1, AAV2.hCHM.Version2a or Aav2.hCHM.Version2b. Western blot analysis with an anti-human REP-1 antibody, showed that REP-1 protein levels were detectable at ~75-80 kDa in all AAV2 (V1, V2a, V2b) transduced samples and in both cells lines (Data not shown). A slightly better protein expression was seen in 84-31 cell line (Table 8). Anti-REP1 antibody detected negligible amount of REP-1 protein in untreated cells. Labeling of the blot with GAPDH antibody detected a band at ~39 kDa in all cell lysates, including the untreated cells.

Densitometric evaluation (quantification of the protein level) of the blots using ImageJ software demonstrated that after normalizing the values to the expression of endogenous GAPDH protein the transduction efficiency was similar in 84-31 and COS-7 cells. (See Table 8 for results.) Based on this, the 84-31 cell line, which is from human origin was used for further experiments.

In conclusion, AAV2.V1, AAV2.V2a and Aav2.V2b induced the production of REP-1 protein in both, 84-31 and COS-7 cells with similar transduction efficiency.

TABLE 8

Densitometric evaluation of Western Blots

| | | REP1 | GAPDH | GAPDH NORMALIZED TO GAPDH OF V1 | REP-1 NORMALIZED TO RESPECTIVE GAPDH | REP-1 NORMALIZED TO REP-1 OF V1 (%) |
| --- | --- | --- | --- | --- | --- | --- |
| 84-31 | AAV2.V1 | 23416.844 | 19350.773 | 1 | 23416.844 | 100 |
| | AAV2.V2b | 36626.765 | 20357.894 | 1.011 | 36203.838 | 154.605 |
| | AAV2.V2a | 31114.844 | 20315.945 | 1.009 | 30819.0684 | 131.610 |
| | | | Molecular weight Marker | | | |
| COS7 | AAV2.V1 | 12880.459 | 15479.288 | 1 | 12880.459 | 100 |
| | AAV2.V2b | 19209.823 | 14321.167 | 0.711 | 26991.925 | 209.557 |
| | AAV2.V2a | 15132.602 | 13145.924 | 0.849 | 17818.595 | 138.338 |

Comparison of the expression of native CHM versus codon-optimized CHM AAV2 vectors in 84-31 cells: Using an anti-human REP-1 antibody, the Western blot analysis of the 84-31 cells transduced with AAV2.hCHM.V2a, V3a, V2b, V3b and V1 detected a band at ~75-80 kDa in all conditions (Data not shown). Anti-REP1 antibody detected negligible amount of REP-1 protein in untreated cells. Labeling of the blot with GAPDH antibody detected a band at ~39 kDa in all cell lysates, including the untreated cells. Densitometric evaluation (quantification of the expression level) of the blots using ImageJ software demonstrated an increase in the expression of AAV2.hCHM.V2a, 3a, 2b, and 3b compared to AAV2.hCHM.V1 after normalizing the values to the production of endogenous GAPDH protein. See Table 9 and 10 for results.

Comparison of the expression of native CHM versus codon-optimized CHM AAV2 vectors in 84-31 cells: Western blot analysis of cells transduced with AAV8.V1, AAV8.V2a, AAV8.V3a, AAV8.2b, AAV8.3b, with anti-human REP-1 antibody detected a band at ~75-80 kDa in all transduced cells (Data not shown). Anti-REP1 antibody detected negligible amount of REP-1 protein in untreated cells. Labeling of the blot with GAPDH antibody detected a band at ~39 kDa in all cell lysates, including the untreated cells. Densitometric evaluation of the blots using ImageJ software demonstrated higher expression of AAV8.hCHM.V2a; 3a; 2b; 3b compared to AAV8.V1. Values are obtained after normalizing the CHM values first, to the expression of the respective endogenous GAPDH protein and then normalized to the expression level of the average of Version 1. See Table 11 and Table 12 for results.

TABLE 9

Values of REP-1 protein in 84-31 cells after transduction with AAV2.hCHM.
V1, Va, V2b, V3a or V3b for PLATE 1 (Western Blot not shown)

| CONSTRUCT | | RAW VALUE | | GAPDH NORMALIZED TO | REP-1 NORMALIZED TO | REP-1 NORMALIZED TO |
|---|---|---|---|---|---|---|
| NAME | LANE NUMBER | REP-1 | GAPDH | GAPDH OF V1 | RESPECTIVE GAPDH | REP-1 OF V1 (%) |
| AAV2.V1 | 1 | 23367.593 | 15155.602 | 1 | 23367.593 | 100 |
| AAV2.V2a | 3 | 26949.421 | 10969.581 | 0.723797115 | 37233.39103 | 159.3377248 |
| AAV2.V3a | 5 | 29867.714 | 14595.894 | 0.963069233 | 31013.0497 | 132.7182038 |
| AAV2.V2b | 7 | 32728.128 | 14133.551 | 0.932562824 | 35094.82381 | 150.1858741 |
| AAV2.V3b | 9 | 33986.543 | 13670.066 | 0.901981063 | 37679.88531 | 161.2484662 |

TABLE 10

Values of REP-1 protein in 84-31 cells after transduction with AAV2.hCHM.
V1, V2a, V2b, V3a or V3b for PLATE 2 (Western blot not shown)

| CONSTRUCT | | RAW VALUE | | GAPDH NORMALIZED TO | REP-1 NORMALIZED TO | REP-1 NORMALIZED TO |
|---|---|---|---|---|---|---|
| NAME | LANE NUMBER | REP-1 | GAPDH | GAPDH OF V1 | RESPECTIVE GAPDH | REP-1 OF V1 (%) |
| AAV2.V1 | 2 | 23128.593 | 11993.823 | 1 | 23128.593 | 100 |
| AAV2.V2a | 4 | 23623.836 | 10982.798 | 0.915704526 | 25798.53582 | 111.5439051 |
| AAV2.V3a | 6 | 28832.543 | 13176.359 | 1.098595419 | 26244.91465 | 113.473892 |
| AAV2.V2b | 8 | 31349.229 | 16028.329 | 1.336381986 | 23458.28463 | 101.4254721 |
| AAV2.V3b | 10 | 33273.856 | 14760 | 1.230633469 | 27037.99047 | 116.9028763 |

TABLE 11

Values of REP-1 protein expression in 84-31 cells after transduction with
AAV8 hCHM Version 1, 2a, 2b, 3a and 3b - PLATE 1 (Western blot not shown)

| CONSTRUCT | | RAW VALUE | | GAPDH NORMALIZED TO | REP-1 NORMALIZED TO | REP-1 NORMALIZED TO |
|---|---|---|---|---|---|---|
| NAME | LANE NUMBER | REP-1 | GAPDH | GAPDH OF V1 | RESPECTIVE GAPDH | REP-1 OF V1 (%) |
| AAV8.V1 | 11 | 3630.589 | 20309.924 | 1 | 3630.589 | 100 |
| AAV8.V2a | 13 | 7133.439 | 17051.48 | 0.839 | 8496.599 | 234.028 |
| AAV8.V3a | 15 | 5828.418 | 15801.045 | 0.777 | 7491.575 | 206.346 |
| AAV8.V2b | 17 | 11411.702 | 19249.681 | 0.947 | 12040.241 | 331.633 |
| AAV8.V3b | 19 | 17610.066 | 18727.024 | 0.922 | 19098.555 | 526.045 |

TABLE 12

Values of REP-1 protein expression in 84-31 cells after transduction with
AAV8 hCHM Version 1, 2a, 2b, 3a and 3b - PLATE 2 (Western blot not shown)

| CONSTRUCT | | RAW VALUE | | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
| NAME | LANE NUMBER | REP-1 | GAPDH | | | |
| AAV8.V1  | 12 | 3507.468  | 19082.681 | 1           | 3507.468    | 100         |
| AAV8.V2a | 14 | 4359.296  | 13274.731 | 0.695642871 | 6266.571801 | 178.6636913 |
| AAV8.V3a | 16 | 6533.246  | 20720.246 | 1.0858142   | 6016.909708 | 171.5456765 |
| AAV8.V2b | 18 | 13962.045 | 17842.167 | 0.934992677 | 14932.7854  | 425.7425983 |
| AAV8.V3b | 20 | 16049.823 | 13836.368 | 0.725074637 | 22135.40811 | 631.0936581 |

Conclusion: Comparative expression studies demonstrated that application of AAV vectors carrying the next generation AAV. hCHM. Version 2a, 2b, 3a and 3b induced increased production of REP-1 protein compared with Version 1 (currently used in clinical trials) in both AAV2 and AAV8 serotype vectors in 84-31 cells.

Example 6: Evaluation of Lambda Stuffer's Effect on AAV Vector Production by qPCR Titer Analysis A single qPCR (quantitative polymerase chain reaction) run was performed on all 8 AAV vectors shown in Table 2, above, in order to assess the effect of lambda stuffer sequences on the amount of DNA impurities. Linearized AAV plasmid standard was used to generate the assay standard. Primer-probe sets were designed on either the CMV/CBA promoter region for quantitation of properly packaged AAV genome or the Kanamycin resistance (KanR) encoding region for reverse packaging. Standards and vector samples were run in two sets, one with the CMV/CBA primer-probe set and the other with the KanR set. Vector sample values (viral genome copy per mL) were determined from each respective standard curve. The effect of the stuffer sequence was assessed by comparing the relative amount of KanR-containing impurities in each vector lot against CMV/CBA containing sequences.

Reagents:
Transgene-Containing Viral Vector Titer:

```
Reference: CMV-CBA Promoter
Primers:
CMV-F:
                                                 (SEQ ID NO: 47)
CCC ACT GGC CAG TAC ATC AA CMV-R:
                                                 (SEQ ID NO: 48)
GCC AAG TAG GAA AGT CCC ATA A FAM-Probe:
                                                 (SEQ ID NO: 49)
/56-FAM/CA TAA TGC C/ZEN/A GGC GGG CCA TTT
AC/3IABkFQ/
```

Impurity-Containing Viral Vector Titer:
Reference: Kanamycin Resistance Gene
Primers:

```
KAN-F:
                                                 (SEQ ID NO: 50)
GAT GGT CGG AAG TGG CAT AA
```

```
KAN-R:
                                                 (SEQ ID NO: 51)
TGC GCC AGA GTT GTT TCT

FAM-Probe:
                                                 (SEQ ID NO: 52)
/56-FAM/CC GTC AGC C/ZEN/A GTT TAG TCT GAC
CA/3IABkFQ/
```

Dilution Reagent: Diluent Q (0.001% PF-68 in nuclease free water): Diluted 1% PF-68 solution 1000-folds with sterile water. Diluent S: Diluent Q+2 ng/µL salmon sperm DNA (Agilent technologies Cat #201190)
ABI TaqMan™ Universal Master Mix (Applied Biosystems 4304437/4326708) Qiagen PCR Product Purification Kit (Qiagen 28104) ABI QuantStudio 6 Flex System Sample Preparation Dnase digest solution was prepared by combining the following: Dnase buffer (10×) 5 µL, Nuclease-free H2O 30 µL, Dnase I (Invitrogen, 18068-015) 5 µL Ten µL of each AAV vector sample was mixed in and incubated at ambient temperature for 10 minutes. The digest mix was inactivated by adding 50 µL of SDS/EDTA/NaCl solution (0.2% SDS/5 mM EDTA/0.2M NaCl) and incubating at 95° C. for 10 minutes. Each AAV vector sample was diluted 10-100,000 fold in Diluent S for qPCR analysis.

qPCR Standard Preparation

Reference standard DNA (linearized) was prepared by digesting plasmid p1008 (low copy transgene plasmid without stuffer) with XhoI and purifying with Qiagen PCR purification kit. Purified material was analyzed on agarose gel to confirm identity, and quantified by Nanodrop. DNA copy number was determined from the stock concentration using the following equivalence: 1 bp=1.096E-21 g. qPCR Standards were prepared according to the following table:

TABLE 13

| DNA Standard | Concentration [Copies/10 µL] | Dilution |
|---|---|---|
| Standard Stock | $2 \times 10^9$ | NA |
| S1 | $2 \times 10^8$ | 10 µL Stock + 190 µL Diluent S |
| S2 | $2 \times 10^7$ | 10 µL S1 + 90 µL Diluent S |
| S3 | $2 \times 10^6$ | 10 µL S2 + 90 µL Diluent S |
| S4 | $2 \times 10^5$ | 10 µL S3 + 90 µL Diluent S |
| S5 | $2 \times 10^4$ | 10 µL S4 + 90 µL Diluent S |
| S6 | $2 \times 10^3$ | 10 µL S5 + 90 µL Diluent S |

PCR Reaction Setup

Extracted DNA samples were analyzed in triplicate (3 wells) in a single qPCR run. The run included reference DNA standards in triplicate, ranging from 103 to 108 copies per well. No-template-control (NTC) was included as negative control. Each AAV vector preparation was analyzed with both CMV/CBA and KanR primer/probe sets. Similarly, for quantitation of each set, the standards were also analyzed with both CMV/CBA and KanR primer/probe sets.

TABLE 14

PCR Reaction Setup

| Regents | Final conc. in Reaction | Volume per 25 μL Reaction |
|---|---|---|
| Universal Master Mix (2x) | 1x | 12.5 μL |
| Optimized Primer Mix (20 μM) | 0.8 μM | 1.0 μL |
| Taqman Probe (10 μM) | 0.2 μM | 0.5 μL |
| Nuclease-Free Water | NA | 1.0 μL |
| Sample/Standard | NA | 10.0 μL |

PCR reaction sequence was set up as follows: 50° C. 2 minutes 1 cycle; 95° C. 10 minutes 1 cycle; 95° C. 15 seconds 40 cycles; 60° C. 1 minutes 40 cycles Run performance. Standards were prepared and run at 103 to 108 DNA copies per well. Lower limit of the assay was set at 1000 copies since assay sensitivity was not an important factor for this experiment. A standard curve was generated for the run using the standard copy numbers and CT (threshold cycle) values of the standards. Linear regression of the standards was performed using the ABI software (data not shown). Standard curve fit had a correlation coefficient (R2 value) of 0.998 or greater indicating a reliable fit model. The slope of the standard curves was −3.5. Slope was used to calculate the efficiency of the amplification reaction, and values between −3.2 and −3.6 represented amplification efficiency between 90% and 110%. Both standard reactions were run with 92.6~93.8% efficiency. Precision of triplicate wells ranged from 2-10%, indicating good agreement among replicates. No-template-control (NTC) resulted in non-quantifiable amplification below the lower limit of the assay.

TABLE 15

Summary of standard curve fit

| Reporter | Target | Slope | Y-intercept | R | Efficiency (%) |
|---|---|---|---|---|---|
| FAM | CMV | −3.513 | 41.896 | 0.998 | 92.597 |
| FAM | KAN | −3.481 | 39.968 | 1.000 | 93.761 |

Results:

Sample value determination: The sample values (AAV genome and reverse-packaging copy number) were interpolated from each matching standard curve (CMV/CBA or KanR), using CT values. Interpolated DNA copy number was corrected for initial dilution and/or digest dilution. Additional correction factor of 2 was applied to account for the difference between double-stranded DNA standards and single-stranded DNA in samples.

Figure 11:
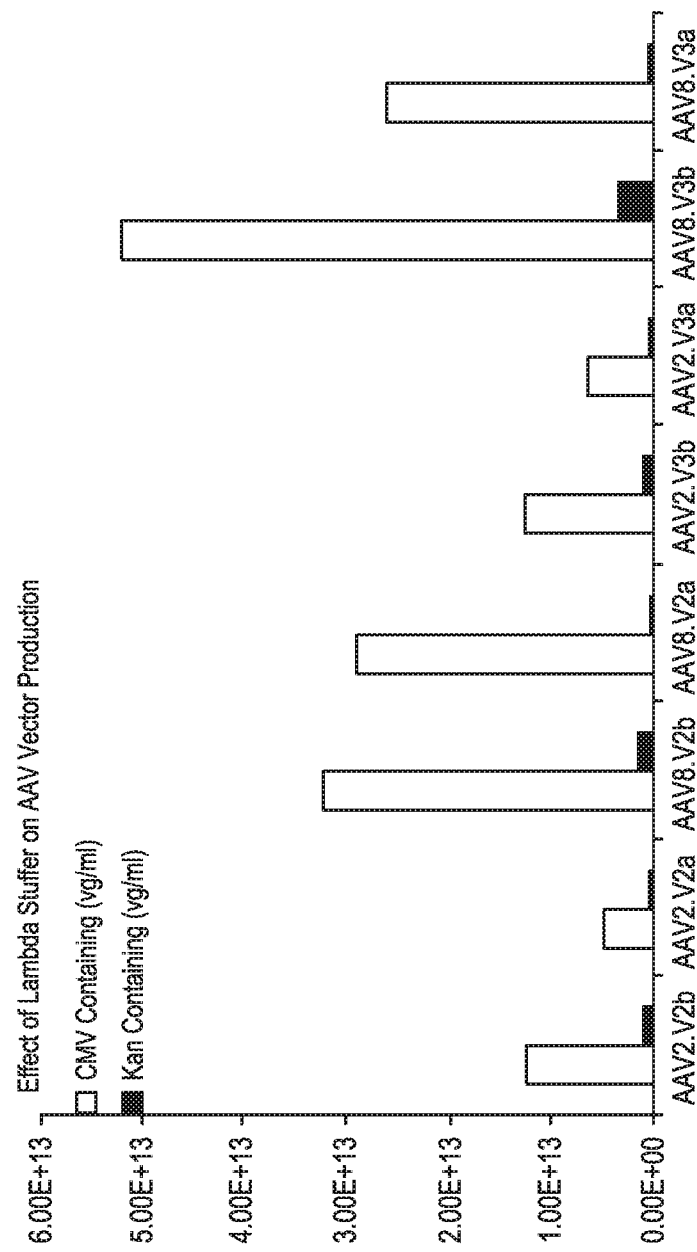
FIG. 11 is a graphic representation of the effect of lambda insert on AAV product impurity. All a-version (lambda containing) vectors have much reduced Kan+ signals from qPCR test.
Figure 13A:
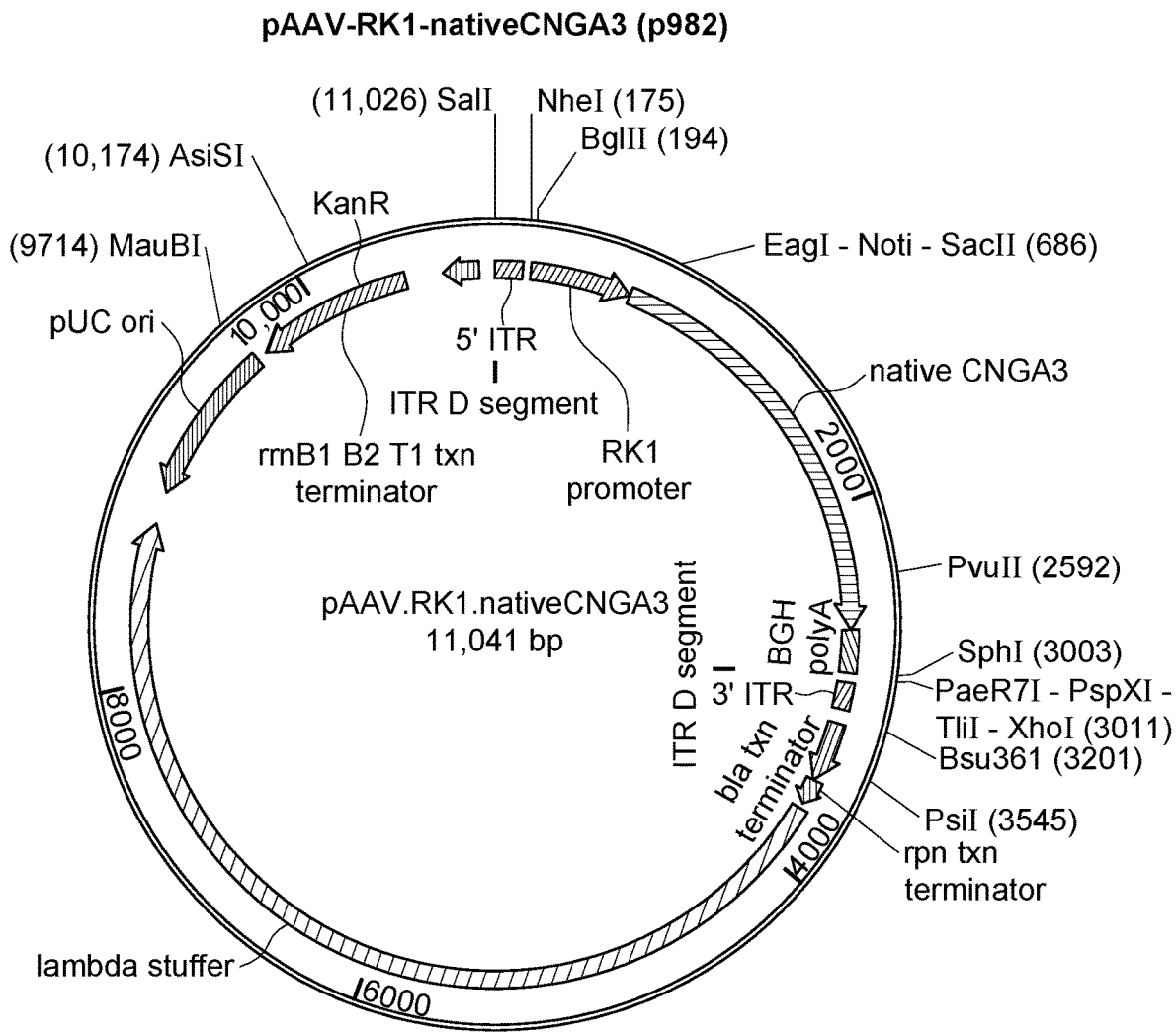
Figure 14A:
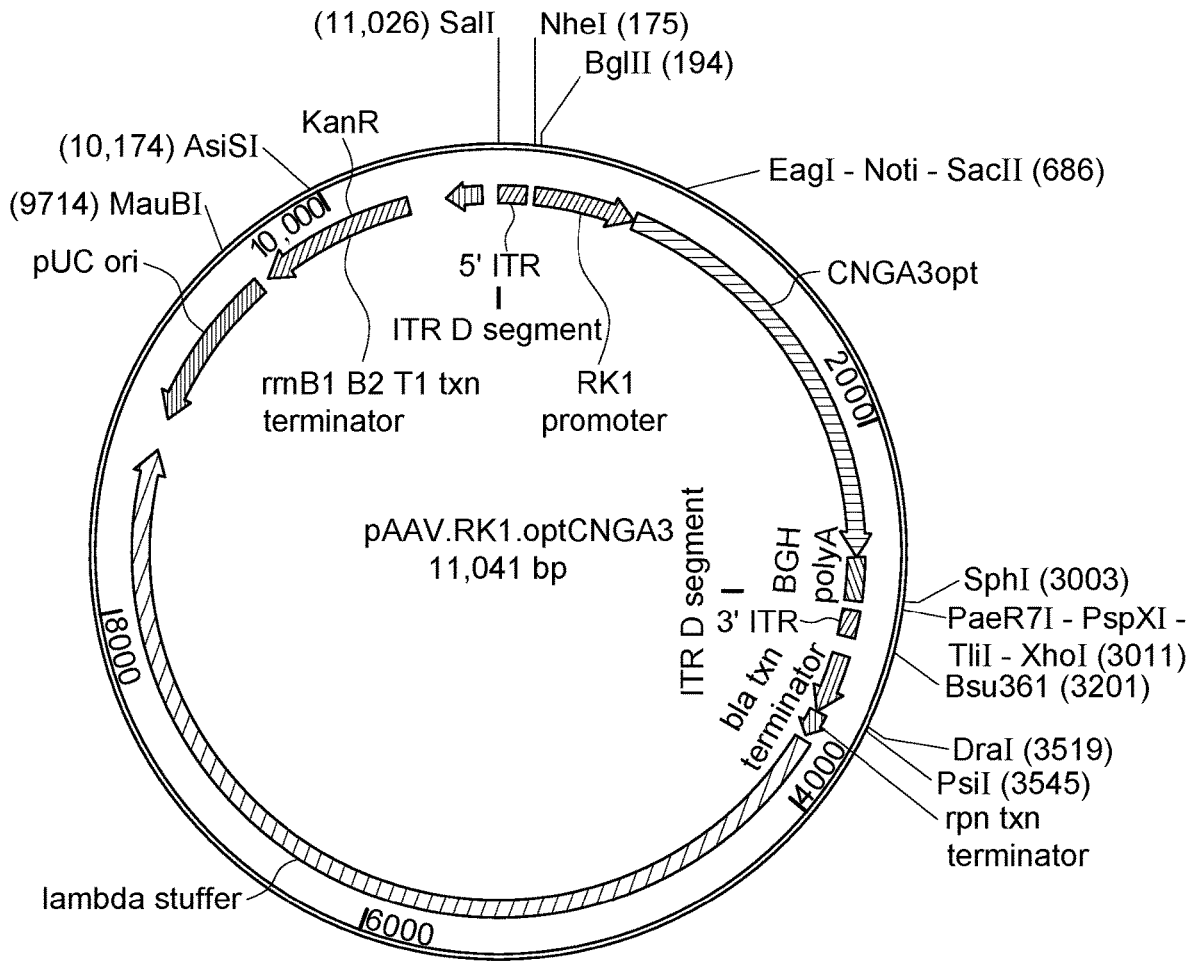
Figure 15A:
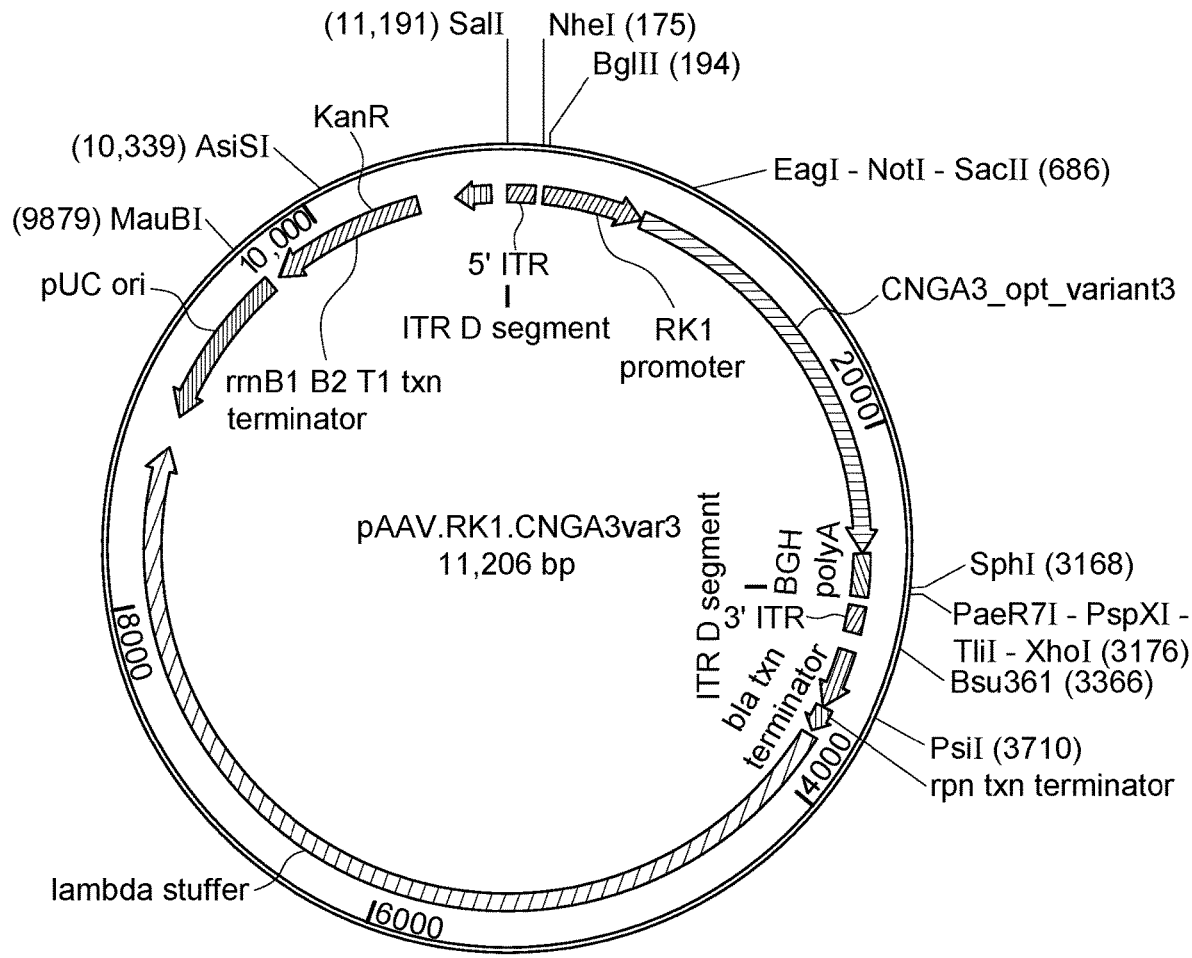
Figure 16A:
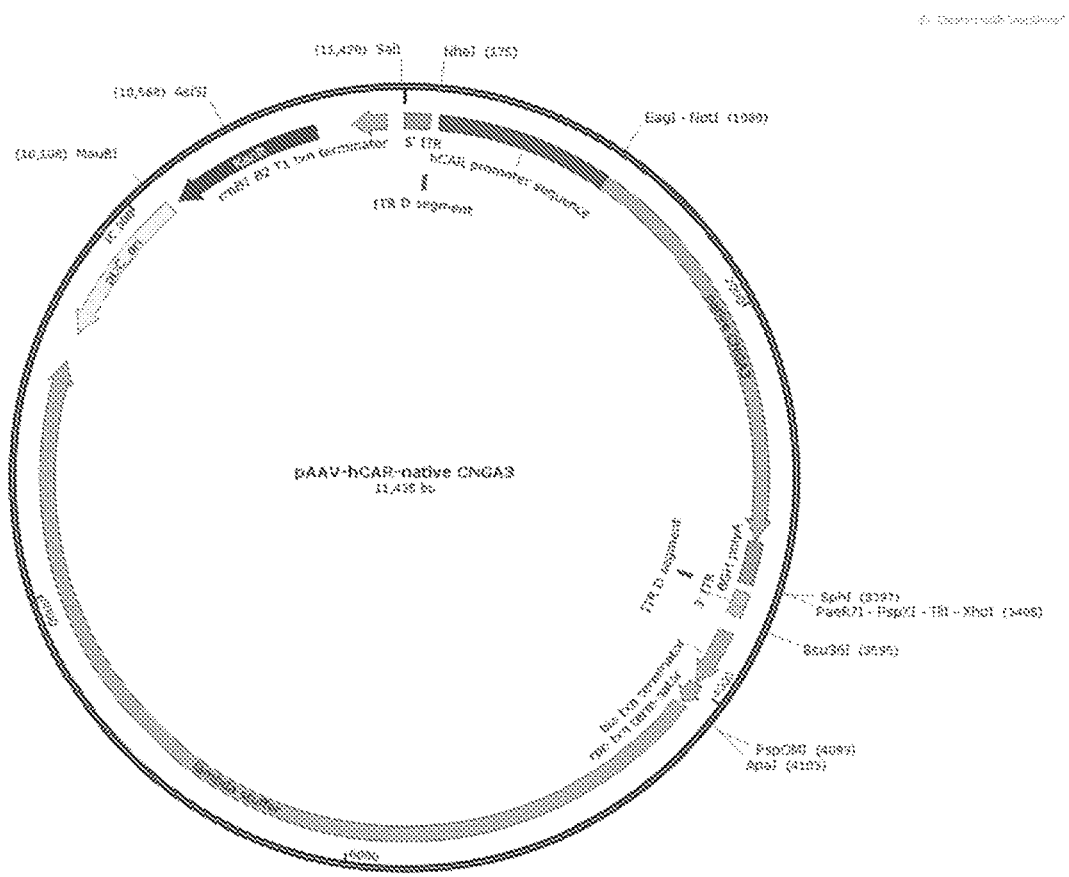
Figure 17A:
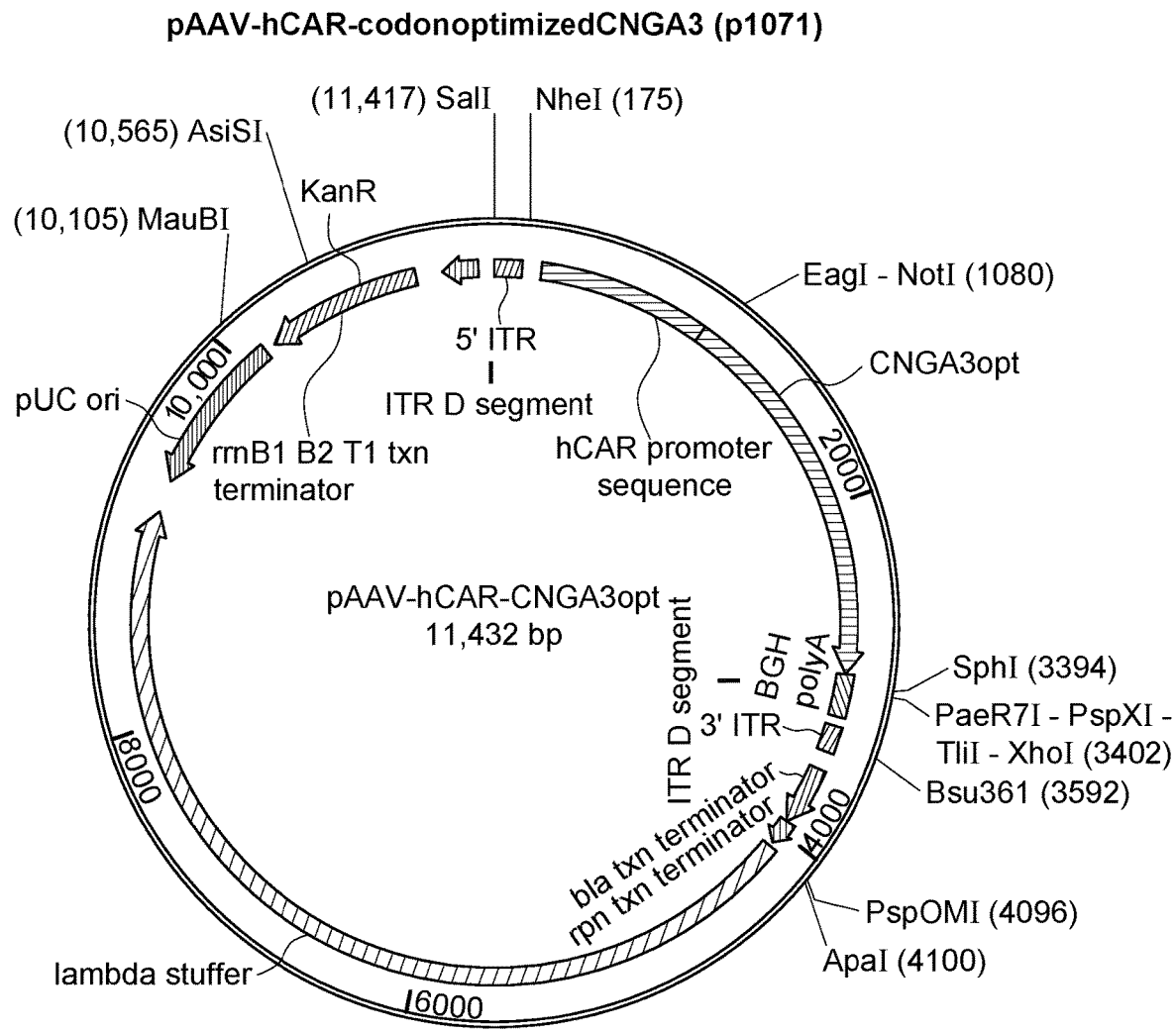
Figure 18A:
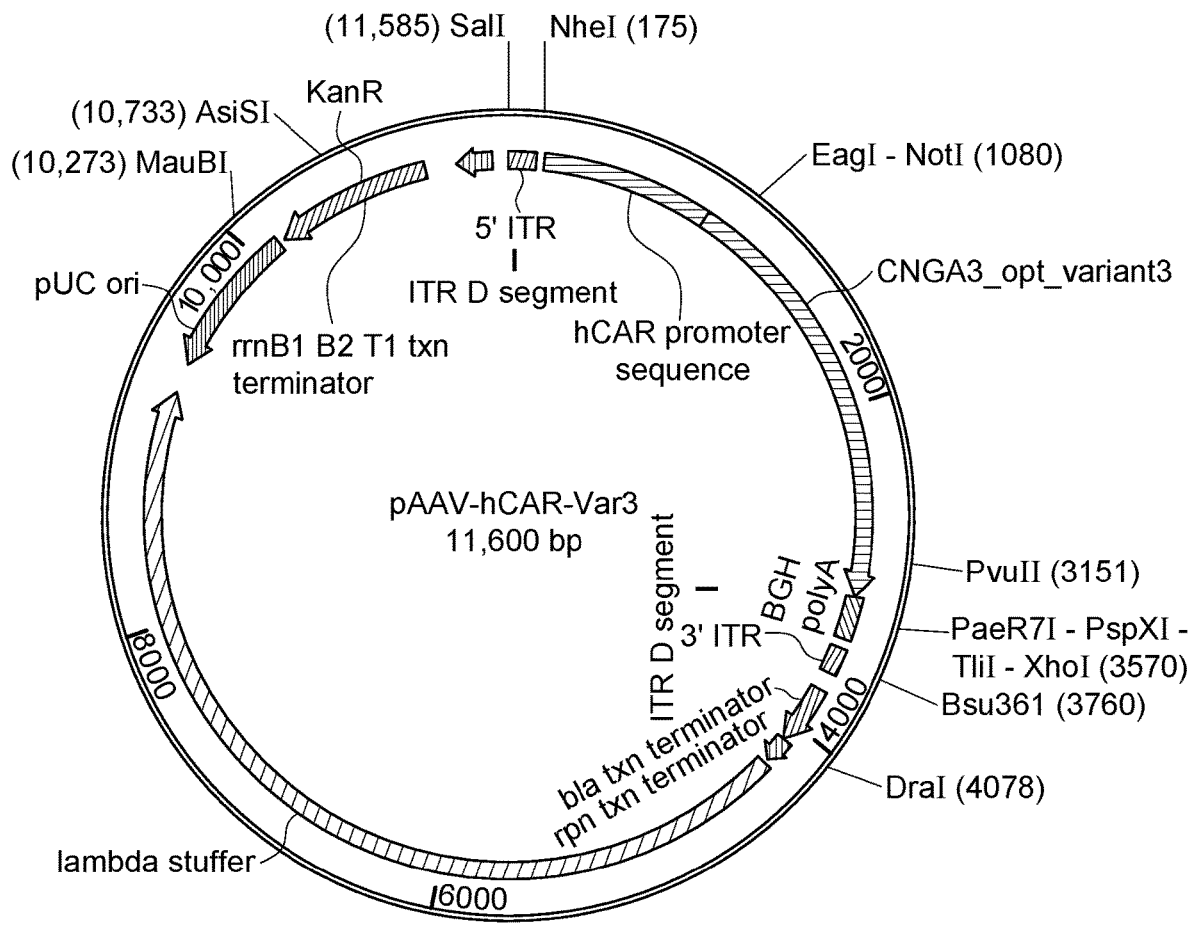
Figure 19A:
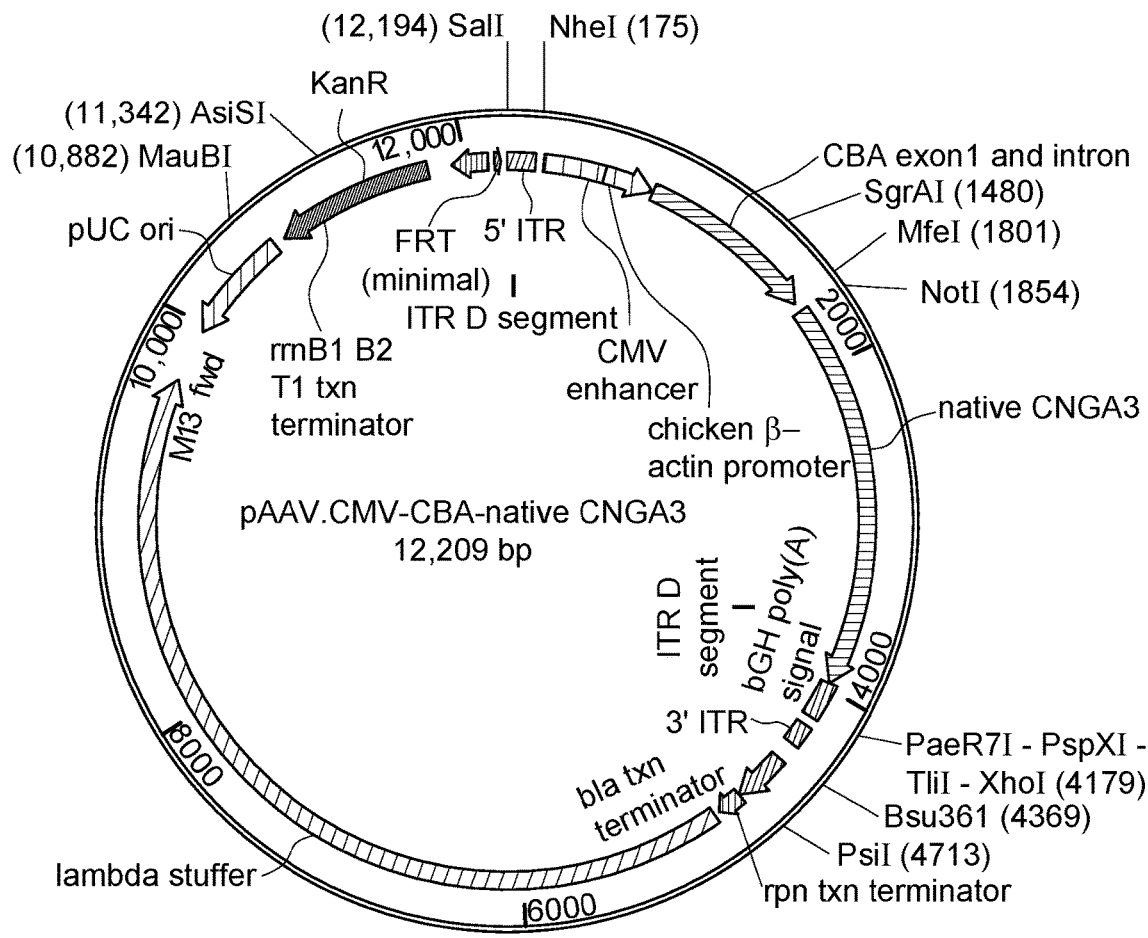
Figure 20A:
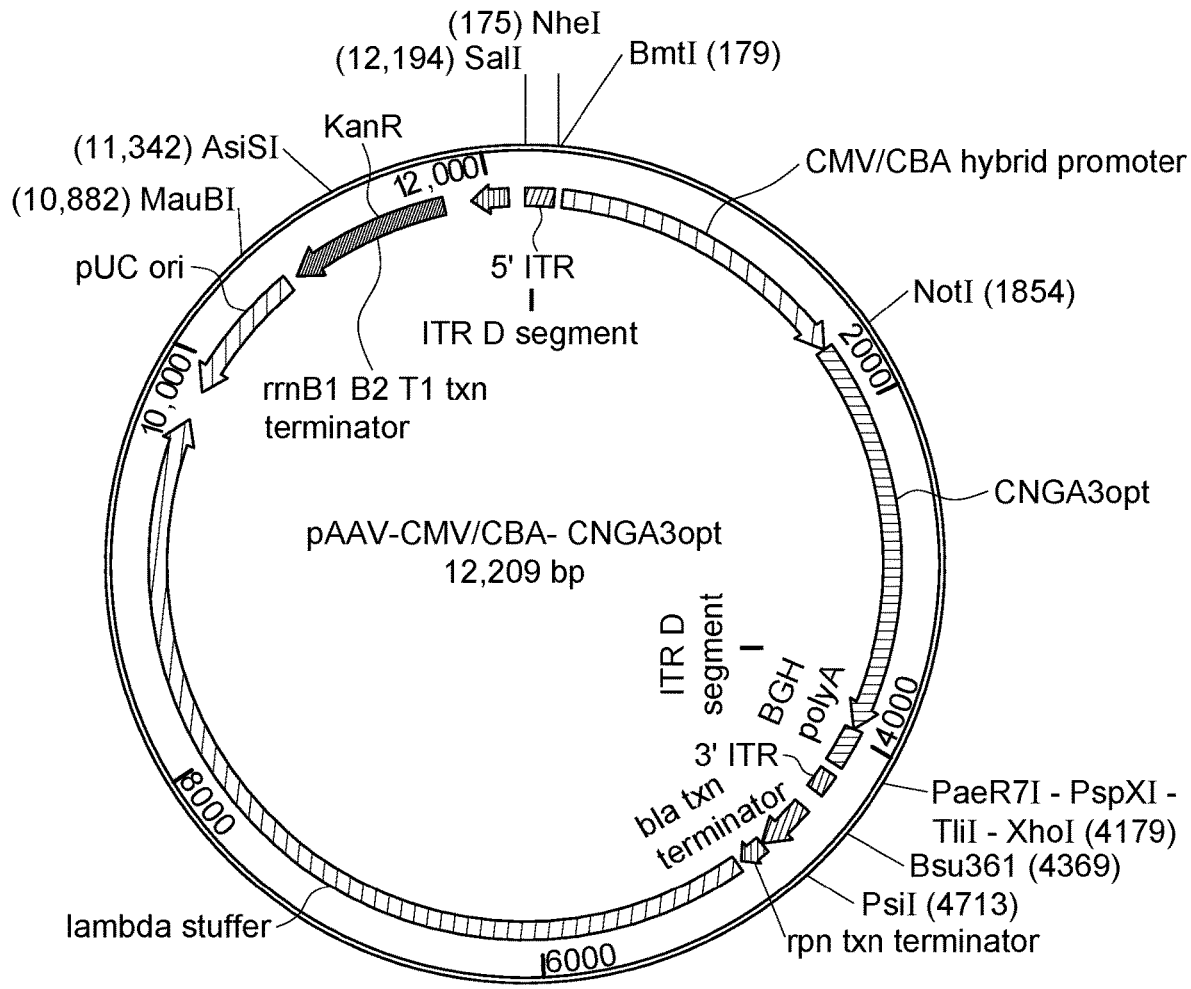
Figure 21A:
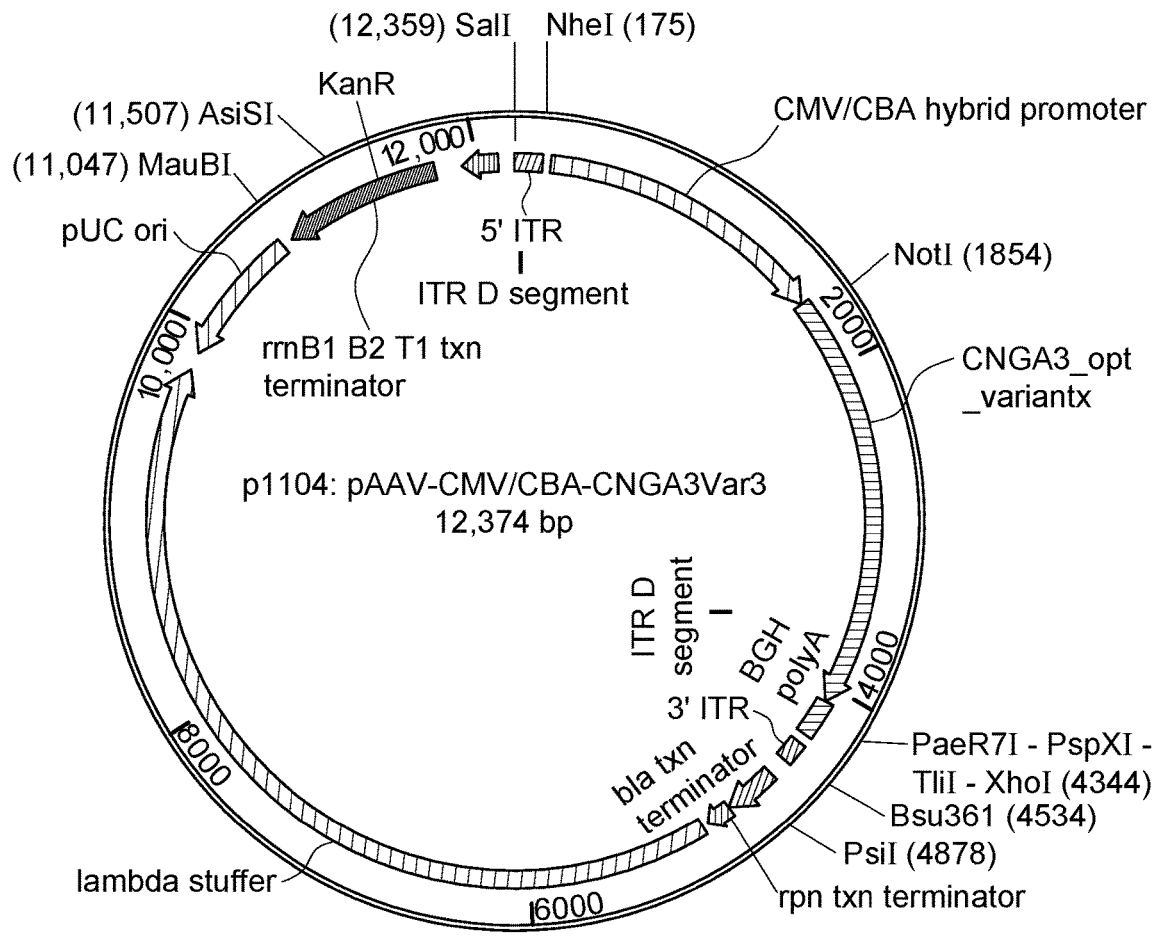
Figure 22A:
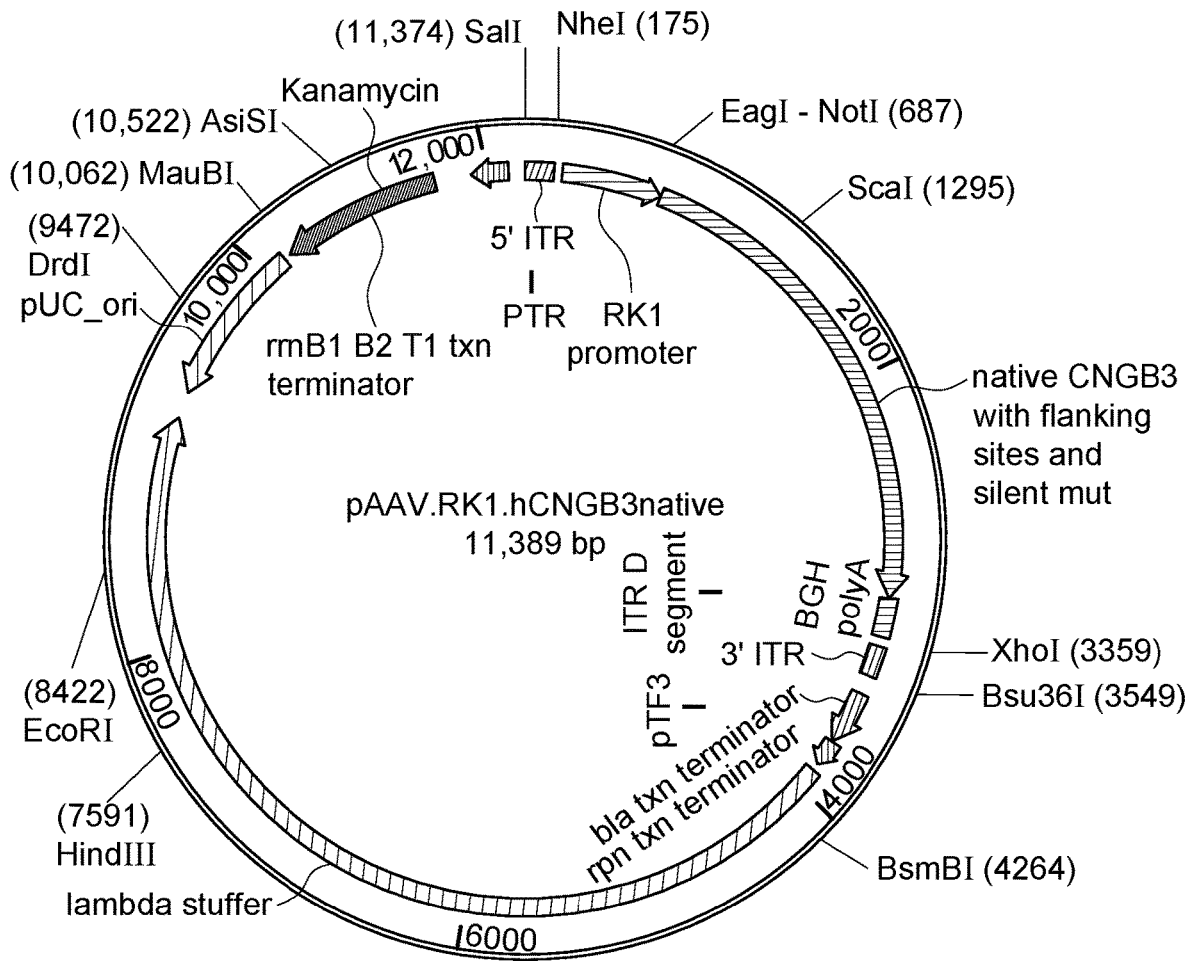
Figure 23A:
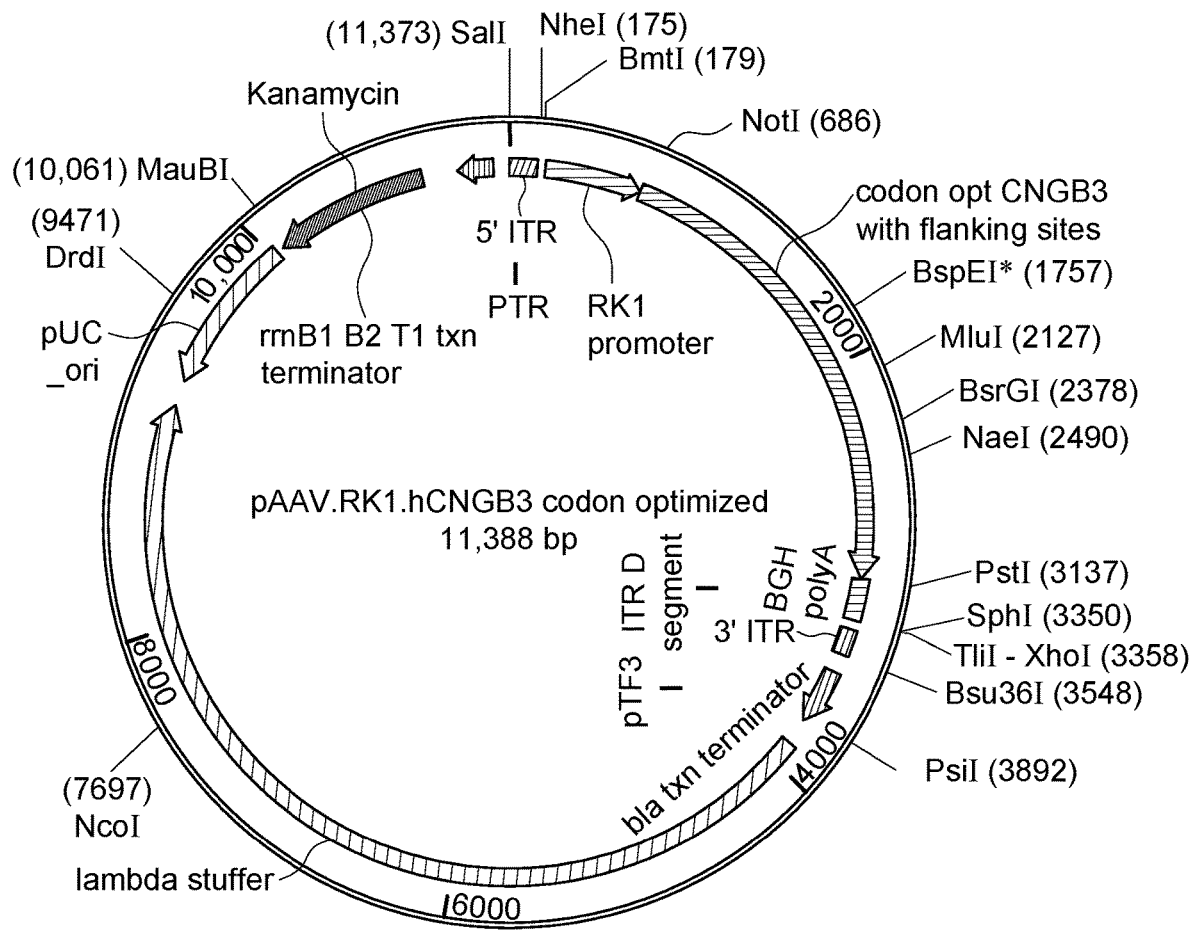
Figure 24A:
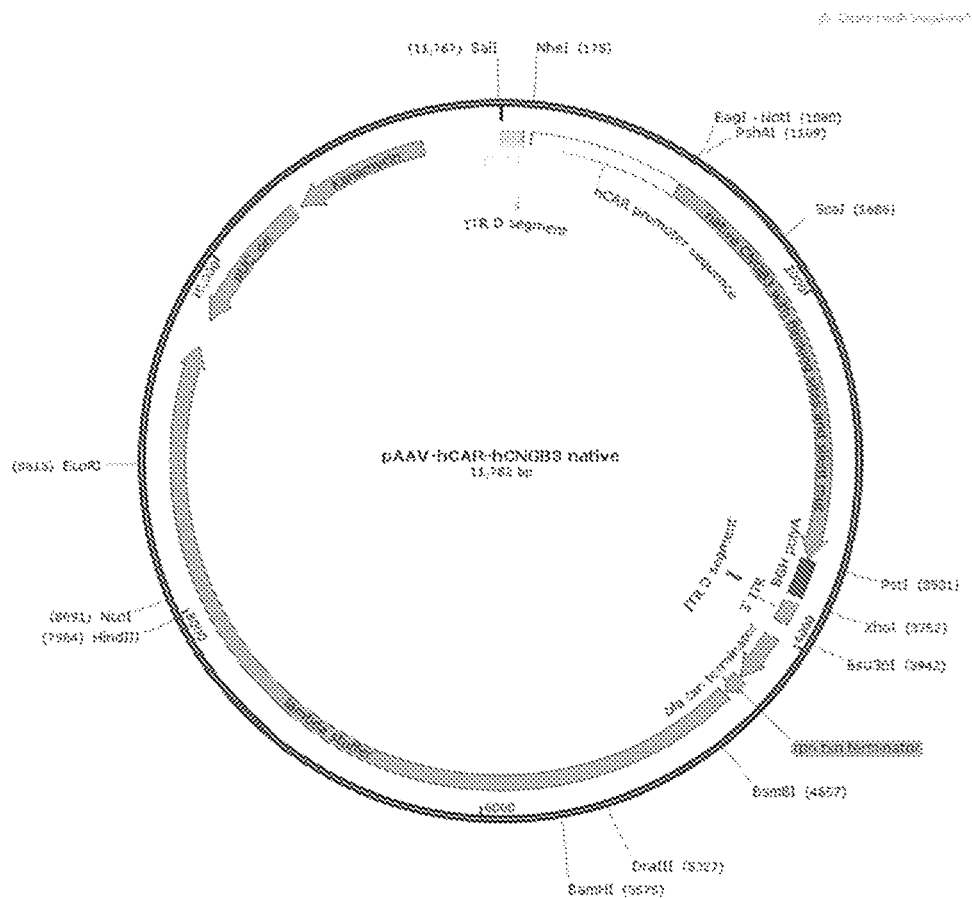
Figure 25A:
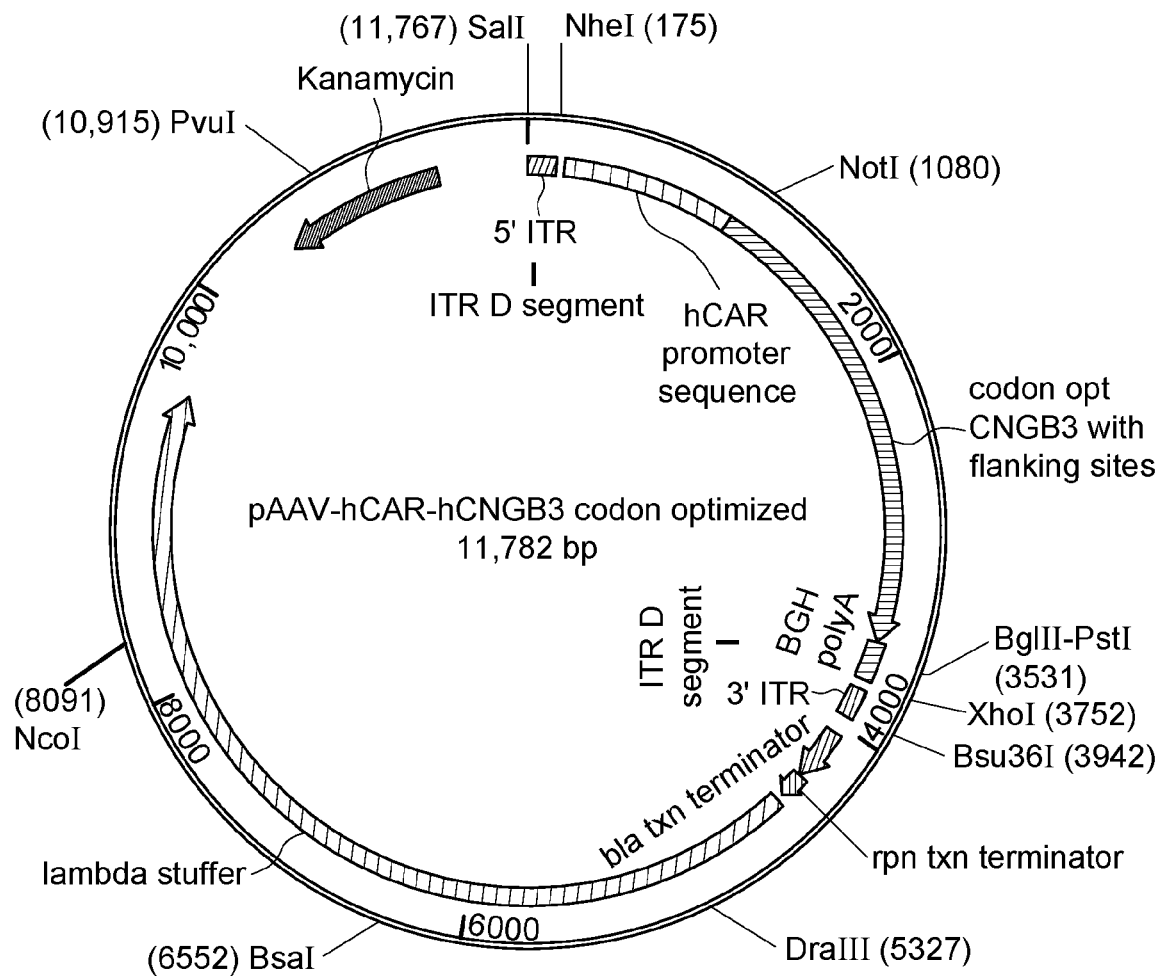
Figure 26A:
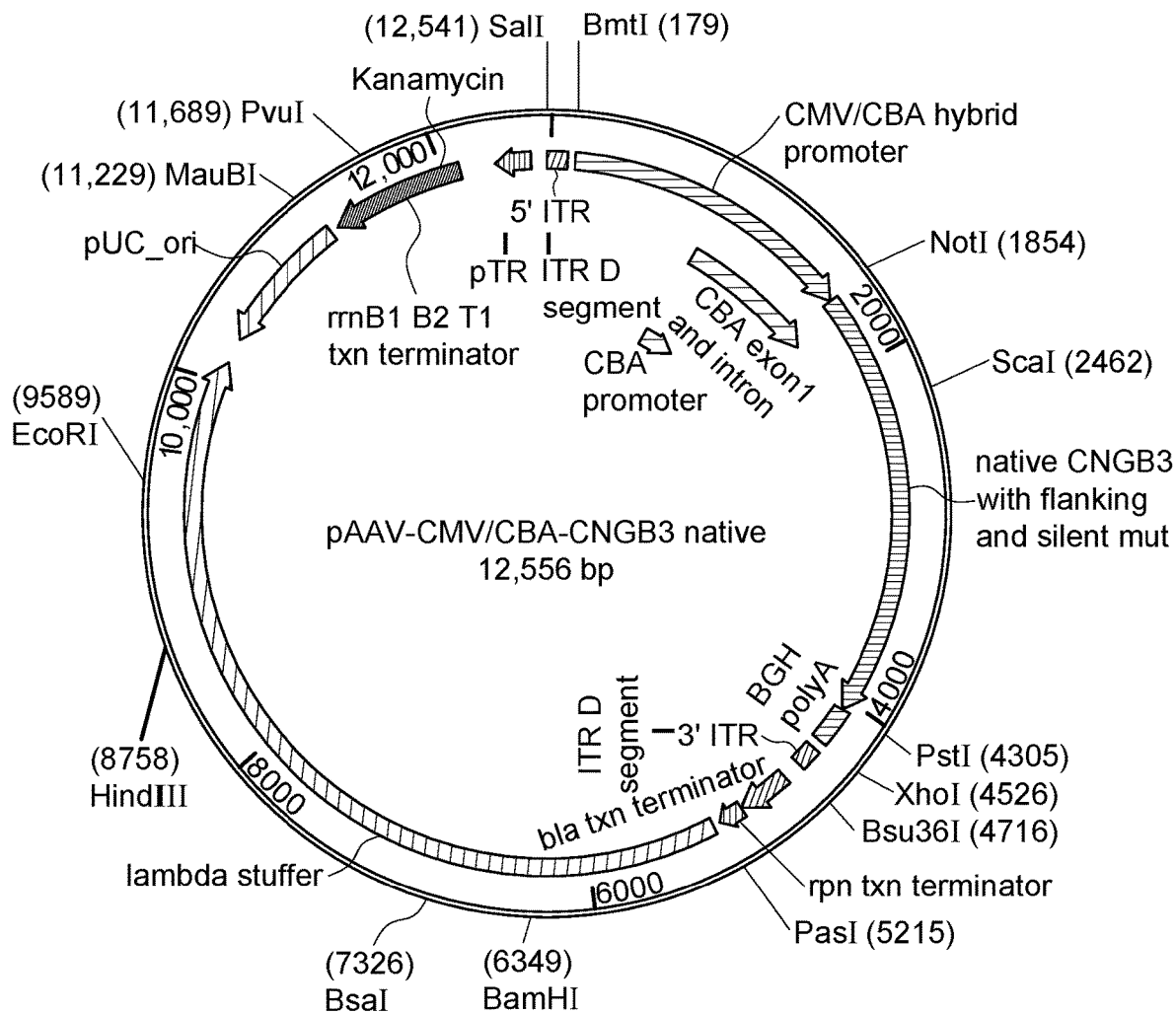
Figure 27A:
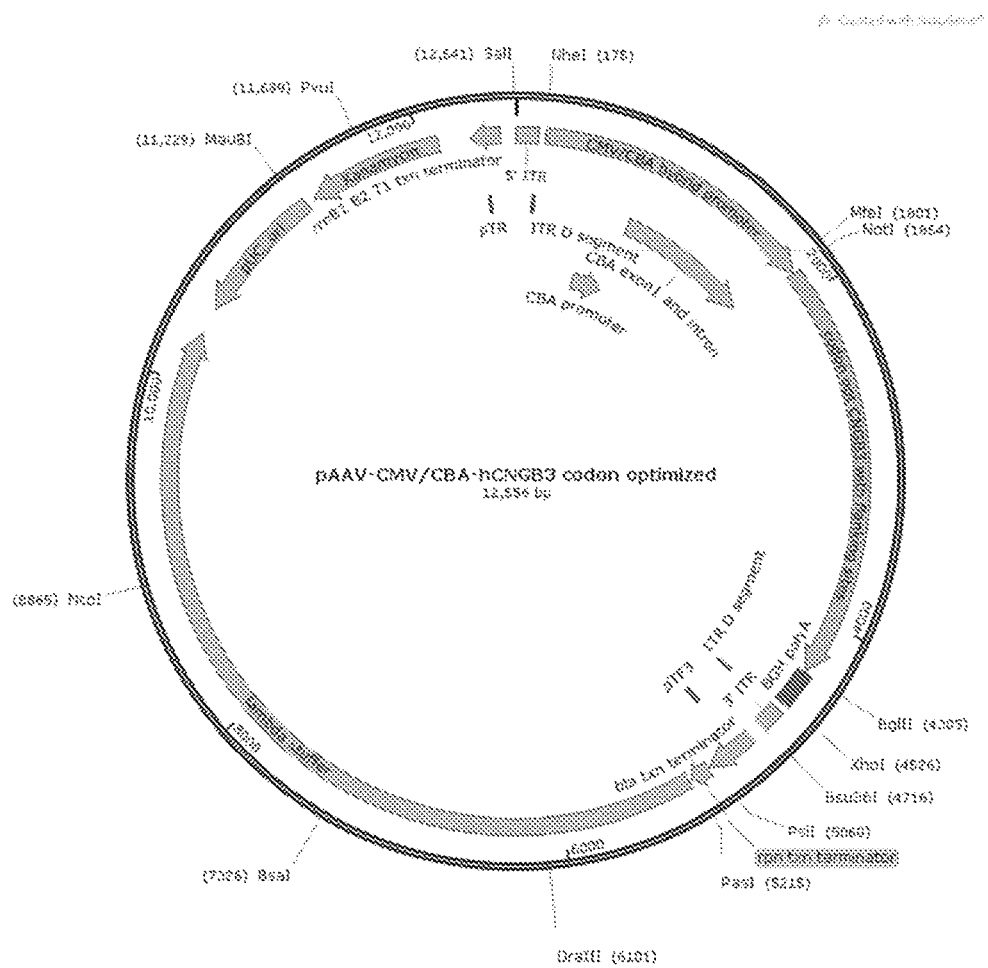

Analysis results for 8 AAV vectors are summarized in the table below, with quantitative comparison between the trans-gene-containing AAV concentration (CMV/CBA) and the KanR-containing impurity concentration. Analysis of results demonstrate that insertion of lambda stuffer into the trans-gene plasmid effectively reduced the occurrence of plasmid-backbone DNA (i.e. KanR) packaging during AAV production from ~7-20 folds (FIG. 11).

TABLE 16 qPCR amplification of kanamycin versus CMV/CBA expressed as percentage

| Sample Name | Lambda Stuffer | CMV/CBA qPCR (vg/ml) | KanR qPCR (vg/ml) | Kan vs. CMV/CBA (%) |
|---|---|---|---|---|
| AAV2.V2b | No | 1.23E+13 | 6.46E+11 | 5.25% |
| AAV2.V2a | Yes | 4.61E+12 | 3.60E+10 | 0.78% |
| AAV8.V2b | No | 3.19E+13 | 1.43E+12 | 4.48% |
| AAV8 V2a | Yes | 2.90E+13 | 1.19E+11 | 0.41% |
| AAV2.V3b | No | 1.26E+13 | 6.69E+11 | 5.31% |
| AAV2.V3a | Yes | 6.33E+12 | 4.56E+10 | 0.72% |
| AAV8.V3b | No | 5.19E+13 | 3.07E+12 | 5.92% |
| AAV8.V3a | Yes | 2.60E+13 | 8.00E+10 | 0.31% |

Example 6: In Vitro Expression of Next Generation AAV8 Vectors in iPS Cells by Western Blot The objective of this study was to evaluate the ability of AAV mediated CHM expression after gene delivery using a series of next generation AAV2 and AAV8 vectors carrying the codon optimized REP-1—encoding gene in induced pluripotent cell lines (iPSC).

Induced pluripotent stem (iPS) cell technology has been successfully utilized as a platform for testing gene therapy vectors in several proof-of-concept and gene therapy studies including ocular diseases. These patient-specific iPS cells provide a valuable in vitro model system to study disease pathogenesis and establish a model to test proof-of-concept of gene therapy where relevant animal models are unavailable. As a preliminary step to test our AAV-mediated gene augmentation therapy for Choroideremia (CHM), we have generated iPS cells from human patients harboring mutations in the causative gene, CHM, which encodes Rab Escort Protein 1 (REP-1) (See example 1) (Method is described in NCP.003). The generated iPS cells were used to evaluate the in vitro expression of our next generation AAV. codon optimized. CHM constructs.

Plasmids and vectors were as described in Example 4. Induced pluripotent stem (iPS) cells are stem cells generated in the laboratory from somatic cells, peripheral blood mononuclear cells, that were reprogrammed back to a pluripotent state. Reprogramming of blood cells enables the development of personalized in vitro cellular models for therapeutic applications. In this report, iPS cells from individuals affected by CHM were used to test the in vitro production of REP-1 protein through western blot analysis. The following table (Table 17) describes the details of iPS cells studied and their respective CHM disease-causing mutations.

TABLE 17

An overview of the iPS cells generated from patients with CHM mutations

| Cell Line | Affected | Mutation in CHM | Method of iPSC generation |
|---|---|---|---|
| JB 588 | Affected | Arg. 555 stop | Sendai virus mediated reprogramming |
| JB 527* | Affected | Exon 2-4 delition | Sendai virus mediated reprogramming |
| JB 500* | Affected | Ex. 10 c.I327_I327 del AT (Needs confirmation) | Sendai virus mediated reprogramming |

*iPS cell line qualification tests are on-going.

Study Design (e.g. Treatment Groups)

1. iPS cells plated on a 12 well cell culture plate are infected with AAV2. hCHM Version 1, Version 2a; Version 2b; Version 3a; Version 3b (AAV2.V1; V2a; V2b; V3a; V3b) at an MOI of either 1E5 or 3E5. After 24 hours of transduction, 1 ml of iPS cell culture media was added to the cells. 36-48 hours of transduction, cells were harvested, lysed and processed for SDS-PAGE followed by Western blot analysis. Production of REP-1 protein was evaluated in cells transduced with all versions of the constructs and compared with untreated controls.

2. As a pilot experiment, three different iPS cell lines plated on a 12 well cell culture plate are transduced with AAV8. hCHM Version 1 and AAV8. hCHM Version 2a (AAV8.V1; AAV8.V2a) at an MOI of 1E6. The iPS cell lines were derived from three CHM affected individuals with unrelated mutations in REP1 gene and were plated in separate plates for this purpose. After 36-48 hours, cells were harvested and lysed and subjected to Western blot analyses compared with untreated cell lysate.

Test Material Administration 3.4.1 Cell Culture

Culturing of iPS cells from CHM patient. In brief, the iPS cells were cultured on Mouse Embryonic Fibroblasts (MEFs, feeders) in iPS cell culture media at 37° C. in an environment supplied with 5% CO2 and 5% O2.

3.4.2 Preparation of Cells for Transduction

The day before seeding the cells, 12-well dishes were coated with Matrigel as described in reference NCP.003 (NCP.003: Culturing of iPS cells from CHM patient and controls). Before transduction of iPS cells with respective AAV2 or AAV8 viral vectors, the cells that are cultured on MEFs were seeded on Matrigel without MEFs (feeder free culturing). Cells were seeded at a density of 4.5+E5 to 6+E5 in 1 ml of iPS cell culture media in each well of a 12-well cell culture dish. Seeded cells were incubated at 37° C. in an environment supplied with 5% CO2, 5% O2.

3.4.3 Transduction

To infect the iPS cells with viral vectors, cells were grown to approximately 50-60% confluence. (This can take 2-4 days in feeder free conditions). Once 50-60% confluence is achieved, one well of the 12-wells is dissociated and cell counts were performed to determine the total number of cells per well. Wells of the iPS cells were then infected with AAV vectors listed below at the predetermined MOI (see Table 18 and 19). Before transduction, the old iPS cell culture media from the plates was removed and a fresh 1 ml of iPS cell culture media was added in each well. Predetermined volumes of the virus from the stock were directly added to each well. See Table 18. And Table 19. For the information on total number of cells infected, MOI and the volume of virus used for infection. Cells were then incubated at 37° C. in an environment supplied with 5% CO2, 5% O2 for 18-24 hours. After 18-24 h of transduction, cells were observed under microscope for any abnormalities or cell death. At this point, another 1 ml of fresh iPS cell culture media was added to each well containing infected and uninfected cells and were further incubated for additional 18-24 hours at 37° C. in an environment supplied with 5% CO2, 5% 02. Cells were observed under the microscope before harvesting to evaluate any cell death or abnormal appearance.

TABLE 18

Infection details and MOIs of next generation AAV2.hCHMV2a, 2B, 3a, 3b Vectors and AAV2.hCHM.V1 vectors in CHM patient-derived iPS cells.

| Vector Used | Cell Line | Cell line number | Cell density | Viral stock concentration (vg/ml) | Vector used (µL) | MOI |
|---|---|---|---|---|---|---|
| AAV2.V2a | iPSC | JB 588 | 6E5 | 2.16E+12 | 30 | 1E5 |
|  | iPSC | JB 588 | 6E5 | 2.16E+12 | 90 | 3E5 |
| AAV2.V2b | iPSC | JB 588 | 6E5 | 7.4E+12 | 8.1 | 1E5 |
|  | iPSC | JB 588 | 6E5 | 7.4E+12 | 24.3 | 3E5 |
| AAV2.V3a | iPSC | JB 588 | 6E5 | 4.82E+12 | 12.4 | 1E5 |
|  | iPSC | JB 588 | 6E5 | 4.82E+12 | 37.3 | 3E5 |
| AAV2.V3b | iPSC | JB 588 | 6E5 | 5.91E+12 | 10.2 | 1E5 |
|  | iPSC | JB 588 | 6E5 | 5.91E+12 | 30.5 | 3E5 |
| AAV2.V1 | iPSC | JB 588 | 6E5 | 4.47E+12 | 30.6 | 1E5 |
|  | iPSC | JB 588 | 6E5 | 4.47E+12 | 40.9 | 3E5 |

TABLE 19

Infection dose of AAV8.V2a and AAV8.V1 vectors in three iPS cell lines derived from 3 different CHM patients.

| Vector Used | Cell Line | Cell line number | Cell density | Viral stock concentration (vg/ml) | Vector used (µL) | MOI |
|---|---|---|---|---|---|---|
| Untreated | iPSC | JB 588 | 4.5E5 |  |  |  |
| AAV8.V2a | iPSC | JB 588 | 4.5E5 | 1.04E+13 | 43 | 1E6 |
| Untreated | iPSC | JB 500 | 4.5E5 |  |  |  |
| AAV8.V1 | iPSC | JB 500 | 4.5E5 | 1.39E+13 | 32 | 1E6 |
| Untreated | iPSC | JB 527 | 4.5E5 |  |  |  |
| AAV8.V1 | iPSC | JB 527 | 4.5E5 | 1.39E+13 | 32 | 1E6 |
| AAV8.V2a | iPSC | JB 527 | 4.5E5 | 1.04E+13 | 43 | 1E6 |

Outcome measurement method—Western blot analysis was performed as described herein.

Results 5.1 Expression of AAV2-hCHM V1, V2a, V2b, V3a, V3b in JB588 iPS cell line: Monoclonal human REP-1-specific antibody, detected one single ~75-80 kDa hREP-1 protein in the transduced JB 588 iPS cells (Data not shown). No band was observed in the case of the untreated control, confirming presence of the disease (data not shown). The intensity of REP-1 protein band at an MOI of 3E5 observed to be stronger in all vectors compared to an MOI of 1E5. Recombinant AAV2. hCHM viral mediated delivery of the hCHM gene, to iPS cells, resulted in a dose-dependent production of REP-1 protein. Probing of the blots with GAPDH antibody showed a band of equal density in all lysates. GAPDH detected a protein at ~39 kDa. Both REP-1 and GAPDH antibodies detected only specific bands of expected molecular weight. No nonspecific bands were observed in the blots.

Expression of AAV8-hCHM. V1, V2a in iPS cells: Monoclonal human REP-1-specific antibody, detected one single ~75-80 kDa REP-1 protein in the transduced JB527, JB500 and JB588 patient derived iPS cells (Data not shown). No protein band was observed in the case of the untreated control. (Data not shown). Probing of the blots with GAPDH antibody showed a band of equal density in all cell lysates including the cell lysates from untreated cells. Anti-GAPDH antibody detected a specific ~39 kDa protein band. Both REP-1 and GAPDH antibodies detected only specific protein bands at the expected size molecular weight. No detectable nonspecific protein bands were observed in the blot.

CONCLUSIONS

The preliminary results presented in the current report revealed the following observations: Western blot analysis confirmed presence of CHM (lack of REP-1 protein) in each one of the three patient-derived iPSCs (JB588, JB500, JB527). In vitro expression studies demonstrated that infecting iPS cells from CHM patients with AAV2.hCHM. Version 2a, 2b, 3a, 3b and AAV2.hCHM Version1 (a current clinical trial candidate) induced the production of REP-1 protein at all tested MOIs. Infecting iPS cells with AAV8. hCHM.Version 2a and AAV8.hCHMVersion1 at an MOI of 1E6 resulted in production of REP1 protein in all three CHM iPS cell lines. Level of REP1 production was higher in the iPSCs infected with AAV8.hCHM.V2a than with AAV8.hCHM.V1.

Example 7: Comparison of In Vivo Expression of AAV8.Codon Optimized.Human CHM Versus AAV.Native.Human CHM Gene therapy for a number of retinal diseases depends on efficient transduction of the appropriate target cells, which for choroideremia, are retinal pigment epithelium (RPE) cells and photoreceptor cells. This study report focuses on the comparison of in vivo expression induced by the native CHM sequence based construct, (Version 1) and four next generation transgene cassettes packaged into an AAV8 backbone in wild type mice. Here we evaluated AAV8 serotype for the purpose of improving gene transfer to photoreceptor cells.

Our experiments were designed to answer the following questions: a. How would these vectors compare for in vivo transduction of photoreceptors: In particular, how efficiently would the next generation AAV8. CHM transduce photoreceptors after subretinal injection of the respective test article compared to version.1.b. Dose response: Would the next generation AAV8. CHM and AAV8. CHM-Version1 vectors differ in dose response of gene expression.

Experimental Details:

Plasmids and vectors were as described in Example 4. Mice (Animals): Wild type, CD1 mice were used to test the in vivo expression of CHM as assessed by production of REP-1 protein. CD1 mouse strain is an outbred Swiss mouse strain which colony we maintain in house. The details of the study are described under CAROT study protocol PCPR02.01.

3.3 Study Design (e.g. Treatment Groups)

3.3.1 Animal Husbandry: Both male and female mice (~3-4 months old) weighing ~20-30 gm were injected with the described test articles. Animals were housed in the University of Pennsylvania's John Morgan University Laboratory Animal Resources (ULAR) facility according to University of Pennsylvania's ULAR regulations. Mice were maintained on a 12-hour light/12-hour dark cycle. Food and water were provided ad libitum. All animals were identified with ear tag numbers.

3.4 Test material administration: The test article formulation provided by the CAROT Vector Core was used for dose administration. The test material was stored at −60 to −80° C. The test material was thawed on ice prior to dosing. For intra-ocular injections, the test article is diluted to the target concentration with phosphate-buffered saline as described in the formulation Table 20. A total of 60 μl of master mix was prepared.

TABLE 20

Dose Formulation table for subretinal injections of test articles.

| Identification | Lot # | Vector Conc (Vg/ml) | Volume (ul) For a total of 60 ul | Volume of PBS (ul) for a total of 60 ul | Injected Conc (vg) | Total vol. inj. (ul) |
|---|---|---|---|---|---|---|
| AAV8.V2a | CT245 | 1.04E+13 | 1.92 | 58.1 | 5E8 | 1.5 μl |
|  |  |  | 19.2 | 40.8 | 5E9 | 1.5 μl |
| AAV8.V2b | CT 244 | 1.11E+13 | 1.8 | 58.2 | 5E8 | 1.5 μl |
|  |  |  | 18 | 42 | 5E9 | 1.5 μl |
| AAV8.V3a | CT 259 | 8.67E+12 | 2.31 | 57.7 | 5E8 | 1.5 μl |
|  |  |  | 23.1 | 36.9 | 5E9 | 1.5 μl |
| AAV8.V3b | CT255 | 1.36E+13 | 1.47 | 58.53 | 5E8 | 1.5 μl |
|  |  |  | 14.7 | 45.3 | 5E9 | 1.5 μl |
| AAV8.V1 | KA8008 | 1.39E+13 | 1.44 | 58.6 | 5E8 | 1.5 μl |
|  |  |  | 14.4 | 45.6 | 5E9 | 1.5 μl |

Preparation of Injection Log Before Subretinal Injections:

An injection log was maintained with the following information before subretinal injection of the test articles:

Cage Number/mouse number

Study Identification

Strain

Date of Birth

Date of injection

Name of investigator/injector

Eye injected into (left or right)

Injection material (vector/serotype)

Dose and Volume

Route of Administration (ROA)

Subretinal injections: Injections were performed by Subretinal Injection by the Surgeon. In brief, animals were anaesthetized before injection. Subretinal injection of the test article was performed using Hamilton 33G syringe. The details of test articles and injections are described in Table 21. From the prepared injection master mix, a volume of 1.5 μl was administered, per injection. One eye per animal was injected with 5E8 vg/eye and the contralateral eye was injected with 5E9 vg/eye.

TABLE 21

Subretinal injection scheme and injection doses

| Gr. No. | Mimimum Number of Animals | ROA | Test Material Identification | Vector Dose (μg/eye) Right Eye | Vector Dose (μg/eye) Left Eye | Dose Volume (μL/eye) Right Eye | Dose Volume (μL/eye) Left Eye | Dosing Day (PD) |
|---|---|---|---|---|---|---|---|---|
| 1 | 2 | Subretinal | AAV8.V2a | 5+E8 | 5+E9 | 1.5 μl | 1.5 μl | Day 90-120 |
| 2 | 2 | Subretinal | AAV8.V2b | 5+E8 | 5+E9 | 1.5 μl | 1.5 μl | Day 90-120 |

TABLE 21-continued

Subretinal injection scheme and injection doses

| Gr. No. | Mimimum Number of Animals | ROA | Test Material Identification | Vector Dose (µg/eye) | | Dose Volume (µL/eye) | | Dosing Day (PD) |
|---|---|---|---|---|---|---|---|---|
| | | | | Right Eye | Left Eye | Right Eye | Left Eye | |
| 3 | 2 | Subretinal | AAV8.V3a | 5+E8 | 5+E9 | 1.5 µl | 1.5 µl | Day 90-120 |
| 4 | 2 | Subretinal | AAV8.V3a | 5+E8 | 5+E9 | 1.5 µl | 1.5 µl | Day 90-120 |
| 5 | 2 | Subretinal | AAV8.V1 | 5+E8 | 5+E9 | 1.5 µl | 1.5 µl | Day 90-120 |
| 6 | 2 | Uninjected | Not Applicable (N/A) | N/A | N/A | N/A | N/A | N/A |

Outcome Measurement Methods

Animal Sacrifice: a. After injecting the animals with the test articles, all animals were observed for 48 hours for any post injection related abnormalities. B. 21-35 days of post injection, the animals were observed for ocular abnormalities using ophthalmoscopy. C. 90-12-days post injection, the animals were sacrificed and eye tissues were collected for evaluating the production of exogenous REP-1 protein by SDS-PAGE followed by western blot analysis.

Collection of Eye Tissue: Eye tissue for western blot analysis was collected after removing the lens from the eye using a sharp surgical blade. The eye (without the lens) was collected in freezer tubes that are labelled appropriately.

Western Blot Analysis

Briefly: 1. Preparation of Tissue Lysate a. Ocular tissue of animals injected with 2 different doses of next generation AAV8. CHM and AAV8.V1 along with the uninjected control animal tissues, were collected after 21-35 days of injection by sacrificing the animals. B. Tissues were then lysed on ice using RIPA buffer with protease inhibitors.

c. Tissue lysates were cleared by centrifuging at 13,000 rpm for 10 min.

2. Quantification and Preparation of Proteins a. Protein quantification of the cell lysates was carried out using ThermoFisher Micro BCA™ Protein Assay Kit following manufacturer's instructions. B. Protein concentration was determined by taking OD reading at 562 nm. C. To evaluate the in vivo expression of CHM, between 20-40 ug of measured protein was loaded on 4-12% Bis-Tris gels.

3. SDS-PAGE and Western Blot

The protein gels were transferred on to a nitrocellulose membrane, blocked in milk and incubated with the primary antibodies. Anti-human REP-1 2F1 antibody (2F1, 1:1000 dilution) and/or anti-GAPDH antibody (1:1000 dilution); were used as primary antibodies. After washing the blot, HRP conjugated anti-mouse IgG antibody and/or anti-rabbit IgG antibody at a concentration of 1:5000 were used as secondary antibodies. The blots were developed by chemiluminescence using ECL reagents according to the manufacturer's instructions.

4. Controls a) Loading controls: Anti-GAPDH antibody was used as loading controls to demonstrate equal loading of protein in each well of the gels. Anti-GAPDH antibody detects a protein of ~39 kDa. B) Positive control: AAV2.V2a transduced COS-7 cell lysates were used as positive controls. C) Negative control: Ocular tissues of uninjected animals were used as negative control.

Sample Value Determination

Quantification of Western blot analysis using Image J software. In brief, densitometric evaluations presented in this report are normalized first, to the levels of endogenous expression of GAPDH protein of the corresponding sample. Then the expression levels are normalized again, to the average REP-1 expression level of uninjected control.

The details of densitometric evaluations and fold change calculations to represent the expression of REP-1 protein are presented as Table 22 and 23.

The description in brief:
1. In table 22 and 23, Column 2 shows the raw values of REP-1 protein and column 3 shows the raw values of GAPDH protein.
2. GAPDH value of each samples was first normalized to the GAPDH values of animal-1 of AAV8.V1 and are shown in Table 22 in 4th column.
3. The values of each sample were also normalized to the GAPDH values of animal-2 of AAV8.V1 and are shown in Table 22 in 5th column.
4. The REP-1 values (Column 2) are then normalized to either to the GAPDH normalized to animal 1 (column 4) or to the GAPDH previously normalized to animal 2 (column 5). These are represented in column 6 and 7 respectively.
5. The normalized REP-1 values are then converted to fold change.
6. The respective REP-1 values are normalized to expression of REP-1 either in animal 1 or animal 2 of the AAV8.V1 injected group and are expressed as fold change (column 8 and 9)
7. Column 10 represents the average fold change in REP-1 protein expression.

Results

Comparison of the CHM expression using the native CHM AAV8.V1 versus the codon optimized CHM vectors: AAV8.V2a, V2b, V3a and V3b. Wild type CD1 mice were injected with two different doses of the each AAV8 vector: a high dose of 5E9 vg/eye and a low dose of 5E8 vg/eye. Following results describe the levels of REP1 protein after injection with high and low doses of AAV8.V1, AAV8.V2a and AAV8.V3a.

Comparison of the expression of AAV8.V1 versus AAV8.V2a and AAV8.V3a (vectors with stuffer) in animals injected with high dose (5E9 vg/eye) of viral vector. Western blot analysis with human anti REP-1 antibody detected a ~75-80 kDa hREP-1 protein band in both (low and high dose injected) ocular tissues of each animal treated with either the next generation AAV8.V2a or V3a or the original AAV8.Version1. A very faint (minimal) band is observed in the case of the uninjected control mice, both. A band of increased intensity was observed in tissues that were transduced with next generation vectors (AAV8V.2a and AAV8.V3a) compared to the tissues transduced with Version. 1. Anti-GAPDH antibodies showed a ~39 kDa band of equal density in all lanes of the western blot including the uninjected controls. Pre-stained protein marker is used to compare the molecular weights of protein of interest. Densitometric evaluation (quantification of the expression level) of the blots using ImageJ software demonstrated that production of REP-1 was increased in animals injected with one of the next generation AAV8. High and low doses constructs (V2a or V3a). (See Table 22 for values.)

through AAV8 results in robust levels of REP-1 protein in comparison with levels produced after injection of AAV8.V3a or AAV8.V1.

Densitometric evaluation (quantification of the expression level) of the blots using ImageJ software further demonstrate an increased production of REP-1 in animals injected with next generation AAV8.CHM constructs (especially V2a) compared with Version 1. See Table 23 for values.

TABLE 22

Quantified REP-1 protein production results for treatment with high dose (5E9vg) AAV8 V1, V2a and V2b

|  | GAPDH | REP-1 | GAPDH Normalized to GAPDH of Version 1 Animal 1 | GAPDH Normalized to GAPDH of Version 1 Animal 2 | REP1 Normalized to respective GAPDH (normalized to animal 1) | REP1 Normalized to respective GAPDH (normalized to animal 2) | Fold change in REP-1 (normalized to animal 1) | Fold change in REP-1 (normalized to animal 2) | Average fold change in REP-1 expression |
|---|---|---|---|---|---|---|---|---|---|
| AAV8.V2a | 12768.589 | 10058.359 | 1.055 | 1.190 | 9533.571 | 8450.521 | 2.335 | 3.742 | 3.038 |
| AAV8.V2a | 11885.518 | 13247.510 | 0.982 | 1.108 | 13489.242 | 11956.812 | 3.303 | 5.294 | 4.299 |
| AAV8.V3a | 12139.418 | 15542.551 | 1.003 | 1.132 | 15495.152 | 13734.843 | 3.794 | 6.081 | 4.938 |
| AAV8V3a | 11113.640 | 7274.388 | 0.918 | 1.036 | 7921.575 | 7021.653 | 1.940 | 3.109 | 2.524 |
| AAV8.V1 | 12102.397 | 4083.761 | 1.000 | 1.128 | 4083.761 | 3619.830 | 1.000 |  |  |
| AAV8.V1 | 10727.518 | 2258.477 | 0.886 | 1.000 | 2547.932 | 2258.477 |  | 1.000 |  |

| Name | REP-1 | GAPDH |
|---|---|---|
| Uninjected Animal-1 | 651.678 | 16633.539 |
| Animal-2 | 253.778 | 13025.397 |

* REP-1 expression values untreated animal was negligible see the values below.

TABLE 23

Quantified REP-1 protein production results for treatment with low dose (5E8 vg) AAV8 V1, V2a and V2b

|  | GAPDH | REP-1 | GAPDH Normalized to GAPDH of Version 1 Animal 1 | GAPDH Normalized to GAPDH of Version 1 Animal 2 | REP1 Normalized to respective GAPDH (normalized to animal 1) | REP1 Normalized to respective GAPDH (normalized to animal 2) | Fold change in REP-1 (normalized to animal 1) | Fold change in REP-1 (normalized to animal 2) | Average fold change in REP-1 expression |
|---|---|---|---|---|---|---|---|---|---|
| AAV8.V2a | 11815.489 | 1194.037 | 0.809 | 0.934 | 13844.203 | 11984.285 | 11.323 | 29.133 | 20.128 |
| AAV8.V2a | 12889.418 | 7162.924 | 0.882 | 1.019 | 8120.634 | 7029.658 | 6.524 | 17.089 | 11.806 |
| AAV8.V3a | 13088.418 | 1516.506 | 0.896 | 1.035 | 1693.128 | 1465.663 | 1.360 | 3.563 | 2.462 |
| AAV8V3a | 9201.075 | 593.192 | 0.630 | 0.727 | 942.048 | 815.519 | 0.757 | 1.982 | 1.370 |
| AAV8.V1 | 14612.782 | 1244.678 | 1.000 | 1.155 | 1244.678 | 1077.460 | 1.000 |  |  |
| AAV8.V1 | 12649.610 | 411.364 | 0.866 | 1.000 | 475.206 | 411.364 |  | 1.000 |  |

|  | REP-1 | GAPDH |
|---|---|---|
| Uninjected Animal-1 | 694.263 | 15930.368 |
| Animal-2 | 254.364 | 13896.246 |

* REP-1 expression values untreated animal was negligible see the values below.

Comparison of the expression of AAV8.V1 versus AAV8.V2a and AAV8.V3a in animals injected with low dose (5E8 vg/eye) of viral vector Human anti REP-1 antibody, the Western blot analysis of the ocular tissues of animals injected with next generation AAV8.V2a,V3a and AAV8.Version1 at a dose of 5E8 detected a ~75-80 kDa hREP-1 protein band in tissues of injected mice. A faint (minimal) band of REP-1 was observed in ocular tissue lysates of the uninjected control mice, both. A band of increased intensity was observed in tissue lysates that are transduced with next generation vectors compared to the lysates that are transduced with Version1. Anti-GAPDH antibody detected an equal intensity protein band at ~39 kDa in all cell lysates. This data demonstrates that delivery of next generation V2a CHM Expression of AAV8.V2b in CD1 mice This current study and the evaluation of lambda stuffer's effect on AAV vector production by qPCR titer analysis were carried out simultaneously. We performed all the animal injections for the in vivo expression study as described in the study protocol PCPR.02 and all samples were harvested. After the qPCR study on the lambda stuffer element was concluded (described above), we decided to carry out the Western blot experiments only to test the expression of AAV vectors without the stuffer such as AAV8.2b and AAV8.3b and exclude them from further analysis (such as comparison with Version 1).

Human anti-REP-1 antibody detected a protein of ~75-80 kDa in ocular tissues of CD-1 mice injected with AAV8.2b at 5E9 (High dose) vector genome copies (FIG. 12A). Animals injected with AAV8.2b at 5E8 (Low dose) showed a very faint protein band at ~75-80 kDa (FIG. 12A). Lysates of ocular tissues from uninjected control animals did not show the presence of REP-1 protein. Anti-GAPDH antibody detected a protein of ~39 kDa in all ocular tissue lysates including the uninjected controls. This data may establish the minimal dose for AAV8.2b.

Expression of AAV8.V3b in CD1 mice

We performed a Western blot analysis on ocular tissues of AAV8.3b injected CD1 mice (2 mice/group) with anti-REP-1 antibody, which revealed the presence of a protein of ~75-80 kDa in one eye injected with low dose and in both eyes injected with high dose of AAV8.3b. In the ocular tissues of uninjected mice there was no REP-1 expression detected (FIG. 12B). The level of REP-1 produced was dose dependent in animals injected with AAV8.3b. Injection with high dose of AAV8.3b (5E9 vector genomes) induced a higher amount of REP-1 compared with the low dose injected eyes (5E8 vector genomes). Anti-GAPDH antibody detected a protein of ~39 kDa in ocular tissue lysates of all injected and uninjected animals.

These results revealed the following observations:
1) The next generation vectors AAV8.Version2a, 2b, 3a and 3b are able to transduce ocular tissues efficiently. 2) Expression of the transgene (codon optimized CHM) was detectable for all of the next generation vectors. 3) Expression of transgene (codon optimized CHM) is dose dependent. 4) AAV8.Version2a and AAV8.Version.2b induced an increased production of REP-1 protein compared to AAV8.Version 1 in ocular tissues of CD-1 mice. 5) There is variation in the exact level of production of the transgenic protein between eyes injected with the same dose reflecting the variability in the surgical delivery procedure. However, differences in levels are large between the low (5E8) and high (5E9) doses. 6) AAV8.CHM.V2a and AAV8.V3a result in much higher levels of REP-1 protein production than AAV8.V1 after in vivo administration of high dose (5E9 vg) vector subretinally in mice.

Example 8: Expression of CNGA3

To maximize the expression of CNGA3, a codon optimized CNGA3 sequence was produced (SEQ ID NO: 9). In addition, a CNGA3 variant was codon optimized (SEQ ID NO: 11). These sequences, as well as the native CNGA3 coding sequence, were incorporated into production plasmids as described herein (SEQ ID Nos: 30-38) and AAV vectors created. Vectors using AAV8 and AAV9 capsids were generated, as described below.

TABLE 24

| | AAV serotype | Transgene cassette |
|---|---|---|
| 1 | AAV8 | RK1-Native CNGA3 |
| 2 | AAV8 | RK1-Codon optimized CNGA3 |
| 3 | AAV8 | RK1-CNGA3 Variant 3 |
| 4 | AAV8 | hCAR-Native CNGA3 |
| 5 | AAV8 | hCAR-Codon optimized CNGA3 |
| 6 | AAV8 | hCAR-CNGA3 Variant 3 |
| 7 | AAV8 | CMV/CBA-Native CNGA3 |
| 8 | AAV8 | CMV/CBA-Codon optimized CNGA3 |
| 9 | AAV8 | CMV/CBA-CNGA3 Variant 3 |
| 10 | AAV8 | hCAR-Native CNGA3 w/WPRE |
| 11 | AAV9 | RK1-Codon optimized CNGA3 |
| 12 | AAV9 | hCAR-Codon optimized CNGA3 |
| 13 | AAV9 | CMV/CBA-Codon optimized CNGA3 |
| 14 | AAV9 | hCAR-Native CNGA3 w/WPRE |

Figure 28:
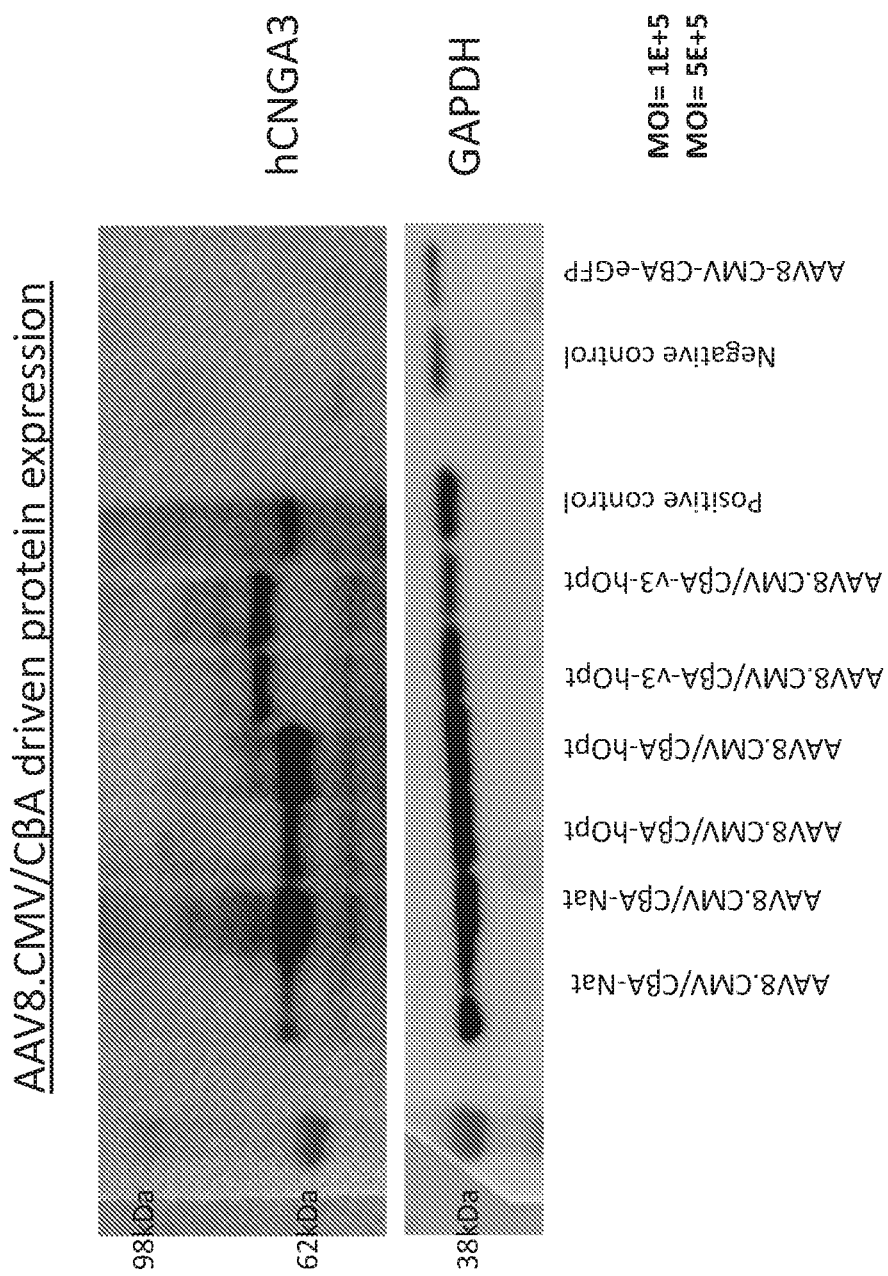
FIG. 28 is a western blot showing hCNGA3 protein expression in 84-31 cells transduced with the noted vectors. 48 hours post transduction, protein was harvested and western blotting was performed. The native and codon optimized (hopt) proteins are expected to be 79 kDa and V3-hopt is expected to be 85 kDa.
Figure 29:
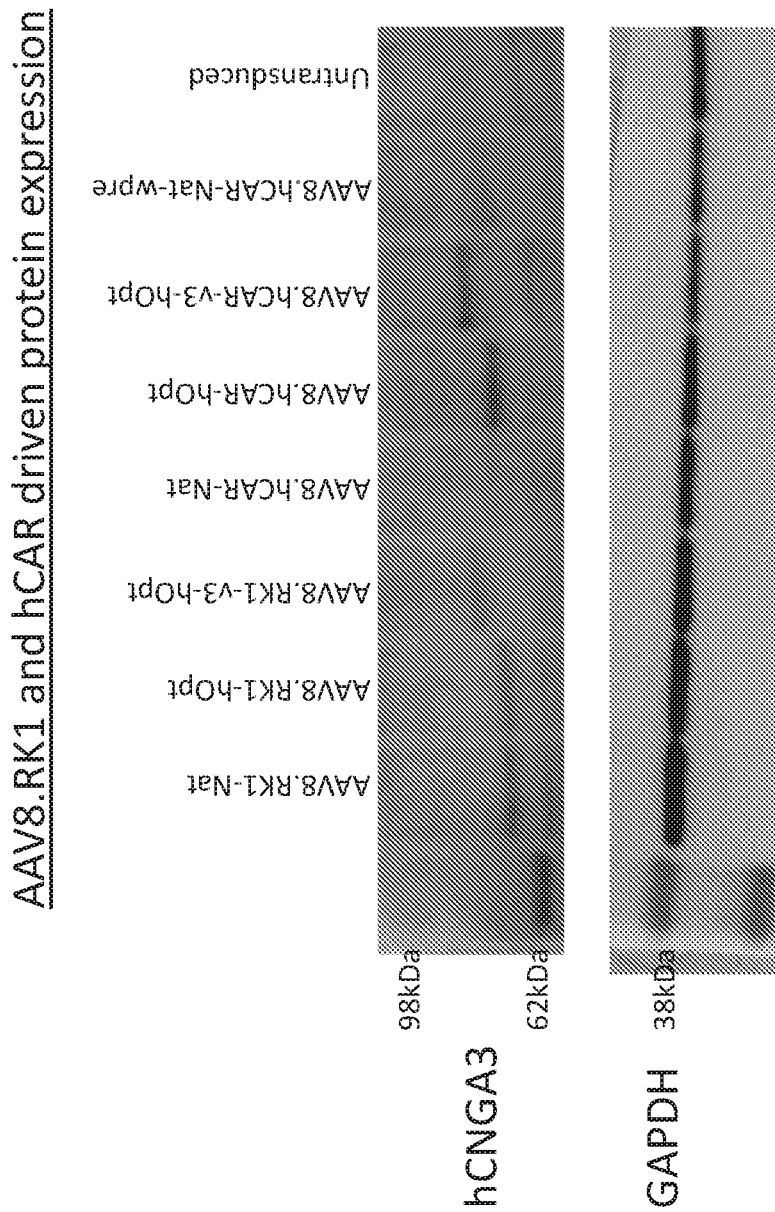
FIG. 29 is a western blot showing hCNGA3 protein expression in 84-31 cells transduced with the noted vectors. 48 hours post transduction, protein was harvested and western blotting was performed. The native and codon optimized (hopt) proteins are expected to be 79 kDa and V3-hopt is expected to be 85 kDa.

Protein expression was assessed, as described above for REP-1. AAV8-CMV-CBA expression is observed in 84-31 cells transduced with each of the 3 CNGA3 vectors at 2 different MOI's. FIG. 28. Positive control used is mouse retinal protein harvested post-injection with AAV8-CMV-CBA-native CNGA3. Codon optimization of CNGA3 plasmid showed enhanced expression with 3 different promoters (CMV/CBA (FIG. 28), RK-1 and hCAR (FIG. 29)). The enhancement with the CMV/CBA promoter is more pronounced at lower dose (presuming saturation at the higher dose).

Exogenous hCNGA3 Expression Using AAV8 & 9 was Tested In Vivo

Figure 30:
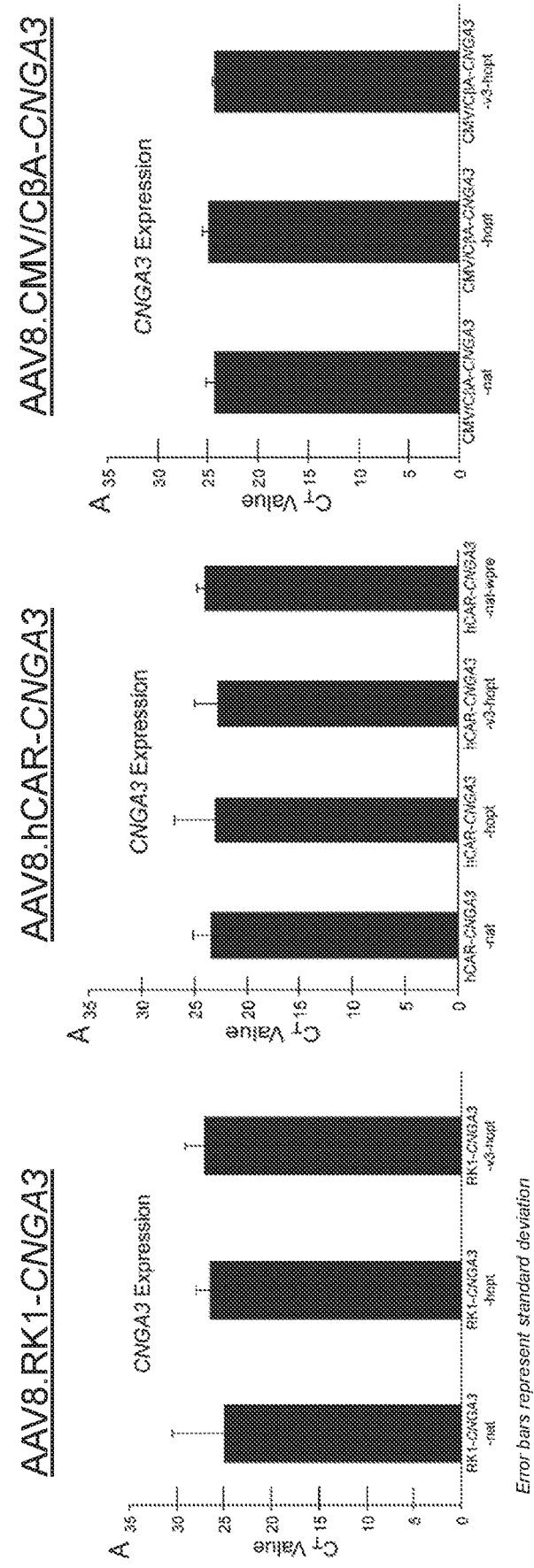
FIG. 30 are three bar graphs showing vector/plasmid expression as measured by RT-PCR for the three noted vectors.

Subretinal injections of 30-120 day old Wt mice were performed. Mice were sacrificed at 3-4 weeks post injection, tissues collected and endpoints measured. In normal mice, expression of CNGA3 measured by qPCR as shown in FIG. 30. In null mice, expression of CNGA3 protein in retina is measured using western and IHC and retinal histopathology is examined.

The CNGA3 mouse model: CNGA3 null mice which have a CPFL5 containing a missense mutation (Exon 5).

Phenotype:

5 weeks: severely reduced cone-specific ERGs 10 weeks: reduction and mislocalization of cone opsin pigments 5 months: Reduced optokinetic reflexes Gene Replacement Therapy for CNGA3-Achromatopsia:

CNGA3 null mice were injected at p16-18, subretinally with one of two doses of noted vectors. Low dose: 8E8 vg/eye; high dose: 8E9 vg/eye. At least 5 animals were injected per group. ERG and OKR were performed at 5-7 weeks and 12-15 weeks. At sacrifice, IHC, western blots and histology were performed.

To provide objective information about the function of retina and to serve as a parameter for efficacy in preclinical studies, electroretinogram (ERG), an electrical response of the cells of the retina to a flash of light, was evaluated in mice according to conventional method and User Manuals. Please see, e.g. Marmor, Michael F., et al. "Standard for clinical electroretinography (2004 update)." *Documenta ophthalinologica* 108.2 (2004): 107-114; and Cronin, Therese, Arkady Lyubarsky, and Jean Bennett "Dark-rearing the rd10 mouse: implications for therapy." *Retinal Degenerative Diseases*. Springer US, 2012. 129-136.

Briefly, an ophthalmoscopic evaluation of animals was completed prior to ERG measurement. Mice with eye defects that may potentially compromise the results of the ERG are excluded. These include corneal opacities such as cataract, corneal injury or inflammation. Mice were then dark-adapted for at least 4 h, weighed under dark conditions and injected anaesthetic intraperitoneally (ketamine/xylazine cocktail with phosphate buffered saline (PBS; pH 7.2), 100 mg/kg and 10 mg/kg respectively). The pupils of pigmented mice were dilated using 1% tropicamide solution while albino mice did need pupil dilation. While the animal was kept on an absorbent bedding on top of the heated platform, the reference electrode was placed to contact with the body of the mouse, and the recording electrodes were positioned over the cornea of respective eyes and contacting with the corneas gently. If necessary, operations using a magnifier was performed.

Stimulator was set as indicated below. Stimuli of any color or achromatic may be used unless indicated. Testing protocol I includes Step 1: 0.01076 scotopic cd s m$^{-2}$ (Candela second per square meter (cd/m$^2$)); Step 2: 500 scotopic cd s m$^{-2}$, achromatic xenon flash; and Step 3: background intensity 100 scotopic cd m$^{-2}$, Stimulus: 500 scotopic cd s m$^{-2}$. In stimulus intensity Set II, for all steps the following stimuli were delivered on a 100 scotopic cd m$^{-2}$ (Candela per square meter (cd/m$^2$)) green (520 nm) background illumination. Testing protocol II includes: Step 1: 500 scotopic cd s m$^{-2}$, achromatic xenon flash; Step 2: 0.0015 cd s m$^{-2}$, UV (365 nm), isi (Interstimulus interval, time interval between consecutive flashes) 1.5 s; Step 3: 0.004 cd s m$^{-2}$, UV (365 nm), isi 1.5 s; Step 4: 0.01 cd s m$^{-2}$, UV (365 nm), isi 2 s; Step 5: 0.03 cd s m$^{-2}$, UV (365 nm), isi 2 s; Step 6: 4scot cd s m$^{-2}$, green (520 nm), isi 2 s; Step 7: 10 scot cd s m$^{-2}$, green (520 nm), isi 2 s; Step 8: 25scot cd s m$^{-2}$, green (520 nm), isi 2 s; and Step 9: 500 scotopic cd s m$^{-2}$, achromatic xenon flash. Testing protocol I and II was run on each animal successively.

The CNG3A/B3 null mice used have normally functioning rods, so the rod-generated ERG was utilized as a signature of the retina condition. The parameter was the amplitude of the saturating a-wave. On stimulation with a bright flash, a fast cornea-negative voltage, was the first (in temporal order) component of the ERG. The amplitude of the a-wave was the difference between the most negative point of the ERG during the time interval of up to 20 ms after the flash and the baseline value of the ERG signal measured at the 3 ms time point after the flash. The choice of the 3 ms data point as the "zero" allowed for exclusion of the flash artifact and minimizing effects of drifts. With incremental increase of stimulus intensity, the amplitude of the a-wave increased until it reached saturation. The a-wave of the mouse ERG is directly proportional to the magnitude of the retinal rod photocurrent (Lyubarsky, Arkady, L., and Edward N, Pugh Jr. "Recovery phase of the murine rod photoresponse reconstructed from electroretinographic recordings." Journal of Neuroscience 16.2 (1996): 563-571), and therefore, is the most direct measure of the rod function.

The amplitude of the a-wave as the voltage difference between baseline and the first trough, which occurs at 7-10 ms after the flash was measured for both eyes using data acquired via testing protocol I. Amplitudes of cone ERGs was measured using the data acquired via testing protocol II. Magnitudes of cone ERGs was divided by the amplitude of the saturating a-wave from the respective eye. If the amplitude of the a-wave from the injected eye was less than 50% of the amplitude of the a-wave from the control eye, this animal was excluded from further processing and counted as severely injured on injection. Results acquired were calculated and normalized. Paired t-test between sets of normalized cone ERGs from the injected and non-injected eye was performed. Statistically significant improvement in the treated eye was to be a signature of successful treatment.

Figure 31:
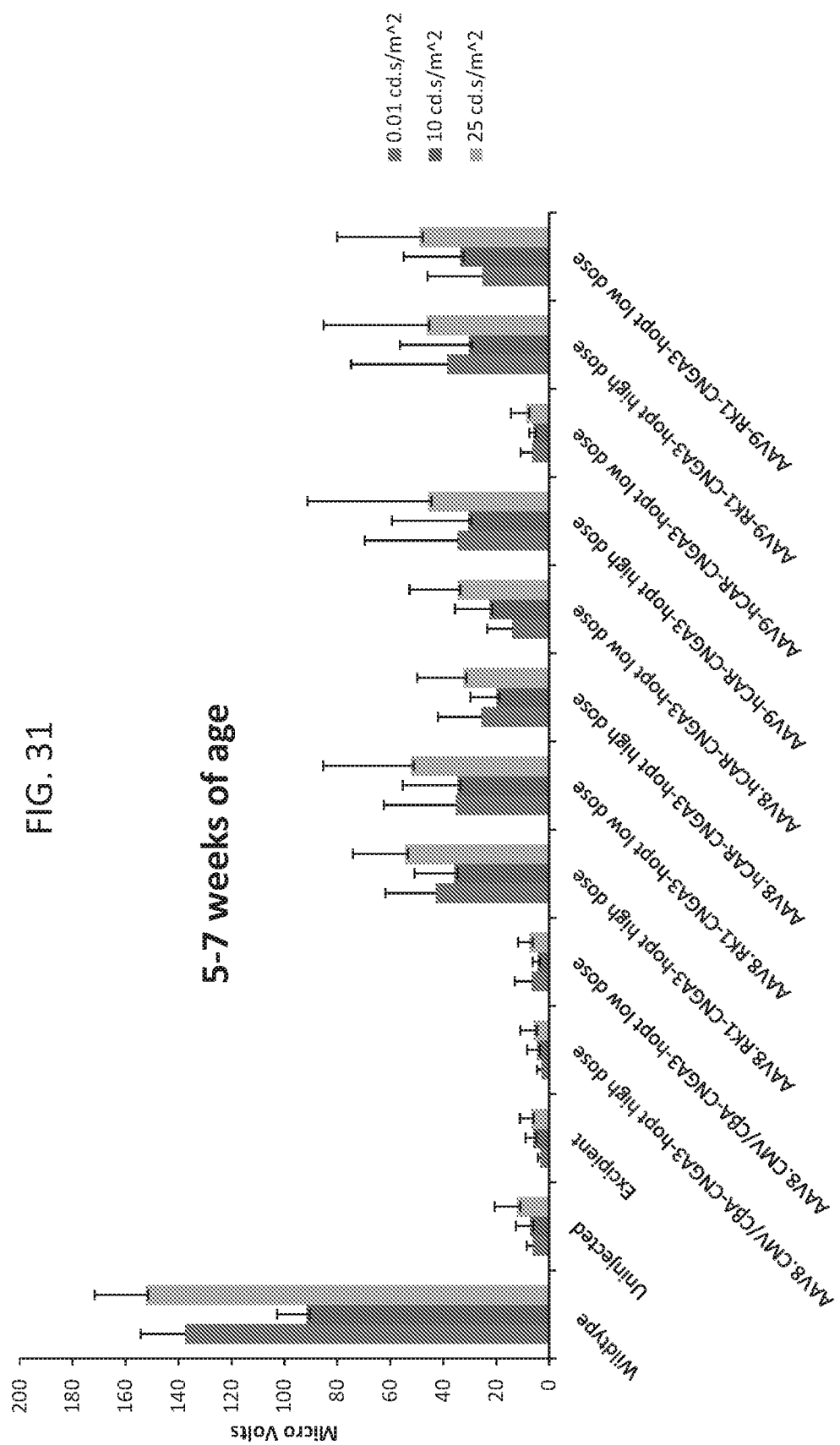
FIG. 31 is a bar graph showing the results of cone ERG for CNGA3 null mice treated with the noted vectors, as described in Example 8. n>5 for all groups, error bars represent standard deviation.

Retinal function was assessed at 5-7 weeks of age following administration of the noted vectors was compared to retinal function of wild type, excipient injected and uninjected eyes. The measured results from three light intensities (0.01 cd·s/m^2, 10 cd·s/m^2 and 25 cd·s/m^2) for each vector/dosage are shown below in Table 25, and in FIG. 31. These results show that RK-1 promoter along with optimized CNGA3 expression cassette is able to correct ERG function in a mouse model.

TABLE 25

| | Student's t-test | | |
|---|---|---|---|
| Uninjected versus: | 0.01 cd·s/m^2 | 10 cd · s/m^2 | 25 cd · s/m^2 |
| Excipient | 4.09E−06 | 0.161284 | 0.007365 |
| AAV8.CMV/CβA-CNGA3-hopt high dose | 0.003812136 | 0.214523 | 0.060289 |
| AAV8.CMV/CβA-CNGA3-hopt low dose | 0.77537772 | 0.305382 | 0.279831 |
| AAV8.RK1-CNGA3-hopt high dose | 5.05248E−07 | 1.02E−06 | 1.72E−07 |
| AAV8.RK1-CNGA3-hopt low dose | 0.001563149 | 0.000454 | 0.000995 |
| AAV8.hCAR-CNGA3-hopt high dose | 0.00051437 | 0.000873 | 0.001657 |
| AAV8.hCAR-CNGA3-hopt low dose | 0.011644961 | 0.002392 | 0.001796 |
| AAV9-hCAR-CNGA3-hopt high dose | 0.010237532 | 0.012328 | 0.020935 |
| AAV9-hCAR-CNGA3-hopt low dose | 0.843706492 | 0.669637 | 0.432698 |
| AAV9-RK1-CNGA3-hopt high dose | 0.004789373 | 0.005494 | 0.009589 |
| AAV9-RK1-CNGA3-hopt low dose | 0.004873537 | 0.000563 | 0.000923 |

P values are shown.

Figure 32A:
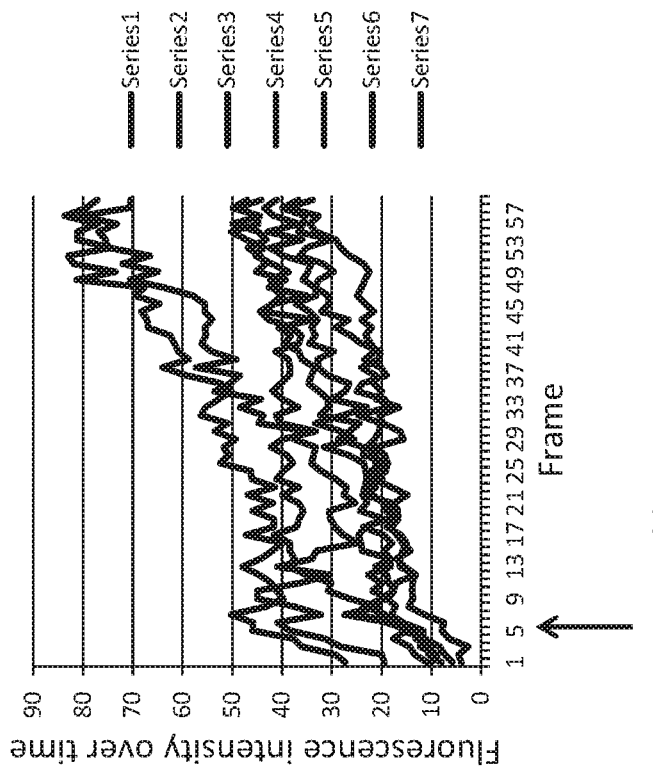
FIG. 32A and FIG. 32B are two line graphs showing fluorescence intensity of untransduced (FIG. 32A) and transduced (FIG. 32B) cells. These results demonstrate calcium uptake in transduced vs. untransduced 84-31 cells after cGMP addition. Each series is a cell.
Figure 32B:
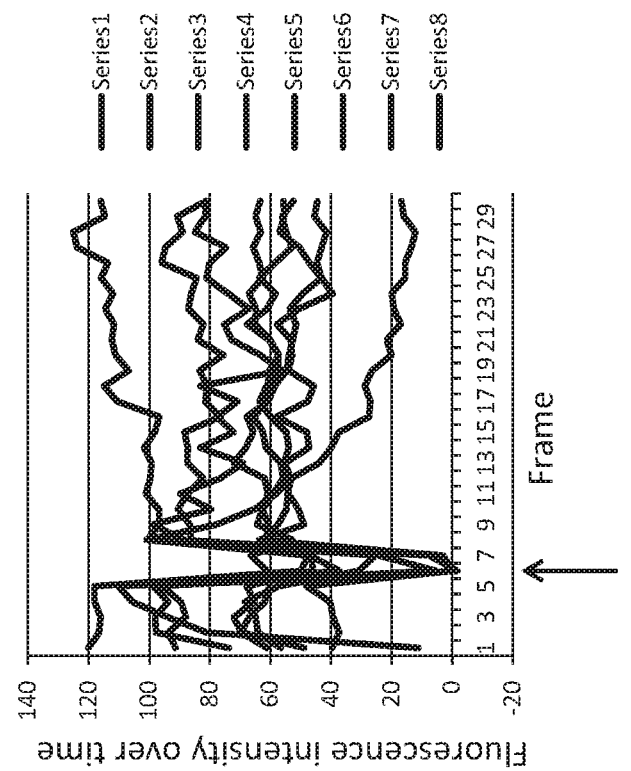

Calcium uptake in transduced vs. untransduced 84-31 cells after cGMP addition is shown in FIG. 32.

Example 9: CNGB3

CNGB3 sequences were incorporated into vectors as described above, for REP-1 and CNGA3. Vectors using AAV8 and AAV9 capsids were generated, as described below.

CNGB3 null mice were injected at p16-18, subretinally with one of two doses of noted vectors. Low dose: 1E9 vg/eye; high dose: 1E10 vg/eye. At least 5 animals were injected per group. ERG and OKR were performed at 5-7 weeks and 12-15 weeks. At sacrifice, IHC, western blots and histology were performed.

Retinal function was assessed at 12-16 weeks of age following administration of the noted vectors was compared to retinal function of wild type, excipient injected and uninjected eyes. The measured results from three light intensities (0.01 cd·s/m^2, 10 cd·s/m^2 and 25 cd·s/m^2) for each vector/dosage are shown below, and in FIG. 33. Series 5, 8 and 9 are light intensities of 0.01 cd·s/m^2, 10 cd·s/m^2 and 25 cd·s/m^2, respectively.

These results show that both hCAR and RK-1 promoter along with optimized CNGB3 expression cassette are able to correct ERG function in the CNGB3 mouse model.

ERG studies suitable for use with the constructs described herein, are described, e.g., in International Patent Application No. PCT/US17/27529, filed Apr. 14, 2017, which is incorporated herein by reference.

Example 10: ELECTRORETINOGRAM (ERG) of MICE

To provide objective information about the function of retina and to serve as a parameter for efficacy in preclinical studies, electroretinogram (ERG), an electrical response of the cells of the retina to a flash of light, was evaluated in mice according to conventional method and User Manuals. Please see, e.g. Marmor, Michael F., et al. "Standard for clinical electroretinography (2004 update)." Documenta ophthalmologica 108.2 (2004): 107-114; and Cronin, Therese, Arkady Lyubarsky, and Jean Bennett. "Dark-rearing the rd10 mouse: implications for therapy." Retinal Degenerative Diseases. Springer US, 2012. 129-136.

Briefly, an ophthalmoscopic evaluation of animals was completed prior to ERG measurement. Mice with eye defects that may potentially compromise the results of the ERG are excluded. These include corneal opacities such as cataract, corneal injury or inflammation. Mice were then dark-adapted for at least 4 h, weighed under dark conditions and injected anaesthetic intraperitoneally (ketamine/xylazine cocktail with phosphate buffered saline (PBS; pH 7.2), 100 mg/kg and 10 mg/kg respectively). The pupils of pigmented mice were dilated using 1% tropicamide solution while albino mice did need pupil dilation. While the animal was kept on an absorbent bedding on top of the heated platform, the reference electrode was placed to contact with the body of the mouse, and the recording electrodes were positioned over the cornea of respective eyes and contacting with the corneas gently. If necessary, operations using a magnifier was performed.

Stimulator was set as indicated below. Stimuli of any color or achromatic may be used unless indicated. Testing protocol I includes Step 1: 0.01076 scotopic cd s m-2 (Candela second per square meter (cd/m2)); Step 2: 500 scotopic cd s m-2, achromatic xenon flash; and Step 3: background intensity 100 scotopic cd m-2, Stimulus: 500 scotopic cd s m-2. In stimulus intensity Set II, for all steps the following stimuli were delivered on a 100 scotopic cd m-2 (Candela per square meter (cd/m2)) green (520 nm) background illumination. Testing protocol II includes: Step 1: 500 scotopic cd s m-2, achromatic xenon flash; Step 2: 0.0015 cd s m-2, UV (365 nm), isi (Interstimulus interval, time interval between consecutive flashes) 1.5 s; Step 3: 0.004 cd s m-2, UV (365 nm), isi 1.5 s; Step 4: 0.01 cd s m-2, UV (365 nm), isi 2 s; Step 5: 0.03 cd s m-2, UV (365 nm), isi 2 s; Step 6: 4scot cd s m-2, green (520 nm), isi 2 s; Step 7: 10 scot cd s m-2, green (520 nm), isi 2 s; Step 8: 25scot cd s m-2, green (520 nm), isi 2 s; and Step 9: 500 scotopic cd s m-2, achromatic xenon flash. Testing protocol I and II was run on each animal successively.

The CNG3 mice used have normally functioning rods, so the rod-generated ERG was utilized as a signature of the retina condition. The parameter was the amplitude of the saturating a-wave. On stimulation with a bright flash, a fast cornea-negative voltage, was the first (in temporal order) component of the ERG. The amplitude of the a-wave was the difference between the most negative point of the ERG during the time interval of up to 20 ms after the flash and the baseline value of the ERG signal measured at the 3 ms time point after the flash. The choice of the 3 ms data point as the "zero" allowed for exclusion of the flash artifact and minimizing effects of drifts. With incremental increase of stimulus intensity, the amplitude of the a-wave increased until it reached saturation. The a-wave of the mouse ERG is directly proportional to the magnitude of the retinal rod photocurrent (Lyubarsky, Arkady L., and Edward N. Pugh Jr. "Recovery phase of the murine rod photoresponse reconstructed from electroretinographic recordings." Journal of Neuroscience 16.2 (1996): 563-571), and therefore, is the most direct measure of the rod function.

The amplitude of the a-wave as the voltage difference between baseline and the first trough, which occurs at 7-10 ms after the flash was measured for both eyes using data acquired via testing protocol I. Amplitudes of cone ERGs was measured using the data acquired via testing protocol II. Magnitudes of cone ERGs was divided by the amplitude of the saturating a-wave from the respective eye. If the amplitude of the a-wave from the injected eye was less than 50% of the amplitude of the a-wave from the control eye, this animal was excluded from further processing and counted as severely injured on injection. Results acquired were calculated and normalized. Paired t-test between sets of normalized cone ERGs from the injected and non-injected eye was performed. Statistically significant improvement in the treated eye was to be a signature of successful treatment.

Example 11: Evaluation of Lambda Stuffer's Effect

Figure 34:
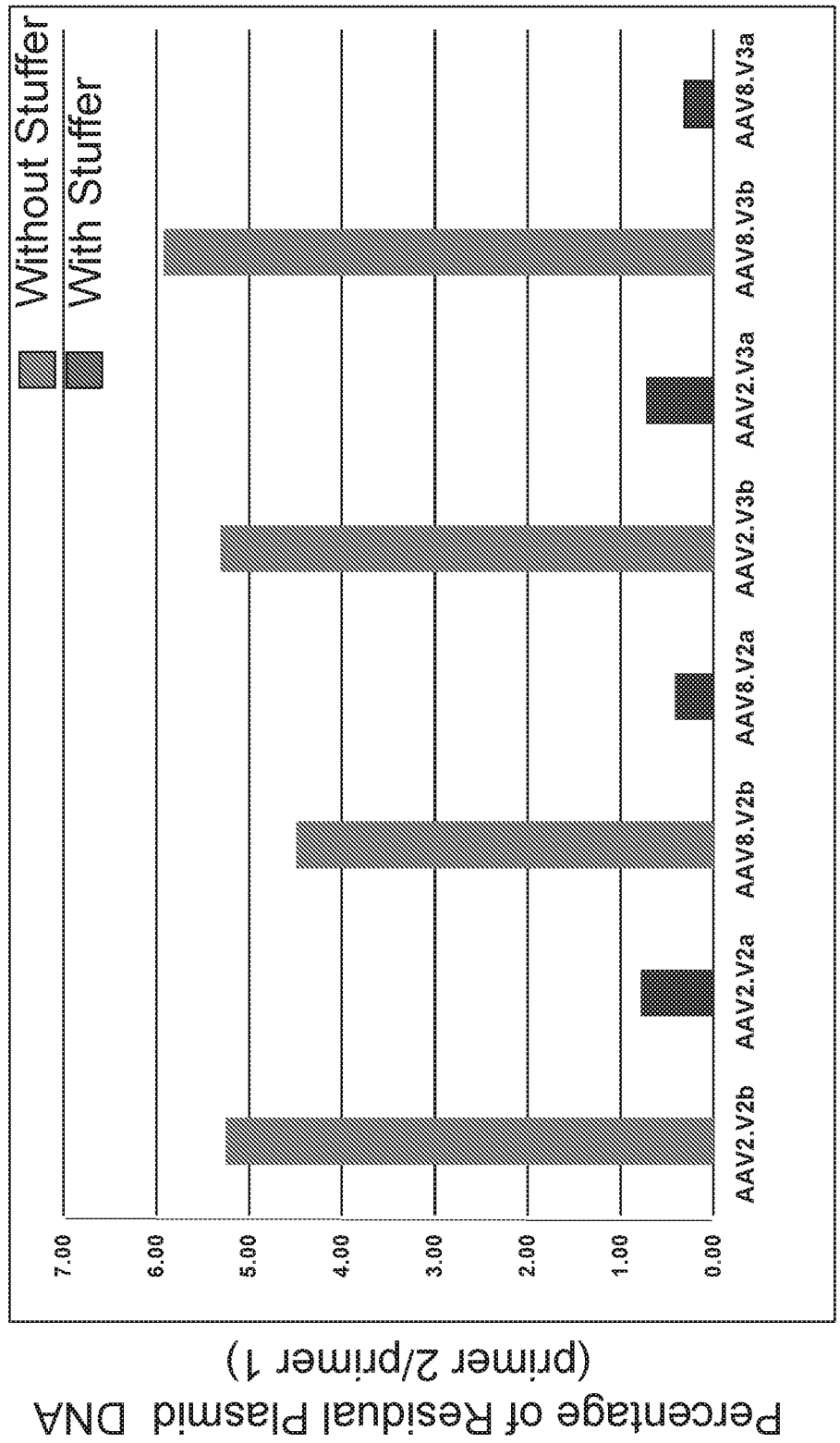
FIG. 34 is a graphic representation of the effect of lambda insert on AAV product impurity.
Figures 35, 36:
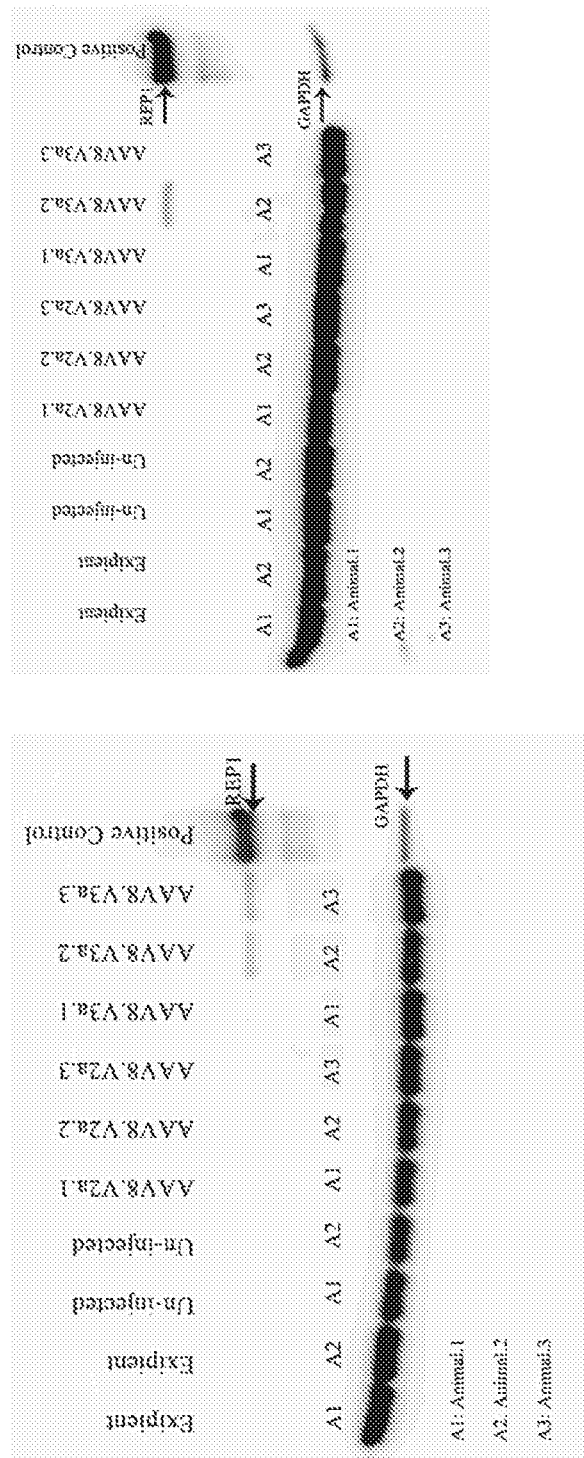
FIG. 35 is a western blot showing human anti-REP-1 antibody detection of a protein of ~75-80 kDa in ocular tissues of CD-1 mice injected with indicated rAAVs at 5E7 vector genome copies per eye. A1, A2 and A3 indicate Animal 1, 2 and 3, respectively.
FIG. 36 is a western blot showing human anti-REP-1 antibody detection of a protein of ~75-80 kDa in ocular tissues of CD-1 mice injected with indicated rAAVs at 1E8 vector genome copies per eye. A1, A2 and A3 indicate Animal 1, 2 and 3, respectively.
Figure 37:
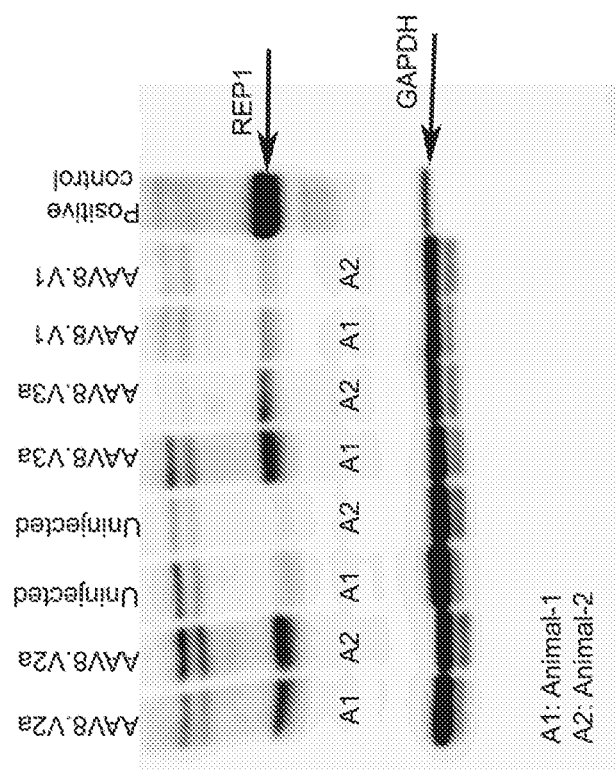
FIG. 37 is a western blot showing human anti-REP-1 antibody detection of a protein of ~75-80 kDa in ocular tissues of CD-1 mice injected with indicated rAAVs at 5E8 vector genome copies per eye. A1 and A2 indicate Animal 1 and 2, respectively.
Figure 38:
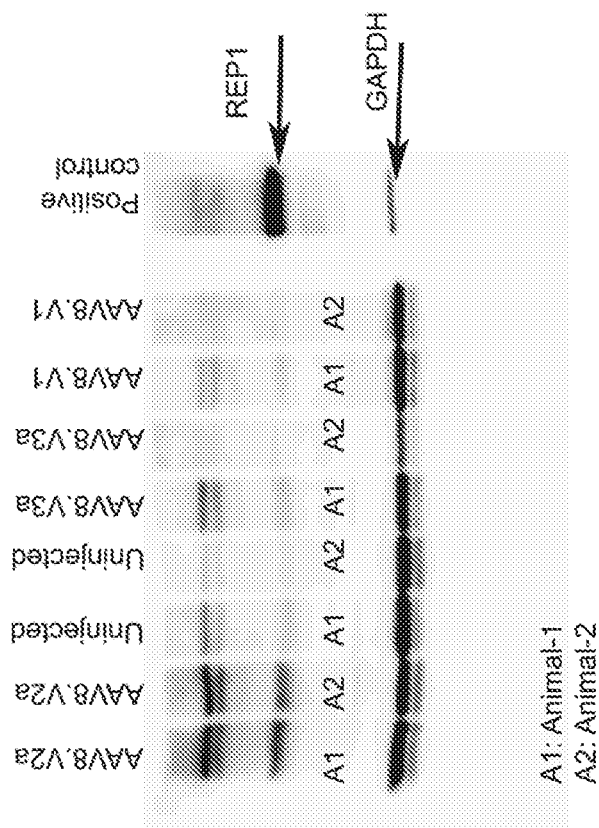
FIG. 38 is a western blot showing human anti-REP-1 antibody detection of a protein of ~75-80 kDa in ocular tissues of CD-1 mice injected with indicated rAAVs at 5E9 vector genome copies per eye. A1 and A2 indicate Animal 1 and 2, respectively.
Figure 39A:
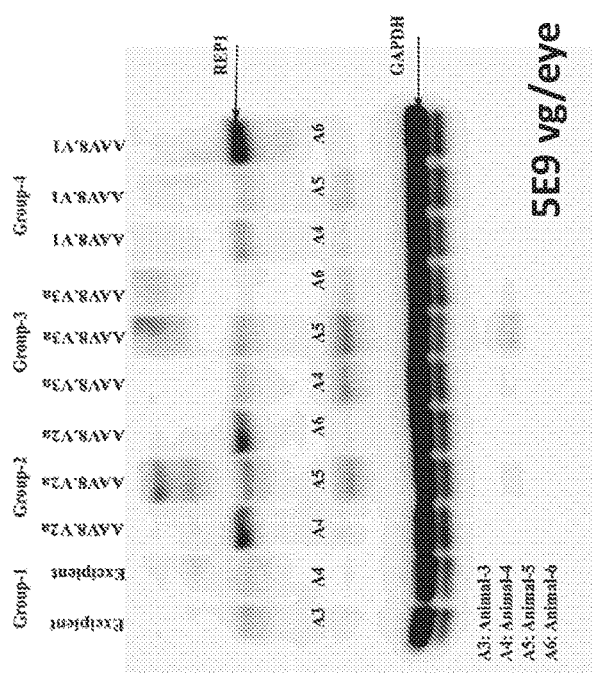
FIGS. 39A and 39B are western blots showing human anti-REP-1 antibody detection of a protein of ~75-80 kDa in ocular tissues of CD-1 mice injected with indicated rAAVs at 5E9 vector genome copies per eye (FIG. 39A) or 1E10 vector genome copies per eye (FIG. 39B). A3, A4, A5, and A6 indicate Animal 3, 4, 5, and 6, respectively.
Figure 39B:
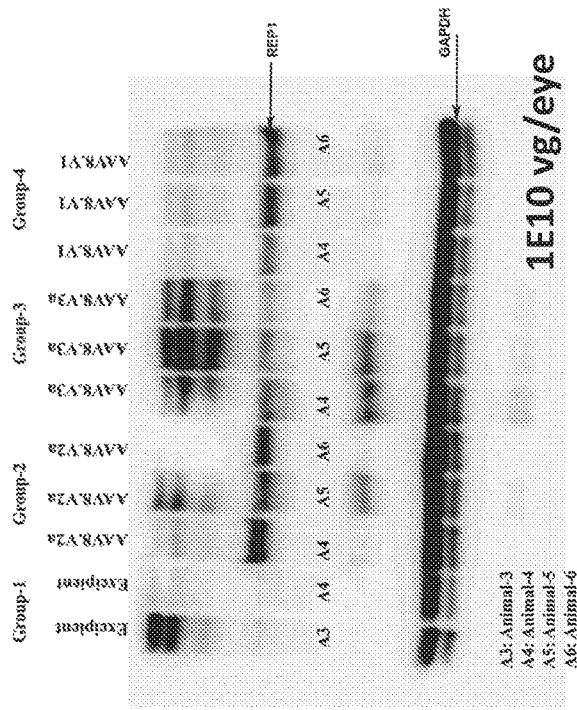

Further to the experiments described in Example 6, percentage of residual plasmid DNA was evaluated and the data acquired was plotted in FIG. 34. Result showed that oversized stuffer sequences reduced DNA impurity by ~80% during triple transfection production for both AAV2 and AAV8.

Example 12: In Vivo Expression of rAAV

Further to the experiments described in Example 7, various dosages (5E7 vector genome copies per eye (vg/eye), 1E8 vg/eye, 5E8 vg/eye, 5E9 vg/eye, and 1E10 vg/eye) of AAV8.V2a, AAV8.V3a and AAV8.V1 were injected to about 3-4-month-old CD-1 mice. Eyeballs were harvested and REP1 protein expressions thereof were evaluated via Western blots. Representative results are shown in FIGS. 35 to 39. Quantifications were performed and indicated in the Tables below. Results showed that compared to AAV8.V1, AAV8.V2a and AAV8.V3a demonstrated higher expression level of REP1 protein at 5E8 vg/eye, 5E9 vg/eye. Subretinal delivery of AAV8.V2a, and AAV8.V3a resulted in robust and reproducible delivery of the CHM transgene to retinal cells. Recombinant AAV8.CHM mediated delivery of the CHM gene resulted in a dose-dependent effect on REP1 protein production.

TABLE 26

| Virus | 5E8 vg/eye Fold Change Relative to AAV8.V1 | 5E9 vg/eye Fold Change Relative to AAV8.V1 |
|---|---|---|
| AAV8.V2a (Animal 1) | 21.17 | 3.04 |
| AAV8.V2a (Animal 2) | 13.39 | 4.58 |
| AAV8.V3a (Animal 1) | 2.62 | 4.90 |
| AAV8.V3a (Animal 2) | 1.78 | 2.57 |

TABLE 27

| Virus | 5E9 Fold Change Relative to AAV8.V1 | 1E10 Fold Change Relative to AAV8.V1 |
|---|---|---|
| AAV8.V2a (Animal 1) | 15.88 | 0.08 |
| AAV8.V2a (Animal 2) | 1.44 | 0.32 |
| AAV8.V2a (Animal 3) | 15.03 | 2.15 |
| AAV8.V2a (Animal 4) | 8.70 | 2.04 |
| AAV8.V2a (Animal 5) | 1.66 | 1.16 |
| AAV8.V2a (Animal 6) | 6.13 | 1.53 |

TABLE 27-continued

| Virus | 5E9 Fold Change Relative to AAV8.V1 | 1E10 Fold Change Relative to AAV8.V1 |
|---|---|---|
| AAV8.V3a (Animal 1) | 9.27 | 0.99 |
| AAV8.V3a (Animal 2) | 4.51 | 0.99 |
| AAV8.V3a (Animal 3) | 0.33 | 0.15 |
| AAV8.V3a (Animal 4) | 0.80 | 0.64 |
| AAV8.V3a (Animal 5) | 0.79 | 0.52 |
| AAV8.V3a (Animal 6) | 0.13 | 0.30 |

Example 13: Retinal Histopathology Upon Injection of rAAVs

Analysis of retinal histopathology was performed on the retina harvested from the mice treated as described in Example 7 and Example 12. H&E staining was performed to reveal changes on photoreceptors as well as presence of immune infiltration. Tunel staining was performed to reveal the presence of apoptosis. Ve treated cells was provided as a positive control. Represented images not shown. A summary of the observation was provided below as a Table. Results indicate that recombinant AAV8.CHM mediated delivery of the CHM-gene resulted in a dose-dependent effect on REP1 protein production and retinal histopathology. Mouse eyes injected with the highest dose of AAV8.V2a, AAV8.V3, and AAV8.V1 showed inflammation, retinal degeneration and apoptosis.

TABLE 28

| Identification | Injected vg/eye | H&E | TUNEL |
|---|---|---|---|
| AAV8.V2a | 5E7 | — | N/A |
| | 1E8 | — | N/A |
| | 5E8 | — | N/A |
| | 5E9 | Mild: Loss of photoreceptors, presence of immune infiltrates | very few +Ve cells |
| | 1E10 | Severe: Loss of photoreceptors, presence of immune infiltrates | +Ve |
| AAV8.V3a | 5E7 | — | N/A |
| | 1E8 | — | N/A |
| | 5E8 | — | N/A |
| | 5E9 | Mild: Loss of photoreceptors, presence of immune infiltrates | very few +Ve cells |
| | 1E10 | Severe: Loss of photoreceptors, presence of immune infiltrates | +Ve |
| AAV8.V1 | 5E8 | — | N/A |
| | 5E9 | Mild: Loss of photoreceptors, presence of immune infiltrates | very few +Ve cells |
| | 1E10 | Severe: Loss of photoreceptors, presence of immune infiltrates | +Ve |

Example 14: iPSCs

Figure 40:
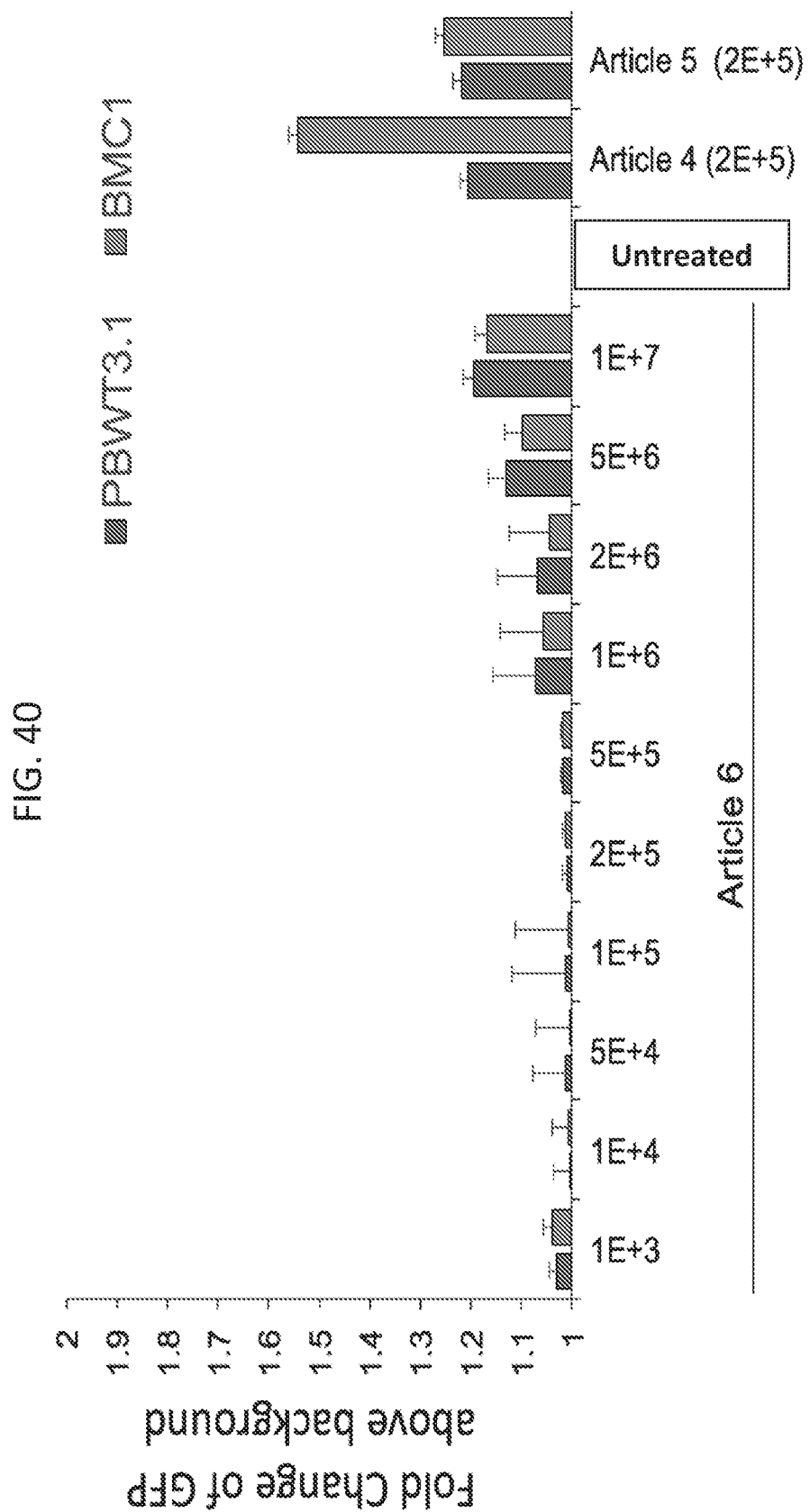
FIG. 40 is a graphic representation of transduction efficiency of AAV8.CMV/CbA-GFP (indicated as Article 6) and AAV2.CMV/CbA-GFP (indicated as Article 5) in PBWT3.1 cells or BMC1 Cells at various dosages. The fold change of GFP above background was plotted in y axis while the dosage with unit vector genome copies were indicated on x axis.

To determine the multiplicity of infection (MOI) required for AAV8 to achieve comparable transduction/expression of a GFP reporter as AAV2 vectors in human iPSCs, and to examine cytotoxicity of AAV8.V2a and AAV8.V3a at high MOI, the following experiments were performed. iPSC Cells were transduced with AAV2.CMV/CßA-GFP and AAV8.CMV/CßA-GFP at multiple MOIs (1E4 to 1E7). The culture wells were imaged and GFP quantified to determine AAV8 MOI comparability of AAV2 vectors. The result was plotted in FIG. 40, indicating that transduction efficiency achieved with 1E7 vg/cell of AAV8.CMV/CßA-GFP) is comparable to AAV2.CMV/CßA-GFP at about 2E5 vg/cell.

Furthermore, cells were transduced at 1E7 vg with AAV8.V2a and AAV8.V3a, and at 2E5 vg with AAV2.V1. Cells were then stained and counted for caspase-3 (an apoptosis marker). Immunofluorescent staining of iPSC treated with 1 uM of Staurosporine, untreated, transduced with 2E5 vector genome copies per cell of AAV2.V2a, transduced with 1E7 vector genome copies per cell of AAV8.V3a, and transduced with 1E7 vector genome copies per cell of AAV8.V1 was performed (images not shown). Staurosporine was used to induce apoptosis. Cells treated thereby were served as positive control. Article 1 is AAV2.V2a; Article 2 is AAV8.V3a; while Article 3 is AAV8.V1.

Figure 41:
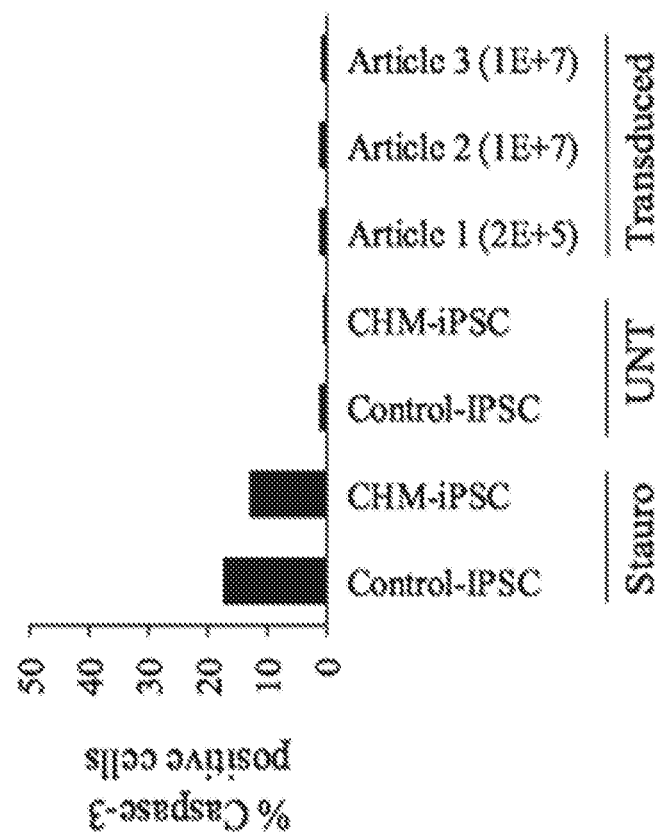
FIG. 41 provides a bar graph showing percentage of caspase-3 positive cells in the cells described in FIG. 44. Stauro indicates Straurosporine-treated cells while UNT are untreated cells. Article 1 is AAV2.V2a; Article 2 is AAV8.V3a; while Article 3 is AAV8.V1.

The data acquired are presented in FIG. 41, showing that AAV8 serotype vectors at an MOI of 1E7 vg/cell resulted in robust transgene expression in transduced iPSCs, and did not lead to apoptosis.

Example 15: Prenylation of RAB

CHM encodes Rab Escort Protein 1 (REP1) while REP1 is required for the prenylation of target RAB proteins. Thus, as described in Example 3, prenylation of target RAB Proteins in CHM patient derived iPSCs after transduction with test rAAVs (using incorporation of a 3H GGPP substrate) was evaluated. The iPSC cells are generated and treated as described in Example 1. Briefly, CHM patient derived iPSC Cell Line JB 588, JB 527 and JB 415 were generated and maintained. Transduction with AAV8.V2a, AAV8.V3a and AAV8.V1 at MOI of 1E7 were performed. Untreated cells served as negative control.

Figure 42:
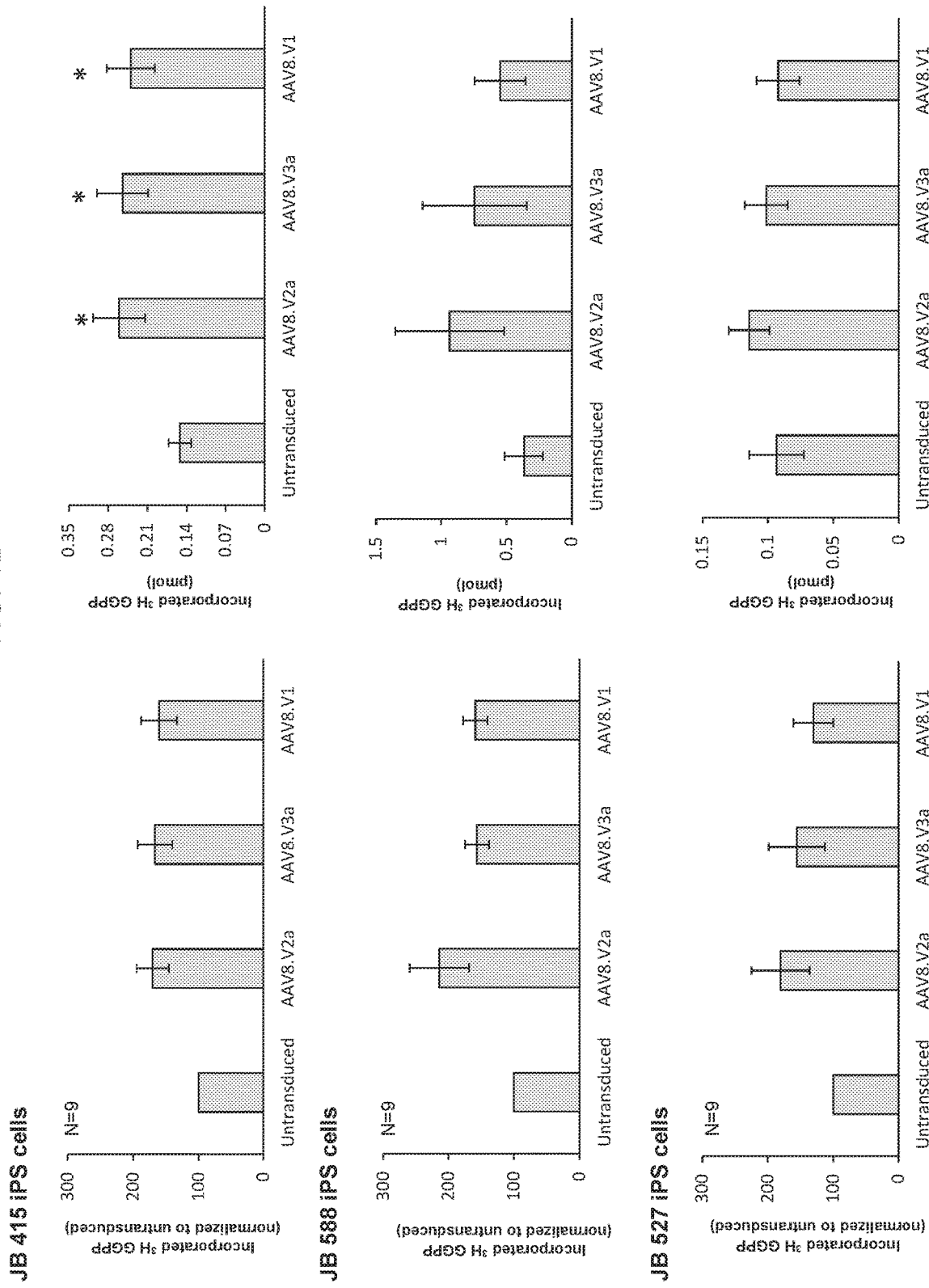
FIG. 42 provides bar graphs showing prenylation of target RAB Proteins in CHM patient derived iPSCs after transduction with AAV8.V2a, AAV8.V3a and AAV8.V1. CHM patient derived iPSC Cell Line JB 588 demonstrates a CHM mutation with Arg 555 Stop (AGA to TGA). CHM patient derived iPSC Cell Line JB 527 demonstrates a deletion of Ex 2-4 of CHM. CHM patient derived iPSC Cell Line JB 415 demonstrates a CHM mutation with Ex 10c.1327-1328 del AT. In the left panels, incorporated 3H GGPP normalized to untransduced iPSC cells was plotted in y axis. In the right panels, amount of incorporated 3H GGPP in pmol was plotted in y axis.
Figure 43A:
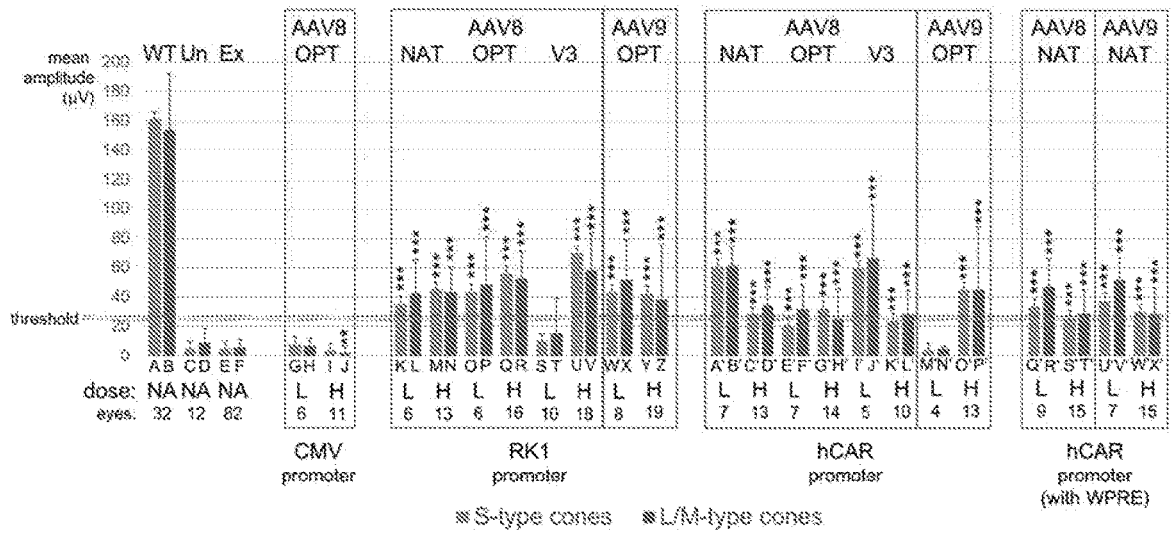
FIG. 43A shows the results of cone response 5-7 weeks post injection for the test articles described in Example 16. WT=wild type, Un=Cnga3 null mice uninjected, Ex=Cnga3 null mice injected with excipient; OPT=codon-optimized, NAT=native, V3=variant 3; NA=not applicable, L=low dose (8E8 vg/eye), H=high dose (8E9 vg/eye); error bars=standard deviation, threshold=4 standard deviations above the excipient mean, * $P<0.05$,  $P<0.01$, * $P<0.001$.
Figure 43B:
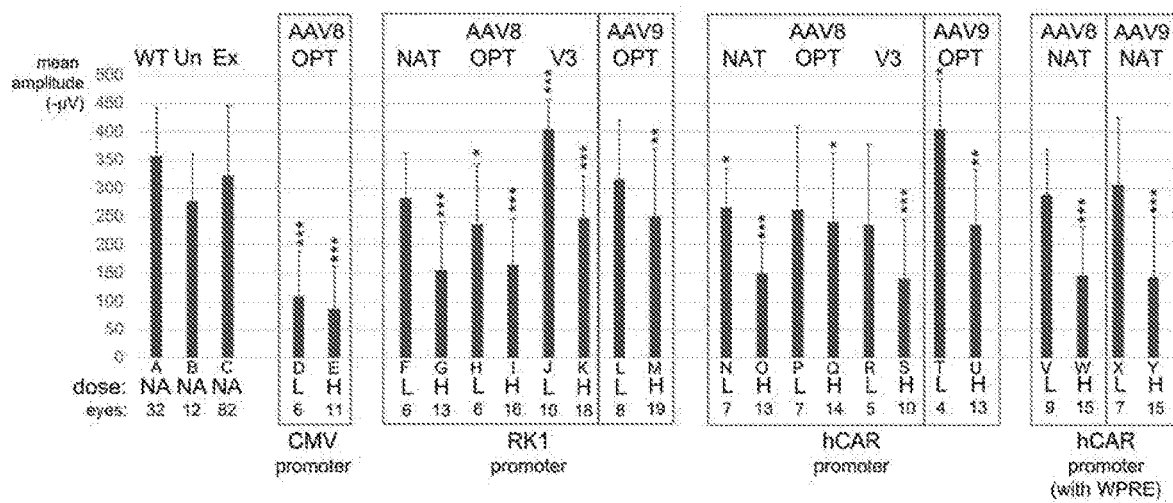
FIG. 43B shows the results of rod response 5-7 weeks post injection for the test articles described in Example 16. WT=wild type, Un=Cnga3 null mice uninjected, Ex=Cnga3 null mice injected with excipient; OPT=codon optimized, NAT=native, V3=variant 3; NA=not applicable, L=low dose (8E8 vg/eye), H=high dose (8E9 vg/eye); error bars=standard deviation, * $P<0.05$,  $P<0.01$, * $P<0.001$.
Figure 44A:
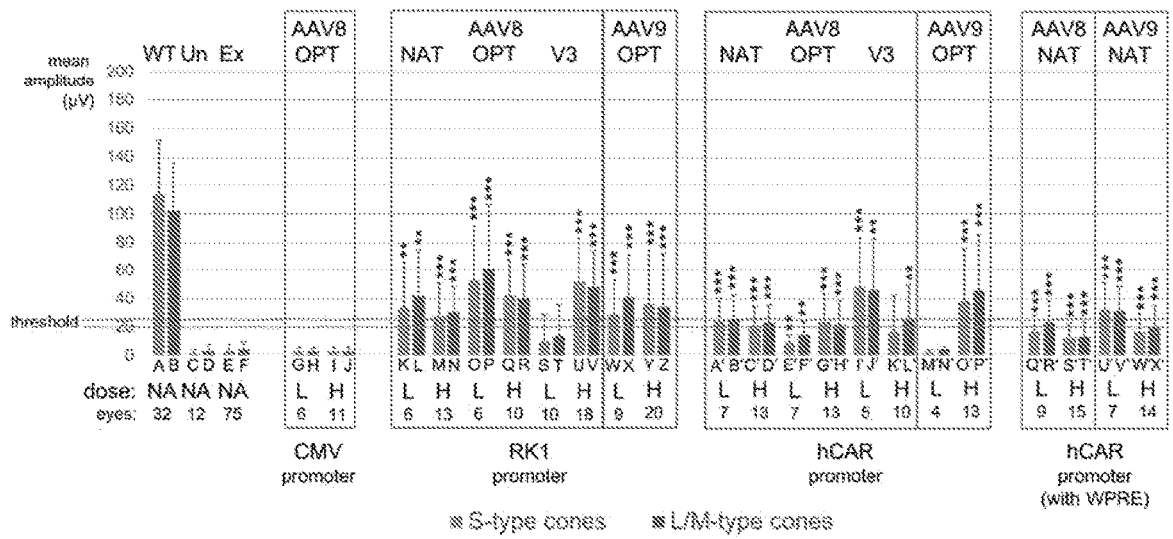
FIG. 44A shows the results of cone response 12-15 weeks post injection for the test articles described in Example 16. WT=wild type, Un=Cnga3 null mice uninjected, Ex=Cnga3 null mice injected with excipient; OPT=codon optimized, NAT=native, V3=variant 3; NA=not applicable, L=low dose (8E8 vg/eye), H=high dose (8E9 vg/eye); error bars=standard deviation, threshold=4 standard deviations above the excipient mean, * $P<0.05$,  $P<0.01$, * $P<0.001$.
Figure 44B:
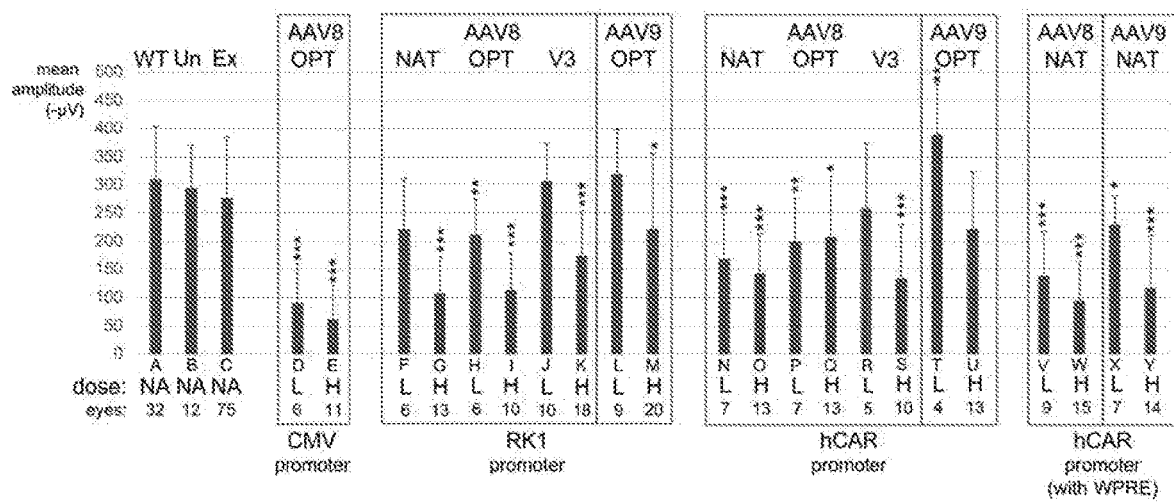
FIG. 44B shows the results of rod response 12-15 weeks post injection for the test articles described in Example 16. WT=wild type, Un=Cnga3 null mice uninjected, Ex=Cnga3 null mice injected with excipient; OPT=codon optimized, NAT=native, V3=variant 3; NA=not applicable, L=low dose (8E8 vg/eye), H=high dose (8E9 vg/eye); error bars=standard deviation, * $P<0.05$,  $P<0.01$, * $P<0.001$.
Figure 45A:
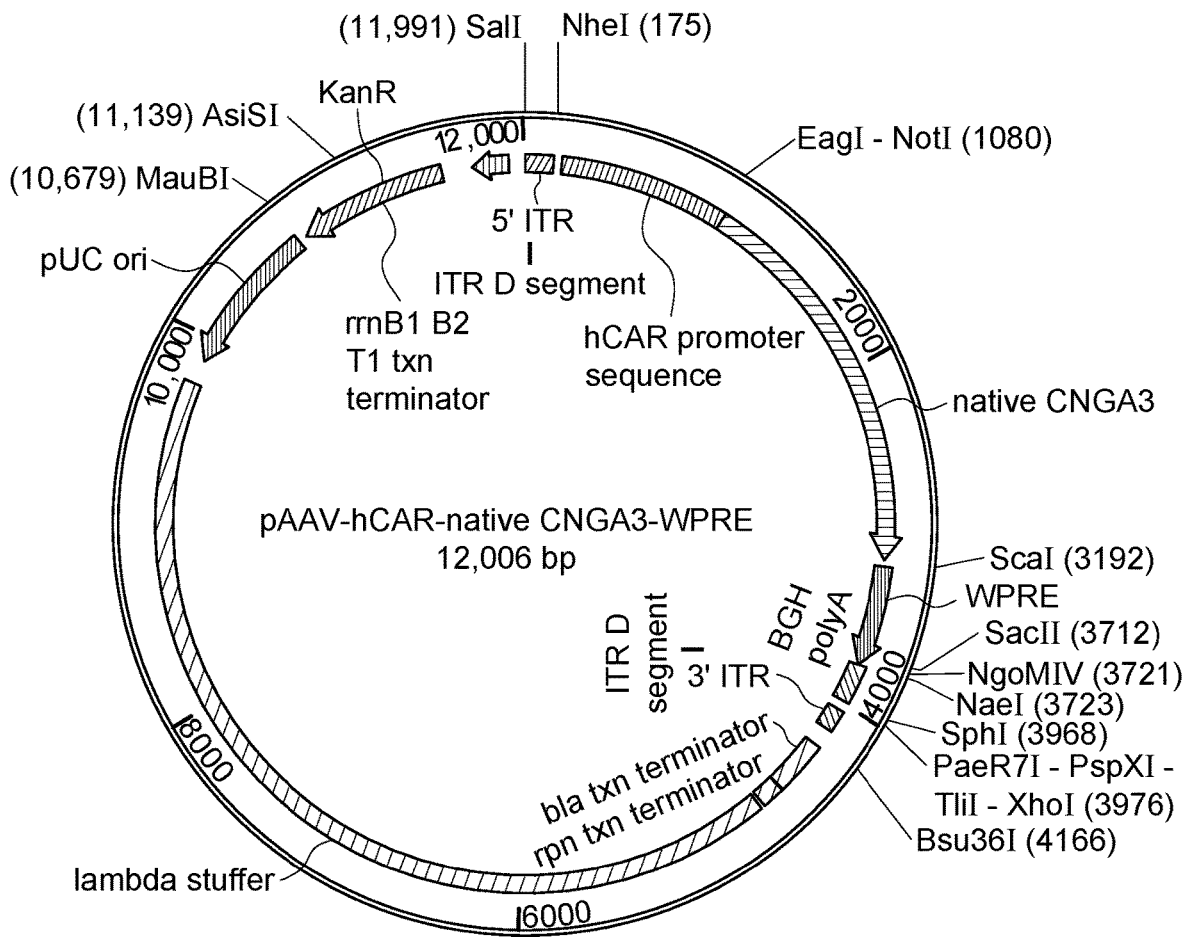

Results are shown in FIG. 42. Compared to untransduced iPSCs, transduced cells showed an increase in both absolute and normalized incorporation of a 3H GGPP substrate.

Example 16: Therapeutic Efficacy of hCNGA3 Gene Therapy on Cnga3 Null Mice

A proof of concept study was performed to test the feasibility of gene augmentation as a therapy for hCNGA3 mediated ACHM disease using a Cnga3 knockout mouse model of ACHM. To do so, we generated 14 unique transgenic cassettes each carrying one of three different promoters (RK1, CMV/CBA, and hCAR) and packaged into either AAV vector serotype 8 or 9. The cDNA sequences used among these 14 test vectors were either native, codon-optimized, or a codon-optimized version of the naturally-occurring variant 3. Subretinal injections of the test articles at either two different doses were performed between P16 and P19, and general clinical observations and ophthalmoscopic examinations were performed on all study animals. Retinal and visual function in the study animals was evaluated by electroretinogram (ERG) and optokinetic reflex (OKR) tests. Cohorts of injected animals were euthanized at study end-point to evaluate retinal histopathology. Additional histological analysis of the retina photoreceptor laminae was performed using TUNEL staining and fluorescent immunohistochemistry for CNGA3.

Ophthalmoscopy performed between 5-7 weeks revealed dose-dependent histopathologic changes. OKR results were inconclusive. ERG analyses revealed improved cone photoreceptor function compared to excipient-treated eyes with dose-dependent effects. Optimal responses were found using transgene cassettes incorporating a photoreceptor-specific promoter.

Results showed that hCNGA3 gene delivery utilizing AA8 and AAV9 viral vectors showed excellent preliminary safety when injected at 8E8 vg/eye. Minimal ocular inflammation was observed and there were no adverse reactions following subretinal delivery of the test articles. Additionally, histopathological analysis of tissue from test article-injected eyes revealed minimal toxicity to the retina at 8E8 vg/eye, with localization of the transgene protein limited to the photoreceptors. In addition, AAV-mediated delivery of hCNGA3 was sufficient to improve cone response with minimal impact on rod response for AAV8.RK1-hCNGA3.Opt and AAV8.hCAR-hCNGA3.V3.

SUMMARY

The in vivo expression and function of hCNGA3 was tested in B6.RHJ-Cnga3$^{cpfl5}$/BocJ (hereafter referred to as Cnga3−/−) mice. The test article consisted of a combination of 3 promoters (RK1, hCAR, and CMV/CβA). The Rhodopsin Kinase (RK1) promoter drives photoreceptor-specific expression, the human Cone Arrestin (hCAR) promoter, with or without the woodchuck posttranscriptional regulatory element (WPRE) enhancer, drives expression in the cones and the cyto megalo virus enhancer with the chicken beta actin promoter (CMV/CβA) drives expression ubiquitously. The 3 alleles used were the native allele (Nat), a codon-optimized allele (Opt), and a naturally occurring variant 3 (V3) which was also codon-optimized. The combinations of these promoter/enhancers and alleles were encapsulated in either AAV8 or AAV9 serotypes. Test article dilutions: All test articles were diluted into an excipient comprised of Dulbecco's phosphate buffered saline and excipient or low dose was injected in the left eye while high dose was injected into the right eye.

Subretinal injections were performed to deliver one of the following test articles: Group 1—an AAV8 encapsidated native human CNGA3 transgene vector controlled by an upstream RK1 promoter sequence; Group 2—an AAV8 encapsidated codon-optimized human CNGA3 transgene vector controlled by an upstream RK1 promoter sequence; Group 3—an AAV8 encapsidated codon-optimized variant 3 CNGA3 transgene vector controlled by an upstream RK1 promoter sequence; Group 4—an AAV8 encapsidated native human CNGA3 transgene vector controlled by an upstream human CAR promoter sequence; Group 5—an AAV8 encapsidated codon-optimized human CNGA3 transgene vector controlled by an upstream human CAR promoter sequence; Group 6—an AAV8 encapsidated codon-optimized human variant 3 CNGA3 transgene vector controlled by an upstream human CAR promoter sequence; Group 8—an AAV8 encapsidated codon-optimized human CNGA3 transgene vector controlled by an upstream cytomegalovirus enhancer/chicken beta actin promoter (CMV/CβA) sequence; Group 10—an AAV8 encapsidated native human CNGA3 transgene vector controlled by an upstream human CAR promoter sequence with the woodchuck posttranscriptional regulatory element (WPRE); Group 11—an AAV9 encapsidated codon-optimized human CNGA3 transgene vector controlled by an upstream RK1 promoter sequence; Group 12—an AAV9 encapsidated codon-optimized human CNGA3 transgene vector controlled by an upstream human CAR promoter sequence; or Group 14—an AAV9 encapsidated native human CNGA3 transgene vector controlled by an upstream human CAR promoter sequence with the woodchuck posttranscriptional regulatory element (WPRE).

General clinical observations, and ophthalmoscopic examinations were performed on all study animals. Visual function in the study animals was evaluated by electroretinogram (ERG) and optokinetic reflex (OKR) tests. Cohorts of injected animals were euthanized at study end-point to process the eyes and stain with Hematoxylin and Eosin (H&E) for histopathology. Additional histological analysis of the retina photoreceptor laminae was performed using TUNEL staining and fluorescent immunohistochemistry for CNGA3.

Results—Summary

Subretinal administration of all test materials carrying hCNGA3 transgenes resulted in minor inflammatory changes in the eyes post-operatively. Zero (0) animals needed to be euthanized as a result of inflammation or adverse reactions to a delivered test article. Of the 182 pups injected with vector, 169 remained in the study at the time of weaning and 162 remained in the study to completion. Ophthalmoscopy performed between 5-7 weeks revealed that most eyes exhibited low to moderate evidence of inflammation associated with degenerative histopathologic change. Specifically, injection of all vectors at the high dose (8E9 vg/eye) resulted in a greater degree of signs of loss of photoreceptors than in eyes injected with vectors at the low dose (8E8 vg/eye). Among eyes injected at the low dose, variations in the degree of retinal changes among eyes of the same cohort likely reflect variability in the surgical delivery procedure. Overall, the best outcomes were observed in eyes that received low dose of AAV8.RK1-hCNGA3 native, AAV8. RK1-hCNGA3 codon-optimized, AAV8.RK1-hCNGA3 codon-optimized variant 3, AAV8.hCAR-hCNGA3 native, and AAV8.hCAR-hCNGA3 codon-optimized variant 3.

Test of retinal and visual function by ERG generally revealed better functioning in eyes injected with the low dose of AAV8.RK1-hCNGA3 native, AAV8.RK1-hCNGA3 codon-optimized, AAV9.RK1-hCNGA3 codon-optimized, and AAV8.hCAR-hCNGA3 variant 3 compared to controls. See FIGS. 43A-44B.

Electroretinogram Results

ERG recordings were gathered following a 12-hour period during which animals were dark-adapted. Each recording consisted of 10 cycles of light stimulation to elicit rod-, S-type, or L/M-type cone-driven responses. Cone responses were used to gauge therapeutic efficacy while rod responses were used to measure toxicity.

Group 1 (AAV8.RK1-hCNGA3 Native):

Eyes injected with 8E8 vg/eye and 8E9 vg/eye showed a robust and significant improvement in cone response at 5-7 and 12-15 weeks post-injection compared to excipient injected controls. There was no change in rod function compared to excipient-injected eyes at 5-7 or 12-15 weeks post-injection for eyes injected with 8E8 vg/eye of vector. However, injection of 8E9 vg/eye resulted in a large and significant decrease in rod function at 5-7 weeks post-injection. Rod function improved slightly by 12-15 weeks post-injection.

Group 2 (AAV8.RK1-hCNGA3 Codon Optimized):

Eyes injected with 8E8 vg/eye and 8E9 vg/eye showed a robust and significant improvement in cone response at 5-7 and 12-15 weeks post-injection compared to excipient-injected controls. There was a mild, but significant, decrease in rod response in eyes injected with 8E8 vg/eye at 5-7 and 12-15 weeks post-injection. The decrease in rod response was even greater for eyes injected with 8E9 vg/eye.

Group 3 (AAV8.RK1-hCNGA3 variant 3):

Eyes injected with 8E8 vg/eye showed no change in cone response at 5-7 and 12-15 weeks post-injection compared to excipient-injected controls but did display a large and significant improvement in rod response at 5-7 weeks. There was a robust and significant improvement in cone response 5-7 and 12-15 weeks post-injection in eyes injected with 8E9 vg/eye compared to excipient-injected controls. However, eyes injected with 8E9 vg showed a large and significant decrease in rod response at 5-7 and 12-15 weeks post-injection.

Group 4 (AAV8.hCAR-hCNGA3 Native):

Eyes injected with 8E8 or 8E9 vg showed a robust and significant improvement in cone response at 5-7 and 12-15 weeks post-injection compared to excipient-injected controls. There was no observed change in rod response 5-7 weeks post-injection in eyes injected with 8E8 vg, though rod response in these eyes did significantly decrease compared to excipient-inject controls by 12-15 weeks post-injection. Eyes injected with 8E9 vg displayed a decrease in rod response at both time points.

Group 5 (AAV8.hCAR-hCNGA3 Codon Optimized):

Eyes injected with 8E8 or 8E9 vg showed a moderate to robust and significant improvement in cone response at 5-7 and 12-15 weeks post-injection compared to excipient-injected controls. While there was no observed change in rod response 5-7 weeks post-injection in eyes that received 8E8 vg, there was a significant decrease in function by 12-15 weeks post injection. Decreased rod response was also observed at both time points in eyes injected with 8E9 vg.

Group 6 (AAV8.hCAR-hCNGA3 Variant 3):

Eyes injected with 8E8 vg showed a robust and significant improvement in cone response at both 5-7 and 12-15 weeks post-injection compared to excipient-injected controls. There was no observed change in rod response in these eyes at either time point. Eyes injected with 8E9 vg showed a robust and significant increase in cone function compared to excipient-injected controls at 5-7 weeks but not 12-15 weeks post-injection. These eyes displayed a significant decrease in rod function at both time points.

Group 8 (AAV8.CMV/CBA-hCNGA3 Codon Optimized):

There was no change in cone response compared to excipient-injected eyes at 5-7 or 12-15 weeks post-injection in eyes injected at either dose. In addition, both doses resulted in a significant decrease in rod response at both time points.

Group 10 (AAV8.hCAR-hCNGA3 Native with WPRE):

Eyes injected with either dose showed a significant improvement in cone response compared to excipient-injected controls at both 5-7 and 12-15 weeks post-injections. Although there was no change in cone response 5-7 weeks post-injection in eyes injected with 8E8 vg, rod response did significantly decrease by 5-7 weeks post-injection in eyes injected with 8E9 vg. In addition, both doses resulted in decreased rod response 12-15 weeks post-injection.

Group 11 (AAV9.RK1-hCNGA3 Codon Optimized):

Eyes injected with 8E8 vg displayed a robust and significant improvement in cone response at both 5-7 and 12-15 weeks post-injection, with no change in rod response. Although eyes injected with 8E9 vg also showed a significant improvement in cone response at both time points, those eyes also exhibited a decrease in rod response.

Group 12 (AAV9.hCAR-hCNGA3 Codon Optimized):

There was not a significant improvement in cone response at either time point in eyes injected with 8E8 vg. Eyes injected with 8E9 vg did show a significant improvement in cone response at both time points, but rod response was significantly decreased by 5-7 weeks post-injection.

Group 14 (AAV9.hCAR-hCNGA3 Native with WPRE):

Eyes injected with 8E8 or 8E9 vg showed a moderate to robust increase in cone response at both 5-7 and 12-15 weeks post-injection. However, injection of either dose resulted in a significant decrease in rod response by 12-15 weeks post-injection.

Low doses (8E8 vg/eye) of AAV in groups 1 (AAV8.RK1-hCNGA3 native), 2 (AAV8.RK1-hCNGA3 codon-optimized), 11 (AAV9.RK1-hCNGA3 codon-optimized), 6 (AAV8.hCAR-hCNGA3 codon-optimized variant 3), and 14 (AAV9.hCAR-hCNGA3 native with WPRE) resulted in retained rod function and improved cone function at both time points post-injection.

There is no significant difference in S- or L/M-type cone function among these test groups.

AAV Group 11 (AAV9.RK1-hCNGA3 codon-optimized) has a significantly lower impact on rod function than AAVs used in groups 1 (AAV8.RK1-hCNGA3 native), 2 (AAV8.RK1-hCNGA3 codon-optimized), and 14 (AAV9.hCAR-hCNGA3 native with WPRE).

High doses (8E9 vg/eye) of AAV in groups 11 (AAV9.RK1-hCNGA3 codon-optimized) and 12 (AAV9.hCAR-hCNGA3 codon-optimized) resulted in retained rod function and improved cone function at both time points.

Rod function is significantly better at 8E8 vg/eye than at 8E9 vg/eye for group 11 (AAV9.RK1-hCNGA3 codon-optimized) at 12-15 weeks post-injection.

There is no difference in rod function at 8E9 vg/eye between groups 11 (AAV9.RK1-hCNGA3 codon-optimized) and 12 (AAV9.hCAR-hCNGA3 codon-optimized) at 12-15 weeks post-injection.

Histology, Immunohistochemistry, and TUNEL Assay Conclusions:

Histological evaluations revealed the loss of photoreceptors, presence of inflammation and abnormal retinal architecture in mice injected with higher dosage of all test articles.

Retinal architecture of mice injected with AAV.hCNGA3, where the expression of hCNGA3 was driven by the promoter CMV.CßA was found to be significantly damaged.

Mice injected at a lower dosage of 8E8 vg/eye of test articles did not reveal the presence of significant histological changes or inflammation.

Mice injected at higher dosage of 8E9 vg/eye of test articles showed significant histological changes or inflammation. Vector to vector variation in effecting the retinal architecture was noted.

Transduction of hCNGA3 null murine retinal tissues with codon-optimized and codon-optimized variant 3 hCNGA3 driven by RK1 and hCAR promoters, respectively, resulted in localization of hCNGA3 to photoreceptors cells. The localization was similar among all test articles at injected dosage.

Variability in the expression of hCNGA3, between mice injected with AAV8.RK1-hCNGA3 codon-optimized and AAV8.hCAR-hCNGA3 codon-optimized variant 3 is relatively low. In mice injected with AAV9.RK1-hCNGA3 codon-optimized, expression of hCNGA3 was found to be inconsistent between animals of the same cohort.

Presence of apoptotic cells was not evident in retinas of mice injected with any given test article.

OVERALL CONCLUSIONS: Subretinal injections of AAV.RK1-hCNGA3, AAV.hCAR-hCNGA3 resulted in robust delivery of the hCNGA3 transgene to photoreceptor cells of the retina. Subretinal delivery of all test articles at higher dose (8E9 vg/eye) resulted in inflammation and degenerative changes in the retina. The severity of the retinal histopathological changes showed a dependency on the promoter used. Vectors where the expression of hCNGA3 was driven by CMV-CßA exerted more severe retinal degenerative changes, followed by the RK1 and then hCAR. Inflammatory changes were also noted after injection with lower doses (8E8 vg/eye) of vectors, but were not as severe. The results of this report establish that delivery of the for hCNGA3 codon-optimized cDNA driven by a photoreceptor-specific promoter by either the AAV8 or AAV9 capsid or of the hCNGA3 codon-optimized variant 3 cDNA driven by a photoreceptor-specific promoter through delivery by the AAV8 capsid, at a viral dose of 8E8 vg/eye is sufficient to for production of hCNGA3 protein in retinal photoreceptors with minimal toxicity.

Post mortem histopathology revealed subretinal delivery of all test articles at the high dose resulted in inflammation and degenerative changes in the retina. Among eyes injected at the low dose, eyes receiving vector with the CMV/CßA promoter displayed severe retinal histopathological changes. Histopathologic findings revealed 108 samples, including those injected with excipient, in which there was cellular infiltrate. The retinal layers were deteriorated in 98 of the retinas, including those injected with excipient. Forty of the 320 eyes scored displayed inflammatory cells in the choroid or vitreous, distributed across all groups, and 32 samples contained rare macrophages that were observed in subretinal spaces.

Three test articles AAV8.CMV/CßA-hCNGA3 native, AAV8.CMV/CßA-hCNGA3 codon-optimized variant 3, and AAV9.CMV/CßA-hCNGA3 codon-optimized, all of which were driven by a constitutive promoter, caused tissue damage and so were not included in this study report. Observed diminished cone function was consistent with the previously reported phenotype of the Cnga3$^{-/-}$ mouse. Ocular inflammation was detected in only one animal following subretinal injections with either gene therapy vectors or excipient controls. The animals receiving viral test articles did not show an increase in morbidity or moribundity. Delivery of 8E8 vg/eye of AAV8.RK1-hCNGA3 codon-optimized or AAV8.hCAR-hCNGA3 codon-optimized variant 3 resulted in a significant preservation of retinal histology and improved visual function compared to excipient-treated eyes. Based on these results we conclude that subretinal delivery of AAV8.RK1-hCNGA3 codon-optimized or AAV8.hCAR-hCNGA3 codon-optimized variant 3 is sufficient to arrest the progression of ACHM in the Cnga3$^{-/-}$ mouse.

All publications cited in this specification, including provisional patent application No. 62/266,789, filed Dec. 14, 2015, provisional patent application No. 62/519,821, filed Jun. 14, 2017, and WO 2017/106202 are incorporated herein by reference in their entirety. Similarly, the SEQ ID Nos which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

Sequence Listing Free Text

The following information is provided for sequences containing free text under numeric identifier <223>

| SEQ ID NO: (containing free text) | Free text under <223> |
|---|---|
| 1 | <223> codon optimized sequence<br><220><br><221> CDS<br><222> (1)..(1962) |
| 2 | <223> Synthetic Construct |
| 5 | <223> constructed plasmid<br><220><br><221> misc_feature<br><222> (1)..(8)<br><223> NotI restriction site for subcloning into proviral plasmid<br><220><br><221> misc_feature<br><222> (4)..(16)<br><223> Kozak consensus sequence<br><220><br><221> CDS<br><222> (13)..(1971)<br><223> codon-optimized open reading frame (ORF)<br><220><br><221> misc_feature<br><222> (1972)..(1977)<br><223> BclI restriction site with embedded stop codon/ site to add optional epitope tag<br><220><br><221> misc_feature<br><222> (1980)..(1985)<br><223> BamHI restriction site for subcloning into proviral plasmid |
| 6 | <223> Synthetic Construct |
| 7 | <223> constructed plasmid<br><220><br><221> misc_feature<br><222> (1)..(145)<br><223> 5' ITR<br><220><br><221> promoter<br><222> (169)..(1786)<br><223> CMV.CBA promoter<br><220><br><221> misc_feature<br><222> (1787)..(1794)<br><223> Not I cloning site, cuts at 1789<br><220><br><221> misc_feature<br><222> (1805)..(1810)<br><223> BamHI cloning site, cuts at 1806<br><220><br><221> polyA_signal<br><222> (1850)..(2052)<br><223> BGH Poly A<br><220><br><221> misc_feature<br><222> (2109)..(2252)<br><223> 3' ITR<br><220><br><221> misc_feature<br><222> (2571)..(6624)<br><223> lambda stuffer<br><220><br><221> misc_feature<br><222> (7314)..(8126)<br><223> Kanamycin resistance (complementary)<br><220><br><221> misc_feature<br><222> (8485)..(9128)<br><223> Origin of replication (complementary) |
| 8 | <223> constructed plasmid |
| 9 | <223> codon optimized sequence<br><220><br><221> CDS<br><222> (1)..(2085)<br><223> codon-optimized ORF |

-continued

| SEQ ID NO: (containing free text) | Free text under <223> |
|---|---|
| 10 | <223> Synthetic Construct |
| 11 | <223> codon optimized sequence |
|  | <220> |
|  | <221> CDS |
|  | <222> (1)..(2250) |
|  | <223> codon-optimized ORF |
| 12 | <223> Synthetic Construct |
|  | <221> CDS |
|  | <222> (1)..(2085) |
| 13 | <223> native open reading frame (ORF) |
| 16 | <223> constructed sequence |
| 17 | <223> constructed sequence |
| 18 | <223> constructed sequence |
| 21 | <223> constructed sequence |
|  | <220> |
|  | <221> CDS |
|  | <222> (1)..(2430) |
| 22 | <223> Synthetic Construct |
| 23 | <223> constructed sequence |
|  | <220 |
|  | <221> misc_feature |
|  | <222> (1)..(12) |
|  | <223> modified end with NotI site and Kozak |
|  | <220 |
|  | <221> misc_feature |
|  | <222> (1)..(8) |
|  | <223> NotI site for subcloning |
|  | <220> |
|  | <221> CDS |
|  | <222> (13)..(2448) |
|  | <223> ORF with silent mutations (stop codon and restriction sites BamHI, PstI, SalI, and NdeI) |
|  | <220> |
|  | <221> misc_feature |
|  | <222> (2440)..(2442) |
|  | <223> modifed stop codon |
|  | <220> |
|  | <221> misc_feature |
|  | <222> (2440)..(2445) |
|  | <223> BclI site to facilitate addition of epitope tag |
|  | <220> |
|  | <221> misc_feature |
|  | <222> (2446)..(2448) |
|  | <223> additional stop codon |
|  | <220> |
|  | <221> misc_feature |
|  | <222> (2449)..(2454) |
|  | <223> PstI site for subcloning |
| 24 | <223> Synthetic Construct |
| 25 | <223> constructed sequence |
|  | <220> |
|  | <221> misc_feature |
|  | <222> (1)..(130) |
|  | <223> 5' ITR |
|  | <220> |
|  | <221> misc_feature |
|  | <222> (241)..(544) |
|  | <223> CMV enhancer |
|  | <220> |
|  | <221> misc_feature |
|  | <222> (546)..(823) |
|  | <223> chicken beta-actin promoter |
|  | <220> |
|  | <221> misc_feature |
|  | <222> (824)..(1795) |
|  | <223> CBA exon 1 and intron |
|  | <220> |
|  | <221> misc_feature |
|  | <222> (1859)..(1864) |
|  | <223> kozak |
|  | <220> |
|  | <221> misc_feature |
|  | <222> (1865)..(3826) |

| SEQ ID NO: (containing free text) | Free text under <223> |
|---|---|
|  | <223> human codon optimized CHM (REP-1) |
|  | <220> |
|  | <221> misc_feature |
|  | <222> (3847)..(4054) |
|  | <223> bGH poly(A) signal |
|  | <220> |
|  | <221> misc_feature |
|  | <222> (4104)..(4233) |
|  | <223> 3' ITR |
| 26 | <223> constructed sequence |
|  | <220> |
|  | <221> misc_feature |
|  | <222> (1)..(130) |
|  | <223> 5' ITR |
|  | <220> |
|  | <221> misc_feature |
|  | <222> (241)..(544) |
|  | <223> CMV enhancer |
|  | <220> |
|  | <221> misc_feature |
|  | <222> (546)..(823) |
|  | <223> chicken beta-actin promoter |
|  | <220> |
|  | <221> misc_feature |
|  | <222> (824)..(1795) |
|  | <223> CBA exon 1 and intron |
|  | <220> |
|  | <221> misc_feature |
|  | <222> (1859)..(1864) |
|  | <223> Kozak |
|  | <220> |
|  | <221> misc_feature |
|  | <222> (1865)..(3826) |
|  | <223> human codon optimized CHM (REM-1) |
|  | <220> |
|  | <221> misc_feature |
|  | <222> (3847)..(4054) |
|  | <223> bGH poly(A) signal |
|  | <220> |
|  | <221> misc_feature |
|  | <222> (4104)..(4233) |
|  | <223> 3' ITR |
| 27 | <223> constructed sequence |
|  | <220> |
|  | <221> misc_feature |
|  | <222> (1)..(130) |
|  | <223> 5' ITR |
|  | <220> |
|  | <221> misc_feature |
|  | <222> (241)..(544) |
|  | <223> CMV Enhancer |
|  | <220> |
|  | <221> misc_feature |
|  | <222> (546)..(823) |
|  | <223> chicken beta-actin promoter |
|  | <220> |
|  | <221> misc_feature |
|  | <222> (824)..(1795) |
|  | <223> CBA exon 1 and intron |
|  | <220> |
|  | <221> misc_feature |
|  | <222> (1859)..(1864) |
|  | <223> kozak |
|  | <220> |
|  | <221> misc_feature |
|  | <222> (1865)..(3826) |
|  | <223> human codon optimized CHM (REP-1) |
|  | <220> |
|  | <221> misc_feature |
|  | <222> (3847)..(4054) |
|  | <223> bGH poly(A) signal |
|  | <220> |
|  | <221> misc_feature |
|  | <222> (4104)..(4233) |

| SEQ ID NO: (containing free text) | Free text under <223> |
|---|---|
| 28 | <223> 3' ITR |
| | <223> constructed sequence |
| | <220> |
| | <221> misc_feature |
| | <222> (1)..(130) |
| | <223> 5' ITR |
| | <220> |
| | <221> misc_feature |
| | <222> (241)..(544) |
| | <223> CMV enhancer |
| | <220> |
| | <221> misc_feature |
| | <222> (546)..(823) |
| | <223> chicken beta actin promoter |
| | <220> |
| | <221> misc_feature |
| | <222> (824)..(1795) |
| | <223> CBA exon 1 and intron |
| | <220> |
| | <221> misc_feature |
| | <222> (1859)..(1864) |
| | <223> kozak |
| | <220> |
| | <221> misc_feature |
| | <222> (1865)..(3826) |
| | <223> human codon optimized CHM (REP-1) |

| SEQ ID NO: (containing free text) | Free text under <223> |
|---|---|
| | <220> |
| | <221> misc_feature |
| | <222> (3847)..(4054) |
| | <223> bGH poly(A) signal |
| | <220> |
| | <221> misc_feature |
| | <222> (4104)..(4233) |
| | <223> 3' ITR |
| 29 | <223> constructed sequence |
| 30 | <223> constructed sequence |
| 31 | <223> constructed sequence |
| 32 | <223> constructed sequence |
| 33 | <223> constructed sequence |
| 34 | <223> constructed sequence |
| 35 | <223> constructed sequence |
| 36 | <223> constructed sequence |
| 37 | <223> constructed sequence |
| 38 | <223> constructed sequence |
| 39 | <223> constructed sequence |
| 40 | <223> constructed sequence |
| 41 | <223> constructed sequence |
| 42 | <223> constructed sequence |
| 43 | <223> constructed sequence |
| 44 | <223> constructed sequence |
| 45 | <223> constructed sequence |
| 46 | <223> constructed sequence |

What is claimed is:

1. An adeno-associated virus (AAV) vector comprising an AAV capsid having encapsidated therein a nucleic acid sequence comprising AAV inverted terminal repeat (ITR) sequences, a nucleic acid sequence comprising nucleotides 10 to 2436 of SEQ ID NO: 45 encoding human cyclic nucleotide gated channel beta 3 (CNGB3), and expression control sequences that direct expression of the CNGB3 in a host cell.

2. The AAV vector of claim 1, wherein the expression control sequences comprise a cytomegalovirus/Chicken Beta Actin (CMV/CBA) promoter, a Rhodopsin Kinase (RK1) promoter, or an human Cone Arrestin (hCAR) promoter.

3. The AAV vector of claim 1, wherein the expression control sequences comprise an ocular cell-specific promoter.

4. A pharmaceutical composition comprising a pharmaceutically acceptable carrier and at least the AAV vector of claim 1.

5. A method for treating achromatopsia in a human subject, said method comprising administering the composition of claim 4 at a dose of at least $1 \times 10^{10}$ AAV vector genome copies/eye subretinally to a subject in need thereof.

6. The method of claim 5, wherein the composition is administered at a dose range of $1 \times 10^{10}$ to $1 \times 10^{12}$ AAV vector genome copies/eye subretinally.

7. The AAV vector of claim 1, wherein the AAV capsid is an AAV2, AAV5, AAV8, AAV9, AAV8 bp, or AAV7m8 capsid.

8. A plasmid comprising a nucleic acid sequence comprising nucleotides 10 to 2436 of SEQ ID NO: 45 encoding CNGB3.

9. The plasmid of claim 8, wherein the nucleic acid sequence comprises nucleotides 175 to 3359 of SEQ ID NO: 40, nucleotides 181 to 3753 of SEQ ID NO: 42, or nucleotides 191 to 4527 of SEQ ID NO: 44.

10. An AAV vector comprising an AAV capsid having encapsidated therein a nucleic acid sequence comprising:
   a) a 5' ITR sequence;
   b) nucleotides 175 to 3359 of SEQ ID NO: 40, nucleotides 181 to 3753 of SEQ ID NO: 42, or nucleotides 191 to 4527 of SEQ ID NO: 44; and
   c) a 3' ITR sequence.

11. The AAV vector of claim 10, wherein the AAV capsid is an AAV2, AAV5, AAV8, AAV9, AAV8 bp, or AAV7m8 capsid.

12. A pharmaceutical composition comprising a pharmaceutically acceptable carrier and at least the AAV vector of claim 10.

13. A method for treating achromatopsia in a human subject, said method comprising administering the composition of claim 12 at a dose of at least $1 \times 10^{10}$ AAV vector genome copies/eye subretinally to a subject in need thereof.

14. The method of claim 13, wherein the composition is administered at a dose range of $1 \times 10^{10}$ to $1 \times 10^{12}$ AAV vector genome copies/eye subretinally.

* * * * *

SEQUENCE LISTING

```
<160> NUMBER OF SEQ ID NOS: 52

<210> SEQ ID NO 1
<211> LENGTH: 1962
<212> TYPE: DNA
<213> ORGANISM: Artificial Sequence
<220> FEATURE:
<223> OTHER INFORMATION: codon optimized sequence
<220> FEATURE:
<221> NAME/KEY: CDS
<222> LOCATION: (1)..(1962)

<400> SEQUENCE: 1 atg gct gat acc ctg ccc tct gaa ttc gac gtg att gtg att gga acc      48
Met Ala Asp Thr Leu Pro Ser Glu Phe Asp Val Ile Val Ile Gly Thr
1               5                   10                  15 gga ctc cct gaa tcg atc atc gcc gcg gcc tgt tcc cgg tcc ggt cgg      96
Gly Leu Pro Glu Ser Ile Ile Ala Ala Ala Cys Ser Arg Ser Gly Arg
                20                  25                  30 cgc gtg ctg cac gtc gat tcg aga agc tac tac gga ggg aat tgg gcc     144
Arg Val Leu His Val Asp Ser Arg Ser Tyr Tyr Gly Gly Asn Trp Ala
            35                  40                  45 tca ttc tcc ttc tcc gga ctg ctc tcc tgg ctg aag gag tat cag gag     192
Ser Phe Ser Phe Ser Gly Leu Leu Ser Trp Leu Lys Glu Tyr Gln Glu
        50                  55                  60 aac tcc gac att gtc tcc gac tca cct gtg tgg cag gac cag atc ctg     240
Asn Ser Asp Ile Val Ser Asp Ser Pro Val Trp Gln Asp Gln Ile Leu
    65                  70                  75                  80 gaa aac gag gaa gca ata gcc ctg agc cgg aag gac aag acc atc cag     288
Glu Asn Glu Glu Ala Ile Ala Leu Ser Arg Lys Asp Lys Thr Ile Gln
                85                  90                  95 cac gtg gag gtg ttc tgt tat gcc tcc caa gac ctc cat gag gac gtg     336
His Val Glu Val Phe Cys Tyr Ala Ser Gln Asp Leu His Glu Asp Val
                100                 105                 110 gaa gag gct gga gcg ttg cag aag aat cat gcc ctc gtg acc tcc gct     384
Glu Glu Ala Gly Ala Leu Gln Lys Asn His Ala Leu Val Thr Ser Ala
```

-continued

|   |   |   |   |   |   |   |   |   |   |   |   |   |   |   |   |
|---|---|---|---|---|---|---|---|---|---|---|---|---|---|---|---|
| | | 115 | | | | 120 | | | | 125 | | | | | |
| aac | tcc | acc | gag | gca | gcc | gac | agc | gcc | ttc | ctg | ccg | acc | gag | gat | gaa | 432
| Asn | Ser | Thr | Glu | Ala | Ala | Asp | Ser | Ala | Phe | Leu | Pro | Thr | Glu | Asp | Glu
| | | 130 | | | | 135 | | | | 140 | | | | |
| tcc | ctg | tca | act | atg | tcg | tgc | gaa | atg | ctg | acc | gaa | cag | act | ccg | agc | 480
| Ser | Leu | Ser | Thr | Met | Ser | Cys | Glu | Met | Leu | Thr | Glu | Gln | Thr | Pro | Ser
| 145 | | | | | 150 | | | | | 155 | | | | | 160
| tcc | gac | ccc | gaa | aac | gcc | ctg | gaa | gtg | aac | gga | gcg | gaa | gtg | acc | ggc | 528
| Ser | Asp | Pro | Glu | Asn | Ala | Leu | Glu | Val | Asn | Gly | Ala | Glu | Val | Thr | Gly
| | | | | 165 | | | | | 170 | | | | | 175 |
| gaa | aag | gag | aac | cat | tgc | gac | gac | aag | act | tgt | gtc | cca | tcc | act | tcc | 576
| Glu | Lys | Glu | Asn | His | Cys | Asp | Asp | Lys | Thr | Cys | Val | Pro | Ser | Thr | Ser
| | | | | 180 | | | | | 185 | | | | | 190 |
| gcg | gag | gac | atg | tcc | gag | aat | gtg | cct | atc | gcc | gag | gac | acc | acc | gaa | 624
| Ala | Glu | Asp | Met | Ser | Glu | Asn | Val | Pro | Ile | Ala | Glu | Asp | Thr | Thr | Glu
| | | | 195 | | | | | 200 | | | | | 205 | |
| cag | ccc | aag | aag | aac | aga | atc | acg | tac | agc | cag | atc | atc | aag | gag | ggg | 672
| Gln | Pro | Lys | Lys | Asn | Arg | Ile | Thr | Tyr | Ser | Gln | Ile | Ile | Lys | Glu | Gly
| | | 210 | | | | | 215 | | | | | 220 | | | |
| cgg | agg | ttt | aac | atc | gat | ctg | gtg | tcg | aag | ctg | ctg | tac | agc | cgc | ggt | 720
| Arg | Arg | Phe | Asn | Ile | Asp | Leu | Val | Ser | Lys | Leu | Leu | Tyr | Ser | Arg | Gly
| 225 | | | | | 230 | | | | | 235 | | | | | 240
| ctg | ctg | atc | gat | ctg | ctc | att | aag | tcg | aac | gtg | tcg | aga | tac | gcc | gag | 768
| Leu | Leu | Ile | Asp | Leu | Leu | Ile | Lys | Ser | Asn | Val | Ser | Arg | Tyr | Ala | Glu
| | | | | 245 | | | | | 250 | | | | | 255 |
| ttc | aag | aac | atc | aca | agg | att | ctc | gcc | ttc | cgg | gaa | gga | aga | gtg | gaa | 816
| Phe | Lys | Asn | Ile | Thr | Arg | Ile | Leu | Ala | Phe | Arg | Glu | Gly | Arg | Val | Glu
| | | | 260 | | | | | 265 | | | | | 270 | |
| caa | gtg | ccg | tgc | tcc | cgg | gcc | gac | gtg | ttc | aac | tca | aag | caa | ctt | acc | 864
| Gln | Val | Pro | Cys | Ser | Arg | Ala | Asp | Val | Phe | Asn | Ser | Lys | Gln | Leu | Thr
| | | 275 | | | | | 280 | | | | | 285 | | | |
| atg | gtg | gaa | aag | cgc | atg | ctg | atg | aaa | ttc | ctg | acc | ttc | tgc | atg | gag | 912
| Met | Val | Glu | Lys | Arg | Met | Leu | Met | Lys | Phe | Leu | Thr | Phe | Cys | Met | Glu
| | 290 | | | | | 295 | | | | | 300 | | | | |
| tac | gaa | aag | tac | cct | gat | gag | tac | aag | ggt | tac | gaa | gaa | att | act | ttc | 960
| Tyr | Glu | Lys | Tyr | Pro | Asp | Glu | Tyr | Lys | Gly | Tyr | Glu | Glu | Ile | Thr | Phe
| 305 | | | | 310 | | | | | 315 | | | | | 320 |
| tac | gag | tac | ctc | aag | acc | cag | aag | ctg | acc | ccg | aat | ctg | cag | tac | att | 1008
| Tyr | Glu | Tyr | Leu | Lys | Thr | Gln | Lys | Leu | Thr | Pro | Asn | Leu | Gln | Tyr | Ile
| | | | | 325 | | | | | 330 | | | | | 335 |
| gtg | atg | cac | tca | atc | gca | atg | acc | tcc | gaa | acc | gcc | tcc | tcg | acc | atc | 1056
| Val | Met | His | Ser | Ile | Ala | Met | Thr | Ser | Glu | Thr | Ala | Ser | Ser | Thr | Ile
| | | | 340 | | | | | 345 | | | | | 350 | |
| gac | ggg | ctc | aag | gcc | acc | aag | aac | ttc | ctg | cac | tgt | ttg | ggg | cgc | tac | 1104
| Asp | Gly | Leu | Lys | Ala | Thr | Lys | Asn | Phe | Leu | His | Cys | Leu | Gly | Arg | Tyr
| | | 355 | | | | | 360 | | | | | 365 | | | |
| ggc | aac | act | ccg | ttc | ctc | ttc | ccg | ctg | tac | ggc | cag | gga | gag | ctg | cct | 1152
| Gly | Asn | Thr | Pro | Phe | Leu | Phe | Pro | Leu | Tyr | Gly | Gln | Gly | Glu | Leu | Pro
| | 370 | | | | | 375 | | | | | 380 | | | | |
| cag | tgt | ttc | tgc | cgg | atg | tgc | gcc | gtg | ttc | ggc | gga | atc | tac | tgt | ctc | 1200
| Gln | Cys | Phe | Cys | Arg | Met | Cys | Ala | Val | Phe | Gly | Gly | Ile | Tyr | Cys | Leu
| 385 | | | | | 390 | | | | | 395 | | | | | 400
| cgc | cac | tcg | gtc | cag | tgc | ctg | gtg | gtg | gac | aag | gaa | tcc | agg | aag | tgc | 1248
| Arg | His | Ser | Val | Gln | Cys | Leu | Val | Val | Asp | Lys | Glu | Ser | Arg | Lys | Cys
| | | | | 405 | | | | | 410 | | | | | 415 |
| aaa | gcc | att | att | gac | cag | ttc | gga | caa | cgg | atc | att | tcc | gag | cac | ttt | 1296
| Lys | Ala | Ile | Ile | Asp | Gln | Phe | Gly | Gln | Arg | Ile | Ile | Ser | Glu | His | Phe
| | | | 420 | | | | | 425 | | | | | 430 | |
| ctt | gtg | gag | gac | tca | tac | ttc | ccg | gag | aac | atg | tgc | tct | cgg | gtc | cag | 1344

```
Leu Val Glu Asp Ser Tyr Phe Pro Glu Asn Met Cys Ser Arg Val Gln
            435                 440                 445 tat cga cag att tcc agg gcg gtg ctc att act gac cgg agc gtc ctc      1392
Tyr Arg Gln Ile Ser Arg Ala Val Leu Ile Thr Asp Arg Ser Val Leu
        450                 455                 460 aag acc gat agc gac cag cag atc tcc atc ctg acc gtg ccg gcg gaa      1440
Lys Thr Asp Ser Asp Gln Gln Ile Ser Ile Leu Thr Val Pro Ala Glu
465                 470                 475                 480 gaa ccc ggc act ttt gcc gtg cgc gtg atc gag ctt tgc tca tcc acc      1488
Glu Pro Gly Thr Phe Ala Val Arg Val Ile Glu Leu Cys Ser Ser Thr
                485                 490                 495 atg act tgc atg aaa ggc act tac ctg gtg cac ctg acg tgc acc tca      1536
Met Thr Cys Met Lys Gly Thr Tyr Leu Val His Leu Thr Cys Thr Ser
            500                 505                 510 tcg aaa acc gct aga gag gac ctg gaa tcc gtc gtc caa aag ctg ttc      1584
Ser Lys Thr Ala Arg Glu Asp Leu Glu Ser Val Val Gln Lys Leu Phe
        515                 520                 525 gtg cct tac acc gag atg gaa att gaa aac gaa caa gtg gag aag ccc      1632
Val Pro Tyr Thr Glu Met Glu Ile Glu Asn Glu Gln Val Glu Lys Pro
530                 535                 540 cgc atc ctt tgg gcc ctg tac ttt aac atg cgc gat tcc tcc gat atc      1680
Arg Ile Leu Trp Ala Leu Tyr Phe Asn Met Arg Asp Ser Ser Asp Ile
545                 550                 555                 560 tcg cgg tcc tgc tat aac gac ttg cct tcg aac gtc tac gtc tgc tcc      1728
Ser Arg Ser Cys Tyr Asn Asp Leu Pro Ser Asn Val Tyr Val Cys Ser
                565                 570                 575 ggg cca gac tgc ggt ctt ggc aac gac aat gcc gtg aag cag gcg gaa      1776
Gly Pro Asp Cys Gly Leu Gly Asn Asp Asn Ala Val Lys Gln Ala Glu
            580                 585                 590 aca ctg ttc caa gag atc tgc cct aac gag gat ttt tgc ccg ccc ccc      1824
Thr Leu Phe Gln Glu Ile Cys Pro Asn Glu Asp Phe Cys Pro Pro Pro
        595                 600                 605 cca aac ccc gag gat atc atc ttg gac gga gac agc ctg cag cca gaa      1872
Pro Asn Pro Glu Asp Ile Ile Leu Asp Gly Asp Ser Leu Gln Pro Glu
610                 615                 620 gca tcc gag tcc agc gcc atc ccg gag gcc aac agc gaa acc ttc aag      1920
Ala Ser Glu Ser Ser Ala Ile Pro Glu Ala Asn Ser Glu Thr Phe Lys
625                 630                 635                 640 gag agc act aac ctg ggc aac ctg gaa gag tcc agc gaa tga              1962
Glu Ser Thr Asn Leu Gly Asn Leu Glu Glu Ser Ser Glu
                645                 650

<210> SEQ ID NO 2
<211> LENGTH: 653
<212> TYPE: PRT
<213> ORGANISM: Artificial Sequence
<220> FEATURE:
<223> OTHER INFORMATION: Synthetic Construct

<400> SEQUENCE: 2

Met Ala Asp Thr Leu Pro Ser Glu Phe Asp Val Ile Val Ile Gly Thr
1               5                   10                  15

Gly Leu Pro Glu Ser Ile Ala Ala Ala Cys Ser Arg Ser Gly Arg
            20                  25                  30

Arg Val Leu His Val Asp Ser Arg Ser Tyr Tyr Gly Gly Asn Trp Ala
        35                  40                  45

Ser Phe Ser Phe Ser Gly Leu Leu Ser Trp Leu Lys Glu Tyr Gln Glu
    50                  55                  60

Asn Ser Asp Ile Val Ser Asp Ser Pro Val Trp Gln Asp Gln Ile Leu
65                  70                  75                  80
```

Glu Asn Glu Glu Ala Ile Ala Leu Ser Arg Lys Asp Lys Thr Ile Gln
            85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
            115                 120                 125

Asn Ser Thr Glu Ala Ala Asp Ser Ala Phe Leu Pro Thr Glu Asp Glu
130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
            165                 170                 175

Glu Lys Glu Asn His Cys Asp Asp Lys Thr Cys Val Pro Ser Thr Ser
            180                 185                 190

Ala Glu Asp Met Ser Glu Asn Val Pro Ile Ala Glu Asp Thr Thr Glu
            195                 200                 205

Gln Pro Lys Lys Asn Arg Ile Thr Tyr Ser Gln Ile Ile Lys Glu Gly
            210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
            245                 250                 255

Phe Lys Asn Ile Thr Arg Ile Leu Ala Phe Arg Glu Gly Arg Val Glu
            260                 265                 270

Gln Val Pro Cys Ser Arg Ala Asp Val Phe Asn Ser Lys Gln Leu Thr
            275                 280                 285

Met Val Glu Lys Arg Met Leu Met Lys Phe Leu Thr Phe Cys Met Glu
            290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
            325                 330                 335

Val Met His Ser Ile Ala Met Thr Ser Glu Thr Ala Ser Ser Thr Ile
            340                 345                 350

Asp Gly Leu Lys Ala Thr Lys Asn Phe Leu His Cys Leu Gly Arg Tyr
            355                 360                 365

Gly Asn Thr Pro Phe Leu Phe Pro Leu Tyr Gly Gln Gly Glu Leu Pro
            370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
            405                 410                 415

Lys Ala Ile Ile Asp Gln Phe Gly Gln Arg Ile Ile Ser Glu His Phe
            420                 425                 430

Leu Val Glu Asp Ser Tyr Phe Pro Glu Asn Met Cys Ser Arg Val Gln
            435                 440                 445

Tyr Arg Gln Ile Ser Arg Ala Val Leu Ile Thr Asp Arg Ser Val Leu
450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
            485                 490                 495

```
Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
    610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 3
<211> LENGTH: 1962
<212> TYPE: DNA
<213> ORGANISM: Homo sapiens
<220> FEATURE:
<221> NAME/KEY: CDS
<222> LOCATION: (1)..(1962)

<400> SEQUENCE: 3 atg gcg gat act ctc cct tcg gag ttt gat gtg atc gta ata ggg acg     48
Met Ala Asp Thr Leu Pro Ser Glu Phe Asp Val Ile Val Ile Gly Thr
1               5                   10                  15 ggt ttg cct gaa tcc atc att gca gct gca tgt tca aga agt ggc cgg     96
Gly Leu Pro Glu Ser Ile Ile Ala Ala Ala Cys Ser Arg Ser Gly Arg
            20                  25                  30 aga gtt ctg cat gtt gat tca aga agc tac tat gga gga aac tgg gcc    144
Arg Val Leu His Val Asp Ser Arg Ser Tyr Tyr Gly Gly Asn Trp Ala
        35                  40                  45 agt ttt agc ttt tca gga cta ttg tcc tgg cta aag gaa tac cag gaa    192
Ser Phe Ser Phe Ser Gly Leu Leu Ser Trp Leu Lys Glu Tyr Gln Glu
    50                  55                  60 aac agt gac att gta agt gac agt cca gtg tgg caa gac cag atc ctt    240
Asn Ser Asp Ile Val Ser Asp Ser Pro Val Trp Gln Asp Gln Ile Leu
65                  70                  75                  80 gaa aat gaa gaa gcc att gct ctt agc agg aag gac aaa act att caa    288
Glu Asn Glu Glu Ala Ile Ala Leu Ser Arg Lys Asp Lys Thr Ile Gln
                85                  90                  95 cat gtg gaa gta ttt tgt tat gcc agt cag gat ttg cat gaa gat gtc    336
His Val Glu Val Phe Cys Tyr Ala Ser Gln Asp Leu His Glu Asp Val
            100                 105                 110 gaa gaa gct ggt gca ctg cag aaa aat cat gct ctt gtg aca tct gca    384
Glu Glu Ala Gly Ala Leu Gln Lys Asn His Ala Leu Val Thr Ser Ala
        115                 120                 125 aac tcc aca gaa gct gca gat tct gcc ttc ctg cct acg gag gat gag    432
Asn Ser Thr Glu Ala Ala Asp Ser Ala Phe Leu Pro Thr Glu Asp Glu
    130                 135                 140 tca tta agc act atg agc tgt gaa atg ctc aca gaa caa act cca agc    480
Ser Leu Ser Thr Met Ser Cys Glu Met Leu Thr Glu Gln Thr Pro Ser
```

```
                    145             150             155             160
agc gat cca gag aat gcg cta gaa gta aat ggt gct gaa gtg aca ggg       528
Ser Asp Pro Glu Asn Ala Leu Glu Val Asn Gly Ala Glu Val Thr Gly
                165             170             175 gaa aaa gaa aac cat tgt gat gat aaa act tgt gtg cca tca act tca       576
Glu Lys Glu Asn His Cys Asp Asp Lys Thr Cys Val Pro Ser Thr Ser
            180             185             190 gca gaa gac atg agt gaa aat gtg cct ata gca gaa gat acc aca gag       624
Ala Glu Asp Met Ser Glu Asn Val Pro Ile Ala Glu Asp Thr Thr Glu
        195             200             205 caa cca aag aaa aac aga att act tac tca caa att att aaa gaa ggc       672
Gln Pro Lys Lys Asn Arg Ile Thr Tyr Ser Gln Ile Ile Lys Glu Gly
    210             215             220 agg aga ttt aat att gat tta gta tca aag ctg ctg tat tct cga gga       720
Arg Arg Phe Asn Ile Asp Leu Val Ser Lys Leu Leu Tyr Ser Arg Gly
225             230             235             240 tta cta att gat ctt cta atc aaa tct aat gtt agt cga tat gca gag       768
Leu Leu Ile Asp Leu Leu Ile Lys Ser Asn Val Ser Arg Tyr Ala Glu
            245             250             255 ttt aaa aat att acc agg att ctt gca ttt cga gaa gga cga gtg gaa       816
Phe Lys Asn Ile Thr Arg Ile Leu Ala Phe Arg Glu Gly Arg Val Glu
        260             265             270 cag gtt ccg tgt tcc aga gca gat gtc ttt aat agc aaa caa ctt act       864
Gln Val Pro Cys Ser Arg Ala Asp Val Phe Asn Ser Lys Gln Leu Thr
    275             280             285 atg gta gaa aag cga atg cta atg aaa ttt ctt aca ttt tgt atg gaa       912
Met Val Glu Lys Arg Met Leu Met Lys Phe Leu Thr Phe Cys Met Glu
290             295             300 tat gag aaa tat cct gat gaa tat aaa gga tat gaa gag atc aca ttt       960
Tyr Glu Lys Tyr Pro Asp Glu Tyr Lys Gly Tyr Glu Glu Ile Thr Phe
305             310             315             320 tat gaa tat tta aag act caa aaa tta acc ccc aac ctc caa tat att      1008
Tyr Glu Tyr Leu Lys Thr Gln Lys Leu Thr Pro Asn Leu Gln Tyr Ile
            325             330             335 gtc atg cat tca att gca atg aca tca gag aca gcc agc agc acc ata      1056
Val Met His Ser Ile Ala Met Thr Ser Glu Thr Ala Ser Ser Thr Ile
        340             345             350 gat ggt ctc aaa gct acc aaa aac ttt ctt cac tgt ctt ggg cgg tat      1104
Asp Gly Leu Lys Ala Thr Lys Asn Phe Leu His Cys Leu Gly Arg Tyr
    355             360             365 ggc aac act cca ttt ttg ttt cct tta tat ggc caa gga gaa ctc ccc      1152
Gly Asn Thr Pro Phe Leu Phe Pro Leu Tyr Gly Gln Gly Glu Leu Pro
370             375             380 cag tgt ttc tgc agg atg tgt gct gtg ttt ggt gga att tat tgt ctt      1200
Gln Cys Phe Cys Arg Met Cys Ala Val Phe Gly Gly Ile Tyr Cys Leu
385             390             395             400 cgc cat tca gta cag tgc ctt gta gtg gac aaa gaa tcc aga aaa tgt      1248
Arg His Ser Val Gln Cys Leu Val Val Asp Lys Glu Ser Arg Lys Cys
            405             410             415 aaa gca att ata gat cag ttt ggt cag aga ata atc tct gag cat ttc      1296
Lys Ala Ile Ile Asp Gln Phe Gly Gln Arg Ile Ile Ser Glu His Phe
        420             425             430 ctc gtg gag gac agt tac ttt cct gag aac atg tgc tca cgt gtg caa      1344
Leu Val Glu Asp Ser Tyr Phe Pro Glu Asn Met Cys Ser Arg Val Gln
    435             440             445 tac agg cag atc tcc agg gca gtg ctg att aca gat aga tct gtc cta      1392
Tyr Arg Gln Ile Ser Arg Ala Val Leu Ile Thr Asp Arg Ser Val Leu
450             455             460 aaa aca gat tca gat caa cag att tcc att ttg aca gtg cca gca gag      1440
Lys Thr Asp Ser Asp Gln Gln Ile Ser Ile Leu Thr Val Pro Ala Glu
```

```
Lys Thr Asp Ser Asp Gln Gln Ile Ser Ile Leu Thr Val Pro Ala Glu
465                 470                 475                 480 gaa cca gga act ttt gct gtt cgg gtc att gag tta tgt tct tca acg    1488
Glu Pro Gly Thr Phe Ala Val Arg Val Ile Glu Leu Cys Ser Ser Thr
                485                 490                 495 atg aca tgc atg aaa ggc acc tat ttg gtt cat ttg act tgc aca tct    1536
Met Thr Cys Met Lys Gly Thr Tyr Leu Val His Leu Thr Cys Thr Ser
            500                 505                 510 tct aaa aca gca aga gaa gat tta gaa tca gtt gtg cag aaa ttg ttt    1584
Ser Lys Thr Ala Arg Glu Asp Leu Glu Ser Val Val Gln Lys Leu Phe
        515                 520                 525 gtt cca tat act gaa atg gag ata gaa aat gaa caa gta gaa aag cca    1632
Val Pro Tyr Thr Glu Met Glu Ile Glu Asn Glu Gln Val Glu Lys Pro
    530                 535                 540 aga att ctg tgg gct ctt tac ttc aat atg aga gat tcg tca gac atc    1680
Arg Ile Leu Trp Ala Leu Tyr Phe Asn Met Arg Asp Ser Ser Asp Ile
545                 550                 555                 560 agc agg agc tgt tat aat gat tta cca tcc aac gtt tat gtc tgc tct    1728
Ser Arg Ser Cys Tyr Asn Asp Leu Pro Ser Asn Val Tyr Val Cys Ser
                565                 570                 575 ggc cca gat tgt ggt tta gga aat gat aat gca gtc aaa cag gct gaa    1776
Gly Pro Asp Cys Gly Leu Gly Asn Asp Asn Ala Val Lys Gln Ala Glu
            580                 585                 590 aca ctt ttc cag gaa atc tgc ccc aat gaa gat ttc tgt ccc cct cca    1824
Thr Leu Phe Gln Glu Ile Cys Pro Asn Glu Asp Phe Cys Pro Pro Pro
        595                 600                 605 cca aat cct gaa gac att atc ctt gat gga gac agt tta cag cca gag    1872
Pro Asn Pro Glu Asp Ile Ile Leu Asp Gly Asp Ser Leu Gln Pro Glu
    610                 615                 620 gct tca gaa tcc agt gcc ata cca gag gct aac tcg gag act ttc aag    1920
Ala Ser Glu Ser Ser Ala Ile Pro Glu Ala Asn Ser Glu Thr Phe Lys
625                 630                 635                 640 gaa agc aca aac ctt gga aac cta gag gag tcc tct gaa taa            1962
Glu Ser Thr Asn Leu Gly Asn Leu Glu Glu Ser Ser Glu
                645                 650

<210> SEQ ID NO 4
<211> LENGTH: 653
<212> TYPE: PRT
<213> ORGANISM: Homo sapiens

<400> SEQUENCE: 4

Met Ala Asp Thr Leu Pro Ser Glu Phe Asp Val Ile Val Ile Gly Thr
1               5                   10                  15

Gly Leu Pro Glu Ser Ile Ile Ala Ala Cys Ser Arg Ser Gly Arg
                20                  25                  30

Arg Val Leu His Val Asp Ser Arg Ser Tyr Tyr Gly Gly Asn Trp Ala
            35                  40                  45

Ser Phe Ser Phe Ser Gly Leu Leu Ser Trp Leu Lys Glu Tyr Gln Glu
        50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
                85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125
```

```
Asn Ser Thr Glu Ala Ala Asp Ser Ala Phe Leu Pro Thr Glu Asp Glu
    130                 135                 140
Ser Leu Ser Thr Met Ser Cys Glu Met Leu Thr Glu Gln Thr Pro Ser
145                 150                 155                 160
Ser Asp Pro Glu Asn Ala Leu Glu Val Asn Gly Ala Glu Val Thr Gly
                165                 170                 175
Glu Lys Glu Asn His Cys Asp Asp Lys Thr Cys Val Pro Ser Thr Ser
                180                 185                 190
Ala Glu Asp Met Ser Glu Asn Val Pro Ile Ala Glu Asp Thr Thr Glu
                195                 200                 205
Gln Pro Lys Lys Asn Arg Ile Thr Tyr Ser Gln Ile Ile Lys Glu Gly
    210                 215                 220
Arg Arg Phe Asn Ile Asp Leu Val Ser Lys Leu Leu Tyr Ser Arg Gly
225                 230                 235                 240
Leu Leu Ile Asp Leu Leu Ile Lys Ser Asn Val Ser Arg Tyr Ala Glu
                245                 250                 255
Phe Lys Asn Ile Thr Arg Ile Leu Ala Phe Arg Glu Gly Arg Val Glu
                260                 265                 270
Gln Val Pro Cys Ser Arg Ala Asp Val Phe Asn Ser Lys Gln Leu Thr
    275                 280                 285
Met Val Glu Lys Arg Met Leu Met Lys Phe Leu Thr Phe Cys Met Glu
    290                 295                 300
Tyr Glu Lys Tyr Pro Asp Glu Tyr Lys Gly Tyr Glu Glu Ile Thr Phe
305                 310                 315                 320
Tyr Glu Tyr Leu Lys Thr Gln Lys Leu Thr Pro Asn Leu Gln Tyr Ile
                325                 330                 335
Val Met His Ser Ile Ala Met Thr Ser Glu Thr Ala Ser Ser Thr Ile
                340                 345                 350
Asp Gly Leu Lys Ala Thr Lys Asn Phe Leu His Cys Leu Gly Arg Tyr
    355                 360                 365
Gly Asn Thr Pro Phe Leu Phe Pro Leu Tyr Gly Gln Gly Glu Leu Pro
    370                 375                 380
Gln Cys Phe Cys Arg Met Cys Ala Val Phe Gly Gly Ile Tyr Cys Leu
385                 390                 395                 400
Arg His Ser Val Gln Cys Leu Val Val Asp Lys Glu Ser Arg Lys Cys
                405                 410                 415
Lys Ala Ile Ile Asp Gln Phe Gly Gln Arg Ile Ile Ser Glu His Phe
                420                 425                 430
Leu Val Glu Asp Ser Tyr Phe Pro Glu Asn Met Cys Ser Arg Val Gln
    435                 440                 445
Tyr Arg Gln Ile Ser Arg Ala Val Leu Ile Thr Asp Arg Ser Val Leu
450                 455                 460
Lys Thr Asp Ser Asp Gln Gln Ile Ser Ile Leu Thr Val Pro Ala Glu
465                 470                 475                 480
Glu Pro Gly Thr Phe Ala Val Arg Val Ile Glu Leu Cys Ser Ser Thr
                485                 490                 495
Met Thr Cys Met Lys Gly Thr Tyr Leu Val His Leu Thr Cys Thr Ser
                500                 505                 510
Ser Lys Thr Ala Arg Glu Asp Leu Glu Ser Val Val Gln Lys Leu Phe
    515                 520                 525
Val Pro Tyr Thr Glu Met Glu Ile Glu Asn Glu Gln Val Glu Lys Pro
    530                 535                 540
Arg Ile Leu Trp Ala Leu Tyr Phe Asn Met Arg Asp Ser Ser Asp Ile
```

```
                    545                 550                 555                 560
            Ser Arg Ser Cys Tyr Asn Asp Leu Pro Ser Asn Val Tyr Val Cys Ser
                                565                 570                 575

Gly Pro Asp Cys Gly Leu Gly Asn Asp Asn Ala Val Lys Gln Ala Glu
                            580                 585                 590

Thr Leu Phe Gln Glu Ile Cys Pro Asn Glu Asp Phe Cys Pro Pro Pro
                        595                 600                 605

Pro Asn Pro Glu Asp Ile Ile Leu Asp Gly Asp Ser Leu Gln Pro Glu
                    610                 615                 620

Ala Ser Glu Ser Ser Ala Ile Pro Glu Ala Asn Ser Glu Thr Phe Lys
            625                 630                 635                 640

Glu Ser Thr Asn Leu Gly Asn Leu Glu Glu Ser Ser Glu
                            645                 650

<210> SEQ ID NO 5
<211> LENGTH: 1985
<212> TYPE: DNA
<213> ORGANISM: Artificial Sequence
<220> FEATURE:
<223> OTHER INFORMATION: constructed plasmid
<220> FEATURE:
<221> NAME/KEY: misc_feature
<222> LOCATION: (1)..(8)
<223> OTHER INFORMATION: NotI restriction site for subcloning into
      proviral plasmid
<220> FEATURE:
<221> NAME/KEY: misc_feature
<222> LOCATION: (4)..(16)
<223> OTHER INFORMATION: Kozak consensus sequence
<220> FEATURE:
<221> NAME/KEY: CDS
<222> LOCATION: (13)..(1971)
<223> OTHER INFORMATION: codon-optimized open reading frame (ORF)
<220> FEATURE:
<221> NAME/KEY: misc_feature
<222> LOCATION: (1972)..(1977)
<223> OTHER INFORMATION: BclI restriction site with embedded stop
      codon/ site to add optional epitope tag
<220> FEATURE:
<221> NAME/KEY: misc_feature
<222> LOCATION: (1980)..(1985)
<223> OTHER INFORMATION: BamHI restriction site for subcloning into
      proviral plasmid

<400> SEQUENCE: 5
gcggccgcca cc atg gct gat acc ctg ccc tct gaa ttc gac gtg att gtg      51
              Met Ala Asp Thr Leu Pro Ser Glu Phe Asp Val Ile Val
                1               5                  10 att gga acc gga ctc cct gaa tcg atc atc gcc gcg gcc tgt tcc cgg        99
Ile Gly Thr Gly Leu Pro Glu Ser Ile Ile Ala Ala Ala Cys Ser Arg
 15                  20                  25 tcc ggt cgg cgc gtg ctg cac gtc gat tcg aga agc tac tac gga ggg       147
Ser Gly Arg Arg Val Leu His Val Asp Ser Arg Ser Tyr Tyr Gly Gly
 30                  35                  40                  45 aat tgg gcc tca ttc tcc ttc tcc gga ctg ctc tcc tgg ctg aag gag       195
Asn Trp Ala Ser Phe Ser Phe Ser Gly Leu Leu Ser Trp Leu Lys Glu
                 50                  55                  60 tat cag gag aac tcc gac att gtc tcc gac tca cct gtg tgg cag gac       243
Tyr Gln Glu Asn Ser Asp Ile Val Ser Asp Ser Pro Val Trp Gln Asp
             65                  70                  75 cag atc ctg gaa aac gag gaa gca ata gcc ctg agc cgg aag gac aag       291
Gln Ile Leu Glu Asn Glu Glu Ala Ile Ala Leu Ser Arg Lys Asp Lys
         80                  85                  90 acc atc cag cac gtg gag gtg ttc tgt tat gcc tcc caa gac ctc cat       339
Thr Ile Gln His Val Glu Val Phe Cys Tyr Ala Ser Gln Asp Leu His
```

-continued

```
                95                  100                 105
gag gac gtg gaa gag gct gga gcg ttg cag aag aat cat gcc ctc gtg         387
Glu Asp Val Glu Glu Ala Gly Ala Leu Gln Lys Asn His Ala Leu Val
110                 115                 120                 125 acc tcc gct aac tcc acc gag gca gcc gac agc gcc ttc ctg ccg acc         435
Thr Ser Ala Asn Ser Thr Glu Ala Ala Asp Ser Ala Phe Leu Pro Thr
                130                 135                 140 gag gat gaa tcc ctg tca act atg tcg tgc gaa atg ctg acc gaa cag         483
Glu Asp Glu Ser Leu Ser Thr Met Ser Cys Glu Met Leu Thr Glu Gln
        145                 150                 155 act ccg agc tcc gac ccc gaa aac gcc ctg gaa gtg aac gga gcg gaa         531
Thr Pro Ser Ser Asp Pro Glu Asn Ala Leu Glu Val Asn Gly Ala Glu
    160                 165                 170 gtg acc ggc gaa aag gag aac cat tgc gac gac aag act tgt gtc cca         579
Val Thr Gly Glu Lys Glu Asn His Cys Asp Asp Lys Thr Cys Val Pro
175                 180                 185 tcc act tcc gcg gag gac atg tcc gag aat gtg cct atc gcc gag gac         627
Ser Thr Ser Ala Glu Asp Met Ser Glu Asn Val Pro Ile Ala Glu Asp
190                 195                 200                 205 acc acc gaa cag ccc aag aag aac aga atc acg tac agc cag atc atc         675
Thr Thr Glu Gln Pro Lys Lys Asn Arg Ile Thr Tyr Ser Gln Ile Ile
                210                 215                 220 aag gag ggg cgg agg ttt aac atc gat ctg gtg tcg aag ctg ctg tac         723
Lys Glu Gly Arg Arg Phe Asn Ile Asp Leu Val Ser Lys Leu Leu Tyr
        225                 230                 235 agc cgc ggt ctg ctg atc gat ctg ctc att aag tcg aac gtg tcg aga         771
Ser Arg Gly Leu Leu Ile Asp Leu Leu Ile Lys Ser Asn Val Ser Arg
    240                 245                 250 tac gcc gag ttc aag aac atc aca agg att ctc gcc ttc cgg gaa gga         819
Tyr Ala Glu Phe Lys Asn Ile Thr Arg Ile Leu Ala Phe Arg Glu Gly
255                 260                 265 aga gtg gaa caa gtg ccg tgc tcc cgg gcc gac gtg ttc aac tca aag         867
Arg Val Glu Gln Val Pro Cys Ser Arg Ala Asp Val Phe Asn Ser Lys
270                 275                 280                 285 caa ctt acc atg gtg gaa aag cgc atg ctg atg aaa ttc ctg acc ttc         915
Gln Leu Thr Met Val Glu Lys Arg Met Leu Met Lys Phe Leu Thr Phe
                290                 295                 300 tgc atg gag tac gaa aag tac cct gat gag tac aag ggt tac gaa gaa         963
Cys Met Glu Tyr Glu Lys Tyr Pro Asp Glu Tyr Lys Gly Tyr Glu Glu
        305                 310                 315 att act ttc tac gag tac ctc aag acc cag aag ctg acc ccg aat ctg        1011
Ile Thr Phe Tyr Glu Tyr Leu Lys Thr Gln Lys Leu Thr Pro Asn Leu
    320                 325                 330 cag tac att gtg atg cac tca atc gca atg acc tcc gaa acc gcc tcc        1059
Gln Tyr Ile Val Met His Ser Ile Ala Met Thr Ser Glu Thr Ala Ser
335                 340                 345 tcg acc atc gac ggg ctc aag gcc acc aag aac ttc ctg cac tgt ttg        1107
Ser Thr Ile Asp Gly Leu Lys Ala Thr Lys Asn Phe Leu His Cys Leu
350                 355                 360                 365 ggg cgc tac ggc aac act ccg ttc ctc ttc ccg ctg tac ggc cag gga        1155
Gly Arg Tyr Gly Asn Thr Pro Phe Leu Phe Pro Leu Tyr Gly Gln Gly
                370                 375                 380 gag ctg cct cag tgt ttc tgc cgg atg tgc gcc gtg ttc ggc gga atc        1203
Glu Leu Pro Gln Cys Phe Cys Arg Met Cys Ala Val Phe Gly Gly Ile
        385                 390                 395 tac tgt ctc cgc cac tcg gtc cag tgc ctg gtg gtg gac aag gaa tcc        1251
Tyr Cys Leu Arg His Ser Val Gln Cys Leu Val Val Asp Lys Glu Ser
    400                 405                 410 agg aag tgc aaa gcc att att gac cag ttc gga caa cgg atc att tcc        1299
```

```
Arg Lys Cys Lys Ala Ile Ile Asp Gln Phe Gly Gln Arg Ile Ile Ser
        415                 420                 425 gag cac ttt ctt gtg gag gac tca tac ttc ccg gag aac atg tgc tct      1347
Glu His Phe Leu Val Glu Asp Ser Tyr Phe Pro Glu Asn Met Cys Ser
430                 435                 440                 445 cgg gtc cag tat cga cag att tcc agg gcg gtg ctc att act gac cgg      1395
Arg Val Gln Tyr Arg Gln Ile Ser Arg Ala Val Leu Ile Thr Asp Arg
                450                 455                 460 agc gtc ctc aag acc gat agc gac cag cag atc tcc atc ctg acc gtg      1443
Ser Val Leu Lys Thr Asp Ser Asp Gln Gln Ile Ser Ile Leu Thr Val
            465                 470                 475 ccg gcg gaa gaa ccc ggc act ttt gcc gtg cgc gtg atc gag ctt tgc      1491
Pro Ala Glu Glu Pro Gly Thr Phe Ala Val Arg Val Ile Glu Leu Cys
        480                 485                 490 tca tcc acc atg act tgc atg aaa ggc act tac ctg gtg cac ctg acg      1539
Ser Ser Thr Met Thr Cys Met Lys Gly Thr Tyr Leu Val His Leu Thr
    495                 500                 505 tgc acc tca tcg aaa acc gct aga gag gac ctg gaa tcc gtc gtc caa      1587
Cys Thr Ser Ser Lys Thr Ala Arg Glu Asp Leu Glu Ser Val Val Gln
510                 515                 520                 525 aag ctg ttc gtg cct tac acc gag atg gaa att gaa aac gaa caa gtg      1635
Lys Leu Phe Val Pro Tyr Thr Glu Met Glu Ile Glu Asn Glu Gln Val
                530                 535                 540 gag aag ccc cgc atc ctt tgg gcc ctg tac ttt aac atg cgc gat tcc      1683
Glu Lys Pro Arg Ile Leu Trp Ala Leu Tyr Phe Asn Met Arg Asp Ser
            545                 550                 555 tcc gat atc tcg cgg tcc tgc tat aac gac ttg cct tcg aac gtc tac      1731
Ser Asp Ile Ser Arg Ser Cys Tyr Asn Asp Leu Pro Ser Asn Val Tyr
        560                 565                 570 gtc tgc tcc ggg cca gac tgc ggt ctt ggc aac gac aat gcc gtg aag      1779
Val Cys Ser Gly Pro Asp Cys Gly Leu Gly Asn Asp Asn Ala Val Lys
    575                 580                 585 cag gcg gaa aca ctg ttc caa gag atc tgc cct aac gag gat ttt tgc      1827
Gln Ala Glu Thr Leu Phe Gln Glu Ile Cys Pro Asn Glu Asp Phe Cys
590                 595                 600                 605 ccg ccc ccc cca aac ccc gag gat atc atc ttg gac gga gac agc ctg      1875
Pro Pro Pro Pro Asn Pro Glu Asp Ile Ile Leu Asp Gly Asp Ser Leu
                610                 615                 620 cag cca gaa gca tcc gag tcc agc gcc atc ccg gag gcc aac agc gaa      1923
Gln Pro Glu Ala Ser Glu Ser Ser Ala Ile Pro Glu Ala Asn Ser Glu
            625                 630                 635 acc ttc aag gag agc act aac ctg ggc aac ctg gaa gag tcc agc gaa      1971
Thr Phe Lys Glu Ser Thr Asn Leu Gly Asn Leu Glu Glu Ser Ser Glu
        640                 645                 650 tgatcatagg atcc                                                       1985

<210> SEQ ID NO 6
<211> LENGTH: 653
<212> TYPE: PRT
<213> ORGANISM: Artificial Sequence
<220> FEATURE:
<223> OTHER INFORMATION: Synthetic Construct

<400> SEQUENCE: 6

Met Ala Asp Thr Leu Pro Ser Glu Phe Asp Val Ile Val Ile Gly Thr
1               5                   10                  15

Gly Leu Pro Glu Ser Ile Ile Ala Ala Ala Cys Ser Arg Ser Gly Arg
            20                  25                  30

Arg Val Leu His Val Asp Ser Arg Ser Tyr Tyr Gly Gly Asn Trp Ala
        35                  40                  45
```

```
Ser Phe Ser Phe Ser Gly Leu Leu Ser Trp Leu Lys Glu Tyr Gln Glu
        50                  55                  60

Asn Ser Asp Ile Val Ser Asp Ser Pro Val Trp Gln Asp Gln Ile Leu
 65              70                  75                      80

Glu Asn Glu Glu Ala Ile Ala Leu Ser Arg Lys Asp Lys Thr Ile Gln
                    85                  90                  95

His Val Glu Val Phe Cys Tyr Ala Ser Gln Asp Leu His Glu Asp Val
                100                 105                 110

Glu Glu Ala Gly Ala Leu Gln Lys Asn His Ala Leu Val Thr Ser Ala
            115                 120                 125

Asn Ser Thr Glu Ala Ala Asp Ser Ala Phe Leu Pro Thr Glu Asp Glu
130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser
                180                 185                 190

Ala Glu Asp Met Ser Glu Asn Val Pro Ile Ala Glu Asp Thr Thr Glu
                195                 200                 205

Gln Pro Lys Lys Asn Arg Ile Thr Tyr Ser Gln Ile Ile Lys Glu Gly
            210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
                245                 250                 255

Phe Lys Asn Ile Thr Arg Ile Leu Ala Phe Arg Glu Gly Arg Val Glu
                260                 265                 270

Gln Val Pro Cys Ser Arg Ala Asp Val Phe Asn Ser Lys Gln Leu Thr
            275                 280                 285

Met Val Glu Lys Arg Met Leu Met Lys Phe Leu Thr Phe Cys Met Glu
            290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
                325                 330                 335

Val Met His Ser Ile Ala Met Thr Ser Glu Thr Ala Ser Ser Thr Ile
                340                 345                 350

Asp Gly Leu Lys Ala Thr Lys Asn Phe Leu His Cys Leu Gly Arg Tyr
                355                 360                 365

Gly Asn Thr Pro Phe Leu Phe Pro Leu Tyr Gly Gln Gly Glu Leu Pro
370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
                405                 410                 415

Lys Ala Ile Ile Asp Gln Phe Gly Gln Arg Ile Ile Ser Glu His Phe
                420                 425                 430

Leu Val Glu Asp Ser Tyr Phe Pro Glu Asn Met Cys Ser Arg Val Gln
                435                 440                 445

Tyr Arg Gln Ile Ser Arg Ala Val Leu Ile Thr Asp Arg Ser Val Leu
450                 455                 460
```

```
Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
            485                 490                 495

Met Thr Cys Met Lys Gly Thr Tyr Leu Val His Leu Thr Cys Thr Ser
        500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
        530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
            565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
            595                 600                 605

Pro Asn Pro Glu Asp Ile Ile Leu Asp Gly Asp Ser Leu Gln Pro Glu
610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 7
<211> LENGTH: 9187
<212> TYPE: DNA
<213> ORGANISM: Artificial Sequence
<220> FEATURE:
<223> OTHER INFORMATION: constructed plasmid
<220> FEATURE:
<221> NAME/KEY: misc_feature
<222> LOCATION: (1)..(145)
<223> OTHER INFORMATION: 5' ITR
<220> FEATURE:
<221> NAME/KEY: promoter
<222> LOCATION: (169)..(1786)
<223> OTHER INFORMATION: CMV.CBA promoter
<220> FEATURE:
<221> NAME/KEY: misc_feature
<222> LOCATION: (1787)..(1794)
<223> OTHER INFORMATION: Not I cloning site, cuts at 1789
<220> FEATURE:
<221> NAME/KEY: misc_feature
<222> LOCATION: (1805)..(1810)
<223> OTHER INFORMATION: BamHI cloning site, cuts at 1806
<220> FEATURE:
<221> NAME/KEY: polyA_signal
<222> LOCATION: (1850)..(2052)
<223> OTHER INFORMATION: BGH PolyA
<220> FEATURE:
<221> NAME/KEY: misc_feature
<222> LOCATION: (2109)..(2252)
<223> OTHER INFORMATION: 3' ITR
<220> FEATURE:
<221> NAME/KEY: misc_feature
<222> LOCATION: (2571)..(6624)
<223> OTHER INFORMATION: lambda stuffer
<220> FEATURE:
<221> NAME/KEY: misc_feature
<222> LOCATION: (7314)..(8126)
<223> OTHER INFORMATION: Kanamycin resistance (complementary)
<220> FEATURE:
<221> NAME/KEY: misc_feature
<222> LOCATION: (8485)..(9128)
<223> OTHER INFORMATION: Origin of replication (complementary)
```

<400> SEQUENCE: 7

```
tcgctcgctc actgaggccg cccgggcaaa gcccgggcgt cgggcgacct ttggtcgccc      60
ggcctcagtg agcgagcgag cgcgcagaga gggagtggcc aactccatca ctaggggttc     120
ctgcggccta gtaggctcag aggcacacag gagtttctgc aaatctagtg caggcgttac     180
ataacttacg gtaaatggcc cgcctggctg accgcccaac gaccccgcc cattgacgtc      240
aataatgacg tatgttccca tagtaacgcc aatagggact ttccattgac gtcaatgggt    300
ggagtattta cggtaaactg cccacttggc agtacatcaa gtgtatcata tgccaagtac    360
gccccctatt gacgtcaatg acggtaaatg gcccgcctgg cattatgccc agtacatgac    420
cttatgggac tttcctactt ggcagtacat ctacgtatta gtcatcgcta ttaacatggt    480
cgaggtgagc cccacgttct gcttcactct ccccatctcc cccccctccc caccccccaat   540
tttgtattta tttatttttt aattattttg tgcagcgatg ggggcggggg ggggggggg    600
gcgcgcgcca ggcggggcgg ggcggggcga ggggcggggc ggggcgaggc ggagaggtgc    660
ggcggcagcc aatcagagcg gcgcgctccg aaagtttcct tttatggcga ggcggcggcg    720
gcggcggccc tataaaaagc gaagcgcgcg gcgggcgggg agtcgctgcg acgctgcctt    780
cgccccgtgc cccgctccgc cgccgcctcg cgccgcccgc cccggctctg actgaccgcg    840
ttactcccac aggtgagcgg gcgggacggc ccttctcctc cgggctgtaa ttagcgcttg    900
gtttaatgac ggcttgtttc ttttctgtgg ctgcgtgaaa gccttgaggg gctccgggag    960
ggcccctttgt gcgggggag cggctcgggg ggtgcgtgcg tgtgtgtgtg cgtgggggagc   1020
gccgcgtgcg gctccgcgct gcccggcggc tgtgagcgct gcgggcgcgg cgcggggctt    1080
tgtgcgctcc gcagtgtgcg cgaggggagc gcggccgggg gcggtgcccc gcggtgcggg    1140
gggggctgcg aggggaacaa aggctgcgtg cggggtgtgt gcgtgggggg gtgagcaggg    1200
ggtgtgggcg cgtcggtcgg gctgcaaccc cccctgcacc ccctcccg agttgctgag      1260
cacggccgg cttcgggtgc gggctccgt acggggcgtg gcgcgggct cgccgtgccg      1320
ggcgggggt ggcggcaggt gggggtgccg ggcggggcgg ggccgcctcg ggccggggag    1380
ggctcggggg aggggcgcgg cggccccgg agcgccggcg gctgtcgagg cgcggcgagc    1440
cgcagccatt gccttttatg gtaatcgtgc gagagggcgc agggacttcc tttgtcccaa    1500
atctgtgcgg agccgaaatc tgggaggcgc cgccgcaccc cctctagcgg gcgcggggcg   1560
aagcggtgcg gcgccggcag gaaggaaatg ggcgggagg gccttcgtgc gtcgccgcgc    1620
cgccgtcccc ttctccctct ccagcctcgg ggctgtccgc ggggggacgg ctgccttcgg    1680
gggggacggg gcagggcggg gttcggcttc tggcgtgtga ccggcggctc tagacaattg    1740
tactaacctt cttctctttc ctctcctgac aggttggtgt acactagcgg ccgcatagta    1800
ctgcggatcc tgcagatctc gagccgaatt cctgcagccc gggggatcag cctcgactgt    1860
gccttctagt tgccagccat ctgttgtttg ccctccccc gtgccttcct tgaccctgga    1920
aggtgccact cccactgtcc tttcctaata aaatgaggaa attgcatcgc attgtctgag    1980
taggtgtcat tctattctgg ggggtggggt ggggcaggac agcaagggg aggattggga   2040
agacaataagc aggcatgctg gggatgcggt gggctctatg gcttctgagg cggaaagaac   2100
cagctggggc tcgagatcca ctagggccgc aggaaccccct agtgatggag ttggccactc   2160
cctctctgcg cgctcgctcg ctcactgagg ccgggcgacc aaaggtcgcc cgacgcccgg    2220
gctttgcccg ggcggcctca gtgagcgagc gacctgcagg ggcagcttga aggaaatact    2280
```

```
aaggcaaagg tactgcaagt gctcgcaaca ttcgcttatg cggattattg ccgtagtgcc    2340
gcgacgccgg gggcaagatg cagagattgc catggtacag gccgtgcggt tgatattgcc    2400
aaaacagagc tgtgggggag agttgtcgag aaagagtgcg gaagatgcaa aggcgtcggc    2460
tattcaagga tgccagcaag cgcagcatat cgcgctgtga cgatgctaat cccaaacctt    2520
acccaaccca cctggtcacg cactgttaag ccgctgtatg acgctctggt ggtgcaatgc    2580
cacaaagaag agtcaatcgc agacaacatt ttgaatgcgg tcacacgtta gcagcatgat    2640
tgccacggat ggcaacatat taacggcatg atattgactt attgaataaa attgggtaaa    2700
tttgactcaa cgatgggtta attcgctcgt tgtggtagtg agatgaaaag aggcggcgct    2760
tactaccgat tccgcctagt tggtcacttc gacgtatcgt ctggaactcc aaccatcgca    2820
ggcagagagg tctgcaaaat gcaatcccga acagttcgc aggtaatagt tagagcctgc    2880
ataacggttt cgggattttt tatatctgca caacaggtaa gagcattgag tcgataatcg    2940
tgaagagtcg gcgagcctgg ttagccagtg ctctttccgt tgtgctgaat taagcgaata    3000
ccggaagcag aaccggatca ccaaatgcgt acaggcgtca tcgccgccca gcaacagcac    3060 aacccaaaact gagccgtagc cactgtctgt cctgaattca ttagtaatag ttacgctgcg    3120
gccttttaca catgaccttc gtgaaagcgg gtggcaggag gtcgcgctaa caacctcctg    3180
ccgttttgcc cgtgcatatc ggtcacgaac aaatctgatt actaaacaca gtagcctgga    3240
tttgttctat cagtaatcga ccttattcct aattaaatag agcaaatccc cttattgggg    3300
gtaagacatg aagatgccag aaaaacatga cctgttggcc gccattctcg cggcaaagga    3360
acaaggcatc ggggcaatcc ttgcgtttgc aatggcgtac cttcgcggca gatataatgg    3420
cggtgcgttt acaaaaacag taatcgacgc aacgatgtgc gccattatcg cctggttcat    3480
tcgtgacctt ctcgacttcg ccggactaag tagcaatctc gcttatataa cgagcgtgtt    3540
tatcggctac atcggtactg actcgattgg ttcgcttatc aaacgcttcg ctgctaaaaa    3600
agccggagta aagatggta gaaatcaata atcaacgtaa ggcgttcctc gatatgctgg    3660
cgtggtcgga gggaactgat aacggacgtc agaaaaccag aaatcatggt tatgacgtca    3720
ttgtaggcgg agagctattt actgattact ccgatcaccc tcgcaaactt gtcacgctaa    3780 acccaaaaact caaatcaaca ggcgccggac gctaccagct tctttcccgt tggtgggatg    3840
cctaccgcaa gcagcttggc ctgaaagact tctctccgaa aagtcaggac gctgtggcat    3900
tgcagcagat taaggagcgt ggcgctttac ctatgattga tcgtggtgat atccgtcagg    3960
caatcgaccg ttgcagcaat atctgggctt cactgccggg cgctggttat ggtcagttcg    4020
agcataaggc tgacagcctg attgcaaaat tcaaagaagc gggcggaacg gtcagagaga    4080
ttgatgtatg agcagagtca ccgcgattat ctccgctctg gttatctgca tcatcgtctg    4140
cctgtcatgg gctgttaatc attaccgtga taacgccatt acctacaaag cccagcgcga    4200
caaaaatgcc agagaactga agctggcgaa cgcggcaatt actgacatgc agatgcgtca    4260
gcgtgatgtt gctgcgctcg atgcaaaata cacgaaggag ttagctgatg ctaaagctga    4320
aaatgatgct ctgcgtgatg atgttgccgc tggtcgtcgt cggttgcaca tcaaagcagt    4380
ctgtcagtca gtgcgtgaag ccaccaccgc ctccggcgtg gataatgcag cctcccccg     4440 actggcagac accgctgaac gggattattt caccctcaga gagaggctga tcactatgca    4500
aaaacaactg gaaggaaccc agaagtatat taatgagcag tgcagataga gttgcccata    4560
tcgatgggca actcatgcaa ttattgtgag caatacacac gcgcttccag cggagtataa    4620
atgcctaaag taataaaacc gagcaatcca tttacgaatg tttgctgggt ttctgtttta    4680
```

```
acaacatttt ctgcgccgcc acaaattttg gctgcatcga cagttttctt ctgcccaatt    4740
ccagaaacga agaaatgatg ggtgatggtt tcctttggtg ctactgctgc cggtttgttt    4800
tgaacagtaa acgtctgttg agcacatcct gtaataagca gggccagcgc agtagcgagt    4860 agcattttt tcatggtgtt attcccgatg cttttgaag ttcgcagaat cgtatgtgta    4920
gaaaattaaa caaaccctaa acaatgagtt gaaatttcat attgttaata tttattaatg    4980
tatgtcaggt gcgatgaatc gtcattgtat tcccggatta actatgtcca cagccctgac    5040
ggggaacttc tctgcgggag tgtccgggaa taattaaaac gatgcacaca gggtttagcg    5100
cgtacacgta ttgcattatg ccaacgcccc ggtgctgaca cggaagaaac cggacgttat    5160
gatttagcgt ggaaagattt gtgtagtgtt ctgaatgctc tcagtaaata gtaatgaatt    5220
atcaaaggta tagtaatatc ttttatgttc atggatattt gtaacccatc ggaaaactcc    5280
tgctttagca agattttccc tgtattgctg aaatgtgatt tctcttgatt tcaacctatc    5340
ataggacgtt tctataagat gcgtgtttct tgagaattta acatttacaa ccttttttaag    5400 tccttttatt aacacggtgt tatcgttttc taacacgatg tgaatattat ctgtggctag    5460
atagtaaata taatgtgaga cgttgtgacg ttttagttca gaataaaaca attcacagtc    5520
taaatctttt cgcacttgat cgaatatttc tttaaaaatg gcaacctgag ccattggtaa    5580
aaccttccat gtgatacgag ggcgcgtagt ttgcattatc gtttttatcg tttcaatctg    5640
gtctgacctc cttgtgtttt gttgatgatt tatgtcaaat attaggaatg ttttcactta    5700
atagtattgg ttgcgtaaca aagtgcggtc ctgctggcat tctggaggga aatacaaccg    5760
acagatgtat gtaaggccaa cgtgctcaaa tcttcataca gaaagatttg aagtaatatt    5820
ttaaccgcta gatgaagagc aagcgcatgg agcgacaaaa tgaataaaga acaatctgct    5880
gatgatccct ccgtggatct gattcgtgta aaaaatatgc ttaatagcac catttctatg    5940
agttaccctg atgttgtaat tgcatgtata gaacataagg tgtctctgga agcattcaga    6000
gcaattgagg cagcgttggt gaagcacgat aataatatga aggattattc cctggtggtt    6060
gactgatcac cataactgct aatcattcaa actatttagt ctgtgacaga gccaacacgc    6120
agtctgtcac tgtcaggaaa gtggtaaaac tgcaactcaa ttactgcaat gccctcgtaa    6180
ttaagtgaat ttacaatatc gtcctgttcg gagggaagaa cgcgggatgt tcattcttca    6240 tcactttaa ttgatgtata tgctctcttt tctgacgtta gtctccgacg gcaggcttca    6300
atgacccagg ctgagaaatt cccggaccct ttttgctcaa gagcgatgtt aatttgttca    6360
atcatttggt taggaaagcg gatgttgcgg gttgttgttc tgcgggttct gttcttcgtt    6420
gacatgaggt tgccccgtat tcagtgtcgc tgatttgtat tgtctgaagt tgtttttacg    6480
ttaagttgat gcagatcaat taatacgata cctgcgtcat aattgattat ttgacgtggt    6540
ttgatggcct ccacgcacgt tgtgatatgt agatgataat cattatcact ttacgggtcc    6600
tttccggtga tccgacaggt tacgcctga tgcggtattt tctccttacg catctgtgcg    6660
gtatttcaca ccgcatacgt caaagcaacc atagtacgcg ccctgtagcg gcgcattaag    6720
cgcggcgggt gtggtggtta cgcgcagcgt gaccgctaca cttgccagcg ccctagcgcc    6780 cgctccttc gctttcttcc cttcctttct cgccacgttc gccggctttc ccgtcaagc    6840 tctaaatcgg gggctccctt tagggttccg atttagtgct ttacggcacc tcgaccccaa    6900
aaaacttgat ttgggtgatg gttcacgtag tgggccatcg ccctgataga cggttttcg    6960 cccctttgacg ttggagtcca cgttctttaa tagtggactc ttgttccaaa ctggaacaac    7020
```

```
actcaaccct atctcgggct attcttttga tttagacctg caggcatgca agcttactgg    7080
ccgtcgtttt acaacgtcgt gactgggaaa accctggcgt tacccaactt aatcgccttg    7140
cagcacatcc cccttttcgcc agctggcgta atagcgaaga ggcccgcacc gatcgccctt    7200
cccaacagtt gcgcagcctg aatggcgaat gcgatttatt caacaaagcc gccgtcccgt    7260
caagtcagcg taatgctctg ccagtgttac aaccaattaa ccaattctga ttagaaaaac    7320
tcatcgagca tcaaatgaaa ctgcaattta ttcatatcag gattatcaat accatatttt    7380
tgaaaaagcc gtttctgtaa tgaaggagaa aactcaccga ggcagttcca taggatggca    7440
agatcctggt atcggtctgc gattccgact cgtccaacat caatacaacc tattaatttc    7500
ccctcgtcaa aataaggtt atcaagtgag aaatcaccat gagtgacgac tgaatccggt    7560
gagaatggca aaagcttatg catttctttc cagacttgtt caacaggcca gccattacgc    7620
tcgtcatcaa aatcactcgc atcaaccaaa ccgttattca ttcgtgattg cgcctgagcg    7680
agacgaaata cgcgatcgct gttaaaagga caattacaaa caggaatcga atgcaaccgg    7740
cgcaggaaca ctgccagcgc atcaacaata ttttcacctg aatcaggata ttcttctaat    7800
acctggaatg ctgttttccc ggggatcgca gtggtgagta accatgcatc atcaggagta    7860
cggataaaat gcttgatggt cggaagaggc ataaattccg tcagccagtt tagtctgacc    7920
atctcatctg taacatcatt ggcaacgcta cctttgccat gtttcagaaa caactctggc    7980
gcatcgggct tcccatacaa tcgatagatt gtcgcacctg attgcccgac attatcgcga    8040
gcccatttat acccatataa atcagcatcc atgttggaat ttaatcgcgg cttcgagcaa    8100
gacgtttccc gttgaatatg gctcataaca ccccttgtat tactgtttat gtaagcagac    8160
agttttattg ttcatgatga tatattttta tcttgtgcaa tgtaacatca gagattttga    8220
gacacaacgt ggctttgttg aataaatcga acttttgctg agttgaagga tcagatcacg    8280
catcttcccg acaacgcaga ccgttccgtg gcaaagcaaa agttcaaaat caccaactgg    8340
tccacctaca acaaagctct catcaaccgt ggctccctca ctttctggct ggatgatggg    8400
gcgattcagg cctggtatga gtcagcaaca ccttcttcac gaggcagacc tctcgacgga    8460
tcgttccact gagcgtcaga ccccgtagaa aagatcaaag gatcttcttg agatcctttt    8520
tttctgcgcg taatctgctg cttgcaaaca aaaaaaccac cgctaccagc ggtggtttgt    8580
ttgccggatc aagagctacc aactcttttt ccgaaggtaa ctggcttcag cagagcgcag    8640
ataccaaata ctgtccttct agtgtagccg tagttaggcc accacttcaa gaactctgta    8700
gcaccgccta catacctcgc tctgctaatc ctgttaccag tggctgctgc cagtggcgat    8760
aagtcgtgtc ttaccgggtt ggactcaaga cgatagttac cggataaggc gcagcggtcg    8820
ggctgaacgg ggggttcgtg cacacagccc agcttggagc gaacgaccta caccgaactg    8880
agatacctac agcgtgagct atgagaaagc gccacgcttc ccgaagggag aaaggcggac    8940
aggtatccgg taagcggcag ggtcggaaca ggagagcgca cgagggagct tccaggggga    9000
aacgcctggt atctttatag tcctgtcggg tttcgccacc tctgacttga gcgtcgattt    9060
ttgtgatgct cgtcaggggg gcggagccta tggaaaaacg ccagcaacgc ggcctttta    9120
cggttcctgg ccttttgctg ccttttgctg cacatgtcct gcaggcagct gcgcgccagc    9180
tgcgcgc                                                              9187
```

<210> SEQ ID NO 8
<211> LENGTH: 11148
<212> TYPE: DNA
<213> ORGANISM: Artificial Sequence
<220> FEATURE:
<223> OTHER INFORMATION: constructed plasmid

<400> SEQUENCE: 8

```
tcgctcgctc actgaggccg cccgggcaaa gcccgggcgt cgggcgacct ttggtcgccc      60
ggcctcagtg agcgagcgag cgcgcagaga gggagtggcc aactccatca ctaggggttc     120
ctgcggccta gtaggctcag aggcacacag gagtttctgc aaatctagtg caggcgttac     180
ataacttacg gtaaatggcc cgcctggctg accgcccaac gaccccgcc cattgacgtc      240
aataatgacg tatgttccca tagtaacgcc aatagggact ttccattgac gtcaatgggt     300
ggagtattta cggtaaactg cccacttggc agtacatcaa gtgtatcata tgccaagtac     360
gccccctatt gacgtcaatg acggtaaatg gcccgcctgg cattatgccc agtacatgac     420
cttatgggac tttcctactt ggcagtacat ctacgtatta gtcatcgcta ttaacatggt     480
cgaggtgagc cccacgttct gcttcactct ccccatctcc cccccctccc caccccaat     540
tttgtattta tttattttt aattattttg tgcagcgatg ggggcggggg ggggggggg      600
gcgcgcgcca ggcggggcgg ggcggggcga ggggcggggc gggcgaggc ggagaggtgc      660
ggcggcagcc aatcagagcg gcgcgctccg aaagtttcct tttatggcga ggcggcggcg     720
gcggcggccc tataaaaagc gaagcgcgcg gcgggcgggg agtcgctgcg acgctgcctt     780
cgccccgtgc cccgctccgc cgccgcctcg cgccgcccgc cccggctctg actgaccgcg     840
ttactcccac aggtgagcgg gcgggacggc ccttctcctc cgggctgtaa ttagcgcttg     900
gtttaatgac ggcttgtttc ttttctgtgg ctgcgtgaaa gccttgaggg gctccgggag     960
ggccctttgt gcgggggggag cggctcgggg ggtgcgtgcg tgtgtgtgtg cgtggggagc    1020
gccgcgtgcg gctccgcgct gcccggcggc tgtgagcgct gcgggcgcgg cgcggggctt    1080
tgtgcgctcc gcagtgtgcg cgaggggagc gcggccgggg gcggtgcccc gcggtgcggg    1140
gggggctgcg aggggaacaa aggctgcgtg cggggtgtgt gcgtggggg gtgagcaggg    1200
ggtgtgggcg cgtcggtcgg gctgcaaccc cccctgcacc cccctccccg agttgctgag    1260
cacggcccgg cttcgggtgc ggggctccgt acggggcgtg gcgcggggct cgccgtgccg    1320
ggcggggggt ggcggcaggt gggggtgccg ggcggggcgg ggccgcctcg ggccggggag    1380
ggctcggggg aggggcgcgg cggccccgg agcgccggcg gctgtcgagg cgcggcgagc    1440
cgcagccatt gccttttatg gtaatcgtgc gagagggcgc agggacttcc tttgtcccaa    1500
atctgtgcgg agccgaaatc tgggaggcgc cgccgcaccc cctctagcgg gcgcggggcg    1560
aagcggtgcg cgcgccggcag gaaggaaatg ggcggggagg gccttcgtgc gtcgccgcgc    1620
cgccgtcccc ttctccctct ccagcctcgg ggctgtccgc ggggggacgg ctgccttcgg    1680
ggggacggg gcagggcggg gttcggcttc tggcgtgtga ccggcggctc tagacaattg    1740
tactaacctt cttctcttc ctctcctgac aggttggtgt acactagcgg ccgccaccat    1800
ggctgatacc ctgccctctg aattcgacgt gattgtgatt ggaaccggac tccctgaatc    1860
gatcatcgcc gcggcctgtt cccggtccgg tcggcgcgtg ctgcacgtcg attcgagaag    1920
ctactacgga gggaattggg cctcattctc cttctccgga ctgctctcct ggctgaagga    1980
gtatcaggag aactccgaca ttgtctccga ctcacctgtg tggcaggacc agatcctgga    2040
aaacgaggaa gcaatagccc tgagccggaa ggacaagacc atccagcacg tggaggtgtt    2100
ctgttatgcc tccaagacc tccatgagga cgtggaagag gctggagcgt tgcagaagaa    2160
tcatgccctc gtgacctccg ctaactccac cgaggcagcc gacagcgcct tcctgccgac    2220
```

```
cgaggatgaa tccctgtcaa ctatgtcgtg cgaaatgctg accgaacaga ctccgagctc    2280
cgaccccgaa aacgccctgg aagtgaacgg agcggaagtg accggcgaaa aggagaacca    2340
ttgcgacgac aagacttgtg tcccatccac ttccgcggag gacatgtccg agaatgtgcc    2400
tatcgccgag gacaccaccg aacagcccaa gaagaacaga atcacgtaca gccagatcat    2460
caaggagggg cggaggttta acatcgatct ggtgtcgaag ctgctgtaca gccgcggtct    2520
gctgatcgat ctgctcatta agtcgaacgt gtcgagatac gccgagttca gaacatcac     2580 aaggattctc gccttccggg aaggaagagt ggaacaagtg ccgtgctccc gggccgacgt    2640
gttcaactca aagcaactta ccatggtgga aaagcgcatg ctgatgaaat tcctgacctt    2700
ctgcatggag tacgaaaagt accctgatga gtacaagggt tacgaagaaa ttactttcta    2760
cgagtacctc aagacccaga agctgacccc gaatctgcag tacattgtga tgcactcaat    2820
cgcaatgacc tccgaaaccg cctcctcgac catcgacggg ctcaaggcca ccaagaactt    2880
cctgcactgt ttggggcgct acggcaacac tccgttcctc ttcccgctgt acggccaggg    2940
agagctgcct cagtgtttct gccggatgtg cgccgtgttc ggcggaatct actgtctccg    3000
ccactcggtc cagtgcctgg tggtggacaa ggaatccagg aagtgcaaag ccattattga    3060
ccagttcgga caacggatca tttccgagca ctttcttgtg gaggactcat acttcccgga    3120
gaacatgtgc tctcgggtcc agtatcgaca gatttccagg gcggtgctca ttactgaccg    3180
gagcgtcctc aagaccgata gcgaccagca gatctccatc ctgaccgtgc cggcggaaga    3240
acccggcact tttgccgtgc gcgtgatcga gctttgctca tccaccatga cttgcatgaa    3300
aggcacttac ctggtgcacc tgacgtgcac ctcatcgaaa accgctagag aggacctgga    3360
atccgtcgtc caaaagctgt tcgtgcctta caccgagatg gaaattgaaa cgaacaagt     3420 ggagaagccc cgcatccttt gggccctgta ctttaacatg cgcgattcct ccgatatctc    3480
gcggtcctgc tataacgact tgccttcgaa cgtctacgtc tgctccgggc cagactgcgg    3540
tcttggcaac gacaatgccg tgaagcaggc ggaaacactg ttccaagaga tctgccctaa    3600
cgaggatttt tgcccgcccc ccccaaaccc cgaggatatc atcttggacg gagacagcct    3660
gcagccagaa gcatccgagt ccagcgccat cccggaggcc aacagcgaaa ccttcaagga    3720
gagcactaac ctgggcaacc tggaagagtc cagcgaatga tcataggatc ctgcagatct    3780
cgagccgaat tcctgcagcc cggggatca gcctcgactg tgccttctag ttgccagcca    3840
tctgttgttt gcccctcccc cgtgccttcc ttgaccctgg aaggtgccac tcccactgtc    3900
ctttcctaat aaaatgagga aattgcatcg cattgtctga gtaggtgtca ttctattctg    3960
gggggtgggg tggggcagga cagcaagggg gaggattggg aagacaatag caggcatgct    4020
ggggatgcgg tgggctctat ggcttctgag gcggaaagaa ccagctgggg ctcgagatcc    4080
actagggccg caggaacccc tagtgatgga gttggccact ccctctctgc gcgctcgctc    4140
gctcactgag gccgggcgac caaaggtcgc ccgacgcccg ggctttgccc gggcggcctc    4200
agtgagcgag cgacctgcag gggcagcttg aaggaaatac taaggcaaag gtactgcaag    4260
tgctcgcaac attcgcttat gcggattatt gccgtagtgc cgcgacgccg ggggcaagat    4320
gcagagattg ccatggtaca ggccgtgcgg ttgatattgc caaaacagag ctgtggggga    4380
gagttgtcga gaaagagtgc ggaagatgca aaggcgtcgg ctattcaagg atgccagcaa    4440
gcgcagcata tcgcgctgtg acgatgctaa tcccaaacct tacccaaccc acctggtcac    4500
gcactgttaa gccgctgtat gacgctctgg tggtgcaatg ccacaaagaa gagtcaatcg    4560
cagacaacat tttgaatgcg gtcacacgtt agcagcatga ttgccacgga tggcaacata    4620
```

```
ttaacggcat gatattgact tattgaataa aatttgggtaa atttgactca acgatgggtt    4680
aattcgctcg ttgtggtagt gagatgaaaa gaggcggcgc ttactaccga ttccgcctag    4740
ttggtcactt cgacgtatcg tctggaactc caaccatcgc aggcagagag gtctgcaaaa    4800
tgcaatcccg aaacagttcg caggtaatag ttagagcctg cataacggtt tcgggatttt    4860
ttatatctgc acaacaggta agagcattga gtcgataatc gtgaagagtc ggcgagcctg    4920
gttagccagt gctcttccg ttgtgctgaa ttaagcgaat accggaagca gaaccggatc    4980
accaaatgcg tacaggcgtc atcgccgccc agcaacagca aacccaaac tgagccgtag    5040 ccactgtctg tcctgaattc attagtaata gttacgctgc ggccttttac acatgacctt    5100
cgtgaaagcg ggtggcagga ggtcgcgcta acaacctcct gccgttttgc ccgtgcatat    5160
cggtcacgaa caaatctgat tactaaacac agtagcctgg atttgttcta tcagtaatcg    5220
accttattcc taattaaata gagcaaatcc ccttattggg ggtaagacat gaagatgcca    5280
gaaaaacatg acctgttggc cgccattctc gcggcaaagg aacaaggcat cggggcaatc    5340
cttgcgtttg caatggcgta ccttcgcggc agatataatg gcggtgcgtt tacaaaaaca    5400
gtaatcgacg caacgatgtg cgccattatc gcctggttca ttcgtgacct tctcgacttc    5460
gccggactaa gtagcaatct cgcttatata acgagcgtgt ttatcggcta catcggtact    5520
gactcgattg gttcgcttat caaacgcttc gctgctaaaa aagccggagt agaagatggt    5580
agaaatcaat aatcaacgta aggcgttcct cgatatgctg gcgtggtcgg agggaactga    5640
taacggacgt cagaaaacca gaaatcatgg ttatgacgtc attgtaggcg gagagctatt    5700
tactgattac tccgatcacc ctcgcaaact tgtcacgcta acccaaaac tcaaatcaac    5760 aggcgccgga cgctaccagc ttctttcccg ttggtgggat gcctaccgca agcagcttgg    5820
cctgaaagac ttctctccga aaagtcagga cgctgtggca ttgcagcaga ttaaggagcg    5880
tggcgcttta cctatgattg atcgtggtga tatccgtcag gcaatcgacc gttgcagcaa    5940
tatctgggct tcactgccgg gcgctggtta tggtcagttc gagcataagg ctgacagcct    6000
gattgcaaaa ttcaaagaag cgggcggaac ggtcagagag attgatgtat gagcagagtc    6060
accgcgatta tctccgctct ggttatctgc atcatcgtct gcctgtcatg ggctgttaat    6120
cattaccgtg ataacgccat tacctacaaa gcccagcgcg acaaaaatgc cagagaactg    6180
aagctggcga acgcggcaat tactgacatg cagatgcgtc agcgtgatgt tgctgcgctc    6240
gatgcaaaat acacgaagga gttagctgat gctaaagctg aaaatgatgc tctgcgtgat    6300
gatgttgccg ctggtcgtcg tcggttgcac atcaaagcag tctgtcagtc agtgcgtgaa    6360
gccaccaccg cctccggcgt ggataatgca gcctcccccc gactggcaga caccgctgaa    6420
cgggattatt tcaccctcag agagaggctg atcactatgc aaaaacaact ggaaggaacc    6480
cagaagtata ttaatgagca gtgcagatag agttgcccat atcgatgggc aactcatgca    6540
attattgtga gcaatacaca cgcgcttcca gcggagtata aatgcctaaa gtaataaaac    6600
cgagcaatcc atttacgaat gtttgctggg tttctgtttt aacaacattt tctgcgccgc    6660
cacaaatttt ggctgcatcg acagttttct tctgcccaat tccagaaacg aagaaatgat    6720
gggtgatggt ttcctttggt gctactgctg ccggtttgtt ttgaacagta aacgtctgtt    6780
gagcacatcc tgtaataagc agggccagcg cagtagcgag tagcattttt ttcatggtgt    6840
tattcccgat gcttttgaa gttcgcagaa tcgtatgtgt agaaaattaa acaaaccct a    6900 aacaatgagt tgaaatttca tattgttaat atttattaat gtatgtcagg tgcgatgaat    6960
```

```
cgtcattgta ttcccggatt aactatgtcc acagccctga cggggaactt ctctgcggga      7020
gtgtccggga ataattaaaa cgatgcacac agggtttagc gcgtacacgt attgcattat      7080
gccaacgccc cggtgctgac acggaagaaa ccggacgtta tgatttagcg tggaaagatt      7140
tgtgtagtgt tctgaatgct ctcagtaaat agtaatgaat tatcaaaggt atagtaaatat     7200 cttttatgtt catggatatt tgtaacccat cggaaaactc ctgctttagc aagattttcc     7260
ctgtattgct gaaatgtgat ttctcttgat ttcaacctat cataggacgt ttctataaga     7320
tgcgtgtttc ttgagaattt aacatttaca acctttttaa gtccttttat taacacggtg     7380
ttatcgtttt ctaacacgat gtgaatatta tctgtggcta gatagtaaat ataatgtgag     7440
acgttgtgac gttttagttc agaataaaac aattcacagt ctaaatcttt tcgcacttga     7500
tcgaatattt cttaaaaaat ggcaacctga gccattggta aaaccttcca tgtgatacga     7560
gggcgcgtag tttgcattat cgtttttatc gtttcaatct ggtctgacct ccttgtgttt     7620
tgttgatgat ttatgtcaaa tattaggaat gttttcactt aatagtattg gttgcgtaac     7680
aaagtgcggt cctgctggca ttctgggggg aaatacaacc gacagatgta tgtaaggcca     7740
acgtgctcaa atcttcatac agaaagattt gaagtaatat tttaaccgct agatgaagag     7800
caagcgcatg gagcgacaaa atgaataaag aacaatctgc tgatgatccc tccgtggatc     7860
tgattcgtgt aaaaaatatg cttaatagca ccatttctat gagttaccct gatgttgtaa     7920
ttgcatgtat agaacataag gtgtctctgg aagcattcag agcaattgag gcagcgttgg     7980
tgaagcacga taataatatg aaggattatt ccctggtggt tgactgatca ccataactgc     8040
taatcattca aactatttag tctgtgacag agccaacacg cagtctgtca ctgtcaggaa     8100
agtggtaaaa ctgcaactca attactgcaa tgccctcgta attaagtgaa tttacaatat     8160
cgtcctgttc ggagggaaga acgcgggatg ttcattcttc atcacttta attgatgtat      8220 atgctctctt ttctgacgtt agtctccgac ggcaggcttc aatgacccag gctgagaaat     8280
tcccggaccc tttttgctca agagcgatgt taatttgttc aatcatttgg ttaggaaagc     8340
ggatgttgcg ggttgttgtt ctgcgggttc tgttcttcgt tgacatgagg ttgccccgta     8400
ttcagtgtcg ctgatttgta ttgtctgaag ttgtttttac gttaagttga tgcagatcaa     8460
ttaatacgat acctgcgtca taattgatta tttgacgtgg tttgatggcc tccacgcacg     8520
ttgtgatatg tagatgataa tcattatcac tttacgggtc cttccggtg atccgacagg     8580 ttacggcctg atgcggtatt ttctccttac gcatctgtgc ggtatttcac accgcatacg     8640
tcaaagcaac catagtacgc gccctgtagc ggcgcattaa gcgcggcggg tgtggtggtt     8700
acgcgcagcg tgaccgctac acttgccagc gccctagcgc ccgctccttt cgctttcttc     8760
ccttcctttc tcgccacgtt cgccggcttt cccgtcaag ctctaaatcg gggctccct      8820 ttaggggttcc gatttagtgc tttacggcac ctcgacccca aaaaacttga tttgggtgat     8880
ggttcacgta gtgggccatc gccctgatag acggttttc gccctttgac gttggagtcc     8940
acgttcttta atagtggact cttgttccaa actggaacaa cactcaaccc tatctcgggc     9000
tattcttttg atttagacct gcaggcatgc aagcttactg gccgtcgttt tacaacgtcg     9060
tgactgggaa aaccctggcg ttacccaact taatcgcctt gcagcacatc cccctttcgc     9120
cagctggcgt aatagcgaag aggcccgcac cgatcgccct tcccaacagt tgcgcagcct     9180
gaatggcgaa tgcgatttat tcaacaaagc cgccgtcccg tcaagtcagc gtaatgctct     9240
gccagtgtta caaccaatta accaattctg attagaaaaa ctcatcgagc atcaaatgaa     9300
actgcaattt attcatatca ggattatcaa taccatattt ttgaaaaagc cgtttctgta     9360
```

```
atgaaggaga aaactcaccg aggcagttcc ataggatggc aagatcctgg tatcggtctg    9420
cgattccgac tcgtccaaca tcaatacaac ctattaattt ccccctcgtca aaataaggt    9480
tatcaagtga aaatcacca tgagtgacga ctgaatccgg tgagaatggc aaaagcttat    9540
gcatttcttt ccagacttgt tcaacaggcc agccattacg ctcgtcatca aaatcactcg    9600
catcaaccaa accgttattc attcgtgatt gcgcctgagc gagacgaaat acgcgatcgc    9660
tgttaaaagg acaattacaa acaggaatcg aatgcaaccg gcgcaggaac actgccagcg    9720
catcaacaat attttcacct gaatcaggat attcttctaa tacctggaat gctgttttcc    9780
cggggatcgc agtggtgagt aaccatgcat catcaggagt acggataaaa tgcttgatgg    9840
tcggaagagg cataaattcc gtcagccagt ttagtctgac catctcatct gtaacatcat    9900
tggcaacgct acctttgcca tgtttcagaa acaactctgg cgcatcgggc ttcccataca    9960
atcgatagat tgtcgcacct gattgcccga cattatcgcg agcccattta tacccatata   10020
aatcagcatc catgttggaa tttaatcgcg gcttcgagca agacgtttcc cgttgaatat   10080
ggctcataac accccttgta ttactgttta tgtaagcaga cagttttatt gttcatgatg   10140
atatattttt atcttgtgca atgtaacatc agagattttg agacacaacg tggctttgtt   10200
gaataaatcg aacttttgct gagttgaagg atcagatcac gcatcttccc gacaacgcag   10260
accgttccgt ggcaaagcaa aagttcaaaa tcaccaactg gtccacctac aacaaagctc   10320
tcatcaaccg tggctccctc actttctggc tggatgatgg ggcgattcag gcctggtatg   10380
agtcagcaac accttcttca cgaggcagac ctctcgacgg atcgttccac tgagcgtcag   10440
accccgtaga aagatcaaa ggatcttctt gagatccttt ttttctgcgc gtaatctgct   10500
gcttgcaaac aaaaaaacca ccgctaccag cggtggtttg tttgccggat caagagctac   10560
caactctttt tccgaaggta actggcttca gcagagcgca gataccaaat actgtccttc   10620
tagtgtagcc gtagttaggc caccacttca agaactctgt agcaccgcct acatacctcg   10680
ctctgctaat cctgttacca gtggctgctg ccagtggcga taagtcgtgt cttaccgggt   10740
tggactcaag acgatagtta ccggataagg cgcagcggtc gggctgaacg ggggggttcgt   10800
gcacacagcc cagcttggag cgaacgacct acaccgaact gagataccta cagcgtgagc   10860
tatgagaaag cgccacgctt cccgaaggga gaaaggcgga caggtatccg gtaagcggca   10920
gggtcgaac aggagagcgc acgagggagc ttccagggg aaacgcctgg tatctttata   10980
gtcctgtcgg gtttcgccac ctctgacttg agcgtcgatt tttgtgatgc tcgtcagggg   11040
ggcggagcct atgaaaaaac gccagcaacg cggcctttttt acggttcctg gccttttgct   11100
ggccttttgc tcacatgtcc tgcaggcagc tgcgcgccag ctgcgcgc                 11148
```

<210> SEQ ID NO 9
<211> LENGTH: 2085
<212> TYPE: DNA
<213> ORGANISM: Artificial Sequence
<220> FEATURE:
<223> OTHER INFORMATION: codon optimized sequence
<220> FEATURE:
<221> NAME/KEY: CDS
<222> LOCATION: (1)..(2085)
<223> OTHER INFORMATION: codon-optimized ORF

<400> SEQUENCE: 9

```
atg gct aag att aac acc cag tac tca cat cca tcc cgc act cac ctc    48
Met Ala Lys Ile Asn Thr Gln Tyr Ser His Pro Ser Arg Thr His Leu
1               5                   10                  15
```

-continued

| | |
|---|---|
| aaa gtc aag acc tcc gat cgg gat ctg aac cgg gct gag aat ggg ctg<br>Lys Val Lys Thr Ser Asp Arg Asp Leu Asn Arg Ala Glu Asn Gly Leu<br>                   20                         25                       30 | 96 |
| tcg cgc gcc cac tcg tcg tcc gag gaa acc agc agc gtg ctc cag ccg<br>Ser Arg Ala His Ser Ser Ser Glu Glu Thr Ser Ser Val Leu Gln Pro<br>        35                        40                       45 | 144 |
| ggc atc gcc atg gaa act agg ggg ctg gcg gac tcc gga cag gga tcc<br>Gly Ile Ala Met Glu Thr Arg Gly Leu Ala Asp Ser Gly Gln Gly Ser<br> 50                        55                       60 | 192 |
| ttc act gga cag ggt att gcc cgg ctg agc aga ctg atc ttc ctg ctt<br>Phe Thr Gly Gln Gly Ile Ala Arg Leu Ser Arg Leu Ile Phe Leu Leu<br>65                      70                       75                   80 | 240 |
| cgc cgc tgg gcg gcc aga cac gtg cac cat cag gac cag gga cct gat<br>Arg Arg Trp Ala Ala Arg His Val His His Gln Asp Gln Gly Pro Asp<br>                   85                       90                   95 | 288 |
| agc ttc ccc gac cgc ttt agg gga gcc gag ctg aaa gaa gtg tca agc<br>Ser Phe Pro Asp Arg Phe Arg Gly Ala Glu Leu Lys Glu Val Ser Ser<br>            100                      105                      110 | 336 |
| cag gag tca aac gcg cag gcc aac gtc ggc agc caa gag cct gca gac<br>Gln Glu Ser Asn Ala Gln Ala Asn Val Gly Ser Gln Glu Pro Ala Asp<br>               115                      120                      125 | 384 |
| cgg gga cgc tcg gca tgg ccg ctc gca aag tgc aac act aac act tcc<br>Arg Gly Arg Ser Ala Trp Pro Leu Ala Lys Cys Asn Thr Asn Thr Ser<br>130                     135                      140 | 432 |
| aac aac acc gaa gag gaa aag aaa acc aag aag aag gat gca att gtg<br>Asn Asn Thr Glu Glu Glu Lys Lys Thr Lys Lys Lys Asp Ala Ile Val<br>145                     150                     155                   160 | 480 |
| gtg gac cct tcc tcc aac ctg tac tac cgc tgg ttg acc gcc atc gcc<br>Val Asp Pro Ser Ser Asn Leu Tyr Tyr Arg Trp Leu Thr Ala Ile Ala<br>                        165                      170                      175 | 528 |
| ctc ccg gtc ttt tac aat tgg tat ctc ctt atc tgc cgg gcc tgc ttc<br>Leu Pro Val Phe Tyr Asn Trp Tyr Leu Leu Ile Cys Arg Ala Cys Phe<br>                   180                      185                      190 | 576 |
| gac gaa ctg caa tca gag tac ctg atg ctg tgg ctg gtg ctg gac tat<br>Asp Glu Leu Gln Ser Glu Tyr Leu Met Leu Trp Leu Val Leu Asp Tyr<br>             195                      200                      205 | 624 |
| agc gcc gat gtg ctc tac gtc ctg gat gtg ctc gtg cgc gcc cgg acc<br>Ser Ala Asp Val Leu Tyr Val Leu Asp Val Leu Val Arg Ala Arg Thr<br>210                     215                     220 | 672 |
| gga ttc ttg gaa caa ggc ctg atg gtg tcc gac acg aat aga ctg tgg<br>Gly Phe Leu Glu Gln Gly Leu Met Val Ser Asp Thr Asn Arg Leu Trp<br>225                     230                     235                   240 | 720 |
| cag cac tat aag acc aca acc cag ttc aag ctt gac gtg ctc agc ctt<br>Gln His Tyr Lys Thr Thr Thr Gln Phe Lys Leu Asp Val Leu Ser Leu<br>                   245                      250                      255 | 768 |
| gtg ccg act gac ctg gcc tac ctg aaa gtc gga act aac tac ccg gaa<br>Val Pro Thr Asp Leu Ala Tyr Leu Lys Val Gly Thr Asn Tyr Pro Glu<br>260                     265                     270 | 816 |
| gtc aga ttc aac cga ctc ctg aag ttc agc agg ctg ttc gag ttc ttt<br>Val Arg Phe Asn Arg Leu Leu Lys Phe Ser Arg Leu Phe Glu Phe Phe<br>               275                      280                      285 | 864 |
| gac cgc acc gag act cgg acc aac tac cct aac atg ttc cgg atc gga<br>Asp Arg Thr Glu Thr Arg Thr Asn Tyr Pro Asn Met Phe Arg Ile Gly<br>290                     295                     300 | 912 |
| aat ctg gtg ctc tac ata ctg att atc atc cat tgg aac gcc tgt atc<br>Asn Leu Val Leu Tyr Ile Leu Ile Ile Ile His Trp Asn Ala Cys Ile<br>305                     310                     315                   320 | 960 |
| tat ttc gcc att tcg aag ttc atc ggt ttc gga acc gat tcc tgg gtg<br>Tyr Phe Ala Ile Ser Lys Phe Ile Gly Phe Gly Thr Asp Ser Trp Val<br>                   325                      330                      335 | 1008 |

```
tac ccc aac atc tcg atc ccc gaa cac ggt cgc ctg tcc cgg aag tac    1056
Tyr Pro Asn Ile Ser Ile Pro Glu His Gly Arg Leu Ser Arg Lys Tyr
            340                 345                 350 atc tac tcc ctg tac tgg tcc act ctg act ctg acc acg atc ggg gaa    1104
Ile Tyr Ser Leu Tyr Trp Ser Thr Leu Thr Leu Thr Thr Ile Gly Glu
        355                 360                 365 acc cct cca ccc gtg aag gac gaa gag tac ctg ttc gtg gtg gtg gac    1152
Thr Pro Pro Pro Val Lys Asp Glu Glu Tyr Leu Phe Val Val Val Asp
    370                 375                 380 ttc ctg gtc gga gtg ttg att ttc gcc acc att gtg gga aac gtg ggc    1200
Phe Leu Val Gly Val Leu Ile Phe Ala Thr Ile Val Gly Asn Val Gly
385                 390                 395                 400 tcc atg atc tcc aac atg aac gcg tcg aga gct gag ttc caa gcc aag    1248
Ser Met Ile Ser Asn Met Asn Ala Ser Arg Ala Glu Phe Gln Ala Lys
                405                 410                 415 atc gac tcc att aag cag tac atg cag ttc aga aag gtc acc aag gac    1296
Ile Asp Ser Ile Lys Gln Tyr Met Gln Phe Arg Lys Val Thr Lys Asp
            420                 425                 430 ctg gaa acc agg gtc atc cgc tgg ttc gac tac ctg tgg gcc aac aaa    1344
Leu Glu Thr Arg Val Ile Arg Trp Phe Asp Tyr Leu Trp Ala Asn Lys
        435                 440                 445 aag act gtg gac gaa aag gaa gtg ctg aag tcg ctg ccg gat aag ctg    1392
Lys Thr Val Asp Glu Lys Glu Val Leu Lys Ser Leu Pro Asp Lys Leu
    450                 455                 460 aag gcc gaa atc gcc att aac gtg cac ctt gac acc ctg aag aaa gtc    1440
Lys Ala Glu Ile Ala Ile Asn Val His Leu Asp Thr Leu Lys Lys Val
465                 470                 475                 480 cgg atc ttc caa gac tgt gaa gcc ggc ctc ctg gtg gag ctc gtg ctc    1488
Arg Ile Phe Gln Asp Cys Glu Ala Gly Leu Leu Val Glu Leu Val Leu
                485                 490                 495 aag ctg cgg ccc acc gtg ttc agc ccg gga gat tac att tgc aag aag    1536
Lys Leu Arg Pro Thr Val Phe Ser Pro Gly Asp Tyr Ile Cys Lys Lys
            500                 505                 510 ggc gat atc ggc aaa gag atg tac atc atc aac gag gga aag ctg gcc    1584
Gly Asp Ile Gly Lys Glu Met Tyr Ile Ile Asn Glu Gly Lys Leu Ala
        515                 520                 525 gtg gtc gcg gac gac ggc gtg acc cag ttc gtg gtg ctg tcc gac gga    1632
Val Val Ala Asp Asp Gly Val Thr Gln Phe Val Val Leu Ser Asp Gly
    530                 535                 540 tcc tac ttc ggt gaa atc tca atc ctc aac atc aag ggg tcc aag tcc    1680
Ser Tyr Phe Gly Glu Ile Ser Ile Leu Asn Ile Lys Gly Ser Lys Ser
545                 550                 555                 560 ggc aac cgg aga act gcc aac att cgc tcc atc gga tac agc gac ctg    1728
Gly Asn Arg Arg Thr Ala Asn Ile Arg Ser Ile Gly Tyr Ser Asp Leu
                565                 570                 575 ttt tgc ctg tcc aag gat gac ctg atg gag gct ctg act gag tac cct    1776
Phe Cys Leu Ser Lys Asp Asp Leu Met Glu Ala Leu Thr Glu Tyr Pro
            580                 585                 590 gaa gcg aag aag gct ttg gag gaa aag ggg cgg cag att ctg atg aag    1824
Glu Ala Lys Lys Ala Leu Glu Glu Lys Gly Arg Gln Ile Leu Met Lys
        595                 600                 605 gac aat ttg atc gac gag gag ctc gca cgg gcc ggc gcc gac ccc aag    1872
Asp Asn Leu Ile Asp Glu Glu Leu Ala Arg Ala Gly Ala Asp Pro Lys
    610                 615                 620 gat ctc gaa gag aag gtc gaa cag ctg ggt tct tcg ctt gat acc ctg    1920
Asp Leu Glu Glu Lys Val Glu Gln Leu Gly Ser Ser Leu Asp Thr Leu
625                 630                 635                 640 caa acc cga ttc gcg cgg ctg ctc gcc gag tac aac gcg acc cag atg    1968
Gln Thr Arg Phe Ala Arg Leu Leu Ala Glu Tyr Asn Ala Thr Gln Met
```

```
                          645                 650                 655
aag atg aag cag aga ctg tca cag ttg gaa tcc caa gtc aag ggc gga         2016
Lys Met Lys Gln Arg Leu Ser Gln Leu Glu Ser Gln Val Lys Gly Gly
            660                 665                 670 ggc gac aag ccg ctg gcg gac ggg gaa gtg ccc ggg gac gcc acc aag         2064
Gly Asp Lys Pro Leu Ala Asp Gly Glu Val Pro Gly Asp Ala Thr Lys
            675                 680                 685 act gag gac aag cag cag tga                                             2085
Thr Glu Asp Lys Gln Gln
            690

<210> SEQ ID NO 10
<211> LENGTH: 694
<212> TYPE: PRT
<213> ORGANISM: Artificial Sequence
<220> FEATURE:
<223> OTHER INFORMATION: Synthetic Construct

<400> SEQUENCE: 10

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
    130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
    210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
```

```
            290                 295                 300
Asn Leu Val Leu Tyr Ile Leu Ile Ile His Trp Asn Ala Cys Ile
305                 310                 315                 320

Tyr Phe Ala Ile Ser Lys Phe Ile Gly Phe Thr Asp Ser Trp Val
                325                 330                 335

Tyr Pro Asn Ile Ser Ile Pro Glu His Gly Arg Leu Ser Arg Lys Tyr
                340                 345                 350

Ile Tyr Ser Leu Tyr Trp Ser Thr Leu Thr Leu Thr Thr Ile Gly Glu
                355                 360                 365

Thr Pro Pro Pro Val Lys Asp Glu Glu Tyr Leu Phe Val Val Val Asp
        370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
                420                 425                 430

Leu Glu Thr Arg Val Ile Arg Trp Phe Asp Tyr Leu Trp Ala Asn Lys
            435                 440                 445

Lys Thr Val Asp Glu Lys Glu Val Leu Lys Ser Leu Pro Asp Lys Leu
        450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
                500                 505                 510

Gly Asp Ile Gly Lys Glu Met Tyr Ile Ile Asn Glu Gly Lys Leu Ala
                515                 520                 525

Val Val Ala Asp Asp Gly Val Thr Gln Phe Val Val Leu Ser Asp Gly
                530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
                580                 585                 590

Glu Ala Lys Lys Ala Leu Glu Glu Lys Gly Arg Gln Ile Leu Met Lys
        595                 600                 605

Asp Asn Leu Ile Asp Glu Glu Leu Ala Arg Ala Gly Ala Asp Pro Lys
        610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
                660                 665                 670

Gly Asp Lys Pro Leu Ala Asp Gly Glu Val Pro Gly Asp Ala Thr Lys
                675                 680                 685

Thr Glu Asp Lys Gln Gln
    690

<210> SEQ ID NO 11
```

```
<211> LENGTH: 2250
<212> TYPE: DNA
<213> ORGANISM: Artificial Sequence
<220> FEATURE:
<223> OTHER INFORMATION: codon optimized sequence
<220> FEATURE:
<221> NAME/KEY: CDS
<222> LOCATION: (1)..(2250)
<223> OTHER INFORMATION: codon-optimized ORF

<400> SEQUENCE: 11 atg gct aag att aac acc cag tac tca cat cca tcc cgc act cac ctc        48
Met Ala Lys Ile Asn Thr Gln Tyr Ser His Pro Ser Arg Thr His Leu
 1               5                  10                  15 aaa gtc aag acc tcc gat cgg gat ctg aac cgg gct gag aat ggg ctg        96
Lys Val Lys Thr Ser Asp Arg Asp Leu Asn Arg Ala Glu Asn Gly Leu
            20                  25                  30 tcg cgc gcc cac tcg tcg tcc gag gaa acc agc agc gtg ctc cag ccg       144
Ser Arg Ala His Ser Ser Ser Glu Glu Thr Ser Ser Val Leu Gln Pro
        35                  40                  45 ggc atc gcc atg gaa act agg ggg ctg gcg gac tcc gga cag gga tcc       192
Gly Ile Ala Met Glu Thr Arg Gly Leu Ala Asp Ser Gly Gln Gly Ser
    50                  55                  60 ttc act gga cag ggt att gcc cgg ttc ggg cgg att cag aag aag tcc       240
Phe Thr Gly Gln Gly Ile Ala Arg Phe Gly Arg Ile Gln Lys Lys Ser
65                  70                  75                  80 cag ccg gag aag gtc gtg cgg gct gcc agc agg ggc agg cca ctc att       288
Gln Pro Glu Lys Val Val Arg Ala Ala Ser Arg Gly Arg Pro Leu Ile
                85                  90                  95 ggt tgg aca cag tgg tgc gct gag gat ggt gga gat gaa tcg gaa atg       336
Gly Trp Thr Gln Trp Cys Ala Glu Asp Gly Gly Asp Glu Ser Glu Met
            100                 105                 110 gca ctg gcc ggc tct ccc gga tgc agc tcg ggc ccc caa ggg aga ctg       384
Ala Leu Ala Gly Ser Pro Gly Cys Ser Ser Gly Pro Gln Gly Arg Leu
        115                 120                 125 agc aga ctg atc ttc ctg ctt cgc cgc tgg gcg gcc aga cac gtg cac       432
Ser Arg Leu Ile Phe Leu Leu Arg Arg Trp Ala Ala Arg His Val His
    130                 135                 140 cat cag gac cag gga cct gat agc ttc ccc gac cgc ttt agg gga gcc       480
His Gln Asp Gln Gly Pro Asp Ser Phe Pro Asp Arg Phe Arg Gly Ala
145                 150                 155                 160 gag ctg aaa gaa gtg tca agc cag gag tca aac gcg cag gcc aac gtc       528
Glu Leu Lys Glu Val Ser Ser Gln Glu Ser Asn Ala Gln Ala Asn Val
                165                 170                 175 ggc agc caa gag cct gca gac cgg gga cgc tcg gca tgg ccg ctc gca       576
Gly Ser Gln Glu Pro Ala Asp Arg Gly Arg Ser Ala Trp Pro Leu Ala
            180                 185                 190 aag tgc aac act aac act tcc aac aac acc gaa gag gaa aag aaa acc       624
Lys Cys Asn Thr Asn Thr Ser Asn Asn Thr Glu Glu Glu Lys Lys Thr
        195                 200                 205 aag aag aag gat gca att gtg gtg gac cct tcc tcc aac ctg tac tac       672
Lys Lys Lys Asp Ala Ile Val Val Asp Pro Ser Ser Asn Leu Tyr Tyr
    210                 215                 220 cgc tgg ttg acc gcc atc gcc ctc ccg gtc ttt tac aat tgg tat ctc       720
Arg Trp Leu Thr Ala Ile Ala Leu Pro Val Phe Tyr Asn Trp Tyr Leu
225                 230                 235                 240 ctt atc tgc cgg gcc tgc ttc gac gaa ctg caa tca gag tac ctg atg       768
Leu Ile Cys Arg Ala Cys Phe Asp Glu Leu Gln Ser Glu Tyr Leu Met
                245                 250                 255 ctg tgg ctg gtg ctg gac tat agc gcc gat gtg ctc tac gtc ctg gat       816
Leu Trp Leu Val Leu Asp Tyr Ser Ala Asp Val Leu Tyr Val Leu Asp
            260                 265                 270
```

```
gtg ctc gtg cgc gcc cgg acc gga ttc ttg gaa caa ggc ctg atg gtg        864
Val Leu Val Arg Ala Arg Thr Gly Phe Leu Glu Gln Gly Leu Met Val
        275                 280                 285 tcc gac acg aat aga ctg tgg cag cac tat aag acc aca acc cag ttc        912
Ser Asp Thr Asn Arg Leu Trp Gln His Tyr Lys Thr Thr Thr Gln Phe
        290                 295                 300 aag ctt gac gtg ctc agc ctt gtg ccg act gac ctg gcc tac ctg aaa        960
Lys Leu Asp Val Leu Ser Leu Val Pro Thr Asp Leu Ala Tyr Leu Lys
305                 310                 315                 320 gtc gga act aac tac ccg gaa gtc aga ttc aac cga ctc ctg aag ttc       1008
Val Gly Thr Asn Tyr Pro Glu Val Arg Phe Asn Arg Leu Leu Lys Phe
            325                 330                 335 agc agg ctg ttc gag ttc ttt gac cgc acc gag act cgg acc aac tac       1056
Ser Arg Leu Phe Glu Phe Phe Asp Arg Thr Glu Thr Arg Thr Asn Tyr
        340                 345                 350 cct aac atg ttc cgg atc gga aat ctg gtg ctc tac ata ctg att atc       1104
Pro Asn Met Phe Arg Ile Gly Asn Leu Val Leu Tyr Ile Leu Ile Ile
        355                 360                 365 atc cat tgg aac gcc tgt atc tat ttc gcc att tcg aag ttc atc ggt       1152
Ile His Trp Asn Ala Cys Ile Tyr Phe Ala Ile Ser Lys Phe Ile Gly
        370                 375                 380 ttc gga acc gat tcc tgg gtg tac ccc aac atc tcg atc ccc gaa cac       1200
Phe Gly Thr Asp Ser Trp Val Tyr Pro Asn Ile Ser Ile Pro Glu His
385                 390                 395                 400 ggt cgc ctg tcc cgg aag tac atc tac tcc ctg tac tgg tcc act ctg       1248
Gly Arg Leu Ser Arg Lys Tyr Ile Tyr Ser Leu Tyr Trp Ser Thr Leu
            405                 410                 415 act ctg acc acg atc ggg gaa acc cct cca ccc gtg aag gac gaa gag       1296
Thr Leu Thr Thr Ile Gly Glu Thr Pro Pro Pro Val Lys Asp Glu Glu
        420                 425                 430 tac ctg ttc gtg gtg gtg gac ttc ctg gtc gga gtg ttg att ttc gcc       1344
Tyr Leu Phe Val Val Val Asp Phe Leu Val Gly Val Leu Ile Phe Ala
        435                 440                 445 acc att gtg gga aac gtg ggc tcc atg atc tcc aac atg aac gcg tcg       1392
Thr Ile Val Gly Asn Val Gly Ser Met Ile Ser Asn Met Asn Ala Ser
450                 455                 460 aga gct gag ttc caa gcc aag atc gac tcc att aag cag tac atg cag       1440
Arg Ala Glu Phe Gln Ala Lys Ile Asp Ser Ile Lys Gln Tyr Met Gln
465                 470                 475                 480 ttc aga aag gtc acc aag gac ctg gaa acc agg gtc atc cgc tgg ttc       1488
Phe Arg Lys Val Thr Lys Asp Leu Glu Thr Arg Val Ile Arg Trp Phe
            485                 490                 495 gac tac ctg tgg gcc aac aaa aag act gtg gac gaa aag gaa gtg ctg       1536
Asp Tyr Leu Trp Ala Asn Lys Lys Thr Val Asp Glu Lys Glu Val Leu
        500                 505                 510 aag tcg ctg ccg gat aag ctg aag gcc gaa atc gcc att aac gtg cac       1584
Lys Ser Leu Pro Asp Lys Leu Lys Ala Glu Ile Ala Ile Asn Val His
        515                 520                 525 ctt gac acc ctg aag aaa gtc cgg atc ttc caa gac tgt gaa gcc ggc       1632
Leu Asp Thr Leu Lys Lys Val Arg Ile Phe Gln Asp Cys Glu Ala Gly
        530                 535                 540 ctc ctg gtg gag ctc gtg ctc aag ctg cgg ccc acc gtg ttc agc ccg       1680
Leu Leu Val Glu Leu Val Leu Lys Leu Arg Pro Thr Val Phe Ser Pro
545                 550                 555                 560 gga gat tac att tgc aag aag ggc gat atc ggc aaa gag atg tac atc       1728
Gly Asp Tyr Ile Cys Lys Lys Gly Asp Ile Gly Lys Glu Met Tyr Ile
            565                 570                 575 atc aac gag gga aag ctg gcc gtg gtc gcg gac gac ggc gtg acc cag       1776
Ile Asn Glu Gly Lys Leu Ala Val Val Ala Asp Asp Gly Val Thr Gln
```

```
ttc gtg gtg ctg tcc gac gga tcc tac ttc ggt gaa atc tca atc ctc    1824
Phe Val Val Leu Ser Asp Gly Ser Tyr Phe Gly Glu Ile Ser Ile Leu
        595                 600                 605 aac atc aag ggg tcc aag tcc ggc aac cgg aga act gcc aac att cgc    1872
Asn Ile Lys Gly Ser Lys Ser Gly Asn Arg Arg Thr Ala Asn Ile Arg
610                 615                 620 tcc atc gga tac agc gac ctg ttt tgc ctg tcc aag gat gac ctg atg    1920
Ser Ile Gly Tyr Ser Asp Leu Phe Cys Leu Ser Lys Asp Asp Leu Met
625                 630                 635                 640 gag gct ctg act gag tac cct gaa gcg aag aag gct ttg gag gaa aag    1968
Glu Ala Leu Thr Glu Tyr Pro Glu Ala Lys Lys Ala Leu Glu Glu Lys
        645                 650                 655 ggg cgg cag att ctg atg aag gac aat ttg atc gac gag gag ctc gca    2016
Gly Arg Gln Ile Leu Met Lys Asp Asn Leu Ile Asp Glu Glu Leu Ala
    660                 665                 670 cgg gcc ggc gcc gac ccc aag gat ctc gaa gag aag gtc gaa cag ctg    2064
Arg Ala Gly Ala Asp Pro Lys Asp Leu Glu Glu Lys Val Glu Gln Leu
675                 680                 685 ggt tct tcg ctt gat acc ctg caa acc cga ttc gcg cgg ctg ctc gcc    2112
Gly Ser Ser Leu Asp Thr Leu Gln Thr Arg Phe Ala Arg Leu Leu Ala
690                 695                 700 gag tac aac gcg acc cag atg aag atg aag cag aga ctg tca cag ttg    2160
Glu Tyr Asn Ala Thr Gln Met Lys Met Lys Gln Arg Leu Ser Gln Leu
705                 710                 715                 720 gaa tcc caa gtc aag ggc gga ggc gac aag ccg ctg gcg gac ggg gaa    2208
Glu Ser Gln Val Lys Gly Gly Gly Asp Lys Pro Leu Ala Asp Gly Glu
                725                 730                 735 gtg ccc ggg gac gcc acc aag act gag gac aag cag cag tga             2250
Val Pro Gly Asp Ala Thr Lys Thr Glu Asp Lys Gln Gln
        740                 745

<210> SEQ ID NO 12
<211> LENGTH: 749
<212> TYPE: PRT
<213> ORGANISM: Artificial Sequence
<220> FEATURE:
<223> OTHER INFORMATION: Synthetic Construct

<400> SEQUENCE: 12

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Phe Gly Arg Ile Gln Lys Lys Ser
65                  70                  75                  80

Gln Pro Glu Lys Val Val Arg Ala Ala Ser Arg Gly Arg Pro Leu Ile
                85                  90                  95

Gly Trp Thr Gln Trp Cys Ala Glu Asp Gly Gly Asp Glu Ser Glu Met
            100                 105                 110

Ala Leu Ala Gly Ser Pro Gly Cys Ser Ser Gly Pro Gln Gly Arg Leu
        115                 120                 125

Ser Arg Leu Ile Phe Leu Leu Arg Arg Trp Ala Ala Arg His Val His
    130                 135                 140
```

```
His Gln Asp Gln Gly Pro Asp Ser Phe Pro Asp Arg Phe Arg Gly Ala
145                 150                 155                 160

Glu Leu Lys Glu Val Ser Ser Gln Glu Ser Asn Ala Gln Ala Asn Val
                165                 170                 175

Gly Ser Gln Glu Pro Ala Asp Arg Gly Arg Ser Ala Trp Pro Leu Ala
            180                 185                 190

Lys Cys Asn Thr Asn Thr Ser Asn Asn Thr Glu Glu Glu Lys Lys Thr
        195                 200                 205

Lys Lys Lys Asp Ala Ile Val Val Asp Pro Ser Ser Asn Leu Tyr Tyr
    210                 215                 220

Arg Trp Leu Thr Ala Ile Ala Leu Pro Val Phe Tyr Asn Trp Tyr Leu
225                 230                 235                 240

Leu Ile Cys Arg Ala Cys Phe Asp Glu Leu Gln Ser Glu Tyr Leu Met
                245                 250                 255

Leu Trp Leu Val Leu Asp Tyr Ser Ala Asp Val Leu Tyr Val Leu Asp
            260                 265                 270

Val Leu Val Arg Ala Arg Thr Gly Phe Leu Glu Gln Gly Leu Met Val
        275                 280                 285

Ser Asp Thr Asn Arg Leu Trp Gln His Tyr Lys Thr Thr Thr Gln Phe
290                 295                 300

Lys Leu Asp Val Leu Ser Leu Val Pro Thr Asp Leu Ala Tyr Leu Lys
305                 310                 315                 320

Val Gly Thr Asn Tyr Pro Glu Val Arg Phe Asn Arg Leu Leu Lys Phe
                325                 330                 335

Ser Arg Leu Phe Glu Phe Phe Asp Arg Thr Glu Thr Arg Thr Asn Tyr
            340                 345                 350

Pro Asn Met Phe Arg Ile Gly Asn Leu Val Leu Tyr Ile Leu Ile Ile
        355                 360                 365

Ile His Trp Asn Ala Cys Ile Tyr Phe Ala Ile Ser Lys Phe Ile Gly
    370                 375                 380

Phe Gly Thr Asp Ser Trp Val Tyr Pro Asn Ile Ser Ile Pro Glu His
385                 390                 395                 400

Gly Arg Leu Ser Arg Lys Tyr Ile Tyr Ser Leu Tyr Trp Ser Thr Leu
                405                 410                 415

Thr Leu Thr Thr Ile Gly Glu Thr Pro Pro Val Lys Asp Glu Glu
            420                 425                 430

Tyr Leu Phe Val Val Asp Phe Leu Val Gly Val Leu Ile Phe Ala
        435                 440                 445

Thr Ile Val Gly Asn Val Gly Ser Met Ile Ser Asn Met Asn Ala Ser
    450                 455                 460

Arg Ala Glu Phe Gln Ala Lys Ile Asp Ser Ile Lys Gln Tyr Met Gln
465                 470                 475                 480

Phe Arg Lys Val Thr Lys Asp Leu Glu Thr Arg Val Ile Arg Trp Phe
                485                 490                 495

Asp Tyr Leu Trp Ala Asn Lys Lys Thr Val Asp Glu Lys Glu Val Leu
            500                 505                 510

Lys Ser Leu Pro Asp Lys Leu Lys Ala Glu Ile Ala Ile Asn Val His
        515                 520                 525

Leu Asp Thr Leu Lys Lys Val Arg Ile Phe Gln Asp Cys Glu Ala Gly
    530                 535                 540

Leu Leu Val Glu Leu Val Leu Lys Leu Arg Pro Thr Val Phe Ser Pro
545                 550                 555                 560

Gly Asp Tyr Ile Cys Lys Lys Gly Asp Ile Gly Lys Glu Met Tyr Ile
```

```
              565                 570                 575
Ile Asn Glu Gly Lys Leu Ala Val Ala Asp Asp Gly Val Thr Gln
            580                 585                 590

Phe Val Leu Ser Asp Gly Ser Tyr Phe Gly Glu Ile Ser Ile Leu
            595                 600                 605

Asn Ile Lys Gly Ser Lys Ser Gly Asn Arg Arg Thr Ala Asn Ile Arg
            610                 615                 620

Ser Ile Gly Tyr Ser Asp Leu Phe Cys Leu Ser Lys Asp Asp Leu Met
625                 630                 635                 640

Glu Ala Leu Thr Glu Tyr Pro Glu Ala Lys Lys Ala Leu Glu Glu Lys
                645                 650                 655

Gly Arg Gln Ile Leu Met Lys Asp Asn Leu Ile Asp Glu Glu Leu Ala
            660                 665                 670

Arg Ala Gly Ala Asp Pro Lys Asp Leu Glu Glu Lys Val Glu Gln Leu
            675                 680                 685

Gly Ser Ser Leu Asp Thr Leu Gln Thr Arg Phe Ala Arg Leu Leu Ala
            690                 695                 700

Glu Tyr Asn Ala Thr Gln Met Lys Met Lys Gln Arg Leu Ser Gln Leu
705                 710                 715                 720

Glu Ser Gln Val Lys Gly Gly Asp Lys Pro Leu Ala Asp Gly Glu
                725                 730                 735

Val Pro Gly Asp Ala Thr Lys Thr Glu Asp Lys Gln Gln
                740                 745

<210> SEQ ID NO 13
<211> LENGTH: 2085
<212> TYPE: DNA
<213> ORGANISM: Homo sapiens
<220> FEATURE:
<221> NAME/KEY: CDS
<222> LOCATION: (1)..(2085)
<223> OTHER INFORMATION: native open reading frame (ORF)

<400> SEQUENCE: 13 atg gcc aag atc aac acc caa tac tcc cac ccc tcc agg acc cac ctc     48
Met Ala Lys Ile Asn Thr Gln Tyr Ser His Pro Ser Arg Thr His Leu
1               5                   10                  15 aag gta aag acc tca gac cgg gat ctc aat cgc gct gaa aat ggc ctc     96
Lys Val Lys Thr Ser Asp Arg Asp Leu Asn Arg Ala Glu Asn Gly Leu
                20                  25                  30 agc aga gcc cac tcg tca agt gag gag aca tcg tca gtg ctg cag ccg    144
Ser Arg Ala His Ser Ser Ser Glu Glu Thr Ser Ser Val Leu Gln Pro
            35                  40                  45 ggg atc gcc atg gag acc aga gga ctg gct gac tcc ggg cag ggc tcc    192
Gly Ile Ala Met Glu Thr Arg Gly Leu Ala Asp Ser Gly Gln Gly Ser
        50                  55                  60 ttc acc ggc cag ggg atc gcc agg ctg tcg cgc ctc atc ttc ttg ctg    240
Phe Thr Gly Gln Gly Ile Ala Arg Leu Ser Arg Leu Ile Phe Leu Leu
65                  70                  75                  80 cgc agg tgg gct gcc agg cat gtg cac cac cag gac cag gga ccg gac    288
Arg Arg Trp Ala Ala Arg His Val His His Gln Asp Gln Gly Pro Asp
                85                  90                  95 tct ttt cct gat cgt ttc cgt gga gcc gag ctt aag gag gtg tcc agc    336
Ser Phe Pro Asp Arg Phe Arg Gly Ala Glu Leu Lys Glu Val Ser Ser
                100                 105                 110 caa gaa agc aat gcc cag gca aat gtg ggc agc cag gag cca gca gac    384
Gln Glu Ser Asn Ala Gln Ala Asn Val Gly Ser Gln Glu Pro Ala Asp
            115                 120                 125
```

| | | |
|---|---|---|
| aga ggg aga agc gcc tgg ccc ctg gcc aaa tgc aac act aac acc agc<br>Arg Gly Arg Ser Ala Trp Pro Leu Ala Lys Cys Asn Thr Asn Thr Ser<br>130                           135                        140 | 432 |
| aac aac acg gag gag gag aag aag acg aaa aag aag gat gcg atc gtg<br>Asn Asn Thr Glu Glu Glu Lys Lys Thr Lys Lys Lys Asp Ala Ile Val<br>145                           150                     155                  160 | 480 |
| gtg gac ccg tcc agc aac ctg tac tac cgc tgg ctg acc gcc atc gcc<br>Val Asp Pro Ser Ser Asn Leu Tyr Tyr Arg Trp Leu Thr Ala Ile Ala<br>                         165                     170                   175 | 528 |
| ctg cct gtc ttc tat aac tgg tat ctg ctt att tgc agg gcc tgt ttc<br>Leu Pro Val Phe Tyr Asn Trp Tyr Leu Leu Ile Cys Arg Ala Cys Phe<br>                   180                     185                   190 | 576 |
| gat gag ctg cag tcc gag tac ctg atg ctg tgg ctg gtc ctg gac tac<br>Asp Glu Leu Gln Ser Glu Tyr Leu Met Leu Trp Leu Val Leu Asp Tyr<br> 195                     200                     205 | 624 |
| tcg gca gat gtc ctg tat gtc ttg gat gtg ctt gta cga gct cgg aca<br>Ser Ala Asp Val Leu Tyr Val Leu Asp Val Leu Val Arg Ala Arg Thr<br>210                         215                     220 | 672 |
| ggt ttt ctt gag caa ggc tta atg gtc agt gat acc aac agg ctg tgg<br>Gly Phe Leu Glu Gln Gly Leu Met Val Ser Asp Thr Asn Arg Leu Trp<br>225                         230                     235                240 | 720 |
| cag cat tac aag acg acc acg cag ttc aag ctg gat gtg ttg tcc ctg<br>Gln His Tyr Lys Thr Thr Thr Gln Phe Lys Leu Asp Val Leu Ser Leu<br>                       245                     250                   255 | 768 |
| gtc ccc acc gac ctg gct tac tta aag gtg ggc aca aac tac cca gaa<br>Val Pro Thr Asp Leu Ala Tyr Leu Lys Val Gly Thr Asn Tyr Pro Glu<br>                260                     265                   270 | 816 |
| gtg agg ttc aac cgc cta ctg aag ttt tcc cgg ctc ttt gaa ttc ttt<br>Val Arg Phe Asn Arg Leu Leu Lys Phe Ser Arg Leu Phe Glu Phe Phe<br>            275                     280                   285 | 864 |
| gac cgc aca gag aca agg acc aac tac ccc aat atg ttc agg att ggg<br>Asp Arg Thr Glu Thr Arg Thr Asn Tyr Pro Asn Met Phe Arg Ile Gly<br>290                         295                     300 | 912 |
| aac ttg gtc ttg tac att ctc atc atc atc cac tgg aat gcc tgc atc<br>Asn Leu Val Leu Tyr Ile Leu Ile Ile Ile His Trp Asn Ala Cys Ile<br>305                         310                     315                 320 | 960 |
| tac ttt gcc att tcc aag ttc att ggt ttt ggg aca gac tcc tgg gtc<br>Tyr Phe Ala Ile Ser Lys Phe Ile Gly Phe Gly Thr Asp Ser Trp Val<br>                   325                     330                   335 | 1008 |
| tac cca aac atc tca atc cca gag cat ggg cgc ctc tcc agg aag tac<br>Tyr Pro Asn Ile Ser Ile Pro Glu His Gly Arg Leu Ser Arg Lys Tyr<br>                       340                     345                   350 | 1056 |
| att tac agt ctc tac tgg tcc acc ttg acc ctt acc acc att ggt gag<br>Ile Tyr Ser Leu Tyr Trp Ser Thr Leu Thr Leu Thr Thr Ile Gly Glu<br>               355                     360                   365 | 1104 |
| acc cca ccc ccc gtg aaa gat gag gag tat ctc ttt gtg gtc gta gac<br>Thr Pro Pro Pro Val Lys Asp Glu Glu Tyr Leu Phe Val Val Val Asp<br>370                         375                     380 | 1152 |
| ttc ttg gtg ggt gtt ctg att ttt gcc acc att gtg ggc aat gtg ggc<br>Phe Leu Val Gly Val Leu Ile Phe Ala Thr Ile Val Gly Asn Val Gly<br>385                         390                     395                400 | 1200 |
| tcc atg atc tcg aat atg aat gcc tca cgg gca gag ttc cag gcc aag<br>Ser Met Ile Ser Asn Met Asn Ala Ser Arg Ala Glu Phe Gln Ala Lys<br>                   405                     410                   415 | 1248 |
| att gat tcc atc aag cag tac atg cag ttc cgc aag gtc acc aag gac<br>Ile Asp Ser Ile Lys Gln Tyr Met Gln Phe Arg Lys Val Thr Lys Asp<br>                 420                     425                   430 | 1296 |
| ttg gag acg cgg gtt atc cgg tgg ttt gac tac ctg tgg gcc aac aag<br>Leu Glu Thr Arg Val Ile Arg Trp Phe Asp Tyr Leu Trp Ala Asn Lys<br>            435                     440                   445 | 1344 |

```
aag acg gtg gat gag aag gag gtg ctc aag agc ctc cca gac aag ctg      1392
Lys Thr Val Asp Glu Lys Glu Val Leu Lys Ser Leu Pro Asp Lys Leu
    450                 455                 460 aag gct gag atc gcc atc aac gtg cac ctg gac acg ctg aag aag gtt      1440
Lys Ala Glu Ile Ala Ile Asn Val His Leu Asp Thr Leu Lys Lys Val
465                 470                 475                 480 cgc atc ttc cag gac tgt gag gca ggg ctg ctg gtg gag ctg gtg ctg      1488
Arg Ile Phe Gln Asp Cys Glu Ala Gly Leu Leu Val Glu Leu Val Leu
                485                 490                 495 aag ctg cga ccc act gtg ttc agc cct ggg gat tat atc tgc aag aag      1536
Lys Leu Arg Pro Thr Val Phe Ser Pro Gly Asp Tyr Ile Cys Lys Lys
            500                 505                 510 gga gat att ggg aag gag atg tac atc atc aac gag ggc aag ctg gcc      1584
Gly Asp Ile Gly Lys Glu Met Tyr Ile Ile Asn Glu Gly Lys Leu Ala
        515                 520                 525 gtg gtg gct gat gat ggg gtc acc cag ttc gtg gtc ctc agc gat ggc      1632
Val Val Ala Asp Asp Gly Val Thr Gln Phe Val Val Leu Ser Asp Gly
    530                 535                 540 agc tac ttc ggg gag atc agc att ctg aac atc aag ggg agc aag tcg      1680
Ser Tyr Phe Gly Glu Ile Ser Ile Leu Asn Ile Lys Gly Ser Lys Ser
545                 550                 555                 560 ggg aac cgc agg acg gcc aac atc cgc agc att ggc tac tca gac ctg      1728
Gly Asn Arg Arg Thr Ala Asn Ile Arg Ser Ile Gly Tyr Ser Asp Leu
                565                 570                 575 ttc tgc ctc tca aag gac gat ctc atg gag gcc ctc acc gag tac ccc      1776
Phe Cys Leu Ser Lys Asp Asp Leu Met Glu Ala Leu Thr Glu Tyr Pro
            580                 585                 590 gaa gcc aag aag gcc ctg gag gag aaa gga cgg cag atc ctg atg aaa      1824
Glu Ala Lys Lys Ala Leu Glu Glu Lys Gly Arg Gln Ile Leu Met Lys
        595                 600                 605 gac aac ctg atc gat gag gag ctg gcc agg gcg ggc gcg gac ccc aag      1872
Asp Asn Leu Ile Asp Glu Glu Leu Ala Arg Ala Gly Ala Asp Pro Lys
    610                 615                 620 gac ctt gag gag aaa gtg gag cag ctg ggg tcc tcc ctg gac acc ctg      1920
Asp Leu Glu Glu Lys Val Glu Gln Leu Gly Ser Ser Leu Asp Thr Leu
625                 630                 635                 640 cag acc agg ttt gca cgc ctc ctg gct gag tac aac gcc acc cag atg      1968
Gln Thr Arg Phe Ala Arg Leu Leu Ala Glu Tyr Asn Ala Thr Gln Met
                645                 650                 655 aag atg aag cag cgt ctc agc caa ctg gaa agc cag gtg aag ggt ggt      2016
Lys Met Lys Gln Arg Leu Ser Gln Leu Glu Ser Gln Val Lys Gly Gly
            660                 665                 670 ggg gac aag ccc ctg gct gat ggg gaa gtt ccc ggg gat gct aca aaa      2064
Gly Asp Lys Pro Leu Ala Asp Gly Glu Val Pro Gly Asp Ala Thr Lys
        675                 680                 685 aca gag gac aaa caa cag tga                                          2085
Thr Glu Asp Lys Gln Gln
        690

<210> SEQ ID NO 14
<211> LENGTH: 694
<212> TYPE: PRT
<213> ORGANISM: Homo sapiens

<400> SEQUENCE: 14

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30
```

```
Ser Arg Ala His Ser Ser Ser Glu Glu Thr Ser Ser Val Leu Gln Pro
         35                  40                  45

Gly Ile Ala Met Glu Thr Arg Gly Leu Ala Asp Ser Gly Gln Gly Ser
 50                  55                  60

Phe Thr Gly Gln Gly Ile Ala Arg Leu Ser Arg Leu Ile Phe Leu Leu
 65                  70                  75                  80

Arg Arg Trp Ala Ala Arg His Val His His Gln Asp Gln Gly Pro Asp
                 85                  90                  95

Ser Phe Pro Asp Arg Phe Arg Gly Ala Glu Leu Lys Glu Val Ser Ser
                100                 105                 110

Gln Glu Ser Asn Ala Gln Ala Asn Val Gly Ser Gln Glu Pro Ala Asp
                115                 120                 125

Arg Gly Arg Ser Ala Trp Pro Leu Ala Lys Cys Asn Thr Asn Thr Ser
130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
                180                 185                 190

Asp Glu Leu Gln Ser Glu Tyr Leu Met Leu Trp Leu Val Leu Asp Tyr
                195                 200                 205

Ser Ala Asp Val Leu Tyr Val Leu Asp Val Leu Val Arg Ala Arg Thr
210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
                260                 265                 270

Val Arg Phe Asn Arg Leu Leu Lys Phe Ser Arg Leu Phe Glu Phe Phe
                275                 280                 285

Asp Arg Thr Glu Thr Arg Thr Asn Tyr Pro Asn Met Phe Arg Ile Gly
                290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
                340                 345                 350

Ile Tyr Ser Leu Tyr Trp Ser Thr Leu Thr Leu Thr Thr Ile Gly Glu
                355                 360                 365

Thr Pro Pro Pro Val Lys Asp Glu Glu Tyr Leu Phe Val Val Val Asp
                370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
                420                 425                 430

Leu Glu Thr Arg Val Ile Arg Trp Phe Asp Tyr Leu Trp Ala Asn Lys
                435                 440                 445

Lys Thr Val Asp Glu Lys Glu Val Leu Lys Ser Leu Pro Asp Lys Leu
```

```
                         450                 455                 460
Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
                500                 505                 510

Gly Asp Ile Gly Lys Glu Met Tyr Ile Ile Asn Glu Gly Lys Leu Ala
            515                 520                 525

Val Val Ala Asp Asp Gly Val Thr Gln Phe Val Val Leu Ser Asp Gly
            530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
                580                 585                 590

Glu Ala Lys Lys Ala Leu Glu Glu Lys Gly Arg Gln Ile Leu Met Lys
            595                 600                 605

Asp Asn Leu Ile Asp Glu Glu Leu Ala Arg Ala Gly Ala Asp Pro Lys
610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
            675                 680                 685

Thr Glu Asp Lys Gln Gln
    690

<210> SEQ ID NO 15
<211> LENGTH: 2085
<212> TYPE: DNA
<213> ORGANISM: Homo sapiens

<400> SEQUENCE: 15
atggccaaga tcaacaccca atactccac ccctccagga cccacctcaa ggtaaagacc        60
tcagaccgag atctcaatcg cgctgaaaat ggcctcagca gagcccactc gtcaagtgag      120
gagacatcgt cagtgctgca gccggggatc gccatggaga ccagaggact ggctgactcc      180
gggcagggct ccttcaccgg ccaggggatc gccaggctgt cgcgcctcat cttcttgctg      240
cgcaggtggg ctgccaggca tgtgcaccac caggaccagg gaccggactc ttttcctgat      300
cgtttccgtg gagccgagct taaggaggtg tccagccaag aaagcaatgc ccaggcaaat      360
gtgggcagcc aggagccagc agacagaggg agaagcgcct ggcccctggc caaatgcaac      420
actaacacca gcaacaacac ggaggaggag aagaagacga aaaagaagga tgcgatcgtg      480
gtggacccgt ccagcaacct gtactaccgc tggctgaccg ccatcgccct gcctgtcttc      540
tataactggt atctgcttat ttgcagggcc tgtttcgatg agctgcagtc cgagtacctg      600
atgctgtggc tggtcctgga ctactcggca gatgtcctgt atgtcttgga tgtgcttgta      660
cgagctcgga caggttttct cgagcaaggc ttaatggtca gtgataccaa caggctgtgg      720
```

-continued

| | |
|---|---|
| cagcattaca agacgaccac gcagttcaag ctggatgtgt tgtccctggt ccccaccgac | 780 |
| ctggcttact taaaggtggg cacaaactac ccagaagtga ggttcaaccg cctactgaag | 840 |
| ttttcccggc tctttgaatt ctttgaccgc acagagacaa ggaccaacta ccccaatatg | 900 |
| ttcaggattg ggaacttggt cttgtacatt ctcatcatca tccactggaa tgcctgcatc | 960 |
| tactttgcca tttccaagtt cattggtttt gggacagact cctgggtcta cccaaacatc | 1020 |
| tcaatcccag agcatgggcg cctctccagg aagtacattt acagtctcta ctggtccacc | 1080 |
| ttgacccctta ccaccattgg tgagaccccca ccccccgtga aagatgagga gtatctctttt | 1140 |
| gtggtcgtag acttcttggt gggtgttctg attttttgcca ccattgtggg caatgtgggc | 1200 |
| tccatgatct cgaatatgaa tgcctcacgg gcagagttcc aggccaagat tgattccatc | 1260 |
| aagcagtaca tgcagttccg caaggtcacc aaggacttgg agacgcgggt tatccggtgg | 1320 |
| tttgactacc tgtgggccaa caagaagacg gtggatgaga aggaggtgct caagagcctc | 1380 |
| ccagacaagc tgaaggctga gatcgccatc aacgtgcacc tggacacgct gaagaaggtt | 1440 |
| cgcatcttcc aggactgtga ggcagggctg ctggtgagc tggtgctgaa gctgcgaccc | 1500 |
| actgtgttca gccctgggga ttatatctgc aagaagggag atattgggaa ggagatgtac | 1560 |
| atcatcaacg agggcaagct ggccgtggtg gctgatgatg gggtcaccca gttcgtggtc | 1620 |
| ctcagcgatg gcagctactt cggggagatc agcattctga acatcaaggg gagcaagtcg | 1680 |
| gggaaccgca ggacgccaa catccgcagc attggctact cagacctgtt ctgcctctca | 1740 |
| aaggacgatc tcatggaggc cctcaccgag taccccgaag ccaagaaggc cctggaggag | 1800 |
| aaaggacggc agatcctgat gaaagacaac ctgatcgatg aggagctggc cagggcgggc | 1860 |
| gcggacccca aggaccttga ggagaaagtg gagcagctgg ggtcctccct ggacaccctg | 1920 |
| cagaccaggt ttgcacgcct cctggctgag tacaacgcca cccagatgaa gatgaagcag | 1980 |
| cgtctcagcc aactggaaag ccaggtgaag ggtggtgggg acaagcccct ggctgatggg | 2040 |
| gaagttcccg gggatgctac aaaaaacagag gacaaacaac agtga | 2085 |

<210> SEQ ID NO 16
<211> LENGTH: 2107
<212> TYPE: DNA
<213> ORGANISM: Artificial Sequence
<220> FEATURE:
<223> OTHER INFORMATION: constructed sequence

<400> SEQUENCE: 16

| | |
|---|---|
| gcggccgcca ccatggctaa gattaacacc cagtactcac atccatcccg cactcacctc | 60 |
| aaagtcaaga cctccgatcg ggatctgaac cgggctgaga atgggctgtc gcgcgcccac | 120 |
| tcgtcgtccg aggaaaccag cagcgtgctc cagcccgggca tcgccatgga aactagggggg | 180 |
| ctggcggact ccggacaggg atccttcact ggacagggta ttgcccggct gagcagactg | 240 |
| atcttcctgc ttcgccgctg ggcggccaga cacgtgcacc atcaggacca gggacctgat | 300 |
| agcttccccg accgctttag gggagccgag ctgaaagaag tgtcaagcca ggagtcaaac | 360 |
| gcgcaggcca acgtcggcag ccaagagcct gcagaccggg gacgctcggc atggccgctc | 420 |
| gcaaagtgca acactaacac ttccaacaac accgaagagg aaaagaaaac caagaagaag | 480 |
| gatgcaattg tggtggaccc ttcctccaac ctgtactacc gctggttgac cgccatcgcc | 540 |
| ctcccggtct tttacaattg gtatctcctt atctgccggg cctgcttcga cgaactgcaa | 600 |
| tcagagtacc tgatgctgtg gctggtgctg gactatagcg ccgatgtgct ctacgtcctg | 660 |
| gatgtgctcg tgcgcgcccg gaccggattc ttggaacaag gcctgatggt gtccgacacg | 720 |

```
aatagactgt ggcagcacta taagaccaca acccagttca agcttgacgt gctcagcctt    780
gtgccgactg acctggccta cctgaaagtc ggaactaact acccggaagt cagattcaac    840
cgactcctga agttcagcag gctgttcgag ttctttgacc gcaccgagac tcggaccaac    900
taccctaaca tgttccggat cggaaatctg gtgctctaca tactgattat catccattgg    960
aacgcctgta tctatttcgc catttcgaag ttcatcggtt tcggaaccga ttcctgggtg   1020 tacccccaaca tctcgatccc cgaacacggt cgcctgtccc ggaagtacat ctactccctg   1080
tactggtcca ctctgactct gaccacgatc ggggaaaccc ctccacccgt gaaggacgaa   1140
gagtacctgt tcgtggtggt ggacttcctg gtcggagtgt tgattttcgc caccattgtg   1200
ggaaacgtgg gctccatgat ctccaacatg aacgcgtcga gagctgagtt ccaagccaag   1260
atcgactcca ttaagcagta catgcagttc agaaaggtca ccaaggacct ggaaaccagg   1320
gtcatccgct ggttcgacta cctgtgggcc aacaaaaaga ctgtggacga aaaggaagtg   1380
ctgaagtcgc tgccggataa gctgaaggcc gaaatcgcca ttaacgtgca ccttgacacc   1440
ctgaagaaag tccggatctt ccaagactgt gaagccggcc tcctggtgga gctcgtgctc   1500
aagctgcggc ccaccgtgtt cagcccggga gattacattt gcaagaaggg cgatatcggc   1560
aaagagatgt acatcatcaa cgagggaaag ctggccgtgg tcgcggacga cggcgtgacc   1620
cagttcgtgg tgctgtccga cggatcctac ttcggtgaaa tctcaatcct caacatcaag   1680
gggtccaagt ccggcaaccg gagaactgcc aacattcgct ccatcggata cagcgacctg   1740
ttttgcctgt ccaaggatga cctgatggag gctctgactg agtaccctga agcgaagaag   1800
gctttggagg aaaaggggcg gcagattctg atgaaggaca atttgatcga cgaggagctc   1860
gcacgggccg cgccgacccc caaggatctc gaagagaagg tcgaacagct gggttcttcg   1920 cttgatacccc tgcaaacccg attcgcgcgg ctgctcgccg agtacaacgc gacccagatg   1980
aagatgaagc agagactgtc acagttggaa tcccaagtca agggcggagg cgacaagccg   2040
ctggcggacg gggaagtgcc cggggacgcc accaagactg aggacaagca gcagtgatca   2100
tagatct                                                             2107
```

<210> SEQ ID NO 17
<211> LENGTH: 2272
<212> TYPE: DNA
<213> ORGANISM: Artificial Sequence
<220> FEATURE:
<223> OTHER INFORMATION: constructed sequence

<400> SEQUENCE: 17

```
gcggccgcca ccatggctaa gattaacacc cagtactcac atccatcccg cactcacctc     60
aaagtcaaga cctccgatcg ggatctgaac cgggctgaga tgggctgtc gcgcgcccac    120 tcgtcgtccg aggaaaccag cagcgtgctc cagccgggca tcgccatgga aactagggg     180 ctggcggact ccgacaggg atccttcact ggacaggta ttgcccggtt cgggcggatt      240
cagaagaagt cccagccgga aaggtcgtg cgggctgcca gcaggggcag gccactcatt    300
ggttggacac agtggtgcgc tgaggatggt ggagatgaat cggaaatggc actggccggc   360
tctcccggat gcagctcggg cccccaaggg agactgagca gactgatctt cctgcttcgc   420
cgctgggcgg ccagacacgt gcaccatcag gaccagggac ctgatagctt ccccgaccgc   480
tttaggggag ccgagctgaa agaagtgtca agccaggagt caaacgcgca ggccaacgtc   540
ggcagccaag agcctgcaga ccggggacgc tcggcatggc cgctcgcaaa gtgcaacact   600
```

-continued

| | |
|---|---|
| aacacttcca caacaccga agaggaaaag aaaaccaaga agaaggatgc aattgtggtg | 660 |
| gacccttcct ccaacctgta ctaccgctgg ttgaccgcca tcgccctccc ggtcttttac | 720 |
| aattggtatc tccttatctg ccgggcctgc ttcgacgaac tgcaatcaga gtacctgatg | 780 |
| ctgtggctgg tgctggacta tagcgccgat gtgctctacg tcctggatgt gctcgtgcgc | 840 |
| gcccggaccg gattcttgga acaaggcctg atggtgtccg acacgaatag actgtggcag | 900 |
| cactataaga ccacaaccca gttcaagctt gacgtgctca gccttgtgcc gactgacctg | 960 |
| gcctacctga aagtcggaac taactacccg gaagtcagat caaccgact cctgaagttc | 1020 |
| agcaggctgt tcgagttctt tgaccgcacc gagactcgga ccaactaccc taacatgttc | 1080 |
| cggatcggaa atctggtgct ctacatactg attatcatcc attggaacgc ctgtatctat | 1140 |
| ttcgccattt cgaagttcat cggtttcgga accgattcct gggtgtaccc caacatctcg | 1200 |
| atccccgaac acggtcgcct gtcccggaag tacatctact ccctgtactg gtccactctg | 1260 |
| actctgacca cgatcgggga aacccctcca cccgtgaagg acgaagagta cctgttcgtg | 1320 |
| gtggtggact tcctggtcgg agtgttgatt ttcgccacca ttgtgggaaa cgtgggctcc | 1380 |
| atgatctcca acatgaacgc gtcgagagct gagttccaag ccaagatcga ctccattaag | 1440 |
| cagtacatgc agttcagaaa ggtcaccaag gacctggaaa ccagggtcat ccgctggttc | 1500 |
| gactacctgt gggccaacaa aaagactgtg gacgaaaagg aagtgctgaa gtcgctgccg | 1560 |
| gataagctga aggccgaaat cgccattaac gtgcaccttg acccctgaa gaaagtccgg | 1620 |
| atcttccaag actgtgaagc cggcctcctg gtggagctcg tgctcaagct gcggcccacc | 1680 |
| gtgttcagcc cggagatta catttgcaag aagggcgata tcggcaaaga gatgtacatc | 1740 |
| atcaacgagg gaaagctggc cgtggtcgcg gacgacggcg tgacccagtt cgtggtgctg | 1800 |
| tccgacggat cctacttcgg tgaaatctca atcctcaaca tcaaggggtc caagtccggc | 1860 |
| aaccggagaa ctgccaacat tcgctccatc ggatacagcg acctgttttg cctgtccaag | 1920 |
| gatgacctga tggaggctct gactgagtac cctgaagcga agaaggcttt ggaggaaaag | 1980 |
| gggcggcaga ttctgatgaa ggacaatttg atcgacgagg agctcgcacg ggccggcgcc | 2040 |
| gaccccaagg atctcgaaga aaggtcgaa cagctgggtt cttcgcttga taccctgcaa | 2100 |
| acccgattcg cgcggctgct cgccgagtac aacgcgaccc agatgaagat gaagcagaga | 2160 |
| ctgtcacagt tggaatccca gtcaagggc ggaggcgaca gccgctggc ggacggggaa | 2220 |
| gtgcccgggg acgccaccaa gactgaggac aagcagcagt gatcatagat ct | 2272 |

<210> SEQ ID NO 18
<211> LENGTH: 2107
<212> TYPE: DNA
<213> ORGANISM: Artificial Sequence
<220> FEATURE:
<223> OTHER INFORMATION: constructed sequence

<400> SEQUENCE: 18

| | |
|---|---|
| gcggccgcca ccatggccaa gatcaacacc caatactccc accctccag gacccacctc | 60 |
| aaggtaaaga cctcagaccg ggatctcaat cgcgctgaaa atggcctcag cagagcccac | 120 |
| tcgtcaagtg aggagacatc gtcagtgctg cagccgggga tcgccatgga gaccagagga | 180 |
| ctggctgact ccgggcaggg ctccttcacc ggccagggga tcgccaggct gtcgcgcctc | 240 |
| atcttcttgc tgcgcaggtg ggctgccagg catgtgcacc accaggacca gggaccggac | 300 |
| tcttttcctg atcgtttccg tggagccgag cttaaggagg tgtccagcca agaaagcaat | 360 |
| gcccaggcaa atgtgggcag ccaggagcca gcagacagag ggagaagcgc ctggcccctg | 420 |

-continued

```
gccaaatgca acactaacac cagcaacaac acggaggagg agaagaagac gaaaaagaag      480
gatgcgatcg tggtggaccc gtccagcaac ctgtactacc gctggctgac cgccatcgcc      540
ctgcctgtct tctataactg gtatctgctt atttgcaggg cctgtttcga tgagctgcag      600
tccgagtacc tgatgctgtg gctggtcctg gactactcgg cagatgtcct gtatgtcttg      660
gatgtgcttg tacgagctcg acaggttttt cttgagcaag cttaatggt cagtgatacc      720 aacaggctgt ggcagcatta aagacgacc acgcagttca agctggatgt gttgtccctg       780
gtccccaccg acctggctta cttaaaggtg ggcacaaact acccagaagt gaggttcaac      840
cgcctactga agttttcccg gctctttgaa ttctttgacc gcacagagac aaggaccaac      900
taccccaata tgttcaggat tgggaacttg gtcttgtaca ttctcatcat catccactgg      960
aatgcctgca tctactttgc catttccaag ttcattggtt ttgggacaga ctcctgggtc     1020
tacccaaaca tctcaatccc agagcatggg cgcctctcca ggaagtacat ttacagtctc     1080
tactggtcca ccttgaccct taccaccatt ggtgagaccc cacccccgt gaaagatgag      1140 gagtatctct ttgtggtcgt agacttcttg gtgggtgttc tgattttgc caccattgtg      1200 ggcaatgtgg gctccatgat ctcgaatatg aatgcctcac gggcagagtt ccaggccaag     1260
attgattcca tcaagcagta catgcagttc cgcaaggtca ccaaggactt ggagacgcgg     1320
gttatccggt ggtttgacta cctgtgggcc aacaagaaga cggtggatga aaggaggtg     1380 ctcaagagcc tcccagacaa gctgaaggct gagatcgcca tcaacgtgca cctggacacg     1440
ctgaagaagg ttcgcatctt ccaggactgt gaggcagggc tgctggtgga gctggtgctg     1500
aagctgcgac ccactgtgtt cagccctggg gattatatct gcaagaaggg agatattggg     1560
aaggagatgt acatcatcaa cgagggcaag ctggccgtgg tggctgatga tggggtcacc     1620
cagttcgtgg tcctcagcga tggcagctac ttcggggaga tcagcattct gaacatcaag     1680
gggagcaagt cggggaaccg caggacggcc aacatccgca gcattggcta ctcagacctg     1740
ttctgcctct caaaggacga tctcatggag ccctcaccg agtaccccga agccaagaag     1800
gccctggagg agaaaggacg gcagatcctg atgaaagaca acctgatcga tgaggagctg     1860
gccagggcgg gcgcggaccc caaggacctt gaggagaaag tggagcagct ggggtcctcc     1920
ctggacaccc tgcagaccag gtttgcacgc ctcctggctg agtacaacgc cacccagatg     1980
aagatgaagc agcgtctcag ccaactggaa agccaggtga agggtggtgg ggacaagccc     2040
ctggctgatg gggaagttcc cggggatgct acaaaaacag aggacaaaca acagtgatca     2100
tagatct                                                               2107
```

```
<210> SEQ ID NO 19
<211> LENGTH: 2430
<212> TYPE: DNA
<213> ORGANISM: Homo sapiens
<220> FEATURE:
<221> NAME/KEY: CDS
<222> LOCATION: (1)..(2430)

<400> SEQUENCE: 19 atg ttt aaa tcg ctg aca aaa gtc aac aag gtg aag cct ata gga gag       48
Met Phe Lys Ser Leu Thr Lys Val Asn Lys Val Lys Pro Ile Gly Glu
 1               5                  10                  15 aac aat gag aat gaa caa agt tct cgt cgg aat gaa gaa ggc tct cac       96
Asn Asn Glu Asn Glu Gln Ser Ser Arg Arg Asn Glu Glu Gly Ser His
             20                  25                  30 cca agt aat cag tct cag caa acc aca gca cag gaa gaa aac aaa ggt      144
```

```
                Pro Ser Asn Gln Ser Gln Gln Thr Ala Gln Glu Glu Asn Lys Gly
                        35                  40                  45 gaa gag aaa tct ctc aaa acc aag tca act cca gtc acg tct gaa gag        192
Glu Glu Lys Ser Leu Lys Thr Lys Ser Thr Pro Val Thr Ser Glu Glu
 50                  55                  60 cca cac acc aac ata caa gac aaa ctc tcc aag aaa aat tcc tct gga        240
Pro His Thr Asn Ile Gln Asp Lys Leu Ser Lys Lys Asn Ser Ser Gly
 65                  70                  75                  80 gat ctg acc aca aac cct gac cct caa aat gca gca gaa cca act gga        288
Asp Leu Thr Thr Asn Pro Asp Pro Gln Asn Ala Ala Glu Pro Thr Gly
                 85                  90                  95 aca gtg cca gag cag aag gaa atg gac ccc ggg aaa gaa ggt cca aac        336
Thr Val Pro Glu Gln Lys Glu Met Asp Pro Gly Lys Glu Gly Pro Asn
            100                 105                 110 agc cca caa aac aaa ccg cct gca gct cct gtt ata aat gag tat gcc        384
Ser Pro Gln Asn Lys Pro Pro Ala Ala Pro Val Ile Asn Glu Tyr Ala
            115                 120                 125 gat gcc cag cta cac aac ctg gtg aaa aga atg cgt caa aga aca gcc        432
Asp Ala Gln Leu His Asn Leu Val Lys Arg Met Arg Gln Arg Thr Ala
130                 135                 140 ctc tac aag aaa aag ttg gta gag gga gat ctc tcc tca ccc gaa gcc        480
Leu Tyr Lys Lys Lys Leu Val Glu Gly Asp Leu Ser Ser Pro Glu Ala
145                 150                 155                 160 agc cca caa act gca aag ccc acg gct gta cca cca gta aaa gaa agc        528
Ser Pro Gln Thr Ala Lys Pro Thr Ala Val Pro Pro Val Lys Glu Ser
                165                 170                 175 gat gat aag cca aca gaa cat tac tac agg ctg ttg tgg ttc aaa gtc        576
Asp Asp Lys Pro Thr Glu His Tyr Tyr Arg Leu Leu Trp Phe Lys Val
            180                 185                 190 aaa aag atg cct tta aca gag tac tta aag cga att aaa ctt cca aac        624
Lys Lys Met Pro Leu Thr Glu Tyr Leu Lys Arg Ile Lys Leu Pro Asn
            195                 200                 205 agc ata gat tca tac aca gat cga ctc tat ctc ctg tgg ctc ttg ctt        672
Ser Ile Asp Ser Tyr Thr Asp Arg Leu Tyr Leu Leu Trp Leu Leu Leu
210                 215                 220 gtc act ctt gcc tat aac tgg aac tgc tgt ttt ata cca ctg cgc ctc        720
Val Thr Leu Ala Tyr Asn Trp Asn Cys Cys Phe Ile Pro Leu Arg Leu
225                 230                 235                 240 gtc ttc cca tat caa acc gca gac aac ata cac tac tgg ctt att gcg        768
Val Phe Pro Tyr Gln Thr Ala Asp Asn Ile His Tyr Trp Leu Ile Ala
                245                 250                 255 gac atc ata tgt gat atc atc tac ctt tat gat atg cta ttt atc cag        816
Asp Ile Ile Cys Asp Ile Ile Tyr Leu Tyr Asp Met Leu Phe Ile Gln
            260                 265                 270 ccc aga ctc cag ttt gta aga gga gga gac ata ata gtg gat tca aat        864
Pro Arg Leu Gln Phe Val Arg Gly Gly Asp Ile Ile Val Asp Ser Asn
            275                 280                 285 gag cta agg aaa cac tac agg act tct aca aaa ttt cag ttg gat gtc        912
Glu Leu Arg Lys His Tyr Arg Thr Ser Thr Lys Phe Gln Leu Asp Val
290                 295                 300 gca tca ata ata cca ttt gat att tgc tac ctc ttc ttt ggg ttt aat        960
Ala Ser Ile Ile Pro Phe Asp Ile Cys Tyr Leu Phe Phe Gly Phe Asn
305                 310                 315                 320 cca atg ttt aga gca aat agg atg tta aag tac act tca ttt ttt gaa       1008
Pro Met Phe Arg Ala Asn Arg Met Leu Lys Tyr Thr Ser Phe Phe Glu
                325                 330                 335 ttt aat cat cac cta gag tct ata atg gac aaa gca tat atc tac aga       1056
Phe Asn His His Leu Glu Ser Ile Met Asp Lys Ala Tyr Ile Tyr Arg
            340                 345                 350
```

```
gtt att cga aca act gga tac ttg ctg ttt att ctg cac att aat gcc   1104
Val Ile Arg Thr Thr Gly Tyr Leu Leu Phe Ile Leu His Ile Asn Ala
        355                 360                 365 tgt gtt tat tac tgg gct tca aac tat gaa gga att ggc act act aga   1152
Cys Val Tyr Tyr Trp Ala Ser Asn Tyr Glu Gly Ile Gly Thr Thr Arg
    370                 375                 380 tgg gtg tat gat ggg gaa gga aac gag tat ctg aga tgt tat tat tgg   1200
Trp Val Tyr Asp Gly Glu Gly Asn Glu Tyr Leu Arg Cys Tyr Tyr Trp
385                 390                 395                 400 gca gtt cga act tta att acc att ggt ggc ctt cca gaa cca caa act   1248
Ala Val Arg Thr Leu Ile Thr Ile Gly Gly Leu Pro Glu Pro Gln Thr
                405                 410                 415 tta ttt gaa att gtt ttt caa ctc ttg aat ttt ttt tct gga gtt ttt   1296
Leu Phe Glu Ile Val Phe Gln Leu Leu Asn Phe Phe Ser Gly Val Phe
            420                 425                 430 gtg ttc tcc agt tta att ggt cag atg aga gat gtg att gga gca gct   1344
Val Phe Ser Ser Leu Ile Gly Gln Met Arg Asp Val Ile Gly Ala Ala
        435                 440                 445 aca gcc aat cag aac tac ttc cgc gcc tgc atg gat gac acc att gcc   1392
Thr Ala Asn Gln Asn Tyr Phe Arg Ala Cys Met Asp Asp Thr Ile Ala
    450                 455                 460 tac atg aac aat tac tcc att cct aaa ctt gtg caa aag cga gtt cgg   1440
Tyr Met Asn Asn Tyr Ser Ile Pro Lys Leu Val Gln Lys Arg Val Arg
465                 470                 475                 480 act tgg tat gaa tat aca tgg gac tct caa aga atg cta gat gag tct   1488
Thr Trp Tyr Glu Tyr Thr Trp Asp Ser Gln Arg Met Leu Asp Glu Ser
                485                 490                 495 gat ttg ctt aag acc cta cca act acg gtc cag tta gcc ctc gcc att   1536
Asp Leu Leu Lys Thr Leu Pro Thr Thr Val Gln Leu Ala Leu Ala Ile
            500                 505                 510 gat gtg aac ttc agc atc atc agc aaa gtc gac ttg ttc aag ggt tgt   1584
Asp Val Asn Phe Ser Ile Ile Ser Lys Val Asp Leu Phe Lys Gly Cys
        515                 520                 525 gat aca cag atg att tat gac atg ttg cta aga ttg aaa tcc gtt ctc   1632
Asp Thr Gln Met Ile Tyr Asp Met Leu Leu Arg Leu Lys Ser Val Leu
    530                 535                 540 tat ttg cct ggt gac ttt gtc tgc aaa aag gga gaa att ggc aag gaa   1680
Tyr Leu Pro Gly Asp Phe Val Cys Lys Lys Gly Glu Ile Gly Lys Glu
545                 550                 555                 560 atg tat atc atc aag cat gga gaa gtc caa gtt ctt gga ggc cct gat   1728
Met Tyr Ile Ile Lys His Gly Glu Val Gln Val Leu Gly Gly Pro Asp
                565                 570                 575 ggt act aaa gtt ctg gtt act ctg aaa gct ggg tcg gtg ttt gga gaa   1776
Gly Thr Lys Val Leu Val Thr Leu Lys Ala Gly Ser Val Phe Gly Glu
            580                 585                 590 atc agc ctt cta gca gca gga gga gga aac cgt cga act gcc aat gtg   1824
Ile Ser Leu Leu Ala Ala Gly Gly Gly Asn Arg Arg Thr Ala Asn Val
        595                 600                 605 gtg gcc cac ggg ttt gcc aat ctt tta act cta gac aaa aag acc ctc   1872
Val Ala His Gly Phe Ala Asn Leu Leu Thr Leu Asp Lys Lys Thr Leu
    610                 615                 620 caa gaa att cta gtg cat tat cca gat tct gaa agg atc ctc atg aag   1920
Gln Glu Ile Leu Val His Tyr Pro Asp Ser Glu Arg Ile Leu Met Lys
625                 630                 635                 640 aaa gcc aga gtg ctt tta aag cag aag gct aag acc gca gaa gca acc   1968
Lys Ala Arg Val Leu Leu Lys Gln Lys Ala Lys Thr Ala Glu Ala Thr
                645                 650                 655 cct cca aga aaa gat ctt gcc ctc ctc ttc cca ccg aaa gaa gag aca   2016
Pro Pro Arg Lys Asp Leu Ala Leu Leu Phe Pro Pro Lys Glu Glu Thr
            660                 665                 670
```

```
ccc aaa ctg ttt aaa act ctc cta gga ggc aca gga aaa gca agt ctt    2064
Pro Lys Leu Phe Lys Thr Leu Leu Gly Gly Thr Gly Lys Ala Ser Leu
            675                 680                 685 gca aga cta ctc aaa ttg aag cga gag caa gca gct cag aag aaa gaa    2112
Ala Arg Leu Leu Lys Leu Lys Arg Glu Gln Ala Ala Gln Lys Lys Glu
    690                 695                 700 aat tct gaa gga gga gag gaa gaa gga aaa gaa aat gaa gat aaa caa    2160
Asn Ser Glu Gly Gly Glu Glu Glu Gly Lys Glu Asn Glu Asp Lys Gln
705                 710                 715                 720 aaa gaa aat gaa gat aaa caa aaa gaa aat gaa gat aaa gga aaa gaa    2208
Lys Glu Asn Glu Asp Lys Gln Lys Glu Asn Glu Asp Lys Gly Lys Glu
                725                 730                 735 aat gaa gat aaa gat aaa gga aga gag cca gaa gag aag cca ctg gac    2256
Asn Glu Asp Lys Asp Lys Gly Arg Glu Pro Glu Glu Lys Pro Leu Asp
            740                 745                 750 aga cct gaa tgt aca gca agt cct att gca gtg gag gaa gaa ccc cac    2304
Arg Pro Glu Cys Thr Ala Ser Pro Ile Ala Val Glu Glu Glu Pro His
        755                 760                 765 tca gtt aga agg aca gtt tta ccc aga ggg act tct cgt caa tca ctc    2352
Ser Val Arg Arg Thr Val Leu Pro Arg Gly Thr Ser Arg Gln Ser Leu
    770                 775                 780 att atc agc atg gct cct tct gct gag ggc gga gaa gag gtt ctt act    2400
Ile Ile Ser Met Ala Pro Ser Ala Glu Gly Gly Glu Glu Val Leu Thr
785                 790                 795                 800 att gaa gtc aaa gaa aag gct aag caa taa                            2430
Ile Glu Val Lys Glu Lys Ala Lys Gln
                805
```

<210> SEQ ID NO 20
<211> LENGTH: 809
<212> TYPE: PRT
<213> ORGANISM: Homo sapiens

<400> SEQUENCE: 20

```
Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
```

```
                180             185             190
Lys Lys Met Pro Leu Thr Glu Tyr Leu Lys Arg Ile Lys Leu Pro Asn
            195             200             205

Ser Ile Asp Ser Tyr Thr Asp Arg Leu Tyr Leu Leu Trp Leu Leu Leu
        210             215             220

Val Thr Leu Ala Tyr Asn Trp Asn Cys Cys Phe Ile Pro Leu Arg Leu
225             230             235             240

Val Phe Pro Tyr Gln Thr Ala Asp Asn Ile His Tyr Trp Leu Ile Ala
            245             250             255

Asp Ile Ile Cys Asp Ile Ile Tyr Leu Tyr Asp Met Leu Phe Ile Gln
            260             265             270

Pro Arg Leu Gln Phe Val Arg Gly Gly Asp Ile Ile Val Asp Ser Asn
        275             280             285

Glu Leu Arg Lys His Tyr Arg Thr Ser Thr Lys Phe Gln Leu Asp Val
        290             295             300

Ala Ser Ile Ile Pro Phe Asp Ile Cys Tyr Leu Phe Phe Gly Phe Asn
305             310             315             320

Pro Met Phe Arg Ala Asn Arg Met Leu Lys Tyr Thr Ser Phe Phe Glu
            325             330             335

Phe Asn His His Leu Glu Ser Ile Met Asp Lys Ala Tyr Ile Tyr Arg
            340             345             350

Val Ile Arg Thr Thr Gly Tyr Leu Leu Phe Ile Leu His Ile Asn Ala
        355             360             365

Cys Val Tyr Tyr Trp Ala Ser Asn Tyr Glu Gly Ile Gly Thr Thr Arg
        370             375             380

Trp Val Tyr Asp Gly Glu Gly Asn Glu Tyr Leu Arg Cys Tyr Tyr Trp
385             390             395             400

Ala Val Arg Thr Leu Ile Thr Ile Gly Gly Leu Pro Glu Pro Gln Thr
            405             410             415

Leu Phe Glu Ile Val Phe Gln Leu Leu Asn Phe Phe Ser Gly Val Phe
            420             425             430

Val Phe Ser Ser Leu Ile Gly Gln Met Arg Asp Val Ile Gly Ala Ala
        435             440             445

Thr Ala Asn Gln Asn Tyr Phe Arg Ala Cys Met Asp Asp Thr Ile Ala
        450             455             460

Tyr Met Asn Asn Tyr Ser Ile Pro Lys Leu Val Gln Lys Arg Val Arg
465             470             475             480

Thr Trp Tyr Glu Tyr Thr Trp Asp Ser Gln Arg Met Leu Asp Glu Ser
            485             490             495

Asp Leu Leu Lys Thr Leu Pro Thr Thr Val Gln Leu Ala Leu Ala Ile
            500             505             510

Asp Val Asn Phe Ser Ile Ile Ser Lys Val Asp Leu Phe Lys Gly Cys
        515             520             525

Asp Thr Gln Met Ile Tyr Asp Met Leu Leu Arg Leu Lys Ser Val Leu
        530             535             540

Tyr Leu Pro Gly Asp Phe Val Cys Lys Lys Gly Glu Ile Gly Lys Glu
545             550             555             560

Met Tyr Ile Ile Lys His Gly Glu Val Gln Val Leu Gly Gly Pro Asp
            565             570             575

Gly Thr Lys Val Leu Val Thr Leu Lys Ala Gly Ser Val Phe Gly Glu
            580             585             590

Ile Ser Leu Leu Ala Ala Gly Gly Gly Asn Arg Arg Thr Ala Asn Val
        595             600             605
```

```
Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
                660                 665                 670

Pro Lys Leu Phe Lys Thr Leu Leu Gly Gly Thr Gly Lys Ala Ser Leu
                675                 680                 685

Ala Arg Leu Leu Lys Leu Lys Arg Glu Gln Ala Ala Gln Lys Lys Glu
    690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Lys Pro Leu Asp
                740                 745                 750

Arg Pro Glu Cys Thr Ala Ser Pro Ile Ala Val Glu Glu Pro His
                755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Val Leu Thr
785                 790                 795                 800

Ile Glu Val Lys Glu Lys Ala Lys Gln
                805

<210> SEQ ID NO 21
<211> LENGTH: 2430
<212> TYPE: DNA
<213> ORGANISM: Artificial Sequence
<220> FEATURE:
<223> OTHER INFORMATION: constructed sequence
<220> FEATURE:
<221> NAME/KEY: CDS
<222> LOCATION: (1)..(2430)

<400> SEQUENCE: 21 atg ttt aaa tcg ctg aca aaa gtc aac aag gtg aag cct ata gga gag    48
Met Phe Lys Ser Leu Thr Lys Val Asn Lys Val Lys Pro Ile Gly Glu
1               5                   10                  15 aac aat gag aat gaa caa agt tct cgt cgg aat gaa gaa ggc tct cac    96
Asn Asn Glu Asn Glu Gln Ser Ser Arg Arg Asn Glu Glu Gly Ser His
                20                  25                  30 cca agt aat cag tct cag caa acc aca gca cag gaa gaa aac aaa ggt   144
Pro Ser Asn Gln Ser Gln Gln Thr Thr Ala Gln Glu Glu Asn Lys Gly
            35                  40                  45 gaa gag aaa tct ctc aaa acc aag tca act cca gtc acg tct gaa gag   192
Glu Glu Lys Ser Leu Lys Thr Lys Ser Thr Pro Val Thr Ser Glu Glu
    50                  55                  60 cca cac acc aac ata caa gac aaa ctc tcc aag aaa aat tcc tct gga   240
Pro His Thr Asn Ile Gln Asp Lys Leu Ser Lys Lys Asn Ser Ser Gly
65                  70                  75                  80 gat ctg acc aca aac cct gac cct caa aat gca gca gaa cca act gga   288
Asp Leu Thr Thr Asn Pro Asp Pro Gln Asn Ala Ala Glu Pro Thr Gly
                85                  90                  95 aca gtg cca gag cag aag gaa atg gac ccc ggg aaa gaa ggt cca aac   336
Thr Val Pro Glu Gln Lys Glu Met Asp Pro Gly Lys Glu Gly Pro Asn
```

|   |   |   |   |   |   |   |   |   |   |   |   |   |   |   |   |   |
|---|---|---|---|---|---|---|---|---|---|---|---|---|---|---|---|---|
|   |   |   | 100 |   |   |   |   | 105 |   |   |   |   | 110 |   |   |   |
| agc | cca | caa | aac | aaa | ccg | cca | gca | gct | cct | gtt | ata | aat | gag | tat | gcc | 384 |
| Ser | Pro | Gln | Asn | Lys | Pro | Pro | Ala | Ala | Pro | Val | Ile | Asn | Glu | Tyr | Ala |   |
|   |   | 115 |   |   |   | 120 |   |   |   |   | 125 |   |   |   |   |   |
| gat | gcc | cag | cta | cac | aac | ctg | gtg | aaa | aga | atg | cgt | caa | aga | aca | gcc | 432 |
| Asp | Ala | Gln | Leu | His | Asn | Leu | Val | Lys | Arg | Met | Arg | Gln | Arg | Thr | Ala |   |
| 130 |   |   |   |   | 135 |   |   |   |   | 140 |   |   |   |   |   |   |
| ctc | tac | aag | aaa | aag | ttg | gta | gag | gga | gat | ctc | tcc | tca | ccc | gaa | gcc | 480 |
| Leu | Tyr | Lys | Lys | Lys | Leu | Val | Glu | Gly | Asp | Leu | Ser | Ser | Pro | Glu | Ala |   |
| 145 |   |   |   | 150 |   |   |   |   | 155 |   |   |   |   | 160 |   |   |
| agc | cca | caa | act | gca | aag | ccc | acg | gct | gta | cca | cca | gta | aaa | gaa | agc | 528 |
| Ser | Pro | Gln | Thr | Ala | Lys | Pro | Thr | Ala | Val | Pro | Pro | Val | Lys | Glu | Ser |   |
|   |   |   | 165 |   |   |   |   | 170 |   |   |   |   | 175 |   |   |   |
| gat | gat | aag | cca | aca | gaa | cat | tac | tac | agg | ctg | ttg | tgg | ttc | aaa | gtc | 576 |
| Asp | Asp | Lys | Pro | Thr | Glu | His | Tyr | Tyr | Arg | Leu | Leu | Trp | Phe | Lys | Val |   |
|   |   |   | 180 |   |   |   |   | 185 |   |   |   |   | 190 |   |   |   |
| aaa | aag | atg | cct | tta | aca | gag | tac | tta | aag | cga | att | aaa | ctt | cca | aac | 624 |
| Lys | Lys | Met | Pro | Leu | Thr | Glu | Tyr | Leu | Lys | Arg | Ile | Lys | Leu | Pro | Asn |   |
|   |   | 195 |   |   |   |   | 200 |   |   |   |   | 205 |   |   |   |   |
| agc | ata | gat | tca | tac | aca | gat | cga | ctc | tat | ctc | ctg | tgg | ctc | ttg | ctt | 672 |
| Ser | Ile | Asp | Ser | Tyr | Thr | Asp | Arg | Leu | Tyr | Leu | Leu | Trp | Leu | Leu | Leu |   |
|   | 210 |   |   |   |   | 215 |   |   |   |   | 220 |   |   |   |   |   |
| gtc | act | ctt | gcc | tat | aac | tgg | aac | tgc | tgt | ttt | ata | cca | ctg | cgc | ctc | 720 |
| Val | Thr | Leu | Ala | Tyr | Asn | Trp | Asn | Cys | Cys | Phe | Ile | Pro | Leu | Arg | Leu |   |
| 225 |   |   |   |   | 230 |   |   |   |   | 235 |   |   |   |   | 240 |   |
| gtc | ttc | cca | tat | caa | acc | gca | gac | aac | ata | cac | tac | tgg | ctt | att | gcg | 768 |
| Val | Phe | Pro | Tyr | Gln | Thr | Ala | Asp | Asn | Ile | His | Tyr | Trp | Leu | Ile | Ala |   |
|   |   |   |   | 245 |   |   |   |   | 250 |   |   |   |   | 255 |   |   |
| gac | atc | atc | tgt | gat | atc | atc | tac | ctt | tat | gat | atg | cta | ttt | atc | cag | 816 |
| Asp | Ile | Ile | Cys | Asp | Ile | Ile | Tyr | Leu | Tyr | Asp | Met | Leu | Phe | Ile | Gln |   |
|   |   |   | 260 |   |   |   |   | 265 |   |   |   |   | 270 |   |   |   |
| ccc | aga | ctc | cag | ttt | gta | aga | gga | gga | gac | ata | ata | gtg | gat | tca | aat | 864 |
| Pro | Arg | Leu | Gln | Phe | Val | Arg | Gly | Gly | Asp | Ile | Ile | Val | Asp | Ser | Asn |   |
|   |   | 275 |   |   |   |   | 280 |   |   |   |   | 285 |   |   |   |   |
| gag | cta | agg | aaa | cac | tac | agg | act | tct | aca | aaa | ttt | cag | ttg | gat | gtc | 912 |
| Glu | Leu | Arg | Lys | His | Tyr | Arg | Thr | Ser | Thr | Lys | Phe | Gln | Leu | Asp | Val |   |
|   | 290 |   |   |   |   | 295 |   |   |   |   | 300 |   |   |   |   |   |
| gca | tca | ata | ata | cca | ttt | gat | att | tgc | tac | ctc | ttc | ttt | ggg | ttt | aat | 960 |
| Ala | Ser | Ile | Ile | Pro | Phe | Asp | Ile | Cys | Tyr | Leu | Phe | Phe | Gly | Phe | Asn |   |
| 305 |   |   |   |   | 310 |   |   |   |   | 315 |   |   |   |   | 320 |   |
| cca | atg | ttt | aga | gca | aat | agg | atg | tta | aag | tac | act | tca | ttt | ttt | gaa | 1008 |
| Pro | Met | Phe | Arg | Ala | Asn | Arg | Met | Leu | Lys | Tyr | Thr | Ser | Phe | Phe | Glu |   |
|   |   |   |   | 325 |   |   |   |   | 330 |   |   |   |   | 335 |   |   |
| ttt | aat | cat | cac | cta | gag | tct | ata | atg | gac | aaa | gca | tat | atc | tac | aga | 1056 |
| Phe | Asn | His | His | Leu | Glu | Ser | Ile | Met | Asp | Lys | Ala | Tyr | Ile | Tyr | Arg |   |
|   |   |   | 340 |   |   |   |   | 345 |   |   |   |   | 350 |   |   |   |
| gtt | att | cga | aca | act | gga | tac | ttg | ctg | ttt | att | ctg | cac | att | aat | gcc | 1104 |
| Val | Ile | Arg | Thr | Thr | Gly | Tyr | Leu | Leu | Phe | Ile | Leu | His | Ile | Asn | Ala |   |
|   |   | 355 |   |   |   |   | 360 |   |   |   |   | 365 |   |   |   |   |
| tgt | gtt | tat | tac | tgg | gct | tca | aac | tat | gaa | gga | att | ggc | act | act | aga | 1152 |
| Cys | Val | Tyr | Tyr | Trp | Ala | Ser | Asn | Tyr | Glu | Gly | Ile | Gly | Thr | Thr | Arg |   |
|   | 370 |   |   |   |   | 375 |   |   |   |   | 380 |   |   |   |   |   |
| tgg | gtg | tat | gat | ggg | gaa | gga | aac | gag | tat | ctg | aga | tgt | tat | tat | tgg | 1200 |
| Trp | Val | Tyr | Asp | Gly | Glu | Gly | Asn | Glu | Tyr | Leu | Arg | Cys | Tyr | Tyr | Trp |   |
| 385 |   |   |   |   | 390 |   |   |   |   | 395 |   |   |   |   | 400 |   |
| gca | gtt | cga | act | tta | att | acc | att | ggt | ggc | ctt | cca | gaa | cca | caa | act | 1248 |
| Ala | Val | Arg | Thr | Leu | Ile | Thr | Ile | Gly | Gly | Leu | Pro | Glu | Pro | Gln | Thr |   |
|   |   |   | 405 |   |   |   |   | 410 |   |   |   |   | 415 |   |   |   |
| tta | ttt | gaa | att | gtt | ttt | caa | ctc | ttg | aat | ttt | ttt | tct | gga | gtt | ttt | 1296 |

-continued

```
                Leu Phe Glu Ile Val Phe Gln Leu Leu Asn Phe Ser Gly Val Phe
                            420                 425                 430 gtg ttc tcc agt tta att ggt cag atg aga gat gtg att gga gca gct    1344
Val Phe Ser Ser Leu Ile Gly Gln Met Arg Asp Val Ile Gly Ala Ala
            435                 440                 445 aca gcc aat cag aac tac ttc cgc gcc tgc atg gat gac acc att gcc    1392
Thr Ala Asn Gln Asn Tyr Phe Arg Ala Cys Met Asp Asp Thr Ile Ala
        450                 455                 460 tac atg aac aat tac tcc att cct aaa ctt gtg caa aag cga gtt cgg    1440
Tyr Met Asn Asn Tyr Ser Ile Pro Lys Leu Val Gln Lys Arg Val Arg
465                 470                 475                 480 act tgg tat gaa tat aca tgg gac tct caa aga atg cta gat gag tct    1488
Thr Trp Tyr Glu Tyr Thr Trp Asp Ser Gln Arg Met Leu Asp Glu Ser
                485                 490                 495 gat ttg ctt aag acc cta cca act acg gtc cag tta gcc ctc gcc att    1536
Asp Leu Leu Lys Thr Leu Pro Thr Thr Val Gln Leu Ala Leu Ala Ile
            500                 505                 510 gat gtg aac ttc agc atc atc agc aaa gtt gac ttg ttc aag ggt tgt    1584
Asp Val Asn Phe Ser Ile Ile Ser Lys Val Asp Leu Phe Lys Gly Cys
        515                 520                 525 gat aca cag atg att tat gac atg ttg cta aga ttg aaa tcc gtt ctc    1632
Asp Thr Gln Met Ile Tyr Asp Met Leu Leu Arg Leu Lys Ser Val Leu
530                 535                 540 tat ttg cct ggt gac ttt gtc tgc aaa aag gga gaa att ggc aag gaa    1680
Tyr Leu Pro Gly Asp Phe Val Cys Lys Lys Gly Glu Ile Gly Lys Glu
545                 550                 555                 560 atg tat atc atc aag cat gga gaa gtc caa gtt ctt gga ggc cct gat    1728
Met Tyr Ile Ile Lys His Gly Glu Val Gln Val Leu Gly Gly Pro Asp
                565                 570                 575 ggt act aaa gtt ctg gtt act ctg aaa gct ggg tcg gtg ttt gga gaa    1776
Gly Thr Lys Val Leu Val Thr Leu Lys Ala Gly Ser Val Phe Gly Glu
            580                 585                 590 atc agc ctt cta gca gca gga gga gga aac cgt cga act gcc aat gtg    1824
Ile Ser Leu Leu Ala Ala Gly Gly Gly Asn Arg Arg Thr Ala Asn Val
        595                 600                 605 gtg gcc cac ggg ttt gcc aat ctt tta act cta gac aaa aag acc ctc    1872
Val Ala His Gly Phe Ala Asn Leu Leu Thr Leu Asp Lys Lys Thr Leu
    610                 615                 620 caa gaa att cta gtg cat tat cca gat tct gaa aga atc ctc atg aag    1920
Gln Glu Ile Leu Val His Tyr Pro Asp Ser Glu Arg Ile Leu Met Lys
625                 630                 635                 640 aaa gcc aga gtg ctt tta aag cag aag gct aag acc gca gaa gca acc    1968
Lys Ala Arg Val Leu Leu Lys Gln Lys Ala Lys Thr Ala Glu Ala Thr
                645                 650                 655 cct cca aga aaa gat ctt gcc ctc ctc ttc cca ccg aaa gaa gag aca    2016
Pro Pro Arg Lys Asp Leu Ala Leu Leu Phe Pro Pro Lys Glu Glu Thr
            660                 665                 670 ccc aaa ctg ttt aaa act ctc cta gga ggc aca gga aaa gca agt ctt    2064
Pro Lys Leu Phe Lys Thr Leu Leu Gly Gly Thr Gly Lys Ala Ser Leu
        675                 680                 685 gca aga cta ctc aaa ttg aag cga gag caa gca gct cag aag aaa gaa    2112
Ala Arg Leu Leu Lys Leu Lys Arg Glu Gln Ala Ala Gln Lys Lys Glu
    690                 695                 700 aat tct gaa gga gga gag gaa gga aaa gaa aat gaa gat aaa caa        2160
Asn Ser Glu Gly Gly Glu Glu Gly Lys Glu Asn Glu Asp Lys Gln
705                 710                 715                 720 aaa gaa aat gaa gat aaa caa aaa gaa aat gaa gat aaa gga aaa gaa    2208
Lys Glu Asn Glu Asp Lys Gln Lys Glu Asn Glu Asp Lys Gly Lys Glu
                725                 730                 735
```

```
aat gaa gat aaa gat aaa gga aga gag cca gaa gag aag cca ctg gac      2256
Asn Glu Asp Lys Asp Lys Gly Arg Glu Pro Glu Glu Lys Pro Leu Asp
            740                 745                 750 aga cct gaa tgt aca gca agt cct att gca gtg gag gaa gaa ccc cac      2304
Arg Pro Glu Cys Thr Ala Ser Pro Ile Ala Val Glu Glu Glu Pro His
        755                 760                 765 tca gtt aga agg aca gtt tta ccc aga ggg act tct cgt caa tca ctc      2352
Ser Val Arg Arg Thr Val Leu Pro Arg Gly Thr Ser Arg Gln Ser Leu
    770                 775                 780 att atc agc atg gct cct tct gct gag ggc gga gaa gag gtt ctt act      2400
Ile Ile Ser Met Ala Pro Ser Ala Glu Gly Gly Glu Glu Val Leu Thr
785                 790                 795                 800 att gaa gtc aaa gaa aag gct aag caa tga                              2430
Ile Glu Val Lys Glu Lys Ala Lys Gln
                805
```

<210> SEQ ID NO 22
<211> LENGTH: 809
<212> TYPE: PRT
<213> ORGANISM: Artificial Sequence
<220> FEATURE:
<223> OTHER INFORMATION: Synthetic Construct

<400> SEQUENCE: 22

```
Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
    210                 215                 220

Val Thr Leu Ala Tyr Asn Trp Asn Cys Cys Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
```

-continued

```
                260                 265                 270
Pro Arg Leu Gln Phe Val Arg Gly Gly Asp Ile Ile Val Asp Ser Asn
            275                 280                 285
Glu Leu Arg Lys His Tyr Arg Thr Ser Thr Lys Phe Gln Leu Asp Val
        290                 295                 300
Ala Ser Ile Ile Pro Phe Asp Ile Cys Tyr Leu Phe Gly Phe Asn
305                 310                 315                 320
Pro Met Phe Arg Ala Asn Arg Met Leu Lys Tyr Thr Ser Phe Phe Glu
                325                 330                 335
Phe Asn His His Leu Glu Ser Ile Met Asp Lys Ala Tyr Ile Tyr Arg
            340                 345                 350
Val Ile Arg Thr Thr Gly Tyr Leu Leu Phe Ile Leu His Ile Asn Ala
        355                 360                 365
Cys Val Tyr Tyr Trp Ala Ser Asn Tyr Glu Gly Ile Gly Thr Thr Arg
    370                 375                 380
Trp Val Tyr Asp Gly Glu Gly Asn Glu Tyr Leu Arg Cys Tyr Tyr Trp
385                 390                 395                 400
Ala Val Arg Thr Leu Ile Thr Ile Gly Gly Leu Pro Glu Pro Gln Thr
                405                 410                 415
Leu Phe Glu Ile Val Phe Gln Leu Leu Asn Phe Phe Ser Gly Val Phe
            420                 425                 430
Val Phe Ser Ser Leu Ile Gly Gln Met Arg Asp Val Ile Gly Ala Ala
        435                 440                 445
Thr Ala Asn Gln Asn Tyr Phe Arg Ala Cys Met Asp Asp Thr Ile Ala
    450                 455                 460
Tyr Met Asn Asn Tyr Ser Ile Pro Lys Leu Val Gln Lys Arg Val Arg
465                 470                 475                 480
Thr Trp Tyr Glu Tyr Thr Trp Asp Ser Gln Arg Met Leu Asp Glu Ser
                485                 490                 495
Asp Leu Leu Lys Thr Leu Pro Thr Thr Val Gln Leu Ala Leu Ala Ile
            500                 505                 510
Asp Val Asn Phe Ser Ile Ile Ser Lys Val Asp Leu Phe Lys Gly Cys
        515                 520                 525
Asp Thr Gln Met Ile Tyr Asp Met Leu Leu Arg Leu Lys Ser Val Leu
    530                 535                 540
Tyr Leu Pro Gly Asp Phe Val Cys Lys Lys Gly Glu Ile Gly Lys Glu
545                 550                 555                 560
Met Tyr Ile Ile Lys His Gly Glu Val Gln Val Leu Gly Gly Pro Asp
                565                 570                 575
Gly Thr Lys Val Leu Val Thr Leu Lys Ala Gly Ser Val Phe Gly Glu
            580                 585                 590
Ile Ser Leu Leu Ala Ala Gly Gly Gly Asn Arg Arg Thr Ala Asn Val
        595                 600                 605
Val Ala His Gly Phe Ala Asn Leu Leu Thr Leu Asp Lys Lys Thr Leu
    610                 615                 620
Gln Glu Ile Leu Val His Tyr Pro Asp Ser Glu Arg Ile Leu Met Lys
625                 630                 635                 640
Lys Ala Arg Val Leu Leu Lys Gln Lys Ala Lys Thr Ala Glu Ala Thr
                645                 650                 655
Pro Pro Arg Lys Asp Leu Ala Leu Leu Phe Pro Pro Lys Glu Glu Thr
            660                 665                 670
Pro Lys Leu Phe Lys Thr Leu Leu Gly Gly Thr Gly Lys Ala Ser Leu
        675                 680                 685
```

```
Ala Arg Leu Leu Lys Leu Lys Arg Glu Gln Ala Ala Gln Lys Lys Glu
        690                 695                 700
Asn Ser Glu Gly Gly Glu Glu Gly Lys Glu Asn Glu Asp Lys Gln
705                 710                 715                 720
Lys Glu Asn Glu Asp Lys Gln Lys Glu Asn Glu Asp Lys Gly Lys Glu
                725                 730                 735
Asn Glu Asp Lys Asp Lys Gly Arg Glu Pro Glu Glu Lys Pro Leu Asp
            740                 745                 750
Arg Pro Glu Cys Thr Ala Ser Pro Ile Ala Val Glu Glu Pro His
        755                 760                 765
Ser Val Arg Arg Thr Val Leu Pro Arg Gly Thr Ser Arg Gln Ser Leu
    770                 775                 780
Ile Ile Ser Met Ala Pro Ser Ala Glu Gly Gly Glu Glu Val Leu Thr
785                 790                 795                 800
Ile Glu Val Lys Glu Lys Ala Lys Gln
                805

<210> SEQ ID NO 23
<211> LENGTH: 2454
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (1)..(12)
<223> OTHER INFORMATION: modified end with NotI site and Kozak
<220> FEATURE:
<221> NAME/KEY: misc_feature
<222> LOCATION: (1)..(8)
<223> OTHER INFORMATION: NotI site for subcloning
<220> FEATURE:
<221> NAME/KEY: CDS
<222> LOCATION: (13)..(2448)
<223> OTHER INFORMATION: ORF with silent mutations (stop codon and
      restriction sites BamHI, PstI, SalI, and NdeI)
<220> FEATURE:
<221> NAME/KEY: misc_feature
<222> LOCATION: (2440)..(2442)
<223> OTHER INFORMATION: modifed stop codon
<220> FEATURE:
<221> NAME/KEY: misc_feature
<222> LOCATION: (2440)..(2445)
<223> OTHER INFORMATION: BclI site to facilitate addition of epitope tag
<220> FEATURE:
<221> NAME/KEY: misc_feature
<222> LOCATION: (2446)..(2448)
<223> OTHER INFORMATION: additional stop codon
<220> FEATURE:
<221> NAME/KEY: misc_feature
<222> LOCATION: (2449)..(2454)
<223> OTHER INFORMATION: PstI site for subcloning

<400> SEQUENCE: 23
gcggccgcca cc atg ttt aaa tcg ctg aca aaa gtc aac aag gtg aag cct      51
              Met Phe Lys Ser Leu Thr Lys Val Asn Lys Val Lys Pro
              1               5                   10 ata gga gag aac aat gag aat gaa caa agt tct cgt cgg aat gaa gaa      99
Ile Gly Glu Asn Asn Glu Asn Glu Gln Ser Ser Arg Arg Asn Glu Glu
    15                  20                  25 ggc tct cac cca agt aat cag tct cag caa acc aca gca cag gaa gaa      147
Gly Ser His Pro Ser Asn Gln Ser Gln Gln Thr Thr Ala Gln Glu Glu
30              35                  40                  45 aac aaa ggt gaa gag aaa tct ctc aaa acc aag tca act cca gtc acg      195
Asn Lys Gly Glu Glu Lys Ser Leu Lys Thr Lys Ser Thr Pro Val Thr
            50                  55                  60
```

-continued

| | | |
|---|---|---|
| tct gaa gag cca cac acc aac ata caa gac aaa ctc tcc aag aaa aat<br>Ser Glu Glu Pro His Thr Asn Ile Gln Asp Lys Leu Ser Lys Lys Asn<br>            65                      70                    75 | 243 | |
| tcc tct gga gat ctg acc aca aac cct gac cct caa aat gca gca gaa<br>Ser Ser Gly Asp Leu Thr Thr Asn Pro Asp Pro Gln Asn Ala Ala Glu<br>        80                      85                    90 | 291 | |
| cca act gga aca gtg cca gag cag aag gaa atg gac ccc ggg aaa gaa<br>Pro Thr Gly Thr Val Pro Glu Gln Lys Glu Met Asp Pro Gly Lys Glu<br>        95                      100                  105 | 339 | |
| ggt cca aac agc cca caa aac aaa ccg cca gca gct cct gtt ata aat<br>Gly Pro Asn Ser Pro Gln Asn Lys Pro Pro Ala Ala Pro Val Ile Asn<br>110                      115                  120                  125 | 387 | |
| gag tat gcc gat gcc cag cta cac aac ctg gtg aaa aga atg cgt caa<br>Glu Tyr Ala Asp Ala Gln Leu His Asn Leu Val Lys Arg Met Arg Gln<br>                      130                  135                  140 | 435 | |
| aga aca gcc ctc tac aag aaa aag ttg gta gag gga gat ctc tcc tca<br>Arg Thr Ala Leu Tyr Lys Lys Lys Leu Val Glu Gly Asp Leu Ser Ser<br>                145                  150                  155 | 483 | |
| ccc gaa gcc agc cca caa act gca aag ccc acg gct gta cca cca gta<br>Pro Glu Ala Ser Pro Gln Thr Ala Lys Pro Thr Ala Val Pro Pro Val<br>160                      165                  170 | 531 | |
| aaa gaa agc gat gat aag cca aca gaa cat tac tac agg ctg ttg tgg<br>Lys Glu Ser Asp Asp Lys Pro Thr Glu His Tyr Tyr Arg Leu Leu Trp<br>        175                      180                    185 | 579 | |
| ttc aaa gtc aaa aag atg cct tta aca gag tac tta aag cga att aaa<br>Phe Lys Val Lys Lys Met Pro Leu Thr Glu Tyr Leu Lys Arg Ile Lys<br>190                      195                  200                  205 | 627 | |
| ctt cca aac agc ata gat tca tac aca gat cga ctc tat ctc ctg tgg<br>Leu Pro Asn Ser Ile Asp Ser Tyr Thr Asp Arg Leu Tyr Leu Leu Trp<br>                      210                  215                  220 | 675 | |
| ctc ttg ctt gtc act ctt gcc tat aac tgg aac tgc tgt ttt ata cca<br>Leu Leu Leu Val Thr Leu Ala Tyr Asn Trp Asn Cys Cys Phe Ile Pro<br>                225                  230                  235 | 723 | |
| ctg cgc ctc gtc ttc cca tat caa acc gca gac aac ata cac tac tgg<br>Leu Arg Leu Val Phe Pro Tyr Gln Thr Ala Asp Asn Ile His Tyr Trp<br>                      240                  245                  250 | 771 | |
| ctt att gcg gac atc atc tgt gat atc atc tac ctt tat gat atg cta<br>Leu Ile Ala Asp Ile Ile Cys Asp Ile Ile Tyr Leu Tyr Asp Met Leu<br>255                      260                  265 | 819 | |
| ttt atc cag ccc aga ctc cag ttt gta aga gga gga gac ata ata gtg<br>Phe Ile Gln Pro Arg Leu Gln Phe Val Arg Gly Gly Asp Ile Ile Val<br>270                      275                  280                  285 | 867 | |
| gat tca aat gag cta agg aaa cac tac agg act tct aca aaa ttt cag<br>Asp Ser Asn Glu Leu Arg Lys His Tyr Arg Thr Ser Thr Lys Phe Gln<br>                      290                  295                  300 | 915 | |
| ttg gat gtc gca tca ata ata cca ttt gat att tgc tac ctc ttc ttt<br>Leu Asp Val Ala Ser Ile Ile Pro Phe Asp Ile Cys Tyr Leu Phe Phe<br>                305                  310                  315 | 963 | |
| ggg ttt aat cca atg ttt aga gca aat agg atg tta aag tac act tca<br>Gly Phe Asn Pro Met Phe Arg Ala Asn Arg Met Leu Lys Tyr Thr Ser<br>        320                      325                    330 | 1011 | |
| ttt ttt gaa ttt aat cat cac cta gag tct ata atg gac aaa gca tat<br>Phe Phe Glu Phe Asn His His Leu Glu Ser Ile Met Asp Lys Ala Tyr<br>335                      340                  345 | 1059 | |
| atc tac aga gtt att cga aca act gga tac ttg ctg ttt att ctg cac<br>Ile Tyr Arg Val Ile Arg Thr Thr Gly Tyr Leu Leu Phe Ile Leu His<br>350                      355                  360                  365 | 1107 | |
| att aat gcc tgt gtt tat tac tgg gct tca aac tat gaa gga att ggc<br>Ile Asn Ala Cys Val Tyr Tyr Trp Ala Ser Asn Tyr Glu Gly Ile Gly | 1155 | |

-continued

```
                     370                 375                 380
act act aga tgg gtg tat gat ggg gaa gga aac gag tat ctg aga tgt   1203
Thr Thr Arg Trp Val Tyr Asp Gly Glu Gly Asn Glu Tyr Leu Arg Cys
            385                 390                 395 tat tat tgg gca gtt cga act tta att acc att ggt ggc ctt cca gaa   1251
Tyr Tyr Trp Ala Val Arg Thr Leu Ile Thr Ile Gly Gly Leu Pro Glu
            400                 405                 410 cca caa act tta ttt gaa att gtt ttt caa ctc ttg aat ttt ttt tct   1299
Pro Gln Thr Leu Phe Glu Ile Val Phe Gln Leu Leu Asn Phe Phe Ser
        415                 420                 425 gga gtt ttt gtg ttc tcc agt tta att ggt cag atg aga gat gtg att   1347
Gly Val Phe Val Phe Ser Ser Leu Ile Gly Gln Met Arg Asp Val Ile
430                 435                 440                 445 gga gca gct aca gcc aat cag aac tac ttc cgc gcc tgc atg gat gac   1395
Gly Ala Ala Thr Ala Asn Gln Asn Tyr Phe Arg Ala Cys Met Asp Asp
                450                 455                 460 acc att gcc tac atg aac aat tac tcc att cct aaa ctt gtg caa aag   1443
Thr Ile Ala Tyr Met Asn Asn Tyr Ser Ile Pro Lys Leu Val Gln Lys
        465                 470                 475 cga gtt cgg act tgg tat gaa tat aca tgg gac tct caa aga atg cta   1491
Arg Val Arg Thr Trp Tyr Glu Tyr Thr Trp Asp Ser Gln Arg Met Leu
            480                 485                 490 gat gag tct gat ttg ctt aag acc cta cca act acg gtc cag tta gcc   1539
Asp Glu Ser Asp Leu Leu Lys Thr Leu Pro Thr Thr Val Gln Leu Ala
        495                 500                 505 ctc gcc att gat gtg aac ttc agc atc atc agc aaa gtt gac ttg ttc   1587
Leu Ala Ile Asp Val Asn Phe Ser Ile Ile Ser Lys Val Asp Leu Phe
510                 515                 520                 525 aag ggt tgt gat aca cag atg att tat gac atg ttg cta aga ttg aaa   1635
Lys Gly Cys Asp Thr Gln Met Ile Tyr Asp Met Leu Leu Arg Leu Lys
                530                 535                 540 tcc gtt ctc tat ttg cct ggt gac ttt gtc tgc aaa aag gga gaa att   1683
Ser Val Leu Tyr Leu Pro Gly Asp Phe Val Cys Lys Lys Gly Glu Ile
        545                 550                 555 ggc aag gaa atg tat atc atc aag cat gga gaa gtc caa gtt ctt gga   1731
Gly Lys Glu Met Tyr Ile Ile Lys His Gly Glu Val Gln Val Leu Gly
            560                 565                 570 ggc cct gat ggt act aaa gtt ctg gtt act ctg aaa gct ggg tcg gtg   1779
Gly Pro Asp Gly Thr Lys Val Leu Val Thr Leu Lys Ala Gly Ser Val
575                 580                 585 ttt gga gaa atc agc ctt cta gca gca gga gga aac cgt cga act   1827
Phe Gly Glu Ile Ser Leu Leu Ala Ala Gly Gly Asn Arg Arg Thr
590                 595                 600                 605 gcc aat gtg gtg gcc cac ggg ttt gcc aat ctt tta act cta gac aaa   1875
Ala Asn Val Val Ala His Gly Phe Ala Asn Leu Leu Thr Leu Asp Lys
                610                 615                 620 aag acc ctc caa gaa att cta gtg cat tat cca gat tct gaa aga atc   1923
Lys Thr Leu Gln Glu Ile Leu Val His Tyr Pro Asp Ser Glu Arg Ile
        625                 630                 635 ctc atg aag aaa gcc aga gtg ctt tta aag cag aag gct aag acc gca   1971
Leu Met Lys Lys Ala Arg Val Leu Leu Lys Gln Lys Ala Lys Thr Ala
            640                 645                 650 gaa gca acc cct cca aga aaa gat ctt gcc ctc ctc ttc cca ccg aaa   2019
Glu Ala Thr Pro Pro Arg Lys Asp Leu Ala Leu Leu Phe Pro Pro Lys
        655                 660                 665 gaa gag aca ccc aaa ctg ttt aaa act ctc cta gga ggc aca gga aaa   2067
Glu Glu Thr Pro Lys Leu Phe Lys Thr Leu Leu Gly Gly Thr Gly Lys
670                 675                 680                 685 gca agt ctt gca aga cta ctc aaa ttg aag cga gag caa gca gct cag   2115
Ala Ser Leu Ala Arg Leu Leu Lys Leu Lys Arg Glu Gln Ala Ala Gln
```

```
Ala Ser Leu Ala Arg Leu Leu Lys Leu Lys Arg Glu Gln Ala Ala Gln
            690             695                 700 aag aaa gaa aat tct gaa gga gga gag gaa gaa gga aaa gaa aat gaa      2163
Lys Lys Glu Asn Ser Glu Gly Gly Glu Glu Glu Gly Lys Glu Asn Glu
            705             710                 715 gat aaa caa aaa gaa aat gaa gat aaa caa aaa gaa aat gaa gat aaa      2211
Asp Lys Gln Lys Glu Asn Glu Asp Lys Gln Lys Glu Asn Glu Asp Lys
            720             725                 730 gga aaa gaa aat gaa gat aaa gat aaa gga aga gag cca gaa gag aag      2259
Gly Lys Glu Asn Glu Asp Lys Asp Lys Gly Arg Glu Pro Glu Glu Lys
            735             740                 745 cca ctg gac aga cct gaa tgt aca gca agt cct att gca gtg gag gaa      2307
Pro Leu Asp Arg Pro Glu Cys Thr Ala Ser Pro Ile Ala Val Glu Glu
750             755             760                 765 gaa ccc cac tca gtt aga agg aca gtt tta ccc aga ggg act tct cgt      2355
Glu Pro His Ser Val Arg Arg Thr Val Leu Pro Arg Gly Thr Ser Arg
                770             775                 780 caa tca ctc att atc agc atg gct cct tct gct gag ggc gga gaa gag      2403
Gln Ser Leu Ile Ile Ser Met Ala Pro Ser Ala Glu Gly Gly Glu Glu
            785             790                 795 gtt ctt act att gaa gtc aaa gaa aag gct aag caa tga tca taa          2448
Val Leu Thr Ile Glu Val Lys Glu Lys Ala Lys Gln     Ser
800             805             810 ctgcag                                                                2454

<210> SEQ ID NO 24
<211> LENGTH: 809
<212> TYPE: PRT
<213> ORGANISM: Artificial Sequence
<220> FEATURE:
<223> OTHER INFORMATION: Synthetic Construct

<400> SEQUENCE: 24

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Asn Ser Ser Gly
65              70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Val Lys Glu Ser
                165                 170                 175

Asp Asp Lys Pro Thr Glu His Tyr Tyr Arg Leu Leu Trp Phe Lys Val
            180                 185                 190
```

```
Lys Lys Met Pro Leu Thr Glu Tyr Leu Lys Arg Ile Lys Leu Pro Asn
            195                 200                 205
Ser Ile Asp Ser Tyr Thr Asp Arg Leu Tyr Leu Leu Trp Leu Leu
    210                 215                 220
Val Thr Leu Ala Tyr Asn Trp Asn Cys Cys Phe Ile Pro Leu Arg Leu
225                 230                 235                 240
Val Phe Pro Tyr Gln Thr Ala Asp Asn Ile His Tyr Trp Leu Ile Ala
                245                 250                 255
Asp Ile Ile Cys Asp Ile Ile Tyr Leu Tyr Asp Met Leu Phe Ile Gln
            260                 265                 270
Pro Arg Leu Gln Phe Val Arg Gly Gly Asp Ile Ile Val Asp Ser Asn
    275                 280                 285
Glu Leu Arg Lys His Tyr Arg Thr Ser Thr Lys Phe Gln Leu Asp Val
    290                 295                 300
Ala Ser Ile Ile Pro Phe Asp Ile Cys Tyr Leu Phe Phe Gly Phe Asn
305                 310                 315                 320
Pro Met Phe Arg Ala Asn Arg Met Leu Lys Tyr Thr Ser Phe Phe Glu
                325                 330                 335
Phe Asn His His Leu Glu Ser Ile Met Asp Lys Ala Tyr Ile Tyr Arg
            340                 345                 350
Val Ile Arg Thr Thr Gly Tyr Leu Leu Phe Ile Leu His Ile Asn Ala
    355                 360                 365
Cys Val Tyr Tyr Trp Ala Ser Asn Tyr Glu Gly Ile Gly Thr Thr Arg
    370                 375                 380
Trp Val Tyr Asp Gly Glu Gly Asn Glu Tyr Leu Arg Cys Tyr Tyr Trp
385                 390                 395                 400
Ala Val Arg Thr Leu Ile Thr Ile Gly Gly Leu Pro Glu Pro Gln Thr
                405                 410                 415
Leu Phe Glu Ile Val Phe Gln Leu Leu Asn Phe Phe Ser Gly Val Phe
            420                 425                 430
Val Phe Ser Ser Leu Ile Gly Gln Met Arg Asp Val Ile Gly Ala Ala
    435                 440                 445
Thr Ala Asn Gln Asn Tyr Phe Arg Ala Cys Met Asp Asp Thr Ile Ala
    450                 455                 460
Tyr Met Asn Asn Tyr Ser Ile Pro Lys Leu Val Gln Lys Arg Val Arg
465                 470                 475                 480
Thr Trp Tyr Glu Tyr Thr Trp Asp Ser Gln Arg Met Leu Asp Glu Ser
                485                 490                 495
Asp Leu Leu Lys Thr Leu Pro Thr Thr Val Gln Leu Ala Leu Ala Ile
            500                 505                 510
Asp Val Asn Phe Ser Ile Ile Ser Lys Val Asp Leu Phe Lys Gly Cys
    515                 520                 525
Asp Thr Gln Met Ile Tyr Asp Met Leu Leu Arg Leu Lys Ser Val Leu
    530                 535                 540
Tyr Leu Pro Gly Asp Phe Val Cys Lys Lys Gly Glu Ile Gly Lys Glu
545                 550                 555                 560
Met Tyr Ile Ile Lys His Gly Glu Val Gln Val Leu Gly Gly Pro Asp
                565                 570                 575
Gly Thr Lys Val Leu Val Thr Leu Lys Ala Gly Ser Val Phe Gly Glu
            580                 585                 590
Ile Ser Leu Leu Ala Ala Gly Gly Gly Asn Arg Arg Thr Ala Asn Val
    595                 600                 605
Val Ala His Gly Phe Ala Asn Leu Leu Thr Leu Asp Lys Lys Thr Leu
```

-continued

```
                610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Lys Glu Glu Thr
                660                 665                 670

Pro Lys Leu Phe Lys Thr Leu Leu Gly Gly Thr Gly Lys Ala Ser Leu
            675                 680                 685

Ala Arg Leu Leu Lys Leu Lys Arg Glu Gln Ala Ala Gln Lys Lys Glu
            690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Glu Lys Pro Leu Asp
            740                 745                 750

Arg Pro Glu Cys Thr Ala Ser Pro Ile Ala Val Glu Glu Pro His
            755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
            805

<210> SEQ ID NO 25
<211> LENGTH: 11714
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (1)..(130)
<223> OTHER INFORMATION: 5' ITR
<220> FEATURE:
<221> NAME/KEY: misc_feature
<222> LOCATION: (241)..(544)
<223> OTHER INFORMATION: CMV enhancer
<220> FEATURE:
<221> NAME/KEY: misc_feature
<222> LOCATION: (546)..(823)
<223> OTHER INFORMATION: chicken beta-actin promoter
<220> FEATURE:
<221> NAME/KEY: misc_feature
<222> LOCATION: (824)..(1795)
<223> OTHER INFORMATION: CBA exon 1 and intron
<220> FEATURE:
<221> NAME/KEY: misc_feature
<222> LOCATION: (1859)..(1864)
<223> OTHER INFORMATION: kozak
<220> FEATURE:
<221> NAME/KEY: misc_feature
<222> LOCATION: (1865)..(3826)
<223> OTHER INFORMATION: human codon optimized CHM (REP-1)
<220> FEATURE:
<221> NAME/KEY: misc_feature
<222> LOCATION: (3847)..(4054)
<223> OTHER INFORMATION: bGH poly(A) signal
<220> FEATURE:
<221> NAME/KEY: misc_feature
<222> LOCATION: (4104)..(4233)
<223> OTHER INFORMATION: 3' ITR

<400> SEQUENCE: 25
```

-continued

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
tagttattaa tagtaatcaa ttacggggtc attagttcat agcccatata tggagttccg     240
cgttacataa cttacggtaa atggcccgcc tggctgaccg cccaacgacc cccgcccatt     300
gacgtcaata atgacgtatg ttcccatagt aacgccaata gggactttcc attgacgtca     360
atgggtggag tatttacggt aaactgccca cttggcagta catcaagtgt atcatatgcc     420
aagtacgccc cctattgacg tcaatgacgg taaatggccc gcctggcatt atgcccagta     480
catgacctta tgggactttc ctacttggca gtacatctac gtattagtca tcgctattaa     540
catggtcgag gtgagcccca cgttctgctt cactctcccc atctccccc cctcccacc      600 cccaattttg tatttattta ttttttaatt attttgtgca gcgatggggg cggggggggg     660 ggggggggcgc gcgccaggcg gggcggggcg gggcgagggg cggggcgggg cgaggcggag     720
aggtgcggcg gcagccaatc agagcggcgc gctccgaaag tttcctttta tggcgaggcg     780 gcggcggcg cggccctata aaaagcgaag cgcgcggcgg gcggggagtc gctgcgacgc     840
tgccttcgcc ccgtgccccg ctccgccgcc ggctcgcgcc gcccgccccg gctctgactg     900
accgcgttac tcccacaggt gagcgggcgg gacggcccctt ctcctccggg ctgtaattag     960
cgcttggttt aatgacggct tgtttctttt ctgtggctgc gtgaaagcct tgagggctc    1020 cgggagggcc ctttgtgcgg ggggagcggc tcgggggtg cgtgcgtgtg tgtgtgcgtg    1080
gggagcgccg cgtgcggctc cgcgctgccc ggcggctgtg agcgctgcgg gcgcggcgcg    1140
gggctttgtg cgctccgcag tgtgcgcgag gggagcgcgg ccggggcgg tgccccgcgg    1200 tgcggggggg gctgcgaggg gaacaaaggc tgcgtgcggg gtgtgtgcgt gggggggtga    1260 gcaggggtg tgggcgcgtc ggtcgggctg caaccccccc tgcaccccc tccccgagtt    1320 gctgagcacg gcccggcttc gggtgcgggg ctccgtacgg ggcgtggcgc ggggctcgcc    1380
gtgccgggcg ggggtggcg gcaggtgggg gtgccgggcg gggcgggcc gcctcgggcc    1440 ggggagggct cggggagggg gcgcggcggc ccccggagcc ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcaccccctc tagcgggcgc    1620
ggggcgaagc ggtgcggcgc cggcaggaag gaaatgggcg gggagggcct tcgtgcgtcg    1680 ccgcgccgc gtccccttct ccctctccag cctcggggct gtccgcgggg gacggctgc    1740 cttcgggggg gacggggcag ggcgggttc ggcttctggc gtgtgaccgg cggctctaga    1800
caattgtact aaccttcttc tctttcctct cctgacaggt tggtgtacac tagcggccgc    1860
caccatggct gataccctgc cctctgaatt cgacgtgatt gtgattggaa ccggactccc    1920
tgaatcgatc atcgccgcgg cctgttcccg gtccggtcgg cgcgtgctgc acgtcgattc    1980
gagaagctac tacggaggga attgggcctc attctccttc tccggactgc tctcctggct    2040
gaaggagtat caggagaact ccgacattgt ctccgactca cctgtgtggc aggaccagat    2100
cctggaaaac gaggaagcaa tagccctgag ccggaaggac aagaccatcc agcacgtgga    2160
ggtgttctgt tatgcctccc aagacctcca tgaggacgtg aagaggctg agcgttgca    2220 gaagaatcat gccctcgtga cctccgctaa ctccaccgag gcagccgaca cgcgccttcct    2280 gccgaccgag gatgaatccc tgtcaactat gtcgtgcgaa atgctgaccg aacagactcc    2340
```

```
gagctccgac cccgaaaacg ccctggaagt gaacggagcg gaagtgaccg gcgaaaagga    2400
gaaccattgc gacgacaaga cttgtgtccc atccacttcc gcggaggaca tgtccgagaa    2460
tgtgcctatc gccgaggaca ccaccgaaca gcccaagaag aacagaatca cgtacagcca    2520
gatcatcaag gaggggcgga ggtttaacat cgatctggtg tcgaagctgc tgtacagccg    2580
cggtctgctg atcgatctgc tcattaagtc gaacgtgtcg agatacgccg agttcaagaa    2640
catcacaagg attctcgcct tccgggaagg aagagtggaa caagtgccgt gctcccgggc    2700
cgacgtgttc aactcaaagc aacttaccat ggtggaaaag cgcatgctga tgaaattcct    2760
gaccttctgc atggagtacg aaaagtaccc tgatgagtac aagggttacg aagaaattac    2820
tttctacgag tacctcaaga cccagaagct gaccccgaat ctgcagtaca ttgtgatgca    2880
ctcaatcgca atgaccctcc gaaaccgcct ctcgaccatc gacgggctca aggccaccaa    2940
gaacttcctg cactgttttgg ggcgctacgg caacactccg ttcctcttcc cgctgtacgg    3000
ccagggagag ctgcctcagt gtttctgccg gatgtgcgcc gtgttcggcg gaatctactg    3060
tctccgccac tcggtccagt gcctggtggt ggacaaggaa tccaggaagt gcaaagccat    3120
tattgaccag ttcggacaac ggatcatttc cgagcacttt cttgtggagg actcatactt    3180 cccgagaac atgtgctctc gggtccagta tcgacagatt tccagggcgg tgctcattac    3240
tgaccggagc gtcctcaaga ccgatagcga ccagcagatc tccatcctga ccgtgccggc    3300
ggaagaaccc ggcactttg ccgtgcgcgt gatcgagctt tgctcatcca ccatgacttg    3360
catgaaaggc acttacctgg tgcacctgac gtgcacctca tcgaaaaccg ctagagagga    3420
cctggaatcc gtcgtccaaa agctgttcgt gccttacacc gagatggaaa ttgaaaacga    3480
acaagtggag aagccccgca tcctttgggc cctgtacttt aacatgcgcg attcctccga    3540
tatctcgcgg tcctgctata cgacttgcc ttcgaacgtc tacgtctgct ccgggccaga    3600
ctgcggtctt ggcaacgaca atgccgtgaa gcaggcggaa acactgttcc aagagatctg    3660
ccctaacgag gattttgcc cgccccccc aaaccccgag gatatcatct tggacggaga    3720
cagcctgcag ccagaagcat ccgagtccag cgccatcccg gaggccaaca gcgaaacctt    3780
caaggagagc actaacctgg gcaacctgga agagtccagc gaatgatcat aggatctctg    3840
cctcgactgt gccttctagt tgccagccat ctgttgtttg cccctcccc gtgccttcct    3900 tgaccctgga aggtgccact cccactgtcc tttcctaata aaatgaggaa attgcatcgc    3960
attgtctgag taggtgtcat tctattctgg ggggtggggt ggggcaggac agcaagggg    4020 aggattggga agacaatagc aggcatgctg gggactcgag ttctacgtag ataagtagca    4080
tggcgggtta atcattaact acaaggaacc cctagtgatg gagttggcca ctccctctct    4140
gcgcgctcgc tcgctcactg aggccgggcg accaaaggtc gcccgacgcc cgggctttgc    4200
ccgggcggcc tcagtgagcg agcgagcgcg cagccttata aggatatggt gcactctcag    4260
tacaatctgc tctgatgccg catagttaag ccagccccga cacccgccaa cacccgctga    4320
cgcgccctga cgggcttgtc tgctcccggc atccgcttac agacaagctg tgaccgtctc    4380
cgggagctgc atgtgtcaga ggttttcacc gtcatcaccg aaacgcgcga gacgaaaggg    4440
cctcgtgata cgcctatttt tataggttaa tgtcatgata ataatggttt cttagacgtc    4500
aggtggcact tttcggggaa atgtgcgcgg aaccctatt tgtttatttt tctaaataca    4560
ttcaaatatg tatccgctca tgagacaata accctgataa atgcttcaat aatattgaaa    4620
aaggaagagt atgagccata ttcaacggga acgtcgagg ccgcgattaa attccaacat    4680
ggatgctgat ttatatgggt ataaatgggc tcgcgataat gtcgggcaat caggtgcgac    4740
```

| | |
|---|---|
| aatctatcgc ttgtatggga agcccgatgc gccagagttg tttctgaaac atggcaaagg | 4800 |
| tagcgttgcc aatgatgtta cagatgagat ggtcagacta aactggctga cggaatttat | 4860 |
| gccacttccg accatcaagc attttatccg tactcctgat gatgcatggt tactcaccac | 4920 |
| tgcgatcccc ggaaaaacag cgttccaggt attagaagaa tatcctgatt caggtgaaaa | 4980 |
| tattgttgat gcgctggcag tgttcctgcg ccggttgcac tcgattcctg tttgtaattg | 5040 |
| tcctttaac agcgatcgcg tatttcgcct cgctcaggcg caatcacgaa tgaataacgg | 5100 |
| tttggttgat gcgagtgatt ttgatgacga gcgtaatggc tggcctgttg aacaagtctg | 5160 |
| gaaagaaatg cataaacttt tgccattctc accggattca gtcgtcactc atggtgattt | 5220 |
| ctcacttgat aaccttattt ttgacgaggg gaaattaata ggttgtattg atgttggacg | 5280 |
| agtcggaatc gcagaccgat accaggatct tgccatccta tggaactgcc tcggtgagtt | 5340 |
| ttctccttca ttacagaaac ggctttttca aaaatatggt attgataatc ctgatatgaa | 5400 |
| taaattgcag tttcatttga tgctcgatga gttttctaa actgtcagac caagtttact | 5460 |
| catatatact ttagattgat ttaaaacttc attttaatt taaaaggatc taggtgaaga | 5520 |
| tccttttga taatctcatg accaaaatcc cttaacgtga gttttcgttc cactgagcgt | 5580 |
| cagacccgt agaaaagatc aaaggatctt cttgagatcc ttttttctg cgcgtaatct | 5640 |
| gctgcttgca acaaaaaaa ccaccgctac cagcggtggt ttgtttgccg gatcaagagc | 5700 |
| taccaactct ttttccgaag gtaactggct tcagcagagc gcagatacca aatactgttc | 5760 |
| ttctagtgta gccgtagtta ggccaccact tcaagaactc tgtagcaccg cctacatacc | 5820 |
| tcgctctgct aatcctgtta ccagtggctg ctgccagtgg cgataagtcg tgtcttaccg | 5880 |
| ggttggactc aagacgatag ttaccggata aggcgcagcg gtcgggctga acggggggtt | 5940 |
| cgtgcacaca gcccagcttg gagcgaacga cctacaccga actgagatac ctacagcgtg | 6000 |
| agctatgaga aagcgccacg cttcccgaag ggagaaaggc ggacaggtat ccggtaagcg | 6060 |
| gcagggtcgg aacaggagag cgcacgaggg agcttccagg gggaaacgcc tggtatcttt | 6120 |
| atagtcctgt cgggtttcgc cacctctgac ttgagcgtcg attttgtga tgctcgtcag | 6180 |
| gggggcggag cctatggaaa aacgccagca acgcggcctt tttacggttc ctggccttt | 6240 |
| gctggccttt tgctcacatg ttctttcctg cgttatcccc tgattctgtg ataaccgta | 6300 |
| ttaccgcctt tgagtgagct gataccgctc gccgcagccg aacgaccgag cgcagcgagt | 6360 |
| cagtgagcga ggaagcggaa gagcgcccaa tacgcaaacc gcctctcccc gcgcgttggc | 6420 |
| cgattcatta atgcaggcgc ctgttgattt gagttttggg tttagcgtga caagtttgcg | 6480 |
| agggtgatcg gagtaatcag taaatagctc tccgcctaca atgacgtcat aaccatgatt | 6540 |
| tctggttttc tgacgtccgt tatcagttcc ctccgaccac gccagcatat cgaggaacgc | 6600 |
| cttacgttga ttattgattt ctaccatctt ctactccggc ttttttagca gcgaagcgtt | 6660 |
| tgataagcga accaatcgag tcagtaccga tgtagccgat aaacacgctc gttatataag | 6720 |
| cgagattgct acttagtccg gcgaagtcga gaaggtcacg aatgaaccag gcgataatgg | 6780 |
| cgcacatcgt tgcgtcgatt actgtttttg taaacgcacc gccattatat ctgccgcgaa | 6840 |
| ggtacgccat tgcaaacgca aggattgccc cgatgccttg ttcctttgcc gcgagaatgg | 6900 |
| cggccaacag gtcatgtttt tctggcatct tcatgtctta cccccaataa ggggatttgc | 6960 |
| tctatttaat taggaataag gtcgattact gatagaacaa atccaggcta ctgtgtttag | 7020 |
| taatcagatt tgttcgtgac cgatatgcac gggcaaaacg gcaggaggtt gttagcgcga | 7080 |

| | |
|---|---|
| cctcctgcca cccgctttca cgaaggtcat gtgtaaaagg ccgcagcgta actattacta | 7140 |
| atgaattcag gacagacagt ggctacggct cagtttgggt tgtgctgttg ctgggcggcg | 7200 |
| atgacgcctg tacgcatttg gtgatccggt tctgcttccg gtattcgctt aattcagcac | 7260 |
| aacggaaaga gcactggcta accaggctcg ccgactcttc acgattatcg actcaatgct | 7320 |
| cttacctgtt gtgcagatat aaaaaatccc gaaaccgtta tgcaggctct aactattacc | 7380 |
| tgcgaactgt ttcgggattg cattttgcag acctctctgc ctgcgatggt tggagttcca | 7440 |
| gacgatacgt cgaagtgacc aactaggcgg aatcggtagt aagcgccgcc tcttttcatc | 7500 |
| tcactaccac aacgagcgaa ttaacccatc gttgagtcaa atttacccaa ttttattcaa | 7560 |
| taagtcaata tcatgccgtt aatatgttgc catccgtggc aatcatgctg ctaacgtgtg | 7620 |
| accgcattca aaatgttgtc tgcgattgac tcttctttgt ggcattgcac caccagagcg | 7680 |
| tcatacagcg gcttaacagt gcgtgaccag gtgggttggg taaggtttgg gattagcatc | 7740 |
| gtcacagcgc gatatgctgc gcttgctggc atccttgaat agccgacgcc tttgcatctt | 7800 |
| ccgcactctt tctcgacaac tctccccac agctctgttt tggcaatatc aaccgcacgg | 7860 |
| cctgtaccat ggcaatctct gcatcttgcc cccggcgtcg cggcactacg gcaataatcc | 7920 |
| gcataagcga atgttgcgag cacttgcagt acctttgcct tagtatttcc ttcaagcttt | 7980 |
| gccacaccac ggtatttccc cgataccttg tgtgcaaatt gcatcagata gttgatagcc | 8040 |
| ttttgtttgt cgttctggct gagttcgtgc ttaccgcaga atgcagccat accgaatccg | 8100 |
| gcttgtgatt gcgccatccc catagcagcc atcacatcag taccggaaag agagtcagaa | 8160 |
| gccgtggccc gtggtgagtc gctcatcatc gggcttttg gcgaatgaaa tttagctacg | 8220 |
| ctttcgagtc tcatgcgcct tctccctgta cctgaatcaa tgttaggttt ccgcagaaca | 8280 |
| ctgcgccggt atcgatatac atttggttgg caaacttgag tggtttcact gctggcgtat | 8340 |
| gaccaaagat gaacgtgtcc gcgcctttga tttctttcac gatcccgttt tgtgagttgc | 8400 |
| tgattcgttc gcggttccag attacctgct gatgatcaac tggctttcca aactcgtatt | 8460 |
| cgtcaaaggg ataatcggcg tggcagataa catatttttt atctttgctc accagttcga | 8520 |
| tgattaacga agttcatct gctttatggg caagagcttt agccagaatt tctttgtcgt | 8580 |
| aatcgagatt aaagaaccag ccaccgccat taagcagcca gtgattaacg tttccacgct | 8640 |
| ctgataagcc atcaatcatc atttgctcat ggtttccacg tacagctctg aaccagggga | 8700 |
| atgtgattaa ttccaggcat tcaacgttct ctgcaccacg atcaaccaaa tcgcccaccg | 8760 |
| agataagcag gtctttttg ttgtcgaatc caatcgtatc cagtttgttc atcaggttcg | 8820 |
| tgtagcatcc gtgcagatcg ccaactaccc aaatatttcg gtatttgctg ccatcaattt | 8880 |
| tttcgtaata gcgcatctct ttcactccat ccgcgatgaa ccatgagaac gtcgttgacg | 8940 |
| atggcgtgca ttttcccgtc tttatcatca acgtattttc tgaccgtacc gcgactacat | 9000 |
| ttcagtctgc gtgctacttc tgtctgattt ccgtatgctt caacgagcat gtctggaatg | 9060 |
| gtttttactg agaacgtcat gcggcctcac ttctgctatt tcgcaggtct ttgagtttct | 9120 |
| gttggtactc tgccttgatc gccttgcact cttcgatagt ccagcgatgg cggttatggt | 9180 |
| ttgattcgat ttcgtctact gcttcctgcc cgatgcggct aatcagttcg acgcgatacg | 9240 |
| gaacgagatt tccgcttttg tgctggttgc acaccacgca ttgcttgtga atattgcgtt | 9300 |
| cattaaatcg gagttgaggt gccgcagcag ttgtccggta atgtccggca tcccactgag | 9360 |
| cagacgtgag cgttccgcac gagatacatg gtaagtcgcg gtctcttct ctgatgaagg | 9420 |
| cgtttacggc ttgttgggct tgtttaatcc agtaactgcg gggctttaag gcgagttttc | 9480 |

```
gaatcttaag tttatctttc tgtttctgct cctctcgtcg tcgtttcttc tctgctgctt    9540
tttccgcttt ttcgcgttct ttacttcgtc gttcgagtgc tatcttggtt ccacactctg    9600
gagagcacca ccactgatta gcgaatgcag ggtgaaacca ttcccggcat tcatcgtttt    9660
tacatcgtct tcgcgctggt ttagccatca tcttcttcct cgtgcatcga gctattcgga    9720
tcgctcatca gttctgcgca gcagtgctca cacacgtgaa cttccagcac atgcagcttc    9780
tgaccgcagt tagcgcacgt taaagctcgc tcgacgcttt cttgttcgta acttcgattt    9840
tggtcaatca ccttgttttc ctcgcacgac gtcttagcca ccggatatcc cacaggtgag    9900
ccgtgtagtt gaaggttttt acgtcagatt cttttgggat tggcttgggt ttatttctgg    9960
tgcgtttcgt tggaaggtat ttgcagtttt cgcagattat gtcggtgata cttcgtcgct   10020
gtctcgccac acgtcctcct tttcctgcgg tagtggtaac accctgttg gtgttctttc    10080 acaccggaga caccatcgat tccagtaagg ttgatttggt cggaagcggt tatcttcttt   10140
gcattcaccg caccgataac atcgcatcat gcagcttccc tcccgaagtc gaaatcaagc   10200
tgccctccaa atatttcgca tgactcagaa caagagccgg tatcgaatct tttagctcgt   10260
accatgtcct gatacagggc ttgataatca ttttctgaat acattttcgc gataccgtcc   10320
agcgacattc ttcctcggta cataatctcc tttggcgttt cccgatgtcc gtcacgcaca   10380
tgggatcccg tgatgacctc attaaaaaca cgctgcaatc cctcctcatc tttgcaggca   10440
agtccgattt tttgcgttga ttttttaatg cagaatatgc agttaccgag atgttccggt   10500
atttgcaaat cgaatggttg ttgcttccac catgcgagga tatcttcctt ctcaaagtct   10560
gacagttcag caagatatct gattccaggc tttggcttta gccgcttcgg ttcatcagct   10620
ctgatgccaa tccacgtggt gtaattccct cgcccgaaat ggtcatcaca gtatttggtg   10680
aagggaacga gttttaatct gtcagtgcag aacgcgccgc cgacgtatgg agtgccatat   10740
ttctttacca tatcgataaa tggcttcaga acaggcattc gcgtctgaat atcctttggt   10800
tcccataccg tataaccatt tggctgtcca agctccgggt tgatatcaac ctgcaatacg   10860
gtgagcggta tatcccagaa cttcacaact tccctgacaa accgatatgt cattggatgt   10920
tcacaacctg tatccatgaa aacgtaatgc acgtctttac ctgcccgtcg cttttgctcc   10980
attagccaga gcaaatatgc tgacgtcctg ccaccggaga aactaacgac atttatcatg   11040
cagccctgtc tccccatctc gctttccact ccagagccag tctcgcttcg tctgaccact   11100
taacgccacg ctctgtaccg aatgcctgta taagctctaa tagctccgca aattcgccta   11160
cacgcatcct gctggttgac tggcctatta ccacaaagcc attcccggca aggttaggaa   11220
caacatcctg ctgctttaat gctgcggtaa acacacactt ccagctttct gcatccagcc   11280
agcgaccatg ccattcaacc tgacgagaga cgtcacctaa gcaggcccat agcttcctgt   11340
tttggtctaa gctgcggttg cgttcctgaa tggttactac gattggtttg gttgggtctg   11400
gaaggatttg ctgtactgcg tgaatagcgt tttgctgatg tgctggagat cgaatttcaa   11460
aggttagttt tttcatgact tccctctccc ccaaataaaa aggctggcac gacaggtttc   11520
ccgactggaa agcgggcagt gagcgcaacg caattaatgt gagttagctc actcattagg   11580 cacccccaggc tttacacttt atgcttccgg ctcgtatgtt gtgtggaatt gtgagcggat   11640
aacaatttca cacaggaaac agctatgacc atgattacgc caagctgtcg actctagagg   11700
atcccctaat aagg                                                     11714
```

<210> SEQ ID NO 26

```
<211> LENGTH: 6647
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (1)..(130)
<223> OTHER INFORMATION: 5' ITR
<220> FEATURE:
<221> NAME/KEY: misc_feature
<222> LOCATION: (241)..(544)
<223> OTHER INFORMATION: CMV enhancer
<220> FEATURE:
<221> NAME/KEY: misc_feature
<222> LOCATION: (546)..(823)
<223> OTHER INFORMATION: chicken beta-actin promoter
<220> FEATURE:
<221> NAME/KEY: misc_feature
<222> LOCATION: (824)..(1795)
<223> OTHER INFORMATION: CBA exon 1 and intron
<220> FEATURE:
<221> NAME/KEY: misc_feature
<222> LOCATION: (1859)..(1864)
<223> OTHER INFORMATION: Kozak
<220> FEATURE:
<221> NAME/KEY: misc_feature
<222> LOCATION: (1865)..(3826)
<223> OTHER INFORMATION: human codon optimized CHM (REM-1)
<220> FEATURE:
<221> NAME/KEY: misc_feature
<222> LOCATION: (3847)..(4054)
<223> OTHER INFORMATION: bGH poly(A) signal
<220> FEATURE:
<221> NAME/KEY: misc_feature
<222> LOCATION: (4104)..(4233)
<223> OTHER INFORMATION: 3' ITR

<400> SEQUENCE: 26
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
tagttattaa tagtaatcaa ttacggggtc attagttcat agcccatata tggagttccg     240
cgttacataa cttacggtaa atggcccgcc tggctgaccg cccaacgacc cccgcccatt     300
gacgtcaata atgacgtatg ttcccatagt aacgccaata gggactttcc attgacgtca     360
atgggtggag tatttacggt aaactgccca cttggcagta catcaagtgt atcatatgcc     420
aagtacgccc cctattgacg tcaatgacgg taaatggccc gcctggcatt atgcccagta     480
catgacctta tgggactttc ctacttggca gtacatctac gtattagtca tcgctattaa     540
catggtcgag gtgagcccca cgttctgctt cactctcccc atctcccccc cctccccacc     600
cccaattttg tatttattta ttttttaatt attttgtgca gcgatggggg cggggggggg     660
gggggggcgc gcgccaggcg gggcggggcg gggcgagggg cggggcgggg cgaggcggag     720
aggtgcggcg gcagccaatc agagcggcgc gctccgaaag tttccttttta tggcgaggcg     780
gcggcggcgg cggccctata aaagcgaag cgcgcggcgg gcgggagtc gctgcgacgc       840
tgccttcgcc ccgtgccccg ctccgccgcc gctcgcgcc gcccgccccg gctctgactg       900
accgcgttac tcccacaggt gagcgggcgg gacggccctt ctcctccggg ctgtaattag      960
cgcttggttt aatgacggct tgtttctttt ctgtggctgc gtgaaagcct tgaggggctc    1020
cgggagggcc ctttgtgcgg ggggagcggc tcggggggtg cgtgcgtgtg tgtgtgcgtg    1080
gggagcgccg cgtgcggctc cgcgctgccc ggcggctgtg agcgctgcgg gcgcggcgcg    1140
gggctttgtg cgctccgcag tgtgcgcgag gggagcgcgg ccggggggcgg tgccccgcgg    1200
```

```
tgcgggggggg gctgcgaggg gaacaaaggc tgcgtgcggg gtgtgtgcgt gggggggtga    1260 gcaggggggtg tgggcgcgtc ggtcgggctg caacccccc tgcaccccc tcccccgagtt    1320 gctgagcacg gcccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggagggg gcgcggcggc ccccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcacccccct tagcgggcgc    1620
ggggcgaagc ggtgcggcgc cggcaggaag gaaatgggcg gggagggcct tcgtgcgtcg    1680
ccgcgccgcc gtccccttct ccctctccag cctcggggct gtccgcgggg ggacggctgc    1740 cttcggggggg gacggggcag ggcggggttc ggcttctggc gtgtgaccgg cggctctaga    1800
caattgtact aaccttcttc tctttcctct cctgacaggt tggtgtacac tagcggccgc    1860
caccatggct gatacccctgc cctctgaatt cgacgtgatt gtgattggaa ccggactccc    1920
tgaatcgatc atcgccgcgg cctgttcccg gtccggtcgg cgcgtgctgc acgtcgattc    1980
gagaagctac tacggaggga attgggcctc attctccttc tccggactgc tctcctggct    2040
gaaggagtat caggagaact ccgacattgt ctccgactca cctgtgtggc aggaccagat    2100
cctggaaaac gaggaagcaa tagccctgag ccggaaggac aagaccatcc agcacgtgga    2160
ggtgttctgt tatgcctccc aagacctcca tgaggacgtg gaagaggctg gagcgttgca    2220
gaagaatcat gccctcgtga cctccgctaa ctccaccgag gcagccgaca gcgccttcct    2280
gccgaccgag gatgaatccc tgtcaactat gtcgtgcgaa atgctgaccg aacagactcc    2340
gagctccgac cccgaaaacg ccctggaagt gaacggagcg gaagtgaccg gcgaaaagga    2400
gaaccattgc gacgacaaga cttgtgtccc atccacttcc gcggaggaca tgtccgagaa    2460
tgtgcctatc gccgaggaca ccaccgaaca gcccaagaag aacagaatca cgtacagcca    2520
gatcatcaag gaggggcgga ggtttaacat cgatctggtg tcgaagctgc tgtacagccg    2580
cggtctgctg atcgatctgc tcattaagtc gaacgtgtcg agatacgccg agttcaagaa    2640
catcacaagg attctcgcct tccgggaagg aagagtggaa caagtgccgt gctcccgggc    2700
cgacgtgttc aactcaaagc aacttaccat ggtggaaaag cgcatgctga tgaaattcct    2760
gaccttctgc atggagtacg aaaagtaccc tgatgagtac aagggttacg aagaaattac    2820
tttctacgag tacctcaaga cccagaagct gaccccgaat ctgcagtaca ttgtgatgca    2880
ctcaatcgca atgacctccg aaaccgcctc ctcgaccatc gacgggctca aggccaccaa    2940
gaacttcctg cactgtttgg ggcgctacgg caacactccg ttcctcttcc cgctgtacgg    3000
ccagggagag ctgcctcagt gtttctgccg gatgtgcgcc gtgttcggcg gaatctactg    3060
tctccgccac tcggtccagt gcctggtggt ggacaaggaa tccaggaagt gcaaagccat    3120
tattgaccag ttcggacaac ggatcatttc gagcactttt cttgtggagg actcatactt    3180
cccggagaac atgtgctctc gggtccagta tcgacagatt tccagggcgg tgctcattac    3240
tgaccggagc gtcctcaaga ccgatagcga ccagcagatc tccatcctga ccgtgccggc    3300
ggaagaaccc ggcactttg ccgtgcgcgt gatcgagctt tgctcatcca ccatgacttg    3360
catgaaaggc acttacctgg tgcacctgac gtgcacctca tcgaaaaccg ctagagagga    3420
cctggaatcc gtcgtccaaa agctgttcgt gccttacacc gagatggaaa ttgaaaacga    3480
acaagtggag aagccccgca tcctttgggc cctgtacttt aacatgcgcg attcctccga    3540
```

```
tatctcgcgg tcctgctata acgacttgcc ttcgaacgtc tacgtctgct ccgggccaga    3600
ctgcggtctt ggcaacgaca atgccgtgaa gcaggcggaa acactgttcc aagagatctg    3660
ccctaacgag gattttttgcc cgccccccccc aaacccccgag gatatcatct tggacggaga    3720
cagcctgcag ccagaagcat ccgagtccag cgccatcccg gaggccaaca gcgaaacctt    3780
caaggagagc actaacctgg gcaacctgga agagtccagc gaatgatcat aggatctctg    3840
cctcgactgt gccttctagt tgccagccat ctgttgtttg cccctccccc gtgccttcct    3900
tgaccctgga aggtgccact cccactgtcc tttcctaata aaatgaggaa attgcatcgc    3960
attgtctgag taggtgtcat tctattctgg ggggtggggt ggggcaggac agcaaggggg    4020
aggattggga agacaatagc aggcatgctg gggactcgag ttctacgtag ataagtagca    4080
tggcgggtta atcattaact acaaggaacc cctagtgatg gagttggcca ctccctctct    4140
gcgcgctcgc tcgctcactg aggccgggcg accaaaggtc gcccgacgcc cgggctttgc    4200
ccgggcggcc tcagtgagcg agcgagcgcg cagccttata aggatatggt gcactctcag    4260
tacaatctgc tctgatgccg catagttaag ccagccccga cacccgccaa cacccgctga    4320
cgcgccctga cgggcttgtc tgctcccggc atccgcttac agacaagctg tgaccgtctc    4380
cgggagctgc atgtgtcaga ggttttcacc gtcatcaccg aaacgcgcga gacgaaaggg    4440
cctcgtgata cgcctatttt tataggttaa tgtcatgata ataatggttt cttagacgtc    4500
aggtggcact tttcggggaa atgtgcgcgg aacccctatt tgtttatttt tctaaataca    4560
ttcaaatatg tatccgctca tgagacaata accctgataa atgcttcaat aatattgaaa    4620
aaggaagagt atgagccata ttcaacggga aacgtcgagg ccgcgattaa attccaacat    4680
ggatgctgat ttatatgggt ataaatgggc tcgcgataat gtcgggcaat caggtgcgac    4740
aatctatcgc ttgtatggga agcccgatgc gccagagttg tttctgaaac atggcaaagg    4800
tagcgttgcc aatgatgtta cagatgagat ggtcagacta aactggctga cggaatttat    4860
gccacttccg accatcaagc attttatccg tactcctgat gatgcatggt tactcaccac    4920
tgcgatcccc ggaaaaacag cgttccaggt attagaagaa tatcctgatt caggtgaaaa    4980
tattgttgat gcgctggcag tgttcctgcg ccggttgcac tcgattcctg tttgtaattg    5040
tccttttaac agcgatcgcg tatttcgcct cgctcaggcg caatcacgaa tgaataacgg    5100
tttggttgat gcgagtgatt ttgatgacga gcgtaatggc tggcctgttg aacaagtctg    5160
gaaagaaatg cataaacttt tgccattctc accggattca gtcgtcactc atggtgattt    5220
ctcacttgat aaccttattt ttgacgaggg gaaattaata ggttgtattg atgttggacg    5280
agtcggaatc gcagaccgat accaggatct tgccatccta tggaactgcc tcggtgagtt    5340
ttctccttca ttacagaaac ggcttttttca aaaatatggt attgataatc ctgatatgaa    5400
taaattgcag tttcatttga tgctcgatga gttttttctaa actgtcagac caagtttact    5460
catatatact ttagattgat ttaaaacttc attttttaatt taaaaggatc taggtgaaga    5520
tcctttttga taatctcatg accaaaatcc cttaacgtga gttttcgttc cactgagcgt    5580
cagacccccgt agaaaagatc aaaggatctt cttgagatcc ttttttttctg cgcgtaatct    5640
gctgcttgca acaaaaaaaa ccaccgctac cagcggtggt ttgtttgccg gatcaagagc    5700
taccaactct ttttccgaag gtaactggct tcagcagagc gcagatacca aatactgttc    5760
ttctagtgta gccgtagtta ggccaccact tcaagaactc tgtagcaccg cctacatacc    5820
tcgctctgct aatcctgtta ccagtggctg ctgccagtgg cgataagtcg tgtcttaccg    5880
ggttggactc aagacgatag ttaccggata aggcgcagcg gtcgggctga acggggggtt    5940
```

```
cgtgcacaca gcccagcttg gagcgaacga cctacaccga actgagatac ctacagcgtg    6000
agctatgaga aagcgccacg cttcccgaag ggagaaaggc ggacaggtat ccggtaagcg    6060
gcagggtcgg aacaggagag cgcacgaggg agcttccagg gggaaacgcc tggtatcttt    6120
atagtcctgt cgggtttcgc cacctctgac ttgagcgtcg attttttgtga tgctcgtcag    6180 gggggcggag cctatggaaa aacgccagca acgcggcctt tttacggttc ctggccttt    6240 gctggccttt tgctcacatg ttctttcctg cgttatcccc tgattctgtg ataaccgta    6300 ttaccgcctt tgagtgagct gataccgctc gccgcagccg aacgaccgag cgcagcgagt    6360
cagtgagcga ggaagcggaa gagcgcccaa tacgcaaacc gcctctcccc gcgcgttggc    6420
cgattcatta atgcagctgg cacgacaggt ttcccgactg gaaagcgggc agtgagcgca    6480
acgcaattaa tgtgagttag ctcactcatt aggcacccca ggctttacac tttatgcttc    6540
cggctcgtat gttgtgtgga attgtgagcg gataacaatt tcacacagga aacagctatg    6600
accatgatta cgccaagctg tcgactctag aggatcccct aataagg              6647
```

<210> SEQ ID NO 27
<211> LENGTH: 11971
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (1)..(130)
<223> OTHER INFORMATION: 5' ITR
<220> FEATURE:
<221> NAME/KEY: misc_feature
<222> LOCATION: (241)..(544)
<223> OTHER INFORMATION: CMV Enhancer
<220> FEATURE:
<221> NAME/KEY: misc_feature
<222> LOCATION: (546)..(823)
<223> OTHER INFORMATION: chicken beta-actin promoter
<220> FEATURE:
<221> NAME/KEY: misc_feature
<222> LOCATION: (824)..(1795)
<223> OTHER INFORMATION: CBA exon 1 and intron
<220> FEATURE:
<221> NAME/KEY: misc_feature
<222> LOCATION: (1859)..(1864)
<223> OTHER INFORMATION: kozak
<220> FEATURE:
<221> NAME/KEY: misc_feature
<222> LOCATION: (1865)..(3826)
<223> OTHER INFORMATION: human codon optimized CHM (REP-1)
<220> FEATURE:
<221> NAME/KEY: misc_feature
<222> LOCATION: (3847)..(4054)
<223> OTHER INFORMATION: bGH poly(A) signal
<220> FEATURE:
<221> NAME/KEY: misc_feature
<222> LOCATION: (4104)..(4233)
<223> OTHER INFORMATION: 3' ITR

<400> SEQUENCE: 27

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gcaagctagc    180
tagttattaa tagtaatcaa ttacggggtc attagttcat agcccatata tggagttccg    240
cgttacataa cttacggtaa atggcccgcc tggctgaccg cccaacgacc cccgcccatt    300
gacgtcaata atgacgtatg ttcccatagt aacgccaata gggactttcc attgacgtca    360
```

```
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattaa    540
catggtcgag gtgagcccca cgttctgctt cactctcccc atctccccc cctcccacc      600
cccaattttg tatttattta ttttttaatt attttgtgca gcgatggggg cggggggggg    660
ggggggcgc gcgccaggcg gggcggggcg gggcgagggg cggggcgggg cgaggcggag     720
aggtgcggcg gcagccaatc agagcggcgc gctccgaaag tttccttttta tggcgaggcg   780
gcggcggcgg cggccctata aaaagcgaag cgcgcggcgg gcggggagtc gctgcgacgc    840
tgccttcgcc ccgtgccccg ctccgccgcc gcctcgcgcc gcccgccccg gctctgactg    900
accgcgttac tcccacaggt gagcgggcgg gacggcccct tcctccgggg ctgtaattag    960
cgcttggttt aatgacggct tgtttctttt ctgtggctgc gtgaaagcct tgagggggctc  1020
cgggagggcc ctttgtgcgg ggggagcggc tcgggggggtg cgtgcgtgtg tgtgtgcgtg  1080
gggagcgccg cgtgcggctc cgcgctgccc ggcggctgtg agcgctgcgg gcgcggcgcg   1140
gggctttgtg cgctccgcag tgtgcgcgag gggagcgcgg ccggggggcgg tgccccgcgg  1200
tgcgggggggg gctgcgaggg gaacaaaggc tgcgtgcggg gtgtgtgcgt gggggggtga  1260
gcagggggtg tgggcgcgtc ggtcgggctg caaccccccc tgcaccccc tccccgagtt    1320
gctgagcacg gcccggcttc gggtgcgggg ctccgtacgg ggcgtggcgc ggggctcgcc   1380
gtgccgggcg gggggtggcg gcaggtgggg gtgccgggcg gggcggggcc gcctcgggcc   1440
ggggagggct cggggggaggg gcgcggcggc ccccggagcg ccggcggctg tcgaggcgcg   1500
gcgagccgca gccattgcct tttatggtaa tcgtgcgaga gggcgcaggg acttcctttg   1560
tcccaaatct gtgcggagcc gaaatctggg aggcgccgcc gcaccccctc tagcgggcgc   1620
ggggcgaagc ggtgcggcgc cggcaggaag gaaatgggcg gggagggcct tcgtgcgtcg   1680
ccgcgccgcc gtcccttct ccctctccag cctcggggct gtccgcgggg ggacggctgc   1740
cttcgggggg gacggggcag ggcggggttc ggcttctggc gtgtgaccgg cggctctaga   1800
caattgtact aaccttcttc tctttcctct cctgacaggt tggtgtacac tagcggccgc   1860
caccatggct gataccctgc cctctgaatt cgacgtgatt gtgattggaa ccggactccc   1920
tgaatcgatc atcgccgcgg cctgttcccg gtccggtcgg cgcgtgctgc acgtcgattc   1980
gagaagctac tacggaggga attgggcctc attctccttc tccggactgc tctcctggct   2040
gaaggagtat caggagaact ccgacattgt ctccgactca cctgtgtggc aggaccagat   2100
cctggaaaac gaggaagcaa tagccctgag ccggaaggac aagaccatcc agcacgtgga   2160
ggtgttctgt tatgcctccc aagacctcca tgaggacgtg gaagaggctg gagcgttgca   2220
gaagaatcat gccctcgtga cctccgctaa ctccaccgag gcagccgaca gcgccttcct   2280
gccgaccgag gatgaatccc tgtcaactat gtcgtgcgaa atgctgaccg aacagactcc   2340
gagctccgac cccgaaaacg ccctggaagt gaacggagcg gaagtgaccg gcgaaaagga   2400
gaaccattgc gacgacaaga cttgtgtccc atccacttcc gcggaggaca tgtccgagaa   2460
tgtgcctatc gccgaggaca ccaccgaaca gcccaagaag aacagaatca cgtacagcca   2520
gatcatcaag gagggggcgga ggtttaacat cgatctggtg tcgaagctgc tgtacagccg   2580
cggtctgctg atcgatctgc tcattaagtc gaacgtgtcg agatacgccg agttcaagaa   2640
catcacaagg attctcgcct tccgggaagg aagagtggaa caagtgccgt gctcccgggc   2700
cgacgtgttc aactcaaagc aacttaccat ggtggaaaag cgcatgctga tgaaattcct   2760
```

```
gaccttctgc atggagtacg aaaagtaccc tgatgagtac aagggttacg aagaaattac   2820
tttctacgag tacctcaaga cccagaagct gaccccgaat ctgcagtaca ttgtgatgca   2880
ctcaatcgca atgacctccg aaaccgcctc ctcgaccatc gacgggctca aggccaccaa   2940
gaacttcctg cactgtttgg ggcgctacgg caacactccg ttcctcttcc cgctgtacgg   3000
ccagggagag ctgcctcagt gtttctgccg gatgtgcgcc gtgttcggcg aatctactg    3060 tctccgccac tcggtccagt gcctggtggt ggacaaggaa tccaggaagt gcaaagccat   3120
tattgaccag ttcggacaac ggatcatttc cgagcacttt cttgtggagg actcatactt   3180 cccgagaac atgtgctctc gggtccagta tcgacagatt tccagggcgg tgctcattac    3240
tgaccggagc gtcctcaaga ccgatagcga ccagcagatc tccatcctga ccgtgccggc   3300
ggaagaaccc ggcacttttg ccgtgcgcgt gatcgagctt tgctcatcca ccatgacttg   3360
catgaaaggc acttacctgg tgcacctgac gtgcacctca tcgaaaaccg ctagagagga   3420
cctggaatcc gtcgtccaaa agctgttcgt gccttacacc gagatggaaa ttgaaaacga   3480
acaagtggag aagccccgca tcctttgggc cctgtacttt aacatgcgcg attcctccga   3540
tatctcgcgg tcctgctata cgacttgcc ttcgaacgtc tacgtctgct ccgggccaga    3600
ctgcggtctt ggcaacgaca atgccgtgaa gcaggcggaa acactgttcc aagagatctg   3660
ccctaacgag gattttgcc cgccccccc aaaccccgag gatatcatct tggacggaga    3720
cagcctgcag ccagaagcat ccgagtccag cgccatcccg gaggccaaca gcgaaacctt   3780
caaggagagc actaacctgg gcaacctgga agagtccagc gaatgatcat aggatctctg   3840
cctcgactgt gccttctagt tgccagccat ctgttgtttg cccctccccc gtgccttcct   3900
tgaccctgga aggtgccact cccactgtcc tttcctaata aaatgaggaa attgcatcgc   3960
attgtctgag taggtgtcat tctattctgg ggggtggggt ggggcaggac agcaagggg    4020 aggattggga agacaatagc aggcatgctg gggactcgag ttctacgtag ataagtagca   4080
tggcgggtta atcattaact acaaggaacc cctagtgatg gagttggcca ctccctctct   4140
gcgcgctcgc tcgctcactg aggccgggcg accaaaggtc gcccgacgcc cgggctttgc   4200
ccgggcggcc tcagtgagcg agcgagcgcg cagccttaat taacctaata aggaaaatga   4260
agggaagttc ctatactttc tagagaatag gaacttctat agggagtcga taagggcga    4320 cacaaaaggt attctaaatg cataataaat actgataaca tcttatagtt tgtattatat   4380
tttgtattat cgttgacatg tataatttg atatcaaaaa ctgattttcc ctttattatt    4440
ttcgagattt attttcttaa ttctctttaa caaactagaa atattgtata tacaaaaaat   4500
cataaataat agatgaatag tttaattata ggtgttcatc aatcgaaaaa gcaacgtatc   4560
ttatttaaag tgcgttgctt ttttctcatt tataaggtta aataattctc atatatcaag   4620
caaagtgaca ggcgccctta aatattctga caaatgctct ttccctaaac tccccccata   4680 aaaaacccg ccgaagcggg tttttacgtt atttgcggat taacgattac tcgttatcag    4740
aaccgcccag gatgcctggc agttccctac tctcgccgct gcgctcggtc gttcggctgc   4800
gggacctcag cgctagcgga gtgtatactg gcttactatg ttggcactga tgagggtgtc   4860
agtgaagtgc ttcatgtggc aggagaaaaa aggctgcacc ggtgcgtcag cagaatatgt   4920
gatacaggat atattccgct tcctcgctca ctgactcgct acgctcggtc gttcgactgc   4980
ggcgagcgga atggcttac gaacggggcg gagatttcct ggaagatgcc aggaagatac    5040
ttaacaggga agtgagaggg ccgcggcaaa gccgtttttc cataggctcc gccccctga    5100
```

```
caagcatcac gaaatctgac gctcaaatca gtggtggcga aacccgacag gactataaag   5160
ataccaggcg tttccccctg gcggctccct cgtgcgctct cctgttcctg cctttcggtt   5220
taccggtgtc attccgctgt tatggccgcg tttgtctcat tccacgcctg acactcagtt   5280
ccgggtaggc agttcgctcc aagctggact gtatgcacga accccccgtt cagtccgacc   5340
gctgcgcctt atccggtaac tatcgtcttg agtccaaccc ggaaagacat gcaaaagcac   5400
cactggcagc agccactggt aattgattta gaggagttag tcttgaagtc atgcgccggt   5460
taaggctaaa ctgaaaggac aagttttggt gactgcgctc ctccaagcca gttacctcgg   5520
ttcaaagagt tggtagctca gagaaccttc gaaaaccgc cctgcaaggc ggttttttcg   5580
ttttcagagc aagagattac gcgcagacca aaacgatctc aagaagatca tcttattaag   5640 ctcctttttta tttggggag agggaagtca tgaaaaaact aacctttgaa attcgatctc   5700
cagcacatca gcaaaacgct attcacgcag tacagcaaat ccttccagac ccaaccaaac   5760
caatcgtagt aaccattcag gaacgcaacc gcagcttaga ccaaaacagg aagctatggg   5820
cctgcttagg tgacgtctct cgtcaggttg aatggcatgg tcgctggctg gatgcagaaa   5880
gctggaagtg tgtgtttacc gcagcattaa agcagcagga tgttgttcct aaccttgccg   5940
ggaatggctt tgtggtaata ggccagtcaa ccagcaggat gcgtgtaggc gaatttgcgg   6000
agctattaga gcttatacag gcattcggta cagagcgtgg cgttaagtgg tcagacgaag   6060
cgagactggc tctggagtgg aaagcgagat ggggagacag ggctgcatga taaatgtcgt   6120
tagtttctcc ggtggcagga cgtcagcata tttgctctgg ctaatggagc aaaagcgacg   6180
ggcaggtaaa gacgtgcatt acgttttcat ggatacaggt tgtgaacatc caatgacata   6240
tcggtttgtc agggaagttg tgaagttctg ggatataccg ctcaccgtat tgcaggttga   6300
tatcaacccg gagcttggac agccaaatgg ttatacggta tgggaaccaa aggatattca   6360
gacgcgaatg cctgttctga agccatttat cgatatggta agaaatatg gcactccata   6420 cgtcggcggc gcgttctgca ctgacagatt aaaactcgtt cccttcacca atactgtga   6480 tgaccatttc gggcgaggga attacaccac gtggattggc atcagagctg atgaaccgaa   6540
gcggctaaag ccaaagcctg gaatcagata tcttgctgaa ctgtcagact ttgagaagga   6600
agatatcctc gcatggtgga agcaacaacc attcgatttg caaataccgg aacatctcgg   6660
taactgcata ttctgcatta aaaatcaac gcaaaaatc ggacttgcct gcaaagatga   6720
ggagggattg cagcgtgttt ttaatgaggt catcacggga tcccatgtgc gtgacggaca   6780 tcggaaacg ccaaggaga ttatgtaccg aggaagaatg tcgctggacg gtatcgcgaa   6840
aatgtattca gaaaatgatt atcaagccct gtatcaggac atggtacgag ctaaaagatt   6900
cgataccggc tcttgttctg agtcatgcga aatatttgga gggcagcttg atttcgactt   6960
cgggagggaa gctgcatgat gcgatgttat cggtgcggtg aatgcaaaga agataaccgc   7020
ttccgaccaa atcaacctta ctggaatcga tggtgtctcc ggtgtgaaag aacaccaaca   7080
ggggtgttac cactaccgca ggaaaaggag gacgtgtggc gagacagcga cgaagtatca   7140
ccgacataat ctgcgaaaac tgcaaatacc ttccaacgaa acgcaccaga aataaaccca   7200
agccaatccc aaaagaatct gacgtaaaaa ccttcaacta cacggctcac ctgtgggata   7260
tccggtggct aagacgtcgt gcgaggaaaa caaggtgatt gaccaaaatc gaagttacga   7320
acaagaaagc gtcgagcgag ctttaacgtg cgctaactgc ggtcagaagc tgcatgtgct   7380
ggaagttcac gtgtgtgagc actgctgcgc agaactgatg agcgatccga atagctcgat   7440
gcacgaggaa gaagatgatg gctaaaccag cgcgaagacg atgtaaaaac gatgaatgcc   7500
```

```
gggaatggtt tcaccctgca ttcgctaatc agtggtggtg ctctccagag tgtggaacca   7560
agatagcact cgaacgacga agtaaagaac gcgaaaaagc ggaaaaagca gcagagaaga   7620
aacgacgacg agaggagcag aaacagaaag ataaacttaa gattcgaaaa ctcgccttaa   7680
agccccgcag ttactggatt aaacaagccc aacaagccgt aaacgccttc atcagagaaa   7740
gagaccgcga cttaccatgt atctcgtgcg aacgctcac gtctgctcag tgggatgccg    7800
gacattaccg gacaactgct gcggcacctc aactccgatt taatgaacgc aatattcaca   7860
agcaatgcgt ggtgtgcaac cagcacaaaa gcggaaatct cgttccgtat cgcgtcgaac   7920
tgattagccg catcgggcag gaagcagtag acgaaatcga atcaaaccat aaccgccatc   7980
gctggactat cgaagagtgc aaggcgatca aggcagagta ccaacagaaa ctcaaagacc   8040
tgcgaaatag cagaagtgag gccgcatgac gttctcagta aaaaccattc cagacatgct   8100
cgttgaagca tacggaaatc agacagaagt agcacgcaga ctgaaatgta gtcgcggtac   8160
ggtcagaaaa tacgttgatg ataaagacgg gaaaatgcac gccatcgtca acgacgttct   8220
catggttcat cgcggatgga gtgaaagaga tgcgctatta cgaaaaaatt gatggcagca   8280
aataccgaaa tatttgggta gttggcgatc tgcacggatg ctacacgaac ctgatgaaca   8340
aactggatac gattggattc gacaacaaaa aagacctgct tatctcggtg ggcgatttgg   8400
ttgatcgtgg tgcagagaac gttgaatgcc tggaattaat cacattcccc tggttcagag   8460
ctgtacgtgg aaaccatgag caaatgatga ttgatggctt atcagagcgt ggaaacgtta   8520
atcactggct gcttaatggc ggtggctggt tctttaatct cgattacgac aaagaaattc   8580
tggctaaagc tcttgcccat aaagcagatg aacttccgtt aatcatcgaa ctggtgagca   8640
aagataaaaa atatgttatc tgccacgccg attatccctt tgacgaatac gagtttggaa   8700
agccagttga tcatcagcag gtaatctgga accgcgaacg aatcagcaac tcacaaaacg   8760
ggatcgtgaa agaaatcaaa ggcgcggaca cgttcatctt tggtcatacg ccagcagtga   8820
aaccactcaa gtttgccaac caaatgtata tcgataccgg cgcagtgttc tgcggaaacc   8880
taacattgat tcaggtacag ggagaaggcg catgagactc gaaagcgtag ctaaatttca   8940
ttcgccaaaa agcccgatga tgagcgactc accacgggcc acggcttctg actctctttc   9000
cggtactgat gtgatggctg ctatggggat ggcgcaatca caagccggat tcggtatggc   9060
tgcattctgc ggtaagcacg aactcagcca gaacgacaaa caaaaggcta tcaactatct   9120
gatgcaattt gcacacaagg tatcgggaa ataccgtggt gtggcaaagc ttgaaggaaa    9180
tactaaggca aaggtactgc aagtgctcgc aacattcgct tatgcggatt attgccgtag   9240
tgccgcgacg ccgggggcaa gatgcagaga ttgccatggt acaggccgtg cggttgatat   9300
tgccaaaaca gagctgtggg ggagagttgt cgagaaagag tgcggaagat gcaaaggcgt   9360
cggctattca aggatgccag caagcgcagc atatcgcgct gtgacgatgc taatcccaaa   9420
ccttacccaa cccacctggt cacgcactgt taagccgctg tatgacgctc tggtggtgca   9480
atgccacaaa gaagagtcaa tcgcagacaa cattttgaat gcggtcacac gttagcagca   9540
tgattgccac ggatggcaac atattaacgg catgatattg acttattgaa taaaattggg   9600
taaatttgac tcaacgatgg gttaattcgc tcgttgtggt agtgagatga aaagaggcgg   9660
cgcttactac cgattccgcc tagttggtca cttcgacgta tcgtctggaa ctccaaccat   9720
cgcaggcaga gaggtctgca aaatgcaatc ccgaaacagt tcgcaggtaa tagttagagc   9780
ctgcataacg gtttcgggat ttttatatc tgcacaacag gtaagagcat tgagtcgata    9840
```

```
atcgtgaaga gtcggcgagc ctggttagcc agtgctcttt ccgttgtgct gaattaagcg    9900
aataccggaa gcagaaccgg atcaccaaat gcgtacaggc gtcatcgccg cccagcaaca    9960
gcacaaccca aactgagccg tagccactgt ctgtcctgaa ttcattagta atagttacgc   10020
tgcggccttt tacacatgac cttcgtgaaa gcgggtggca ggaggtcgcg ctaacaacct   10080
cctgccgttt tgcccgtgca tatcggtcac gaacaaatct gattactaaa cacagtagcc   10140
tggatttgtt ctatcagtaa tcgacccttat tcctaattaa atagagcaaa tccccttatt   10200
gggggtaaga catgaagatg ccagaaaaac atgacctgtt ggccgccatt ctcgcggcaa   10260
aggaacaagg catcggggca atccttgcgt ttgcaatggc gtaccttcgc ggcagatata   10320
atggcggtgc gtttacaaaa acagtaatcg acgcaacgat gtgcgccatt atcgcctggt   10380
tcattcgtga ccttctcgac ttcgccggac taagtagcaa tctcgcttat ataacgagcg   10440
tgtttatcgg ctacatcggt actgactcga ttggttcgct tatcaaacgc ttcgctgcta   10500
aaaaagccgg agtagaagat ggtagaaatc aataatcaac gtaaggcgtt cctcgatatg   10560
ctggcgtggt cggagggaac tgataacgga cgtcagaaaa ccagaaatca tggttatgac   10620
gtcattgtag gcggagagct atttactgat tactccgatc accctcgcaa acttgtcacg   10680
ctaaacccaa aactcaaatc aacaggcgca gcttttagaa aaactcatcg agcatcaaat   10740
gaaactgcaa tttattcata tcaggattat caataccata tttttgaaaa agccgtttct   10800
gtaatgaagg agaaaactca ccgaggcagt tccataggat ggcaagatcc tggtatcggt   10860
ctgcgattcc gactcgtcca acatcaatac aacctattaa tttcccctcg tcaaaaataa   10920
ggttatcaag tgagaaatca ccatgagtga cgactgaatc cggtgagaat ggcaaaagtt   10980
tatgcatttc tttccagact tgttcaacag gccagccatt acgctcgtca tcaaaatcac   11040
tcgcatcaac caaaccgtta ttcattcgtg attgcgcctg agcgaggcga atacgcgat   11100
cgctgttaaa aggacaatta caaacaggaa tcgagtgcaa ccggcgcagg aacactgcca   11160
gcgcatcaac aatatttttca cctgaatcag gatattcttc taatacctgg aacgctgttt   11220
ttccggggat cgcagtggtg agtaaccatg catcatcagg agtacggata aaatgcttga   11280
tggtcggaag tggcataaat tccgtcagcc agtttagtct gaccatctca tctgtaacat   11340
cattggcaac gctacctttg ccatgtttca gaaacaactc tggcgcatcg gcttcccat   11400
acaagcgata gattgtcgca cctgattgcc cgacattatc gcgagcccat ttatacccat   11460
ataaatcagc atccatgttg gaatttaatc gcggcctcga cgtttcccgt tgaatatggc   11520
tcatattctt cctttttcaa tattattgaa gcatttatca gggttattgt ctcatgagcg   11580
gatacatatt tgaatgtatt tagaaaaata aacaaatagg ggtcagtgtt acaaccaatt   11640
aaccaattct gaacattatc gcgagcccat ttatacctga atatggctca taacacccct   11700
tgtttgcctg gcggcagtag cgcggtggtc ccacctgacc ccatgccgaa ctcagaagtg   11760
aaacgccgta gcgccgatgg tagtgtgggg actccccatg cgagagtagg gaactgccag   11820
gcatcaaata aaacgaaagg ctcagtcgaa agactgggcc tttcgcccgg ctaattagg   11880
gggtgtcgcc cttattcgac tctataggga agttcctatt ctctagaaag tataggaact   11940
tctgaagggg ggtcgatcga cttaattaag g                                 11971
```

<210> SEQ ID NO 28
<211> LENGTH: 6900
<212> TYPE: DNA
<213> ORGANISM: Artificial Sequence
<220> FEATURE:
<223> OTHER INFORMATION: constructed sequence

```
<220> FEATURE:
<221> NAME/KEY: misc_feature
<222> LOCATION: (1)..(130)
<223> OTHER INFORMATION: 5' ITR
<220> FEATURE:
<221> NAME/KEY: misc_feature
<222> LOCATION: (241)..(544)
<223> OTHER INFORMATION: CMV enhancer
<220> FEATURE:
<221> NAME/KEY: misc_feature
<222> LOCATION: (546)..(823)
<223> OTHER INFORMATION: chicken beta actin promoter
<220> FEATURE:
<221> NAME/KEY: misc_feature
<222> LOCATION: (824)..(1795)
<223> OTHER INFORMATION: CBA exon 1 and intron
<220> FEATURE:
<221> NAME/KEY: misc_feature
<222> LOCATION: (1859)..(1864)
<223> OTHER INFORMATION: kozak
<220> FEATURE:
<221> NAME/KEY: misc_feature
<222> LOCATION: (1865)..(3826)
<223> OTHER INFORMATION: human codon optimized CHM (REP-1)
<220> FEATURE:
<221> NAME/KEY: misc_feature
<222> LOCATION: (3847)..(4054)
<223> OTHER INFORMATION: bGH poly(A) signal
<220> FEATURE:
<221> NAME/KEY: misc_feature
<222> LOCATION: (4104)..(4233)
<223> OTHER INFORMATION: 3' ITR

<400> SEQUENCE: 28
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
tagttattaa tagtaatcaa ttacggggtc attagttcat agcccatata tggagttccg     240
cgttacataa cttacggtaa atggcccgcc tggctgaccg cccaacgacc cccgcccatt     300
gacgtcaata atgacgtatg ttcccatagt aacgccaata gggactttcc attgacgtca     360
atgggtggag tatttacggt aaactgccca cttggcagta catcaagtgt atcatatgcc     420
aagtacgccc cctattgacg tcaatgacgg taaatggccc gcctggcatt atgcccagta     480
catgacctta tgggactttc ctacttggca gtacatctac gtattagtca tcgctattaa     540
catggtcgag gtgagcccca cgttctgctt cactctcccc atctcccccc cctccccacc     600
cccaattttg tatttattta ttttttaatt attttgtgca gcgatggggg cggggggggg     660 ggggggcgc gcgccaggcg gggcggggcg gggcgagggg cggggcgggg cgaggcggag     720
aggtgcggcg gcagccaatc agagcggcgc gctccgaaag tttccttttt atggcgaggcg     780 gcggcggcg cggccctata aaagcgaag cgcgcggcgg gcgggagtc gctgcgacgc     840 tgccttcgcc ccgtgccccg ctccgccgcc gcctcgcgcc gcccgccccg gctctgactg     900
accgcgttac tcccacaggt gagcgggcgg gacggccctt ctcctccggg ctgtaattag     960
cgcttggttt aatgacggct tgtttctttt ctgtggctgc gtgaaagcct tgaggggctc    1020
cgggagggcc ctttgtgcgg ggggagcggc tcggggggtg cgtgcgtgtg tgtgtgcgtg    1080
gggagcgccg cgtgcggctc cgcgctgccc ggcggctgtg agcgctgcgg gcgcggcgcg    1140
gggctttgtg cgctccgcag tgtgcgcgag gggagcgcgg ccggggcggg tgccccgcgg    1200 tgcgggggg gctgcgaggg gaacaaaggc tgcgtgcggg gtgtgtgcgt gggggggtga    1260 gcaggggtg tgggcgcgtc ggtcgggctg caaccccccc tgcacccccc tccccgagtt    1320
```

```
gctgagcacg gcccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggagggg gcgcggcggc ccccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcacccctc tagcgggcgc     1620 ggggcgaagc ggtgcggcgc cggcaggaag gaaatgggcg gggagggcct tcgtgcgtcg    1680
ccgcgccgcc gtccccttct ccctctccag cctcggggct gtccgcgggg ggacggctgc    1740 cttcggggggg gacggggcag ggcggggttc ggcttctggc gtgtgaccgg cggctctaga   1800
caattgtact aaccttcttc tctttcctct cctgacaggt tggtgtacac tagcggccgc    1860
caccatggct gataccctgc cctctgaatt cgacgtgatt gtgattggaa ccggactccc    1920
tgaatcgatc atcgccgcgg cctgttcccg gtccggtcgg cgcgtgctgc acgtcgattc    1980
gagaagctac tacggaggga attgggcctc attctccttc tccggactgc tctcctggct    2040
gaaggagtat caggagaact ccgacattgt ctccgactca cctgtgtggc aggaccagat    2100
cctggaaaac gaggaagcaa tagccctgag ccggaaggac aagaccatcc agcacgtgga    2160
ggtgttctgt tatgcctccc aagacctcca tgaggacgtg gaagaggctg gagcgttgca    2220
gaagaatcat gccctcgtga cctccgctaa ctccaccgag gcagccgaca gcgccttcct    2280
gccgaccgag gatgaatccc tgtcaactat gtcgtgcgaa atgctgaccg aacagactcc    2340
gagctccgac cccgaaaacg ccctggaagt gaacggagcg gaagtgaccg gcgaaaagga    2400
gaaccattgc gacgacaaga cttgtgtccc atccacttcc gcggaggaca tgtccgagaa    2460
tgtgcctatc gccgaggaca ccaccgaaca gcccaagaag aacagaatca cgtacagcca    2520
gatcatcaag gaggggcgga ggtttaacat cgatctggtg tcgaagctgc tgtacagccg    2580
cggtctgctg atcgatctgc tcattaagtc gaacgtgtcg agatacgccg agttcaagaa    2640
catcacaagg attctcgcct tccgggaagg aagagtggaa caagtgccgt gctcccgggc    2700
cgacgtgttc aactcaaagc aacttaccat ggtggaaaag cgcatgctga tgaaattcct    2760
gaccttctgc atggagtacg aaaagtaccc tgatgagtac aagggttacg aagaaattac    2820
tttctacgag tacctcaaga cccagaagct gaccccgaat ctgcagtaca ttgtgatgca    2880
ctcaatcgca atgaccctcg aaaccgcctc ctcgaccatc gacgggctca aggccaccaa    2940
gaacttcctg cactgtttgg ggcgctacgg caacactccg ttcctcttcc cgctgtacgg    3000
ccagggagag ctgcctcagt gtttctgccg gatgtgcgcc gtgttcggcg gaatctactg    3060
tctccgccac tcggtccagt gcctggtggt ggacaaggaa tccaggaagt gcaaagccat    3120
tattgaccag ttcggacaac ggatcatttc cgagcacttt cttgtggagg actcatactt    3180
cccggagaac atgtgctctc gggtccagta tcgacagatt tccagggcgg tgctcattac    3240
tgaccggagc gtcctcaaga ccgatagcga ccagcagatc tccatcctga ccgtgccggc    3300
ggaagaaccc ggcactttttg ccgtgcgcgt gatcgagctt tgctcatcca ccatgacttg    3360
catgaaaggc acttacctgg tgcacctgac gtgcacctca tcgaaaaccg ctagagagga    3420
cctggaatcc gtcgtccaaa agctgttcgt gccttacacc gagatggaaa ttgaaaacga    3480
acaagtggag aagccccgca tcctttgggc cctgtacttt aacatgcgcg attcctccga    3540
tatctcgcgg tcctgctata acgacttgcc ttcgaacgtc tacgtctgct ccgggccaga    3600
ctgcggtctt ggcaacgaca atgccgtgaa gcaggcggaa acactgttcc aagagatctg    3660
ccctaacgag gattttttgcc cgcccccccc aaaccccgag gatatcatct ggacggaga   3720
```

-continued

```
cagcctgcag ccagaagcat ccgagtccag cgccatcccg gaggccaaca gcgaaacctt    3780
caaggagagc actaacctgg gcaacctgga agagtccagc gaatgatcat aggatctctg    3840
cctcgactgt gccttctagt tgccagccat ctgttgtttg cccctccccc gtgccttcct    3900
tgaccctgga aggtgccact cccactgtcc tttcctaata aaatgaggaa attgcatcgc    3960
attgtctgag taggtgtcat tctattctgg ggggtggggt ggggcaggac agcaaggggg    4020
aggattggga agacaatagc aggcatgctg gggactcgag ttctacgtag ataagtagca    4080
tggcgggtta atcattaact acaaggaacc cctagtgatg gagttggcca ctccctctct    4140
gcgcgctcgc tcgctcactg aggccgggcg accaaaggtc gcccgacgcc cgggctttgc    4200
ccgggcggcc tcagtgagcg agcgagcgcg cagccttaat taacctaata aggaaaatga    4260
agggaagttc ctatactttc tagagaatag gaacttctat agggagtcga ataagggcga    4320
cacaaaaggt attctaaatg cataataaat actgataaca tcttatagtt tgtattatat    4380
tttgtattat cgttgacatg tataattttg atatcaaaaa ctgattttcc ctttattatt    4440
ttcgagattt attttcttaa ttctctttaa caaactagaa atattgtata tacaaaaaat    4500
cataaataat agatgaatag tttaattata ggtgttcatc aatcgaaaaa gcaacgtatc    4560
ttatttaaag tgcgttgctt ttttctcatt tataaggtta aataattctc atatatcaag    4620
caaagtgaca gcgcccctta aatattctga caaatgctct ttccctaaac tccccccata    4680
aaaaaacccg ccgaagcggg ttttttacgtt atttgcggat taacgattac tcgttatcag    4740
aaccgcccag gatgcctggc agttccctac tctcgccgct cgctcggtc gttcggctgc     4800 gggacctcag cgctagcgga gtgtatactg gcttactatg ttggcactga tgagggtgtc    4860
agtgaagtgc ttcatgtggc aggagaaaaa aggctgcacc ggtgcgtcag cagaatatgt    4920
gatacaggat atattccgct tcctcgctca ctgactcgct acgctcggtc gttcgactgc    4980
ggcgagcgga aatggcttac gaacggggcg gagatttcct ggaagatgcc aggaagatac    5040
ttaacaggga agtgagaggg ccgcggcaaa gccgttttc cataggctcc gcccccctga     5100
caagcatcac gaaatctgac gctcaaatca gtggtggcga aacccgacag gactataaag    5160
ataccaggcg tttccccctg gcggctccct cgtgcgctct cctgttcctg cctttcggtt    5220
taccggtgtc attccgctgt tatggccgcg tttgtctcat tccacgcctg acactcagtt    5280
ccgggtaggc agttcgctcc aagctggact gtatgcacga accccccgtt cagtccgacc    5340
gctgcgcctt atccggtaac tatcgtcttg agtccaaccc ggaaagacat gcaaaagcac    5400
cactggcagc agccactggt aattgattta gaggagttag tcttgaagtc atgcgccggt    5460
taaggctaaa ctgaaaggac aagttttggt gactgcgctc ctccaagcca gttacctcgg    5520
ttcaaagagt tggtagctca gagaaccttc gaaaaaccgc cctgcaaggc ggttttttcg    5580
ttttcagagc aagagattac gcgcagacca aaacgatctc aagaagatca tcttattaag    5640
cttttagaaa aactcatcga gcatcaaatg aaactgcaat ttattcatat caggattatc    5700
aataccatat ttttgaaaaa gccgtttctg taatgaagga gaaaactcac cgaggcagtt    5760
ccataggatg gcaagatcct ggtatcggtc tgcgattccg actcgtccaa catcaataca    5820
acctattaat ttcccctcgt caaaaataag gttatcaagt gagaaatcac catgagtgac    5880
gactgaatcc ggtgagaatg gcaaaagttt atgcatttct ttccagactt gttcaacagg    5940
ccagccatta cgctcgtcat caaaatcact cgcatcaacc aaaccgttat tcattcgtga    6000
ttgcgcctga gcgaggcgaa atacgcgatc gctgttaaaa ggacaattac aaacaggaat    6060
```

| cgagtgcaac | cggcgcagga | acactgccag | cgcatcaaca | atattttcac | ctgaatcagg | 6120 |
| atattcttct | aataccrgga | acgctgtttt | tccggggatc | gcagtggtga | gtaaccatgc | 6180 |
| atcatcagga | gtacggataa | aatgcttgat | ggtcggaagt | ggcataaatt | ccgtcagcca | 6240 |
| gtttagtctg | accatctcat | ctgtaacatc | attggcaacg | ctacctttgc | catgtttcag | 6300 |
| aaacaactct | ggcgcatcgg | gcttcccata | caagcgatag | attgtcgcac | ctgattgccc | 6360 |
| gacattatcg | cgagcccatt | tatacccata | taaatcagca | tccatgttgg | aatttaatcg | 6420 |
| cggcctcgac | gtttcccgtt | gaatatggct | catattcttc | cttttcaat | attattgaag | 6480 |
| catttatcag | ggttattgtc | tcatgagcgg | atacatattt | gaatgtattt | agaaaaataa | 6540 |
| acaaataggg | gtcagtgtta | caaccaatta | accaattctg | aacattatcg | cgagcccatt | 6600 |
| tatacctgaa | tatggctcat | aacaccccctt | gtttgcctgg | cggcagtagc | gcggtggtcc | 6660 |
| cacctgaccc | catgccgaac | tcagaagtga | acgccgtag | cgccgatggt | agtgtgggga | 6720 |
| ctccccatgc | gagagtaggg | aactgccagg | catcaaataa | aacgaaaggc | tcagtcgaaa | 6780 |
| gactgggcct | ttcgcccggg | ctaattaggg | ggtgtcgccc | ttattcgact | ctataggaa | 6840 |
| gttcctattc | tctagaaagt | ataggaactt | ctgaaggggg | gtcgatcgac | ttaattaagg | 6900 |

<210> SEQ ID NO 29
<211> LENGTH: 12074
<212> TYPE: DNA
<213> ORGANISM: Artificial Sequence
<220> FEATURE:
<223> OTHER INFORMATION: constructed sequence

<400> SEQUENCE: 29

| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctacgta | gcaagctagc | 180 |
| tagttattaa | tagtaatcaa | ttacggggtc | attagttcat | agcccatata | tggagttccg | 240 |
| cgttacataa | cttacggtaa | atggcccgcc | tggctgaccg | cccaacgacc | cccgcccatt | 300 |
| gacgtcaata | atgacgtatg | ttcccatagt | aacgccaata | gggactttcc | attgacgtca | 360 |
| atgggtggag | tatttacggt | aaactgccca | cttggcagta | catcaagtgt | atcatatgcc | 420 |
| aagtacgccc | cctattgacg | tcaatgacgg | taaatggccc | gcctggcatt | atgcccagta | 480 |
| catgacctta | tgggactttc | ctacttggca | gtacatctac | gtattagtca | tcgctattaa | 540 |
| catggtcgag | gtgagcccca | cgttctgctt | cactctcccc | atctcccccc | cctccccacc | 600 |
| cccaattttg | tatttattta | ttttttaatt | attttgtgca | gcgatggggg | cggggggggg | 660 |
| gggggggcgc | gcgccaggcg | gggcggggcg | gggcgagggg | cggggcgggg | cgaggcggag | 720 |
| aggtgcggcg | gcagccaatc | agagcggcgc | gctccgaaag | tttccttta | tggcgaggcg | 780 |
| gcggcggcgg | cggcccctata | aaaagcgaag | cgcgcggcgg | gcgggagtc | gctgcgacgc | 840 |
| tgccttcgcc | ccgtgcccg | ctccgccgcc | gcctcgcgcc | gcccgcccg | gctctgactg | 900 |
| accgcgttac | tcccacaggt | gagcgggcgg | gacggccctt | ctcctccggg | ctgtaattag | 960 |
| cgcttggttt | aatgacggct | tgtttctttt | ctgtggctgc | gtgaaagcct | tgaggggctc | 1020 |
| cgggagggcc | ctttgtgcgg | gggagcggc | tcggggggtg | cgtgcgtgtg | tgtgtgcgtg | 1080 |
| gggagcgccg | cgtgcggctc | cgcgctgccc | ggcggctgtg | agcgctgcgg | gcgcggcgcg | 1140 |
| gggctttgtg | cgctccgcag | tgtgcgcgag | gggagcgcgg | ccggggcgg | tgccccgcgg | 1200 |
| tgcgggggg | gctgcgaggg | gaacaaaggc | tgcgtgcggg | gtgtgtgcgt | gggggggtga | 1260 |

```
gcaggggggtg tgggcgcgtc ggtcgggctg caaccccccc tgcaccccccc tcccgagtt    1320 gctgagcacg gcccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggggaggg gcgcggcggc ccccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcaccccctc tagcgggcgc    1620
ggggcgaagc ggtgcggcgc cggcaggaag gaaatgggcg gggagggcct tcgtgcgtcg    1680
ccgcgccgcc gtccccttct ccctctccag cctcggggct gtccgcgggg ggacggctgc    1740
cttcgggggg gacggggcag ggcggggttc ggcttctggc gtgtgaccgg cggctctaga    1800
caattgtact aaccttcttc tctttcctct cctgacaggt tggtgtacac tagcggccgc    1860
atggcggata ctctcccttc ggagtttgat gtgatcgtaa tagggacggg tttgcctgaa    1920
tccatcattg cagctgcatg ttcaagaagt ggccggagag ttctgcatgt tgattcaaga    1980
agctactatg gaggaaactg gccagttttt agcttttcag gactattgtc ctggctaaag    2040
gaataccagg aaaacagtga cattgtaagt gacagtccag tgtggcaaga ccagatcctt    2100
gaaaatgaag aagccattgc tcttagcagg aaggacaaaa ctattcaaca tgtggaagta    2160 tttttgttatg ccagtcagga tttgcatgaa gatgtcgaag aagctggtgc actgcagaaa    2220
aatcatgctc ttgtgacatc tgcaaactcc acagaagctg cagattctgc cttcctgcct    2280
acggaggatg agtcattaag cactatgagc tgtgaaatgc tcacagaaca aactccaagc    2340
agcgatccag agaatgcgct agaagtaaat ggtgctgaag tgacagggga aaaagaaaac    2400
cattgtgatg ataaaaacttg tgtgccatca acttcagcag aagacatgag tgaaaatgtg    2460
cctatagcag aagataccac agagcaacca agaaaaaaca gaattactta ctcacaaatt    2520
attaaagaag gcaggagatt taatattgat ttagtatcaa agctgctgta ttctcgagga    2580
ttactaattg atcttctaat caaatctaat gttagtcgat atgcagagtt taaaaatatt    2640
accaggattc ttgcatttcg agaaggacga gtggaacagg ttccgtgttc cagagcagat    2700
gtctttaata gcaaacaact tactatggta gaaaagcgaa tgctaatgaa atttcttaca    2760
ttttgtatgg aatatgagaa atatcctgat gaatataaag gatatgaaga gatcacattt    2820
tatgaatatt taaagactca aaaattaacc cccaacctcc aatatattgt catgcattca    2880
attgcaatga catcagagac agccagcagc accatagatg gtctcaaagc taccaaaaac    2940
tttcttcact gtcttgggcg gtatggcaac actccatttt tgtttccttt atatggccaa    3000
ggagaactcc cccagtgttt ctgcaggatg tgtgctgtgt ttggtggaat ttattgtctt    3060
cgccattcag tacagtgcct tgtagtggac aaagaatcca gaaaatgtaa agcaattata    3120
gatcagtttg gtcagagaat aatctctgag catttcctcg tggaggacag ttactttcct    3180
gagaacatgt gctcacgtgt gcaatacagg cagatctcca gggcagtgct gattacagat    3240
agatctgtcc taaaaacaga ttcagatcaa cagatttcca ttttgacagt gccagcagag    3300
gaaccaggaa ctttttgctgt tcgggtcatt gagttatgtt cttcaacgat gacatgcatg    3360
aaaggcacct atttggttca tttgacttgc acatcttcta aaacagcaag agaagattta    3420
gaatcagttg tgcagaaatt gtttgttcca tatactgaaa tggagataga aaatgaacaa    3480
gtagaaaagc caagaattct gtgggctctt tacttcaata tgagagattc gtcagacatc    3540
agcaggagct gttataatga tttaccatcc aacgtttatg tctgctctgg cccagattgt    3600
```

```
ggtttaggaa atgataatgc agtcaaacag gctgaaacac ttttccagga aatctgcccc    3660
aatgaagatt tctgtcccc tccaccaaat cctgaagaca ttatccttga tggagacagt    3720
ttacagccag aggcttcaga atccagtgcc ataccagagg ctaactcgga gactttcaag    3780
gaaagcacaa accttggaaa cctagaggag tcctctgaat aaggatctgc ctcgactgtg    3840
ccttctagtt gccagccatc tgttgtttgc ccctcccccg tgccttcctt gaccctggaa    3900
ggtgccactc ccactgtcct ttcctaataa aatgaggaaa ttgcatcgca ttgtctgagt    3960
aggtgtcatt ctattctggg gggtggggtg gggcaggaca gcaaggggga ggattgggaa    4020
gacaatagca ggcatgctgg ggactcgagt tctacgtaga taagtagcat ggcgggttaa    4080
tcattaacta caaggaaccc ctagtgatgg agttggccac tccctctctg cgcgctcgct    4140
cgctcactga ggccgggcga ccaaaggtcg cccgacgccc gggctttgcc cgggcggcct    4200
cagtgagcga gcgagcgcgc agccttaatt aacctaagga aaatgaagtg aagttcctat    4260
actttctaga aataggaac ttctatagtg agtcgaataa gggcgacaca aaatttattc    4320
taaatgcata ataaatactg ataacatctt atagtttgta ttatattttg tattatcgtt    4380
gacatgtata attttgatat caaaaactga ttttcccttt attatttccg agattatttt    4440
tcttaattct ctttaacaaa ctagaaatat tgtatataca aaaaatcata aataatagat    4500
gaatagttta attataggtg ttcatcaatc gaaaagcaa cgtatcttat ttaaagtgcg    4560
ttgctttttt ctcatttata aggttaaata attctcatat atcaagcaaa gtgacaggcg    4620
cccttaaata ttctgacaaa tgctcttttc ctaaactccc cccataaaaa aacccgccga    4680
agcgggtttt tacgttattt gcggattaac gattactcgt tatcagaacc gcccagggg    4740 cccgagctta acctttttat ttgggggaga gggaagtcat gaaaaaacta acctttgaaa    4800
ttcgatctcc agcacatcag caaaacgcta ttcacgcagt acagcaaatc cttccagacc    4860
caaccaaacc aatcgtagta accattcagg aacgcaaccg cagcttagac caaaacagga    4920
agctatgggc ctgcttaggt gacgtctctc gtcaggttga atggcatggt cgctggctgg    4980
atgcagaaag ctggaagtgt gtgtttaccg cagcattaaa gcagcaggat gttgttccta    5040
accttgccgg gaatggcttt gtggtaatag gccagtcaac cagcaggatg cgtgtaggcg    5100
aatttgcgga gctattagag cttatacagg cattcggtac agagcgtggc gttaagtggt    5160
cagacgaagc gagactggct ctggagtgga aagcagatg gggagacagg gctgcatgat    5220
aaatgtcgtt agtttctccg gtggcaggac gtcagcatat ttgctctggc taatggagca    5280
aaagcgacgg gcaggtaaag acgtgcatta cgttttcatg gatacaggtt gtgaacatcc    5340
aatgacatat cggtttgtca gggaagttgt gaagttctgg gatataccgc tcaccgtatt    5400
gcaggttgat atcaacccgg agcttggaca gccaaatggt tatacggtat gggaaccaaa    5460
ggatattcag acgcgaatgc ctgttctgaa gccatttatc gatatggtaa agaaatatgg    5520
cactccatac gtcggcggcg cgttctgcac tgacagatta aaactcgttc ccttcaccaa    5580
atactgtgat gaccatttcg ggcgagggaa ttacaccacg tggattggca tcagagctga    5640
tgaaccgaag cggctaaagc caaagcctgg aatcagatat cttgctgaac tgtcagactt    5700
tgagaaggaa gatatcctcg catggtggaa gcaacaacca ttcgatttgc aaataccgga    5760
acatctcggt aactgcatat tctgcattaa aaaatcaacg caaaaatcg gacttgcctg    5820 caaagatgag gagggattgc agcgtgtttt taatgaggtc atcacgggat cccatgtgcg    5880
tgacggacat cgggaaacgc caaaggagat tatgtaccga ggaagaatgt cgctggacgg    5940
tatcgcgaaa atgtattcag aaaatgatta tcaagccctg tatcaggaca tggtacgagc    6000
```

```
taaaagattc gataccggct cttgttctga gtcatgcgaa atatttggag ggcagcttga      6060
tttcgacttc gggagggaag ctgcatgatg cgatgttatc ggtgcggtga atgcaaagaa      6120
gataaccgct tccgaccaaa tcaaccttac tggaatcgat ggtgtctccg gtgtgaaaga      6180
acaccaacag gggtgttacc actaccgcag gaaaaggagg acgtgtggcg agacagcgac      6240
gaagtatcac cgacataatc tgcgaaaact gcaaatacct tccaacgaaa cgcaccagaa      6300
ataaacccaa gccaatccca aaagaatctg acgtaaaaac cttcaactac acggctcacc      6360
tgtgggatat ccggtggcta agacgtcgtg cgaggaaaac aaggtgattg accaaaatcg      6420
aagttacgaa caagaaagcg tcgagcgagc tttaacgtgc gctaactgcg gtcagaagct      6480
gcatgtgctg gaagttcacg tgtgtgagca ctgctgcgca gaactgatga gcgatccgaa      6540
tagctcgatg cacgaggaag aagatgatgg ctaaaccagc gcgaagacga tgtaaaaacg      6600
atgaatgccg ggaatggttt caccctgcat tcgctaatca gtggtggtgc tctccagagt      6660
gtggaaccaa gatagcactc gaacgacgaa gtaaagaacg cgaaaaagcg gaaaaagcag      6720
cagagaagaa acgacgacga gaggagcaga aacagaaaga taaacttaag attcgaaaac      6780
tcgccttaaa gccccgcagt tactggatta acaagcccca acaagccgta aacgccttca      6840
tcagagaaag agaccgcgac ttaccatgta tctcgtgcgg aacgctcacg tctgctcagt      6900
gggatgccgg acattaccgg acaactgctg cggcacctca actccgattt aatgaacgca      6960
atattcacaa gcaatgcgtg gtgtgcaacc agcacaaaag cggaaatctc gttccgtatc      7020
gcgtcgaact gattagccgc atcgggcagg aagcagtaga cgaaatcgaa tcaaaccata      7080
accgccatcg ctggactatc gaagagtgca aggcgatcaa ggcagagtac caacagaaac      7140
tcaaagacct gcgaaatagc agaagtgagg ccgcatgacg ttctcagtaa aaaccattcc      7200
agacatgctc gttgaagcat acggaaatca gacagaagta gcacgcagac tgaaatgtag      7260
tcgcggtacg gtcagaaaat acgttgatga taaagacggg aaaatgcacg ccatcgtcaa      7320
cgacgttctc atggttcatc gcggatggag tgaaagagat gcgctattac gaaaaaattg      7380
atggcagcaa ataccgaaat atttgggtag ttggcgatct gcacggatgc tacacgaacc      7440
tgatgaacaa actggatacg attggattcg acaacaaaaa agacctgctt atctcggtgg      7500
gcgatttggt tgatcgtggt gcagagaacg ttgaatgcct ggaattaatc acattcccct      7560
ggttcagagc tgtacgtgga aaccatgagc aaatgatgat tgatggctta tcagagcgtg      7620
gaaacgttaa tcactggctg cttaatggcg gtggctggtt ctttaatctc gattacgaca      7680
aagaaattct ggctaaagct cttgcccata agcagatga acttccgtta atcatcgaac      7740
tggtgagcaa agataaaaaa tatgttatct gccacgccga ttatcccttt gacgaatacg      7800
agtttggaaa gccagttgat catcagcagg taatctggaa ccgcgaacga atcagcaact      7860
cacaaaacgg gatcgtgaaa gaaatcaaag cgcggacac gttcatcttt ggtcatacgc      7920
cagcagtgaa accactcaag tttgccaacc aaatgtatat cgataccggc gcagtgttct      7980
gcggaaacct aacattgatt caggtacagg gagaaggcgc atgagactcg aaagcgtagc      8040
taaatttcat tcgccaaaaa gcccgatgat gagcgactca ccacgggcca cggcttctga      8100 ctctcttttcc ggtactgatg tgatggctgc tatgggatg gcgcaatcac aagccggatt      8160
cggtatggct gcattctgcg gtaagcacga actcagccag aacgacaaac aaaaggctat      8220
caactatctg atgcaatttg cacacaaggt atcgggaaa taccgtggtg tggcaaagct      8280
tgaaggaaat actaaggcaa aggtactgca agtgctcgca acattcgctt atgcggatta      8340
```

-continued

```
ttgccgtagt gccgcgacgc cggggggcaag atgcagagat tgccatggta caggccgtgc   8400
ggttgatatt gccaaaacag agctgtgggg gagagttgtc gagaaagagt gcggaagatg   8460
caaaggcgtc ggctattcaa ggatgccagc aagcgcagca tatcgcgctg tgacgatgct   8520
aatcccaaac cttacccaac ccacctggtc acgcactgtt aagccgctgt atgacgctct   8580
ggtggtgcaa tgccacaaag aagagtcaat cgcagacaac attttgaatg cggtcacacg   8640
ttagcagcat gattgccacg gatggcaaca tattaacggc atgatattga cttattgaat   8700
aaaattgggt aaatttgact caacgatggg ttaattcgct cgttgtggta gtgagatgaa   8760
aagaggcggc gcttactacc gattccgcct agttggtcac ttcgacgtat cgtctggaac   8820
tccaaccatc gcaggcagag aggtctgcaa aatgcaatcc cgaaacagtt cgcaggtaat   8880
agttagagcc tgcataacgg tttcgggatt ttttatatct gcacaacagg taagagcatt   8940
gagtcgataa tcgtgaagag tcggcgagcc tggttagcca gtgctctttc cgttgtgctg   9000
aattaagcga ataccggaag cagaaccgga tcaccaaatg cgtacaggcg tcatcgccgc   9060
ccagcaacag cacaacccaa actgagccgt agccactgtc tgtcctgaat tcattagtaa   9120
tagttacgct gcggccttttt acacatgacc ttcgtgaaag cgggtggcag gaggtcgcgc   9180
taacaacctc ctgccgtttt gcccgtgcat atcggtcacg aacaaatctg attactaaac   9240
acagtagcct ggatttgttc tatcagtaat cgaccttatt cctaattaaa tagagcaaat   9300
ccccttattg ggggtaagac atgaagatgc cagaaaaaca tgacctgttg gccgccattc   9360
tcgcggcaaa ggaacaaggc atcggggcaa tccttgcgtt tgcaatggcg taccttcgcg   9420
gcagatataa tggcggtgcg tttacaaaaa cagtaatcga cgcaacgatg tgcgccatta   9480
tcgcctggtt cattcgtgac cttctcgact tcgccggact aagtagcaat ctcgcttata   9540
taacgagcgt gtttatcggc tacatcggta ctgactcgat tggttcgctt atcaaacgct   9600
tcgctgctaa aaaagccgga gtagaagatg gtagaaatca ataatcaacg taaggcgttc   9660
ctcgatatgc tggcgtggtc ggagggaact gataacggac gtcagaaaac cagaaatcat   9720
ggttatgacg tcattgtagg cggagagcta tttactgatt actccgatca ccctcgcaaa   9780
cttgtcacgc taaacccaaa actcaaatca acaggcgctt aagactggcc gtcgttttac   9840
aacacagaaa gagtttgtag aaacgcaaaa aggccatccg tcagggggcct tctgcttagt   9900
ttgatgcctg gcagttccct actctcgcct tccgcttcct cgctcactga ctcgctgcgc   9960
tcggtcgttc ggctgcggcg agcggtatca gctcactcaa aggcggtaat acggttatcc  10020
acagaatcag gggataacgc aggaaagaac atgtgagcaa aaggccagca aaaggccagg  10080
aaccgtaaaa aggccgcgtt gctggcgttt ttccataggc tccgcccccc tgacgagcat  10140
cacaaaaatc gacgctcaag tcagaggtgg cgaaacccga caggactata agataccagg  10200
gcgtttcccc ctggaagctc cctcgtgcgc tctcctgttc cgaccctgcc gcttaccgga  10260
tacctgtccg cctttctccc ttcgggaagc gtggcgcttt ctcatagctc acgctgtagg  10320
tatctcagtt cggtgtaggt cgttcgctcc aagctgggct gtgtgcacga accccccgtt  10380
cagcccgacc gctgcgcctt atccggtaac tatcgtcttg agtccaaccc ggtaagacac  10440
gacttatcgc cactggcagc agccactggt aacaggatta gcagagcgag gtatgtaggc  10500
ggtgctacag agttcttgaa gtggtgggct aactacggct acactagaag aacagtattt  10560
ggtatctgcg ctctgctgaa gccagttacc ttcggaaaaa gagttggtag ctcttgatcc  10620
ggcaaacaaa ccaccgctgg tagcggtggt ttttttgttt gcaagcagca gattacgcgc  10680
agaaaaaaag gatctcaaga agatcctttg atcttttcta cggggtctga cgctcagtgg  10740
```

```
aacgacgcgc gcgtaactca cgttaaggga ttttggtcat gagcttgcgc cgtcccgtca    10800
agtcagcgta atgctctgct tttagaaaaa ctcatcgagc atcaaatgaa actgcaattt    10860
attcatatca ggattatcaa taccatattt ttgaaaaagc cgtttctgta atgaaggaga    10920
aaactcaccg aggcagttcc ataggatggc aagatcctgg tatcggtctg cgattccgac    10980
tcgtccaaca tcaatacaac ctattaattt cccctcgtca aaaataaggt tatcaagtga    11040
gaaatcacca tgagtgacga ctgaatccgg tgagaatggc aaaagtttat gcatttcttt    11100
ccagacttgt tcaacaggcc agccattacg ctcgtcatca aaatcactcg catcaaccaa    11160
accgttattc attcgtgatt gcgcctgagc gaggcgaaat acgcgatcgc tgttaaaagg    11220
acaattacaa acaggaatcg agtgcaaccg gcgcaggaac actgccagcg catcaacaat    11280
attttcacct gaatcaggat attcttctaa tacctggaac gctgttttttc cggggatcgc    11340 agtggtgagt aaccatgcat catcaggagt acggataaaa tgcttgatgg tcggaagtgg    11400
cataaattcc gtcagccagt ttagtctgac catctcatct gtaacatcat ggcaacgct    11460 accttttgcca tgtttcagaa acaactctgg cgcatcgggc ttcccataca agcgatagat    11520
tgtcgcacct gattgcccga cattatcgcg agcccattta tacccatata aatcagcatc    11580
catgttggaa tttaatcgcg gcctcgacgt ttcccgttga atatggctca tattcttcct    11640
ttttcaatat tattgaagca tttatcaggg ttattgtctc atgagcggat acatatttga    11700
atgtatttag aaaaataaac aaatagggt cagtgttaca accaattaac caattctgaa    11760
cattatcgcg agcccattta tacctgaata tggctcataa cacccccttgt ttgcctggcg    11820 gcagtagcgc ggtggtccca cctgaccccca tgccgaactc agaagtgaaa cgccgtagcg    11880
ccgatggtag tgtggggact ccccatgcga gagtagggaa ctgccaggca tcaaataaaa    11940
cgaaaggctc agtcgaaaga ctgggccttt cgcccgggct aattaggggg tgtcgccctt    12000
attcgactct atagtgaagt tcctattctc tagaaagtat aggaacttct gaagtggggt    12060
cgacttaatt aagg                                                      12074
```

<210> SEQ ID NO 30
<211> LENGTH: 11041
<212> TYPE: DNA
<213> ORGANISM: Artificial Sequence
<220> FEATURE:
<223> OTHER INFORMATION: constructed sequence

<400> SEQUENCE: 30

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctacgta gcaagctagc      180
aagatccaag ctcagatctc gatcgagttg ggccccagaa gcctggtggt tgtttgtcct      240
tctcagggga aaagtgaggc ggcccccttgg aggaagggc cgggcagaat gatctaatcg      300
gattccaagc agctcagggg attgtctttt tctagcacct tcttgccact cctaagcgtc      360
ctccgtgacc ccggctggga tttagcctgg tgctgtgtca gccccggtct cccaggggct      420
tcccagtggt cccaggaac cctcgacagg gcccggtctc tctcgtccag caagggcagg      480
gacgggccac aggccaaggg ccctcgatcg aggaactgaa aaaccagaaa gttaactggt      540
aagtttagtc ttttttgtctt ttattttcagg tcccggatcc ggtggtggtg caaatcaaag      600
aactgctcct cagtggatgt tgcctttact tctaggcctg tacggaagtg ttacttctgc      660
```

```
tctaaaagct gcggaattgt acccgcggcc gccaccatgg ccaagatcaa cacccaatac      720 tcccaccect ccaggaccca cctcaaggta aagacctcag accgggatct caatcgcgct      780
gaaaatggcc tcagcagagc ccactcgtca agtgaggaga catcgtcagt gctgcagccg      840
gggatcgcca tggagaccag aggactggct gactccgggc agggctcctt caccggccag      900
gggatcgcca ggctgtcgcg cctcatcttc ttgctgcgca ggtgggctgc caggcatgtg      960
caccaccagg accagggacc ggactctttt cctgatcgtt ccgtggagc cgagcttaag      1020 gaggtgtcca gccaagaaag caatgcccag gcaaatgtgg gcagccagga gccagcagac     1080
agagggagaa gcgcctggcc cctggccaaa tgcaacacta acaccagcaa caacacggag     1140
gaggagaaga agacgaaaaa gaaggatgcg atcgtggtgg acccgtccag caacctgtac     1200
taccgctggc tgaccgccat cgccctgcct gtcttctata actggtatct gcttatttgc     1260
agggcctgtt tcgatgagct gcagtccgag tacctgatgc tgtggctggt cctggactac     1320
tcggcagatg tcctgtatgt cttggatgtg cttgtacgag ctcggacagg ttttcttgag     1380
caaggcttaa tggtcagtga taccaacagg ctgtggcagc attacaagac gaccacgcag     1440
ttcaagctgg atgtgttgtc cctggtcccc accgacctgg cttacttaaa ggtgggcaca     1500
aactacccag aagtgaggtt caaccgccta ctgaagtttt cccggctctt tgaattcttt     1560
gaccgcacag agacaaggac caactacccc aatatgttca ggattgggaa cttggtcttg     1620
tacattctca tcatcatcca ctggaatgcc tgcatctact tgccatttc caagttcatt     1680 ggttttggga cagactcctg ggtctaccca acatctcaa tcccagagca tgggcgcctc     1740
tccaggaagt acatttacag tctctactgg tccaccttga cccttaccac cattggtgag     1800 acccacccc ccgtgaaaga tgaggagtat ctctttgtgg tcgtagactt cttggtgggt     1860
gttctgattt tgccaccat tgtgggcaat gtgggctcca tgatctcgaa tatgaatgcc     1920
tcacgggcag agttccaggc caagattgat tccatcaagc agtacatgca gttccgcaag     1980
gtcaccaagg acttggagac gcgggttatc cggtggtttg actacctgtg gccaacaag     2040 aagacggtgg atgagaagga ggtgctcaag agcctcccag acaagctgaa ggctgagatc     2100
gccatcaacg tgcacctgga cacgctgaag aaggttcgca tcttccagga ctgtgaggca     2160
gggctgctgg tggagctggt gctgaagctg cgacccactg tgttcagccc tgggattat    2220 atctgcaaga agggagatat tgggaaggag atgtacatca tcaacgaggg caagctggcc     2280
gtggtggctg atgatggggt cacccagttc gtggtcctca gcgatggcag ctacttcggg     2340
gagatcagca ttctgaacat caaggggagc aagtcgggga accgcaggac ggccaacatc     2400
cgcagcattg gctactcaga cctgttctgc ctctcaaagg acgatctcat ggaggccctc     2460
accgagtacc ccgaagccaa gaaggccctg gaggagaaag acggcagat cctgatgaaa     2520 gacaacctga tcgatgagga gctggccagg gcgggcgcgg accccaagga ccttgaggag     2580
aaagtggagc agctggggtc ctccctggac accctgcaga ccaggtttgc acgcctcctg     2640
gctgagtaca cgccacccca gatgaagatg aagcagcgtc tcagccaact ggaaagccag     2700
gtgaagggtg gtggggacaa gcccctggct gatggggaag ttcccgggga tgctacaaaa     2760
acagaggaca acaacagtg atcatagatc gatctgcctc gactgtgcct tctagttgcc     2820
agccatctgt tgtttgcccc tcccccgtgc cttccttgac cctggaaggt gccactccca     2880
ctgtcctttc ctaataaaat gaggaaattg catcgcattg tctgagtagg tgtcattcta     2940
ttctgggggg tggggtgggg caggacagca agggggagga ttgggaagac aatagcaggc     3000
atgctgggga ctcgagttct acgtagataa gtagcatggc gggttaatca ttaactacaa     3060
```

```
ggaacccta gtgatggagt tggccactcc ctctctgcgc gctcgctcgc tcactgaggc    3120
cgggcgacca aaggtcgccc gacgcccggg ctttgcccgg gcggcctcag tgagcgagcg    3180
agcgcgcagc cttaattaac ctaaggaaaa tgaagtgaag ttcctatact ttctagagaa    3240
taggaacttc tatagtgagt cgaataaggg cgacacaaaa tttattctaa atgcataata    3300
aatactgata acatcttata gtttgtatta tattttgtat tatcgttgac atgtataatt    3360
ttgatatcaa aaactgattt tccctttatt attttcgaga tttattttct taattctctt    3420
taacaaacta gaaatattgt atatacaaaa aatcataaat aatagatgaa tagtttaatt    3480
ataggtgttc atcaatcgaa aaagcaacgt atcttattta aagtgcgttg ctttttttctc   3540 atttataagg ttaataatt ctcatatatc aagcaaagtg acaggcgccc ttaaatattc     3600
tgacaaatgc tctttcccta aactccccc ataaaaaaac ccgccgaagc gggttttac     3660 gttatttgcg gattaacgat tactcgttat cagaaccgcc caggggccc gagcttaacc    3720 tttttatttg ggggagaggg aagtcatgaa aaaactaacc tttgaaattc gatctccagc    3780
acatcagcaa aacgctattc acgcagtaca gcaaatcctt ccagacccaa ccaaaccaat    3840
cgtagtaacc attcaggaac gcaaccgcag cttagaccaa acaggaagc tatgggcctg     3900 cttaggtgac gtctctcgtc aggttgaatg gcatggtcgc tggctggatg cagaaagctg    3960
gaagtgtgtg tttaccgcag cattaaagca gcaggatgtt gttcctaacc ttgccgggaa    4020
tggctttgtg gtaataggcc agtcaaccag caggatgcgt gtaggcgaat ttgcggagct    4080
attagagctt atacaggcat tcggtacaga gcgtggcgtt aagtggtcag acgaagcgag    4140
actggctctg gagtggaaag cgagatgggg agacagggct gcatgataaa tgtcgttagt    4200
ttctccggtg gcaggacgtc agcatatttg ctctggctaa tggagcaaaa gcgacgggca    4260
ggtaaagacg tgcattacgt tttcatggat acaggttgtg aacatccaat gacatatcgg    4320
tttgtcaggg aagttgtgaa gttctgggat ataccgctca ccgtattgca ggttgatatc    4380
aacccggagc ttggacagcc aaatggttat acggtatggg aaccaaagga tattcagacg    4440
cgaatgcctg ttctgaagcc atttatcgat atggtaaaga aatatggcac tccatacgtc    4500
ggcggcgcgt tctgcactga cagattaaaa ctcgttccct tcaccaaata ctgtgatgac    4560
catttcgggc gagggaatta caccacgtgg attggcatca gagctgatga accgaagcgg    4620
ctaaagccaa agcctggaat cagatatctt gctgaactgt cagactttga gaggaagat    4680 atcctcgcat ggtggaagca acaaccattc gatttgcaaa taccggaaca tctcggtaac    4740
tgcatattct gcattaaaaa atcaacgcaa aaatcggac ttgcctgcaa agatgaggag    4800
ggattgcagc gtgttttaa tgaggtcatc acgggatccc atgtgcgtga cggacatcgg    4860
gaaacgccaa aggagattat gtaccgagga agaatgtcgc tggacggtat cgcgaaaatg    4920
tattcagaaa atgattatca agccctgtat caggacatgg tacgagctaa aagattcgat    4980
accggctctt gttctgagtc atgcgaaata tttggagggc agcttgattt cgacttcggg    5040
agggaagctg catgatgcga tgttatcggt gcggtgaatg caaagaagat aaccgcttcc    5100
gaccaaatca accttactgg aatcgatggt gtctccggtg tgaaagaaca ccaacagggg    5160
tgttaccact accgcaggaa aaggaggacg tgtggcgaga cagcgacgaa gtatcaccga    5220
cataatctgc gaaaactgca ataccttcc aacgaaacgc accagaaata aacccaagcc    5280
aatcccaaaa gaatctgacg taaaaacctt caactacacg gctcacctgt gggatatccg    5340
gtggctaaga cgtcgtgcga ggaaaacaag gtgattgacc aaaatcgaag ttacgaacaa    5400
```

```
gaaagcgtcg agcgagcttt aacgtgcgct aactgcggtc agaagctgca tgtgctggaa    5460
gttcacgtgt gtgagcactg ctgcgcagaa ctgatgagcg atccgaatag ctcgatgcac    5520
gaggaagaag atgatggcta aaccagcgcg aagacgatgt aaaaacgatg aatgccggga    5580
atggtttcac cctgcattcg ctaatcagtg gtggtgctct ccagagtgtg gaaccaagat    5640
agcactcgaa cgacgaagta aagaacgcga aaaagcggaa aaagcagcag agaagaaacg    5700
acgacgagag gagcagaaac agaaagataa acttaagatt cgaaaactcg ccttaaagcc    5760
ccgcagttac tggattaaac aagcccaaca agccgtaaac gccttcatca gagaaagaga    5820
ccgcgactta ccatgtatct cgtgcggaac gctcacgtct gctcagtggg atgccggaca    5880
ttaccggaca actgctgcgg cacctcaact ccgatttaat gaacgcaata ttcacaagca    5940
atgcgtggtg tgcaaccagc acaaaagcgg aaatctcgtt ccgtatcgcg tcgaactgat    6000
tagccgcatc gggcaggaag cagtagacga aatcgaatca aaccataacc gccatcgctg    6060
gactatcgaa gagtgcaagg cgatcaaggc agagtaccaa cagaaactca aagacctgcg    6120
aaatagcaga agtgaggccg catgacgttc tcagtaaaaa ccattccaga catgctcgtt    6180
gaagcatacg gaaatcagac agaagtagca cgcagactga aatgtagtcg cggtacggtc    6240
agaaaatacg ttgatgataa agacgggaaa atgcacgcca tcgtcaacga cgttctcatg    6300
gttcatcgcg gatggagtga aagagatgcg ctattacgaa aaaattgatg gcagcaaata    6360
ccgaaatatt tgggtagttg cgatctgca cggatgctac acgaacctga tgaacaaact    6420
ggatacgatt ggattcgaca acaaaaaaga cctgcttatc tcggtgggcg atttggttga    6480
tcgtggtgca gagaacgttg aatgcctgga attaatcaca ttcccctggt tcagagctgt    6540
acgtggaaac catgagcaaa tgatgattga tggcttatca gagcgtggaa acgttaatca    6600
ctggctgctt aatggcggtg gctggttctt taatctcgat tacgcaaaag aaattctggc    6660
taaagctctt gcccataaag cagatgaact tccgttaatc atcgaactgg tgagcaaaga    6720
taaaaaatat gttatctgcc acgccgatta tcccctttgac gaatacgagt ttggaaagcc    6780
agttgatcat cagcaggtaa tctggaaccg cgaacgaatc agcaactcac aaaacgggat    6840
cgtgaaagaa atcaaaggcg cggacacgtt catctttggt catacgccag cagtgaaacc    6900
actcaagttt gccaaccaaa tgtatatcga taccggcgca gtgttctgcg gaaacctaac    6960
attgattcag gtacagggag aaggcgcatg agactcgaaa gcgtagctaa atttcattcg    7020
ccaaaaagcc cgatgatgag cgactcacca cgggccacgg cttctgactc tctttccggt    7080
actgatgtga tggctgctat ggggatggcg caatcacaag ccggattcgg tatggctgca    7140
ttctgcggta agcacgaact cagccagaac gacaaacaaa aggctatcaa ctatctgatg    7200
caatttgcac acaaggtatc ggggaaatac cgtggtgtgg caaagcttga aggaaatact    7260
aaggcaaagg tactgcaagt gctcgcaaca ttcgcttatg cggattattg ccgtagtgcc    7320
gcgacgccgg gggcaagatg cagagattgc catggtacag gccgtgcggt tgatattgcc    7380
aaaacagagc tgtgggggag agttgtcgag aaagagtgcg gaagatgcaa aggcgtcggc    7440
tattcaagga tgccagcaag cgcagcatat cgcgctgtga cgatgctaat cccaaacctt    7500
acccaaccca cctggtcacg cactgttaag ccgctgtatg acgctctggt ggtgcaatgc    7560
cacaaagaag agtcaatcgc agacaacatt ttgaatgcgg tcacacgtta gcagcatgat    7620
tgccacggat ggcaacatat taacggcatg atattgactt attgaataaa attgggtaaa    7680
tttgactcaa cgatgggtta attcgctcgt tgtggtagtg agatgaaaag aggcggcgct    7740
tactaccgat tccgcctagt tggtcacttc gacgtatcgt ctggaactcc aaccatcgca    7800
```

```
ggcagagagg tctgcaaaat gcaatcccga aacagttcgc aggtaatagt tagagcctgc    7860
ataacggttt cgggattttt tatatctgca caacaggtaa gagcattgag tcgataatcg    7920
tgaagagtcg gcgagcctgg ttagccagtg ctctttccgt tgtgctgaat taagcgaata    7980
ccggaagcag aaccggatca ccaaatgcgt acaggcgtca tcgccgccca gcaacagcac    8040
aacccaaact gagccgtagc cactgtctgt cctgaattca ttagtaatag ttacgctgcg    8100
gccttttaca catgaccttc gtgaaagcgg gtggcaggag gtcgcgctaa caacctcctg    8160
ccgttttgcc cgtgcatatc ggtcacgaac aaatctgatt actaaacaca gtagcctgga    8220
tttgttctat cagtaatcga ccttattcct aattaaatag agcaaatccc cttattgggg    8280
gtaagacatg aagatgccag aaaaacatga cctgttggcc gccattctcg cggcaaagga    8340
acaaggcatc ggggcaatcc ttgcgtttgc aatggcgtac cttcgcggca gataataagg    8400
cggtgcgttt acaaaaacag taatcgacgc aacgatgtgc gccattatcg cctggttcat    8460
tcgtgacctt ctcgacttcg ccggactaag tagcaatctc gcttatataa cgagcgtgtt    8520
tatcggctac atcggtactg actcgattgg ttcgcttatc aaacgcttcg ctgctaaaaa    8580
agccggagta gaagatggta gaaatcaata atcaacgtaa ggcgttcctc gatatgctgg    8640
cgtggtcgga gggaactgat aacggacgtc agaaaaccag aaatcatggt tatgacgtca    8700
ttgtaggcgg agagctattt actgattact ccgatcaccc tcgcaaactt gtcacgctaa    8760
acccaaaact caaatcaaca ggcgcttaag actggccgtc gttttacaac acagaaagag    8820
tttgtagaaa cgcaaaaagg ccatccgtca ggggccttct gcttagtttg atgcctggca    8880
gttccctact ctcgccttcc gcttcctcgc tcactgactc gctgcgctcg tcgttcggc    8940 tgcggcgagc ggtatcagct cactcaaagg cggtaatacg gttatccaca gaatcagggg    9000
ataacgcagg aaagaacatg tgagcaaaag gccagcaaaa ggccaggaac cgtaaaaagg    9060
ccgcgttgct ggcgtttttc cataggctcc gcccccctga cgagcatcac aaaaatcgac    9120
gctcaagtca gaggtggcga aacccgacag gactataaag ataccaggcg tttccccctg    9180
gaagctccct cgtgcgctct cctgttccga ccctgccgct taccggatac ctgtccgcct    9240
ttctcccttc gggaagcgtg gcgctttctc atagctcacg ctgtaggtat ctcagttcgg    9300
tgtaggtcgt tcgctccaag ctgggctgtg tgcacgaacc ccccgttcag cccgaccgct    9360
gcgccttatc cggtaactat cgtcttgagt ccaacccggt aagacacgac ttatcgccac    9420
tggcagcagc cactggtaac aggattagca gagcgaggta tgtaggcggt gctacagagt    9480
tcttgaagtg gtgggctaac tacggctaca ctagaagaac agtatttggt atctgcgctc    9540
tgctgaagcc agttaccttc ggaaaaagag ttggtagctc ttgatccggc aaacaaacca    9600
ccgctggtag cggtggtttt tttgtttgca agcagcagat tacgcgcaga aaaaaaggat    9660
ctcaagaaga tcctttgatc ttttctacgg ggtctgacgc tcagtggaac gacgcgcgcg    9720
taactcacgt taagggattt tggtcatgag cttgcgccgt cccgtcaagt cagcgtaatg    9780
ctctgctttt agaaaaactc atcgagcatc aaatgaaact gcaatttatt catatcagga    9840
ttatcaatac catattttg aaaaagccgt ttctgtaatg aaggagaaaa ctcaccgagg    9900
cagttccata ggatggcaag atcctggtat cggtctgcga ttccgactcg tccaacatca    9960
atacaaccta ttaatttccc ctcgtcaaaa ataaggttat caagtgagaa atcaccatga    10020
gtgacgactg aatccggtga gaatggcaaa agtttatgca tttctttcca gacttgttca    10080
acaggccagc cattacgctc gtcatcaaaa tcactcgcat caaccaaacc gttattcatt    10140
```

```
cgtgattgcg cctgagcgag gcgaaatacg cgatcgctgt taaaaggaca attacaaaca    10200
ggaatcgagt gcaaccggcg caggaacact gccagcgcat caacaatatt ttcacctgaa    10260
tcaggatatt cttctaatac ctggaacgct gttttccgg ggatcgcagt ggtgagtaac    10320
catgcatcat caggagtacg gataaaatgc ttgatggtcg gaagtggcat aaattccgtc    10380
agccagttta gtctgaccat ctcatctgta acatcattgg caacgctacc tttgccatgt    10440
ttcagaaaca actctggcgc atcgggcttc ccatacaagc gatagattgt cgcacctgat    10500
tgcccgacat tatcgcgagc ccatttatac ccatataaat cagcatccat gttggaattt    10560
aatcgcggcc tcgacgtttc ccgttgaata tggctcatat tcttcctttt tcaatattat    10620
tgaagcattt atcagggtta ttgtctcatg agcggataca tatttgaatg tatttagaaa    10680
aataaacaaa tagggtcag tgttacaacc aattaaccaa ttctgaacat tatcgcgagc    10740
ccatttatac ctgaatatgg ctcataacac cccttgtttg cctggcggca gtagcgcggt    10800
ggtcccacct gaccccatgc cgaactcaga agtgaaacgc cgtagcgccg atggtagtgt    10860
ggggactccc catgcgagag tagggaactg ccaggcatca aataaaacga aaggctcagt    10920
cgaaagactg ggcctttcgc ccgggctaat tagggggtgt cgcccttatt cgactctata    10980
gtgaagttcc tattctctag aaagtatagg aacttctgaa gtggggtcga cttaattaag    11040
g                                                                    11041
```

<210> SEQ ID NO 31
<211> LENGTH: 11041
<212> TYPE: DNA
<213> ORGANISM: Artificial Sequence
<220> FEATURE:
<223> OTHER INFORMATION: constructed sequence

<400> SEQUENCE: 31

```
ctgcgcgctc gctcgctcac tgaggccgcc cgggcaaagc ccgggcgtcg gcgacctttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
aagatccaag ctcagatctc gatcgagttg gccccagaa gcctggtggt tgtttgtcct     240
tctcagggga aaagtgaggc ggccccttgg aggaaggggc cgggcagaat gatctaatcg     300
gattccaagc agctcagggg attgtctttt tctagcacct tcttgccact cctaagcgtc     360
ctccgtgacc ccggctggga tttagcctgg tgctgtgtca gccccggtct cccaggggct     420
tcccagtggt ccccaggaac cctcgacagg gcccggtctc tctcgtccag caagggcagg     480
gacgggccac aggccaaggg ccctcgatcg aggaactgaa aaaccagaaa gttaactggt     540
aagtttagtc tttttgtctt ttatttcagg tcccggatcc ggtggtggtg caaatcaaag     600
aactgctcct cagtggatgt tgcctttact tctaggcctg tacggaagtg ttacttctgc     660
tctaaaagct gcggaattgt acccgcggcc gccaccatgg ctaagattaa cacccagtac     720
tcacatccat cccgcactca cctcaaagtc aagacctccg atcgggatct gaaccgggct     780
gagaatgggc tgtcgcgcgc ccactcgtcg tccgaggaaa ccagcagcgt gctccagccg     840
ggcatcgcca tggaaactag ggggctggcg gactccggac agggatcctt cactggacag     900
ggtattgccc ggctgagcag actgatcttc ctgcttcgcc gctgggcggc cagacacgtg     960
caccatcagg accagggacc tgatagcttc cccgaccgct ttaggggagc cgagctgaaa    1020
gaagtgtcaa gccaggagtc aaacgcgcag gccaacgtcg gcagccaaga gcctgcagac    1080
cggggacgct cggcatggcc gctcgcaaag tgcaacacta acacttccaa caacaccgaa    1140
```

```
gaggaaaaga aaaccaagaa gaaggatgca attgtggtgg acccttcctc caacctgtac    1200
taccgctggt tgaccgccat cgccctcccg gtcttttaca attggtatct ccttatctgc    1260
cgggcctgct tcgacgaact gcaatcagag tacctgatgc tgtggctggt gctggactat    1320
agcgccgatg tgctctacgt cctggatgtg ctcgtgcgcg cccggaccgg attcttggaa    1380
caaggcctga tggtgtccga cacgaataga ctgtggcagc actataagac cacaacccag    1440
ttcaagcttg acgtgctcag ccttgtgccg actgacctgg cctacctgaa agtcggaact    1500
aactacccgg aagtcagatt caaccgactc ctgaagttca gcaggctgtt cgagttcttt    1560
gaccgcaccg agactcggac caactaccct aacatgttcc ggatcggaaa tctggtgctc    1620
tacatactga ttatcatcca ttggaacgcc tgtatctatt tcgccatttc gaagttcatc    1680
ggtttcggaa ccgattcctg ggtgtacccc aacatctcga tccccgaaca cggtcgcctg    1740
tcccggaagt acatctactc cctgtactgg tccactctga ctctgaccac gatcggggaa    1800
acccctccac ccgtgaagga cgaagagtac ctgttcgtgg tggtggactt cctggtcgga    1860
gtgttgattt tcgccaccat tgtgggaaac gtgggctcca tgatctccaa catgaacgcg    1920
tcgagagctg agttccaagc caagatcgac tccattaagc agtacatgca gttcagaaag    1980
gtcaccaagg acctggaaac cagggtcatc cgctggttcg actacctgtg ggccaacaaa    2040
aagactgtgg acgaaaagga agtgctgaag tcgctgccgg ataagctgaa ggccgaaatc    2100
gccattaacg tgcaccttga caccctgaag aaagtccgga tcttccaaga ctgtgaagcc    2160
ggcctcctgg tggagctcgt gctcaagctg cggcccaccg tgttcagccc gggagattac    2220
atttgcaaga agggcgatat cggcaaagag atgtacatca tcaacgaggg aaagctggcc    2280
gtggtcgcgg acgacggcgt gacccagttc gtggtgctgt ccgacggatc ctacttcggt    2340
gaaatctcaa tcctcaacat caaggggtcc aagtccggca accggagaac tgccaacatt    2400
cgctccatcg gatacagcga cctgttttgc ctgtccaagg atgacctgat ggaggctctg    2460
actgagtacc ctgaagcgaa gaaggctttg gaggaaaagg ggcggcagat tctgatgaag    2520
gacaatttga tcgacgagga gctcgcacgg gccggcgccg accccaagga tctcgaagag    2580
aaggtcgaac agctgggttc ttcgcttgat accctgcaaa cccgattcgc gcggctgctc    2640
gccgagtaca acgcgaccca gatgaagatg aagcagagac tgtcacagtt ggaatcccaa    2700
gtcaagggcg gaggcgacaa gccgctggcg gacggggaag tgcccgggga cgccaccaag    2760
actgaggaca gcagcagtg atcatagatc gatctgcctc gactgtgcct tctagttgcc    2820
agccatctgt tgtttgcccc tccccgtgc cttccttgac cctggaaggt gccactccca    2880
ctgtcctttc ctaataaaat gaggaaattg catcgcattg tctgagtagg tgtcattcta    2940
ttctgggggg tggggtgggg caggacagca agggggagga ttgggaagac aatagcaggc    3000
atgctgggga ctcgagttct acgtagataa gtagcatggc gggttaatca ttaactacaa    3060 ggaacccta gtgatggagt tggccactcc ctctctgcgc gctcgctcgc tcactgaggc    3120
cgggcgacca aggtcgcccg acgcccggg ctttgcccgg gcggcctcag tgagcgagcg    3180
agcgcgcagc cttaattaac ctaaggaaaa tgaagtgaag ttcctatact ttctagagaa    3240
taggaacttc tatagtgagt cgaataaggg cgacacaaaa tttattctaa atgcataata    3300
aatactgata acatcttata gtttgtatta tattttgtat tatcgttgac atgtataatt    3360
ttgatatcaa aaactgattt tccctttatt attttcgaga tttatttct taattctctt    3420 taacaaacta gaaatattgt atatacaaaa aatcataaat aatagatgaa tagtttaatt    3480
```

| | |
|---|---|
| ataggtgttc atcaatcgaa aaagcaacgt atcttattta aagtgcgttg cttttttctc | 3540 |
| atttataagg ttaaataatt ctcatatatc aagcaaagtg acaggcgccc ttaaatattc | 3600 |
| tgacaaatgc tctttcccta aactcccccc ataaaaaaac ccgccgaagc gggtttttac | 3660 |
| gttatttgcg gattaacgat tactcgttat cagaaccgcc caggggggccc gagcttaacc | 3720 |
| tttttatttg ggggagaggg aagtcatgaa aaaactaacc tttgaaattc gatctccagc | 3780 |
| acatcagcaa aacgctattc acgcagtaca gcaaatcctt ccagacccaa ccaaaccaat | 3840 |
| cgtagtaacc attcaggaac gcaaccgcag cttagaccaa aacaggaagc tatgggcctg | 3900 |
| cttaggtgac gtctctcgtc aggttgaatg catggtcgc tggctggatg cagaaagctg | 3960 |
| gaagtgtgtg tttaccgcag cattaaagca gcaggatgtt gttcctaacc ttgccgggaa | 4020 |
| tggctttgtg gtaataggcc agtcaaccag caggatgcgt gtaggcgaat ttgcggagct | 4080 |
| attagagctt atacaggcat tcggtacaga gcgtggcgtt aagtggtcag acgaagcgag | 4140 |
| actggctctg gagtggaaag cgagatgggg agacagggct gcatgataaa tgtcgttagt | 4200 |
| ttctccggtg gcaggacgtc agcatatttg ctctggctaa tggagcaaaa gcgacgggca | 4260 |
| ggtaaagacg tgcattacgt tttcatggat acaggttgtg aacatccaat gacatatcgg | 4320 |
| tttgtcaggg aagttgtgaa gttctgggat ataccgctca ccgtattgca ggttgatatc | 4380 |
| aacccggagc ttggacagcc aaatggttat acggtatggg aaccaaagga tattcagacg | 4440 |
| cgaatgcctg ttctgaagcc atttatcgat atggtaaaga aatatggcac tccatacgtc | 4500 |
| ggcggcgcgt tctgcactga cagattaaaa ctcgttccct tcaccaaata ctgtgatgac | 4560 |
| catttcgggc gagggaatta caccacgtgg attggcatca gagctgatga accgaagcgg | 4620 |
| ctaaagccaa agcctggaat cagatatctt gctgaactgt cagactttga gaggaagat | 4680 |
| atcctcgcat ggtggaagca acaaccattc gatttgcaaa taccggaaca tctcggtaac | 4740 |
| tgcatattct gcattaaaaa atcaacgcaa aaaatcggac ttgcctgcaa agatgaggag | 4800 |
| ggattgcagc gtgtttttaa tgaggtcatc acgggatccc atgtgcgtga cggacatcgg | 4860 |
| gaaacgccaa aggagattat gtaccgagga agaatgtcgc tggacggtat cgcgaaaatg | 4920 |
| tattcagaaa atgattatca agccctgtat caggacatgg tacgagctaa aagattcgat | 4980 |
| accggctctt gttctgagtc atgcgaaata tttggagggc agcttgattt cgacttcggg | 5040 |
| agggaagctg catgatgcga tgttatcggt gcggtgaatg caaagaagat aaccgcttcc | 5100 |
| gaccaaatca accttactgg aatcgatggt gtctccggtg tgaaagaaca ccaacagggg | 5160 |
| tgttaccact accgcaggaa aaggaggacg tgtggcgaga cagcgacgaa gtatcaccga | 5220 |
| cataatctgc gaaaactgca aataccttcc aacgaaacgc accagaaata acccaagcc | 5280 |
| aatcccaaaa gaatctgacg taaaaacctt caactacacg gctcacctgt gggatatccg | 5340 |
| gtggctaaga cgtcgtgcga ggaaaacaag gtgattgacc aaaatcgaag ttacgaacaa | 5400 |
| gaaagcgtcg agcgagcttt aacgtgcgct aactgcggtc agaagctgca tgtgctggaa | 5460 |
| gttcacgtgt gtgagcactg ctgcgcagaa ctgatgagcg atccgaatag ctcgatgcac | 5520 |
| gaggaagaag atgatggcta aaccagcgcg aagacgatgt aaaaacgatg aatgccggga | 5580 |
| atggtttcac cctgcattcg ctaatcagtg gtggtgctct ccagagtgtg gaaccaagat | 5640 |
| agcactcgaa cgacgaagta aagaacgcga aaaagcggaa aaagcagcag agaagaaacg | 5700 |
| acgacgagag gagcagaaac agaaagataa acttaagatt cgaaaactcg ccttaaagcc | 5760 |
| ccgcagttac tggattaaac aagcccaaca agccgtaaac gccttcatca gagaaagaga | 5820 |
| ccgcgactta ccatgtatct cgtgcggaac gctcacgtct gctcagtggg atgccggaca | 5880 |

```
ttaccggaca actgctgcgg cacctcaact ccgatttaat gaacgcaata ttcacaagca    5940
atgcgtggtg tgcaaccagc acaaaagcgg aaatctcgtt ccgtatcgcg tcgaactgat    6000
tagccgcatc gggcaggaag cagtagacga aatcgaatca aaccataacc gccatcgctg    6060
gactatcgaa gagtgcaagg cgatcaaggc agagtaccaa cagaaactca aagacctgcg    6120
aaatagcaga agtgaggccg catgacgttc tcagtaaaaa ccattccaga catgctcgtt    6180
gaagcatacg gaaatcagac agaagtagca cgcagactga aatgtagtcg cggtacggtc    6240
agaaaatacg ttgatgataa agacgggaaa atgcacgcca tcgtcaacga cgttctcatg    6300
gttcatcgcg gatggagtga aagagatgcg ctattacgaa aaaattgatg gcagcaaata    6360
ccgaaatatt tgggtagttg gcgatctgca cggatgctac acgaacctga tgaacaaact    6420
ggatacgatt ggattcgaca acaaaaaaga cctgcttatc tcggtgggcg atttggttga    6480
tcgtggtgca gagaacgttg aatgcctgga attaatcaca ttcccctggt tcagagctgt    6540
acgtggaaac catgagcaaa tgatgattga tggcttatca gagcgtggaa acgttaatca    6600
ctggctgctt aatggcggtg gctggttctt taatctcgat tacgacaaag aaattctggc    6660
taaagctctt gcccataaag cagatgaact tccgttaatc atcgaactgg tgagcaaaga    6720
taaaaaatat gttatctgcc acgccgatta tcccttttgac gaatacgagt ttggaaagcc    6780
agttgatcat cagcaggtaa tctggaaccg gaacgaatc agcaactcac aaaacgggat    6840
cgtgaaagaa atcaaaggcg cggacacgtt catctttggt catacgccag cagtgaaacc    6900
actcaagttt gccaaccaaa tgtatatcga taccggcgca gtgttctgcg gaaacctaac    6960
attgattcag gtacagggag aaggcgcatg agactcgaaa gcgtagctaa atttcattcg    7020
ccaaaaagcc cgatgatgag cgactcacca cgggccacgg cttctgactc tctttccggt    7080
actgatgtga tggctgctat ggggatggcg caatcacaag ccggattcgg tatggctgca    7140
ttctgcggta agcacgaact cagccagaac gacaaacaaa aggctatcaa ctatctgatg    7200
caatttgcac acaaggtatc ggggaaatac cgtggtgtgg caaagcttga aggaaatact    7260
aaggcaaagg tactgcaagt gctcgcaaca ttcgcttatg cggattattg ccgtagtgcc    7320
gcgacgccgg gggcaagatg cagagattgc catggtacga gccgtgcggt tgatattgcc    7380
aaaacagagc tgtgggggag agttgtcgag aaagagtgcg gaagatgcaa aggcgtcggc    7440
tattcaagga tgccagcaag cgcagcatat cgcgctgtga cgatgctaat cccaaacctt    7500
acccaaccca cctggtcacg cactgttaag ccgctgtatg acgctctggt ggtgcaatgc    7560
cacaaagaag agtcaatcgc agacaacatt ttgaatgcgg tcacacgtta gcagcatgat    7620
tgccacggat ggcaacatat taacggcatg atattgactt attgaataaa attgggtaaa    7680
tttgactcaa cgatgggtta attcgctcgt tgtggtagtg agatgaaaag aggcggcgct    7740
tactaccgat tccgcctagt tggtcacttc gacgtatcgt ctggaactcc aaccatcgca    7800
ggcagagagg tctgcaaaat gcaatcccga aacagttcgc aggtaatagt tagagcctgc    7860
ataacggttt cgggatttt tatatctgca caacaggtaa gagcattgag tcgataatcg    7920
tgaagagtcg gcgagcctgg ttagccagtg ctctttccgt tgtgctgaat taagcgaata    7980
ccggaagcag aaccggatca ccaaatgcgt acaggcgtca tcgccgccca gcaacagcac    8040 aacccaaaact gagccgtagc cactgtctgt cctgaattca ttagtaatag ttacgctgcg    8100
gccttttaca catgaccttc gtgaaagcgg gtggcaggag gtcgcgctaa caacctcctg    8160
ccgttttgcc cgtgcatatc ggtcacgaac aaatctgatt actaaacaca gtagcctgga    8220
```

```
tttgttctat cagtaatcga ccttattcct aattaaatag agcaaatccc cttattgggg    8280
gtaagacatg aagatgccag aaaaacatga cctgttggcc gccattctcg cggcaaagga    8340
acaaggcatc ggggcaatcc ttgcgtttgc aatggcgtac cttcgcggca gatataatgg    8400
cggtgcgttt acaaaaacag taatcgacgc aacgatgtgc gccattatcg cctggttcat    8460
tcgtgacctt ctcgacttcg ccggactaag tagcaatctc gcttatataa cgagcgtgtt    8520
tatcggctac atcggtactg actcgattgg ttcgcttatc aaacgcttcg ctgctaaaaa    8580
agccggagta aagatggta gaaatcaata atcaacgtaa ggcgttcctc gatatgctgg    8640
cgtggtcgga gggaactgat aacggacgtc agaaaaccag aaatcatggt tatgacgtca    8700
ttgtaggcgg agagctattt actgattact ccgatcaccc tcgcaaactt gtcacgctaa    8760
acccaaaact caaatcaaca ggcgcttaag actggccgtc gttttacaac acagaaagag    8820
tttgtagaaa cgcaaaaagg ccatccgtca ggggccttct gcttagtttg atgcctggca    8880
gttccctact ctcgccttcc gcttcctcgc tcactgactc gctgcgctcg gtcgttcggc    8940
tgcggcgagc ggtatcagct cactcaaagg cggtaatacg ttatccaca gaatcagggg    9000
ataacgcagg aaagaacatg tgagcaaaag gccagcaaaa ggccaggaac cgtaaaaagg    9060
ccgcgttgct ggcgtttttc cataggctcc gcccccctga cgagcatcac aaaaatcgac    9120
gctcaagtca gaggtggcga aacccgacag gactataaag ataccaggcg tttccccctg    9180
gaagctccct cgtgcgctct cctgttccga cctgccgct taccggatac ctgtccgcct    9240
ttctccctc gggaagcgtg gcgctttctc atagctcacg ctgtaggtat ctcagttcgg    9300
tgtaggtcgt tcgctccaag ctgggctgtg tgcacgaacc ccccgttcag cccgaccgct    9360
gcgccttatc cggtaactat cgtcttgagt ccaacccggt aagacacgac ttatcgccac    9420
tggcagcagc cactggtaac aggattagca gagcgaggta tgtaggcggt gctacagagt    9480
tcttgaagtg gtgggctaac tacggctaca ctagaagaac agtatttggt atctgcgctc    9540
tgctgaagcc agttaccttc ggaaaaagag ttggtagctc ttgatccggc aaacaaacca    9600
ccgctggtag cggtggtttt tttgtttgca agcagcagat tacgcgcaga aaaaaaggat    9660
ctcaagaaga tccttttgatc ttttctacgg ggtctgacgc tcagtggaac gacgcgcgcg    9720
taactcacgt taagggatt tggtcatgag cttgcgccgt cccgtcaagt cagcgtaatg    9780
ctctgctttt agaaaaactc atcgagcatc aaatgaaact gcaatttatt catatcagga    9840
ttatcaatac catattttg aaaaagccgt ttctgtaatg aaggagaaaa ctcaccgagg    9900
cagttccata ggatgcaag atcctggtat cggtctgcga ttccgactcg tccaacatca    9960
atacaaccta ttaatttccc ctcgtcaaaa ataaggttat caagtgagaa atcaccatga   10020
gtgacgactg aatccggtga gaatggcaaa agtttatgca tttctttcca gacttgttca   10080
acaggccagc cattacgctc gtcatcaaaa tcactcgcat caaccaaacc gttattcatt   10140
cgtgattgcg cctgagcgag gcgaaatacg cgatcgctgt taaaaggaca attacaaaca   10200
ggaatcgagt gcaaccggcg caggaacact gccagcgcat caacaatatt ttcacctgaa   10260
tcaggatatt cttctaatac ctggaacgct gttttccgg ggatcgcagt ggtgagtaac   10320
catgcatcat caggagtacg gataaaatgc ttgatggtcg gaagtggcat aaattccgtc   10380
agccagttta gtctgaccat ctcatctgta acatcattgg caacgctacc tttgccatgt   10440
ttcagaaaca actctggcgc atcgggcttc ccatacaagc gatagattgt cgcacctgat   10500
tgcccgacat tatcgcgagc ccatttatac ccatataaat cagcatccat gttggaattt   10560
aatcgcggcc tcgacgtttc ccgttgaata tggctcatat tcttcctttt tcaatattat   10620
```

-continued

```
tgaagcattt atcagggtta ttgtctcatg agcggataca tatttgaatg tatttagaaa    10680
aataaacaaa taggggtcag tgttacaacc aattaaccaa ttctgaacat tatcgcgagc    10740
ccatttatac ctgaatatgg ctcataacac cccttgtttg cctggcggca gtagcgcggt    10800
ggtcccacct gaccccatgc cgaactcaga agtgaaacgc cgtagcgccg atggtagtgt    10860
ggggactccc catgcgagag tagggaactg ccaggcatca aataaaacga aaggctcagt    10920
cgaaagactg ggcctttcgc ccgggctaat taggggggtgt cgcccttatt cgactctata    10980
gtgaagttcc tattctctag aaagtatagg aacttctgaa gtggggtcga cttaattaag    11040
g                                                                    11041
```

<210> SEQ ID NO 32
<211> LENGTH: 11206
<212> TYPE: DNA
<213> ORGANISM: Artificial Sequence
<220> FEATURE:
<223> OTHER INFORMATION: constructed sequence

<400> SEQUENCE: 32

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
aagatccaag ctcagatctc gatcgagttg ggccccagaa gcctggtggt tgtttgtcct     240
tctcagggga aaagtgaggc ggccccttgg aggaagggggc cgggcagaat gatctaatcg     300
gattccaagc agctcagggg attgtctttt tctagcacct tcttgccact cctaagcgtc     360
ctccgtgacc ccggctggga tttagcctgg tgctgtgtca gccccggtct cccaggggct     420
tcccagtggt ccccaggaac cctcgacagg gcccggtctc tctcgtccag caagggcagg     480
gacgggccac aggccaaggg ccctcgatcg aggaactgaa aaaccagaaa gttaactggt     540
aagtttagtc ttttttgtctt ttatttcagg tcccggatcc ggtggtggtg caaatcaaag     600
aactgctcct cagtggatgt tgcctttact tctaggcctg tacggaagtg ttacttctgc     660
tctaaaagct gcggaattgt acccgcggcc gccaccatgg ctaagattaa cacccagtac     720
tcacatccat cccgcactca cctcaaagtc aagacctccg atcgggatct gaaccgggct     780
gagaatgggc tgtcgcgcgc ccactcgtcg tccgaggaaa ccagcagcgt gctccagccg     840
ggcatcgcca tggaaactag ggggctggcg gactccggac agggatcctt cactggacag     900
ggtattgccc ggtcgggcg gattcagaag aagtcccagc cggagaaggt cgtgcgggct     960
gccagcaggg gcaggccact cattggttgg acacagtggt gcgctgagga tggtggagat    1020
gaatcggaaa tggcactggc cggctctccc ggatgcagct cgggccccca agggagactg    1080
agcagactga tcttcctgct tcgccgctgg gcggccagac acgtgcacca tcaggaccag    1140
ggacctgata gcttccccga ccgctttagg ggagccgagc tgaaagaagt gtcaagccag    1200
gagtcaaacg cgcaggccaa cgtcggcagc caagagcctg cagaccgggg acgctcggca    1260
tggccgctcg caaagtgcaa cactaacact tccaacaaca ccgaagagga aagaaaaacc    1320
aagaagaagg atgcaattgt ggtggaccct tcctccaacc tgtactaccg ctggttgacc    1380
gccatcgccc tccggtctt ttacaattgg tatctcctta tctgccgggc ctgcttcgac    1440
gaactgcaat cagagtacct gatgctgtgg ctggtgctgg actatagcgc cgatgtgctc    1500
tacgtcctgg atgtgctcgt gcgcgcccgg accggattct tggaacaagg cctgatggtg    1560
```

```
tccgacacga atagactgtg gcagcactat aagaccacaa cccagttcaa gcttgacgtg   1620
ctcagccttg tgccgactga cctggcctac ctgaaagtcg gaactaacta cccggaagtc   1680
agattcaacc gactcctgaa gttcagcagg ctgttcgagt tctttgaccg caccgagact   1740
cggaccaact accctaacat gttccggatc ggaaatctgg tgctctacat actgattatc   1800
atccattgga acgcctgtat ctatttcgcc atttcgaagt tcatcggttt cggaaccgat   1860
tcctgggtgt accccaacat ctcgatcccc gaacacggtc gcctgtcccg gaagtacatc   1920
tactccctgt actggtccac tctgactctg accacgatcg gggaaacccc tccacccgtg   1980
aaggacgaag agtacctgtt cgtggtggtg gacttcctgg tcggagtgtt gattttcgcc   2040
accattgtgg gaaacgtggg ctccatgatc tccaacatga acgcgtcgag agctgagttc   2100
caagccaaga tcgactccat taagcagtac atgcagttca gaaaggtcac caaggacctg   2160
gaaaccaggg tcatccgctg gttcgactac ctgtgggcca acaaaaagac tgtggacgaa   2220
aaggaagtgc tgaagtcgct gccggataag ctgaaggccg aaatcgccat taacgtgcac   2280
cttgacaccc tgaagaaagt ccggatcttc aagactgtg aagccggcct cctggtggag   2340
ctcgtgctca agctgcggcc caccgtgttc agcccgggag attacatttg caagaagggc   2400
gatatcggca aagagatgta catcatcaac gagggaaagc tggccgtggt cgcggacgac   2460
ggcgtgaccc agttcgtggt gctgtccgac ggatcctact tcggtgaaat ctcaatcctc   2520
aacatcaagg gtccaagtc cggcaaccgg agaactgcca acattcgctc catcggatac   2580
agcgacctgt tttgcctgtc caaggatgac ctgatggagg ctctgactga gtaccctgaa   2640
gcgaagaagg ctttggagga aaaggggcgg cagattctga tgaaggacaa tttgatcgac   2700
gaggagctcg cacgggccgg cgccgacccc aaggatctcg aagagaaggt cgaacagctg   2760
ggttcttcgc ttgatacccct gcaaacccga ttcgcgcggc tgctcgccga gtacaacgcg   2820
acccagatga agatgaagca gagactgtca cagttggaat cccaagtcaa gggcggaggc   2880
gacaagccgc tggcggacgg ggaagtgccc ggggacgcca ccaagactga ggacaagcag   2940
cagtgatcat agatcgatct gcctcgactg tgccttctag ttgccagcca tctgttgttt   3000
gccccctcccc cgtgccttcc ttgacccctgg aaggtgccac tcccactgtc ctttcctaat   3060
aaaatgagga aattgcatcg cattgtctga gtaggtgtca ttctattctg gggggtgggg   3120
tggggcagga cagcaagggg gaggattggg aagacaatag caggcatgct ggggactcga   3180
gttctacgta gataagtagc atggcgggtt aatcattaac tacaaggaac ccctagtgat   3240
ggagttggcc actccctctc tgcgcgctcg ctcgctcact gaggccgggc gaccaaaggt   3300
cgcccgacgc ccgggctttg cccggcggc ctcagtgagc gagcgagcgc gcagccttaa   3360
ttaacctaag gaaaatgaag tgaagttcct atactttcta gagaatagga acttctatag   3420
tgagtcgaat aagggcgaca caaaatttat tctaaatgca taataaatac tgataacatc   3480
ttatagtttg tattatattt tgtattatcg ttgacatgta aattttgat atcaaaaact   3540
gatttccct ttattatttt cgagatttat tttcttaatt ctctttaaca aactagaaat   3600
attgtatata caaaaaatca taaataatag atgaatagtt taattatagg tgttcatcaa   3660
tcgaaaaagc aacgtatctt atttaaagtg cgttgctttt ttctcattta taaggttaaa   3720
taattctcat atatcaagca aagtgacagg cgcccttaaa tattctgaca aatgctcttt   3780
ccctaaactc ccccataaa aaacccgcc gaagcgggtt tttacgttat ttgcggatta   3840
acgattactg gttatcagaa ccgcccaggg ggccgagct taaccttttt atttggggga   3900
gagggaagtc atgaaaaaac taacctttga aattcgatct ccagcacatc agcaaaacgc   3960
```

```
tattcacgca gtacagcaaa tccttccaga cccaaccaaa ccaatcgtag taaccattca    4020
ggaacgcaac cgcagcttag accaaaacag gaagctatgg gcctgcttag gtgacgtctc    4080
tcgtcaggtt gaatggcatg gtcgctggct ggatgcagaa agctggaagt gtgtgtttac    4140
cgcagcatta aagcagcagg atgttgttcc taaccttgcc gggaatggct ttgtggtaat    4200
aggccagtca accagcagga tgcgtgtagg cgaatttgcg gagctattag agcttataca    4260
ggcattcggt acagagcgtg gcgttaagtg gtcagacgaa gcgagactgg ctctggagtg    4320
gaaagcgaga tggggagaca gggctgcatg ataaatgtcg ttagtttctc cggtggcagg    4380
acgtcagcat atttgctctg gctaatggag caaaagcgac gggcaggtaa agacgtgcat    4440
tacgttttca tggatacagg ttgtgaacat ccaatgacat atcggtttgt cagggaagtt    4500
gtgaagttct gggatatacc gctcaccgta ttgcaggttg atatcaaccc ggagcttgga    4560
cagccaaatg gttatacggt atgggaacca aaggatattc agacgcgaat gcctgttctg    4620
aagccattta tcgatatggt aaagaaatat ggcactccat acgtcggcgg cgcgttctgc    4680
actgacagat taaaactcgt tcccttcacc aaatactgtg atgaccattt cgggcgaggg    4740
aattacacca cgtggattgg catcagagct gatgaaccga agcggctaaa gccaaagcct    4800
ggaatcagat atcttgctga actgtcagac tttgagaagg aagatatcct cgcatggtgg    4860
aagcaacaac cattcgattt gcaaataccg gaacatctcg gtaactgcat attctgcatt    4920
aaaaaatcaa cgcaaaaaat cggacttgcc tgcaaagatg aggagggatt gcagcgtgtt    4980
tttaatgagg tcatcacggg atcccatgtg cgtgacggac atcgggaaac gccaaaggag    5040
attatgtacc gaggaagaat gtcgctggac ggtatcgcga aaatgtattc agaaaatgat    5100
tatcaagccc tgtatcagga catggtacga gctaaaagat tcgataccgg ctcttgttct    5160
gagtcatgcg aaatatttgg agggcagctt gatttcgact tcgggaggga agctgcatga    5220
tgcgatgtta tcggtgcggt gaatgcaaag aagataaccg cttccgacca aatcaacctt    5280
actggaatcg atggtgtctc cggtgtgaaa gaacaccaac aggggtgtta ccactaccgc    5340
aggaaaagga ggacgtgtgg cgagacagcg acgaagtatc accgacataa tctgcgaaaa    5400
ctgcaaatac cttccaacga aacgcaccag aaataaaccc aagccaatcc caaaagaatc    5460
tgacgtaaaa accttcaact acacggctca cctgtgggat atccggtggc taagacgtcg    5520
tgcgaggaaa acaaggtgat tgaccaaaat cgaagttacg aacaagaaag cgtcgagcga    5580
gctttaacgt gcgctaactg cggtcagaag ctgcatgtgc tggaagttca cgtgtgtgag    5640
cactgctgcg cagaactgat gagcgatccg aatagctcga tgcacgagga agaagatgat    5700
ggctaaacca gcgcgaagac gatgtaaaaa cgatgaatgc cgggaatggt ttcaccctgc    5760
attcgctaat cagtggtggt gctctccaga gtgtggaacc aagatagcac tcgaacgacg    5820
aagtaaagaa cgcgaaaaag cggaaaaagc agcagagaag aaacgacgac gagaggagca    5880
gaaacagaaa gataaactta agattcgaaa actcgcctta aagccccgca gttactggat    5940
taaacaagcc caacaagccg taaacgcctt catcagagaa agagaccgcg acttaccatg    6000
tatctcgtgc ggaacgctca cgtctgctca gtgggatgcc ggacattacc ggacaactgc    6060
tgcggcacct caactccgat ttaatgaacg caatattcac aagcaatgcg tggtgtgcaa    6120
ccagcacaaa agcggaaatc tcgttccgta tcgcgtcgaa ctgattagcc gcatcgggca    6180
ggaagcagta gacgaaatcg aatcaaacca taaccgccat cgctggacta tcgaagagtg    6240
caaggcgatc aaggcagagt accaacagaa actcaaagac ctgcgaaata gcagaagtga    6300
```

```
ggccgcatga cgttctcagt aaaaaccatt ccagacatgc tcgttgaagc atacggaaat   6360
cagacagaag tagcacgcag actgaaatgt agtcgcggta cggtcagaaa atacgttgat   6420
gataaagacg ggaaaatgca cgccatcgtc aacgacgttc tcatggttca tcgcggatgg   6480
agtgaaagag atgcgctatt acgaaaaaat tgatggcagc aaataccgaa atatttgggt   6540
agttggcgat ctgcacggat gctacacgaa cctgatgaac aaactggata cgattggatt   6600
cgacaacaaa aaagacctgc ttatctcggt gggcgatttg gttgatcgtg gtgcagagaa   6660
cgttgaatgc ctggaattaa tcacattccc ctggttcaga gctgtacgtg gaaaccatga   6720
gcaaatgatg attgatggct tatcagagcg tggaaacgtt aatcactggc tgcttaatgg   6780
cggtggctgg ttctttaatc tcgattacga caaagaaatt ctggctaaag ctcttgccca   6840
taaagcagat gaacttccgt taatcatcga actggtgagc aaagataaaa aatatgttat   6900
ctgccacgcc gattatccct tgacgaata cgagtttgga aagccagttg atcatcagca   6960
ggtaatctgg aaccgcgaac gaatcagcaa ctcacaaaac gggatcgtga agaaatcaa   7020 aggcgcggac acgttcatct tggtcatac gccagcagtg aaaccactca gtttgccaa   7080 ccaaatgtat atcgataccg gcgcagtgtt ctgcggaaac ctaacattga ttcaggtaca   7140
gggagaaggc gcatgagact cgaaagcgta gctaaatttc attcgccaaa aagcccgatg   7200
atgagcgact caccacgggc cacggcttct gactctcttt ccggtactga tgtgatggct   7260
gctatgggga tggcgcaatc acaagccgga ttcggtatgg ctgcattctg cggtaagcac   7320
gaactcagcc agaacgacaa acaaaaggct atcaactatc tgatgcaatt tgcacacaag   7380
gtatcgggga ataccgtgg tgtggcaaag cttgaaggaa atactaaggc aaaggtactg   7440
caagtgctcg caacattcgc ttatgcggat tattgccgta gtgccgcgac gccgggggca   7500
agatgcagag attgccatgg tacaggccgt gcggttgata ttgccaaaac agagctgtgg   7560
gggagagttg tcgagaaaga gtgcggaaga tgcaaaggcg tcggctattc aaggatgcca   7620
gcaagcgcag catatcgcgc tgtgacgatg ctaatcccaa accttaccca acccacctgg   7680
tcacgcactg ttaagccgct gtatgacgct ctggtggtgc aatgccacaa agaagagtca   7740
atcgcagaca acatttttgaa tgcggtcaca cgttagcagc atgattgcca cggatggcaa   7800
catattaacg gcatgatatt gacttattga ataaaattgg gtaaatttga ctcaacgatg   7860
ggttaattcg ctcgttgtgg tagtgagatg aaaagaggcg gcgcttacta ccgattccgc   7920
ctagttggtc acttcgacgt atcgtctgga actccaacca tcgcaggcag agaggtctgc   7980
aaaatgcaat cccgaaacag ttcgcaggta atagttagag cctgcataac ggtttcggga   8040 tttttatat ctgcacaaca ggtaagagca ttgagtcgat aatcgtgaag agtcggcgag   8100
cctggttagc cagtgctctt tccgttgtgc tgaattaagc gaataccgga agcagaaccg   8160
gatcaccaaa tgcgtacagg cgtcatcgcc gcccagcaac agcacaaccc aaactgagcc   8220
gtagccactg tctgtcctga attcattagt aatagttacg ctgcggcctt ttacacatga   8280
ccttcgtgaa agcgggtggc aggaggtcgc gctaacaacc tcctgccgtt ttgcccgtgc   8340
atatcggtca cgaacaaatc tgattactaa acacagtagc ctggatttgt tctatcagta   8400
atcgacctta ttcctaatta aatagagcaa atcccttat tggggtaag acatgaagat   8460 gccagaaaaa catgacctgt tggccgccat tctcgcggca aaggaacaag gcatcgggc   8520 aatccttgcg tttgcaatgg cgtaccttcg cggcagatat aatggcggtg cgtttacaaa   8580
aacagtaatc gacgcaacga tgtgcgccat tatcgcctgg ttcattcgtg accttctcga   8640
cttcgccgga ctaagtagca atctcgctta tataacgagc gtgtttatcg gctacatcgg   8700
```

```
tactgactcg attggttcgc ttatcaaacg cttcgctgct aaaaaagccg gagtagaaga    8760
tggtagaaat caataatcaa cgtaaggcgt tcctcgatat gctggcgtgg tcggagggaa    8820
ctgataacgg acgtcagaaa accagaaatc atggttatga cgtcattgta ggcggagagc    8880
tatttactga ttactccgat caccctcgca aacttgtcac gctaaaccca aaactcaaat    8940
caacaggcgc ttaagactgg ccgtcgtttt acaacacaga aagagtttgt agaaacgcaa    9000
aaaggccatc cgtcagggc cttctgctta gtttgatgcc tggcagttcc ctactctcgc    9060
cttccgcttc ctcgctcact gactcgctgc gctcggtcgt tcggctgcgg cgagcggtat    9120
cagctcactc aaaggcggta atacggttat ccacagaatc aggggataac gcaggaaaga    9180
acatgtgagc aaaaggccag caaaaggcca ggaaccgtaa aaaggccgcg ttgctggcgt    9240
tttccatag gctccgcccc cctgacgagc atcacaaaaa tcgacgctca agtcagaggt    9300
ggcgaaaccc gacaggacta taaagatacc aggcgtttcc ccctggaagc tccctcgtgc    9360
gctctcctgt tccgaccctg ccgcttaccg gatacctgtc cgcctttctc ccttcgggaa    9420
gcgtggcgct ttctcatagc tcacgctgta ggtatctcag ttcggtgtag gtcgttcgct    9480
ccaagctggg ctgtgtgcac gaaccccccg ttcagcccga ccgctgcgcc ttatccggta    9540
actatcgtct gagtccaac ccggtaagac acgacttatc gccactggca gcagccactg    9600
gtaacaggat tagcagagcg aggtatgtag gcggtgctac agagttcttg aagtggtggg    9660
ctaactacgg ctacactaga agaacagtat ttggtatctg cgctctgctg aagccagtta    9720
ccttcggaaa aagagttggt agctcttgat ccggcaaaca aaccaccgct ggtagcggtg    9780
gtttttttgt ttgcaagcag cagattacgc gcagaaaaaa aggatctcaa gaagatcctt    9840
tgatcttttc tacggggtct gacgctcagt ggaacgacgc gcgcgtaact cacgttaagg    9900
gattttggtc atgagcttgc gccgtcccgt caagtcagcg taatgctctg cttttagaaa    9960
aactcatcga gcatcaaatg aaactgcaat ttattcatat caggattatc aataccatat   10020
ttttgaaaaa gccgtttctg taatgaagga gaaaactcac cgaggcagtt ccataggatg   10080
gcaagatcct ggtatcggtc tgcgattccg actcgtccaa catcaataca acctattaat   10140
ttcccctcgt caaaaataag gttatcaagt gagaaatcac catgagtgac gactgaatcc   10200
ggtgagaatg gcaaaagttt atgcatttct ttccagactt gttcaacagg ccagccatta   10260
cgctcgtcat caaaatcact cgcatcaacc aaaccgttat tcattcgtga ttgcgcctga   10320
gcgaggcgaa atacgcgatc gctgttaaaa ggacaattac aaacaggaat cgagtgcaac   10380
cggcgcagga acactgccag cgcatcaaca atatttcac ctgaatcagg atattcttct   10440
aatacctgga acgctgtttt tccggggatc gcagtggtga gtaaccatgc atcatcagga   10500
gtacggataa aatgcttgat ggtcggaagt ggcataaatt ccgtcagcca gtttagtctg   10560
accatctcat ctgtaacatc attggcaacg ctacctttgc catgtttcag aaacaactct   10620
ggcgcatcgg gcttcccata caagcgatag attgtcgcac ctgattgccc gacattatcg   10680
cgagcccatt tatacccata taaatcagca tccatgttgg aatttaatcg cggcctcgac   10740
gtttcccgtt gaatatggct catattcttc ctttttcaat attattgaag catttatcag   10800
ggttattgtc tcatgagcgg atacatattt gaatgtattt agaaaaataa acaaataggg   10860
gtcagtgtta caaccaatta accaattctg aacattatcg cgagcccatt tatacctgaa   10920
tatggctcat aacaccccctt gtttgcctgg cggcagtagc gcggtggtcc cacctgaccc   10980
catgccgaac tcagaagtga aacgccgtag cgccgatggt agtgtgggga ctccccatgc   11040
```

```
gagagtaggg aactgccagg catcaaataa acgaaaggc tcagtcgaaa gactgggcct    11100
ttcgcccggg ctaattaggg ggtgtcgccc ttattcgact ctatagtgaa gttcctattc    11160
tctagaaagt ataggaactt ctgaagtggg gtcgacttaa ttaagg                   11206
```

<210> SEQ ID NO 33
<211> LENGTH: 11435
<212> TYPE: DNA
<213> ORGANISM: Artificial Sequence
<220> FEATURE:
<223> OTHER INFORMATION: constructed sequence

<400> SEQUENCE: 33

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
ctgaagagac agaaatatct ctaattccat gagcggtcat acgaggcaag agaagccgct     240
tagagcatgg acttagttag tttcaggat tggacagagt caagagctgg ggtgaggagg      300
ttaccctcgg tagggtgac acagatgtca accgccatt ccctccacat gcatgtcctg      360
ccagaagaac ctgtccctgg gctgggaatc ttatattacc ttcctctcca atgagaagag     420
aagttcaagg ctcacagaca tgtgcataca caagctcaat gcactcaaga ttcccctcca     480
ccactcctgc ccccactacc tacaggagat tgactcctgc tgtgcacata agctgggata     540
atcagggttt ctaaacatca gcttcaaaag tccaatgtcc aaagtggtgg ggggccgggg     600
aacgaggtac tctttccata cccttggctt ttgtgtggcc tggagccgct gatatagaga     660
ttggagtggg acacgaggta ttcctttcaa aaacacaaag gcctatactt tgagccctcc     720
catttcaatc ccccaccatg cttcaccttt aagacctcca actccacttt gatcccagtt     780
ctcaggttca ggcctcacaa ggccaaaatc tgaagttac ccttctcaaa ctcccttgcc      840
tttaacatca tcagaatcaa cctcctaccc ccactctgtc ccagcagcaa tagcctgcta     900 atctttagc actaatcttt taggcactaa tctgcttcc aaactcttgg cacctgaact       960
atttataagc agtgttttat gcccccccac caaagaaccc tattctttc ccatgacccc     1020 accaatcaaa acactcagag gactgtgggt ataagaggct ggggaggcag gcatagcagc    1080
ggccgccacc atggccaaga tcaacaccca atactcccac ccctccagga cccacctcaa    1140
ggtaaagacc tcagaccggg atctcaatcg cgctgaaaat ggcctcagca gagcccactc    1200
gtcaagtgag gagacatcgt cagtgctgca gccggggatc gccatggaga ccagaggact    1260
ggctgactcc gggcagggct ccttcaccgg ccaggggatc gccaggctgt cgcgcctcat    1320
cttcttgctg cgcaggtggg ctgccaggca tgtgcaccac caggaccagg accggactc     1380 ttttcctgat cgtttccgtg gagccgagct taaggaggtg tccagccaag aaagcaatgc    1440
ccaggcaaat gtgggcagcc aggagccagc agacagaggg agaagcgcct ggcccctggc    1500
caaatgcaac actaacacca gcaacaacac ggaggaggag aagaagacga aaaagaagga    1560
tgcgatcgtg gtggacccgt ccagcaacct gtactaccgc tggctgaccg ccatcgccct    1620
gcctgtcttc tataactggt atctgcttat ttgcagggcc tgtttcgatg agctgcagtc    1680
cgagtacctg atgctgtggc tggtcctgga ctactcggca gatgtcctgt atgtcttgga    1740
tgtgcttgta cgagctcgga caggttttct tgagcaaggc ttaatggtca gtgataccaa    1800
caggctgtgg cagcattaca agacgaccac gcagttcaag ctggatgtgt tgtccctggt    1860
ccccaccgac ctggcttact aaaggtgggg cacaaactac ccagaagtga ggttcaaccg    1920
```

```
cctactgaag ttttcccggc tctttgaatt ctttgaccgc acagagacaa ggaccaacta   1980
ccccaatatg ttcaggattg ggaacttggt cttgtacatt ctcatcatca tccactggaa   2040
tgcctgcatc tactttgcca tttccaagtt cattggtttt gggacagact cctgggtcta   2100
cccaaacatc tcaatcccag agcatgggcg cctctccagg aagtacattt acagtctcta   2160
ctggtccacc ttgacccttha ccaccattgg tgagacccca cccccgtga aagatgagga   2220 gtatctcttt gtggtcgtag acttcttggt gggtgttctg attttgcca ccattgtggg   2280 caatgtgggc tccatgatct cgaatatgaa tgcctcacgg gcagagttcc aggccaagat   2340
tgattccatc aagcagtaca tgcagttccg caaggtcacc aaggacttgg agacgcgggt   2400
tatccggtgg tttgactacc tgtgggccaa caagaagacg gtggatgaga aggaggtgct   2460
caagagcctc ccagacaagc tgaaggctga gatcgccatc aacgtgcacc tggacacgct   2520
gaagaaggtt cgcatcttcc aggactgtga ggcagggctg ctggtggagc tggtgctgaa   2580
gctgcgaccc actgtgttca gccctgggga ttatatctgc aagaagggag atattgggaa   2640
ggagatgtac atcatcaacg agggcaagct ggccgtggtg gctgatgatg ggtcaccca   2700 gttcgtggtc ctcagcgatg gcagctactt cggggagatc agcattctga acatcaaggg   2760
gagcaagtcg gggaaccgca ggacggccaa catccgcagc attggctact cagacctgtt   2820
ctgcctctca aggacgatc tcatggaggc cctcaccgag tacccgaagc caagaaggc   2880 cctggaggag aaaggacggc agatcctgat gaaagacaac ctgatcgatg aggagctggc   2940
cagggcgggc gcggaccca aggaccttga ggagaaagtg gagcagctgg ggtcctccct   3000
ggacaccctg cagaccaggt ttgcacgcct cctggctgag tacaacgcca cccagatgaa   3060
gatgaagcag cgtctcagcc aactggaaag ccaggtgaag ggtggtgggg acaagcccct   3120
ggctgatggg gaagttcccg gggatgctac aaaaacagag gacaaacaac agtgatcata   3180
gatcgatctg cctcgactgt gccttctagt tgccagccat ctgttgttg cccctcccc   3240 gtgccttcct tgaccctgga aggtgccact cccactgtcc tttcctaata aaatgaggaa   3300
attgcatcgc attgtctgag taggtgtcat tctattctgg ggggtggggt ggggcaggac   3360
agcaaggggg aggattggga agacaatagc aggcatgctg gggactcgag ttctacgtag   3420
ataagtagca tggcgggtta atcattaact acaaggaacc cctagtgatg gagttggcca   3480
ctccctctct gcgcgctcgc tcgctcactg aggccgggcg accaaaggtc gcccgacgcc   3540
cgggctttgc ccgggcggcc tcagtgagcg agcgagcgcg cagccttaat taacctaagg   3600
aaaatgaagt gaagttccta tactttctag agaataggaa cttctatagt gagtcgaata   3660
agggcgacac aaaatttatt ctaaatgcat aataaatact gataacatct tatagtttgt   3720
attatatttt gtattatcgt tgacatgtat aattttgata tcaaaactg attttcccctt   3780 tattattttc gagatttatt ttcttaattc tctttaacaa actagaaata ttgtatatac   3840
aaaaaatcat aaataataga tgaatagttt aattataggt gttcatcaat cgaaaaagca   3900
acgtatctta tttaaagtgc gttgctttt tctcatttat aaggttaaat aattctcata   3960
tatcaagcaa agtgacaggc gcccttaaat attctgacaa atgctctttc cctaaactcc   4020
ccccataaaa aaacccgccg aagcgggttt ttacgttatt tgcggattaa cgattactcg   4080
ttatcagaac cgcccagggg gcccgagctt aacctttta tttggggag agggaagtca   4140 tgaaaaaact aacctttgaa attcgatctc cagcacatca gcaaaacgct attcacgcag   4200
tacagcaaat ccttccagac ccaaccaaac caatcgtagt aaccattcag gaacgcaacc   4260
```

```
gcagcttaga ccaaaacagg aagctatggg cctgcttagg tgacgtctct cgtcaggttg    4320
aatggcatgg tcgctggctg gatgcagaaa gctggaagtg tgtgtttacc gcagcattaa    4380
agcagcagga tgttgttcct aaccttgccg ggaatggctt tgtggtaata ggccagtcaa    4440
ccagcaggat gcgtgtaggc gaatttgcgg agctattaga gcttatacag gcattcggta    4500
cagagcgtgg cgttaagtgg tcagacgaag cgagactggc tctggagtgg aaagcgagat    4560
ggggagacag ggctgcatga taaatgtcgt tagtttctcc ggtggcagga cgtcagcata    4620
tttgctctgg ctaatggagc aaaagcgacg ggcaggtaaa gacgtgcatt acgttttcat    4680
ggatacaggt tgtgaacatc caatgacata tcggtttgtc agggaagttg tgaagttctg    4740
ggatataccg ctcaccgtat tgcaggttga tatcaacccg gagcttggac agccaaatgg    4800
ttatacggta tgggaaccaa aggatattca gacgcgaatg cctgttctga agccatttat    4860
cgatatggta aagaaatatg gcactccata cgtcggcggc gcgttctgca ctgacagatt    4920
aaaactcgtt cccttcacca atactgtga tgaccatttc gggcgaggga attacaccac     4980
gtggattggc atcagagctg atgaaccgaa gcggctaaag ccaaagcctg aatcagata    5040 tcttgctgaa ctgtcagact ttgagaagga agatatcctc gcatggtgga agcaacaacc    5100
attcgatttg caaataccgg aacatctcgg taactgcata ttctgcatta aaaaatcaac    5160
gcaaaaaatc ggacttgcct gcaaagatga ggagggattg cagcgtgttt ttaatgaggt    5220
catcacggga tcccatgtgc gtgacggaca tcggaaacg ccaaggaga ttatgtaccg     5280 aggaagaatg tcgctggacg gtatcgcgaa aatgtattca gaaaatgatt atcaagccct    5340
gtatcaggac atggtacgag ctaaaagatt cgataccggc tcttgttctg agtcatgcga    5400
aatatttgga gggcagcttg atttcgactt cgggagggaa gctgcatgat gcgatgttat    5460
cggtgcggta aatgcaaaga agataaccgc ttccgaccaa atcaacctta ctggaatcga    5520
tggtgtctcc ggtgtgaaag aacaccaaca ggggtgttac cactaccgca ggaaaaggag    5580
gacgtgtggc gagacagcga cgaagtatca ccgacataat ctgcgaaaac tgcaaatacc    5640
ttccaacgaa acgcaccaga aataaaccca agccaatccc aaaagaatct gacgtaaaaa    5700
ccttcaacta cacggctcac ctgtgggata tccgtggct aagacgtcgt gcgaggaaaa     5760
caaggtgatt gaccaaaatc gaagttacga acaagaaagc gtcgagcgag ctttaacgtg    5820
cgctaactgc ggtcagaagc tgcatgtgct ggaagttcac gtgtgtgagc actgctgcgc    5880
agaactgatg agcgatccga atagctcgat gcacgaggaa gaagatgatg gctaaaccag    5940
cgcgaagacg atgtaaaaac gatgaatgcc gggaatggtt tcaccctgca ttcgctaatc    6000
agtggtggtg ctctccagag tgtggaacca agatagcact cgaacgacga agtaaagaac    6060 gcgaaaagc ggaaaaagca gcagagaaga acgacgacg agaggagcag aaacagaaag      6120
ataaacttaa gattcgaaaa ctcgccttaa agccccgcag ttactggatt aaacaagccc    6180
aacaagccgt aaacgccttc atcagagaaa gagaccgcga cttaccatgt atctcgtgcg    6240
gaacgctcac gtctgctcag tgggatgccg gacattaccg acaactgct gcggcacctc     6300 aactccgatt taatgaacgc aatattcaca agcaatgcgt ggtgtgcaac cagcacaaaa    6360
gcggaaatct cgttccgtat cgcgtcgaac tgattagccg catcgggcag gaagcagtag    6420
acgaaatcga atcaaaccat aaccgccatc gctggactat cgaagagtgc aaggcgatca    6480
aggcagagta ccaacagaaa ctcaaagacc tgcgaaatag cagaagtgag gccgcatgac    6540
gttctcagta aaaaccattc cagacatgct cgttgaagca tacggaaatc agacagaagt    6600
agcacgcaga ctgaaatgta gtcgcggtac ggtcagaaaa tacgttgatg ataaagacgg    6660
```

```
gaaaatgcac gccatcgtca acgacgttct catggttcat cgcggatgga gtgaaagaga   6720
tgcgctatta cgaaaaaatt gatggcagca aataccgaaa tatttgggta gttggcgatc   6780
tgcacggatg ctacacgaac ctgatgaaca aactggatac gattggattc gacaacaaaa   6840
aagacctgct tatctcggtg ggcgatttgg ttgatcgtgg tgcagagaac gttgaatgcc   6900
tggaattaat cacattcccc tggttcagag ctgtacgtgg aaaccatgag caaatgatga   6960
ttgatggctt atcagagcgt ggaaacgtta atcactggct gcttaatggc ggtggctggt   7020
tctttaatct cgattacgac aaagaaattc tggctaaagc tcttgcccat aaagcagatg   7080
aacttccgtt aatcatcgaa ctggtgagca agataaaaa atatgttatc tgccacgccg   7140
attatccctt tgacgaatac gagtttggaa agccagttga tcatcagcag gtaatctgga   7200
accgcgaacg aatcagcaac tcacaaaacg ggatcgtgaa agaaatcaaa ggcgcggaca   7260
cgttcatctt tggtcatacg ccagcagtga aaccactcaa gtttgccaac caaatgtata   7320
tcgataccgg cgcagtgttc tgcggaaacc taacattgat tcaggtacag ggagaaggcg   7380
catgagactc gaaagcgtag ctaaatttca ttcgccaaaa agcccgatga tgagcgactc   7440
accacgggcc acggcttctg actctctttc cggtactgat gtgatggctg ctatggggat   7500
ggcgcaatca caagccggat tcggtatggc tgcattctgc ggtaagcacg aactcagcca   7560
gaacgacaaa caaaaggcta tcaactatct gatgcaattt gcacacaagg tatcggggaa   7620
ataccgtggt gtggcaaagc ttgaaggaaa tactaaggca aaggtactgc aagtgctcgc   7680
aacattcgct tatgcggatt attgccgtag tgccgcgacg ccgggggcaa gatgcagaga   7740
ttgccatggt acaggccgtg cggttgatat tgccaaaaca gagctgtggg ggagagttgt   7800
cgagaaagag tgcggaagat gcaaaggcgt cggctattca aggatgccag caagcgcagc   7860
atatcgcgct gtgacgatgc taatcccaaa ccttacccaa cccacctggt cacgcactgt   7920
taagccgctg tatgacgctc tggtggtgca atgccacaaa gaagagtcaa tcgcagacaa   7980
cattttgaat gcggtcacac gttagcagca tgattgccac ggatggcaac atattaacgg   8040
catgatattg acttattgaa taaaattggg taaatttgac tcaacgatgg gttaattcgc   8100
tcgttgtggt agtgagatga aaagaggcgg cgcttactac cgattccgcc tagttggtca   8160
cttcgacgta tcgtctggaa ctccaaccat cgcaggcaga gaggtctgca aaatgcaatc   8220
ccgaaacagt tcgcaggtaa tagttagagc ctgcataacg gtttcgggat tttttatatc   8280
tgcacaacag gtaagagcat tgagtcgata atcgtgaaga gtcggcgagc ctggttagcc   8340
agtgctcttt ccgttgtgct gaattaagcg aataccggaa gcagaaccgg atcaccaaat   8400
gcgtacaggc gtcatcgccg cccagcaaca gcacaaccca aactgagccg tagccactgt   8460
ctgtcctgaa ttcattagta atagttacgc tgcggccttt tacacatgac cttcgtgaaa   8520
gcgggtggca ggaggtcgcg ctaacaacct cctgccgttt tgcccgtgca tatcggtcac   8580
gaacaaatct gattactaaa cacagtagcc tggatttgtt ctatcagtaa tcgacccttat  8640
tcctaattaa atagagcaaa tccccttatt gggggtaaga catgaagatg ccagaaaaac   8700
atgacctgtt ggccgccatt ctcgcggcaa aggaacaagg catcgggca atccttgcgt    8760
ttgcaatggc gtaccttcgc ggcagatata atggcggtgc gtttacaaaa acagtaatcg   8820
acgcaacgat gtgcgccatt atcgcctggt tcattcgtga ccttctcgac ttcgccggac   8880
taagtagcaa tctcgcttat ataacgagcg tgtttatcgg ctacatcggt actgactcga   8940
ttggttcgct tatcaaacgc ttcgctgcta aaaaagccgg agtagaagat ggtagaaatc   9000
```

```
aataatcaac gtaaggcgtt cctcgatatg ctggcgtggt cggagggaac tgataacgga    9060
cgtcagaaaa ccagaaatca tggttatgac gtcattgtag gcggagagct atttactgat    9120
tactccgatc accctcgcaa acttgtcacg ctaaacccaa aactcaaatc aacaggcgct    9180
taagactggc cgtcgtttta caacacgaaa agagtttgta gaaacgcaaa aaggccatcc    9240 gtcagggcc ttctgcttag tttgatgcct ggcagttccc tactctcgcc ttccgcttcc     9300
tcgctcactg actcgctgcg ctcggtcgtt cggctgcggc gagcggtatc agctcactca    9360
aaggcggtaa tacggttatc cacagaatca ggggataacg caggaaagaa catgtgagca    9420
aaaggccagc aaaaggccag gaaccgtaaa aaggccgcgt tgctggcgtt tttccatagg    9480
ctccgccccc ctgacgagca tcacaaaaat cgacgctcaa gtcagaggtg gcgaaacccg    9540
acaggactat aaagatacca ggcgtttccc cctggaagct ccctcgtgcg ctctcctgtt    9600
ccgaccctgc cgcttaccgg atacctgtcc gcctttctcc cttcgggaag cgtggcgctt    9660
tctcatagct cacgctgtag gtatctcagt tcggtgtagg tcgttcgctc caagctgggc    9720
tgtgtgcacg aaccccccgt tcagcccgac cgctgcgcct tatccggtaa ctatcgtctt    9780
gagtccaacc cggtaagaca cgacttatcg ccactggcag cagccactgg taacaggatt    9840
agcagagcga ggtatgtagg cggtgctaca gagttcttga agtggtgggc taactacggc    9900
tacactagaa gaacagtatt tggtatctgc gctctgctga agccagttac cttcggaaaa    9960
agagttggta gctcttgatc cggcaaacaa accaccgctg gtagcggtgg tttttttgtt   10020
tgcaagcagc agattacgcg cagaaaaaaa ggatctcaag aagatccttt gatcttttct   10080
acggggtctg acgctcagtg gaacgacgcg cgcgtaactc acgttaaggg attttggtca   10140
tgagcttgcg ccgtcccgtc aagtcagcgt aatgctctgc ttttagaaaa actcatcgag   10200
catcaaatga aactgcaatt tattcatatc aggattatca ataccatatt tttgaaaaag   10260
ccgtttctgt aatgaaggag aaaactcacc gaggcagttc cataggatgg caagatcctg   10320
gtatcggtct gcgattccga ctcgtccaac atcaatacaa cctattaatt cccctcgtc    10380 aaaaataagg ttatcaagtg agaaatcacc atgagtgacg actgaatccg gtgagaatgg   10440
caaaagttta tgcatttctt tccagacttg ttcaacaggc cagccattac gctcgtcatc   10500
aaaatcactc gcatcaacca accgttatt cattcgtgat tgcgcctgag cgaggcgaaa    10560
tacgcgatcg ctgttaaaag gacaattaca acaggaatc gagtgcaacc ggcgcaggaa    10620
cactgccagc gcatcaacaa tattttcacc tgaatcagga tattcttcta atacctggaa   10680
cgctgttttt ccggggatcg cagtggtgag taaccatgca tcatcaggag tacgataaa    10740 atgcttgatg gtcggaagtg gcataaattc cgtcagccag tttagtctga ccatctcatc   10800
tgtaacatca ttggcaacgc tacctttgcc atgtttcaga aacaactctg gcgcatcggg   10860
cttcccatac aagcgataga ttgtcgcacc tgattgcccg acattatcgc gagcccattt   10920
atacccatat aaatcagcat ccatgttgga atttaatcgc ggcctcgacg tttcccgttg   10980
aatatggctc atattcttcc ttttcaata ttattgaagc atttatcagg gttattgtct    11040
catgagcgga tacatatttg aatgtattta gaaaaataaa caaatagggg tcagtgttac   11100
aaccaattaa ccaattctga acattatcgc gagcccattt atacctgaat atggctcata   11160 acacccttg tttgcctggc ggcagtagcg cggtggtccc acctgacccc atgccgaact    11220
cagaagtgaa acgccgtagc gccgatggta gtgtggggac tccccatgcg agagtaggga   11280
actgccaggc atcaaataaa acgaaaggct cagtcgaaag actgggcctt tcgccggc    11340 taattagggg gtgtcgccct tattcgactc tatagtgaag ttcctattct ctagaaagta   11400
```

-continued taggaacttc tgaagtgggg tcgacttaat taagg    11435

<210> SEQ ID NO 34
<211> LENGTH: 11432
<212> TYPE: DNA
<213> ORGANISM: Artificial Sequence
<220> FEATURE:
<223> OTHER INFORMATION: constructed sequence

<400> SEQUENCE: 34
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gcaagctagc   180
ctgaagagac agaaatatct ctaattccat gagcggtcat acgaggcaag agaagccgct   240
tagagcatgg acttagttag tttcagggat tggacagagt caagagctgg ggtgaggagg   300
ttaccctcgg taggggtgac acagatgtca accgccatt cctccacat gcatgtcctg     360
ccagaagaac ctgtccctgg gctgggaatc ttatattacc ttcctctcca atgagaagag   420
aagttcaagg ctcacagaca tgtgcataca caagctcaat gcactcaaga ttcccctcca   480
ccactcctgc ccccactacc tacaggagat tgactcctgc tgtgcacata agctgggata   540
atcagggttt ctaaacatca gcttcaaaag tccaatgtcc aaagtggtgg ggggccgggg   600
aacgaggtac tctttccata cccttggctt ttgtgtggcc tggagccgct gatatagaga   660
ttggagtggg acacgaggta ttcctttcaa aaacacaaag gcctatactt tgagccctcc   720
catttcaatc ccccaccatg cttcaccttt aagacctcca actccacttt gatcccagtt   780
ctcaggttca ggcctcacaa ggccaaaatc ctgaagttac ccttctcaaa ctcccttgcc   840
tttaacatca tcagaatcaa cctcctaccc ccactctgtc ccagcagcaa tagcctgcta   900
atcttttagc actaatcttt taggcactaa tctgctttcc aaactcttgg cacctgaact   960
atttataagc agtgttttat gccccccac caaagaaccc tattcttttc ccatgacccc    1020
accaatcaaa acactcagag gactgtgggt ataagaggct gggaggcag gcatagcagc    1080
ggccgccacc atggctaaga ttaacaccca gtactcacat ccatcccgca ctcacctcaa   1140
agtcaagacc tccgatcggg atctgaaccg ggctgagaat gggctgtcgc gcgcccactc   1200
gtcgtccgag gaaaccagca gcgtgctcca gccgggcatc gccatggaaa ctaggggct    1260
ggcggactcc ggacagggat ccttcactgg acagggtatt gcccggctga gcagactgat   1320
cttcctgctt cgccgctggg cggccagaca cgtgcaccat caggaccagg gacctgatag   1380
cttcccccgac cgctttaggg gagccgagct gaaagaagtg tcaagccagg agtcaaacgc   1440
gcaggccaac gtcggcagcc aagagcctgc agaccgggga cgctcggcat ggccgctcgc   1500
aaagtgcaac actaacactt ccaacaacac cgaagaggaa aagaaaacca agaagaagga   1560
tgcaattgtg gtggaccctt cctccaacct gtactaccgc tggttgaccg ccatcgccct   1620
cccggtcttt tacaattggt atctccttat ctgccgggcc tgcttcgacg aactgcaatc   1680
agagtacctg atgctgtggc tggtgctgga ctatagcgcc gatgtgctct acgtcctgga   1740
tgtgctcgtg cgcgcccgga ccggattctt ggaacaaggc ctgatggtgt ccgacacgaa   1800
tagactgtgg cagcactata agaccacaac ccagttcaag cttgacgtgc tcagccttgt   1860
gccgactgac ctggcctacc tgaaagtcgg aactaactac ccggaagtca gattcaaccg   1920
actcctgaag ttcagcaggc tgttcgagtt ctttgaccgc accgagactc ggaccaacta   1980

```
ccctaacatg ttccggatcg gaaatctggt gctctacata ctgattatca tccattggaa    2040
cgcctgtatc tatttcgcca tttcgaagtt catcggtttc ggaaccgatt cctgggtgta    2100
ccccaacatc tcgatccccg aacacggtcg cctgtcccgg aagtacatct actccctgta    2160
ctggtccact ctgactctga ccacgatcgg ggaaacccct ccacccgtga aggacgaaga    2220
gtacctgttc gtggtggtgg acttcctggt cggagtgttg atttttcgcca ccattgtggg    2280
aaacgtgggc tccatgatct ccaacatgaa cgcgtcgaga gctgagttcc aagccaagat    2340
cgactccatt aagcagtaca tgcagttcag aaaggtcacc aaggacctgg aaaccagggt    2400
catccgctgg ttcgactacc tgtgggccaa caaaaagact gtggacgaaa aggaagtgct    2460
gaagtcgctg ccggataagc tgaaggccga aatcgccatt aacgtgcacc ttgacaccct    2520
gaagaaagtc cggatcttcc aagactgtga agccggcctc ctggtggagc tcgtgctcaa    2580
gctgcggccc accgtgttca gcccgggaga ttacatttgc aagaagggcg atatcggcaa    2640
agagatgtac atcatcaacg agggaaagct ggccgtggtc gcggacgacg gcgtgaccca    2700
gttcgtggtg ctgtccgacg gatcctactt cggtgaaatc tcaatcctca acatcaaggg    2760
gtccaagtcc ggcaaccgga gaactgccaa cattcgctcc atcggataca gcgacctgtt    2820
ttgcctgtcc aaggatgacc tgatggaggc tctgactgag taccctgaag cgaagaaggc    2880
tttgaggaa aaggggcggc agattctgat gaaggacaat ttgatcgacg aggagctcgc    2940
acgggccggc gccgacccca aggatctcga agagaaggtc gaacagctgg ttcttcgct    3000
tgataccctg caaacccgat tcgcgcggct gctcgccgag tacaacgcga cccagatgaa    3060
gatgaagcag agactgtcac agttggaatc ccaagtcaag gcggaggcg acaagccgct    3120
ggcggacggg gaagtgcccg ggacgccac caagactgag gacaagcagc agtgatcata    3180
gatcctgcct cgactgtgcc ttctagttgc cagccatctg ttgtttgccc ctccccgtg    3240
ccttccttga ccctggaagg tgccactccc actgtccttt cctaataaaa tgaggaaatt    3300
gcatcgcatt gtctgagtag gtgtcattct attctggggg gtggggtggg caggacagc    3360
aaggggagg attgggaaga caatagcagg catgctgggg actcgagttc tacgtagata    3420
agtagcatgg cggttaatc attaactaca aggaacccct agtgatggag ttggccactc    3480
cctctctgcg cgctcgctcg ctcactgagg ccggcgacc aaaggtcgcc cgacgcccgg    3540
gctttgcccg gcggcctca gtgagcgagc gagcgcgcag ccttaattaa cctaaggaaa    3600
atgaagtgaa gttcctatac tttctagaga ataggaactt ctatagtgag tcgaataagg    3660
gcgacacaaa atttattcta aatgcataat aaatactgat aacatcttat agtttgtatt    3720
atattttgta ttatcgttga catgtataat tttgatatca aaaactgatt ttcccttat    3780
tatttttcgag atttattttc ttaattctct ttaacaaact agaaatattg tatatacaaa    3840
aaatcataaa taatagatga atagtttaat tataggtgtt catcaatcga aaaagcaacg    3900
tatcttattt aaagtgcgtt gctttttct catttataag gttaaataat tctcatatat    3960
caagcaaagt gacaggcgcc cttaaatatt ctgacaaatg ctctttccct aaactcccc    4020
cataaaaaaa cccgccgaag cgggtttta cgttatttgc ggattaacga ttactcgtta    4080
tcagaaccgc ccagggggcc cgagcttaac cttttattt gggggagagg gaagtcatga    4140
aaaactaac ctttgaaatt cgatctccag cacatcagca aaacgctatt cacgcagtac    4200
agcaaatcct tccagaccca accaaaccaa tcgtagtaac cattcaggaa cgcaaccgca    4260
gcttagacca aaacaggaag ctatgggcct gcttaggtga cgtctctcgt caggttgaat    4320
ggcatggtcg ctggctggat gcagaaagct ggaagtgtgt gtttaccgca gcattaaagc    4380
```

```
agcaggatgt tgttcctaac cttgccggga atggctttgt ggtaataggc cagtcaacca   4440
gcaggatgcg tgtaggcgaa tttgcggagc tattagagct tatacaggca ttcggtacag   4500
agcgtggcgt taagtggtca gacgaagcga gactggctct ggagtggaaa gcgagatggg   4560
gagacagggc tgcatgataa atgtcgttag tttctccggt ggcaggacgt cagcatattt   4620
gctctggcta atggagcaaa agcgacgggc aggtaaagac gtgcattacg ttttcatgga   4680
tacaggttgt gaacatccaa tgacatatcg gtttgtcagg gaagttgtga agttctggga   4740
tataccgctc accgtattgc aggttgatat caacccggag cttggacagc caaatggtta   4800
tacggtatgg gaaccaaagg atattcgac gcgaatgcct gttctgaagc catttatcga   4860
tatggtaaag aaatatggca ctccatacgt cggcggcgcg ttctgcactg acagattaaa   4920
actcgttccc ttcaccaaat actgtgatga ccatttcggg cgagggaatt acaccacgtg   4980
gattggcatc agagctgatg aaccgaagcg gctaaagcca aagcctggaa tcagatatct   5040
tgctgaactg tcagactttg agaaggaaga tatcctcgca tggtggaagc aacaaccatt   5100
cgatttgcaa ataccggaac atctcggtaa ctgcatattc tgcattaaaa aatcaacgca   5160
aaaaatcgga cttgcctgca aagatgagga gggattgcag cgtgttttta atgaggtcat   5220
cacgggatcc catgtgcgtg acggacatcg ggaaacgcca aaggagatta tgtaccgagg   5280
aagaatgtcg ctgacggta tcgcgaaaat gtattcagaa aatgattatc aagccctgta   5340
tcaggacatg gtacgagcta aaagattcga taccggctct tgttctgagt catgcgaaat   5400
atttggaggg cagcttgatt tcgacttcgg gagggaagct gcatgatgcg atgttatcgg   5460
tgcggtgaat gcaagaagaa taaccgcttc cgaccaaatc aaccttactg gaatcgatgg   5520
tgtctccggt gtgaaagaac accaacaggg gtgttaccac taccgcagga aaaggaggac   5580
gtgtggcgag acagcgacga agtatcaccg acataatctg cgaaaactgc aaataccttc   5640
caacgaaacg caccagaaat aaacccaagc caatcccaaa agaatctgac gtaaaaacct   5700
tcaactacac ggctcacctg tgggatatcc ggtggctaag acgtcgtgcg aggaaaacaa   5760
ggtgattgac caaaatcgaa gttacgaaca agaaagcgtc gagcgagctt aacgtgcgc   5820 taactgcggt cagaagctgc atgtgctgga agttcacgtg tgtgagcact gctgcgcaga   5880
actgatgagc gatccgaata gctcgatgca cgaggaagaa gatgatggct aaaccagcgc   5940
gaagacgatg taaaaacgat gaatgccggg aatggtttca ccctgcattc gctaatcagt   6000
ggtggtgctc tccagagtgt ggaaccaaga tagcactcga acgacgaagt aaagaacgcg   6060
aaaaagcgga aaaagcagca gagaagaaac gacgacgaga ggagcagaaa cagaaagata   6120
aacttaagat tcgaaaactc gccttaaagc cccgcagtta ctggattaaa caagcccaac   6180
aagccgtaaa cgccttcatc agagaaagag accgcgactt accatgtatc tcgtgcggaa   6240
cgctcacgtc tgctcagtgg gatgccggac attaccggac aactgctgcg gcacctcaac   6300
tccgatttaa tgaacgcaat attcacaagc aatgcgtggt gtgcaaccag cacaaaagcg   6360
gaaatctcgt tccgtatcgc gtcgaactga ttagccgcat cgggcaggaa gcagtagacg   6420
aaatcgaatc aaaccataac cgccatcgct ggactatcga agagtgcaag gcgatcaagg   6480
cagagtacca acagaaactc aaagacctgc gaaatagcag aagtgaggcc gcatgacgtt   6540
ctcagtaaaa accattccag acatgctcgt tgaagcatac ggaaatcaga cagaagtagc   6600
acgcagactg aaatgtagtc gcggtacggt cagaaaatac gttgatgata aagacgggaa   6660
aatgcacgcc atcgtcaacg acgttctcat ggttcatcgc ggatggagtg aaagagatgc   6720
```

```
gctattacga aaaaattgat ggcagcaaat accgaaatat ttgggtagtt ggcgatctgc    6780
acggatgcta cacgaacctg atgaacaaac tggatacgat tggattcgac aacaaaaaag    6840
acctgcttat ctcggtgggc gatttggttg atcgtggtgc agagaacgtt gaatgcctgg    6900
aattaatcac attccctgg ttcagagctg tacgtgaaaa ccatgagcaa atgatgattg     6960
atggcttatc agagcgtgga aacgttaatc actggctgct taatggcggt ggctggttct    7020
ttaatctcga ttcgacaaa gaaattctgg ctaaagctct tgcccataaa gcagatgaac     7080
ttccgttaat catcgaactg gtgagcaaag ataaaaaata tgttatctgc cacgccgatt    7140
atccctttga cgaatacgag tttgaaagc cagttgatca tcagcaggta atctggaacc     7200
gcgaacgaat cagcaactca caaaacggga tcgtgaaaga aatcaaaggc gcggacacgt    7260
tcatctttgg tcatacgcca gcagtgaaac cactcaagtt tgccaaccaa atgtatatcg    7320
ataccggcgc agtgttctgc ggaaacctaa cattgattca ggtacaggga aaggcgcat    7380 gagactcgaa agcgtagcta aatttcattc gccaaaaagc ccgatgatga gcgactcacc    7440
acgggccacg gcttctgact ctcttccgg tactgatgtg atggctgcta tggggatggc     7500
gcaatcacaa gccggattcg gtatggctgc attctgcggt aagcacgaac tcagccagaa    7560
cgacaaacaa aaggctatca actatctgat gcaatttgca cacaaggtat cggggaaata    7620
ccgtggtgtg gcaaagcttg aaggaaatac taaggcaaag gtactgcaag tgctcgcaac    7680
attcgcttat gcggattatt gccgtagtgc cgcgacgccg ggggcaagat gcagagattg    7740
ccatggtaca ggccgtgcgg ttgatattgc caaaacagag ctgtggggga gagttgtcga    7800
gaaagagtgc ggaagatgca aaggcgtcgg ctattcaagg atgccagcaa gcgcagcata    7860
tcgcgctgtg acgatgctaa tcccaaacct tacccaaccc acctggtcac gcactgttaa    7920
gccgctgtat gacgctctgg tggtgcaatg ccacaaagaa gagtcaatcg cagacaacat    7980
tttgaatgcg gtcacacgtt agcagcatga ttgccacgga tggcaacata ttaacggcat    8040
gatattgact tattgaataa aattgggtaa atttgactca acgatgggtt aattcgctcg    8100
ttgtggtagt gagatgaaaa gaggcggcgc ttactaccga ttccgcctag ttggtcactt    8160
cgacgtatcg tctggaactc caaccatcgc aggcagagag gtctgcaaaa tgcaatcccg    8220
aaacagttcg caggtaatag ttagagcctg cataacggtt tcgggatttt ttatatctgc    8280
acaacaggta agagcattga gtcgataatc gtgaagagtc ggcgagcctg gttagccagt    8340
gctctttccg ttgtgctgaa ttaagcgaat accggaagca gaaccggatc accaaatgcg    8400
tacaggcgtc atcgccgccc agcaacagca caacccaaac tgagccgtag ccactgtctg    8460
tcctgaattc attagtaata gttacgctgc ggccttttac acatgacctt cgtgaaagcg    8520
ggtggcagga ggtcgcgcta acaacctcct gccgttttgc ccgtgcatat cggtcacgaa    8580
caaatctgat tactaaacac agtagcctgg atttgttcta tcagtaatcg accttattcc    8640
taattaaata gagcaaatcc ccttattggg ggtaagacat gaagatgcca gaaaacatg     8700 acctgttggc cgccattctc gcggcaaagg aacaaggcat cggggcaatc cttgcgtttg    8760
caatggcgta ccttcgcggc agatataatg gcggtgcgtt tacaaaaaca gtaatcgacg    8820
caacgatgtg cgccattatc gcctggttca ttcgtgacct tctcgacttc gccggactaa    8880
gtagcaatct cgcttatata acgagcgtgt ttatcggcta catcggtact gactcgattg    8940
gttcgcttat caaacgcttc gctgctaaaa aagccggagt agaagatggt agaaatcaat    9000
aatcaacgta aggcgttcct cgatatgctg gcgtggtcgg agggaactga taacggacgt    9060
cagaaaacca gaaatcatgg ttatgacgtc attgtaggcg gagagctatt tactgattac    9120
```

```
tccgatcacc ctcgcaaact tgtcacgcta aacccaaaac tcaaatcaac aggcgcttaa    9180
gactggccgt cgttttacaa cacagaaaga gtttgtagaa acgcaaaaag gccatccgtc    9240 agggggccttc tgcttagttt gatgcctggc agttccctac tctcgccttc cgcttcctcg   9300
ctcactgact cgctgcgctc ggtcgttcgg ctgcggcgag cggtatcagc tcactcaaag    9360
gcggtaatac ggttatccac agaatcaggg gataacgcag gaaagaacat gtgagcaaaa    9420
ggccagcaaa aggccaggaa ccgtaaaaag gccgcgttgc tggcgttttt ccataggctc    9480
cgcccccctg acgagcatca aaaaatcga cgctcaagtc agaggtggcg aaacccgaca     9540
ggactataaa gataccaggc gtttccccct ggaagctccc tcgtgcgctc tcctgttccg    9600
accctgccgc ttaccggata cctgtccgcc tttctccctt cgggaagcgt ggcgctttct    9660
catagctcac gctgtaggta tctcagttcg gtgtaggtcg ttcgctccaa gctgggctgt    9720
gtgcacgaac cccccgttca gcccgaccgc tgcgccttat ccggtaacta tcgtcttgag    9780
tccaacccgg taagacacga cttatcgcca ctggcagcag ccactggtaa caggattagc    9840
agagcgaggt atgtaggcgg tgctacagag ttcttgaagt ggtgggctaa ctacggctac    9900
actagaagaa cagtatttgg tatctgcgct ctgctgaagc cagttacctt cggaaaaaga    9960
gttggtagct cttgatccgg caaacaaacc accgctggta gcggtggttt ttttgtttgc   10020
aagcagcaga ttacgcgcag aaaaaaagga tctcaagaag atcctttgat cttttctacg   10080
gggtctgacg ctcagtggaa cgacgcgcgc gtaactcacg ttaagggatt ttggtcatga   10140
gcttgcgccg tcccgtcaag tcagcgtaat gctctgcttt tagaaaaact catcgagcat   10200
caaatgaaac tgcaatttat tcatatcagg attatcaata ccatatttt gaaaaagccg   10260 tttctgtaat gaaggagaaa actcaccgag gcagttccat aggatggcaa gatcctggta   10320
tcggtctgcg attccgactc gtccaacatc aatacaacct attaatttcc cctcgtcaaa   10380
aataaggtta tcaagtgaga atcaccatg agtgacgact gaatccggtg agaatggcaa    10440
aagtttatgc atttctttcc agacttgttc aacaggccag ccattacgct cgtcatcaaa   10500
atcactcgca tcaaccaaac cgttattcat tcgtgattgc gcctgagcga ggcgaaatac   10560
gcgatcgctg ttaaaaggac aattacaaac aggaatcgag tgcaaccggc gcaggaacac   10620
tgccagcgca tcaacaatat tttcacctga atcaggatat tcttctaata cctggaacgc   10680 tgttttttccg gggatcgcag tggtgagtaa ccatgcatca tcaggagtac ggataaaatg   10740
cttgatggtc ggaagtggca taaattccgt cagccagttt agtctgacca tctcatctgt   10800
aacatcattg gcaacgctac ctttgccatg tttcagaaac aactctggcg catcgggctt   10860
cccatacaag cgatagattg tcgcacctga ttgcccgaca ttatcgcgag cccatttata   10920
cccatataaa tcagcatcca tgttggaatt taatcgcggc ctcgacgttt ccgttgaat    10980 atggctcata ttcttccttt ttcaatatta ttgaagcatt tatcagggtt attgtctcat   11040
gagcggatac atatttgaat gtatttagaa aaataaacaa ataggggtca gtgttacaac   11100
caattaacca attctgaaca ttatcgcgag cccatttata cctgaatatg gctcataaca   11160 cccccttgttt gcctggcggc agtagcgcgg tggtcccacc tgaccccatg ccgaactcag   11220
aagtgaaacg ccgtagcgcc gatggtagtg tgggggactcc ccatgcgaga gtagggaact   11280
gccaggcatc aaataaaacg aaaggctcag tcgaaagact gggcctttcg cccgggctaa   11340 ttaggggtg tcgcccttat tcgactctat agtgaagttc ctattctcta gaaagtatag   11400
gaacttctga agtggggtcg acttaattaa gg                                  11432
```

<210> SEQ ID NO 35
<211> LENGTH: 11600
<212> TYPE: DNA
<213> ORGANISM: Artificial Sequence
<220> FEATURE:
<223> OTHER INFORMATION: constructed sequence

<400> SEQUENCE: 35

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
ctgaagagac agaaatatct ctaattccat gagcggtcat acgaggcaag agaagccgct     240
tagagcatgg acttagttag tttcagggat tggacagagt caagagctgg ggtgaggagg     300
ttaccctcgg taggggtgac acagatgtca accgcctatt ccctccacat gcatgtcctg     360
ccagaagaac ctgtccctgg gctgggaatc ttatattacc ttcctctcca atgagaagag     420
aagttcaagg ctcacagaca tgtgcataca caagctcaat gcactcaaga ttcccctcca     480
ccactcctgc ccccactacc tacaggagat tgactcctgc tgtgcacata agctgggata     540
atcagggttt ctaaacatca gcttcaaaag tccaatgtcc aaagtggtgg ggggccgggg     600
aacgaggtac tctttccata cccttggctt ttgtgtggcc tggagccgct gatatagaga     660
ttggagtggg acacgaggta ttcctttcaa aaacacaaag gcctatactt tgagccctcc     720
catttcaatc ccccaccatg cttcaccttt aagacctcca actccacttt gatcccagtt     780
ctcaggttca ggcctcacaa ggccaaaatc ctgaagttac ccttctcaaa ctcccttgcc     840
tttaacatca tcagaatcaa cctcctaccc ccactctgtc ccagcagcaa tagcctgcta     900
atcttttagc actaatcttt taggcactaa tctgctttcc aaactcttgg cacctgaact     960
atttataagc agtgttttat gcccccccac caaagaaccc tattcttttc ccatgacccc    1020
accaatcaaa acactcagag gactgtgggt ataagaggct ggggaggcag gcatagcagc    1080
ggccgccacc atggctaaga ttaacaccca gtactcacat ccatcccgca ctcacctcaa    1140
agtcaagacc tccgatcggg atctgaaccg ggctgagaat gggctgtcgc gcgcccactc    1200
gtcgtccgag gaaaccagca gcgtgctcca gccgggcatc gccatggaaa ctaggggggct    1260
ggcggactcc ggacagggat ccttcactgg acagggtatt gcccggttcg ggcggattca    1320
gaagaagtcc cagccggaga aggtcgtgcg ggctgccagc aggggcaggc cactcattgg    1380
ttggacacag tggtgcgctg aggatggtgg agatgaatcg gaaatggcac tggccggctc    1440
tcccggatgc agctcgggcc cccaagggag actgagcaga ctgatcttcc tgcttcgccg    1500
ctgggcggcc agacacgtgc accatcagga ccagggacct gatagcttcc ccgaccgctt    1560
taggggagcc gagctgaaag aagtgtcaag ccaggagtca aacgcgcagg ccaacgtcgg    1620
cagccaagag cctgcagacc ggggacgctc ggcatggccg ctcgcaaagt gcaacactaa    1680
cacttccaac aacaccgaag aggaaaagaa accaagaag aaggatgcaa ttgtggtgga    1740
cccttcctcc aacctgtact accgctggtt gaccgccatc gccctcccgg tcttttacaa    1800
ttggtatctc cttatctgcc gggcctgctt cgacgaactg caatcagagt acctgatgct    1860
gtggctggtg ctggactata gcgccgatgt gctctacgtc ctggatgtgc tcgtgcgcgc    1920
ccggaccgga ttcttggaac aaggcctgat ggtgtccgac acgaatagac tgtggcagca    1980
ctataagacc acaacccagt tcaagcttga cgtgctcagc cttgtgccga ctgacctggc    2040
ctacctgaaa gtcggaacta actacccgga agtcagattc aaccgactcc tgaagttcag    2100
```

```
caggctgttc gagttctttg accgcaccga gactcggacc aactacccta acatgttccg    2160
gatcggaaat ctggtgctct acatactgat tatcatccat tggaacgcct gtatctattt    2220
cgccatttcg aagttcatcg gtttcggaac cgattcctgg gtgtacccca acatctcgat    2280
ccccgaacac ggtcgcctgt cccggaagta catctactcc ctgtactggt ccactctgac    2340
tctgaccacg atcggggaaa cccctccacc cgtgaaggac gaagagtacc tgttcgtggt    2400
ggtggacttc ctggtcggag tgttgatttt cgccaccatt gtgggaaacg tgggctccat    2460
gatctccaac atgaacgcgt cgagagctga gttccaagcc aagatcgact ccattaagca    2520
gtacatgcag ttcagaaagg tcaccaagga cctggaaacc agggtcatcc gctggttcga    2580
ctacctgtgg gccaacaaaa agactgtgga cgaaaaggaa gtgctgaagt cgctgccgga    2640
taagctgaag gccgaaatcg ccattaacgt gcaccttgac accctgaaga agtccggat    2700 cttccaagac tgtgaagccg gcctcctggt ggagctcgtg ctcaagctgc ggcccaccgt    2760
gttcagcccg ggagattaca tttgcaagaa gggcgatatc ggcaaagaga tgtacatcat    2820
caacgaggga aagctggccg tggtcgcgga cgacggcgtg acccagttcg tggtgctgtc    2880
cgacggatcc tacttcggtg aaatctcaat cctcaacatc aaggggtcca agtccggcaa    2940
ccggagaact gccaacattc gctccatcgg atacagcgac ctgttttgcc tgtccaagga    3000
tgacctgatg gaggctctga ctgagtaccc tgaagcgaag aaggctttgg aggaaaaggg    3060
gcggcagatt ctgatgaagg acaatttgat cgacgaggag ctcgcacggg ccggcgccga    3120
ccccaaggat ctcgaagaga aggtcgaaca gctgggttct tcgcttgata ccctgcaaac    3180
ccgattcgcg cggctgctcg ccgagtacaa cgcgacccag atgaagatga agcagagact    3240
gtcacagttg gaatcccaag tcaagggcgg aggcgacaag ccgctggcgg acggggaagt    3300
gcccggggac gccaccaaga ctgaggacaa gcagcagtga tcatagatcg atctgcctcg    3360
actgtgcctt ctagttgcca gccatctgtt gtttgcccct ccccgtgcc ttccttgacc    3420 ctggaaggtg ccactcccac tgtcctttcc taataaaatg aggaaattgc atcgcattgt    3480
ctgagtaggt gtcattctat tctgggggt ggggtgggc aggacagcaa ggggaggat    3540 tgggaagaca atagcaggca tgctggggac tcgagttcta cgtagataag tagcatggcg    3600
ggttaatcat taactacaag gaacccctag tgatggagtt ggccactccc tctctgcgcg    3660
ctcgctcgct cactgaggcc gggcgaccaa aggtcgcccg acgcccgggc tttgcccggg    3720
cggcctcagt gagcgagcga gcgcgcagcc ttaattaacc taaggaaaat gaagtgaagt    3780
tcctatactt tctagagaat aggaacttct atagtgagtc gaataagggc gacacaaaat    3840
ttattctaaa tgcataataa atactgataa catcttatag tttgtattat attttgtatt    3900
atcgttgaca tgtataattt tgatatcaaa aactgatttt ccctttatta ttttcgagat    3960
ttattttctt aattctcttt aacaaactag aaatattgta tatacaaaaa atcataaata    4020
atagatgaat agtttaatta taggtgttca tcaatcgaaa aagcaacgta tcttatttaa    4080
agtgcgttgc ttttttctca tttataaggt taaataattc tcatatatca agcaaagtga    4140
caggcgccct taaatattct gacaaatgct ctttccctaa actcccccca taaaaaaacc    4200
cgccgaagcg ggttttacg ttatttgcgg attaacgatt actcgttatc agaaccgccc    4260
agggggcccg agcttaacct ttttatttgg gggagaggga agtcatgaaa aaactaacct    4320
ttgaaattcg atctccagca catcagcaaa acgctattca cgcagtacag caaatccttc    4380
cagacccaac caaaccaatc gtagtaacca ttcaggaacg caaccgcagc ttagaccaaa    4440
```

```
acaggaagct atgggcctgc ttaggtgacg tctctcgtca ggttgaatgg catggtcgct    4500
ggctggatgc agaaagctgg aagtgtgtgt ttaccgcagc attaaagcag caggatgttg    4560
ttcctaacct tgccgggaat ggctttgtgg taataggcca gtcaaccagc aggatgcgtg    4620
taggcgaatt tgcggagcta ttagagctta tacaggcatt cggtacagag cgtggcgtta    4680
agtggtcaga cgaagcgaga ctggctctgg agtggaaagc gagatgggga gacagggctg    4740
catgataaat gtcgttagtt tctccggtgg caggacgtca gcatatttgc tctggctaat    4800
ggagcaaaag cgacgggcag gtaaagacgt gcattacgtt ttcatggata caggttgtga    4860
acatccaatg acatatcggt ttgtcaggga agttgtgaag ttctgggata taccgctcac    4920
cgtattgcag gttgatatca acccggagct tggacagcca aatggttata cggtatggga    4980
accaaaggat attcagacgc gaatgcctgt tctgaagcca tttatcgata tggtaaagaa    5040
atatggcact ccatacgtcg gcggcgcgtt ctgcactgac agattaaaac tcgttccctt    5100
caccaaatac tgtgatgacc atttcgggcg agggaattac accacgtgga ttggcatcag    5160
agctgatgaa ccgaagcggc taaagccaaa gcctggaatc agatatcttg ctgaactgtc    5220
agactttgag aaggaagata tcctcgcatg gtggaagcaa caaccattcg atttgcaaat    5280
accggaacat ctcggtaact gcatattctg cattaaaaaa tcaacgcaaa aaatcggact    5340
tgcctgcaaa gatgaggagg gattgcagcg tgtttttaat gaggtcatca cgggatccca    5400
tgtgcgtgac ggacatcggg aaacgccaaa ggagattatg taccgaggaa gaatgtcgct    5460
ggacggtatc gcgaaaatgt attcagaaaa tgattatcaa gccctgtatc aggacatggt    5520
acgagctaaa agattcgata ccggctcttg ttctgagtca tgcgaaatat ttggagggca    5580
gcttgatttc gacttcggga gggaagctgc atgatgcgat gttatcggtg cggtgaatgc    5640
aaagaagata accgcttccg accaaatcaa ccttactgga atcgatggtg tctccggtgt    5700
gaaagaacac caacaggggt gttaccacta ccgcaggaaa aggaggacgt gtggcgagac    5760
agcgacgaag tatcaccgac ataatctgcg aaaactgcaa ataccttcca acgaaacgca    5820
ccagaaataa acccaagcca atcccaaaag aatctgacgt aaaaaccttc aactacacgg    5880
ctcacctgtg ggatatccgg tggctaagac gtcgtgcgag gaaaacaagg tgattgacca    5940
aaatcgaagt tacgaacaag aaagcgtcga gcgagcttta acgtgcgcta actgcggtca    6000
gaagctgcat gtgctggaag ttcacgtgtg tgagcactgc tgcgcagaac tgatgagcga    6060
tccgaatagc tcgatgcacg aggaagaaga tgatggctaa ccagcgcga agacgatgta    6120 aaaacgatga atgccgggaa tggtttcacc ctgcattcgc taatcagtgg tggtgctctc    6180
cagagtgtgg aaccaagata gcactcgaac gacgaagtaa agaacgcgaa aaagcggaaa    6240
aagcagcaga gaagaaacga cgacgagagg agcagaaaca gaaagataaa cttaagattc    6300
gaaaactcgc cttaaagccc cgcagttact ggattaaaca agcccaacaa gccgtaaacg    6360
ccttcatcag agaagagac cgcgacttac catgtatctc gtgcggaacg ctcacgtctg    6420
ctcagtggga tgccggacat taccggacaa ctgctgcggc acctcaactc cgatttaatg    6480
aacgcaatat tcacaagcaa tgcgtggtgt gcaaccagca caaaagcgga atctcgttc    6540 cgtatcgcgt cgaactgatt agccgcatcg ggcaggaagc agtagacgaa atcgaatcaa    6600
accataaccg ccatcgctgg actatcgaag agtgcaaggc gatcaaggca gagtaccaac    6660
agaaactcaa agacctgcga aatagcagaa gtgaggccgc atgacgttct cagtaaaaac    6720
cattccagac atgctcgttg aagcatacgg aaatcagaca gaagtagcac gcagactgaa    6780
atgtagtcgc ggtacggtca gaaaatacgt tgatgataaa gacgggaaaa tgcacgccat    6840
```

| | |
|---|---|
| cgtcaacgac gttctcatgg ttcatcgcgg atggagtgaa agagatgcgc tattacgaaa | 6900 |
| aaattgatgg cagcaaatac cgaaatattt gggtagttgg cgatctgcac ggatgctaca | 6960 |
| cgaacctgat gaacaaactg gatacgattg gattcgacaa caaaaaagac ctgcttatct | 7020 |
| cggtgggcga tttggttgat cgtgtgtcag agaacgttga atgcctggaa ttaatcacat | 7080 |
| tccctggtt cagagctgta cgtggaaacc atgagcaaat gatgattgat ggcttatcag | 7140 |
| agcgtggaaa cgttaatcac tggctgctta atggcggtgg ctggttcttt aatctcgatt | 7200 |
| acgacaaaga aattctggct aaagctcttg cccataaagc agatgaactt ccgttaatca | 7260 |
| tcgaactggt gagcaaagat aaaaaatatg ttatctgcca cgccgattat ccctttgacg | 7320 |
| aatacgagtt tggaaagcca gttgatcatc agcaggtaat ctggaaccgc gaacgaatca | 7380 |
| gcaactcaca aaacgggatc gtgaaagaaa tcaaaggcgc ggacacgttc atctttggtc | 7440 |
| atacgccagc agtgaaacca ctcaagtttg ccaaccaaat gtatatcgat accggcgcag | 7500 |
| tgttctgcgg aaacctaaca ttgattcagg tacagggaga aggcgcatga gactcgaaag | 7560 |
| cgtagctaaa tttcattcgc caaaaagccc gatgatgagc gactcaccac gggccacggc | 7620 |
| ttctgactct ctttccggta ctgatgtgat ggctgctatg gggatggcgc aatcacaagc | 7680 |
| cggattcggt atggctgcat tctgcggtaa gcacgaactc agccagaacg acaaacaaaa | 7740 |
| ggctatcaac tatctgatgc aatttgcaca caaggtatcg gggaaatacc gtggtgtggc | 7800 |
| aaagcttgaa ggaaatacta aggcaaaggt actgcaagtg ctcgcaacat tcgcttatgc | 7860 |
| ggattattgc cgtagtgccg cgacgccggg ggcaagatgc agagattgcc atggtacagg | 7920 |
| ccgtgcggtt gatattgcca aaacagagct gtggggggaga gttgtcgaga aagagtgcgg | 7980 |
| aagatgcaaa ggcgtcggct attcaaggat gccagcaagc gcagcatatc gcgctgtgac | 8040 |
| gatgctaatc ccaaacctta cccaacccac ctggtcacgc actgttaagc cgctgtatga | 8100 |
| cgctctggtg gtgcaatgcc acaaagaaga gtcaatcgca gacaacattt tgaatgcggt | 8160 |
| cacacgttag cagcatgatt gccacggatg gcaacatatt aacggcatga tattgactta | 8220 |
| ttgaataaaa ttgggtaaat ttgactcaac gatgggttaa ttcgctcgtt gtggtagtga | 8280 |
| gatgaaaaga ggcggcgctt actaccgatt ccgcctagtt ggtcacttcg acgtatcgtc | 8340 |
| tggaactcca accatcgcag gcagagaggt ctgcaaaatg caatcccgaa acagttcgca | 8400 |
| ggtaatagtt agagcctgca taacggtttc gggattttt atatctgcac aacaggtaag | 8460 |
| agcattgagt cgataatcgt gaagagtcgg cgagcctggt tagccagtgc tctttccgtt | 8520 |
| gtgctgaatt aagcgaatac cggaagcaga accggatcac caaatgcgta caggcgtcat | 8580 |
| cgccgcccag caacagcaca acccaaactg agccgtagcc actgtctgtc ctgaattcat | 8640 |
| tagtaatagt tacgctgcgg ccttttacac atgaccttcg tgaaagcggg tggcaggagg | 8700 |
| tcgcgctaac aacctcctgc cgttttgccc gtgcatatcg gtcacgaaca atctgatta | 8760 |
| ctaaacacag tagcctggat ttgttctatc agtaatcgac cttattccta attaaataga | 8820 |
| gcaaatcccc ttattggggg taagacatga agatgccaga aaaacatgac ctgttggccg | 8880 |
| ccattctcgc ggcaaaggaa caaggcatcg gggcaatcct tgcgtttgca atggcgtacc | 8940 |
| ttcgcggcag atataatggc ggtgcgttta caaaaacagt aatcgacgca acgatgtgcg | 9000 |
| ccattatcgc ctggttcatt cgtgaccttc tcgacttcgc cggactaagt agcaatctcg | 9060 |
| cttatataac gagcgtgttt atcggctaca tcggtactga ctcgattggt tcgcttatca | 9120 |
| aacgcttcgc tgctaaaaaa gccggagtag aagatggtag aaatcaataa tcaacgtaag | 9180 |

```
gcgttcctcg atatgctggc gtggtcggag ggaactgata acggacgtca gaaaaccaga   9240
aatcatggtt atgacgtcat tgtaggcgga gagctattta ctgattactc cgatcaccct   9300
cgcaaacttg tcacgctaaa cccaaaactc aaatcaacag gcgcttaaga ctggccgtcg   9360
ttttacaaca cagaaagagt ttgtagaaac gcaaaaaggc catccgtcag gggccttctg   9420
cttagtttga tgcctggcag ttccctactc tcgccttccg cttcctcgct cactgactcg   9480
ctgcgctcgg tcgttcggct gcggcgagcg gtatcagctc actcaaaggc ggtaatacgg   9540
ttatccacag aatcagggga taacgcagga agaacatgt gagcaaaagg ccagcaaaag    9600
gccaggaacc gtaaaaaggc cgcgttgctg cgttttttcc ataggctccg ccccctgac    9660
gagcatcaca aaaatcgacg ctcaagtcag aggtggcgaa acccgacagg actataaaga   9720
taccaggcgt ttcccctgg aagctccctc gtgcgctctc ctgttccgac cctgccgctt    9780
accggatacc tgtccgcctt tctcccttcg ggaagcgtgg cgctttctca tagctcacgc   9840
tgtaggtatc tcagttcggt gtaggtcgtt cgctccaagc tgggctgtgt gcacgaaccc   9900
cccgttcagc ccgaccgctg cgccttatcc ggtaactatc gtcttgagtc caacccggta   9960
agacacgact tatcgccact ggcagcagcc actggtaaca ggattagcag agcgaggtat  10020
gtaggcggtg ctacagagtt cttgaagtgg tgggctaact acggctacac tagaagaaca  10080
gtatttggta tctgcgctct gctgaagcca gttaccttcg gaaaagagt tggtagctct   10140
tgatccggca aacaaaccac cgctggtagc ggtggttttt ttgtttgcaa gcagcagatt  10200
acgcgcagaa aaaaggatc tcaagaagat cctttgatct tttctacggg gtctgacgct   10260
cagtggaacg acgcgcgcgt aactcacgtt aagggatttt ggtcatgagc ttgcgccgtc  10320
ccgtcaagtc agcgtaatgc tctgctttta gaaaaactca tcgagcatca aatgaaactg  10380
caatttattc atatcaggat tatcaatacc atattttga aaaagccgtt tctgtaatga    10440
aggagaaaac tcaccgaggc agttccatag gatggcaaga tcctggtatc ggtctgcgat  10500
tccgactcgt ccaacatcaa tacaacctat taatttcccc tcgtcaaaaa taaggttatc  10560
aagtgagaaa tcaccatgag tgacgactga atccggtgag aatggcaaaa gtttatgcat  10620
ttctttccag acttgttcaa caggccagcc attacgctcg tcatcaaaat cactcgcatc  10680
aaccaaaccg ttattcattc gtgattgcgc ctgagcgagg cgaaatacgc gatcgctgtt  10740
aaaaggacaa ttacaaacag gaatcgagtg caaccggcgc aggaacactg ccagcgcatc  10800
aacaatattt tcacctgaat caggatattc ttctaatacc tggaacgctg ttttttccggg 10860
gatcgcagtg tgagtaacc atgcatcatc aggagtacgg ataaaatgct tgatggtcgg   10920
aagtggcata aattccgtca gccagtttag tctgaccatc tcatctgtaa catcattggc   10980
aacgctacct ttgccatgtt tcagaaacaa ctctggcgca tcgggcttcc catacaagcg   11040
atagattgtc gcacctgatt gcccgacatt atcgcgagcc catttatacc catataaatc   11100
agcatccatg ttggaattta atcgcggcct cgacgtttcc cgttaatat ggctcatatt    11160
cttccttttt caatattatt gaagcattta tcagggttat tgtctcatga gcggatacat   11220
atttgaatgt atttagaaaa ataaacaaat aggggtcagt gttacaacca attaaccaat   11280
tctgaacatt atcgcgagcc catttatacc tgaatatggc tcataacacc ccttgtttgc   11340
ctggcggcag tagcgcggtg gtcccacctg accccatgcc gaactcagaa gtgaaacgcc   11400
gtagcgccga tggtagtgtg gggactcccc atgcgagagt agggaactgc caggcatcaa   11460
ataaaacgaa aggctcagtc gaaagactgg gcctttcgcc cgggctaatt aggggggtgtc   11520
gcccttattc gactctatag tgaagttcct attctctaga aagtatagga acttctgaag   11580
```

```
tggggtcgac ttaattaagg                                             11600
```

<210> SEQ ID NO 36
<211> LENGTH: 12209
<212> TYPE: DNA
<213> ORGANISM: Artificial Sequence
<220> FEATURE:
<223> OTHER INFORMATION: constructed sequence

<400> SEQUENCE: 36

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gcaagctagc    180
tagttattaa tagtaatcaa ttacggggtc attagttcat agcccatata tggagttccg    240
cgttacataa cttacggtaa atggcccgcc tggctgaccg cccaacgacc cccgcccatt    300
gacgtcaata atgacgtatg ttcccatagt aacgccaata gggactttcc attgacgtca    360
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattaa    540
catggtcgag gtgagcccca cgttctgctt cactctcccc atctcccccc cctccccacc    600
cccaattttg tatttattta ttttttaatt attttgtgca gcgatggggg cggggggggg    660
gggggggcgc gcgccaggcg gggcggggcg gggcgagggg cggggcgggg cgaggcggag    720
aggtgcggcg gcagccaatc agagcggcgc gctccgaaag tttcctttta tggcgaggcg    780
gcggcggcgg cggcccctata aaaagcgaag cgcgcggcgg gcggggagtc gctgcgacgc    840
tgccttcgcc ccgtgccccg ctccgccgcc gcctcgcgcc gcccgccccg gctctgactg    900
accgcgttac tcccacaggt gagcgggcgg gacggccctt ctcctccggg ctgtaattag    960
cgcttggttt aatgacggct tgtttctttt ctgtggctgc gtgaaagcct tgaggggctc   1020
cgggagggcc ctttgtgcgg ggggagcggc tcggggggtg cgtgcgtgtg tgtgtgcgtg   1080
gggagcgccg cgtgcggctc cgcgctgccc ggcggctgtg agcgctgcgg gcgcggcgcg   1140
gggctttgtg cgctccgcag tgtgcgcgag gggagcgcgg ccgggggcgg tgccccgcgg   1200
tgcggggggg gctgcgaggg gaacaaaggc tgcgtgcggg gtgtgtgcgt gggggggtga   1260
gcagggggtg tgggcgcgtc ggtcgggctg caacccccccc tgcaccccccc tccccgagtt   1320
gctgagcacg gccggcttc gggtgcgggg ctccgtacgg ggcgtggcgc ggggctcgcc   1380
gtgccgggcg gggggtggcg gcaggtgggg gtgccgggcg gggcggggcc gcctcgggcc   1440
ggggagggct cggggaggg gcgcggcggc cccggagcg ccggcggctg tcgaggcgcg   1500
gcgagccgca gccattgcct tttatggtaa tcgtgcgaga gggcgcaggg acttcctttg   1560
tcccaaatct gtgcggagcc gaaatctggg aggcgccgcc gcaccccctc tagcgggcgc   1620
ggggcgaagc ggtgcggcgc cggcaggaag gaaatgggcg gggagggcct tcgtgcgtcg   1680
ccgcgccgcc gtccccttct ccctctccag cctcggggct gtccgcgggg gacggctgc   1740
cttcgggggg gacggggcag ggcggggttc ggcttctggc gtgtgaccgg cggctctaga   1800
caattgtact aaccttcttc tcttttcctct cctgacaggt tggtgtacac tagcggccgc   1860
caccatggcc aagatcaaca cccaatactc cacccctcc aggacccacc tcaaggtaaa   1920
gacctcagac cgggatctca atcgcgctga aaatggcctc agcagagccc actcgtcaag   1980
```

```
tgaggagaca tcgtcagtgc tgcagccggg gatcgccatg gagaccagag gactggctga    2040
ctccgggcag ggctccttca ccggccaggg gatcgccagg ctgtcgcgcc tcatcttctt    2100
gctgcgcagg tgggctgcca ggcatgtgca ccaccaggac cagggaccgg actctttcc     2160 tgatcgtttc cgtggagccg agcttaagga ggtgtccagc caagaaagca atgcccaggc    2220
aaatgtgggc agccaggagc cagcagacag agggagaagc gcctggcccc tggccaaatg    2280
caacactaac accagcaaca cacggagga  ggagaagaag acgaaaaaga aggatgcgat     2340
cgtggtggac ccgtccagca acctgtacta ccgctggctg accgccatcg ccctgcctgt    2400
cttctataac tggtatctgc ttatttgcag ggcctgtttc gatgagctgc agtccgagta    2460
cctgatgctg tggctggtcc tggactactc ggcagatgtc ctgtatgtct tggatgtgct    2520
tgtacgagct cggacaggtt ttcttgagca aggcttaatg gtcagtgata ccaacaggct    2580
gtggcagcat tacaagacga ccacgcagtt caagctggat gtgttgtccc tggtccccac    2640
cgacctggct tacttaaagg tgggcacaaa ctacccagaa gtgaggttca accgcctact    2700
gaagttttcc cggctctttg aattctttga ccgcacagag acaaggacca actaccccaa    2760
tatgttcagg attgggaact tggtcttgta cattctcatc atcatccact ggaatgcctg    2820
catctacttt gccatttcca agttcattgg ttttgggaca gactcctggg tctacccaaa    2880
catctcaatc ccagagcatg ggcgcctctc caggaagtac atttacagtc tctactggtc    2940 cacctt gacc cttaccacca ttggtgagac cccacccccc gtgaaagatg aggagtatct    3000
ctttgtggtc gtagacttct tggtgggtgt tctgattttt gccaccattg tgggcaatgt    3060
gggctccatg atctcgaata tgaatgcctc acgggcagag ttccaggcca agattgattc    3120
catcaagcag tacatgcagt tccgcaaggt caccaaggac ttggagacgc gggttatccg    3180
gtggtttgac tacctgtggg ccaacaagaa gacggtggat gagaaggagg tgctcaagag    3240
cctcccagac aagctgaagg ctgagatcgc catcaacgtg cacctggaca cgctgaagaa    3300
ggttcgcatc ttccaggact gtgaggcagg gctgctggtg gagctggtgc tgaagctgcg    3360
acccactgtg ttcagccctg ggattatat  ctgcaagaag ggagatattg ggaaggagat    3420
gtacatcatc aacgagggca agctggccgt ggtggctgat gatgggggtca cccagttcgt    3480 ggtcctcagc gatggcagct acttcgggga gatcagcatt ctgaacatca aggggagcaa    3540
gtcggggaac cgcaggacgg ccaacatccg cagcattggc tactcagacc tgttctgcct    3600
ctcaaaggac gatctcatgg aggccctcac cgagtacccc gaagccaaga aggccctgga    3660
ggagaaagga cggcagatcc tgatgaaaga caacctgatc gatgaggagc tggcagggc     3720 gggcgcggac cccaaggacc ttgaggagaa agtggagcag ctggggtcct ccctggacac    3780
cctgcagacc aggtttgcac gcctcctggc tgagtacaac gccacccaga tgaagatgaa    3840
gcagcgtctc agccaactgg aaagccaggt gaagggtggt ggggacaagc ccctggctga    3900
tggggaagtt cccggggatg ctacaaaaac agaggacaaa caacagtgat catagatcga    3960
tctgcctcga ctgtgccttc tagttgccag ccatctgttg tttgcccctc ccccgtgcct    4020
tccttgaccc tggaaggtgc cactcccact gtcctttcct aataaaatga ggaaattgca    4080
tcgcattgtc tgagtaggtg tcattctatt ctggggggtg ggtgggca   ggacagcaag    4140 ggggaggatt gggaagacaa tagcaggcat gctgggact  cgagttctac gtagataagt    4200
agcatggcgg gttaatcatt aactacaagg aaccctagt  gatggagttg gccactccct    4260
ctctgcgcgc tcgctcgctc actgaggccg ggcgaccaaa ggtcgcccga cgcccgggct    4320
ttgcccgggc ggcctcagtg agcgagcgag cgcgcagcct taattaacct aaggaaaatg    4380
```

```
aagtgaagtt cctatacttt ctagagaata ggaacttcta tagtgagtcg aataagggcg    4440
acacaaaatt tattctaaat gcataataaa tactgataac atcttatagt ttgtattata    4500
ttttgtatta tcgttgacat gtataatttt gatatcaaaa actgattttc cctttattat    4560
tttcgagatt tattttctta attctcttta acaaactaga aatattgtat atacaaaaaa    4620
tcataaataa tagatgaata gtttaattat aggtgttcat caatcgaaaa agcaacgtat    4680
cttatttaaa gtgcgttgct tttttctcat ttataaggtt aaataattct catatatcaa    4740
gcaaagtgac aggcgcccct aaatattctg acaaatgctc tttccctaaa ctccccccat    4800
aaaaaaaccc gccgaagcgg ttttttacgt tatttgcgga ttaacgatta ctcgttatca    4860
gaaccgccca gggggcccga gcttaacctt tttatttggg ggagagggaa gtcatgaaaa    4920
aactaacctt tgaaattcga tctccagcac atcagcaaaa cgctattcac gcagtacagc    4980
aaatccttcc agacccaacc aaaccaatcg tagtaaccat tcaggaacgc aaccgcagct    5040
tagaccaaaa caggaagcta tgggcctgct taggtgacgt ctctcgtcag gttgaatggc    5100
atggtcgctg gctggatgca gaaagctgga agtgtgtgtt taccgcagca ttaaagcagc    5160
aggatgttgt tcctaacctt gccgggaatg gctttgtggt aataggccag tcaaccagca    5220
ggatgcgtgt aggcgaattt gcggagctat tagagcttat acaggcattc ggtacagagc    5280
gtggcgttaa gtggtcagac gaagcgagac tggctctgga gtggaaagcg agatggggag    5340
acagggctgc atgataaatg tcgttagttt ctccggtggc aggacgtcag catatttgct    5400
ctggctaatg gagcaaaagc gacgggcagg taaagacgtg cattacgttt tcatggatac    5460
aggttgtgaa catccaatga catatcggtt tgtcagggaa gttgtgaagt tctgggatat    5520
accgctcacc gtattgcagg ttgatatcaa cccggagctt ggacagccaa atggttatac    5580
ggtatgggaa ccaaaggata ttcagacgcg aatgcctgtt ctgaagccat ttatcgatat    5640
ggtaaagaaa tatggcactc catacgtcgg cggcgcgttc tgcactgaca gattaaaact    5700
cgttcccttc accaaatact gtgatgacca tttcgggcga gggaattaca ccacgtggat    5760
tggcatcaga gctgatgaac cgaagcggct aaagccaaag cctggaatca gatatcttgc    5820
tgaactgtca gactttgaga aggaagatat cctcgcatgg tggaagcaac aaccattcga    5880
tttgcaaata ccggaacatc tcggtaactg catattctgc attaaaaaat caacgcaaaa    5940
aatcggactt gcctgcaaag atgaggaggg attgcagcgt gttttttaatg aggtcatcac    6000 gggatcccat gtgcgtgacg gacatcggga aacgccaaag gagattatgt accgaggaag    6060
aatgtcgctg gacggtatcg cgaaaatgta ttcagaaaat gattatcaag ccctgtatca    6120
ggacatggta cgagctaaaa gattcgatac cggctcttgt tctgagtcat gcgaaatatt    6180
tggagggcag cttgatttcg acttcgggag ggaagctgca tgatgcgatg ttatcggtgc    6240
ggtgaatgca aagaagataa ccgcttccga ccaaatcaac cttactggaa tcgatggtgt    6300
ctccggtgtg aaagaacacc aacagggtgt taccactac cgcaggaaaa ggaggacgtg    6360
tggcgagaca gcgacgaagt atcaccgaca taatctgcga aaactgcaaa taccttccaa    6420
cgaaacgcac cagaaataaa cccaagccaa tcccaaaaga atctgacgta aaaaccttca    6480
actacacggc tcacctgtgg gatatccggt ggctaagacg tcgtgcgagg aaaacaaggt    6540
gattgaccaa aatcgaagtt acgaacaaga aagcgtcgag cgagctttaa cgtgcgctaa    6600
ctgcggtcag aagctgcatg tgctggaagt tcacgtgtgt gagcactgct gcgcagaact    6660
gatgagcgat ccgaatagct cgatgcacga ggaagaagat gatggctaaa ccagcgcgaa    6720
```

```
gacgatgtaa aaacgatgaa tgccgggaat ggtttcaccc tgcattcgct aatcagtggt    6780
ggtgctctcc agagtgtgga accaagatag cactcgaacg acgaagtaaa gaacgcgaaa    6840
aagcggaaaa agcagcagag aagaaacgac gacgagagga gcagaaacag aaagataaac    6900
ttaagattcg aaaactcgcc ttaaagcccc gcagttactg gattaaacaa gcccaacaag    6960
ccgtaaacgc cttcatcaga gaaagagacc gcgacttacc atgtatctcg tgcggaacgc    7020
tcacgtctgc tcagtgggat gccggacatt accggacaac tgctgcggca cctcaactcc    7080
gatttaatga acgcaatatt cacaagcaat gcgtggtgtg caaccagcac aaaagcggaa    7140
atctcgttcc gtatcgcgtc gaactgatta gccgcatcgg gcaggaagca gtagacgaaa    7200
tcgaatcaaa ccataaccgc catcgctgga ctatcgaaga gtgcaaggcg atcaaggcag    7260
agtaccaaca gaaactcaaa gacctgcgaa atagcagaag tgaggccgca tgacgttctc    7320
agtaaaaacc attccagaca tgctcgttga agcatacgga aatcagacag aagtagcacg    7380
cagactgaaa tgtagtcgcg gtacggtcag aaaatacgtt gatgataaag acgggaaaat    7440
gcacgccatc gtcaacgacg ttctcatggt tcatcgcgga tggagtgaaa gagatgcgct    7500
attacgaaaa aattgatggc agcaaatacc gaaatatttg ggtagttggc gatctgcacg    7560
gatgctcacg gaacctgatg aacaaactgg atacgattgg attcgacaac aaaaaagacc    7620
tgcttatctc ggtgggcgat ttggttgatc gtggtgcaga gaacgttgaa tgcctggaat    7680
taatcacatt cccctggttc agagctgtac gtggaaacca tgagcaaatg atgattgatg    7740
gcttatcaga gcgtggaaac gttaatcact ggctgcttaa tggcggtggc tggttcttta    7800
atctcgatta cgacaaagaa attctggcta aagctcttgc ccataaagca gatgaacttc    7860
cgttaatcat cgaactggtg agcaaagata aaaatatgt tatctgccac gccgattatc    7920
cctttgacga atacgagttt ggaaagccag ttgatcatca gcaggtaatc tggaaccgcg    7980
aacgaatcag caactcacaa aacgggatcg tgaaagaaat caaggcgcg acacgttca    8040
tctttggtca tacgccagca gtgaaaccac tcaagtttgc caaccaaatg tatatcgata    8100
ccggcgcagt gttctgcgga aacctaacat tgattcaggt acagggagaa ggcgcatgag    8160
actcgaaagc gtagctaaat tcattcgcc aaaaagcccg atgatgagcg actcaccacg    8220
ggccacggct tctgactctc tttccggtac tgatgtgatg gctgctatgg ggatggcgca    8280
atcacaagcc ggattcggta tggctgcatt ctgcggtaag cacgaactca gccagaacga    8340
caaacaaaag gctatcaact atctgatgca atttgcacac aaggtatcgg ggaaataccg    8400
tggtgtggca aagcttgaag gaaatactaa ggcaaaggta ctgcaagtgc tcgcaacatt    8460
cgcttatgcg gattattgcc gtagtgccgc gacgccgggg gcaagatgca gagattgcca    8520
tggtacaggc cgtgcggttg atattgccaa aacagagctg tggggagag ttgtcgagaa    8580
agagtgcgga agatgcaaag gcgtcggcta ttcaaggatg ccagcaagcg cagcatatcg    8640
cgctgtgacg atgctaatcc caaaccttac ccaacccacc tggtcacgca ctgttaagcc    8700
gctgtatgac gctctggtgg tgcaatgcca caaagaagag tcaatcgcag acaacatttt    8760
gaatgcggtc acacgttagc agcatgattg ccacggatgg caacatatta acggcatgat    8820
attgacttat tgaataaaat tgggtaaatt tgactcaacg atgggttaat tcgctcgttg    8880
tggtagtgag atgaaaagag gcggcgctta ctaccgattc cgcctagttg gtcacttcga    8940
cgtatcgtct ggaactccaa ccatcgcagg cagagaggtc tgcaaaatgc aatcccgaaa    9000
cagttcgcag gtaatagtta gagcctgcat aacggtttcg ggattttta tatctgcaca    9060
acaggtaaga gcattgagtc gataatcgtg aagagtcggc gagcctggtt agccagtgct    9120
```

```
ctttccgttg tgctgaatta agcgaatacc ggaagcagaa ccggatcacc aaatgcgtac    9180
aggcgtcatc gccgcccagc aacagcacaa cccaaactga gccgtagcca ctgtctgtcc    9240
tgaattcatt agtaatagtt acgctgcggc cttttacaca tgaccttcgt gaaagcgggt    9300
ggcaggaggt cgcgctaaca acctcctgcc gttttgcccg tgcatatcgg tcacgaacaa    9360
atctgattac taaacacagt agcctggatt tgttctatca gtaatcgacc ttattcctaa    9420
ttaaatagag caaatcccct tattgggggt aagacatgaa gatgccagaa aaacatgacc    9480
tgttggccgc cattctcgcg gcaaaggaac aaggcatcgg gcaatccttg cgtttgcaa    9540 tggcgtacct tcgcggcaga tataatggcg gtgcgtttac aaaaacagta atcgacgcaa    9600
cgatgtgcgc cattatcgcc tggttcattc gtgaccttct cgacttcgcc ggactaagta    9660
gcaatctcgc ttatataacg agcgtgttta tcggctacat cggtactgac tcgattggtt    9720
cgcttatcaa acgcttcgct gctaaaaaag ccggagtaga agatggtaga aatcaataat    9780
caacgtaagg cgttcctcga tatgctggcg tggtcggagg gaactgataa cggacgtcag    9840
aaaaccagaa atcatggtta tgacgtcatt gtaggcggag agctatttac tgattactcc    9900
gatcaccctc gcaaacttgt cacgctaaac ccaaaactca aatcaacagg cgcttaagac    9960
tggccgtcgt tttacaacac agaaagagtt tgtagaaacg caaaaaggcc atccgtcagg   10020
ggccttctgc ttagtttgat gcctggcagt tccctactct cgccttccgc ttcctcgctc   10080
actgactcgc tgcgctcggt cgttcggctg cggcgagcgg tatcagctca ctcaaaggcg   10140
gtaatacggt tatccacaga atcaggggat aacgcaggaa agaacatgtg agcaaaaggc   10200
cagcaaaagg ccaggaaccg taaaaaggcc gcgttgctgg cgttttttcca taggctccgc   10260 cccccctgacg agcatcacaa aaatcgacgc tcaagtcaga ggtggcgaaa cccgacagga   10320
ctataaagat accaggcgtt tccccctgga agctccctcg tgcgctctcc tgttccgacc   10380
ctgccgctta ccggatacct gtccgccttt ctcccttcgg gaagcgtggc gctttctcat   10440
agctcacgct gtaggtatct cagttcggtg taggtcgttc gctccaagct gggctgtgtg   10500
cacgaacccc ccgttcagcc cgaccgctgc gccttatccg gtaactatcg tcttgagtcc   10560
aacccggtaa gacacgactt atcgccactg gcagcagcca ctggtaacag gattagcaga   10620
gcgaggtatg taggcggtgc tacagagttc ttgaagtggt gggctaacta cggctacact   10680
agaagaacag tatttggtat ctgcgctctg ctgaagccag ttaccttcgg aaaaagagtt   10740
ggtagctctt gatccggcaa acaaaccacc gctggtagcg gtggtttttt tgtttgcaag   10800
cagcagatta cgcgcagaaa aaaaggatct caagaagatc ctttgatctt ttctacgggg   10860
tctgacgctc agtggaacga cgcgcgcgta actcacgtta agggattttg gtcatgagct   10920
tgcgccgtcc cgtcaagtca gcgtaatgct ctgcttttag aaaaactcat cgagcatcaa   10980
atgaaactgc aatttattca tatcaggatt atcaatacca tattttgaa aaagccgttt   11040 ctgtaatgaa ggagaaaact caccgaggca gttccatagg atggcaagat cctggtatcg   11100
gtctgcgatt ccgactcgtc aacatcaat acaacctatt aatttcccct cgtcaaaaat   11160
aaggttatca agtgagaaat caccatgagt gacgactgaa tccggtgaga atggcaaaag   11220
tttatgcatt tctttccaga cttgttcaac aggccagcca ttacgctcgt catcaaaatc   11280
actcgcatca accaaaccgt tattcattcg tgattgcgcc tgagcgaggc gaaatacgcg   11340
atcgctgtta aaaggacaat tacaaacagg aatcgagtgc aaccggcgca ggaacactgc   11400
cagcgcatca acaatatttt cacctgaatc aggatattct tctaataccg ggaacgctgt   11460
```

| | |
|---|---|
| ttttccgggg atcgcagtgg tgagtaacca tgcatcatca ggagtacgga taaaatgctt | 11520 |
| gatggtcgga agtggcataa attccgtcag ccagtttagt ctgaccatct catctgtaac | 11580 |
| atcattggca acgctacctt tgccatgttt cagaaacaac tctggcgcat cgggcttccc | 11640 |
| atacaagcga tagattgtcg cacctgattg cccgacatta tcgcgagccc atttataccc | 11700 |
| atataaatca gcatccatgt tggaatttaa tcgcggcctc gacgtttccc gttgaatatg | 11760 |
| gctcatattc ttcctttttc aatattattg aagcatttat cagggttatt gtctcatgag | 11820 |
| cggatacata tttgaatgta tttagaaaaa taaacaaata ggggtcagtg ttacaaccaa | 11880 |
| ttaaccaatt ctgaacatta tcgcgagccc atttatacct gaatatggct cataacaccc | 11940 |
| cttgtttgcc tggcggcagt agcgcggtgg tcccacctga ccccatgccg aactcagaag | 12000 |
| tgaaacgccg tagcgccgat ggtagtgtgg ggactcccca tgcgagagta gggaactgcc | 12060 |
| aggcatcaaa taaaacgaaa ggctcagtcg aaagactggg cctttcgccc gggctaatta | 12120 |
| gggggtgtcg cccttattcg actctatagt gaagttccta ttctctagaa agtataggaa | 12180 |
| cttctgaagt ggggtcgact taattaagg | 12209 |

<210> SEQ ID NO 37
<211> LENGTH: 12209
<212> TYPE: DNA
<213> ORGANISM: Artificial Sequence
<220> FEATURE:
<223> OTHER INFORMATION: constructed sequence

<400> SEQUENCE: 37

| | |
|---|---|
| ctgcgcgctc gctcgctcac tgaggccgcc cgggcaaagc ccgggcgtcg ggcgacccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gcaagctagc | 180 |
| tagttattaa tagtaatcaa ttacggggtc attagttcat agcccatata tggagttccg | 240 |
| cgttacataa cttacggtaa atggcccgcc tggctgaccg cccaacgacc cccgcccatt | 300 |
| gacgtcaata atgacgtatg ttcccatagt aacgccaata gggactttcc attgacgtca | 360 |
| atgggtggag tatttacggt aaactgccca cttggcagta catcaagtgt atcatatgcc | 420 |
| aagtacgccc cctattgacg tcaatgacgg taaatggccc gcctggcatt atgcccagta | 480 |
| catgacctta tgggactttc ctacttggca gtacatctac gtattagtca tcgctattaa | 540 |
| catggtcgag gtgagcccca cgttctgctt cactctcccc atctccccc cctccccacc | 600 |
| cccaattttg tatttattta ttttttaatt attttgtgca gcgatggggg cggggggggg | 660 |
| ggggggcgc gcgccaggcg gggcggggcg gggcgagggg cggggcgggg cgaggcggag | 720 |
| aggtgcggcg gcagccaatc agagcggcgc gctccgaaag tttccttttta tggcgaggcg | 780 |
| gcggcggcgg cggccctata aaagcgaag cgcgcggcgg gcgggagtc gctgcgacgc | 840 |
| tgccttcgcc ccgtgccccg ctccgccgcc gcctcgcgcc gcccgcccg gctctgactg | 900 |
| accgcgttac tcccacaggt gagcgggcgg gacggccctt ctcctccggg ctgtaattag | 960 |
| cgcttggttt aatgacggct tgtttctttt ctgtggctgc gtgaaagcct tgaggggctc | 1020 |
| cgggagggcc ctttgtgcgg ggggagcggc tcggggggtg cgtgcgtgtg tgtgtgcgtg | 1080 |
| gggagcgccg cgtgcggctc cgcgctgccc ggcggctgtg agcgctgcgg gcgcggcgcg | 1140 |
| gggctttgtg cgctccgcag tgtgcgcgag gggagcgcgg ccgggggcgg tgccccgcgg | 1200 |
| tgcggggggg gctgcgaggg gaacaaaggc tgcgtgcggg gtgtgtgcgt gggggggtga | 1260 |
| gcaggggggtg tgggcgcgtc ggtcgggctg caaccccccc tgcaccccccc tccccgagtt | 1320 |

```
gctgagcacg gcccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggggaggg gcgcggcggc ccccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcaccccctc tagcgggcgc    1620
ggggcgaagc ggtgcggcgc cggcaggaag gaaatgggcg gggagggcct tcgtgcgtcg    1680
ccgcgccgcc gtccccttct ccctctccag cctcggggct gtccgcgggg ggacggctgc    1740 cttcggggggg gacggggcag ggcggggttc ggcttctggc gtgtgaccgg cggctctaga    1800
caattgtact aaccttcttc tctttcctct cctgacaggt tggtgtacac tagcggccgc    1860
caccatggct aagattaaca cccagtactc acatccatcc cgcactcacc tcaaagtcaa    1920
gacctccgat cgggatctga accgggctga gaatgggctg tcgcgcgccc actcgtcgtc    1980
cgaggaaacc agcagcgtgc tccagccggg catcgccatg gaaactaggg ggctggcgga    2040
ctccggacag ggatccttca ctggacaggg tattgcccgg ctgagcagac tgatcttcct    2100
gcttcgccgc tgggcggcca gacacgtgca ccatcaggac cagggacctg atagcttccc    2160
cgaccgcttt aggggagccg agctgaaaga agtgtcaagc caggagtcaa acgcgcaggc    2220
caacgtcggc agccaagagc ctgcagaccg gggacgctcg gcatggccgc tcgcaaagtg    2280
caacactaac acttccaaca acaccgaaga ggaaaagaaa accaagaaga aggatgcaat    2340
tgtggtggac ccttcctcca acctgtacta ccgctggttg accgccatcg ccctcccggt    2400
cttttacaat tggtatctcc ttatctgccg ggcctgcttc gacgaactgc aatcagagta    2460
cctgatgctg tggctggtgc tggactatag cgccgatgtg ctctacgtcc tggatgtgct    2520
cgtgcgcgcc cggaccggat tcttggaaca aggcctgatg gtgtccgaca cgaatagact    2580
gtggcagcac tataagacca caacccagtt caagcttgac gtgctcagcc ttgtgccgac    2640
tgacctggcc tacctgaaag tcggaactaa ctacccggaa gtcagattca accgactcct    2700
gaagttcagc aggctgttcg agttctttga ccgcaccgag actcggacca actaccctaa    2760
catgttccgg atcggaaatc tggtgctcta catactgatt atcatccatt ggaacgcctg    2820
tatctatttc gccatttcga agttcatcgg tttcggaacc gattcctggg tgtaccccaa    2880
catctcgatc cccgaacacg gtcgcctgtc ccggaagtac atctactccc tgtactggtc    2940
cactctgact ctgaccacga tcgggggaaac ccctccaccc gtgaaggacg aagagtacct    3000
gttcgtggtg gtggacttcc tggtcggagt gttgattttc gccaccattg tgggaaacgt    3060
gggctccatg atctccaaca tgaacgcgtc gagagctgag ttccaagcca agatcgactc    3120
cattaagcag tacatgcagt tcagaaaggt caccaaggac ctgaaaccca gggtcatccg    3180
ctggttcgac tacctgtggg ccaacaaaaa gactgtggac gaaaaggaag tgctgaagtc    3240
gctgccggat aagctgaagg ccgaaatcgc cattaacgtg caccttgaca ccctgaagaa    3300
agtccggatc ttccaagact gtgaagccgg cctcctggtg gagctcgtgc tcaagctgcg    3360
gcccaccgtg ttcagcccgg gagattacat ttgcaagaag ggcgatatcg gcaaagagat    3420
gtacatcatc aacgagggaa agctggccgt ggtcgcggac gacggcgtga cccagttcgt    3480
ggtgctgtcc gacggatcct acttcggtga aatctcaatc ctcaacatca gggggtccaa    3540
gtccggcaac cggagaactg ccaacattcg ctccatcgga tacagcgacc tgttttgcct    3600
gtccaaggat gacctgatgg aggctctgac tgagtaccct gaagcgaaga aggctttgga    3660
```

```
ggaaaagggg cggcagattc tgatgaagga caatttgatc gacgaggagc tcgcacgggc    3720
cggcgccgac cccaaggatc tcgaagagaa ggtcgaacag ctgggttctt cgcttgatac    3780
cctgcaaacc cgattcgcgc ggctgctcgc cgagtacaac gcgacccaga tgaagatgaa    3840
gcagagactg tcacagttgg aatcccaagt caagggcgga ggcgacaagc cgctggcgga    3900
cggggaagtg cccggggacg ccaccaagac tgaggacaag cagcagtgat catagatcga    3960
tctgcctcga ctgtgccttc tagttgccag ccatctgttg tttgcccctc cccgtgcct     4020 tccttgaccc tggaaggtgc cactcccact gtcctttcct aataaaatga ggaaattgca    4080
tcgcattgtc tgagtaggtg tcattctatt ctggggggtg gggtgggggca ggacagcaag   4140 ggggaggatt gggaagacaa tagcaggcat gctggggact cgagttctac gtagataagt    4200
agcatggcgg gttaatcatt aactacaagg aacccctagt gatggagttg cccactccct    4260
ctctgcgcgc tcgctcgctc actgaggccg ggcgaccaaa ggtcgcccga cgcccgggct    4320
ttgcccgggc ggcctcagtg agcgagcgag cgcgcagcct taattaacct aaggaaaatg    4380
aagtgaagtt cctatacttt ctagagaata ggaacttcta tagtgagtcg aataagggcg    4440
acacaaaatt tattctaaat gcataataaa tactgataac atcttatagt ttgtattata    4500
ttttgtatta tcgttgacat gtataatttt gatatcaaaa actgattttc cctttattat    4560
tttcgagatt tattttctta attctctttta acaaactaga aatattgtat atacaaaaaa   4620
tcataaataa tagatgaata gtttaattat aggtgttcat caatcgaaaa agcaacgtat    4680
cttatttaaa gtgcgttgct tttttctcat ttataaggtt aaataattct catatatcaa    4740
gcaaagtgac aggcgccctt aaatattctg acaaatgctc tttccctaaa ctccccccat    4800 aaaaaaccc gccgaagcgg gttttacgt tatttgcgga ttaacgatta ctcgttatca     4860
gaaccgccca gggggcccga gcttaacctt tttatttggg ggagagggaa gtcatgaaaa    4920
aactaacctt tgaaattcga tctccagcac atcagcaaaa cgctattcac gcagtacagc    4980
aaatccttcc agacccaacc aaaccaatcg tagtaaccat tcaggaacgc aaccgcagct    5040
tagaccaaaa caggaagcta tgggcctgct taggtgacgt ctctcgtcag gttgaatggc    5100
atggtcgctg gctggatgca gaaagctgga agtgtgtgtt taccgcagca ttaaagcagc    5160
aggatgttgt tcctaacctt gccgggaatg gctttgtggt aataggccag tcaaccagca    5220
ggatgcgtgt aggcgaattt gcggagctat tagagcttat acaggcattc ggtacagagc    5280
gtggcgttaa gtggtcagac gaagcgagac tggctctgga gtggaaagcg agatggggag    5340
acagggctgc atgataaatg tcgttagttt ctccggtggc aggacgtcag catatttgct    5400
ctggctaatg gagcaaaagc gacgggcagg taaagacgtg cattacgttt tcatggatac    5460
aggttgtgaa catccaatga catatcggtt tgtcagggaa gttgtgaagt tctgggatat    5520
accgctcacc gtattgcagg ttgatatcaa cccggagctt ggacagccaa atggttatac    5580
ggtatgggaa ccaaaggata ttcagacgcg aatgcctgtt ctgaagccat ttatcgatat    5640
ggtaaagaaa tatggcactc catacgtcgg cggcgcgttc tgcactgaca gattaaaact    5700
cgttcccttc accaaatact gtgatgacca tttcgggcga gggaattaca ccacgtggat    5760
tggcatcaga gctgatgaac cgaagcggct aaagccaaag cctggaatca gatatcttgc    5820
tgaactgtca gactttgaga aggaagatat cctcgcatgg tggaagcaac aaccattcga    5880
tttgcaaata ccggaacatc tcggtaactg catattctgc attaaaaaat caacgcaaaa    5940
aatcggactt gcctgcaaag atgaggaggg attgcagcgt gtttttaatg aggtcatcac    6000
gggatcccat gtgcgtgacg gacatcggga aacgccaaag gagattatgt accgaggaag    6060
```

```
aatgtcgctg gacggtatcg cgaaaatgta ttcagaaaat gattatcaag ccctgtatca    6120
ggacatggta cgagctaaaa gattcgatac cggctcttgt tctgagtcat gcgaaatatt    6180
tggagggcag cttgatttcg acttcgggag ggaagctgca tgatgcgatg ttatcggtgc    6240
ggtgaatgca aagaagataa ccgcttccga ccaaatcaac cttactggaa tcgatggtgt    6300
ctccggtgtg aaagaacacc aacaggggtg ttaccactac cgcaggaaaa ggaggacgtg    6360
tggcgagaca gcgacgaagt atcaccgaca taatctgcga aaactgcaaa taccttccaa    6420
cgaaacgcac cagaaataaa cccaagccaa tcccaaaaga atctgacgta aaaaccttca    6480
actacacggc tcacctgtgg gatatccggt ggctaagacg tcgtgcgagg aaaacaaggt    6540
gattgaccaa aatcgaagtt acgaacaaga aagcgtcgag cgagctttaa cgtgcgctaa    6600
ctgcggtcag aagctgcatg tgctggaagt tcacgtgtgt gagcactgct gcgcagaact    6660
gatgagcgat ccgaatagct cgatgcacga ggaagaagat gatggctaaa ccagcgcgaa    6720
gacgatgtaa aaacgatgaa tgccgggaat ggtttcaccc tgcattcgct aatcagtggt    6780
ggtgctctcc agagtgtgga accaagatag cactcgaacg acgaagtaaa gaacgcgaaa    6840
aagcggaaaa agcagcagag aagaaacgac gacgagagga gcagaaacag aaagataaac    6900
ttaagattcg aaaactcgcc ttaaagcccc gcagttactg gattaaacaa gcccaacaag    6960
ccgtaaacgc cttcatcaga gaaagagacc gcgacttacc atgtatctcg tgcggaacgc    7020
tcacgtctgc tcagtgggat gccggacatt accggacaac tgctgcggca cctcaactcc    7080
gatttaatga acgcaatatt cacaagcaat gcgtggtgtg caaccagcac aaaagcggaa    7140
atctcgttcc gtatcgcgtc gaactgatta gccgcatcgg gcaggaagca gtagacgaaa    7200
tcgaatcaaa ccataaccgc catcgctgga ctatcgaaga gtgcaaggcg atcaaggcag    7260
agtaccaaca gaaactcaaa gacctgcgaa atagcagaag tgaggccgca tgacgttctc    7320
agtaaaaacc attccagaca tgctcgttga agcatacgga aatcagacag aagtagcacg    7380
cagactgaaa tgtagtcgcg gtacggtcag aaaatacgtt gatgataaag acgggaaaat    7440
gcacgccatc gtcaacgacg ttctcatggt tcatcgcgga tggagtgaaa gagatgcgct    7500
attacgaaaa aattgatggc agcaaatacc gaaatatttg ggtagttggc gatctgcacg    7560
gatgctacac gaacctgatg aacaaactgg atacgattgg attcgacaac aaaaaagacc    7620
tgcttatctc ggtgggcgat ttggttgatc gtggtgcaga gaacgttgaa tgcctggaat    7680
taatcacatt cccctggttc agagctgtac gtggaaacca tgagcaaatg atgattgatg    7740
gcttatcaga gcgtggaaac gttaatcact ggctgcttaa tggcggtggc tggttctta    7800 atctcgatta cgacaaagaa attctggcta agctcttgc ccataaagca gatgaacttc    7860
cgttaatcat cgaactggtg agcaaagata aaaatatgt tatctgccac gccgattatc    7920
cctttgacga atacgagttt ggaaagccag ttgatcatca gcaggtaatc tggaaccgcg    7980
aacgaatcag caactcacaa aacgggatcg tgaaagaaat caaggcgcg gacacgttca    8040 tctttggtca tacgccagca gtgaaaccac tcaagtttgc caaccaaatg tatatcgata    8100
ccggcgcagt gttctgcgga aacctaacat tgattcaggt acagggagaa ggcgcatgag    8160
actcgaaagc gtagctaaat tcattcgcc aaaaagcccg atgatgagcg actcaccacg    8220
ggccacggct tctgactctc tttccggtac tgatgtgatg gctgctatgg ggatggcgca    8280
atcacaagcc ggattcggta tggctgcatt ctgcggtaag cacgaactca gccagaacga    8340
caaacaaaag gctatcaact atctgatgca atttgcacac aaggtatcgg ggaaataccg    8400
```

-continued

```
tggtgtggca aagcttgaag gaaatactaa ggcaaaggta ctgcaagtgc tcgcaacatt   8460
cgcttatgcg gattattgcc gtagtgccgc gacgccgggg gcaagatgca gagattgcca   8520
tggtacaggc cgtgcggttg atattgccaa acagagctg  tgggggagag ttgtcgagaa   8580
agagtgcgga agatgcaaag gcgtcggcta ttcaaggatg ccagcaagcg cagcatatcg   8640
cgctgtgacg atgctaatcc caaaccttac ccaacccacc tggtcacgca ctgttaagcc   8700
gctgtatgac gctctggtgg tgcaatgcca caaagaagag tcaatcgcag acaacatttt   8760
gaatgcggtc acacgttagc agcatgattg ccacggatgg caacatatta acggcatgat   8820
attgacttat tgaataaaat tgggtaaatt tgactcaacg atgggttaat tcgctcgttg   8880
tggtagtgag atgaaaagag gcggcgctta ctaccgattc cgcctagttg gtcacttcga   8940
cgtatcgtct ggaactccaa ccatcgcagg cagagaggtc tgcaaaatgc aatcccgaaa   9000
cagttcgcag gtaatagtta gagcctgcat aacggtttcg ggatttttta tatctgcaca   9060
acaggtaaga gcattgagtc gataatcgtg aagagtcggc gagcctggtt agccagtgct   9120
ctttccgttg tgctgaatta agcgaatacc ggaagcagaa ccggatcacc aaatgcgtac   9180
aggcgtcatc gccgcccagc aacagcacaa cccaaactga gccgtagcca ctgtctgtcc   9240
tgaattcatt agtaatagtt acgctgcggc cttttacaca tgaccttcgt gaaagcgggt   9300
ggcaggaggt cgcgctaaca acctcctgcc gttttgcccg tgcatatcgg tcacgaacaa   9360
atctgattac taaacacagt agcctggatt tgttctatca gtaatcgacc ttattcctaa   9420
ttaaatagag caaatcccct tattgggggt aagacatgaa gatgccagaa aaacatgacc   9480
tgttggccgc cattctcgcg gcaaaggaac aaggcatcgg gcaatcctt  gcgtttgcaa   9540
tggcgtacct tcgcggcaga tataatggcg gtgcgtttac aaaaacagta atcgacgcaa   9600
cgatgtgcgc cattatcgcc tggttcattc gtgaccttct cgacttcgcc ggactaagta   9660
gcaatctcgc ttatataacg agcgtgttta tcggctacat cggtactgac tcgattggtt   9720
cgcttatcaa acgcttcgct gctaaaaaag ccggagtaga agatggtaga aatcaataat   9780
caacgtaagg cgttcctcga tatgctggcg tggtcggagg gaactgataa cggacgtcag   9840
aaaaccagaa atcatggtta tgacgtcatt gtaggcggag agctatttac tgattactcc   9900
gatcaccctc gcaaacttgt cacgctaaac ccaaaactca aatcaacagg cgcttaagac   9960
tggccgtcgt tttacaacac agaaagagtt tgtagaaacg caaaaaggcc atccgtcagg  10020
ggccttctgc ttagtttgat gcctggcagt tccctactct cgccttccgc ttcctcgctc  10080
actgactcgc tgcgctcggt cgttcggctg cggcgagcgg tatcagctca ctcaaaggcg  10140
gtaatacggt tatccacaga atcaggggat aacgcaggaa agaacatgtg agcaaaaggc  10200
cagcaaaagg ccaggaaccg taaaaaggcc gcgttgctgg cgttttttcca taggctccgc  10260
cccctgacg  agcatcacaa aaatcgacgc tcaagtcaga ggtggcgaaa cccgacagga  10320
ctataaagat accaggcgtt tcccctggaa gctccctcg  tgcgctctcc tgttccgacc  10380
ctgccgctta ccggatacct gtccgccttt ctcccttcgg gaagcgtggc gctttctcat  10440
agctcacgct gtaggtatct cagttcggtg taggtcgttc gctccaagct gggctgtgtg  10500
cacgaacccc ccgttcagcc cgaccgctgc gccttatccg gtaactatcg tcttgagtcc  10560
aacccggtaa gacacgactt atcgccactg gcagcagcca ctggtaacag gattagcaga  10620
gcgaggtatg taggcggtgc tacagagttc ttgaagtggt gggctaacta cggctacact  10680
agaagaacag tatttggtat ctgcgctctg ctgaagccag ttaccttcgg aaaaagagtt  10740
ggtagctctt gatccggcaa acaaaccacc gctggtagcg gtggtttttt tgtttgcaag  10800
```

```
cagcagatta cgcgcagaaa aaaaggatct caagaagatc ctttgatctt ttctacgggg    10860
tctgacgctc agtggaacga cgcgcgcgta actcacgtta agggattttg gtcatgagct    10920
tgcgccgtcc cgtcaagtca gcgtaatgct ctgcttttag aaaaactcat cgagcatcaa    10980
atgaaactgc aatttattca tatcaggatt atcaatacca tattttgaa aaagccgttt     11040 ctgtaatgaa ggagaaaact caccgaggca gttccatagg atggcaagat cctggtatcg    11100
gtctgcgatt ccgactcgtc caacatcaat acaacctatt aatttcccct cgtcaaaaat    11160
aaggttatca agtgagaaat caccatgagt gacgactgaa tccggtgaga atggcaaaag    11220
tttatgcatt tctttccaga cttgttcaac aggccagcca ttacgctcgt catcaaaatc    11280
actcgcatca accaaaccgt tattcattcg tgattgcgcc tgagcgaggc gaaatacgcg    11340
atcgctgtta aaaggacaat tacaaacagg aatcgagtgc aaccggcgca ggaacactgc    11400
cagcgcatca acaatatttt cacctgaatc aggatattct tctaatacct ggaacgctgt    11460
ttttccgggg atcgcagtgg tgagtaacca tgcatcatca ggagtacgga taaaatgctt    11520
gatggtcgga agtggcataa attccgtcag ccagtttagt ctgaccatct catctgtaac    11580
atcattggca acgctacctt tgccatgttt cagaaacaac tctggcgcat cgggcttccc    11640
atacaagcga tagattgtcg cacctgattg cccgacatta tcgcgagccc atttataccc    11700
atataaatca gcatccatgt tggaatttaa tcgcggcctc gacgtttccc gttgaatatg    11760
gctcatattc ttccttttc aatattattg aagcatttat cagggttatt gtctcatgag    11820
cggatacata tttgaatgta tttagaaaaa taaacaaata gggtcagtg ttacaaccaa     11880 ttaaccaatt ctgaacatta tcgcgagccc atttataccg gaatatggct cataacaccc    11940
cttgtttgcc tggcggcagt agcgcggtgg tcccacctga ccccatgccg aactcagaag    12000
tgaaacgccg tagcgccgat ggtagtgtgg ggactcccca tgcgagagta gggaactgcc    12060
aggcatcaaa taaaacgaaa ggctcagtcg aaagactggg cctttcgccc gggctaatta    12120
gggggtgtcg cccttattcg actctatagt gaagttccta ttctctagaa agtataggaa    12180
cttctgaagt ggggtcgact taattaagg                                      12209
```

<210> SEQ ID NO 38
<211> LENGTH: 12374
<212> TYPE: DNA
<213> ORGANISM: Artificial Sequence
<220> FEATURE:
<223> OTHER INFORMATION: constructed sequence

<400> SEQUENCE: 38

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctacgta gcaagctagc    180
tagttattaa tagtaatcaa ttacggggtc attagttcat agcccatata tggagttccg    240
cgttacataa cttacggtaa atggcccgcc tggctgaccg cccaacgacc cccgcccatt    300
gacgtcaata atgacgtatg ttcccatagt aacgccaata gggactttcc attgacgtca    360
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattaa    540
catggtcgag gtgagcccca cgttctgctt cactctcccc atctccccc cctcccacc      600
```

```
cccaatttttg tatttattta ttttttaatt attttgtgca gcgatggggg cggggggggg    660
gggggggcgc gcgccaggcg gggcggggcg gggcgagggg cggggcgggg cgaggcggag    720
aggtgcggcg gcagccaatc agagcggcgc gctccgaaag tttccttttta tggcgaggcg   780
gcggcggcgc cggccctata aaaagcgaag cgcgcggcgg gcggggagtc gctgcgacgc    840
tgccttcgcc ccgtgccccg ctccgccgcc gcctcgcgcc gcccgccccg gctctgactg    900
accgcgttac tcccacaggt gagcgggcgg gacggcccctt ctcctccggg ctgtaattag   960
cgcttggttt aatgacggct tgtttcttttt ctgtggctgc gtgaaagcct tgagggggctc 1020
cgggagggcc ctttgtgcgg ggggagcggc tcgggggtg cgtgcgtgtg tgtgtgcgtg   1080
gggagcgccg cgtgcggctc cgcgctgccc ggcggctgtg agcgctgcgg gcgcggcgcg   1140
gggctttgtg cgctccgcag tgtgcgcgag gggagcgcgg ccggggcgg tgccccgcgg   1200
tgcggggggg gctgcgaggg gaacaaaggc tgcgtgcggg gtgtgtgcgt ggggggggtga 1260
gcagggggtg tgggcgcgtc ggtcgggctg caaccccccc tgcaccccccc tcccccgagtt 1320
gctgagcacg gcccggcttc gggtgcgggg ctccgtacgg ggcgtggcgc ggggctcgcc   1380
gtgccgggcg gggggtggcg gcaggtgggg gtgccgggcg gggcggggcc gcctcgggcc   1440
ggggagggct cggggggaggg gcgcggcggc ccccggagcg ccggcggctg tcgaggcgcg  1500
gcgagccgca gccattgcct tttatggtaa tcgtgcgaga gggcgcaggg acttcctttg   1560
tcccaaatct gtgcggagcc gaaatctggg aggcgccgcc gcaccccctc tagcgggcgc   1620
ggggcgaagc ggtgcggcgc cggcaggaag gaaatgggcg gggagggcct tcgtgcgtcg   1680
ccgcgccgcc gtcccttct ccctctccag cctcggggct gtccgcgggg ggacggctgc   1740
cttcgggggg gacggggcag ggcggggttc ggcttctggc gtgtgaccgg cggctctaga   1800
caattgtact aaccttcttc tcttttcctct cctgacaggt tggtgtacac tagcggccgc   1860
caccatggct aagattaaca cccagtactc acatccatcc cgcactcacc tcaaagtcaa   1920
gacctccgat cgggatctga accgggctga gaatgggctg tcgcgcgccc actcgtcgtc   1980
cgaggaaacc agcagcgtgc tccagccggg catcgccatg gaaactaggg ggctggcgga   2040
ctccggacag ggatccttca ctggacaggg tattgcccgg ttcgggcgga ttcagaagaa   2100
gtcccagccg gagaaggtcg tgcgggctgc cagcaggggc aggccactca ttggttggac   2160
acagtggtgc gctgaggatg gtggagatga atcggaaatg gcactggccg gctctcccgg   2220
atgcagctcg ggccccccaag ggagactgag cagactgatc ttcctgcttc gccgctgggc  2280
ggccagacac gtgcaccatc aggaccaggg acctgatagc ttccccgacc gctttagggg   2340
agccgagctg aaagaagtgt caagccagga gtcaaacgcg caggccaacg tcggcagcca   2400
agagcctgca gaccggggac gctcggcatg gccgctcgca aagtgcaaca ctaacacttc   2460
caacaacacc gaagaggaaa agaaaaaccaa gaagaaggat gcaattgtgg tggaccccttc 2520
ctccaacctg tactaccgct ggttgaccgc catcgccctc ccggtctttt acaattggta   2580
tctccttatc tgccgggcct gcttcgacga actgcaatca gagtacctga tgctgtggct   2640
ggtgctggac tatagcgccg atgtgctcta cgtcctggat gtgctcgtgc gcgcccggac   2700
cggattcttg gaacaaggcc tgatggtgtc cgacacgaat agactgtggc agcactataa   2760
gaccacaacc cagttcaagc ttgacgtgct cagccttgtg ccgactgacc tggcctacct   2820
gaaagtcgga actaactacc cggaagtcag attcaaccga ctcctgaagt tcagcaggct   2880
gttcgagttc tttgaccgca ccgagactcg gaccaactac cctaacatgt tccggatcgg   2940
aaatctggtg ctctacatac tgattatcat ccattggaac gcctgtatct atttcgccat   3000
```

```
ttcgaagttc atcggtttcg gaaccgattc ctgggtgtac cccaacatct cgatccccga    3060
acacggtcgc ctgtcccgga agtacatcta ctccctgtac tggtccactc tgactctgac    3120
cacgatcggg gaaaccccte cacccgtgaa ggacgaagag tacctgttcg tggtggtgga    3180
cttcctggtc ggagtgttga ttttcgccac cattgtggga aacgtgggct ccatgatctc    3240
caacatgaac gcgtcgagag ctgagttcca agccaagatc gactccatta agcagtacat    3300
gcagttcaga aaggtcacca aggacctgga aaccagggtc atccgctggt tcgactacct    3360
gtgggccaac aaaaagactg tggacgaaaa ggaagtgctg aagtcgctgc cggataagct    3420
gaaggccgaa atcgccatta acgtgcacct tgacaccctg aagaaagtcc ggatcttcca    3480
agactgtgaa gccggcctcc tggtggagct cgtgctcaag ctgcggccca ccgtgttcag    3540
cccgggagat tacatttgca gaagggcga tatcggcaaa gagatgtaca tcatcaacga    3600
gggaaagctg gccgtggtcg cggacgacgg cgtgacccag ttcgtggtgc tgtccgacgg    3660
atcctacttc ggtgaaatct caatcctcaa catcaagggg tccaagtccg caaccggag    3720 aactgccaac attcgctcca tcggatacag cgacctgttt tgcctgtcca aggatgacct    3780
gatggaggct ctgactgagt accctgaagc gaagaaggct ttggaggaaa aggggcggca    3840
gattctgatg aaggacaatt tgatcgacga ggagctcgca cgggccggcg ccgacccaa    3900 ggatctcgaa gagaaggtcg aacagctggg ttcttcgctt gatacccge aaacccgatt    3960 cgcgcggctg ctcgccgagt acaacgcgac ccagatgaag atgaagcaga gactgtcaca    4020
gttggaatcc caagtcaagg gcggaggcga caagccgctg gcggacgggg aagtgcccgg    4080
ggacgccacc aagactgagg acaagcagca gtgatcatag atcgatctgc ctcgactgtg    4140
ccttctagtt gccagccatc tgttgtttgc ccctccccg tgccttcctt gaccctggaa    4200
ggtgccactc ccactgtcct ttcctaataa aatgaggaaa ttgcatcgca ttgtctgagt    4260
aggtgtcatt ctattctggg gggtggggtg gggcaggaca gcaaggggga ggattgggaa    4320
gacaatagca ggcatgctgg ggactcgagt tctacgtaga taagtagcat ggcgggttaa    4380
tcattaacta caaggaaccc ctagtgatgg agttggccac tccctctctg cgcgctcgct    4440
cgctcactga ggccgggcga ccaaaggtcg cccgacgccc gggctttgcc cggcggcct    4500 cagtgagcga gcgagcgcgc agccttaatt aacctaagga aaatgaagtg aagttcctat    4560
actttctaga gaataggaac ttctatagtg agtcgaataa gggcgacaca aaatttattc    4620
taaatgcata taaatactg ataacatctt atagtttgta ttatattttg tattatcgtt    4680
gacatgtata attttgatat caaaaactga ttttcccttt attattttcg agatttattt    4740
tcttaattct ctttaacaaa ctagaaatat tgtatataca aaaatcata ataatagat    4800 gaatagttta attataggtg ttcatcaatc gaaaagcaa cgtatcttat ttaaagtgcg    4860
ttgctttttt ctcatttata aggttaaata attctcatat atcaagcaaa gtgacaggcg    4920
cccttaaata ttctgacaaa tgctctttcc ctaaactccc cccataaaaa acccgccga    4980 agcgggtttt tacgttattt gcggattaac gattactcgt tatcagaacc gcccagggg    5040 cccgagctta acctttttat ttgggggaga gggaagtcat gaaaaaacta acctttgaaa    5100
ttcgatctcc agcacatcag caaaacgcta ttcacgcagt acagcaaatc cttccagacc    5160
caaccaaacc aatcgtagta accattcagg aacgcaaccg cagcttagac caaaacagga    5220
agctatgggc ctgcttaggt gacgtctctc gtcaggttga atggcatggt cgctggctgg    5280
atgcagaaag ctggaagtgt gtgtttaccg cagcattaaa gcagcaggat gttgttccta    5340
```

-continued

```
accttgccgg gaatggcttt gtggtaatag gccagtcaac cagcaggatg cgtgtaggcg    5400
aatttgcgga gctattagag cttatacagg cattcggtac agagcgtggc gttaagtggt    5460
cagacgaagc gagactggct ctggagtgga aagcgagatg gggagacagg gctgcatgat    5520
aaatgtcgtt agtttctccg gtggcaggac gtcagcatat ttgctctggc taatggagca    5580
aaagcgacgg gcaggtaaag acgtgcatta cgttttcatg gatacaggtt gtgaacatcc    5640
aatgacatat cggtttgtca gggaagttgt gaagttctgg gatataccgc tcaccgtatt    5700
gcaggttgat atcaacccgg agcttggaca gccaaatggt tatacggtat gggaaccaaa    5760
ggatattcag acgcgaatgc ctgttctgaa gccatttatc gatatggtaa agaaatatgg    5820
cactccatac gtcggcggcg cgttctgcac tgacagatta aaactcgttc ccttcaccaa    5880
atactgtgat gaccatttcg ggcgagggaa ttacaccacg tggattggca tcagagctga    5940
tgaaccgaag cggctaaagc caaagcctgg aatcagatat cttgctgaac tgtcagactt    6000
tgagaaggaa gatatcctcg catggtggaa gcaacaacca ttcgatttgc aaataccgga    6060
acatctcggt aactgcatat tctgcattaa aaaatcaacg caaaaaatcg gacttgcctg    6120
caaagatgag gagggattgc agcgtgtttt taatgaggtc atcacgggat cccatgtgcg    6180
tgacggacat cgggaaacgc caaaggagat tatgtaccga ggaagaatgt cgctggacgg    6240
tatcgcgaaa atgtattcag aaaatgatta tcaagccctg tatcaggaca tggtacgagc    6300
taaaagattc gataccggct cttgttctga gtcatgcgaa atatttggag gcagcttga    6360 tttcgacttc ggagggaag ctgcatgatg cgatgttatc ggtgcggtga atgcaaagaa    6420
gataaccgct tccgaccaaa tcaaccttac tggaatcgat ggtgtctccg gtgtgaaaga    6480
acaccaacag gggtgttacc actaccgcag gaaaaggagg acgtgtggcg agacagcgac    6540
gaagtatcac cgacataatc tgcgaaaact gcaaatacct tccaacgaaa cgcaccagaa    6600
ataaacccaa gccaatccca aaagaatctg acgtaaaaac cttcaactac acggctcacc    6660
tgtgggatat ccgtggcta agacgtcgtc gaggaaaaac aaggtgattg accaaaatcg    6720
aagttacgaa caagaaagcg tcgagcgagc tttaacgtgc gctaactgcg gtcagaagct    6780
gcatgtgctg gaagttcacg tgtgtgagca ctgctgcgca gaactgatga gcgatccgaa    6840
tagctcgatg cacgaggaag aagatgatgg ctaaaccagc gcgaagacga tgtaaaaacg    6900
atgaatgccg ggaatggttt caccctgcat tcgctaatca gtggtggtgc ctctccagagt    6960 gtggaaccaa gatagcactc gaacgacgaa gtaaagaacg cgaaaaagcg gaaaaagcag    7020
cagagaagaa acgacgacga gaggagcaga aacagaaaga taaacttaag attcgaaaac    7080
tcgccttaaa gccccgcagt tactggatta aacaagccca acaagccgta aacgccttca    7140
tcagagaaag agaccgcgac ttaccatgta tctcgtgcgg aacgctcacg tctgctcagt    7200
gggatgccgg acattaccgg acaactgctg cggcacctca actccgattt aatgaacgca    7260
atattcacaa gcaatgcgtg gtgtgcaacc agcacaaaag cggaaatctc gttccgtatc    7320
gcgtcgaact gattagccgc atcgggcagg aagcagtaga cgaaatcgaa tcaaaccata    7380
accgccatcg ctggactatc gaagagtgca aggcgatcaa ggcagagtac caacagaaac    7440
tcaaagacct gcgaaatagc agaagtgagg ccgcatgacg ttctcagtaa aaaccattcc    7500
agacatgctc gttgaagcat acggaaatca gacagaagta gcacgcagac tgaaatgtag    7560
tcgcggtacg gtcagaaaat acgttgatga taaagacggg aaaatgcacg ccatcgtcaa    7620
cgacgttctc atggttcatc gcggatggag tgaaagagat gcgctattac gaaaaaattg    7680
atggcagcaa ataccgaaat atttgggtag ttggcgatct gcacggatgc tacacgaacc    7740
```

```
tgatgaacaa actggatacg attggattcg acaacaaaaa agacctgctt atctcggtgg    7800
gcgatttggt tgatcgtggt gcagagaacg ttgaatgcct ggaattaatc acattcccct    7860
ggttcagagc tgtacgtgga aaccatgagc aaatgatgat tgatggctta tcagagcgtg    7920
gaaacgttaa tcactggctg cttaatggcg gtggctggtc ctttaatctc gattacgaca    7980
aagaaattct ggctaaagct cttgcccata aagcagatga acttccgtta atcatcgaac    8040
tggtgagcaa agataaaaaa tatgttatct gccacgccga ttatcccttt gacgaatacg    8100
agtttggaaa gccagttgat catcagcagg taatctggaa ccgcgaacga atcagcaact    8160
cacaaaacgg gatcgtgaaa gaaatcaaag gcgcggacac gttcatcttt ggtcatacgc    8220
cagcagtgaa accactcaag tttgccaacc aaatgtatat cgataccggc gcagtgttct    8280
gcggaaacct aacattgatt caggtacagg agaaggcgc atgagactcg aaagcgtagc     8340
taaatttcat tcgccaaaaa gcccgatgat gagcgactca ccacgggcca cggcttctga    8400 ctctcttttcc ggtactgatg tgatggctgc tatggggatg gcgcaatcac aagccggatt   8460
cggtatggct gcattctgcg gtaagcacga actcagccag aacgacaaac aaaaggctat    8520
caactatctg atgcaatttg cacacaaggt atcggggaaa taccgtggtg tggcaaagct    8580
tgaaggaaat actaaggcaa aggtactgca agtgctcgca acattcgctt atgcggatta    8640
ttgccgtagt gccgcgacgc cgggggcaag atgcagagat tgccatggta caggccgtgc    8700
ggttgatatt gccaaaacag agctgtgggg gagagttgtc gagaaagagt gcggaagatg    8760
caaaggcgtc ggctattcaa ggatgccagc aagcgcagca tatcgcgctg tgacgatgct    8820
aatcccaaac cttacccaac ccacctggtc acgcactgtt aagccgctgt atgacgctct    8880
ggtggtgcaa tgccacaaag aagagtcaat cgcagacaac attttgaatg cggtcacacg    8940
ttagcagcat gattgccacg gatggcaaca tattaacggc atgatattga cttattgaat    9000
aaaattgggt aaatttgact caacgatggg ttaattcgct cgttgtggta gtgagatgaa    9060
aagaggcggc gcttactacc gattccgcct agttggtcac ttcgacgtat cgtctggaac    9120
tccaaccatc gcaggcagag aggtctgcaa aatgcaatcc cgaaacagtt cgcaggtaat    9180
agttagagcc tgcataacgg tttcgggatt ttttatatct gcacaacagg taagagcatt    9240
gagtcgataa tcgtgaagag tcggcgagcc tggttagcca gtgctctttc cgttgtgctg    9300
aattaagcga ataccggaag cagaaccgga tcaccaaatg cgtacaggcg tcatcgccgc    9360
ccagcaacag cacaacccaa actgagccgt agccactgtc tgtcctgaat tcattagtaa    9420
tagttacgct gcggcctttt acacatgacc ttcgtgaaag cgggtggcag gaggtcgcgc    9480
taacaacctc ctgccgtttt gcccgtgcat atcggtcacg aacaaatctg attactaaac    9540
acagtagcct ggatttgttc tatcagtaat cgaccttatt cctaattaaa tagagcaaat    9600
ccccttattg ggggtaagac atgaagatgc cagaaaaaca tgacctgttg gccgccattc    9660
tcgcggcaaa ggaacaaggc atcggggcaa tccttgcgtt tgcaatggcg taccttcgcg    9720
gcagatataa tggcggtgcg tttacaaaaa cagtaatcga cgcaacgatg tgcgccatta    9780
tcgcctggtt cattcgtgac cttctcgact tcgccggact aagtagcaat ctcgcttata    9840
taacgagcgt gtttatcggc tacatcggta ctgactcgat tggttcgctt atcaaacgct    9900
tcgctgctaa aaaagccgga gtagaagatg gtagaaatca ataatcaacg taaggcgttc    9960
ctcgatatgc tggcgtggtc ggagggaact gataacggac gtcagaaaac cagaaatcat    10020
ggttatgacg tcattgtagg cggagagcta tttactgatt actccgatca ccctcgcaaa    10080
```

-continued

```
cttgtcacgc taaacccaaa actcaaatca acaggcgctt aagactggcc gtcgttttac   10140
aacacagaaa gagtttgtag aaacgcaaaa aggccatccg tcaggggcct tctgcttagt   10200
ttgatgcctg gcagttccct actctcgcct tccgcttcct cgctcactga ctcgctgcgc   10260
tcggtcgttc ggctgcggcg agcggtatca gctcactcaa aggcggtaat acggttatcc   10320
acagaatcag gggataacgc aggaaagaac atgtgagcaa aaggccagca aaaggccagg   10380
aaccgtaaaa aggccgcgtt gctggcgttt ttccataggc tccgcccccc tgacgagcat   10440
cacaaaaatc gacgctcaag tcagaggtgg cgaaacccga caggactata agataccag   10500
gcgtttcccc ctggaagctc cctcgtgcgc tctcctgttc cgaccctgcc gcttaccgga   10560
tacctgtccg cctttctccc ttcgggaagc gtggcgcttt ctcatagctc acgctgtagg   10620
tatctcagtt cggtgtaggt cgttcgctcc aagctgggct gtgtgcacga accccccgtt   10680
cagcccgacc gctgcgcctt atccggtaac tatcgtcttg agtccaaccc ggtaagacac   10740
gacttatcgc cactggcagc agccactggt aacaggatta gcagagcgag gtatgtaggc   10800
ggtgctacag agttcttgaa gtggtgggct aactacggct acactagaag aacagtattt   10860
ggtatctgcg ctctgctgaa gccagttacc ttcggaaaaa gagttggtag ctcttgatcc   10920
ggcaaacaaa ccaccgctgg tagcggtggt ttttttgttt gcaagcagca gattacgcgc   10980
agaaaaaaag gatctcaaga agatcctttg atcttttcta cggggtctga cgctcagtgg   11040
aacgacgcgc gcgtaactca cgttaaggga ttttggtcat gagcttgcgc cgtcccgtca   11100
agtcagcgta atgctctgct tttagaaaaa ctcatcgagc atcaaatgaa actgcaattt   11160
attcatatca ggattatcaa taccatattt ttgaaaaagc cgtttctgta atgaaggaga   11220
aaactcaccg aggcagttcc ataggatggc aagatcctgg tatcggtctg cgattccgac   11280
tcgtccaaca tcaatacaac ctattaattt cccctcgtca aaaataaggt tatcaagtga   11340
gaaatcacca tgagtgacga ctgaatccgg tgagaatggc aaaagtttat gcatttcttt   11400
ccagacttgt tcaacaggcc agccattacg ctcgtcatca aaatcactcg catcaaccaa   11460
accgttattc attcgtgatt gcgcctgagc gaggcgaaat acgcgatcgc tgttaaaagg   11520
acaattacaa acaggaatcg agtgcaaccg gcgcaggaac actgccagcg catcaacaat   11580
attttcacct gaatcaggat attcttctaa tacctggaac gctgttttc cggggatcgc   11640
agtggtgagt aaccatgcat catcaggagt acggataaaa tgcttgatgg tcggaagtgg   11700
cataaattcc gtcagccagt ttagtctgac catctcatct gtaacatcat tggcaacgct   11760
acctttgcca tgtttcagaa acaactctgg cgcatcgggc ttcccataca agcgatagat   11820
tgtcgcacct gattgcccga cattatcgcg agcccattta tacccatata atcagcatc    11880
catgttggaa tttaatcgcg gcctcgacgt ttcccgttga atatggctca tattcttcct   11940
ttttcaatat tattgaagca tttatcaggg ttattgtctc atgagcggat acatatttga   12000
atgtatttag aaaaataaac aaataggggg cagtgttaca accaattaac caattctgaa   12060
cattatcgcg agcccattta tacctgaata tggctcataa caccccttgt ttgcctggcg   12120
gcagtagcgc ggtggtccca cctgacccca tgccgaactc agaagtgaaa cgccgtagcg   12180
ccgatggtag tgtggggact ccccatgcga gagtagggaa ctgccaggca tcaaataaaa   12240
cgaaaggctc agtcgaaaga ctgggccttt cgccggggct aattaggggg tgtcgccctt   12300
attcgactct atagtgaagt tcctattctc tagaaagtat aggaacttct gaagtggggt   12360
cgacttaatt aagg                                                     12374
```

<210> SEQ ID NO 39
<211> LENGTH: 11389
<212> TYPE: DNA
<213> ORGANISM: Artificial Sequence
<220> FEATURE:
<223> OTHER INFORMATION: constructed sequence

<400> SEQUENCE: 39

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctacgta | gcaagctagc | 180 |
| aagatccaag | ctcagatctc | gatcgagttg | gccccagaa | gcctggtggt | tgtttgtcct | 240 |
| tctcagggga | aaagtgaggc | ggccccttgg | aggaagggc | cgggcagaat | gatctaatcg | 300 |
| gattccaagc | agctcagggg | attgtctttt | tctagcacct | tcttgccact | cctaagcgtc | 360 |
| ctccgtgacc | ccggctggga | tttagcctgg | tgctgtgtca | gccccggtct | cccaggggct | 420 |
| tcccagtggt | ccccaggaac | cctcgacagg | gcccggtctc | tctcgtccag | caagggcagg | 480 |
| gacgggccac | aggccaaggg | ccctcgatcg | aggaactgaa | aaaccagaaa | gttaactggt | 540 |
| aagtttagtc | tttttgtctt | ttatttcagg | tcccggatcc | ggtggtggtg | caaatcaaag | 600 |
| aactgctcct | cagtggatgt | tgcctttact | tctaggcctg | tacggaagtg | ttacttctgc | 660 |
| tctaaaagct | gcggaattgt | acccggcggc | cgccaccatg | tttaaatcgc | tgacaaaagt | 720 |
| caacaaggtg | aagcctatag | gagagaacaa | tgagaatgaa | caagttctc | gtcggaatga | 780 |
| agaaggctct | cacccaagta | atcagtctca | gcaaaccaca | gcacaggaag | aaaacaaagg | 840 |
| tgaagagaaa | tctctcaaaa | ccaagtcaac | tccagtcacg | tctgaagagc | cacacaccaa | 900 |
| catacaagac | aaactctcca | agaaaaattc | ctctggagat | ctgaccacaa | accctgaccc | 960 |
| tcaaaatgca | gcagaaccaa | ctggaacagt | gccagagcag | aaggaaatgg | accccgggaa | 1020 |
| agaaggtcca | aacagcccac | aaaacaaacc | gccagcagct | cctgttataa | atgagtatgc | 1080 |
| cgatgcccag | ctacacaacc | tggtgaaaag | aatgcgtcaa | agaacagccc | tctacaagaa | 1140 |
| aaagttggta | gagggagatc | tctcctcacc | cgaagccagc | ccacaaactg | caaagcccac | 1200 |
| ggctgtacca | ccagtaaaag | aaagcgatga | taagccaaca | gaacattact | acaggctgtt | 1260 |
| gtggttcaaa | gtcaaaaaga | tgcctttaac | agagtactta | aagcgaatta | aacttccaaa | 1320 |
| cagcatagat | tcatacacag | atcgactcta | tctcctgtgg | ctcttgcttg | tcactcttgc | 1380 |
| ctataactgg | aactgctgtt | ttataccact | gcgcctcgtc | ttcccatatc | aaaccgcaga | 1440 |
| caacatacac | tactggctta | ttgcggacat | catctgtgat | atcatctacc | tttatgatat | 1500 |
| gctatttatc | cagcccagac | tccagtttgt | aagaggagga | gacataatag | tggattcaaa | 1560 |
| tgagctaagg | aaaacactaca | ggacttctac | aaaatttcag | ttggatgtcg | catcaataat | 1620 |
| accatttgat | atttgctacc | tcttctttgg | gtttaatcca | atgtttagag | caaataggat | 1680 |
| gttaaagtac | acttcatttt | ttgaatttaa | tcatcaccta | gagtctataa | tggacaaagc | 1740 |
| atatatctac | agagttattc | gaacaactgg | atacttgctg | tttattctgc | acattaatgc | 1800 |
| ctgtgtttat | tactgggctt | caaactatga | aggaattggc | actactagat | gggtgtatga | 1860 |
| tggggaagga | aacgagtatc | tgagatgtta | ttattgggca | gttcgaactt | taattaccat | 1920 |
| tggtggcctt | ccagaaccac | aaactttatt | tgaaattgtt | tttcaactct | gaatttttt | 1980 |
| ttctggagtt | tttgtgttct | ccagtttaat | tggtcagatg | agagatgtga | ttggagcagc | 2040 |
| tacagccaat | cagaactact | tccgcgcctg | catggatgac | accattgcct | acatgaacaa | 2100 |

```
ttactccatt cctaaacttg tgcaaaagcg agttcggact tggtatgaat atacatggga    2160
ctctcaaaga atgctagatg agtctgattt gcttaagacc ctaccaacta cggtccagtt    2220
agccctcgcc attgatgtga acttcagcat catcagcaaa gttgacttgt tcaagggttg    2280
tgatacacag atgatttatg acatgttgct aagattgaaa tccgttctct atttgcctgg    2340
tgactttgtc tgcaaaaagg gagaaattgg caaggaaatg tatatcatca agcatggaga    2400
agtccaagtt cttggaggcc ctgatggtac taaagttctg gttactctga agctgggtc    2460 ggtgttgga gaaatcagcc ttctagcagc aggaggagga aaccgtcgaa ctgccaatgt    2520
ggtggcccac gggtttgcca atcttttaac tctagacaaa aagaccctcc aagaaattct    2580
agtgcattat ccagattctg aaagaatcct catgaagaaa gccagagtgc ttttaaagca    2640
gaaggctaag accgcagaag caacccctcc aagaaaagat cttgccctcc tcttcccacc    2700
gaaagaagag acacccaaac tgttaaaac tctcctagga ggcacaggaa aagcaagtct    2760
tgcaagacta ctcaaattga agcgagagca agcagctcag aagaaagaaa attctgaagg    2820
aggagaggaa aaggaaaaag aaaatgaaga taaacaaaaa gaaaatgaag ataaacaaaa    2880
agaaaatgaa gataaaggaa aagaaaatga agataaagat aaaggaagag agccagaaga    2940
gaagccactg gacagacctg aatgtacagc aagtcctatt gcagtggagg aagaacccca    3000
ctcagttaga aggacagttt tacccagagg gacttctcgt caatcactca ttatcagcat    3060 ggctcccttct gctgagggcg gagaagaggt tcttactatt gaagtcaaag aaaaggctaa    3120
gcaatgatca taactgcaga tctgcctcga ctgtgccttc tagttgccag ccatctgttg    3180
tttgcccctc cccgtgcct tccttgaccc tggaaggtgc cactcccact gtcctttcct    3240
aataaaatga ggaaattgca tcgcattgtc tgagtaggtg tcattctatt ctggggggtg    3300
gggtggggca ggacagcaag ggggaggatt gggaagacaa tagcaggcat gctgggact    3360 cgagttctac gtagataagt agcatggcgg gttaatcatt aactacaagg acccctagt    3420 gatggagttg gccactccct ctctgcgcgc tcgctcgctc actgaggccg gcgaccaaa    3480 ggtcgcccga cgcccgggct tgcccgggc ggcctcagtg agcgagcgag cgcgcagcct    3540
taattaacct aaggaaatg aagtgaagtt cctatacttt ctagagaata ggaacttcta    3600
tagtgagtcg ataagggcg acacaaaatt tattctaaat gcataataaa tactgataac    3660
atcttatagt ttgtattata ttttgtatta tcgttgacat gtataatttt gatatcaaaa    3720
actgattttc cctttattat tttcgagatt tattttctta attctcttta acaaactaga    3780
aatattgtat atacaaaaaa tcataaataa tagatgaata gttaattat aggtgttcat    3840 caatcgaaaa agcaacgtat cttatttaaa gtgcgttgct ttttctcat ttataaggtt    3900 aaataattct catatatcaa gcaaagtgac aggcgccctt aaatattctg acaaatgctc    3960
tttccctaaa ctcccccca taaaaaaccc gccgaagcgg ttttttacgt tatttgcgga    4020
ttaacgatta ctcgttatca gaaccgccca ggggcccga gcttaacctt tttatttggg    4080
ggagagggaa gtcatgaaaa actaaccttt gaaattcga tctccagcac atcagcaaaa    4140
cgctattcac gcagtacagc aaatccttcc agacccaacc aaaccaatcg tagtaaccat    4200
tcaggaacgc aaccgcagct tagaccaaaa caggaagcta tgggcctgct taggtgacgt    4260
ctctcgtcag gttgaatggc atggtcgctg gctggatgca gaaagctgga gtgtgtgtt    4320 taccgcagca ttaaagcagc aggatgttgt tcctaacctt gccgggaatg gctttgtggt    4380
aataggccag tcaaccagca ggatgcgtgt aggcgaattt gcggagctat tagagcttat    4440
acaggcattc ggtacagagc gtggcgttaa gtggtcagac gaagcgagac tggctctgga    4500
```

```
gtggaaagcg agatggggag acagggctgc atgataaatg tcgttagttt ctccggtggc   4560
aggacgtcag catatttgct ctggctaatg gagcaaaagc gacgggcagg taaagacgtg   4620
cattacgttt tcatggatac aggttgtgaa catccaatga catatcggtt tgtcagggaa   4680
gttgtgaagt tctgggatat accgctcacc gtattgcagg ttgatatcaa cccggagctt   4740
ggacagccaa atggttatac ggtatgggaa ccaaaggata ttcagacgcg aatgcctgtt   4800
ctgaagccat ttatcgatat ggtaaagaaa tatggcactc catacgtcgg cggcgcgttc   4860
tgcactgaca gattaaaact cgttcccttc accaaatact gtgatgacca tttcgggcga   4920
gggaattaca ccacgtggat tggcatcaga gctgatgaac cgaagcggct aaagccaaag   4980
cctggaatca gatatcttgc tgaactgtca gactttgaga aggaagatat cctcgcatgg   5040
tggaagcaac aaccattcga tttgcaaata ccggaacatc tcggtaactg catattctgc   5100
attaaaaaat caacgcaaaa aatcggactt gcctgcaaag atgaggaggg attgcagcgt   5160
gtttttaatg aggtcatcac gggatcccat gtgcgtgacg gacatcggga aacgccaaag   5220
gagattatgt accgaggaag aatgtcgctg acggtatcg cgaaaatgta ttcagaaaat   5280
gattatcaag ccctgtatca ggacatggta cgagctaaaa gattcgatac cggctcttgt   5340
tctgagtcat gcgaaatatt tggagggcag cttgatttcg acttcgggag ggaagctgca   5400
tgatgcgatg ttatcggtgc ggtgaatgca aagaagataa ccgcttccga ccaaatcaac   5460
cttactggaa tcgatggtgt ctccggtgtg aaagaacacc aacaggggtg ttaccactac   5520
cgcaggaaaa ggaggacgtg tggcgagaca gcgacgaagt atcaccgaca taatctgcga   5580
aaactgcaaa taccttccaa cgaaacgcac cagaaataaa cccaagccaa tcccaaaaga   5640
atctgacgta aaaaccttca actacacggc tcacctgtgg gatatccggt ggctaagacg   5700
tcgtgcgagg aaaacaaggt gattgaccaa aatcgaagtt acgaacaaga aagcgtcgag   5760
cgagctttaa cgtgcgctaa ctgccggtcag aagctgcatg tgctggaagt tcacgtgtgt   5820
gagcactgct gcgcagaact gatgagcgat ccgaatagct cgatgcacga ggaagaagat   5880
gatggctaaa ccagcgcgaa gacgatgtaa aaacgatgaa tgccgggaat ggtttcaccc   5940
tgcattcgct aatcagtggt ggtgctctcc agagtgtgga accaagatag cactcgaacg   6000
acgaagtaaa gaacgcgaaa aagcggaaaa agcagcagag aagaaacgac gacgagagga   6060
gcagaaacag aaagataaac ttaagattcg aaaactcgcc ttaaagcccc gcagttactg   6120
gattaaacaa gcccaacaag ccgtaaacgc cttcatcaga gaaagagacc gcgacttacc   6180
atgtatctcg tgcggaacgc tcacgtctgc tcagtgggat gccggacatt accggacaac   6240
tgctgcggca cctcaactcc gatttaatga acgcaatatt cacaagcaat gcgtggtgtg   6300
caaccagcac aaaagcggaa atctcgttcc gtatcgcgtc gaactgatta gccgcatcgg   6360
gcaggaagca gtagacgaaa tcgaatcaaa ccataaccgc catcgctgga ctatcgaaga   6420
gtgcaaggca atcaaggcag agtaccaaca gaaactcaaa gacctgcgaa atagcagaag   6480
tgaggccgca tgacgttctc agtaaaaacc attccagaca tgctcgttga agcatacgga   6540
aatcagacag aagtagcacg cagactgaaa tgtagtcgcg gtacggtcag aaaatacgtt   6600
gatgataaag acgggaaaat gcacgccatc gtcaacgacg ttctcatggt tcatcgcgga   6660
tggagtgaaa gagatgcgct attacgaaaa aattgatggc agcaaatacc gaaatatttg   6720
ggtagttggc gatctgcacg gatgctacac gaacctgatg aacaaactgg atacgattgg   6780
attcgacaac aaaaaagacc tgcttatctc ggtgggcgat ttggttgatc gtggtgcaga   6840
```

```
gaacgttgaa tgcctggaat taatcacatt ccoctggttc agagctgtac gtggaaacca      6900
tgagcaaatg atgattgatg cttatcaga gcgtggaaac gttaatcact ggctgcttaa       6960
tggcggtggc tggttcttta atctcgatta cgacaaagaa attctggcta aagctcttgc      7020
ccataaagca gatgaacttc cgttaatcat cgaactggtg agcaaagata aaaatatgt      7080 tatctgccac gccgattatc cctttgacga atacgagttt ggaaagccag ttgatcatca     7140
gcaggtaatc tggaaccgcg aacgaatcag caactcacaa aacgggatcg tgaaagaaat    7200
caaaggcgcg gacacgttca tctttggtca tacgccagca gtgaaaccac tcaagtttgc    7260
caaccaaatg tatatcgata ccggcgcagt gttctgcgga aacctaacat tgattcaggt    7320
acagggagaa ggcgcatgag actcgaaagc gtagctaaat ttcattcgcc aaaaagcccg   7380
atgatgagcg actcaccacg ggccacggct tctgactctc tttccggtac tgatgtgatg    7440
gctgctatgg ggatggcgca atcacaagcc ggattcggta tggctgcatt ctgcggtaag   7500
cacgaactca gccagaacga caaacaaaag gctatcaact atctgatgca atttgcacac    7560
aaggtatcgg ggaaataccg tggtgtggca aagcttgaag gaaatactaa ggcaaaggta   7620
ctgcaagtgc tcgcaacatt cgcttatgcg gattattgcc gtagtccgc gacgccgggg   7680 gcaagatgca gagattgcca tggtacaggc cgtgcgttg atattgccaa aacagagctg   7740 tggggagag ttgtcgagaa agagtgcgga agatgcaaag gcgtcggcta ttcaaggatg    7800
ccagcaagcc cagcatatcg cgctgtgacg atgctaatcc caaaccttac ccaacccacc   7860
tggtcacgca ctgttaagcc gctgtatgac gctctggtgg tgcaatgcca caagaagag   7920 tcaatcgcag acaacattt gaatgcgtc acacgttagc agcatgattg ccacggatgg   7980
caacatatta acggcatgat attgacttat tgaataaaat tgggtaaatt tgactcaacg   8040
atgggttaat tcgctcgttg tggtagtgag atgaaaagag gcggcgctta ctaccgattc   8100
cgcctagttg gtcacttcga cgtatcgtct ggaactccaa ccatcgcagg cagagaggtc   8160
tgcaaaatgc aatcccgaaa cagttcgcag gtaatagtta gagcctgcat aacgtttcg    8220 ggatttttta tatctgcaca acaggtaaga gcattgagtc gataatcgtg aagagtcggc  8280
gagcctggtt agccagtgct ctttccgttg tgctgaatta agcgaatacc ggaagcagaa  8340
ccggatcacc aaatgcgtac aggcgtcatc gccgcccagc aacagcacaa cccaaactga  8400
gccgtagcca ctgtctgtcc tgaattcatt agtaatagtt acgctgcggc cttttacaca   8460
tgaccttcgt gaaagcgggt ggcaggaggt cgcgctaaca acctcctgcc gttttgcccg  8520
tgcatatcgg tcacgaacaa atctgattac taaacacagt agcctggatt tgttctatca   8580
gtaatcgacc ttattcctaa ttaaatagag caaatcccct tattgggggt aagacatgaa   8640
gatgccagaa aaacatgacc tgttggccgc cattctcgcg gcaaaggaac aaggcatcgg  8700
ggcaatcctt gcgtttgcaa tggcgtacct tcgcggcaga tataatggcg gtgcgtttac  8760
aaaaacagta atcgacgcaa cgatgtgcgc cattatcgcc tggttcattc gtgaccttct  8820
cgacttcgcc ggactaagta gcaatctcgc ttatataacg agcgtgttta tcggctacat   8880
cggtactgac tcgattggtt cgcttatcaa acgcttcgct gctaaaaaag ccggagtaga  8940
agatggtaga aatcaataat caacgtaagg cgttcctcga tatgctggcg tggtcggagg   9000
gaactgataa cggacgtcag aaaaccagaa atcatggtta tgacgtcatt gtaggcggag  9060
agctatttac tgattactcc gatcaccctc gcaaacttgt cacgctaaac ccaaaactca   9120
aatcaacagc cgcttaagac tggccgtcgt tttacaacac agaaagagtt tgtagaaacg   9180
caaaaaggcc atccgtcagg ggccttctgc ttagtttgat gcctggcagt tccctactct   9240
```

```
cgccttccgc ttcctcgctc actgactcgc tgcgctcggt cgttcggctg cggcgagcgg    9300
tatcagctca ctcaaaggcg gtaatacggt tatccacaga atcaggggat aacgcaggaa    9360
agaacatgtg agcaaaaggc cagcaaaagg ccaggaaccg taaaaaggcc gcgttgctgg    9420
cgtttttcca taggctccgc ccccctgacg agcatcacaa aaatcgacgc tcaagtcaga    9480
ggtggcgaaa cccgacagga ctataaagat accaggcgtt tccccctgga agctccctcg    9540
tgcgctctcc tgttccgacc ctgccgctta ccggatacct gtccgccttt ctcccttcgg    9600
gaagcgtggc gctttctcat agctcacgct gtaggtatct cagttcggtg taggtcgttc    9660
gctccaagct gggctgtgtg cacgaacccc ccgttcagcc cgaccgctgc gccttatccg    9720
gtaactatcg tcttgagtcc aacccggtaa gacacgactt atcgccactg gcagcagcca    9780
ctggtaacag gattagcaga gcgaggtatg taggcggtgc tacagagttc ttgaagtggt    9840
gggctaacta cggctacact agaagaacag tatttggtat ctgcgctctg ctgaagccag    9900
ttaccttcgg aaaaagagtt ggtagctctt gatccggcaa acaaaccacc gctggtagcg    9960
gtggtttttt tgtttgcaag cagcagatta cgcgcagaaa aaaaggatct caagaagatc   10020
ctttgatctt ttctacgggg tctgacgctc agtggaacga cgcgcgcgta actcacgtta   10080
agggattttg gtcatgagct tgcgccgtcc cgtcaagtca gcgtaatgct ctgcttttag   10140
aaaaactcat cgagcatcaa atgaaactgc aatttattca tatcaggatt atcaatacca   10200
tatttttgaa aaagccgttt ctgtaatgaa ggagaaaact caccgaggca gttccatagg   10260
atggcaagat cctggtatcg gtctgcgatt ccgactcgtc caacatcaat acaacctatt   10320
aatttcccct cgtcaaaaat aaggttatca agtgagaaat caccatgagt gacgactgaa   10380
tccggtgaga atggcaaaag tttatgcatt tctttccaga cttgttcaac aggccagcca   10440
ttacgctcgt catcaaaatc actcgcatca accaaaccgt tattcattcg tgattgcgcc   10500
tgagcgaggc gaaatacgcg atcgctgtta aaaggacaat acaaacagg aatcgagtgc    10560 aaccggcgca ggaacactgc cagcgcatca acaatatttt cacctgaatc aggatattct   10620
tctaatacct ggaacgctgt ttttccgggg atcgcagtgg tgagtaacca tgcatcatca   10680
ggagtacgga taaaatgctt gatggtcgga agtggcataa attccgtcag ccagtttagt   10740
ctgaccatct catctgtaac atcattggca acgctacctt tgccatgttt cagaaacaac   10800
tctggcgcat cgggcttccc atacaagcga tagattgtcg cacctgattg cccgacatta   10860
tcgcgagccc atttataccc atataaatca gcatccatgt tggaatttaa tcgcggcctc   10920
gacgtttccc gttgaatatg gctcatattc ttcctttttc aatattattg aagcatttat   10980
cagggttatt gtctcatgag cggatacata tttgaatgta tttagaaaaa taaacaaata   11040
ggggtcagtg ttacaaccaa ttaaccaatt ctgaacatta tcgcgagccc atttatacct   11100
gaatatggct cataacaccc cttgtttgcc tggcggcagt agcgcggtgg tcccacctga   11160
ccccatgccg aactcagaag tgaaacgccg tagcgccgat ggtagtgtgg ggactcccca   11220
tgcgagagta gggaactgcc aggcatcaaa taaaacgaaa ggctcagtcg aaagactggg   11280
cctttcgccc gggctaatta gggggtgtcg cccttattcg actctatagt gaagttccta   11340
ttctctagaa agtataggaa cttctgaagt ggggtcgact taattaagg               11389
```

<210> SEQ ID NO 40
<211> LENGTH: 11388
<212> TYPE: DNA
<213> ORGANISM: Artificial Sequence
<220> FEATURE:

<223> OTHER INFORMATION: constructed sequence

<400> SEQUENCE: 40

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
aagatccaag ctcagatctc gatcgagttg ggccccagaa gcctggtggt tgtttgtcct     240
tctcagggga aaagtgaggc ggccccttgg aggaaggggc cgggcagaat gatctaatcg     300
gattccaagc agctcagggg attgtctttt tctagcacct tcttgccact cctaagcgtc     360
ctccgtgacc ccggctggga tttagcctgg tgctgtgtca gccccggtct cccagggct      420
tcccagtggt ccccaggaac cctcgacagg gcccggtctc tctcgtccag caagggcagg     480
gacgggccac aggccaaggg ccctcgatcg aggaactgaa aaaccagaaa gttaactggt     540
aagtttagtc tttttgtctt ttatttcagg tcccggatcc ggtggtggtg caaatcaaag     600
aactgctcct cagtggatgt tgcctttact tctaggcctg tacggaagtg ttacttctgc     660
tctaaaagct gcggaattgt acccgcggcc gccaccatgt tcaagtccct caccaaagtc     720
aacaaggtca agcccatcgg agagaacaac gagaatgagc agagctctcg gcgcaacgaa     780
gaaggatccc atccgtcgaa ccagtcacag cagactaccg cacaggagga gaacaaggga     840
gaagaaaagt cgctcaagac taagtccacc cccgtgacct cggaagaacc gcacacgaac     900
attcaggaca agctgtccaa gaagaactcc tccggcgatc tcacgactaa cccggacccc     960
cagaatgccg ctgaacctac tgggaccgtg cctgagcaaa aggagatgga ccccggaaag    1020
gagggtccta actccccca aaacaagccc ccggccgcgc cggtcatcaa tgagtacgcg    1080
gacgcgcaac tgcataacct cgtgaagcgg atgcggcaaa gaaccgccct ctacaagaag    1140
aaactggtgg agggcgacct gagctcacct gaagccagcc cacagaccgc caaacccacc    1200
gccgtgccgc ctgtgaagga gtccgatgac aagcctaccg agcactacta ccgcctgctg    1260
tggttcaagg tcaagaagat gccctgaccc gaatacctca agcggatcaa gctgccgaac    1320
agcatcgaca gctacaccga ccggctttac ttgctctggc tgctgcttgt gaccctggct    1380
tacaactgga actgttgttt cattccctg cggctggtgt tcccttacca aaccgcggat     1440
aacattcact actggctgat tgccgacatc atttgcgaca tcatctacct gtacgatatg    1500
ctttttatcc aaccgcggct gcaattcgtc cgcggggag acatcattgt ggactccaac    1560
gagctgcgca gcattaccg gacctcgaca aagttccagc tggatgtggc ctccatcatc    1620
ccgttcgata tctgttacct gttctttggc ttcaacccga tgttcagggc gaacaggatg    1680
ctgaagtaca cttccttctt cgaattcaac caccacctgg agtccatcat ggacaaggct    1740
tacatctacc gcgtgatccg gaccactggt tacctcctgt tcatcctgca catcaacgcc    1800
tgcgtctatt actgggcctc aaactacgaa ggcattggta ccacccgctg ggtgtacgac    1860
ggggagggaa acgagtatct gcgctgctac tactgggccg tgcgaaccct cataactatt    1920
ggcggcctcc cggaaccgca gaccctgttc gagatcgtgt tccaactcct caacttcttc    1980
tcgggagtgt tcgtgttttc aagcttgatt ggacagatgc gggacgtgat cggtgcagca    2040
actgccaacc agaactactt tcgcgcctgc atggacgaca ctatcgcgta catgaacaac    2100
tattcgatcc ccaagctggt gcagaaacgc gtgcggactt ggtatgagta cacttgggac    2160
tcccagagaa tgcttgacga gtccgatctg ctcaagaccc tgcctactac cgtgcagctg    2220
gcactcgcca tcgatgtgaa cttctccatt atctcgaaag tcgatctgtt caagggctgc    2280
```

```
gacacccaga tgatctacga catgctgctg agactcaagt ccgtgttgta cctccctggc   2340
gacttcgtgt gcaagaaggg cgaaatcggg aaggagatgt acattatcaa gcacggagaa   2400
gtccaggtgc tgggggacc agacggtacc aaggtccttg tcaccctgaa ggccgggtcc    2460
gtgttcggcg aaatttccct gttggccgcc ggcggtggca acaggagaac cgcaaatgtg   2520
gtggcccacg gcttcgcaaa ccttctgacc ctggacaaga aaaccctcca ggaaatcctc   2580
gtgcactacc cggatagcga gcggatcctg atgaagaaag cccgggtgct gctgaagcaa   2640
aaggccaaga ccgccgaagc caccccgcct cggaaggacc tggctctgct gttcccaccc   2700
aaggaggaga ctcccaaact gtttaagacc ctcttgggcg ggacgggaaa ggcctccctc   2760
gctcgcttgc ttaagttgaa gagggagcag gccgcgcaga agaaggaaaa ctccgaagga   2820
ggggaagaag agggaaagga aaacgaagat aagcagaagg agaacgagga taagcaaaag   2880
gaaaatgagg acaaggggaa agaaaacgag gacaaggata agggtcgcga acctgaagag   2940
aagccgctgg atcggccaga gtgcactgcc tcgcctatcg cggtcgaaga ggaaccccat   3000
agcgtgcgca gaaccgtgct gcctagaggc acatcgaggc agtcactgat tatctctatg   3060
gcaccaagcg ccgagggagg agaggaagtg ctcaccatcg aggtcaagga aaaagcgaag   3120
cagtgatcat aactgcagat ctgcctcgac tgtgccttct agttgccagc catctgttgt   3180
ttgcccctcc cccgtgcctt ccttgaccct ggaaggtgcc actccactg tcctttccta    3240
ataaaatgag gaaattgcat cgcattgtct gagtaggtgt cattctattc tggggggtgg   3300
ggtggggcag gacagcaagg gggaggattg gaagacaat agcaggcatg ctggggactc    3360
gagttctacg tagataagta gcatggcggg ttaatcatta actacaagga acccctagtg   3420
atggagttgg ccactccctc tctgcgcgct cgctcgctca ctgaggccgg gcgaccaaag   3480
gtcgcccgac gcccgggctt tgcccgggcg gcctcagtga gcgagcgagc gcgcagcctt   3540
aattaaccta aggaaaatga agtgaagttc ctatactttc tagagaatag gaacttctat   3600
agtgagtcga taagggcga cacaaaattt attctaaatg cataataaat actgataaca    3660
tcttatagtt tgtattatat tttgtattat cgttgacatg tataattttg atatcaaaaa   3720
ctgattttcc ctttattatt ttcgagattt attttcttaa ttctctttaa caaactagaa   3780
atattgtata tacaaaaaat cataaataat agatgaatag tttaattata ggtgttcatc   3840
aatcgaaaaa gcaacgtatc ttatttaaag tgcgttgctt ttttctcatt tataaggtta   3900
ataattctc atatatcaag caaagtgaca ggcgccctta atattctga caaatgctct     3960
ttccctaaac tccccccata aaaaacccg ccgaagcggg ttttacgtt atttgcggat     4020
taacgattac tcgttatcag aaccgcccag ggggcccgag cttaaccttt ttatttgggg   4080
gagagggaag tcatgaaaaa actaaccttt gaaattcgat ctccagcaca tcagcaaaac   4140
gctattcacg cagtacagca aatccttcca gacccaacca aaccaatcgt agtaaccatt   4200
caggaacgca accgcagctt agaccaaaac aggaagctat gggcctgctt aggtgacgtc   4260
tctcgtcagg ttgaatggca tggtcgctgg ctggatgcag aaagctggaa gtgtgtgttt   4320
accgcagcat taaagcagca ggatgttgtt cctaaccttg ccgggaatgg ctttgtggta   4380
ataggccagt caaccagcag gatgcgtgta ggcgaatttg cggagctatt agagcttata   4440
caggcattcg gtacagagcg tggcgttaag tggtcagacg aagcgagact ggctctggag   4500
tggaaagcga gatggggaga cagggctgca tgataaatgt cgttagtttc tccggtggca   4560
ggacgtcagc atatttgctc tggctaatgg agcaaaagcg acgggcaggt aaagacgtgc   4620
```

```
attacgtttt catggataca ggttgtgaac atccaatgac atatcggttt gtcagggaag   4680
ttgtgaagtt ctgggatata ccgctcaccg tattgcaggt tgatatcaac ccggagcttg   4740
gacagccaaa tggttatacg gtatgggaac caaaggatat tcagacgcga atgcctgttc   4800
tgaagccatt tatcgatatg gtaaagaaat atggcactcc atacgtcggc ggcgcgttct   4860
gcactgacag attaaaactc gttcccttca ccaaatactg tgatgaccat ttcgggcgag   4920
ggaattacac cacgtggatt ggcatcagag ctgatgaacc gaagcggcta aagccaaagc   4980
ctggaatcag atatcttgct gaactgtcag actttgagaa ggaagatatc ctcgcatggt   5040
ggaagcaaca accattcgat ttgcaaatac cggaacatct cggtaactgc atattctgca   5100
ttaaaaaatc aacgcaaaaa atcggacttg cctgcaaaga tgaggaggga ttgcagcgtg   5160
tttttaatga ggtcatcacg ggatcccatg tgcgtgacgg acatcgggaa acgccaaagg   5220
agattatgta ccgaggaaga atgtcgctgg acggtatcgc gaaaatgtat tcagaaaatg   5280
attatcaagc cctgtatcag gacatggtac gagctaaaag attcgatacc ggctcttgtt   5340
ctgagtcatg cgaaatattt ggagggcagc ttgatttcga cttcgggagg gaagctgcat   5400
gatgcgatgt tatcggtgcg gtgaatgcaa agaagataac cgcttccgac caaatcaacc   5460
ttactggaat cgatggtgtc tccggtgtga agaacacaca cagggggtgt taccactacc   5520
gcaggaaaag gaggacgtgt ggcgagacag cgacgaagta tcaccgacat aatctgcgaa   5580
aactgcaaat accttccaac gaaacgcacc agaaataaac ccaagccaat cccaaaagaa   5640
tctgacgtaa aaaccttcaa ctacacggct cacctgtggg atatccggtg ctaagacgt   5700
cgtgcgagga aaacaaggtg attgaccaaa atcgaagtta cgaacaagaa agcgtcgagc   5760
gagctttaac gtgcgctaac tgcggtcaga agctgcatgt gctggaagtt cacgtgtgtg   5820
agcactgctg cgcagaactg atgagcgatc cgaatagctc gatgcacgag gaagaagatg   5880
atggctaaac cagcgcgaag acgatgtaaa aacgatgaat gccgggaatg gtttcaccct   5940
gcattcgcta atcagtggtg gtgctctcca gagtgtggaa ccaagatagc actcgaacga   6000
cgaagtaaag aacgcgaaaa agcggaaaaa gcagcagaga agaaacgacg acgagaggag   6060
cagaaacaga aagataaact taagattcga aaactcgcct taaagccccg cagttactgg   6120
attaaacaag cccaacaagc cgtaaacgcc ttcatcagag aaagagaccg cgacttacca   6180
tgtatctcgt gcggaacgct cacgtctgct cagtgggatg ccggacatta ccggacaact   6240
gctgcggcac ctcaactccg atttaatgaa cgcaatattc acaagcaatg cgtggtgtgc   6300
aaccagcaca aaagcggaaa tctcgttccg tatcgcgtcg aactgattag ccgcatcggg   6360
caggaagcag tagacgaaat cgaatcaaac cataaccgcc atcgctggac tatcgaagag   6420
tgcaaggcga tcaaggcaga gtaccaacag aaactcaaag acctgcgaaa tagcagaagt   6480
gaggccgcat gacgttctca gtaaaaacca ttccagacat gctcgttgaa gcatacggaa   6540
atcagacaga agtagcacgc agactgaaat gtagtcgcgg tacggtcaga aaatacgttg   6600
atgataaaga cgggaaaatg cacgccatcg tcaacgacgt tctcatggtt catcgcggat   6660
ggagtgaaag agatgcgcta ttacgaaaaa attgatggca gcaaataccg aaatatttgg   6720
gtagttggcg atctgcacgg atgctacacg aacctgatga acaaactgga tacgattgga   6780
ttcgacaaca aaaaagacct gcttatctcg gtgggcgatt tggttgatcg tggtgcagag   6840
aacgttgaat gcctggaatt aatcacattc ccctggttca gagctgtacg tggaaaccat   6900
gagcaaatga tgattgatgg cttatcagag cgtggaaacg ttaatcactg gctgcttaat   6960
ggcggtggct ggttctttaa tctcgattac gacaaagaaa ttctggctaa agctcttgcc   7020
```

```
cataaagcag atgaacttcc gttaatcatc gaactggtga gcaaagataa aaaatatgtt   7080
atctgccacg ccgattatcc ctttgacgaa tacgagtttg aaagccagt tgatcatcag    7140 caggtaatct ggaaccgcga acgaatcagc aactcacaaa acgggatcgt gaaagaaatc   7200
aaaggcgcgg acacgttcat ctttggtcat acgccagcag tgaaaccact caagtttgcc   7260
aaccaaatgt atatcgatac cggcgcagtg ttctgcggaa acctaacatt gattcaggta   7320
cagggagaag gcgcatgaga ctcgaaagcg tagctaaatt tcattcgcca aaaagcccga   7380
tgatgagcga ctcaccacgg gccacggctt ctgactctct ttccggtact gatgtgatgg   7440
ctgctatggg gatggcgcaa tcacaagccg gattcggtat ggctgcattc tgcggtaagc   7500
acgaactcag ccagaacgac aaacaaaagg ctatcaacta tctgatgcaa tttgcacaca   7560
aggtatcggg gaaataccgt ggtgtggcaa agcttgaagg aaatactaag gcaaaggtac   7620
tgcaagtgct cgcaacattc gcttatgcgg attattgccg tagtgccgcg acgccggggg   7680
caagatgcag agattgccat ggtacaggcc gtgcggttga tattgccaaa acagagctgt   7740
gggggagagt tgtcgagaaa gagtgcggaa gatgcaaagg cgtcggctat tcaaggatgc   7800
cagcaagcgc agcatatcgc gctgtgacga tgctaatccc aaaccttacc caacccacct   7860
ggtcacgcac tgttaagccg ctgtatgacg ctctggtggt gcaatgccac aaagaagagt   7920
caatcgcaga caacattttg aatgcggtca cacgttagca gcatgattgc cacggatggc   7980
aacatattaa cggcatgata ttgacttatt gaataaaatt gggtaaattt gactcaacga   8040
tgggttaatt cgctcgttgt ggtagtgaga tgaaaagagg cggcgcttac taccgattcc   8100
gcctagttgg tcacttcgac gtatcgtctg gaactccaac catcgcaggc agagaggtct   8160
gcaaaatgca atcccgaaac agttcgcagg taatagttag agcctgcata acggtttcgg   8220 gatttttat atctgcacaa caggtaagag cattgagtcg ataatcgtga agagtcggcg    8280
agcctggtta gccagtgctc tttccgttgt gctgaattaa gcgaataccg gaagcagaac   8340
cggatcacca aatgcgtaca ggcgtcatcg ccgcccagca acagcacaac ccaaactgag   8400
ccgtagccac tgtctgtcct gaattcatta gtaatagtta cgctgcggcc ttttacacat   8460
gaccttcgtg aaagcgggtg gcaggaggtc gcgctaacaa cctcctgccg ttttgcccgt   8520
gcatatcggt cacgaacaaa tctgattact aaacacagta gcctggattt gttctatcag   8580
taatcgacct tattcctaat taaatagagc aaatccccctt attgggggta agacatgaag   8640
atgccagaaa aacatgacct gttggccgcc attctcgcgg caaaggaaca aggcatcggg   8700
gcaatccttg cgtttgcaat ggcgtacctt cgcggcagat ataatggcgg tgcgtttaca   8760
aaaacagtaa tcgacgcaac gatgtgcgcc attatcgcct ggttcattcg tgaccttctc   8820
gacttcgccg gactaagtag caatctcgct tatataacga gcgtgtttat cggctacatc   8880
ggtactgact cgattggttc gcttatcaaa cgcttcgctg ctaaaaaagc cggagtagaa   8940
gatggtagaa atcaataatc aacgtaaggc gttcctcgat atgctggcgt ggtcggaggg   9000
aactgataac ggacgtcaga aaaccagaaa tcatggttat gacgtcattg taggcggaga   9060
gctatttact gattactccg atcaccctcg caaacttgtc acgctaaacc caaaactcaa   9120
atcaacaggc gcttaagact ggccgtcgtt ttacaacaca gaaagagttt gtagaaacgc   9180
aaaaaggcca tccgtcaggg gccttctgct tagtttgatg cctggcagtt ccctactctc   9240
gccttccgct tcctcgctca ctgactcgct gcgctcggtc gttcggctgc ggcgagcggt   9300
atcagctcac tcaaaggcgg taatacggtt atccacagaa tcagggggata acgcaggaaa   9360
```

```
gaacatgtga gcaaaaggcc agcaaaaggc caggaaccgt aaaaaggccg cgttgctggc    9420 gttttttccat aggctccgcc ccctgacga gcatcacaaa aatcgacgct caagtcagag    9480
gtggcgaaac ccgacaggac tataaagata ccaggcgttt ccccctggaa gctccctcgt    9540
gcgctctcct gttccgaccc tgccgcttac cggatacctg tccgcctttc tcccttcggg    9600
aagcgtggcg ctttctcata gctcacgctg taggtatctc agttcggtgt aggtcgttcg    9660
ctccaagctg ggctgtgtgc acgaaccccc cgttcagccc gaccgctgcg ccttatccgg    9720
taactatcgt cttgagtcca acccggtaag acacgactta tcgccactgg cagcagccac    9780
tggtaacagg attagcagag cgaggtatgt aggcggtgct acagagttct tgaagtggtg    9840
ggctaactac ggctacacta agaacagt atttggtatc tgcgctctgc tgaagccagt    9900
taccttcgga aaaagagttg gtagctcttg atccggcaaa caaaccaccg ctggtagcgg    9960
tggttttttt gtttgcaagc agcagattac gcgcagaaaa aaggatctc aagaagatcc    10020 tttgatcttt tctacggggt ctgacgctca gtggaacgac gcgcgcgtaa ctcacgttaa    10080
gggattttgg tcatgagctt gcgccgtccc gtcaagtcag cgtaatgctc tgcttttaga    10140
aaaactcatc gagcatcaaa tgaaactgca atttattcat atcaggatta tcaataccat    10200
atttttgaaa aagccgtttc tgtaatgaag agaaaactc accgaggcag ttccatagga    10260
tggcaagatc ctggtatcgg tctgcgattc cgactcgtcc aacatcaata caacctatta    10320
atttcccctc gtcaaaaata aggttatcaa gtgagaaatc accatgagtg acgactgaat    10380
ccggtgagaa tggcaaaagt ttatgcattt cttccagac ttgttcaaca ggccagccat    10440
tacgctcgtc atcaaaatca ctcgcatcaa ccaaaccgtt attcattcgt gattgcgcct    10500
gagcgaggcg aaatacgcga tcgctgttaa aaggacaatt acaaacagga atcgagtgca    10560
accggcgcag gaacactgcc agcgcatcaa caatattttc acctgaatca ggatattctt    10620
ctaatacctg gaacgctgtt tttccgggga tcgcagtggt gagtaaccat gcatcatcag    10680
gagtacggat aaaatgcttg atggtcggaa gtggcataaa ttccgtcagc cagtttagtc    10740
tgaccatctc atctgtaaca tcattggcaa cgctacctt gccatgtttc agaaacaact    10800
ctggcgcatc gggcttccca tacaagcgat agattgtcgc acctgattgc ccgacattat    10860
cgcgagccca tttatacccc tataaatcag catccatgtt ggaatttaat cgcggcctcg    10920
acgtttcccg ttgaatatgg ctcatattct cctttttca atattattga agcatttatc    10980
agggttattg tctcatgagc ggatacatat ttgaatgtat ttagaaaaat aaacaaatag    11040
gggtcagtgt tacaaccaat taaccaattc tgaacattat cgcgagccca tttataccctg   11100 aatatggctc ataacacccc ttgtttgcct ggcggcagta gcgcggtggt cccacctgac    11160
cccatgccga actcagaagt gaaacgccgt agcgccgatg gtagtgtggg gactccccat    11220
gcgagagtag ggaactgcca ggcatcaaat aaaacgaaag gctcagtcga aagactgggc    11280
ctttcgcccg gctaattag ggggtgtcgc ccttattcga ctctatagtg aagttcctat    11340
tctctagaaa gtataggaac ttctgaagtg gggtcgactt aattaagg                  11388
```

<210> SEQ ID NO 41
<211> LENGTH: 11782
<212> TYPE: DNA
<213> ORGANISM: Artificial Sequence
<220> FEATURE:
<223> OTHER INFORMATION: constructed sequence

<400> SEQUENCE: 41

```
ctgcgcgctc gctcgctcac tgaggccgcc cgggcaaagc ccgggcgtcg gcgacctttt    60
```

```
ggtcgcccgg cctcagtgag cgagcgagcg cgcagagagg gagtggccaa ctccatcact    120
aggggttcct tgtagttaat gattaacccg ccatgctact tatctacgta gcaagctagc    180
ctgaagagac agaaatatct ctaattccat gagcggtcat acgaggcaag agaagccgct    240
tagagcatgg acttagttag tttcagggat tggacagagt caagagctgg ggtgaggagg    300
ttaccctcgg taggggtgac acagatgtca accgcctatt ccctccacat gcatgtcctg    360
ccagaagaac ctgtccctgg gctgggaatc ttatattacc ttcctctcca atgagaagag    420
aagttcaagg ctcacagaca tgtgcataca caagctcaat gcactcaaga ttcccctcca    480
ccactcctgc ccccactacc tacaggagat tgactcctgc tgtgcacata agctgggata    540
atcagggttt ctaaacatca gcttcaaaag tccaatgtcc aaagtggtgg ggggccgggg    600
aacgaggtac tctttccata cccttggctt ttgtgtggcc tggagccgct gatatagaga    660
ttggagtggg acacgaggta ttcctttcaa aaacacaaag gcctatactt tgagccctcc    720
catttcaatc ccccaccatg cttcaccttt aagacctcca actccacttt gatcccagtt    780
ctcaggttca ggcctcacaa ggccaaaatc ctgaagttac ccttctcaaa ctcccttgcc    840
tttaacatca tcagaatcaa cctcctaccc ccactctgtc ccagcagcaa tagcctgcta    900
atcttttagc actaatcttt taggcactaa tctgctttcc aaactcttgg cacctgaact    960
atttataagc agtgttttat gccccccac caaagaaccc tattcttttc ccatgacccc    1020
accaatcaaa acactcagag gactgtgggt ataagaggct ggggaggcag gcatagcagc    1080
ggccgccacc atgtttaaat cgctgacaaa agtcaacaag gtgaagccta taggagagaa    1140
caatgagaat gaacaaagtt ctcgtcggaa tgaagaaggc tctcacccaa gtaatcagtc    1200
tcagcaaacc acagcacagg aagaaaacaa aggtgaagag aaatctctca aaaccaagtc    1260
aactccagtc acgtctgaag agccacacac caacatacaa gacaaactct ccaagaaaaa    1320
ttcctctgga gatctgacca caaacccctga ccctcaaaat gcagcagaac caactggaac    1380
agtgccagag cagaaggaaa tggaccccgg gaaagaaggt ccaaacagcc cacaaaacaa    1440
accgccagca gctcctgtta taatgagta tgccgatgcc cagctacaca acctggtgaa    1500
aagaatgcgt caaagaacag ccctctacaa gaaaaagttg gtagagggag atctctcctc    1560
acccgaagcc agcccacaaa ctgcaaagcc cacggctgta ccaccagtaa aagaaagcga    1620
tgataagcca acagaacatt actacaggct gttgtggttc aaagtcaaaa agatgccttt    1680
aacagagtac ttaaagcgaa ttaaacttcc aaacagcata gattcataca cagatcgact    1740
ctatctcctg tggctcttgc ttgtcactct tgcctataac tggaactgct gttttatacc    1800
actgcgcctc gtcttcccat atcaaaccgc agacaacata cactactggc ttattgcgga    1860
catcatctgt gatatcatct acctttatga tatgctattt atccagccca gactccagtt    1920
tgtaagagga ggagacataa tagtggattc aaatgagcta aggaaacact acaggacttc    1980
tacaaaattt cagttggatg tcgcatcaat aataccattt gatatttgct acctcttctt    2040
tgggtttaat ccaatgttta gagcaaatag gatgttaaag tacacttcat tttttgaatt    2100
taatcatcac ctagagtcta taatggacaa agcatatatc tacagagtta ttcgaacaac    2160
tggatacttg ctgtttattc tgcacattaa tgcctgtgtt tattactggg cttcaaacta    2220
tgaaggaatt ggcactacta gatgggtgta tgatgggaa ggaaacgagt atctgagatg    2280
ttattattgg gcagttcgaa cttttaattac cattggtggc cttccagaac cacaaacttt    2340
atttgaaatt gttttcaac tcttgaattt tttttctgga gtttttgtgt tctccagttt    2400
```

```
aattggtcag atgagagatg tgattggagc agctacagcc aatcagaact acttccgcgc    2460
ctgcatggat gacaccattg cctacatgaa caattactcc attcctaaac ttgtgcaaaa    2520
gcgagttcgg acttggtatg aatatacatg ggactctcaa agaatgctag atgagtctga    2580
tttgcttaag accctaccaa ctacggtcca gttagccctc gccattgatg tgaacttcag    2640
catcatcagc aaagttgact tgttcaaggg ttgtgataca cagatgattt atgacatgtt    2700
gctaagattg aaatccgttc tctatttgcc tggtgacttt gtctgcaaaa agggagaaat    2760
tggcaaggaa atgtatatca tcaagcatgg agaagtccaa gttcttggag ccctgatgg     2820
tactaaagtt ctggttactc tgaaagctgg gtcggtgttt ggagaaatca gccttctagc    2880
agcaggagga ggaaaccgtc gaactgccaa tgtggtggcc cacgggtttg ccaatctttt    2940
aactctagac aaaaagaccc tccaagaaat tctagtgcat tatccagatt ctgaaagaat    3000
cctcatgaag aaagccagag tgcttttaaa gcagaaggct aagaccgcag aagcaacccc    3060
tccaagaaaa gatcttgccc tcctcttccc accgaaagaa gagacaccca aactgtttaa    3120
aactctccta ggaggcacag gaaaagcaag tcttgcaaga ctactcaaat tgaagcgaga    3180
gcaagcagct cagaagaaag aaaattctga aggaggagag gaagaaggaa aagaaaatga    3240
agataaacaa aaagaaaatg aagataaaca aaagaaaat  gaagataaag gaaaagaaaa    3300
tgaagataaa gataaaggaa gagagccaga gagaagcca  ctggacagac ctgaatgtac    3360
agcaagtcct attgcagtgg aggaagaacc ccactcagtt agaaggacag ttttacccag    3420
agggacttct cgtcaatcac tcattatcag catggctcct tctgctgagg gcggagaaga    3480
ggttcttact attgaagtca aagaaaaggc taagcaatga tcataactgc agatctgcct    3540
cgactgtgcc ttctagttgc cagccatctg ttgtttgccc ctcccccgtg ccttccttga    3600
ccctggaagg tgccactccc actgtccttt cctaataaaa tgaggaaatt gcatcgcatt    3660
gtctgagtag gtgtcattct attctggggg gtggggtggg gcaggacagc aaggggagg     3720
attgggaaga caatagcagg catgctgggg actcgagttc tacgtagata agtagcatgg    3780
cgggttaatc attaactaca aggaacccct agtgatggag ttggccactc cctctctgcg    3840
cgctcgctcg ctcactgagg ccgggcgacc aaaggtcgcc cgacgcccgg gctttgcccg    3900
ggcggcctca gtgagcgagc gagcgcgcag ccttaattaa cctaaggaaa atgaagtgaa    3960
gttcctatac tttctagaga ataggaactt ctatagtgag tcgaataagg gcgacacaaa    4020
atttattcta aatgcataat aaatactgat aacatcttat agtttgtatt atattttgta    4080
ttatcgttga catgtataat tttgatatca aaaactgatt ttcccttat tattttcgag     4140
atttattttc ttaattctct ttaacaaact agaaatattg tatatacaaa aaatcataaa    4200
taatagatga atagttaat tataggtgtt catcaatcga aaagcaacg tatcttattt      4260
aaagtgcgtt gcttttttct catttataag gttaaataat tctcatatat caagcaaagt    4320
gacaggcgcc cttaaatatt ctgacaaatg ctctttccct aaactccccc cataaaaaaa    4380
cccgccgaag cgggttttta cgttatttgc ggattaacga ttactcgtta tcagaaccgc    4440
ccagggggcc cgagcttaac cttttattt ggggagagg  gaagtcatga aaaaactaac    4500
ctttgaaatt cgatctccag cacatcagca aaacgctatt cacgcagtac agcaaatcct    4560
tccagaccca accaaaccaa tcgtagtaac cattcaggaa cgcaaccgca gcttagacca    4620
aaacaggaag ctatgggcct gcttaggtga cgtctctcgt caggttgaat ggcatggtcg    4680
ctggctggat gcagaaagct ggaagtgtgt gtttaccgca gcattaaagc agcaggatgt    4740
tgttcctaac cttgccggga atggctttgt ggtaataggc cagtcaacca gcaggatgcg    4800
```

```
tgtaggcgaa tttgcggagc tattagagct tatacaggca ttcggtacag agcgtggcgt    4860
taagtggtca gacgaagcga gactggctct ggagtggaaa gcgagatggg gagacagggc    4920
tgcatgataa atgtcgttag ttttctccggt ggcaggacgt cagcatattt gctctggcta    4980
atggagcaaa agcgacgggc aggtaaagac gtgcattacg ttttcatgga tacaggttgt    5040
gaacatccaa tgacatatcg gtttgtcagg gaagttgtga agttctggga tataccgctc    5100
accgtattgc aggttgatat caacccggag cttggacagc caaatggtta tacgqtatgg    5160 gaaccaaagg atattcagac gcgaatgcct gttctgaagc catttatcga tatggtaaag    5220
aaatatggca ctccatacgt cggcggcgcg ttctgcactg acagattaaa actcgttccc    5280
ttcaccaaat actgtgatga ccatttcggg cgagggaatt acaccacgtg gattggcatc    5340
agagctgatg aaccgaagcg gctaaagcca aagcctggaa tcagatatct tgctgaactg    5400
tcagactttg agaaggaaga tatcctcgca tggtggaagc aacaaccatt cgatttgcaa    5460
ataccggaac atctcggtaa ctgcatattc tgcattaaaa aatcaacgca aaaaatcgga    5520
cttgcctgca aagatgagga gggattgcag cgtgttttta atgaggtcat cacgggatcc    5580
catgtgcgtg acgacatcg ggaaacgcca aaggagatta tgtaccgagg aagaatgtcg    5640
ctggacggta tcgcgaaaat gtattcagaa aatgattatc aagccctgta tcaggacatg    5700
gtacgagcta aaagattcga taccggctct tgttctgagt catgcgaaat atttggaggg    5760
cagcttgatt tcgacttcgg gagggaagct gcatgatgcg atgttatcgg tgcggtgaat    5820
gcaaagaaga taaccgcttc cgaccaaatc aaccttactg gaatcgatgg tgtctccggt    5880
gtgaaagaac accaacaggg gtgttaccac taccgcagga aaaggaggac gtgtggcgag    5940
acagcgacga agtatcaccg acataatctg cgaaaactgc aaataccttc caacgaaacg    6000
caccagaaat aaacccaagc caatcccaaa agaatctgac gtaaaaacct tcaactacac    6060
ggctcacctg tgggatatcc ggtggctaag acgtcgtgcg aggaaaacaa ggtgattgac    6120
caaaatcgaa gttacgaaca agaaagcgtc gagcgagctt taacgtgcgc taactgcggt    6180
cagaagctgc atgtgctgga agttcacgtg tgtgagcact gctgcgcaga actgatgagc    6240
gatccgaata gctcgatgca cgaggaagaa gatgatggct aaaccagcgc gaagacgatg    6300
taaaaacgat gaatgccggg aatggtttca ccctgcattc gctaatcagt ggtggtgctc    6360
tccagagtgt ggaaccaaga tagcactcga acgacgaagt aaagaacgcg aaaaagcgga    6420
aaaagcagca gagaagaaac gacgacgaga ggagcagaaa cagaaagata aacttaagat    6480
tcgaaaactc gccttaaagc cccgcagtta ctggattaaa caagcccaac aagccgtaaa    6540
cgccttcatc agagaaagag accgcgactt accatgtatc tcgtgcggaa cgctcacgtc    6600
tgctcagtgg gatgccggac attaccggac aactgctgcg gcacctcaac tccgatttaa    6660
tgaacgcaat attcacaagc aatgcgtggt gtgcaaccag cacaaaagcg gaaatctcgt    6720
tccgtatcgc gtcgaactga ttagccgcat cgggcaggaa gcagtagacg aaatcgaatc    6780
aaaccataac cgccatcgct ggactatcga agagtgcaag gcgatcaagg cagagtacca    6840
acagaaactc aaagacctgc gaaatagcag aagtgaggcc gcatgacgtt ctcagtaaaa    6900
accattccag acatgctcgt tgaagcatac ggaaatcaga cagaagtagc acgcagactg    6960
aaatgtagtc gcggtacggt cagaaaatac gttgatgata agacgggaa aatgcacgcc    7020 atcgtcaacg acgttctcat ggttcatcgc ggatggagtg aaagagatgc gctattacga    7080
aaaaattgat ggcagcaaat accgaaatat ttgggtagtt ggcgatctgc acggatgcta    7140
```

```
cacgaacctg atgaacaaac tggatacgat tggattcgac aacaaaaaag acctgcttat    7200
ctcggtgggc gatttggttg atcgtggtgc agagaacgtt gaatgcctgg aattaatcac    7260
attcccctgg ttcagagctg tacgtggaaa ccatgagcaa atgatgattg atggcttatc    7320
agagcgtgga aacgttaatc actggctgct taatggcggt ggctggttct ttaatctcga    7380
ttacgacaaa gaaattctgg ctaaagctct tgcccataaa gcagatgaac ttccgttaat    7440
catcgaactg gtgagcaaag ataaaaaata tgttatctgc cacgccgatt atcccctttga   7500 cgaatacgag tttggaaagc cagttgatca tcagcaggta atctggaacc gcgaacgaat    7560
cagcaactca caaaacggga tcgtgaaaga aatcaaaggc gcggacacgt tcatctttgg    7620
tcatacgcca gcagtgaaac cactcaagtt tgccaaccaa atgtatatcg ataccggcgc    7680
agtgttctgc ggaaacctaa cattgattca ggtacaggga gaaggcgcat gagactcgaa    7740
agcgtagcta aatttcattc gccaaaaagc ccgatgatga gcgactcacc acgggccacg    7800
gcttctgact ctctttccgg tactgatgtg atggctgcta tggggatggc gcaatcacaa    7860
gccggattcg gtatggctgc attctgcggt aagcacgaac tcagccagaa cgacaaacaa    7920
aaggctatca actatctgat gcaatttgca cacaaggtat cggggaaata ccgtggtgtg    7980
gcaaagcttg aaggaaatac taaggcaaag gtactgcaag tgctcgcaac attcgcttat    8040
gcggattatt gccgtagtgc cgcgacgccg ggggcaagat gcagagattg ccatggtaca    8100
ggccgtgcgt tgatattgc caaaacgag ctgtggggga gagttgtcga aaagagtgc      8160 ggaagatgca aaggcgtcgg ctattcaagg atgccagcaa gcgcagcata tcgcgctgtg    8220
acgatgctaa tcccaaacct tacccaaccc acctggtcac gcactgttaa gccgctgtat    8280
gacgctctgg tggtgcaatg ccacaaagaa gagtcaatcg cagacaacat tttgaatgcg    8340
gtcacacgtt agcagcatga ttgccacgga tggcaacata ttaacggcat gatattgact    8400
tattgaataa aattgggtaa atttgactca acgatgggtt aattcgctcg ttgtggtagt    8460
gagatgaaaa gaggcggcgc ttactaccga ttccgcctag ttggtcactt cgacgtatcg    8520
tctggaactc caaccatcgc aggcagagag gtctgcaaaa tgcaatcccg aaacagttcg    8580
caggtaatag ttagagcctg cataacggtt tcgggatttt ttatatctgc acaacaggta    8640
agagcattga gtcgataatc gtgaagagtc ggcgagcctg gttagccagt gctctttccg    8700
ttgtgctgaa ttaagcgaat accggaagca gaaccggatc accaaatgcg tacaggcgtc    8760
atcgccgccc agcaacagca caacccaaac tgagccgtag ccactgtctg tcctgaattc    8820
attagtaata gttacgctgc ggccttttac acatgacctt cgtgaaagcg ggtggcagga    8880
ggtcgcgcta acaacctcct gccgttttgc ccgtgcatat cggtcacgaa caaatctgat    8940
tactaaacac agtagcctgg atttgttcta tcagtaatcg accttattcc taattaaata    9000
gagcaaatcc ccttattggg ggtaagacat gaagatgcca gaaaaacatg acctgttggc    9060
cgccattctc gcggcaaagg aacaaggcat cggggcaatc cttgcgtttg caatggcgta    9120
ccttcgcggc agatataatg gcggtgcgtt tacaaaaaca gtaatcgacg caacgatgtg    9180
cgccattatc gcctggttca ttcgtgacct tctcgacttc gccggactaa gtagcaatct    9240
cgcttatata acgagcgtgt ttatcggcta catcggtact gactcgattg gttcgcttat    9300
caaacgcttc gctgctaaaa aagccggagt agaagatggt agaaatcaat aatcaacgta    9360
aggcgttcct cgatatgctg gcgtggtcgg agggaactga taacggacgt cagaaaacca    9420
gaaatcatgt ttatgacgtc attgtaggcg gagagctatt tactgattac tccgatcacc    9480
ctcgcaaact tgtcacgcta aacccaaaac tcaaatcaac aggcgcttaa gactggccgt    9540
```

```
cgttttacaa cacagaaaga gtttgtagaa acgcaaaaag gccatccgtc agggggccttc    9600 tgcttagttt gatgcctggc agttccctac tctcgccttc cgcttcctcg ctcactgact    9660
cgctgcgctc ggtcgttcgg ctgcggcgag cggtatcagc tcactcaaag gcggtaatac    9720
ggttatccac agaatcaggg gataacgcag gaaagaacat gtgagcaaaa ggccagcaaa    9780
aggccaggaa ccgtaaaaag gccgcgttgc tggcgttttt ccataggctc cgcccccctg    9840
acgagcatca caaaaatcga cgctcaagtc agaggtggcg aaacccgaca ggactataaa    9900
gataccaggc gtttccccct ggaagctccc tcgtgcgctc tcctgttccg accctgccgc    9960
ttaccggata cctgtccgcc tttctccctt cgggaagcgt ggcgctttct catagctcac   10020
gctgtaggta tctcagttcg gtgtaggtcg ttcgctccaa gctgggctgt gtgcacgaac   10080 ccccgttca gcccgaccgc tgcgccttat ccggtaacta tcgtcttgag tccaacccgg   10140
taagacacga cttatcgcca ctggcagcag ccactggtaa caggattagc agagcgaggt   10200
atgtaggcgg tgctacagag ttcttgaagt ggtgggctaa ctacggctac actagaagaa   10260
cagtatttgg tatctgcgct ctgctgaagc cagttacctt cggaaaaaga gttggtagct   10320
cttgatccgg caaacaaacc accgctggta gcggtggttt ttttgtttgc aagcagcaga   10380
ttacgcgcag aaaaaaagga tctcaagaag atcctttgat cttttctacg ggtctgacg   10440 ctcagtggaa cgacgcgcgc gtaactcacg ttaagggatt ttggtcatga gcttgcgccg   10500
tcccgtcaag tcagcgtaat gctctgcttt tagaaaaact catcgagcat caaatgaaac   10560
tgcaatttat tcatatcagg attatcaata ccatattttt gaaaaagccg tttctgtaat   10620
gaaggagaaa actcaccgag gcagttccat aggatggcaa gatcctggta tcggtctgcg   10680
attccgactc gtccaacatc aatacaacct attaatttcc cctcgtcaaa ataaggtta   10740 tcaagtgaga atcaccatg agtgacgact gaatccggtg agaatggcaa aagtttatgc   10800
atttctttcc agacttgttc aacaggccag ccattacgct cgtcatcaaa atcactcgca   10860
tcaaccaaac cgttattcat tcgtgattgc gcctgagcga ggcgaaatac gcgatcgctg   10920
ttaaaaggac aattacaaac aggaatcgag tgcaaccggc gcaggaacac tgccagcgca   10980
tcaacaatat tttcacctga atcaggatat tcttctaata cctggaacgc tgttttttccg   11040 gggatcgcag tggtgagtaa ccatgcatca tcaggagtac ggataaaatg cttgatggtc   11100
ggaagtggca taaattccgt cagccagttt agtctgacca tctcatctgt aacatcattg   11160
gcaacgctac ctttgccatg tttcagaaac aactctggcg catcgggctt cccatacaag   11220
cgatagattg tcgcacctga ttgcccgaca ttatcgcgag cccatttata cccatataaa   11280
tcagcatcca tgttggaatt taatcgcggc ctcgacgttt ccgttgaat atggctcata   11340 ttcttccttt tcaatattat tgaagcatt tatcagggtt attgtctcat gagcggatac   11400
atatttgaat gtatttagaa aaataaacaa ataggggtca gtgttacaac caattaacca   11460
attctgaaca ttatcgcgag cccatttata cctgaatatg gctcataaca ccccttgttt   11520
gcctggcggc agtagcgcgg tggtcccacc tgaccccatg ccgaactcag aagtgaaacg   11580
ccgtagcgcc gatggtagtg tggggactcc ccatgcgaga gtaggaaact gccaggcatc   11640
aaataaaacg aaaggctcag tcgaaagact gggcctttcg cccgggctaa ttaggggtg    11700 tcgcccttat tcgactctat agtgaagttc ctattctcta gaaagtatag gaacttctga   11760
agtggggtcg acttaattaa gg                                            11782
```

<210> SEQ ID NO 42

<211> LENGTH: 11782
<212> TYPE: DNA
<213> ORGANISM: Artificial Sequence
<220> FEATURE:
<223> OTHER INFORMATION: constructed sequence

<400> SEQUENCE: 42

```
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctacgta gcaagctagc       180
ctgaagagac agaaatatct ctaattccat gagcggtcat acgaggcaag agaagccgct       240
tagagcatgg acttagttag tttcagggat tggacagagt caagagctgg ggtgaggagg       300
ttaccctcgg tagggtgac acagatgtca accgccatt ccctccacat gcatgtcctg        360
ccagaagaac ctgtccctgg gctgggaatc ttatattacc ttcctctcca atgagaagag       420
aagttcaagg ctcacagaca tgtgcataca caagctcaat gcactcaaga ttcccctcca       480
ccactcctgc ccccactacc tacaggagat tgactcctgc tgtgcacata agctgggata       540
atcagggttt ctaaacatca gcttcaaaag tccaatgtcc aaagtggtgg ggggccgggg       600
aacgaggtac tctttccata cccttggctt ttgtgtggcc tggagccgct gatatagaga       660
ttggagtggg acacgaggta ttcctttcaa aaacacaaag gcctatactt tgagccctcc       720
catttcaatc ccccaccatg cttcaccttt aagacctcca actccacttt gatcccagtt       780
ctcaggttca ggcctcacaa ggccaaaatc ctgaagttac ccttctcaaa ctcccttgcc       840
tttaacatca tcagaatcaa cctcctaccc ccactctgtc ccagcagcaa tagcctgcta       900
atctttagc actaatcttt taggcactaa tctgctttcc aaactcttgg cacctgaact       960
atttataagc agtgttttat gccccccac caaagaaccc tattcttttc ccatgacccc      1020
accaatcaaa acactcagag gactgtgggt ataagaggct ggggaggcag gcatagcagc      1080
ggccgccacc atgttcaagt ccctcaccaa agtcaacaag gtcaagccca tcggagagaa      1140
caacgagaat gagcagagct ctcggcgcaa cgaagaagga tcccatccgt cgaaccagtc      1200
acagcagact accgcacagg aggagaacaa gggagaagaa aagtcgctca agactaagtc      1260
caccccgtg acctcggaag aaccgcacac gaacattcag gacaagctgt ccaagaagaa      1320
ctcctccggc gatctcacga ctaacccgga ccccagaat gccgctgaac ctactgggac      1380
cgtgcctgag caaaaggaga tggaccccgg aaaggagggt cctaactccc cccaaaacaa      1440
gccccggcc gcgccggtca tcaatgagta cgcggacgcg caactgcata acctcgtgaa      1500
gcggatgcgg caaagaaccg ccctctacaa gaagaaactg gtggagggcg acctgagctc      1560
acctgaagcc agcccacaga ccgccaaacc caccgccgtg ccgcctgtga aggagtccga      1620
tgacaagcct accgagcact actaccgcct gctgtggttc aaggtcaaga agatgcccct      1680
gaccgaatac ctcaagcgga tcaagctgcc gaacagcatc gacagctaca ccgaccggct      1740
ttacttgctc tggctgctgc ttgtgaccct ggcttacaac tggaactgtt gtttcattcc      1800
cctgcggctg gtgttcccctt accaaaccgc ggataacatt cactactggc tgattgccga      1860
catcatttgc gacatcatct acctgtacga tatgcttttt atccaaccgc ggctgcaatt      1920
cgtccgcggg ggagacatca ttgtggactc caacgagctg cgcaagcatt accggacctc      1980
gacaaagttc cagctggatg tggcctccat catcccgttc gatatctgtt acctgttctt      2040
tggcttcaac ccgatgttca gggcgaacag gatgctgaag tacacttcct tcttcgaatt      2100
caaccaccac ctggagtcca tcatggacaa ggcttacatc taccgcgtga tccggaccac      2160
```

```
tggttacctc ctgttcatcc tgcacatcaa cgcctgcgtc tattactggg cctcaaacta   2220
cgaaggcatt ggtaccaccc gctgggtgta cgacggggag ggaaacgagt atctgcgctg   2280
ctactactgg gccgtgcgaa ccctcataac tattggcggc ctcccggaac cgcagaccct   2340
gttcgagatc gtgttccaac tcctcaactt cttctcggga gtgttcgtgt tttcaagctt   2400
gattggacag atgcgggacg tgatcggtgc agcaactgcc aaccagaact actttcgcgc   2460
ctgcatggac gacactatcg cgtacatgaa caactattcg atcccaagc tggtgcagaa    2520 acgcgtgcgg acttggtatg agtacacttg ggactcccag agaatgcttg acgagtccga   2580
tctgctcaag accctgccta ctaccgtgca gctggcactc gccatcgatg tgaacttctc   2640
cattatctcg aaagtcgatc tgttcaaggg ctgcgacacc cagatgatct acgacatgct   2700
gctgagactc aagtccgtgt tgtacctccc tggcgacttc gtgtgcaaga agggcgaaat   2760
cgggaaggag atgtacatta tcaagcacgg agaagtccag gtgctggggg gaccagacgg   2820
taccaaggtc cttgtcaccc tgaaggccgg gtccgtgttc ggcgaaattt ccctgttggc   2880
cgccggcggt ggcaacagga gaaccgcaaa tgtggtggcc cacggcttcg caaaccttct   2940
gaccctggac aagaaaaccc tccaggaaat cctcgtgcac tacccggata gcagcggat    3000 cctgatgaag aaagcccggg tgctgctgaa gcaaaaggcc aagaccgccg aagccacccc   3060
gcctcggaag gacctggctc tgctgttccc acccaaggag gagactccca aactgtttaa   3120
gaccctcttg ggcgggacgg gaaaggcctc cctcgctcgc ttgcttaagt tgaagaggga   3180
gcaggccgcg cagaagaagg aaaactccga aggaggggaa gaagagggaa aggaaaacga   3240
agataagcag aaggagaacg aggataagca aaaggaaaat gaggacaagg ggaaagaaaa   3300
cgaggacaag gataagggtc gcgaacctga agagaagccg ctggatcggc cagagtgcac   3360
tgcctcgcct atcgcggtcg aagaggaacc ccatagcgtg cgcagaaccg tgctgcctag   3420
aggcacatcg aggcagtcac tgattatctc tatggcacca agcgccgagg gaggagagga   3480
agtgctcacc atcgaggtca aggaaaaagc gaagcagtga tcataactgc agatctgcct   3540
cgactgtgcc ttctagttgc cagccatctg ttgtttgccc ctcccccgtg ccttccttga   3600
ccctggaagg tgccactccc actgtccttt cctaataaaa tgaggaaatt gcatcgcatt   3660
gtctgagtag gtgtcattct attctggggg gtggggtggg gcaggacagc aaggggagg    3720 attgggaaga caatagcagg catgctgggg actcgagttc tacgtagata agtagcatgg   3780
cgggttaatc attaactaca aggaacccct agtgatggag ttggccactc cctctctgcg   3840
cgctcgctcg ctcactgagg ccgggcgacc aaaggtcgcc cgacgcccgg ctttgcccg    3900 ggcggcctca gtgagcgagc gagcgcgcag ccttaattaa cctaaggaaa atgaagtgaa   3960
gttcctatac tttctagaga ataggaactt ctatagtgag tcgaataagg gcgacacaaa   4020
atttattcta aatgcataat aaatactgat aacatcttat agtttgtatt atattttgta   4080
ttatcgttga catgtataat tttgatatca aaaactgatt ttcccttat tattttcgag     4140 atttattttc ttaattctct ttaacaaact agaaatattg tatatacaaa aatcataaa    4200 taatagatga atagtttaat tataggtgtt catcaatcga aaagcaacg tatcttattt    4260 aaagtgcgtt gcttttttct catttataag gttaaataat tctcatatat caagcaaagt   4320
gacaggcgcc cttaaatatt ctgacaaatg ctctttccct aaactccccc cataaaaaaa   4380
cccgccgaag cggttttta cgttatttgc ggattaacga ttactcgtta tcagaaccgc    4440 ccaggggcc cgagcttaac ctttttattt gggggagagg gaagtcatga aaaaactaac   4500
```

```
ctttgaaatt cgatctccag cacatcagca aaacgctatt cacgcagtac agcaaatcct    4560
tccagaccca accaaaccaa tcgtagtaac cattcaggaa cgcaaccgca gcttagacca    4620
aaacaggaag ctatgggcct gcttaggtga cgtctctcgt caggttgaat ggcatggtcg    4680
ctggctggat gcagaaagct ggaagtgtgt gtttaccgca gcattaaagc agcaggatgt    4740
tgttcctaac cttgccggga atggctttgt ggtaataggc cagtcaacca gcaggatgcg    4800
tgtaggcgaa tttgcggagc tattagagct tatacaggca ttcggtacag agcgtggcgt    4860
taagtggtca gacgaagcga gactggctct ggagtggaaa gcgagatggg gagacagggc    4920
tgcatgataa atgtcgttag tttctccggt ggcaggacgt cagcatattt gctctggcta    4980
atggagcaaa agcgacgggc aggtaaagac gtgcattacg ttttcatgga tacaggttgt    5040
gaacatccaa tgacatatcg gtttgtcagg gaagttgtga agttctggga tataccgctc    5100
accgtattgc aggttgatat caacccggag cttggacagc caaatggtta tacggtatgg    5160
gaaccaaagg atattcagac gcgaatgcct gttctgaagc catttatcga tatggtaaag    5220
aaatatggca ctccatacgt cggcggcgcg ttctgcactg acagattaaa actcgttccc    5280
ttcaccaaat actgtgatga ccatttcggg cgagggaatt acaccacgtg gattggcatc    5340
agagctgatg aaccgaagcg gctaaagcca aagcctggaa tcagatatct tgctgaactg    5400
tcagactttg agaaggaaga tatcctcgca tggtggaagc aacaaccatt cgatttgcaa    5460
ataccggaac atctcggtaa ctgcatattc tgcattaaaa aatcaacgca aaaaatcgga    5520
cttgcctgca agatgagga gggattgcag cgtgttttta atgaggtcat cacgggatcc    5580
catgtgcgtg acgacatcg ggaaacgcca aggagatta tgtaccgagg aagaatgtcg    5640
ctggacggta tcgcgaaaat gtattcagaa aatgattatc aagccctgta tcaggacatg    5700
gtacgagcta aaagattcga taccggctct tgttctgagt catgcgaaat atttggaggg    5760
cagcttgatt tcgacttcgg gagggaagct gcatgatgcg atgttatcgg tgcggtgaat    5820
gcaaagaaga taaccgcttc cgaccaaatc aaccttactg gaatcgatgg tgtctccggt    5880
gtgaaagaac accaacaggg gtgttaccac taccgcagga aaaggaggac gtgtggcgag    5940
acagcgacga agtatcaccg acataatctg cgaaaactgc aaataccttc caacgaaacg    6000
caccagaaat aaacccaagc caatcccaaa agaatctgac gtaaaaacct tcaactacac    6060
ggctcacctg tgggatatcc ggtggctaag acgtcgtgcg aggaaaacaa ggtgattgac    6120
caaaatcgaa gttacgaaca agaaagcgtc gagcgagctt taacgtgcgc taactgcggt    6180
cagaagctgc atgtgctgga agttcacgtg tgtgagcact gctgcgcaga actgatgagc    6240
gatccgaata gctcgatgca cgaggaagaa gatgatggct aaaccagcgc gaagacgatg    6300
taaaaacgat gaatgccggg aatggtttca ccctgcattc gctaatcagt ggtggtgctc    6360
tccagagtgt ggaaccaaga tagcactcga acgacgaagt aaagaacgcg aaaaagcgga    6420
aaaagcagca gagaagaaac gacgacgaga ggagcagaaa cagaaagata aacttaagat    6480
tcgaaaactc gccttaaagc cccgcagtta ctggattaaa caagcccaac aagccgtaaa    6540
cgccttcatc agagaaagag accgcgactt accatgtatc tcgtgcggaa cgctcacgtc    6600
tgctcagtgg gatgccggac attaccggac aactgctgcg gcacctcaac tccgatttaa    6660
tgaacgcaat attcacaagc aatgcgtggt gtgcaaccag cacaaaagcg gaaatctcgt    6720
tccgtatcgc gtcgaactga ttagccgcat cgggcaggaa gcagtagacg aaatcgaatc    6780
aaaccataac cgccatcgct ggactatcga agagtgcaag gcgatcaagg cagagtacca    6840
acagaaactc aaagacctgc gaaatagcag aagtgaggcc gcatgacgtt ctcagtaaaa    6900
```

-continued

```
accattccag acatgctcgt tgaagcatac ggaaatcaga cagaagtagc acgcagactg    6960
aaatgtagtc gcggtacggt cagaaaatac gttgatgata agacgggaa aatgcacgcc    7020 atcgtcaacg acgttctcat ggttcatcgc ggatggagtg aaagagatgc gctattacga    7080
aaaaattgat ggcagcaaat accgaaatat ttgggtagtt ggcgatctgc acggatgcta    7140
cacgaacctg atgaacaaac tggatacgat tggattcgac aacaaaaaag acctgcttat    7200
ctcggtgggc gatttggttg atcgtggtgc agagaacgtt gaatgcctgg aattaatcac    7260
attcccctgg ttcagagctg tacgtggaaa ccatgagcaa atgatgattg atggcttatc    7320
agagcgtgga aacgttaatc actggctgct taatggcggt ggctggttct ttaatctcga    7380
ttacgacaaa gaaattctgg ctaaagctct tgcccataaa gcagatgaac ttccgttaat    7440
catcgaactg gtgagcaaag ataaaaaata tgttatctgc cacgccgatt atccctttga    7500
cgaatacgag tttggaaagc cagttgatca tcagcaggta atctggaacc gcgaacgaat    7560
cagcaactca caaaacggga tcgtgaaaga aatcaaaggc gcggacacgt tcatctttgg    7620
tcatacgcca gcagtgaaac cactcaagtt tgccaaccaa atgtatatcg ataccggcgc    7680
agtgttctgc ggaaacctaa cattgattca ggtacaggga gaaggcgcat gagactcgaa    7740
agcgtagcta aatttcattc gccaaaaagc ccgatgatga gcgactcacc acgggccacg    7800
gcttctgact ctctttccgg tactgatgtg atggctgcta tggggatggc gcaatcacaa    7860
gccggattcg gtatggctgc attctgcggt aagcacgaac tcagccagaa cgacaaacaa    7920
aaggctatca actatctgat gcaatttgca cacaaggtat cggggaaata ccgtggtgtg    7980
gcaaagcttg aaggaaatac taaggcaaag gtactgcaag tgctcgcaac attcgcttat    8040
gcggattatt gccgtagtgc cgcgacgccg ggggcaagat gcagagattg ccatggtaca    8100
ggccgtgcgg ttgatattgc caaaacagag ctgtggggga gagttgtcga aaagagtgc    8160 ggaagatgca aaggcgtcgg ctattcaagg atgccagcaa gcgcagcata tcgcgctgtg    8220
acgatgctaa tcccaaacct tacccaaccc acctggtcac gcactgttaa gccgctgtat    8280
gacgctctgg tggtgcaatg ccacaaagaa gagtcaatcg cagacaacat tttgaatgcg    8340
gtcacacgtt agcagcatga ttgccacgga tggcaacata ttaacggcat gatattgact    8400
tattgaataa aattgggtaa atttgactca acgatgggtt aattcgctcg ttgtggtagt    8460
gagatgaaaa gaggcggcgc ttactaccga ttccgcctag ttggtcactt cgacgtatcg    8520
tctggaactc caaccatcgc aggcagagag gtctgcaaaa tgcaatcccg aaacagttcg    8580
caggtaatag ttagagcctg cataacggtt tcgggatttt ttatatctgc acaacaggta    8640
agagcattga gtcgataatc gtgaagagtc ggcgagcctg gttagccagt gctctttccg    8700
ttgtgctgaa ttaagcgaat accggaagca gaaccggatc accaaatgcg tacaggcgtc    8760
atcgccgccc agcaacagca caacccaaac tgagccgtag ccactgtctg tcctgaattc    8820
attagtaata gttacgctgc ggccttttac acatgacctt cgtgaaagcg ggtggcagga    8880
ggtcgcgcta acaacctcct gccgttttgc ccgtgcatat cggtcacgaa caaatctgat    8940
tactaaacac agtagcctgg atttgttcta tcagtaatcg accttattcc taattaaata    9000
gagcaaatcc ccttattggg ggtaagacat gaagatgcca gaaaaacatg acctgttggc    9060
cgccattctc gcggcaaagg aacaaggcat cggggcaatc cttgcgtttg caatggcgta    9120
ccttcgcggc agatataatg gcggtgcgtt tacaaaaaca gtaatcgacg caacgatgtg    9180
cgccattatc gcctggttca ttcgtgacct tctcgacttc gccggactaa gtagcaatct    9240
```

-continued

| | |
|---|---|
| cgcttatata acgagcgtgt ttatcggcta catcggtact gactcgattg gttcgcttat | 9300 |
| caaacgcttc gctgctaaaa aagccggagt agaagatggt agaaatcaat aatcaacgta | 9360 |
| aggcgttcct cgatatgctg gcgtggtcgg agggaactga taacggacgt cagaaaacca | 9420 |
| gaaatcatgg ttatgacgtc attgtaggcg gagagctatt tactgattac tccgatcacc | 9480 |
| ctcgcaaact tgtcacgcta aacccaaaac tcaaatcaac aggcgcttaa gactggccgt | 9540 |
| cgttttacaa cacagaaaga gtttgtagaa acgcaaaaag gccatccgtc agggccttc | 9600 |
| tgcttagttt gatgcctggc agttccctac tctcgccttc cgcttcctcg ctcactgact | 9660 |
| cgctgcgctc ggtcgttcgg ctgcggcgag cggtatcagc tcactcaaag gcggtaatac | 9720 |
| ggttatccac agaatcaggg gataacgcag gaaagaacat gtgagcaaaa ggccagcaaa | 9780 |
| aggccaggaa ccgtaaaaag gccgcgttgc tggcgttttt ccataggctc cgcccccctg | 9840 |
| acgagcatca caaaaatcga cgctcaagtc agaggtggcg aaacccgaca ggactataaa | 9900 |
| gataccaggc gtttccccct ggaagctccc tcgtgcgctc tcctgttccg accctgccgc | 9960 |
| ttaccggata cctgtccgcc tttctccctt cgggaagcgt ggcgctttct catagctcac | 10020 |
| gctgtaggta tctcagttcg gtgtaggtcg ttcgctccaa gctgggctgt gtgcacgaac | 10080 |
| cccccgttca gcccgaccgc tgcgccttat ccggtaacta tcgtcttgag tccaacccgg | 10140 |
| taagacacga cttatcgcca ctggcagcag ccactggtaa caggattagc agagcgaggt | 10200 |
| atgtaggcgg tgctacagag ttcttgaagt ggtgggctaa ctacggctac actagaagaa | 10260 |
| cagtatttgg tatctgcgct ctgctgaagc cagttacctt cggaaaaaga gttggtagct | 10320 |
| cttgatccgg caaacaaacc accgctggta gcggtggttt ttttgtttgc aagcagcaga | 10380 |
| ttacgcgcag aaaaaaagga tctcaagaag atcctttgat cttttctacg gggtctgacg | 10440 |
| ctcagtggaa cgacgcgcgc gtaactcacg ttaagggatt ttggtcatga gcttgcgccg | 10500 |
| tcccgtcaag tcagcgtaat gctctgcttt tagaaaaact catcgagcat caaatgaaac | 10560 |
| tgcaatttat tcatatcagg attatcaata ccatattttt gaaaaagccg tttctgtaat | 10620 |
| gaaggagaaa actcaccgag gcagttccat aggatggcaa gatcctggta tcggtctgcg | 10680 |
| attccgactc gtccaacatc aatacaacct attaatttcc cctcgtcaaa ataaggtta | 10740 |
| tcaagtgaga atcaccatg agtgacgact gaatccggtg agaatggcaa agtttatgc | 10800 |
| atttcttttcc agacttgttc aacaggccag ccattacgct cgtcatcaaa atcactcgca | 10860 |
| tcaaccaaac cgttattcat tcgtgattgc gcctgagcga ggcgaaatac gcgatcgctg | 10920 |
| ttaaaaggac aattacaaac aggaatcgag tgcaaccggc gcaggaacac tgccagcgca | 10980 |
| tcaacaatat tttcacctga atcaggatat tcttctaata cctggaacgc tgttttttccg | 11040 |
| gggatcgcag tggtgagtaa ccatgcatca tcaggagtac ggataaaatg cttgatggtc | 11100 |
| ggaagtggca taaattccgt cagccagttt agtctgacca tctcatctgt aacatcattg | 11160 |
| gcaacgctac ctttgccatg tttcagaaac aactctggcg catcgggctt cccatacaag | 11220 |
| cgatagattg tcgcacctga ttgcccgaca ttatcgcgag cccatttata cccatataaa | 11280 |
| tcagcatcca tgttggaatt taatcgcggc ctcgacgttt cccgttgaat atggctcata | 11340 |
| ttcttccttt tcaatatta ttgaagcatt tatcagggtt attgtctcat gagcggatac | 11400 |
| atatttgaat gtatttagaa aaataaacaa ataggggtca gtgttacaac caattaacca | 11460 |
| attctgaaca ttatcgcgag cccatttata cctgaatatg gctcataaca cccttgttt | 11520 |
| gcctggcggc agtagcgcgg tggtcccacc tgacccccatg ccgaactcag aagtgaaacg | 11580 |
| ccgtagcgcc gatggtagtg tggggactcc ccatgcgaga gtagggaact gccaggcatc | 11640 |

<210> SEQ ID NO 43
<211> LENGTH: 12556
<212> TYPE: DNA
<213> ORGANISM: Artificial Sequence
<220> FEATURE:
<223> OTHER INFORMATION: constructed sequence

<400> SEQUENCE: 43

```
aaataaaacg aaaggctcag tcgaaagact gggcctttcg cccgggctaa ttaggggggtg    11700
tcgcccttat tcgactctat agtgaagttc ctattctcta gaaagtatag gaacttctga    11760
agtggggtcg acttaattaa gg                                              11782
```

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gcaagctagc     180
tagttattaa tagtaatcaa ttacggggtc attagttcat agcccatata tggagttccg     240
cgttacataa cttacggtaa atggcccgcc tggctgaccg cccaacgacc cccgcccatt     300
gacgtcaata atgacgtatg ttcccatagt aacgccaata gggactttcc attgacgtca     360
atgggtggag tatttacggt aaactgccca cttggcagta catcaagtgt atcatatgcc     420
aagtacgccc cctattgacg tcaatgacgg taaatggccc gcctggcatt atgcccagta     480
catgacctta tgggactttc ctacttggca gtacatctac gtattagtca tcgctattaa     540
catggtcgag gtgagcccca cgttctgctt cactctcccc atctcccccc cctccccacc     600
cccaattttg tatttattta ttttttaatt attttgtgca gcgatggggg cggggggggg     660
ggggggcgc gcgccaggcg gggcggggcg gggcgagggg cggggcgggg cgaggcggag     720
aggtgcggcg gcagccaatc agagcggcgc gctccgaaag tttccttttta tggcgaggcg     780
gcggcggcgg cggccctata aaaagcgaag cgcgcggcgg gcggggagtc gctgcgacgc     840
tgccttcgcc ccgtgccccg ctccgccgcc gcctcgcgcc gcccgccccg gctctgactg     900
accgcgttac tcccacaggt gagcgggcgg gacggccctt ctcctccggg ctgtaattag     960
cgcttggttt aatgacggct tgtttctttt ctgtggctgc gtgaaagcct tgaggggctc    1020
cgggagggcc ctttgtgcgg ggggagcggc tcgggggtg cgtgcgtgtg tgtgtgcgtg    1080
gggagcgccg cgtgcggctc cgcgctgccc ggcggctgtg agcgctgcgg gcgcggcgcg    1140
gggctttgtg cgctccgcag tgtgcgcgag gggagcgcgg ccgggggcgg tgccccgcgg    1200
tgcggggggg gctgcgaggg gaacaaaggc tgcgtgcggg gtgtgtgcgt gggggggtga    1260
gcagggggtg tgggcgcgtc ggtcgggctg caaccccccc tgcacccccc tccccgagtt    1320
gctgagcacg gcccggcttc gggtgcgggg ctccgtacgg ggcgtggcgc ggggctcgcc    1380
gtgccgggcg gggggtggcg gcaggtgggg gtgccgggcg gggcggggcc gcctcgggcc    1440
ggggagggct cggggaggg gcgcggcggc cccggagcg ccggcggctg tcgaggcgcg    1500
gcgagccgca gccattgcct tttatggtaa tcgtgcgaga gggcgcaggg acttcctttg    1560
tcccaaatct gtgcggagcc gaaatctggg aggcgccgcc gcaccccctc tagcgggcgc    1620
ggggcgaagc ggtgcggcgc cggcaggaag gaaatgggcg ggagggcct tcgtgcgtcg    1680
ccgcgccgcc gtccccttct ccctctccag cctcggggct gtccgcgggg gacggctgc    1740
cttcgggggg gacggggcag ggcggggttc ggcttctggc gtgtgaccgg cggctctaga    1800
caattgtact aaccttcttc tctttcctct cctgacaggt tggtgtacac tagcggccgc    1860
```

| | |
|---|---|
| caccatgttt aaatcgctga caaaagtcaa caaggtgaag cctataggag agaacaatga | 1920 |
| gaatgaacaa agttctcgtc ggaatgaaga aggctctcac ccaagtaatc agtctcagca | 1980 |
| aaccacagca caggaagaaa acaaaggtga agagaaatct ctcaaaacca agtcaactcc | 2040 |
| agtcacgtct gaagagccac acaccaacat acaagacaaa ctctccaaga aaaattcctc | 2100 |
| tggagatctg accacaaacc ctgaccctca aaatgcagca gaaccaactg aacagtgcc | 2160 |
| agagcagaag gaaatggacc ccgggaaaga aggtccaaac agcccacaaa acaaaccgcc | 2220 |
| agcagctcct gttataaatg agtatgccga tgcccagcta cacaacctgg tgaaaagaat | 2280 |
| gcgtcaaaga acagccctct acaagaaaaa gttggtagag ggagatctct cctcacccga | 2340 |
| agccagccca caaactgcaa agcccacggc tgtaccacca gtaaaagaaa gcgatgataa | 2400 |
| gccaacagaa cattactaca ggctgttgtg gttcaaagtc aaaaagatgc ctttaacaga | 2460 |
| gtacttaaag cgaattaaac ttccaaacag catagattca tacacagatc gactctatct | 2520 |
| cctgtggctc ttgcttgtca ctcttgccta taactggaac tgctgtttta taccactgcg | 2580 |
| cctcgtcttc ccatatcaaa ccgcagacaa catacactac tggcttattg cggacatcat | 2640 |
| ctgtgatatc atctaccttt atgatatgct atttatccag cccagactcc agtttgtaag | 2700 |
| aggaggagac ataatagtgg attcaaatga gctaaggaaa cactcagga cttctacaaa | 2760 |
| atttcagttg gatgtcgcat caataatacc atttgatatt tgctacctct tctttgggtt | 2820 |
| taatccaatg tttagagcaa ataggatgtt aaagtacact tcattttttg aatttaatca | 2880 |
| tcacctagag tctataatgg acaaagcata tatctacaga gttattcgaa caactggata | 2940 |
| cttgctgttt attctgcaca ttaatgcctg tgtttattac tgggcttcaa actatgaagg | 3000 |
| aattggcact actagatggg tgtatgatgg ggaaggaaac gagtatctga tgttatta | 3060 |
| ttgggcagtt cgaactttaa ttaccattgg tggccttcca gaaccacaaa ctttatttga | 3120 |
| aattgttttt caactcttga attttttttc tggagttttt gtgttctcca gtttaattgg | 3180 |
| tcagatgaga gatgtgattg gagcagctac agccaatcag aactacttcc gcgcctgcat | 3240 |
| ggatgacacc attgcctaca tgaacaatta ctccattcct aaacttgtgc aaaagcgagt | 3300 |
| tcggacttgg tatgaatata catgggactc tcaaagaatg ctagatgagt ctgatttgct | 3360 |
| taagacccta ccaactacgg tccagttagc cctcgccatt gatgtgaact tcagcatcat | 3420 |
| cagcaaagtt gacttgttca agggttgtga tacacagatg attttatgaca tgttgctaag | 3480 |
| attgaaatcc gttctctatt tgcctggtga ctttgtctgc aaaaagggag aaattggcaa | 3540 |
| ggaaatgtat atcatcaagc atggagaagt ccaagttctt ggaggccctg atggtactaa | 3600 |
| agttctggtt actctgaaag ctgggtcggt gtttggagaa atcagccttc tagcagcagg | 3660 |
| aggaggaaac cgtcgaactg ccaatgtggt ggcccacggg tttgccaatc ttttaactct | 3720 |
| agacaaaaag accctccaag aaattctagt gcattatcca gattctgaaa gaatcctcat | 3780 |
| gaagaaagcc agagtgcttt taaagcagaa ggctaagacc gcagaagcaa ccctccaag | 3840 |
| aaaagatctt gccctcctct tcccaccgaa agaagagaca cccaaactgt ttaaaactct | 3900 |
| cctaggaggc acaggaaaag caagtcttgc aagactactc aaattgaagc gagagcaagc | 3960 |
| agctcagaag aaagaaaatt ctgaaggagg agaggaagaa ggaaaagaaa atgaagataa | 4020 |
| acaaaaagaa aatgaagata acaaaaagaa aaatgaagat aaaggaaaag aaaatgaaga | 4080 |
| taaagataaa ggaagagagc cagaagagaa gccactggac agacctgaat gtacagcaag | 4140 |
| tcctattgca gtggaggaag aaccccactc agttagaagg acagttttac ccagagggac | 4200 |
| ttctcgtcaa tcactcatta tcagcatggc tccttctgct gagggcggag aagaggttct | 4260 |

```
tactattgaa gtcaaagaaa aggctaagca atgatcataa ctgcagatct gcctcgactg    4320
tgccttctag ttgccagcca tctgttgttt gcccctcccc cgtgccttcc ttgaccctgg    4380
aaggtgccac tcccactgtc ctttcctaat aaaatgagga aattgcatcg cattgtctga    4440
gtaggtgtca ttctattctg gggggtgggg tggggcagga cagcaagggg gaggattggg    4500
aagacaatag caggcatgct ggggactcga gttctacgta gataagtagc atggcgggtt    4560
aatcattaac tacaaggaac ccctagtgat ggagttggcc actccctctc tgcgcgctcg    4620
ctcgctcact gaggccgggc gaccaaaggt cgcccgacgc ccgggctttg cccgggcggc    4680
ctcagtgagc gagcgagcgc gcagccttaa ttaacctaag aaaatgaag tgaagttcct     4740 atactttcta gagaatagga acttctatag tgagtcgaat aagggcgaca caaaatttat    4800
tctaaatgca taataaatac tgataacatc ttatagtttg tattatattt tgtattatcg    4860
ttgacatgta aattttgat atcaaaaact gattttccct ttattatttt cgagatttat     4920
tttcttaatt ctctttaaca aactagaaat attgtatata caaaaaatca taataatag     4980 atgaatagtt taattatagg tgttcatcaa tcgaaaaagc aacgtatctt atttaaagtg    5040
cgttgctttt ttctcattta taaggttaaa taattctcat atatcaagca aagtgacagg    5100
cgcccttaaa tattctgaca aatgctcttt ccctaaactc cccccataaa aaacccgcc     5160 gaagcgggtt tttacgttat ttgcggatta acgattactc gttatcagaa ccgcccaggg    5220
ggcccgagct taacctttt atttggggga gagggaagtc atgaaaaaac taacctttga     5280
aattcgatct ccagcacatc agcaaaacgc tattcacgca gtacagcaaa tccttccaga    5340
cccaaccaaa ccaatcgtag taaccattca ggaacgcaac cgcagcttag accaaaacag    5400
gaagctatgg gcctgcttag gtgacgtctc tcgtcaggtt gaatggcatg gtcgctggct    5460
ggatgcagaa agctggaagt gtgtgtttac cgcagcatta aagcagcagg atgttgttcc    5520
taaccttgcc gggaatggct ttgtggtaat aggccagtca accagcagga tgcgtgtagg    5580
cgaatttgcg gagctattag agcttataca ggcattcggt acagagcgtg gcgttaagtg    5640
gtcagacgaa gcgagactgg ctctggagtg gaaagcgaga tggggagaca gggctgcatg    5700
ataaatgtcg ttagtttctc cggtggcagg acgtcagcat atttgctctg gctaatggag    5760
caaaagcgac gggcaggtaa agacgtgcat tacgttttca tggatacagg ttgtgaacat    5820
ccaatgacat atcggtttgt cagggaagtt gtgaagttct gggatatacc gctcaccgta    5880
ttgcaggttg atatcaaccc ggagcttgga cagccaaatg ttatacggt atgggaacca     5940 aaggatattc agacgcgaat gcctgttctg aagccatta tcgatatggt aaagaaatat     6000
ggcactccat acgtcggcgg cgcgttctgc actgacagat taaaactcgt tcccttcacc    6060
aaatactgtg atgaccattt cgggcgaggg aattacacca cgtggattgg catcagagct    6120
gatgaaccga agcggctaaa gccaaagcct ggaatcagat atcttgctga actgtcagac    6180
tttgagaagg aagatatcct cgcatggtgg aagcaacaac cattcgattt gcaaataccg    6240
gaacatctcg gtaactgcat attctgcatt aaaaaatcaa cgcaaaaaat cggacttgcc    6300
tgcaaagatg aggagggatt gcagcgtgtt tttaatgagg tcatcacggg atcccatgtg    6360
cgtgacggac atcgggaaac gccaaggag attatgtacc gaggaagaat gtcgctggac     6420
ggtatcgcga aaatgtattc agaaaatgat tatcaagccc tgtatcagga catggtacga    6480
gctaaaagat tcgataccgg ctcttgttct gagtcatgcg aaatatttgg agggcagctt    6540
gatttcgact tcgggaggga agctgcatga tgcgatgtta tcggtgcggt gaatgcaaag    6600
```

```
aagataaccg cttccgacca aatcaacctt actggaatcg atggtgtctc cggtgtgaaa   6660
gaacaccaac aggggtgtta ccactaccgc aggaaaagga ggacgtgtgg cgagacagcg   6720
acgaagtatc accgacataa tctgcgaaaa ctgcaaatac cttccaacga aacgcaccag   6780
aaataaaccc aagccaatcc caaaagaatc tgacgtaaaa accttcaact acacggctca   6840
cctgtgggat atccggtggc taagacgtcg tgcgaggaaa acaaggtgat tgaccaaaat   6900
cgaagttacg aacaagaaag cgtcgagcga gctttaacgt gcgctaactg cggtcagaag   6960
ctgcatgtgc tggaagttca cgtgtgtgag cactgctgcg cagaactgat gagcgatccg   7020
aatagctcga tgcacgagga agaagatgat ggctaaacca gcgcgaagac gatgtaaaaa   7080
cgatgaatgc cgggaatggt ttcaccctgc attcgctaat cagtggtggt gctctccaga   7140
gtgtggaacc aagatagcac tcgaacgacg aagtaaagaa cgcgaaaaag cggaaaaagc   7200
agcagagaag aaacgacgac gagaggagca gaaacagaaa gataaactta agattcgaaa   7260
actcgcctta aagccccgca gttactggat taaacaagcc caacaagccg taaacgcctt   7320
catcagagaa agagaccgcg acttaccatg tatctcgtgc ggaacgctca cgtctgctca   7380
gtgggatgcc ggacattacc ggacaactgc tgcggcacct caactccgat ttaatgaacg   7440
caatattcac aagcaatgcg tggtgtgcaa ccagcacaaa agcggaaatc tcgttccgta   7500
tcgcgtcgaa ctgattagcc gcatcgggca ggaagcagta gacgaaatcg aatcaaacca   7560
taaccgccat cgctggacta tcgaagagtg caaggcgatc aaggcagagt accaacagaa   7620
actcaaagac ctgcgaaata gcagaagtga ggccgcatga cgttctcagt aaaaaccatt   7680
ccagacatgc tcgttgaagc atacggaaat cagacagaag tagcacgcag actgaaatgt   7740
agtcgcggta cggtcagaaa atacgttgat gataaagacg ggaaaatgca cgccatcgtc   7800
aacgacgttc tcatggttca tcgcggatgg agtgaaagaa atgcgctatt acgaaaaaat   7860
tgatggcagc aaataccgaa atatttgggt agttggcgat ctgcacggat gctacacgaa   7920
cctgatgaac aaactggata cgattggatt cgacaacaaa aaagacctgc ttatctcggt   7980
gggcgatttg gttgatcgtg gtgcagagaa cgttgaatgc ctggaattaa tcacattccc   8040
ctggttcaga gctgtacgtg gaaaccatga gcaaatgatg attgatggct atcagagcg   8100 tggaaacgtt aatcactggc tgcttaatgg cggtggctgg ttctttaatc tcgattacga   8160
caaagaaatt ctggctaaag ctcttgccca taaagcagat gaacttccgt taatcatcga   8220
actggtgagc aaagataaaa aatatgttat ctgccacgcc gattatccct ttgacgaata   8280
cgagtttgga aagccagttg atcatcagca ggtaatctgg aaccgcgaac gaatcagcaa   8340
ctcacaaaac gggatcgtga agaaatcaa aggcgcggac acgttcatct tggtcatac   8400 gccagcagtg aaaccactca gtttgccaa ccaaatgtat atcgataccg gcgcagtgtt   8460
ctgcggaaac ctaacattga ttcaggtaca gggagaaggc gcatgagact cgaaagcgta   8520
gctaaatttc attcgccaaa aagcccgatg atgagcgact caccacgggc cacggcttct   8580
gactctcttt ccggtactga tgtgatggct gctatgggga tggcgcaatc acaagccgga   8640
ttcggtatgg ctgcattctg cggtaagcac gaactcagcc agaacgacaa acaaaaggct   8700
atcaactatc tgatgcaatt tgcacacaag gtatcgggga ataccgtgg tgtggcaaag   8760 cttgaaggaa atactaaggc aaaggtactg caagtgctcg caacattcgc ttatgcggat   8820
tattgccgta gtgccgcgac gccgggggca agatgcagag attgccatgg tacaggccgt   8880
gcggttgata ttgccaaaac agagctgtgg gggagagttg tcgagaaaga gtgcggaaga   8940
tgcaaaggcg tcggctattc aaggatgcca gcaagcgcag catatcgcgc tgtgacgatg   9000
```

```
ctaatcccaa accttaccca acccacctgg tcacgcactg ttaagccgct gtatgacgct    9060
ctggtggtgc aatgccacaa agaagagtca atcgcagaca acattttgaa tgcggtcaca    9120
cgttagcagc atgattgcca cggatggcaa catattaacg gcatgatatt gacttattga    9180
ataaaattgg gtaaatttga ctcaacgatg ggttaattcg ctcgttgtgg tagtgagatg    9240
aaaagaggcg gcgcttacta ccgattccgc ctagttggtc acttcgacgt atcgtctgga    9300
actccaacca tcgcaggcag agaggtctgc aaaatgcaat cccgaaacag ttcgcaggta    9360
atagttagag cctgcataac ggtttcggga ttttttatat ctgcacaaca ggtaagagca    9420
ttgagtcgat aatcgtgaag agtcggcgag cctggttagc cagtgctctt tccgttgtgc    9480
tgaattaagc gaataccgga agcagaaccg gatcaccaaa tgcgtacagg cgtcatcgcc    9540
gcccagcaac agcacaaccc aaactgagcc gtagccactg tctgtcctga attcattagt    9600
aatagttacg ctgcggcctt ttacacatga ccttcgtgaa agcgggtggc aggaggtcgc    9660
gctaacaacc tcctgccgtt ttgcccgtgc atatcggtca cgaacaaatc tgattactaa    9720
acacagtagc ctggatttgt tctatcagta atcgacctta ttcctaatta aatagagcaa    9780
atcccttat tgggggtaag acatgaagat gccagaaaaa catgacctgt tggccgccat    9840
tctcgcggca aggaacaag gcatcggggc aatccttgcg tttgcaatgg cgtaccttcg    9900
cggcagatat aatggcggtg cgtttacaaa acagtaatc gacgcaacga tgtgcgccat    9960
tatcgcctgg ttcattcgtg accttctcga cttcgccgga ctaagtagca atctcgctta   10020
tataacgagc gtgtttatcg gctacatcgg tactgactcg attggttcgc ttatcaaacg   10080
cttcgctgct aaaaaagccg gagtagaaga tggtagaaat caataatcaa cgtaaggcgt   10140
tcctcgatat gctggcgtgg tcggaggaa ctgataacgg acgtcagaaa accagaaatc   10200
atggttatga cgtcattgta ggcggagagc tatttactga ttactccgat caccctcgca   10260
aacttgtcac gctaaaccca aaactcaaat caacaggcgc ttaagactgg ccgtcgtttt   10320
acaacacaga aagagtttgt agaaacgcaa aaaggccatc cgtcagggc cttctgctta   10380
gtttgatgcc tggcagttcc ctactctcgc cttccgcttc ctcgctcact gactcgctgc   10440
gctcggtcgt tcggctgcgg cgagcggtat cagctcactc aaaggcggta atacggttat   10500
ccacagaatc agggataac gcaggaaaga acatgtgagc aaaaggccag caaaaggcca   10560
ggaaccgtaa aaaggccgcg ttgctggcgt ttttccatag gctccgcccc cctgacgagc   10620
atcacaaaaa tcgacgctca agtcagaggt ggcgaaaccc gacaggacta taaagatacc   10680
aggcgtttcc ccctggaagc tccctcgtgc gctctcctgt tccgaccctg ccgcttaccg   10740
gatacctgtc cgcctttctc ccttcgggaa gcgtggcgct ttctcatagc tcacgctgta   10800
ggtatctcag ttcggtgtag gtcgttcgct ccaagctggg ctgtgtgcac gaaccccccg   10860
ttcagcccga ccgctgcgcc ttatccggta actatcgtct tgagtccaac ccggtaagac   10920
acgacttatc gccactggca gcagccactg gtaacaggat tagcagagcg aggtatgtag   10980
gcggtgctac agagttcttg aagtggtggg ctaactacgg ctacactaga agaacagtat   11040
ttggtatctg cgctctgctg aagccagtta ccttcggaaa aagagttggt agctcttgat   11100
ccggcaaaca aaccaccgct ggtagcggtg gttttttttgt ttgcaagcag cagattacgc   11160
gcagaaaaaa aggatctcaa gaagatcctt tgatcttttc tacggggtct gacgctcagt   11220
ggaacgacgc gcgcgtaact cacgttaagg gattttggtc atgagcttgc gccgtcccgt   11280
caagtcagcg taatgctctg cttttagaaa aactcatcga gcatcaaatg aaactgcaat   11340
```

```
ttattcatat caggattatc aataccatat ttttgaaaaa gccgtttctg taatgaagga    11400
gaaaactcac cgaggcagtt ccataggatg gcaagatcct ggtatcggtc tgcgattccg    11460
actcgtccaa catcaataca acctattaat ttccctcgt caaaaataag gttatcaagt     11520
gagaaatcac catgagtgac gactgaatcc ggtgagaatg gcaaaagttt atgcatttct    11580
ttccagactt gttcaacagg ccagccatta cgctcgtcat caaaatcact cgcatcaacc    11640
aaaccgttat tcattcgtga ttgcgcctga gcgaggcgaa atacgcgatc gctgttaaaa    11700
ggacaattac aaacaggaat cgagtgcaac cggcgcagga acactgccag cgcatcaaca    11760
atattttcac ctgaatcagg atattcttct aatacctgga acgctgtttt tccggggatc    11820
gcagtggtga gtaaccatgc atcatcagga gtacggataa aatgcttgat ggtcggaagt    11880
ggcataaatt ccgtcagcca gtttagtctg accatctcat ctgtaacatc attggcaacg    11940
ctacctttgc catgtttcag aaacaactct ggcgcatcgg gcttcccata caagcgatag    12000
attgtcgcac ctgattgccc gacattatcg cgagcccatt tatacccata taaatcagca    12060
tccatgttgg aatttaatcg cggcctcgac gtttcccgtt gaatatggct catattcttc    12120 cttttcaat attattgaag catttatcag ggttattgtc tcatgagcgg atacatattt     12180
gaatgtattt agaaaaataa acaaataggg gtcagtgtta caaccaatta accaattctg    12240
aacattatcg cgagcccatt tatacctgaa tatggctcat aacacccctt gtttgcctgg    12300
cggcagtagc gcggtggtcc cacctgaccc catgccgaac tcagaagtga acgccgtag    12360 cgccgatggt agtgtgggga ctccccatgc gagagtaggg aactgccagg catcaaataa    12420
aacgaaaggc tcagtcgaaa gactgggcct ttcgccccgg gctaattaggg ggtgtcgccc   12480 ttattcgact ctatagtgaa gttcctattc tctagaaagt ataggaactt ctgaagtggg    12540
gtcgacttaa ttaagg                                                    12556
```

<210> SEQ ID NO 44
<211> LENGTH: 12556
<212> TYPE: DNA
<213> ORGANISM: Artificial Sequence
<220> FEATURE:
<223> OTHER INFORMATION: constructed sequence

<400> SEQUENCE: 44

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact     120
aggggttcct tgtagttaat gattaacccg ccatgctact tatctacgta gcaagctagc    180
tagttattaa tagtaatcaa ttacggggtc attagttcat agcccatata tggagttccg    240
cgttacataa cttacggtaa atggcccgcc tggctgaccg cccaacgacc cccgcccatt    300
gacgtcaata atgacgtatg ttcccatagt aacgccaata gggactttcc attgacgtca    360
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattaa    540
catggtcgag gtgagcccca cgttctgctt cactctcccc atctcccccc cctccccacc    600
cccaattttg tatttattta ttttttaatt attttgtgca gcgatggggg cggggggggg    660
gggggggcgc gcgccaggcg gggcggggcg gggcgagggg cggggcgggg cgaggcggag    720
aggtgcggcg gcagccaatc agagcggcgc gctccgaaag tttccttta tggcgaggcg     780 gcggcggcgg cggccctata aaaagcgaag cgcgcggcgg gcgggagtc gctgcgacgc      840
```

```
tgccttcgcc ccgtgccccg ctccgccgcc gcctcgcgcc gcccgccccg gctctgactg    900
accgcgttac tcccacaggt gagcgggcgg gacggcccct ctcctccggg ctgtaattag    960
cgcttggttt aatgacggct tgtttctttt ctgtggctgc gtgaaagcct tgaggggctc   1020
cgggagggcc ctttgtgcgg ggggagcggc tcgggggtg cgtgcgtgtg tgtgtgcgtg    1080
gggagcgccg cgtgcggctc cgcgctgccc ggcggctgtg agcgctgcgg gcgcggcgcg   1140
gggctttgtg cgctccgcag tgtgcgcgag gggagcgcgg ccggggggcgg tgccccgcgg   1200
tgcgggggg gctgcgaggg gaacaaaggc tgcgtgcggg gtgtgtgcgt ggggggtga     1260
gcaggggtg tgggcgcgtc ggtcgggctg caaccccccc tgcaccccc tccccgagtt    1320
gctgagcacg gccggcttc gggtgcgggg ctccgtacgg ggcgtggcgc ggggctcgcc    1380
gtgccgggcg ggggtggcg gcaggtgggg gtgccgggcg gggcgggcc gcctcgggcc    1440
ggggagggct cggggaggg gcgcggcggc ccccggagcg ccggcggctg tcgaggcgcg    1500
gcgagccgca gccattgcct tttatggtaa tcgtgcgaga gggcgcaggg acttcctttg   1560
tcccaaatct gtgcggagcc gaaatctggg aggcgccgcc gcaccccctc tagcgggcgc   1620
ggggcgaagc ggtgcggcgc cggcaggaag gaaatgggcg gggagggcct tcgtgcgtcg   1680
ccgcgccgcc gtccccttct ccctctccag cctcggggct gtccgcgggg ggacggctgc   1740
cttcgggggg gacggggcag ggcgggggttc ggcttctggc gtgtgaccgg cggctctaga   1800
caattgtact aaccttcttc tcttttcctct cctgacaggt tggtgtacac tagcggccgc   1860
caccatgttc aagtccctca ccaaagtcaa caaggtcaag cccatcggag agaacaacga   1920
gaatgagcag agctctcggc gcaacgaaga aggatcccat ccgtcgaacc agtcacagca   1980
gactaccgca caggaggaga acaagggaga agaaaagtcg ctcaagacta agtccacccc   2040
cgtgacctcg gaagaaccgc acacgaacat tcaggacaag ctgtccaaga gaactcctc    2100
cggcgatctc acgactaacc cggaccccca gaatgccgct gaacctactg ggaccgtgcc   2160
tgagcaaaag gagatggacc ccggaaagga gggtcctaac tccccccaaa acaagccccc   2220
ggccgcgccg gtcatcaatg agtacgcgga cgcgcaactg cataacctcg tgaagcggat   2280
gcggcaaaga accgccctct acaagaagaa actggtggag ggcgacctga gctcacctga   2340
agccagccca cagaccgcca aacccaccgc cgtgccgcct gtgaaggagt ccgatgacaa   2400
gcctaccgag cactactacc gcctgctgtg gttcaaggtc aagaagatgc ccctgaccga   2460
atacctcaag cggatcaagc tgccgaacag catcgacagc tacaccgacc ggctttactt   2520
gctctgctgt ctgcttgtga ccctggctta caactggaac tgttgtttca ttcccctgcg   2580
gctggtgttc ccttaccaaa ccgcggataa cattcactac tggctgattg ccgacatcat   2640
ttgcgacatc atctacctgt acgatatgct ttttatccaa ccgcggctgc aattcgtccg   2700
cggggagac atcattgtgg actccaacga gctgcgcaag cattaccgga cctcgacaaa   2760
gttccagctg gatgtggcct ccatcatccc gttcgatatc tgttacctgt ctttggctt    2820
caacccgatg ttcagggcga acaggatgct gaagtacact tccttcttcg aattcaacca   2880
ccacctggag tccatcatgg acaaggctta catctaccgc gtgatccgga ccactggtta   2940
cctcctgttc atcctgcaca tcaacgcctg cgtctattac tgggcctcaa actacgaagg   3000
cattggtacc acccgctggg tgtacgacgg ggagggaaac gagtatctgc gctgctacta   3060
ctgggccgtg cgaaccctca taactattgg cggcctcccg gaaccgcaga ccctgttcga   3120
gatcgtgttc caactcctca acttcttctc gggagtgttc gtgttttcaa gcttgattgg   3180
```

```
acagatgcgg gacgtgatcg gtgcagcaac tgccaaccag aactactttc gcgcctgcat    3240 ggacgcacact atcgcgtaca tgaacaacta ttcgatcccc aagctggtgc agaaacgcgt   3300
gcggacttgg tatgagtaca cttgggactc ccagagaatg cttgacgagt ccgatctgct   3360
caagaccctg cctactaccg tgcagctggc actcgccatc gatgtgaact tctccattat   3420
ctcgaaagtc gatctgttca agggctgcga cacccagatg atctacgaca tgctgctgag   3480
actcaagtcc gtgttgtacc tccctggcga cttcgtgtgc aagaagggcg aaatcgggaa   3540
ggagatgtac attatcaagc acggagaagt ccaggtgctg gggggaccag acggtaccaa   3600
ggtccttgtc accctgaagg ccgggtccgt gttcggcgaa atttccctgt ggccgccgg    3660 cggtggcaac aggagaaccg caaatgtggt ggcccacggc ttcgcaaacc ttctgaccct   3720
ggacaagaaa accctccagg aaatcctcgt gcactaccg gatagcgagc ggatcctgat    3780
gaagaaagcc cggggtgctgc tgaagcaaaa ggccaagacc gccgaagcca ccccgcctcg  3840
gaaggacctg gctctgctgt tcccacccaa ggaggagact cccaaactgt ttaagaccct   3900
cttgggcggg acgggaaagg cctccctcgc tcgcttgctt aagttgaaga gggagcaggc   3960
cgcgcagaag aaggaaaact ccgaaggagg ggaagaagag ggaaaggaaa acgaagataa   4020
gcagaaggag aacgaggata gcaaaaggaa aaatgaggac aaggggaaag aaaacgagga   4080
caaggataag ggtcgcgaac ctgaagagaa gccgctggat cggccagagt gcactgcctc   4140
gcctatcgcg gtcgaagagg aaccccatag cgtgcgcaga accgtgctgc ctagaggcac   4200
atcgaggcag tcactgatta tctctatggc accaagcgcc gagggaggag aggaagtgct   4260
caccatcgag gtcaaggaaa aagcgaagca gtgatcataa ctgcagatct gcctcgactg   4320
tgccttctag ttgccagcca tctgttgttt gcccctcccc cgtgccttcc ttgaccctgg   4380
aaggtgccac tcccactgtc ctttcctaat aaaatgagga aattgcatcg cattgtctga   4440
gtaggtgtca ttctattctg gggggtgggg tggggcagga cagcaagggg gaggattggg   4500
aagacaatag caggcatgct ggggactcga gttctacgta gataagtagc atggcgggtt   4560
aatcattaac tacaaggaac ccctagtgat ggagttggcc actccctctc tgcgcgctcg   4620
ctcgctcact gaggccgggc gaccaaaggt cgcccgacgc ccgggctttg cccgggcggc   4680
ctcagtgagc gagcgagcgc gcagccttaa ttaacctaag gaaaatgaag tgaagttcct   4740
atactttcta gagaatagga acttctatag tgagtcgaat aagggcgaca caaaatttat   4800
tctaaatgca taataaatac tgataacatc ttatagtttg tattatatt tgtattatcg    4860 ttgacatgta taattttgat atcaaaaact gattttccct ttattatttt cgagatttat   4920
tttcttaatt ctctttaaca aactagaaat attgtatata caaaaaatca taaataatag   4980
atgaatagtt taattatagg tgttcatcaa tcgaaaaagc aacgtatctt atttaaagtg   5040
cgttgctttt ttctcatttta taaggttaaa taattctcat atatcaagca aagtgacagg   5100
cgcccttaaa tattctgaca aatgctcttt ccctaaactc cccccataaa aaacccgcc    5160 gaagcgggtt tttacgttat ttgcggatta acgattactc gttatcagaa ccgcccaggg   5220
ggcccgagct taacctttt atttggggga gagggaagtc atgaaaaaac taacctttga    5280
aattcgatct ccagcacatc agcaaaacgc tattcacgca gtacagcaaa tccttccaga   5340
cccaaccaaa ccaatcgtag taaccattca ggaacgcaac cgcagcttag accaaaacag   5400
gaagctatgg gcctgcttag gtgacgtctc tcgtcaggtt gaatggcatg gtcgctggct   5460
ggatgcagaa agctggaagt gtgtgtttac cgcagcatta aagcagcagg atgttgttcc   5520
taaccttgcc gggaatggct ttgtggtaat aggccagtca accagcagga tgcgtgtagg   5580
```

```
cgaatttgcg gagctattag agcttataca ggcattcggt acagagcgtg gcgttaagtg    5640
gtcagacgaa gcgagactgg ctctggagtg gaaagcgaga tggggagaca gggctgcatg    5700
ataaatgtcg ttagtttctc cggtggcagg acgtcagcat atttgctctg gctaatggag    5760
caaaagcgac gggcaggtaa agacgtgcat tacgttttca tggatacagg ttgtgaacat    5820
ccaatgacat atcggtttgt cagggaagtt gtgaagttct gggatatacc gctcaccgta    5880
ttgcaggttg atatcaaccc ggagcttgga cagccaaatg ttatacggt atgggaacca    5940 aaggatattc agacgcgaat gcctgttctg aagccattta tcgatatggt aaagaaatat    6000
ggcactccat acgtcggcgg cgcgttctgc actgacagat aaaactcgt tcccttcacc    6060 aaatactgtg atgaccattt cgggcgaggg aattacacca cgtggattgg catcagagct    6120
gatgaaccga agcggctaaa gccaaagcct ggaatcagat atcttgctga actgtcagac    6180
tttgagaagg aagatatcct cgcatggtgg aagcaacaac cattcgattt gcaaataccg    6240
gaacatctcg gtaactgcat attctgcatt aaaaaatcaa cgcaaaaaat cggacttgcc    6300
tgcaaagatg aggagggatt gcagcgtgtt tttaatgagg tcatcacggg atcccatgtg    6360
cgtgacggac atcgggaaac gccaaaggag attatgtacc gaggaagaat gtcgctggac    6420
ggtatcgcga aaatgtattc agaaaatgat tatcaagccc tgtatcagga catggtacga    6480
gctaaaagat tcgataccgg ctcttgttct gagtcatgcg aaatatttgg agggcagctt    6540
gatttcgact tcgggaggga agctgcatga tgcgatgtta tcggtgcggt gaatgcaaag    6600
aagataaccg cttccgacca aatcaacctt actggaatcg atggtgtctc cggtgtgaaa    6660
gaacaccaac aggggtgtta ccactaccgc aggaaaagga ggacgtgtgg cgagacagcg    6720
acgaagtatc accgacataa tctgcgaaaa ctgcaaatac cttccaacga aacgcaccag    6780
aaataaaccc aagccaatcc caaaagaatc tgacgtaaaa accttcaact acacggctca    6840
cctgtgggat atccggtggc taagacgtcg tgcgaggaaa acaaggtgat tgaccaaaat    6900
cgaagttacg aacaagaaag cgtcgagcga gctttaacgt gcgctaactg cggtcagaag    6960
ctgcatgtgc tggaagttca cgtgtgtgag cactgctgcg cagaactgat gagcgatccg    7020
aatagctcga tgcacgagga agaagatgat ggctaaacca gcgcgaagac gatgtaaaaa    7080
cgatgaatgc cgggaatggt ttcaccctgc attcgctaat cagtggtggt gctctccaga    7140
gtgtggaacc aagatagcac tcgaacgacg aagtaaagaa cgcgaaaaag cggaaaaagc    7200
agcagagaag aaacgacgac gagaggagca gaaacagaaa gataaactta agattcgaaa    7260
actcgcctta aagcccgca gttactggat taaacaagcc caacaagccg taaacgcctt    7320
catcagagaa agagaccgcg acttaccatg tatctcgtgc ggaacgctca cgtctgctca    7380
gtgggatgcc ggacattacc ggacaactgc tgcggcacct caactccgat ttaatgaacg    7440
caatattcac aagcaatgcg tggtgtgcaa ccagcacaaa agcggaaatc tcgttccgta    7500
tcgcgtcgaa ctgattagcc gcatcgggca ggaagcagta gacgaaatcg aatcaaacca    7560
taaccgccat cgctggacta tcgaagagtg caaggcgatc aaggcagagt accaacagaa    7620
actcaaagac ctgcgaaata gcagaagtga ggccgcatga cgttctcagt aaaaaccatt    7680
ccagacatgc tcgttgaagc atacggaaat cagacagaag tagcacgcag actgaaatgt    7740
agtcgcggta cggtcagaaa atacgttgat gataaagacg ggaaaatgca cgccatcgtc    7800
aacgacgttc tcatggttca tcgcggatgg agtgaaagag atgcgctatt acgaaaaaat    7860
tgatggcagc aaataccgaa atatttgggt agttggcgat ctgcacggat gctacacgaa    7920
```

```
cctgatgaac aaactggata cgattggatt cgacaacaaa aaagacctgc ttatctcggt    7980
gggcgatttg gttgatcgtg gtgcagagaa cgttgaatgc ctggaattaa tcacattccc    8040
ctggttcaga gctgtacgtg gaaaccatga gcaaatgatg attgatggct tatcagagcg    8100
tggaaacgtt aatcactggc tgcttaatgg cggtggctgg ttctttaatc tcgattacga    8160
caaagaaatt ctggctaaag ctcttgccca taaagcagat gaacttccgt taatcatcga    8220
actggtgagc aaagataaaa aatatgttat ctgccacgcc gattatccct ttgacgaata    8280
cgagtttgga aagccagttg atcatcagca ggtaatctgg aaccgcgaac gaatcagcaa    8340
ctcacaaaac gggatcgtga agaaatcaa aggcgcggac acgttcatct ttggtcatac    8400
gccagcagtg aaaccactca gtttgccaa ccaaatgtat atcgataccg cgcagtgtt    8460
ctgcggaaac ctaacattga ttcaggtaca gggagaaggc gcatgagact cgaaagcgta    8520
gctaaatttc attcgccaaa aagcccgatg atgagcgact caccacgggc cacggcttct    8580
gactctcttt ccggtactga tgtgatggct gctatgggga tggcgcaatc acaagccgga    8640
ttcggtatgg ctgcattctg cggtaagcac gaactcagcc agaacgacaa acaaaaggct    8700
atcaactatc tgatgcaatt tgcacacaag gtatcgggga ataccgtgg tgtggcaaag    8760
cttgaaggaa atactaaggc aaaggtactg caagtgctcg caacattcgc ttatgcggat    8820
tattgccgta gtgccgcgac gccgggggca agatgcagag attgccatgg tacaggccgt    8880
gcggttgata ttgccaaaac agagctgtgg gggagagttg tcgagaaaga gtgcggaaga    8940
tgcaaaggcg tcggctattc aaggatgcca gcaagcgcag catatcgcgc tgtgacgatg    9000
ctaatcccaa accttaccca acccacctgg tcacgcactg ttaagccgct gtatgacgct    9060
ctggtggtgc aatgccacaa agaagagtca atcgcagaca acattttgaa tgcggtcaca    9120
cgttagcagc atgattgcca cggatggcaa catattaacg gcatgatatt gacttattga    9180
ataaaattgg gtaaatttga ctcaacgatg ggttaattcg ctcgttgtgg tagtgagatg    9240
aaaagaggcg gcgcttacta ccgattccgc ctagttggtc acttcgacgt atcgtctgga    9300
actccaacca tcgcaggcag agaggtctgc aaaatgcaat cccgaaacag ttcgcaggta    9360
atagttagag cctgcataac ggtttcggga tttttttatat ctgcacaaca ggtaagagca    9420
ttgagtcgat aatcgtgaag agtcggcgag cctggttagc cagtgctctt tccgttgtgc    9480
tgaattaagc gaataccgga agcagaaccg gatcaccaaa tgcgtacagg cgtcatcgcc    9540
gcccagcaac agcacaaccc aaactgagcc gtagccactg tctgtcctga attcattagt    9600
aatagttacg ctgcggcctt ttacacatga ccttcgtgaa agcgggtggc aggaggtcgc    9660
gctaacaacc tcctgccgtt tgcccgtgc atatcggtca cgaacaaatc tgattactaa    9720
acacagtagc ctggatttgt tctatcagta atcgacctta ttcctaatta aatagagcaa    9780
atcccttat tgggggtaag acatgaagat gccagaaaaa catgacctgt tggccgccat    9840
tctcgcggca aaggaacaag gcatcgggc aatccttgcg tttgcaatgg cgtaccttcg    9900
cggcagatat aatggcggtg cgtttacaaa aacagtaatc gacgcaacga tgtgcgccat    9960
tatcgcctgg ttcattcgtg accttctcga cttcgccgga ctaagtagca atctcgctta   10020
tataacgagc gtgtttatcg gctacatcgg tactgactcg attggttcgc ttatcaaacg   10080
cttcgctgct aaaaaagccg gagtagaaga tggtagaaat caataatcaa cgtaaggcgt   10140
tcctcgatat gctggcgtgg tcggagggaa ctgataacgg acgtcagaaa accagaaatc   10200
atggttatga cgtcattgta ggcggagagc tatttactga ttactccgat caccctcgca   10260
aacttgtcac gctaaaccca aaactcaaat caacaggcgc ttaagactgg ccgtcgtttt   10320
```

```
acaacacaga aagagtttgt agaaacgcaa aaaggccatc cgtcaggggc cttctgctta    10380
gtttgatgcc tggcagttcc ctactctcgc cttccgcttc ctcgctcact gactcgctgc    10440
gctcggtcgt tcggctgcgg cgagcggtat cagctcactc aaaggcggta atacggttat    10500
ccacagaatc aggggataac gcaggaaaga acatgtgagc aaaaggccag caaaaggcca    10560
ggaaccgtaa aaaggccgcg ttgctggcgt ttttccatag gctccgcccc cctgacgagc    10620
atcacaaaaa tcgacgctca agtcagaggt ggcgaaaccc gacaggacta taaagatacc    10680
aggcgtttcc ccctggaagc tccctcgtgc gctctcctgt tccgaccctg ccgcttaccg    10740
gatacctgtc cgcctttctc ccttcgggaa gcgtggcgct ttctcatagc tcacgctgta    10800
ggtatctcag ttcggtgtag gtcgttcgct ccaagctggg ctgtgtgcac gaaccccccg    10860
ttcagcccga ccgctgcgcc ttatccggta actatcgtct tgagtccaac ccggtaagac    10920
acgacttatc gccactggca gcagccactg gtaacaggat tagcagagcg aggtatgtag    10980
gcggtgctac agagttcttg aagtggtggg ctaactacgg ctacactaga agaacagtat    11040
ttggtatctg cgctctgctg aagccagtta ccttcggaaa aagagttggt agctcttgat    11100
ccggcaaaca aaccaccgct ggtagcggtg gttttttgt ttgcaagcag cagattacgc    11160
gcagaaaaaa aggatctcaa gaagatcctt tgatcttttc tacggggtct gacgctcagt    11220
ggaacgacgc gcgcgtaact cacgttaagg gattttggtc atgagcttgc gccgtcccgt    11280
caagtcagcg taatgctctg cttttagaaa aactcatcga gcatcaaatg aaactgcaat    11340
ttattcatat caggattatc aataccatat ttttgaaaaa gccgtttctg taatgaagga    11400
gaaaactcac cgaggcagtt ccataggatg gcaagatcct ggtatcggtc tgcgattccg    11460
actcgtccaa catcaataca acctattaat ttcccctcgt caaaaataag gttatcaagt    11520
gagaaatcac catgagtgac gactgaatcc ggtgagaatg gcaaaagttt atgcatttct    11580
ttccagactt gttcaacagg ccagccatta cgctcgtcat caaaatcact cgcatcaacc    11640
aaaccgttat tcattcgtga ttgcgcctga gcgaggcgaa atacgcgatc gctgttaaaa    11700
ggacaattac aaacaggaat cgagtgcaac cggcgcagga acactgccag cgcatcaaca    11760
atattttcac ctgaatcagg atattcttct aatacctgga acgctgtttt tccgggatc     11820 gcagtggtga gtaaccatgc atcatcagga gtacggataa aatgcttgat ggtcggaagt    11880
ggcataaatt ccgtcagcca gtttagtctg accatctcat ctgtaacatc attggcaacg    11940
ctacctttgc catgtttcag aaacaactct ggcgcatcgg gcttcccata caagcgatag    12000
attgtcgcac ctgattgccc gacattatcg cgagcccatt tatacccata taatcagca    12060 tccatgttgg aatttaatcg cggcctcgac gtttcccgtt gaatatggct catattcttc    12120 cttttcaat attattgaag catttatcag ggttattgtc tcatgagcgg atacatattt    12180
gaatgtattt agaaaaataa acaaataggg gtcagtgtta caaccaatta accaattctg    12240
aacattatcg cgagcccatt tatacctgaa tatggctcat aacacccctt gtttgcctgg    12300
cggcagtagc gcggtggtcc cacctgaccc catgccgaac tcagaagtga aacgccgtag    12360
cgccgatggt agtgtgggga ctccccatgc gagagtaggg aactgccagg catcaaataa    12420
aacgaaaggc tcagtcgaaa gactgggcct ttcgccggg ctaattaggg ggtgtcgccc     12480
ttattcgact ctatagtgaa gttcctattc tctagaaagt ataggaactt ctgaagtggg    12540
gtcgacttaa ttaagg                                                    12556
```

<210> SEQ ID NO 45

<211> LENGTH: 2450
<212> TYPE: DNA
<213> ORGANISM: Artificial Sequence
<220> FEATURE:
<223> OTHER INFORMATION: constructed sequence

<400> SEQUENCE: 45

| | | | | | |
|---|---|---|---|---|---|
| gccgccacca | tgttcaagtc | cctcaccaaa | gtcaacaagg | tcaagcccat | cggagagaac | 60 |
| aacgagaatg | agcagagctc | tcggcgcaac | gaagaaggat | cccatccgtc | gaaccagtca | 120 |
| cagcagacta | ccgcacagga | ggagaacaag | ggagaagaaa | agtcgctcaa | gactaagtcc | 180 |
| accccgtga | cctcggaaga | accgcacacg | aacattcagg | acaagctgtc | caagaagaac | 240 |
| tcctccggcg | atctcacgac | taacccggac | ccccagaatg | ccgctgaacc | tactgggacc | 300 |
| gtgcctgagc | aaaaggagat | ggaccccgga | aggagggtc | ctaactcccc | ccaaaacaag | 360 |
| cccccggccg | cgccggtcat | caatgagtac | gcggacgcgc | aactgcataa | cctcgtgaag | 420 |
| cggatgcggc | aaagaaccgc | cctctacaag | aagaaactgg | tggagggcga | cctgagctca | 480 |
| cctgaagcca | gcccacagac | cgccaaaccc | accgccgtgc | cgcctgtgaa | ggagtccgat | 540 |
| gacaagccta | ccgagcacta | ctaccgcctg | ctgtggttca | aggtcaagaa | gatgcccctg | 600 |
| accgaatacc | tcaagcggat | caagctgccg | aacagcatcg | acagctacac | cgaccggctt | 660 |
| tacttgctct | ggctgctgct | tgtgaccctg | gcttacaact | ggaactgttg | tttcattccc | 720 |
| ctgcggctgg | tgttcccta | ccaaaccgcg | gataacattc | actactggct | gattgccgac | 780 |
| atcatttgcg | acatcatcta | cctgtacgat | atgcttttta | tccaaccgcg | gctgcaattc | 840 |
| gtccgcgggg | gagacatcat | tgtggactcc | aacgagctgc | gcaagcatta | ccggacctcg | 900 |
| acaaagttcc | agctggatgt | ggcctccatc | atcccgttcg | atatctgtta | cctgttcttt | 960 |
| ggcttcaacc | cgatgttcag | ggcgaacagg | atgctgaagt | acacttcctt | cttcgaattc | 1020 |
| aaccaccacc | tggagtccat | catggacaag | gcttacatct | accgcgtgat | ccggaccact | 1080 |
| ggttacctcc | tgttcatcct | gcacatcaac | gcctgcgtct | attactgggc | tcaaaactac | 1140 |
| gaaggcattg | gtaccacccg | ctgggtgtac | gacggggagg | gaaacgagta | tctgcgctgc | 1200 |
| tactactggg | ccgtgcgaac | cctcataact | attggcggcc | tcccggaacc | gcagaccctg | 1260 |
| ttcgagatcg | tgttccaact | cctcaacttc | ttctcgggag | tgttcgtgtt | ttcaagcttg | 1320 |
| attggacaga | tgcgggacgt | gatcggtgca | gcaactgcca | accagaacta | ctttcgcgcc | 1380 |
| tgcatggacg | acactatcgc | gtacatgaac | aactattcga | tccccaagct | ggtgcagaaa | 1440 |
| cgcgtgcgga | cttggtatga | gtacacttgg | gactcccaga | gaatgcttga | cgagtccgat | 1500 |
| ctgctcaaga | ccctgcctac | taccgtgcag | ctggcactcg | ccatcgatgt | gaacttctcc | 1560 |
| attatctcga | aagtcgatct | gttcaagggc | tgcgacaccc | agatgatcta | cgacatgctg | 1620 |
| ctgagactca | agtccgtgtt | gtacctccct | ggcgacttcg | tgtgcaagaa | gggcgaaatc | 1680 |
| gggaaggaga | tgtacattat | caagcacgga | gaagtccagg | tgctggggg | accagacggt | 1740 |
| accaaggtcc | ttgtcaccct | gaaggccggg | tccgtgttcg | gcgaaatttc | cctgttggcc | 1800 |
| gccggcggtg | gcaacaggag | aaccgcaaat | gtggtggccc | acggcttcgc | aaaccttctg | 1860 |
| accctggaca | agaaaaccct | ccaggaaatc | ctcgtgcact | accggatag | cgagcggatc | 1920 |
| ctgatgaaga | agcccgggt | gctgctgaag | caaaaggcca | agaccgccga | agccaccccg | 1980 |
| cctcggaagg | acctggctct | gctgttccca | cccaaggagg | agactcccaa | actgtttaag | 2040 |
| accctcttgg | gcgggacggg | aaaggcctcc | ctcgctcgct | tgcttaagtt | gaagagggag | 2100 |
| caggccgcgc | agaagaagga | aaactccgaa | ggagggaag | aagagggaaa | ggaaaacgaa | 2160 |

| | |
|---|---|
| gataagcaga aggagaacga ggataagcaa aaggaaaatg aggacaaggg gaaagaaaac | 2220 |
| gaggacaagg ataagggtcg cgaacctgaa gagaagccgc tggatcggcc agagtgcact | 2280 |
| gcctcgccta tcgcggtcga agaggaaccc catagcgtgc gcagaaccgt gctgcctaga | 2340 |
| ggcacatcga ggcagtcact gattatctct atggcaccaa cgccgaggg aggagaggaa | 2400 |
| gtgctcacca tcgaggtcaa ggaaaaagcg aagcagtgat cataactgca | 2450 |

<210> SEQ ID NO 46
<211> LENGTH: 12006
<212> TYPE: DNA
<213> ORGANISM: Artificial Sequence
<220> FEATURE:
<223> OTHER INFORMATION: constructed sequence

<400> SEQUENCE: 46

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gcaagctagc | 180 |
| ctgaagagac agaaatatct ctaattccat gagcggtcat acgaggcaag agaagccgct | 240 |
| tagagcatgg acttagttag tttcagggat tggacagagt caagagctgg ggtgaggagg | 300 |
| ttaccctcgg taggggtgac acagatgtca accgccatt ccctccacat gcatgtcctg | 360 |
| ccagaagaac ctgtccctgg gctgggaatc ttatattacc ttcctctcca atgagaagag | 420 |
| aagttcaagg ctcacagaca tgtgcataca caagctcaat gcactcaaga ttcccctcca | 480 |
| ccactcctgc ccccactacc tacaggagat tgactcctgc tgtgcacata agctgggata | 540 |
| atcagggttt ctaaacatca gcttcaaaag tccaatgtcc aaagtggtgg ggggccgggg | 600 |
| aacgaggtac tctttccata cccttggctt ttgtgtggcc tggagccgct gatatagaga | 660 |
| ttggagtggg acacgaggta ttcctttcaa aaacacaaag gcctatactt tgagccctcc | 720 |
| catttcaatc ccccaccatg cttcacccttt aagacctcca actccacttt gatcccagtt | 780 |
| ctcaggttca ggcctcacaa ggccaaaatc ctgaagttac ccttctcaaa ctcccttgcc | 840 |
| tttaacatca tcagaatcaa cctcctaccc ccactctgtc ccagcagcaa tagcctgcta | 900 |
| atcttttagc actaatcttt taggcactaa tctgcttttcc aaactcttgg cacctgaact | 960 |
| atttataagc agtgttttat gcccccccac caaagaaccc tattcttttc ccatgacccc | 1020 |
| accaatcaaa acactcagag gactgtgggt ataagaggct ggggaggcag gcatagcagc | 1080 |
| ggccgccacc atggccaaga tcaacaccca atactcccac ccctccagga cccacctcaa | 1140 |
| ggtaaagacc tcagaccggg atctcaatcg cgctgaaaat ggcctcagca gagcccactc | 1200 |
| gtcaagtgag gagacatcgt cagtgctgca gccggggatc gccatggaga ccagaggact | 1260 |
| ggctgactcc gggcagggct ccttcaccgg ccaggggatc gccaggctgt cgcgcctcat | 1320 |
| cttcttgctg cgcaggtggg ctgccaggca tgtgcaccac caggaccagg gaccggactc | 1380 |
| ttttcctgat cgtttccgtg gagccgagct taaggaggtg tccagccaag aaagcaatgc | 1440 |
| ccaggcaaat gtgggcagcc aggagccagc agacagaggg agaagcgcct ggcccctggc | 1500 |
| caaatgcaac actaacacca gcaacaacac ggaggaggag aagaagacga aaagaagga | 1560 |
| tgcgatcgtg gtggacccgt ccagcaacct gtactaccgc tggctgaccg ccatcgccct | 1620 |
| gcctgtcttc tataactggt atctgcttat ttgcagggcc tgtttcgatg agctgcagtc | 1680 |
| cgagtacctg atgctgtggc tggtcctgga ctactcggca gatgtcctgt atgtcttgga | 1740 |

-continued

```
tgtgcttgta cgagctcgga caggttttct tgagcaaggc ttaatggtca gtgataccaa      1800
caggctgtgg cagcattaca agacgaccac gcagttcaag ctggatgtgt tgtccctggt      1860
ccccaccgac ctggcttact taaaggtggg cacaaactac ccagaagtga ggttcaaccg      1920
cctactgaag ttttcccggc tctttgaatt ctttgaccgc acagagacaa ggaccaacta      1980
ccccaatatg ttcaggattg ggaacttggt cttgtacatt ctcatcatca tccactggaa      2040
tgcctgcatc tactttgcca tttccaagtt cattggtttt gggacagact cctgggtcta      2100
cccaaacatc tcaatcccag agcatgggcg cctctccagg aagtacattt acagtctcta      2160
ctggtccacc ttgacccctta ccaccattgg tgagacccca cccccgtga aagatgagga      2220 gtatctcttt gtggtcgtag acttcttggt gggtgttctg attttttgcca ccattgtggg      2280 caatgtgggc tccatgatct cgaatatgaa tgcctcacgg gcagagttcc aggccaagat      2340
tgattccatc aagcagtaca tgcagttccg caaggtcacc aaggacttgg agacgcgggt      2400
tatccggtgg tttgactacc tgtgggccaa caagaagacg gtggatgaga aggaggtgct      2460
caagagcctc ccagacaagc tgaaggctga gatcgccatc aacgtgcacc tggacacgct      2520
gaagaaggtt cgcatcttcc aggactgtga ggcagggctg ctggtggagc tggtgctgaa      2580
gctgcgaccc actgtgttca gccctgggga ttatatctgc aagaagggag atattgggaa      2640
ggagatgtac atcatcaacg agggcaagct ggccgtggtg gctgatgatg gggtcacccca     2700 gttcgtggtc ctcagcgatg gcagctactt cggggagatc agcattctga acatcaaggg      2760
gagcaagtcg gggaaccgca ggacggccaa catccgcagc attggctact cagacctgtt      2820
ctgcctctca aaggacgatc tcatggaggc cctcaccgag tacccgaagc caagaaggc      2880 cctggaggag aaaggacggc agatcctgat gaaagacaac ctgatcgatg aggagctggc      2940
cagggcgggc gcggaccccca aggaccttga ggagaaagtg gagcagctgg ggtcctccct      3000
ggacaccctg cagaccaggt ttgcacgcct cctggctgag tacaacgcca cccagatgaa      3060
gatgaagcag cgtctcagcc aactggaaag ccaggtgaag ggtggtgggg acaagccccct     3120 ggctgatggg gaagttcccg gggatgctac aaaaacagag gacaaacaac agtgatcata      3180
gggccgcata gtactgcgga tccgatccaa tcaacctctg gattacaaaa tttgtgaaag      3240
attgactggt attcttaact atgttgctcc ttttacgcta tgtggatacg ctgctttaat      3300
gcctttgtat catgctattg cttcccgtat ggctttcatt ttctcctcct tgtataaatc      3360
ctggttgctg tctctttatg aggagttgtg gcccgttgtc aggcaacgtg gcgtggtgtg      3420
cactgtgttt gctgacgcaa ccccccactgg ttggggcatt gccaccacct gtcagctcct      3480
ttccgggact ttcgctttcc ccctccctat gccacggcg gaactcatcg ccgcctgcct      3540
tgcccgctgc tggacagggg ctcggctgtt gggcactgac aattccgtgg tgttgtcggg      3600
gaaatcatcg tcctttcctt ggctgctcgc ctgtgttgcc acctggattc tgcgcgggac      3660
gtccttctgc tacgtccctt cggccctcaa tccagcggac cttccttccc gcggcctgct      3720
gccggctctg cggcctcttc cgcgtcttcg agatcgatct gcctcgactg tgccttctag      3780
ttgccagcca tctgttgttt gcccctcccc cgtgccttcc ttgaccctgg aaggtgccac      3840
tcccactgtc ctttcctaat aaaatgagga aattgcatcg cattgtctga gtaggtgtca      3900
ttctattctg gggggtgggg tggggcagga cagcaagggg gaggattggg aagacaatag      3960
caggcatgct ggggactcga gttctacgta gataagtagc atggcgggtt aatcattaac      4020
tacaaggaac cctagtgatg ggagttgcc actccctctc tgcgcgctcg ctcgctcact      4080
gaggccgggc gaccaaaggt cgcccgacgc ccgggctttg cccgggcggc ctcagtgagc      4140
```

```
gagcgagcgc gcagccttaa ttaacctaag gaaaatgaag tgaagttcct atactttcta   4200
gagaatagga acttctatag tgagtcgaat aagggcgaca caaaatttat tctaaatgca   4260
taataaatac tgataacatc ttatagtttg tattatattt tgtattatcg ttgacatgta   4320
taattttgat atcaaaaact gattttccct ttattatttt cgagatttat tttcttaatt   4380
ctctttaaca aactagaaat attgtatata caaaaaatca taaataatag atgaatagtt   4440
taattatagg tgttcatcaa tcgaaaaagc aacgtatctt atttaaagtg cgttgctttt   4500
ttctcattta taaggttaaa taattctcat atatcaagca aagtgacagg cgcccttaaa   4560
tattctgaca aatgctcttt ccctaaactc cccccataaa aaacccgcc gaagcgggtt    4620
tttacgttat ttgcggatta acgattactc gttatcagaa ccgcccaggg ggcccgagct   4680
taacctttt atttggggga gagggaagtc atgaaaaaac taacctttga aattcgatct    4740
ccagcacatc agcaaaacgc tattcacgca gtacagcaaa tccttccaga cccaaccaaa   4800
ccaatcgtag taaccattca ggaacgcaac cgcagcttag accaaaacag gaagctatgg   4860
gcctgcttag gtgacgtctc tcgtcaggtt gaatggcatg gtcgctggct ggatgcagaa   4920
agctggaagt gtgtgtttac cgcagcatta aagcagcagg atgttgttcc taaccttgcc   4980
gggaatggct ttgtggtaat aggccagtca accagcagga tgcgtgtagg cgaatttgcg   5040
gagctattag agcttataca ggcattcggt acagagcgtg gcgttaagtg gtcagacgaa   5100
gcgagactgg ctctggagtg gaaagcgaga tggggagaca gggctgcatg ataaatgtcg   5160
ttagtttctc cggtggcagg acgtcagcat atttgctctg gctaatggag caaaagcgac   5220
gggcaggtaa agacgtgcat tacgttttca tggatacagg ttgtgaacat ccaatgacat   5280
atcggtttgt cagggaagtt gtgaagttct gggatatacc gctcaccgta ttgcaggttg   5340
atatcaaccc ggagcttgga cagccaaatg gttatacggt atgggaacca aaggatattc   5400
agacgcgaat gcctgttctg aagccattta tcgatatggt aaagaaatat ggcactccat   5460
acgtcggcgg cgcgttctgc actgacagat taaaactcgt tcccttcacc aaatactgtg   5520
atgaccattt cgggcgaggg aattacacca cgtggattgg catcagagct gatgaaccga   5580
agcggctaaa gccaaagcct ggaatcagat atcttgctga actgtcagac tttgagaagg   5640
aagatatcct cgcatggtgg aagcaacaac cattcgattt gcaaataccg aacatctcg    5700
gtaactgcat attctgcatt aaaaaatcaa cgcaaaaaat cggacttgcc tgcaaagatg   5760
aggagggatt gcagcgtgtt tttaatgagg tcatcacggg atcccatgtg cgtgacggac   5820
atcgggaaac gccaaaggag attatgtacc gaggaagaat gtcgctggac ggtatcgcga   5880
aaatgtattc agaaaatgat tatcaagccc tgtatcagga catggtacga gctaaaagat   5940
tcgataccgg ctcttgttct gagtcatgcg aaatatttgg agggcagctt gatttcgact   6000
tcgggaggga agctgcatga tgcgatgtta tcggtgcggt gaatgcaaag aagataaccg   6060
cttccgacca aatcaacctt actggaatcg atggtgtctc cggtgtgaaa gaacaccaac   6120
aggggtgtta ccactaccgc aggaaaagga ggacgtgtgg cgagacagcg acgaagtatc   6180
accgacataa tctgcgaaaa ctgcaaatac cttccaacga aacgcaccag aaataaaccc   6240
aagccaatcc caaagaatc tgacgtaaaa accttcaact acacggctca cctgtgggat    6300
atccggtggc taagacgtcg tgcgaggaaa acaaggtgat tgaccaaaat cgaagttacg   6360
aacaagaaag cgtcgagcga gctttaacgt gcgctaactg cggtcagaag ctgcatgtgc   6420
tggaagttca cgtgtgtgag cactgctgcg cagaactgat gagcgatccg aatagctcga   6480
```

```
tgcacgagga agaagatgat ggctaaacca gcgcgaagac gatgtaaaaa cgatgaatgc    6540
cgggaatggt ttcaccctgc attcgctaat cagtggtggt gctctccaga gtgtggaacc    6600
aagatagcac tcgaacgacg aagtaaagaa cgcgaaaaag cggaaaaagc agcagagaag    6660 aaacgcgac gagaggagca gaaacagaaa gataaactta agattcgaaa actcgcctta    6720
aagccccgca gttactggat taaacaagcc caacaagccg taaacgcctt catcagagaa    6780
agagaccgcg acttaccatg tatctcgtgc ggaacgctca cgtctgctca gtgggatgcc    6840
ggacattacc ggacaactgc tgcggcacct caactccgat ttaatgaacg caatattcac    6900
aagcaatgcg tggtgtgcaa ccagcacaaa agcggaaatc tcgttccgta tcgcgtcgaa    6960
ctgattagcc gcatcgggca ggaagcagta gacgaaatcg aatcaaacca taaccgccat    7020
cgctggacta tcgaagagtg caaggcgatc aaggcagagt accaacgaaa actcaaagac    7080
ctgcgaaata gcagaagtga ggccgcatga cgttctcagt aaaaaccatt ccagacatgc    7140
tcgttgaagc atacgaaat cagacagaag tagcacgcag actgaaatgt agtcgcggta    7200
cggtcagaaa atacgttgat gataaagacg ggaaaatgca cgccatcgtc aacgacgttc    7260
tcatggttca tcgcggatgg agtgaaagag atgcgctatt acgaaaaaat tgatggcagc    7320
aaataccgaa atatttgggt agttggcgat ctgcacggat gctacacgaa cctgatgaac    7380
aaactggata cgattggatt cgacaacaaa aaagacctgc ttatctcggt gggcgatttg    7440
gttgatcgtg gtgcagagaa cgttgaatgc ctggaattaa tcacattccc ctggttcaga    7500
gctgtacgtg gaaaccatga gcaaatgatg attgatggct tatcagagcg tggaaacgtt    7560
aatcactggc tgcttaatgg cggtggctgg ttctttaatc tcgattacga caagaaaatt    7620
ctggctaaag ctcttgccca taaagcagat gaacttccgt taatcatcga actggtgagc    7680
aaagataaaa aatatgttat ctgccacgcc gattatccct ttgacgaata cgagtttgga    7740
aagccagttg atcatcagca ggtaatctgg aaccgcgaac gaatcagcaa ctcacaaaac    7800
gggatcgtga agaaatcaa aggcgcggac acgttcatct tggtcatac gccagcagtg    7860 aaaccactca gttttgccaa ccaaatgtat atcgataccg gcgcagtgtt ctgcggaaac    7920
ctaacattga ttcaggtaca gggagaaggc gcatgagact cgaaagcgta gctaaatttc    7980
attcgccaaa aagcccgatg atgagcgact caccacgggc cacggcttct gactctcttt    8040
ccggtactga tgtgatggct gctatgggga tggcgcaatc acaagccgga ttcggtatgg    8100
ctgcattctg cggtaagcac gaactcagcc agaacgacaa acaaaaggct atcaactatc    8160
tgatgcaatt tgcacacaag gtatcgggga aataccgtgg tgtggcaaag cttgaaggaa    8220
atactaaggc aaaggtactg caagtgctcg caacattcgc ttatgcggat tattgccgta    8280
gtgccgcgac gccgggggca agatgcagag attgccatgg tacaggccgt gcggttgata    8340
ttgccaaaac agagctgtgg gggagagttg tcgagaaaga gtgcggaaga tgcaaaggcg    8400
tcggctattc aaggatgcca gcaagcgcag catatcgcgc tgtgacgatg ctaatcccaa    8460
accttaccca acccacctgg tcacgcactg ttaagccgct gtatgacgct ctggtggtgc    8520
aatgccacaa agaagagtca atcgcagaca acattttgaa tgcggtcaca cgttagcagc    8580
atgattgcca cggatggcaa catattaacg gcatgatatt gacttattga ataaaattgg    8640
gtaaatttga ctcaacgatg ggttaattcg ctcgttgtgg tagtgagatg aaaagaggcg    8700
gcgcttacta ccgattccgc ctagttggtc acttcgacgt atcgtctgga actccaacca    8760
tcgcaggcag agaggtctgc aaaatgcaat cccgaaacag ttcgcaggta atagttagag    8820
cctgcataac ggtttcggga ttttttatat ctgcacaaca ggtaagagca ttgagtcgat    8880
```

```
aatcgtgaag agtcggcgag cctggttagc cagtgctctt tccgttgtgc tgaattaagc    8940
gaataccgga agcagaaccg gatcaccaaa tgcgtacagg cgtcatcgcc gcccagcaac    9000
agcacaaccc aaactgagcc gtagccactg tctgtcctga attcattagt aatagttacg    9060
ctgcggcctt ttacacatga ccttcgtgaa agcgggtggc aggaggtcgc gctaacaacc    9120
tcctgccgtt ttgcccgtgc atatcggtca cgaacaaatc tgattactaa acacagtagc    9180
ctggatttgt tctatcagta atcgacctta ttcctaatta aatagagcaa atccccttat    9240
tgggggtaag acatgaagat gccagaaaaa catgacctgt tggccgccat tctcgcggca    9300
aaggaacaag gcatcggggc aatccttgcg tttgcaatgg cgtaccttcg cggcagatat    9360
aatggcggtg cgtttacaaa aacagtaatc gacgcaacga tgtgcgccat tatcgcctgg    9420
ttcattcgtg accttctcga cttcgccgga ctaagtagca atctcgctta taacgagc     9480
gtgtttatcg gctacatcgg tactgactcg attggttcgc ttatcaaacg cttcgctgct    9540
aaaaagccg gagtagaaga tggtagaaat caataatcaa cgtaaggcgt tcctcgatat    9600
gctggcgtgg tcggagggaa ctgataacgg acgtcagaaa accagaaatc atggttatga    9660
cgtcattgta ggcggagagc tatttactga ttactccgat caccctcgca aacttgtcac    9720
gctaaaccca aaactcaaat caacaggcgc ttaagactgg ccgtcgtttt acaacacaga    9780
aagagtttgt agaaacgcaa aaaggccatc cgtcaggggc cttctgctta gtttgatgcc    9840
tggcagttcc ctactctcgc cttccgcttc ctcgctcact gactcgctgc gctcggtcgt    9900
tcggctgcgg cgagcggtat cagctcactc aaaggcggta atacggttat ccacagaatc    9960
aggggataac gcaggaaaga acatgtgagc aaaaggccag caaaaggcca ggaaccgtaa   10020
aaaggccgcg ttgctggcgt ttttccatag gctccgcccc cctgacgagc atcacaaaaa   10080
tcgacgctca agtcagaggt ggcgaaaccc gacaggacta taaagatacc aggcgtttcc   10140
ccctggaagc tccctcgtgc gctctcctgt tccgaccctg ccgcttaccg gatacctgtc   10200
cgcctttctc ccttcgggaa gcgtggcgct ttctcatagc tcacgctgta ggtatctcag   10260
ttcggtgtag tcgttcgct  ccaagctggg ctgtgtgcac gaaccccccg ttcagcccga   10320
ccgctgcgcc ttatccggta actatcgtct tgagtccaac ccggtaagac acgacttatc   10380
gccactggca gcagccactg gtaacaggat tagcagagcg aggtatgtag cggtgctac    10440
agagttcttg aagtggtggg ctaactacgg ctacactaga agaacagtat ttggtatctg    10500
cgctctgctg aagccagtta ccttcggaaa aagagttggt agctcttgat ccggcaaaca   10560
aaccaccgct ggtagcggtg gtttttttgt ttgcaagcag cagattacgc gcagaaaaaa   10620
aggatctcaa gaagatcctt tgatcttttc tacggggtct gacgctcagt ggaacgacgc   10680
gcgcgtaact cacgttaagg gattttggtc atgagcttgc gccgtccgt  caagtcagcg   10740
taatgctctg cttttagaaa aactcatcga gcatcaaatg aaactgcaat ttattcatat   10800
caggattatc aataccatat ttttgaaaaa gccgtttctg taatgaagga gaaaactcac   10860
cgaggcagtt ccataggatg gcaagatcct ggtatcggtc tgcgattccg actcgtccaa   10920
catcaataca acctattaat ttcccctcgt caaaaataag gttatcaagt gagaaatcac   10980
catgagtgac gactgaatcc ggtgagaatg gcaaaagttt atgcatttct ttccagactt   11040
gttcaacagg ccagccatta cgctcgtcat caaaatcact cgcatcaacc aaaccgttat   11100
tcattcgtga ttgcgcctga gcgaggcgaa atacgcgatc gctgttaaaa ggacaattac   11160
aaacaggaat cgagtgcaac cggcgcagga acactgccag cgcatcaaca atattttcac   11220
```

```
ctgaatcagg atattcttct aatacctgga acgctgtttt tccggggatc gcagtggtga    11280
gtaaccatgc atcatcagga gtacggataa aatgcttgat ggtcggaagt ggcataaatt    11340
ccgtcagcca gtttagtctg accatctcat ctgtaacatc attggcaacg ctacctttgc    11400
catgtttcag aaacaactct ggcgcatcgg gcttcccata caagcgatag attgtcgcac    11460
ctgattgccc gacattatcg cgagcccatt tatacccata taaatcagca tccatgttgg    11520
aatttaatcg cggcctcgac gtttcccgtt gaatatggct catattcttc ctttttcaat    11580
attattgaag catttatcag ggttattgtc tcatgagcgg atacatattt gaatgtattt    11640
agaaaaataa acaaataggg gtcagtgtta caaccaatta accaattctg aacattatcg    11700
cgagcccatt tatacctgaa tatggctcat aacacccctt gtttgcctgg cggcagtagc    11760
gcggtggtcc cacctgaccc catgccgaac tcagaagtga aacgccgtag cgccgatggt    11820
agtgtgggga ctccccatgc gagagtaggg aactgccagg catcaaataa aacgaaaggc    11880
tcagtcgaaa gactgggcct ttcgcccggg ctaattaggg ggtgtcgccc ttattcgact    11940
ctatagtgaa gttcctattc tctagaaagt ataggaactt ctgaagtggg gtcgacttaa    12000
ttaagg                                                              12006
```

```
<210> SEQ ID NO 47
<211> LENGTH: 20
<212> TYPE: DNA
<213> ORGANISM: Artificial Sequence
<220> FEATURE:
<223> OTHER INFORMATION: primer sequence

<400> SEQUENCE: 47
cccacttggc agtacatcaa                                               20

<210> SEQ ID NO 48
<211> LENGTH: 22
<212> TYPE: DNA
<213> ORGANISM: Artificial Sequence
<220> FEATURE:
<223> OTHER INFORMATION: primer sequence

<400> SEQUENCE: 48
gccaagtagg aaagtcccat aa                                            22

<210> SEQ ID NO 49
<211> LENGTH: 24
<212> TYPE: DNA
<213> ORGANISM: Artificial Sequence
<220> FEATURE:
<223> OTHER INFORMATION: probe sequence
<220> FEATURE:
<221> NAME/KEY: misc_feature
<222> LOCATION: (1)..(1)
<223> OTHER INFORMATION: 6-FAM fluorescent label
<220> FEATURE:
<221> NAME/KEY: misc_feature
<222> LOCATION: (9)..(10)
<223> OTHER INFORMATION: ZEN quencher
<220> FEATURE:
<221> NAME/KEY: misc_feature
<222> LOCATION: (24)..(24)
<223> OTHER INFORMATION: Iowa Black FQ quencher

<400> SEQUENCE: 49
cataatgcca ggcgggccat ttac                                          24

<210> SEQ ID NO 50
<211> LENGTH: 20
```

```
<212> TYPE: DNA
<213> ORGANISM: Artificial Sequence
<220> FEATURE:
<223> OTHER INFORMATION: primer sequence

<400> SEQUENCE: 50
gatggtcgga agtggcataa                                                    20

<210> SEQ ID NO 51
<211> LENGTH: 18
<212> TYPE: DNA
<213> ORGANISM: Artificial Sequence
<220> FEATURE:
<223> OTHER INFORMATION: primer sequence

<400> SEQUENCE: 51
tgcgccagag ttgtttct                                                      18

<210> SEQ ID NO 52
<211> LENGTH: 24
<212> TYPE: DNA
<213> ORGANISM: Artificial Sequence
<220> FEATURE:
<223> OTHER INFORMATION: probe sequence
<220> FEATURE:
<221> NAME/KEY: misc_feature
<222> LOCATION: (1)..(1)
<223> OTHER INFORMATION: 6-FAM fluorescent label
<220> FEATURE:
<221> NAME/KEY: misc_feature
<222> LOCATION: (9)..(10)
<223> OTHER INFORMATION: ZEN quencher
<220> FEATURE:
<221> NAME/KEY: misc_feature
<222> LOCATION: (24)..(24)
<223> OTHER INFORMATION: Iowa Black FQ quencher

<400> SEQUENCE: 52
ccgtcagcca gtttagtctg acca                                               24
```